US 9,546,155 B2
Jan. 17, 2017

(12) United States Patent
Saruta et al.

(54) AROMATIC HETEROCYCLIC COMPOUND

(71) Applicant: MITSUBISHI TANABE PHARMA CORPORATION, Osaka-shi, Osaka (JP)

(72) Inventors: Kunio Saruta, Osaka (JP); Norimitsu Hayashi, Osaka (JP); Osamu Sakurai, Osaka (JP); Hiroaki Sawamoto, Osaka (JP); Eri Ooboki, Osaka (JP)

(73) Assignee: MITSUBISHI TANABE PHARMA CORPORATION, Osaka-shi (JP)

( * ) Notice: Subject to any disclaimer, the term of this patent is extended or adjusted under 35 U.S.C. 154(b) by 0 days.

(21) Appl. No.: 14/407,282

(22) PCT Filed: Jun. 14, 2013

(86) PCT No.: PCT/JP2013/066431
§ 371 (c)(1),
(2) Date: Dec. 11, 2014

(87) PCT Pub. No.: WO2013/187496
PCT Pub. Date: Dec. 19, 2013

(65) Prior Publication Data
US 2015/0158844 A1    Jun. 11, 2015

Related U.S. Application Data

(60) Provisional application No. 61/660,129, filed on Jun. 15, 2012, provisional application No. 61/660,137, filed on Jun. 15, 2012.

(51) Int. Cl.
C07D 401/04 (2006.01)
C07D 401/14 (2006.01)
C07D 413/14 (2006.01)
C07D 401/10 (2006.01)
C07D 409/14 (2006.01)
C07D 417/14 (2006.01)
C07D 249/08 (2006.01)
C07D 405/14 (2006.01)
C07D 249/14 (2006.01)

(52) U.S. Cl.
CPC ........... *C07D 401/14* (2013.01); *C07D 249/08* (2013.01); *C07D 249/14* (2013.01); *C07D 401/04* (2013.01); *C07D 401/10* (2013.01); *C07D 405/14* (2013.01); *C07D 409/14* (2013.01); *C07D 413/14* (2013.01); *C07D 417/14* (2013.01)

(58) Field of Classification Search
CPC .................................................. C07D 401/04
USPC ........................................ 546/256; 514/333
See application file for complete search history.

(56) References Cited

U.S. PATENT DOCUMENTS

| | | |
|---|---|---|
| 5,340,810 A | 8/1994 | Clitherow et al. |
| 5,459,148 A | 10/1995 | Yanagisawa et al. |
| 5,463,071 A | 10/1995 | Himmelsbach et al. |
| 2003/0114457 A1 | 6/2003 | Hu et al. |
| 2005/0004175 A1 | 1/2005 | Nakamura et al. |
| 2008/0096895 A1 | 4/2008 | Kamboj et al. |
| 2008/0182861 A1 | 7/2008 | Souers et al. |
| 2011/0034506 A1 | 2/2011 | Sun |
| 2011/0319403 A1 | 12/2011 | Zhou et al. |
| 2012/0101100 A1* | 4/2012 | Bist et al. ................. 514/236.8 |

FOREIGN PATENT DOCUMENTS

| | | |
|---|---|---|
| EP | 0 525 629 A2 | 2/1993 |
| JP | 6-116251 A | 4/1994 |
| JP | 2008-513514 A | 5/2008 |
| JP | 2008-255024 A | 10/2008 |
| JP | 2010-511058 A | 4/2010 |
| RU | 2109736 | 4/1998 |
| WO | WO 95/15594 A1 | 6/1995 |
| WO | WO 99/58518 A2 | 11/1999 |
| WO | WO 00/59506 A1 | 10/2000 |
| WO | WO 00/66578 A1 | 11/2000 |
| WO | WO 00/78726 A1 | 12/2000 |
| WO | WO 03/006011 A1 | 1/2003 |
| WO | WO 03/006670 A2 | 1/2003 |
| WO | WO 03/064410 A1 | 8/2003 |
| WO | WO 03/093248 A1 | 11/2003 |
| WO | WO 2004/099168 A2 | 11/2004 |
| WO | WO 2004/100881 A2 | 11/2004 |
| WO | WO 2006/034440 A3 | 3/2006 |
| WO | WO 2007/016538 A2 | 2/2007 |
| WO | WO 2008/067257 A2 | 6/2008 |
| WO | WO 2009/011285 A1 | 1/2009 |

(Continued)

OTHER PUBLICATIONS

International Search Report issued in PCT/JP2013/066431, mailed on Sep. 17, 2013.
"MEDI 315," Division of Medicinal Chemistry Scientific Abstracts for the 239th National Meeting and Exposition, Mar. 21-25, 2010.
Cases et al., "Identification of a gene encoding an acyl CoA:diacylglycerol acyltransferase, a key enzyme in triacylglycerol synthesis," Proc. Natl. Acad. Sci., vol. 95, Oct. 1998, pp. 13018-13023.
Chen et al., "Increased insulin and leptin sensitivity in mice lacking acyl CoA:diacylglycerol acyltransferase 1," The Journal of Clinical Investigation, vol. 109, No. 8, Apr. 2002, pp. 1049-1055.

(Continued)

*Primary Examiner* — Patricia L Morris
(74) *Attorney, Agent, or Firm* — Birch, Stewart, Kolasch & Birch, LLP

(57) ABSTRACT

The compound represented by the general formula: wherein ring A is benzene which may be substituted and the like; ring B is benzene which may be substituted and the like; X is a single bond and the like; Y is alkyl which may be substituted and the like; Z is $CR^1$ or nitrogen atom; $R^1$ is hydrogen and the like; $R^2$ is alkyl which may be substituted and the like or a pharmaceutically acceptable salt thereof is useful as a prevention/treatment agent of obesity, diabetes, and the like.

5 Claims, No Drawings

(56) References Cited

FOREIGN PATENT DOCUMENTS

| WO | WO 2009/079593 A1 | 6/2009 |
| WO | WO 2009/126861 A2 | 10/2009 |
| WO | WO 2010/107765 A1 | 9/2010 |
| WO | WO 2011/002067 A1 | 1/2011 |
| WO | WO 2012/009217 A1 | 1/2012 |
| WO | WO 2012/015693 A1 | 2/2012 |
| WO | WO 2012/044567 A2 | 4/2012 |
| WO | WO 2012/044567 A3 | 4/2012 |
| WO | WO 2012/047772 A2 | 4/2012 |
| WO | WO 2012/081736 A1 | 6/2012 |

OTHER PUBLICATIONS

Chen et al., "Inhibition of Triglyceride Synthesis as a Treatment Strategy for Obesity," Arterioscler Thromb Vasc Biol., Mar. 2005, pp. 482-486.

Gilcrest, T. Heterocyclic Chemistry Addision Wesley Longman 1997, p. 257.

International Preliminary Report on Patentability and Written Opinion issued Jun. 27, 2013, in PCT International Application No. PCT/JP2011/079958.

International Search Report issued in PCT/JP2011/079958, mailed on Feb. 14, 2012.

Liu et al., Discovery of Potent, Selective, Orally Bioavailable Stearoyl-CoA Desaturase 1 Inhibitors, J. Med. Chem., 50(13), pp. 3086-3100 (2007).

Nanzando's Medical Dictionary 19th Edition, Nanzando Company, Limited, 2006, pp. 2112-2113 and Partial English translation.

Sulsky et al., "Potent and selective biphenyl azole inhibitors of adipocyte fatty acid binding protein (aFABP)," Bioorganic & Medicinal Chemistry Letters 17, 2007, pp. 3511-3515.

Written Opinion of the International Searching Authority issued in PCT/JP2011/079958, mailed on Feb. 14, 2012.

Yen et al., "MGAT2, a Monoacylglycerol Acyltransferase Expressed in the Small Intestine," The Journal of Biological Chemistry, vol. 278, No. 20, May 16, 2003, pp. 18532-18537.

Al-Soud et el., "Synthesis and Biological Evaluation of Phenyl Substituted 1H-1,2,4-Triazoles as Non-Steroidal Inhibitors of 17β-Hydroxysteroid Dehydrogenase Type 2," Arch. Pharm. Chem. Life Sci., vol. 345, No. 8, Apr. 25, 2012, pp. 610-621. XP055215409.

Extended European Search Report, dated Oct. 8, 2015, for European Application No. 13804940.8.

U.S. Appl. No. 13/994,543, filed Jun. 14, 2013.

* cited by examiner

AROMATIC HETEROCYCLIC COMPOUND

CROSS REFERENCE TO RELATED APPLICATIONS

This application is the National Phase of PCT International Application No. PCT/JP2013/066431, filed on Jun. 14, 2013, which claims priority under 35 U.S.C. 119(e) to U.S. Provisional Application No. 61/660,129, filed on Jun. 15, 2012, and to U.S. Provisional Application No. 61/660,137, filed on Jun. 15, 2012, all of which are hereby expressly incorporated by reference into the present application.

TECHNICAL FIELD

The present invention relates to an aromatic heterocyclic compound or a pharmaceutically acceptable salt thereof having an acylcoenzyme A: diacylglycerolacyltransferase (DGAT) 1 inhibitory activity.

BACKGROUND ART

Obesity is a condition wherein fat is excessively accumulated in a body (Non-Patent Document 1), and may lead to hyperlipidemia, hypertriglycemia, lipid metabolism disorder, fatty liver, diabetes, hypertension, arteriosclerosis, cerebrovascular disorder, coronary artery disease, dyspnoea, lumbago, gonarthrosis, and the like. Among obesity, those having these diseases or those which may possibly cause these diseases in the future are defined as adiposity, and regarded as one of diseases.

DGAT is an enzyme catalyzing a reaction from diacylglyerol to TG, which reaction is the final stage of triacylglycerol (TG) synthesis, and it is known that DGAT has two kinds of subtypes, DGAT1 and DGAT2. Among these, DGAT1 is known to exist in liver, skeletal muscle, adipocytes, and the like, and is involved in the TG synthesis in each tissue (Non-Patent Document 2).

Further, when TG is absorbed in the small intestine, TG is decomposed by pancreatic lipase in the lumen of the small intestine to fatty acid and mono acylglycerol, then incorporated into small intestinal epithelial cells, and absorbed after it is resynthesized to TG in the epithelial cells, and it has been known that DGAT1 is also involved in the final stage of TG resynthesis in the small intestinal epithelial cells (Non-Patent Document 3).

Therefore, a compound which inhibits DGAT1 is expected to improve the pathology of obesity since it not only inhibits TG synthesis in adipocyte, liver and the like by inhibiting the final step of TG synthesis but also suppresses the TG absorption in small intestines by suppressing the TG resynthesis in small intestine (Non-Patent Document 4).

Further, a theory that the accumulation of TG in liver, skeletal muscle, and the like (ectopic fat accumulation) is a cause of insulin resistance in type 2 diabetes mellitus accompanying obesity has been widely accepted, and a compound which inhibits DGAT1 is expected to improve the insulin sensitivity and has the therapeutic effect on type 2 diabetes mellitus by alleviating the ectopic fat accumulation (Non-Patent Document 4). Furthermore, in a mouse deleted in DGAT1 by genetic manipulation (DGAT1 knockout mouse), it was reported that the improvement in the insulin sensitivity was observed as compared with a wild type mouse (Non-Patent Document 5). It was recently reported that a compound which inhibits DGAT1 stimulates the action of glucagon-like peptide-1 (GLP-1) and a protein which causes anorexia (Non-Patent Document 6).

As a compound having a continuous aromatic ring structure, the following has been known. For example, in Patent Document 1, (2S)-2-[4'-(1-benzyl-1H-benzimidazole-2-yl)-biphenyl-4-yloxy]-3-phenyl-propionic acid (Example 70) and the like are disclosed as a compound which inhibits protein-tyrosine phosphatase (PTPases) and is useful for the treatment of insulin resistance accompanying obesity, glucose intolerance, diabetes, hypertension, or ischemic disease.

In Patent Document 2, as a compound having an inhibitory activity against protein-tyrosine phosphatase 1B (PTP-1B) which is useful for the treatment of type 2 diabetes mellitus, 2-benzyl-4-[4'-(2-benzyl-benzofuran-3-yl)-biphenyl-4-yl]-4-oxo-butyric acid (Example 1), ({4'-(3-benzylamino)imidazo[1,2-a]pyridin-2-yl)biphenyl-4-yl}oxy) (phenyl)acetic acid, {[4'-(5-methyl-1H-indol-1-yl)biphenyl-4-yl]oxy}(phenyl) acetic acid (Example 3), and the like are disclosed.

In Patent Document 3, Patent Document 4 and Patent Document 5, a compound having an inhibitory activity against Factor VIIa, Factor IXa, Factor Xa, and/or Factor XIa which has a structure wherein biphenyl and nitrogen-containing fused heterocyclic ring are bonded is disclosed. However, the chemical structure is restricted to those having a structure wherein the nitrogen-containing fused heterocyclic ring is bonded at the 3-position of the biphenyl.

In Patent Document 6, 2-[[2'-(5-phenyl-1H-imidazol-2-yl)[1,1'-biphenyl]-3-yl]oxy]acetic acid (Example 46) and the like as a compound having the therapeutic effect on obesity and diabetes by inhibiting adipocyte fatty acid-binding protein (aP2) are disclosed.

In Non-Patent Document 7, 2-[[2'-(1-ethyl-4,5-diphenyl-1H-imidazol-2-yl) [1,1'-biphenyl]-3-yl]oxy]acetic acid, 2-[[2'-(4,5-diphenyl-1H-imidazol-2-yl)[1,1'-biphenyl]-3-yl] oxy]acetic acid, and the like as a compound which binds to adipocyte fatty acid-binding protein (aFABP) are reported.

As another compound having a continuous ring structure, those in, for example, Patent Documents 7 to 14 and Non-Patent Document 8 are known.

Also, as a compound having DGAT1 inhibitory activity, for example, heteroarylbenzene derivatives (Patent Document 15), bicyclic heterocyclic compounds (Patent Document 16), triazolopyridine derivatives (Patent Document 17), imidazole derivatives (Patent Documents 18 to 20), spiro-ring compounds (Patent Document 21), and biaryl compounds (Patent Document 22) are known.

PRIOR ART DOCUMENTS

Patent Documents

Patent Document 1: WO99/58518A
Patent Document 2: WO2004/99168A
Patent Document 3: WO2003/6670A
Patent Document 4: WO2003/6011A
Patent Document 5: US2003/0114457A
Patent Document 6: WO00/59506A
Patent Document 7: WO2006/034440
Patent Document 8: WO2011/002067
Patent Document 9: JP1994/116251
Patent Document 10: WO2003/093248
Patent Document 11: WO2000/066578
Patent Document 12: WO2009/079593
Patent Document 13: WO1995/015594
Patent Document 14: WO2003/064410
Patent Document 15: WO2009/011285
Patent Document 16: WO2010/107765

Patent Document 17: WO2009/126861
Patent Document 18: WO2012/015693
Patent Document 19: WO2012/047772
Patent Document 20: WO2012/044567
Patent Document 21: WO2012/009217
Patent Document 22: WO2008/067257

Non-Patent Documents

Non-Patent Document 1: Nanzando's Medical Dictionary (19th Edition), page 2113, 2006
Non-Patent Document 2: Proc. Natl. Acad. Sci. USA, Vol. 95, page 13018, 1998
Non-Patent Document 3: J. Biol. Chem. Vol. 278, page 18532, 2003
Non-Patent Document 4: Arterioscler. Thromb. Vasc. Biol. Vol. 25, page 482, 2005
Non-Patent Document 5: The Journal of Clinical Investigation, 109(8) 1049-1055 (2002)
Non-Patent Document 6: American Chemical Society National Meeting Abst. MEDI 315 (2010)
Non-Patent Document 7: Bioorganic & Medicinal Chemistry Letters 17(12) 3511-3515, 2007
Non-Patent Document 8: J. Med. Chem. 50(13), 3086-3100 (2007)

DISCLOSURE OF THE INVENTION

Problems to be Solved by the Invention

An object of the present invention is to provide an aromatic heterocyclic compound or a pharmaceutically acceptable salt thereof having DGAT1 inhibitory activity, and a DGAT1 inhibitor which is useful for the prevention and/or treatment of obesity, or hyperlipidemia, hypertriglyceridemia, lipid metabolism disorder, fatty liver, hypertension, arteriosclerosis, diabetes, and the like caused by obesity.

Means to Solve the Problems

As a result that the inventors of present invention have conducted earnest studies to solve the aforementioned problems, and as a result they have found the aromatic heterocyclic compound or a pharmaceutically acceptable salt thereof represented by a formula as below has an excellent DGAT1 inhibitory activity and accomplished the present invention.

Namely, the present invention is as follows:
1. A compound represented by the general formula (1):

[Chemical Formula 1]

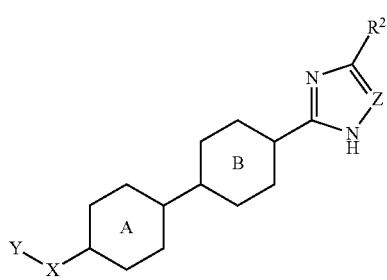

(1)

[wherein ring A is benzene which may be substituted or 6-membered monocyclic aromatic heterocycle which may be substituted;
ring B is benzene which may be substituted or 6-membered monocyclic aromatic heterocycle which may be substituted;
X is a single bond or —O—;
Y is alkyl which may be substituted or cycloalkyl which may be substituted;
Z is $CR^1$ or nitrogen atom;
$R^1$ is hydrogen, halogen atom, alkoxy, or alkyl which may be substituted;
(i) when Z is $CR^1$, $R^2$ is the formula as below:

[Chemical Formula 2]

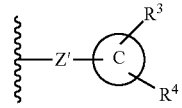

{wherein Z' represents a single bond, alkylene, -Alk-O—, or -$Alk^1$-O-$Alk^2$-,
(wherein Alk, $Alk^1$, and $Alk^2$ each independently represent alkylene, and the bond at the right end represents a bond to ring C),
ring C represents an aromatic hydrocarbon group or an aromatic heterocyclic group},
$R^3$ and $R^4$ each independently represent hydrogen, halogen atom, alkyl which may be substituted, alkoxy which may be substituted, alkyl substituted with non-aromatic heterocycle, or carbonyl substituted with non-aromatic heterocycle); (ii) when Z is nitrogen atom, $R^2$ is alkyl which may be substituted, alkoxy which may be substituted, alkylthio, an aromatic hydrocarbon group which may be substituted, a non-aromatic heterocyclic group which may be substituted, cycloalkyl which may be substituted, aryloxy which may be substituted, heteroaryloxy which may be substituted, cycloalkyloxy, or cycloalkylalkoxy],
or a pharmaceutically acceptable salt thereof.
2. The compound according to the above 1, wherein the compound is represented by the general formula (1-A):

[Chemical Formula 3]

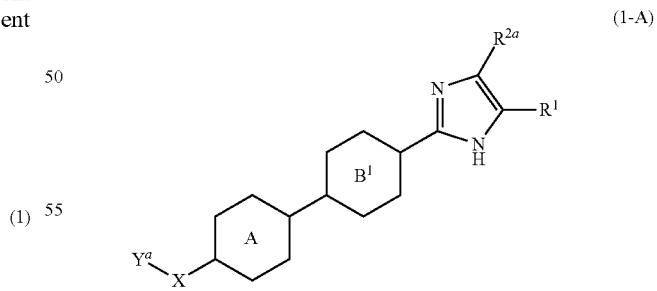

(1-A)

[wherein ring A is benzene which may be substituted or 6-membered monocyclic aromatic heterocycle which may be substituted;
ring $B^1$ is benzene which may be substituted or 6-membered monocyclic aromatic heterocycle which may be substituted;
$R^1$ is hydrogen, halogen atom, alkoxy, or alkyl which may be substituted;

$R^{2a}$ is the formula as below:

[Chemical Formula 4]

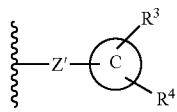

{wherein Z' represents a single bond, alkylene, -Alk-O—, or -Alk$^1$-O-Alk$^2$-,
(wherein Alk, Alk$^1$, and Alk$^2$ each independently represent alkylene, and the bond at the right end represents a bond to ring C),
ring C represents an aromatic hydrocarbon group or an aromatic heterocyclic group,
R$^3$ and R$^4$ each independently represent hydrogen, halogen atom, alkyl which may be substituted, alkoxy which may be substituted, alkyl substituted with non-aromatic heterocycle, or carbonyl substituted with non-aromatic heterocycle};
X is a single bond or —O—;
Y$^a$ is alkyl which may be substituted or cycloalkyl which may be substituted];
or a pharmaceutically acceptable salt thereof.

3. The compound according to the above 2 wherein ring A is benzene which may be substituted or pyridine which may be substituted, or a pharmaceutically acceptable salt thereof.

4. The compound according to the above 2 or 3 wherein ring B$^1$ is benzene which may be substituted, pyridine which may be substituted, or pyrimidine which may be substituted, or a pharmaceutically acceptable salt thereof.

5. The compound according to any one of the above 2 to 4 wherein X is —O—; and Y$^a$ is alkyl substituted with carboxy, or a pharmaceutically acceptable salt thereof.

6. The compound according to the above 2 which is selected from
1-{[(5'-fluoro-4-methyl-6'-{5-[2-(trifluoromethoxy)phenyl]-1H-imidazol-2-yl}-3,3'-bipyridin-6-yl)oxy]methyl}cyclopropanecarboxylic acid,
2,2-dimethyl-3-{[4-methyl-5-(2-{5-[2-(trifluoromethyl)phenyl]-1H-imidazol-2-yl}-pyrimidin-5-yl)pyridin-2-yl]oxy}propanoic acid,
3-{[5'-fluoro-4-methyl-6'-(5-phenyl-1H-imidazol-2-yl)-3,3'-bipyridin-6-yl]oxy}-2,2-dimethylpropanoic acid,
2-ethyl-2-[({5-[6-(5-phenyl-1H-imidazol-2-yl)pyridin-3-yl]pyrazin-2-yl}oxy)methyl]-butanoic acid,
3-[4-(5-{5-[4-(difluoromethoxy)phenyl]-1H-imidazol-2-yl}pyridin-2-yl)phenoxy]-2,2-dimethylpropanoic acid,
2,2-dimethyl-3-[4-(5-{5-[2-(trifluoromethoxy)phenyl]-1H-imidazol-2-yl}pyridin-2-yl)-phenoxy]propanoic acid,
2,2-dimethyl-3-(4-{5-[5-(2-phenoxyethyl)-1H-imidazol-2-yl]pyridin-2-yl}phenoxy)-propanoic acid,
2,2-dimethyl-3-({4-methyl-5-[2-(5-phenyl-1H-imidazol-2-yl)pyrimidin-5-yl]pyridin-2-yl}oxy)propanoic acid,
2,2-dimethyl-3-({4-methyl-5-[3-methyl-4-(5-phenyl-1H-imidazol-2-yl)phenyl]pyridin-2-yl}oxy)propanoic acid,
2,2-dimethyl-3-({5-[3-methyl-4-(5-phenyl-1H-imidazol-2-yl)phenyl]pyridin-2-yl}oxy)-propanoic acid,
3-(4-{5-[5-(2,4-difluorophenyl)-1H-imidazol-2-yl]pyridin-2-yl}phenoxy)-2,2-dimethylpropanoic acid,
2-ethyl-2-[({4-methyl-5-[2-(5-phenyl-1H-imidazol-2-yl)pyrimidin-5-yl]pyridin-2-yl}-oxy)methyl]butanoic acid,
1-[({4-methyl-5-[2-(5-phenyl-1H-imidazol-2-yl)pyrimidin-5-yl]pyridin-2-yl}oxy)-methyl]cyclobutanecarboxylic acid,
2,2-dimethyl-3-({5-[4-(5-phenyl-1H-imidazol-2-yl)phenyl]pyridin-2-yl}oxy)propanoic acid,
3-[(5-{4-[5-(4-methoxyphenyl)-1H-imidazol-2-yl]phenyl}pyridin-2-yl)oxy]-2,2-dimethylpropanoic acid,
1-({[5'-fluoro-4-methyl-6'-(5-phenyl-1H-imidazol-2-yl)-3,3'-bipyridin-6-yl]oxy}-methyl)cyclopropanecarboxylic acid,
3-[(5-{3-cyano-4-[4-(4-methoxyphenyl)-1H-imidazol-2-yl]phenyl}-4-methylpyridin-2-yl)oxy]-2,2-dimethylpropanoic acid,
2,2-dimethyl-3-[4-(5-{5-[2-(trifluoromethyl)benzyl]-1H-imidazol-2-yl}pyridin-2-yl)-phenoxy]propanoic acid,
3-(4-{5-[5-(4-methoxyphenyl)-1H-imidazol-2-yl]pyridin-2-yl}phenoxy)-2,2-dimethylpropanoic acid,
2,2-dimethyl-3-({4-methyl-5-[4-(5-phenyl-1H-imidazol-2-yl)phenyl]pyridin-2-yl}oxy)-propanoic acid,
3-[4-(5-{5-[(benzyloxy)methyl]-1H-imidazol-2-yl}pyridin-2-yl)phenoxy]-2,2-dimethylpropanoic acid,
3-{4-[5-(4-chloro-5-phenyl-1H-imidazol-2-yl)pyridin-2-yl]phenoxy}-2,2-dimethylpropanoic acid,
2,2-dimethyl-3-(4-{5-[5-(thiophen-2-yl)-1H-imidazol-2-yl]pyridin-2-yl}phenoxy)-propanoic acid,
3-[(5-{4-[5-(4-methoxyphenyl)-1H-imidazol-2-yl]phenyl}-4-methylpyridin-2-yl)oxy]-2,2-dimethylpropanoic acid, and
2,2-dimethyl-3-{4-[5-(5-phenyl-1H-imidazol-2-yl)pyridin-2-yl]phenoxy}propanoic acid,
or a pharmaceutically acceptable salt thereof.

7. The compound according to the above 1 wherein the compound is represented by the general formula (1-B):

[Chemical Formula 5]

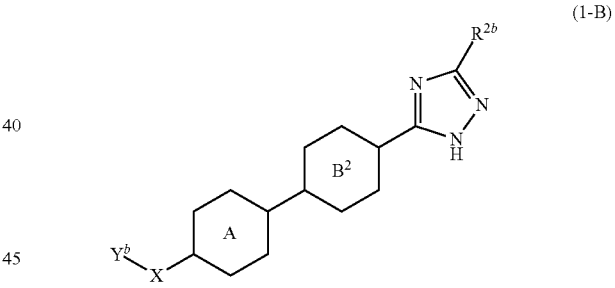

(wherein ring A represents benzene which may be substituted or 6-membered monocyclic aromatic heterocycle which may be substituted;
ring B$^2$ represents benzene which may be substituted or 6-membered monocyclic aromatic heterocycle which may be substituted;
R$^{2b}$ represents alkyl which may be substituted, alkoxy which may be substituted, alkylthio, an aromatic hydrocarbon group which may be substituted, a non-aromatic heterocyclic group which may be substituted, cycloalkyl which may be substituted, aryloxy which may be substituted, heteroaryloxy which may be substituted, cycloalkyloxy, or cycloalkylalkoxy,
X represents a single bond or —O—;
Y$^b$ represents alkyl which may be substituted or cycloalkyl which may be substituted);
or a pharmaceutically acceptable salt thereof.

8. The compound according to the above 7 wherein ring A is benzene which may be substituted or pyridine which may be substituted, or a pharmaceutically acceptable salt thereof.

9. The compound according to the above 7 or 8 wherein ring $B^2$ is benzene which may be substituted, pyridine which may be substituted or pyrimidine which may be substituted, or a pharmaceutically acceptable salt thereof.

10. The compound according to any one of the above 7 to 9 wherein $R^{2b}$ is alkyl which may be substituted, alkoxy which may be substituted, an aromatic hydrocarbon group which may be substituted, or aryloxy which may be substituted, or a pharmaceutically acceptable salt thereof.

11. The compound according to any one of the above 7 to 10 wherein X is —O—, and $Y^b$ is alkyl which may be substituted with carboxy, or a pharmaceutically acceptable salt thereof.

12. The compound according to the above 7 which is selected from 2,2-dimethyl-3-[(5-{4-[3-(propan-2-yloxy)-1H-1,2,4-triazol-5-yl]phenyl}-pyridin-2-yl)oxy]propanoic acid, 3-[(5-{3-fluoro-4-[3-(propan-2-yloxy)-1H-1,2,4-triazol-5-yl]phenyl}-4-methylpyridin-2-yl)oxy]-2,2-dimethylpropanoic acid, 2,2-dimethyl-3-({4'-methyl-5-[3-(propan-2-yloxy)-1H-1,2,4-triazol-5-yl]-2,3'-bipyridin-6'-yl}oxy)propanoic acid, 3-[(5-{4-[3-(4-fluorophenoxy)-1H-1,2,4-triazol-5-yl]phenyl}pyridin-2-yl)oxy]-2,2-dimethylpropanoic acid, 3-[(5-{4-[3-(4-cyanophenoxy)-1H-1,2,4-triazol-5-yl]phenyl}pyridin-2-yl)oxy]-2,2-dimethylpropanoic acid, 2,2-dimethyl-3-[(5-{4-[3-(2,2,3,3,3-pentafluoropropoxy)-1H-1,2,4-triazol-5-yl]phenyl}pyridin-2-yl)oxy]propanoic acid sodium salt, (trans-4-{4'-[3-(trifluoromethyl)-1H-1,2,4-triazol-5-yl]biphenyl-4-yl}cyclohexyl)acetic acid, (trans-4-{4-{5-[3-(trifluoromethyl)-1H-1,2,4-triazol-5-yl]pyridin-2-yl}phenyl)-cyclohexyl]acetic acid,

[4-(5-{4-[3-(trifluoromethyl)-1H-1,2,4-triazol-5-yl]phenyl}pyridin-2-yl)cyclohexyl]-acetic acid, 2,2-dimethyl-3-({5-[4-(5-phenyl-4H-1,2,4-triazol-3-yl)phenyl]pyridin-2-yl}oxy)-propanoic acid, (4-{5-[4-(3-ethoxy-1H-1,2,4-triazol-5-yl)phenyl]pyridin-2-yl}cyclohexyl)acetic acid, 3-({5-[4-(3-ethoxy-1H-1,2,4-triazol-5-yl)phenyl]-4-methylpyridin-2-yl}oxy)-2,2-dimethylpropanoic acid, 2,2-dimethyl-3-({4-methyl-6'-[3-(propan-2-yloxy)-1H-1,2,4-triazol-5-yl]-3,3'-bipyridin-6-yl}oxy)propanoic acid, 3-[(5-{4-[3-(2,4-difluorophenoxy)-1H-1,2,4-triazol-5-yl]phenyl}pyridin-2-yl)oxy]-2,2-dimethylpropanoic acid, and 3-[(5-{3-fluoro-4-[3-(4-fluorophenoxy)-1H-1,2,4-triazol-5-yl]phenyl}-4-methylpyridin-2-yl)oxy]-2,2-dimethylpropanoic acid, or a pharmaceutically acceptable salt thereof.

13. A diacylglycerol acyltransferase (DGAT) 1 inhibitor comprising the compound according to any one of the above 1 to 12 or a pharmaceutically acceptable salt thereof as active ingredient.

14. The DGAT 1 inhibitor according to the above 13 which is a prophylactic or treatment agent of obesity.

15. The DGAT 1 inhibitor according to the above 13 which is a prophylactic or treatment agent of hyperlipidemia, hypertriglyceridemia, lipid metabolism disorder or fatty liver.

16. The DGAT 1 inhibitor according to the above 13 wherein the agent is a prevention/treatment agent of type 2 diabetes mellitus, diabetic complication (including diabetic peripheral neuropathy, diabetic nephropathy, diabetic retinopathy and diabetic macroangiopathy), arteriosclerosis, hypertension, cerebrovascular disorder, coronary artery disease, dyspnoea, lumbago or gonarthrosis.

17. The DGAT 1 inhibitor according to the above 13 wherein the agent is a prevention/treatment agent of type 2 diabetes mellitus or diabetic complication.

18. The DGAT 1 inhibitor according to the above 13 wherein the agent is a prevention/treatment agent of familial hyperchylomicronemia.

19. Use of the compound according to any one of the above 1 to 12 or a pharmaceutically acceptable salt thereof for the prevention/treatment of hyperlipidemia, hypertriglyceridemia, lipid metabolism disorder, fatty liver, type 2 diabetes mellitus, diabetic complication (including diabetic peripheral neuropathy, diabetic nephropathy, diabetic retinopathy and diabetic macroangiopathy), arteriosclerosis, hypertension, cerebrovascular disorder, coronary artery disease, dyspnoea, lumbago or gonarthrosis.

20. Use of the compound according to any one of the above 1 to 12 or a pharmaceutically acceptable salt thereof for the prevention/treatment of familial hyperchylomicronemia.

21. A method for the prevention/treatment of hyperlipidemia, hypertriglyceridemia, lipid metabolism disorder, fatty liver, type 2 diabetes mellitus, diabetic complication (including diabetic peripheral neuropathy, diabetic nephropathy, diabetic retinopathy and diabetic macroangiopathy), arteriosclerosis, hypertension, cerebrovascular disorder, coronary artery disease, dyspnoea, lumbago or gonarthrosis, characterized by administering the compound according to any one of the above 1 to 12 or a pharmaceutically acceptable salt thereof to a patient.

22. A method for the prevention/treatment of familial hyperchylomicronemia, characterized by administering the compound according to any one of the above 1 to 12 or a pharmaceutically acceptable salt thereof to a patient.

Another aspect of the present invention includes a compound represented by the general formula (A) as below:

[Chemical Formula 6]

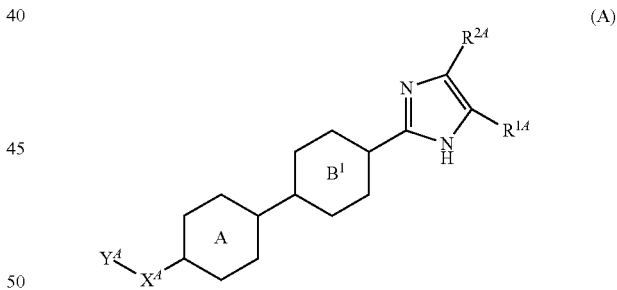

[wherein ring A represents benzene which may be substituted or 6-membered monocyclic aromatic heterocycle which may be substituted;

ring $B^1$ represents benzene which may be substituted or 6-membered monocyclic aromatic heterocycle which may be substituted;

$X^A$ represents a single bond or —O—;

$Y^A$ represents:

(1) cycloalkyl which may be substituted with the group selected from (i) to (v) as below:

(i) carboxy,
(ii) carboxyalkyl
(iii) alkoxyalkyl
(iv) aminocarbonyl, and
(v) alkoxycarbonylalkyl, or (2) alkyl which may be substituted with a group selected from (i) and (ii) as below:
  (i) carboxy, and
  (ii) aminocarbonyl which may be mono- or di-substituted with alkyl which may be substituted with 1 to 3 hydroxyls,
$R^{1A}$ represents hydrogen, alkyl, or halogen atom; and
$R^{2A}$ represents (1) alkyl which may be substituted with a group selected from halogen atom, alkoxy, and hydroxy, (2) halogen atom, (3) cyano, (4) aminocarbonyl which may be mono- or di-substituted with alkyl, (5) alkoxycarbonyl, or (6) tetrahydropyranyl;
with the proviso that when $R^{1A}$ is hydrogen atom; $R^{2A}$ is alkyl which may be substituted with halogen atom; ring A is:

[Chemical Formula 7]

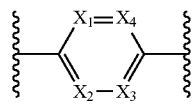

(wherein a bond at the right end represents a bond to ring B, $X_1$ represents N or $CRX_1$, $X_2$ represents N or $CRX_2$, $X_3$ represents N or $CRX_3$, $X_4$ represents N or $CRX_4$, $RX_1$, $RX_2$, $RX_3$ and $RX_4$ each represents hydrogen, straight or branched alkyl which may be substituted with halogen atom, alkyl having a cyclic structure which may be substituted with halogen atom, straight or branched alkoxy, halogen atom, or cyano),
then an aspect wherein $Y^A$ is alkyl substituted with carboxy, and $X^A$ is —O— is excluded,
or a pharmaceutically acceptable salt thereof.]

Another aspect of the present invention includes a compound represented by the general formula (B) as below:

[Chemical Formula 8]

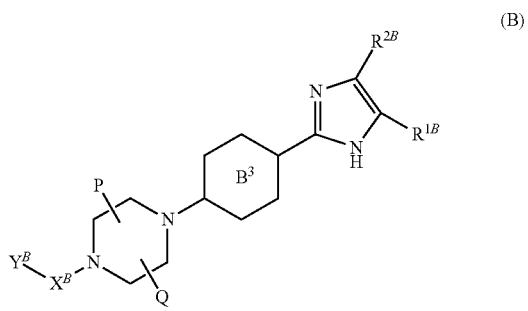

(wherein ring $B^3$ represents 6-membered monocyclic aromatic heterocycle which may be substituted;
P represents hydrogen or alkyl,
Q represents hydrogen, or a group which forms carbonyl together with P,
$X^B$ represents a single bond or —CH$_2$CO— wherein a bond at the right end represents a bond to piperazine,
$Y^B$ represents:
(1) phenyl which may be substituted with a group selected from (i) to (vi) as below:
  (i) halogen atom,
  (ii) alkyl,
  (iii) carboxyalkyl
  (iv) hydroxyalkyl
  (v) alkoxycarbonylalkyl which may be substituted with a group selected from hydroxy, aralkyloxy, and 2,2-dimethyl-1,3-dioxolane, and (vi) aminocarbonylalkyl which may be mono- or di-substituted with alkyl which may be substituted with a group selected from hydroxy and 2,2-dimethyl-1,3-dioxolane,
(2) pyridyl which may be substituted with alkyl, or
(3) alkyl which may be substituted with carboxy,
$R^{1B}$ represents hydrogen or alkyl, and
$R^{2B}$ represents cycloalkyl or alkyl which may be substituted with halogen),
or a pharmaceutically acceptable salt thereof.

Another aspect of the present invention also includes a compound represented by the general formula (C) as below:

[Chemical Formula 9]

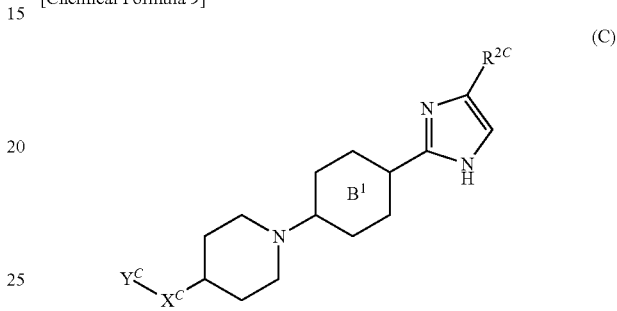

[wherein ring $B^1$ represents benzene which may be substituted or 6-membered monocyclic aromatic heterocycle which may be substituted,
$X^C$ represents a single bond, —O—, —OCH$_2$— (wherein a bond at the right end represents a bond to piperazine, or alkylene),
$Y^C$ represents:
(1) phenyl which may be substituted with a group selected from (i) to (v) as below:
  (i) halogen atom,
  (ii) alkyl,
  (iii) carboxyalkyl
  (iv) carboxy, and
  (v) alkoxy, or
(2) alkyl which may be substituted with carboxy, and
$R^{2C}$ represents alkyl which may be substituted with halogen],
or a pharmaceutically acceptable salt thereof.

Further, another aspect of the present invention includes a compound represented by the general formula (D) as below:

[Chemical Formula 10]

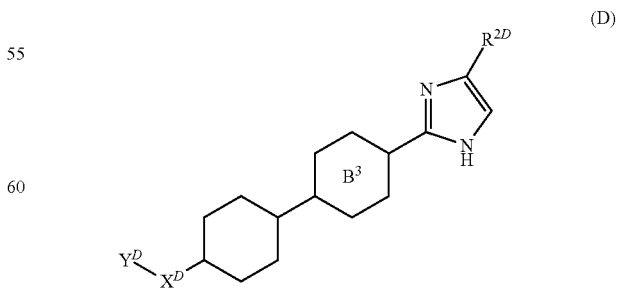

[wherein ring $B^3$ represents 6-membered monocyclic aromatic heterocyclic ring which may be substituted, $X^D$ represents a single bond, —OCH$_2$— or —O— (wherein a bond at the right end represents a bond to cyclohexane), $Y^D$ represents:
(1) phenyl which may be substituted with a group selected from (i) to (iv) as below:
  (i) halogen atom,
  (ii) alkyl,
  (iii) carboxyalkyl, and
  (iv) carboxy
(2) pyridyl which may be substituted with carboxy, or
(3) alkyl which may be substituted with carboxy, and $R^{2D}$ represents alkyl which may be substituted with halogen], or a pharmaceutically acceptable salt thereof.

The groups represented by each symbol in the present specification are explained below. The abbreviations used in the present specification each have the meanings as below.
Ac: acetyl
Bn: benzyl
Boc: t-butoxycarbonyl
EDC: 1-ethyl-3-(3-dimethylaminopropyl)carbodiimide
Et: ethyl
HOBt: 1-hydroxybenzotriazole
Me: methyl
MOM: methoxymethyl
Ph: phenyl
SEM: 2-(trimethylsilyl)ethoxymethyl
TBS: t-butyldimethylsilyl
t-Bu: t-butyl
Tf: trifluoromethanesulfonyl
TFA: trifluoroacetic acid
THF: tetrahydrofuran
TMS: trimethylsilyl As "halogen atom", fluorine atom, chlorine atom, bromine atom, and iodine atom can be mentioned. Among them, fluorine atom and chlorine atom are preferred.

As "alkyl", for example, straight or branched alkyl having 1 to 8 carbon atom, preferably 1 to 6 carbon atoms, can be mentioned, and specifically, methyl, ethyl, propyl, isopropyl, butyl, t-butyl, isobutyl, pentyl, hexyl, 2-methylpropyl, 2-ethylbutyl, 2-propylpentyl, and the like can be mentioned.

As "cycloalkane", for example, cycloalkane having 3 to 8 carbon atoms, preferably 3 to 6 carbon atoms, can be mentioned, and specifically, cyclopropane, cyclobutane, cyclopentane, cyclohexane, cycloheptane, and the like can be mentioned.

As "cycloalkyl", for example, cycloalkyl having 3 to 8 carbon atoms, preferably 3 to 6 carbon atom, can be mentioned, and specifically, cyclopropyl, cyclobutyl, cyclopentyl, cyclohexyl, cycloheptyl, and the like can be mentioned.

As "alkoxy", for example, straight or branched alkoxy having 1 to 8 carbon atom, preferably 1 to 6 carbon atoms, can be mentioned, and specifically, methoxy, ethoxy, propoxy, isopropoxy, butoxy, t-butoxy, isobutoxy, pentyloxy, hexyloxy, and the like can be mentioned.

As "alkylene", for example, straight or branched alkylene having 1 to 6 carbon atom, preferably 1 to 3 carbon atoms, can be mentioned, and specifically, methylene, ethylene, propylene, isopropylene, butylene, isobutylene, and the like can be mentioned.

As "alkoxycarbony", for example, straight or branched alkoxycarbonyl having 2 to 9 carbon atoms, can be mentioned, and specifically, methoxycarbonyl, ethoxycarbonyl, propoxycarbonyl, isopropoxycarbonyl, butoxycarbonyl, pentyloxycarbonyl, hexyloxycarbonyl, and the like can be mentioned.

As "alkoxycarbonylalkyl", for example, the above "alkyl" substituted with the above "alkoxycarbonyl" can be mentioned, and specifically, methoxycarbonylmethyl, methoxycarbonylethyl, ethoxycarbonylmethyl, ethoxycarbonylethyl, and the like can be mentioned.

As "carboxyalkyl", for example, the above "alkyl" substituted with carboxy can be mentioned, and specifically, carboxymethyl, carboxyethyl, carboxypropyl, carboxyisopropyl, carboxy-t-butyl, carboxyhexyl, and the like can be mentioned.

As "alkoxyalkyl", for example, the above "alkyl" substituted with the above "alkoxy" can be mentioned, and specifically, methoxymethyl, methoxyethyl, ethoxymethyl, ethoxyethyl, t-butoxymethyl, and the like can be mentioned.

As "hydroxyalkyl", for example, the above "alkyl" substituted with hydroxy can be mentioned, and specifically, hydroxymethyl, 1-hydroxyethyl, 2-hydroxypropyl, 2-hydroxyethyl, 3-hydroxypropyl, and the like can be mentioned.

As "aminocarbonylalkyl", for example, the above "alkyl" substituted with aminocarbonyl can be mentioned, and specifically, aminocarbonylmethyl, aminocarbonylethyl, and the like can be mentioned.

As "aromatic hydrocarbon group", for example, 6 to 14 membered monocyclic, bicyclic, or tricyclic aromatic hydrocarbon group can be mentioned, specifically, phenyl, naphthyl, phenanthryl, anthryl, and the like can be mentioned, and phenyl is particularly preferred.

As "aromatic heterocyclic group", for example, 5 to 14 membered mono-cyclic or bi-cyclic aromatic heterocyclic group containing 1 to 4 heteroatoms selected from nitrogen atom, sulfur atom and oxygen atom other than carbon atom as an annular atom can be mentioned, and specifically, pyrrolyl, imidazolyl, triazolyl, tetrazolyl, pyridyl, pyrazinyl, pyrimidinyl, pyridazinyl, triazinyl, azepinyl, diazepinyl, furyl, pyranyl, oxepinyl, thienyl, thiopyranyl, oxazolyl, isoxazolyl, thiazolyl, isothiazolyl, furazanyl, oxadiazolyl, oxazinyl, oxadiazinyl, oxazepinyl, oxadiazepinyl, thiadiazolyl, thiazinyl, indolyl, isoindolyl, benzofuryl, benzothienyl, indazolyl, quinolinyl, isoquinolinyl, quinoxalinyl, quinazolinyl, benzoxazolyl, benzothiazolyl, benzimidazolyl, and the like can be mentioned.

As "non-aromatic heterocyclic group", for example, 5 to 14 membered mono-cyclic or bi-cyclic non-aromatic heterocyclic group containing 1 to 4 heteroatoms selected from nitrogen atom, sulfur atom and oxygen atom other than carbon atoms as an annular atom can be mentioned. Specifically, pyrrolidinyl, pyrazolidinyl, piperidinyl, piperazinyl, morpholinyl, thiomorpholinyl, homopiperidinyl, oxazolidinyl, thiazolidinyl, imidazolidinyl, imidazolinyl, tetrahydrofuryl, dihydrofuryl, tetrahydrothienyl, dihydrothienyl, tetrahydropyridyl, dihydrobenzofuryl, dihydrobenzothienyl, and the like can be mentioned.

As "alkylthio", for example, straight or branched alkylthio having 1 to 8 carbon atom, preferably 1 to 4 carbon atoms can be mentioned, and specifically, methylthio, ethylthio, propylthio, butylthio, and the like can be mentioned.

Aryl in "aryloxy" has the same meaning as in the above "aromatic hydrocarbon group", and phenyl is particularly preferred. As a specific example for "aryloxy", phenyloxy, naphthyloxy, and the like can be mentioned.

Heteroaryl in "heteroaryloxy" has the same meaning as in the above "aromatic heterocyclic group", and 5 to 6-membered monocyclic aromatic heterocyclic group containing 1 to 4 heteroatoms selected from nitrogen atom, sulfur atom and oxygen atom other than carbon atoms as an annular atom is particularly preferred. As a specific example for "heteroaryloxy", pyridyloxy, pyrimidinyloxy, pyrazyloxy, and the like can be mentioned.

As "cycloalkyloxy", for example, cycloalkyloxy having 3 to 8 carbon atoms, preferably 3 to 6 carbon atoms can be mentioned, and specifically, cyclopropyloxy, cyclobutyloxy, cyclopentyloxy, cyclohexyloxy, cycloheptyloxy, and the like can be mentioned.

As "cycloalkylalkoxy", the above "alkoxy" substituted with the above "cycloalkyl" can be mentioned, and specifically, cyclopropylmethoxy, cyclopropylethoxy, cyclobutylmethoxy, cyclopentylmethoxy, cyclohexylmethoxy, cycloheptylmethoxy, and the like can be mentioned.

As "aralkyloxy", for example, the above "alkoxy" substituted with the above "aromatic hydrocarbon group" can be mentioned, and specifically, benzyloxy, phenethyloxy, 1-naphthylmethoxy, 2-naphthylmethoxy, and the like can be mentioned.

As "aralkyloxycarbonyl", for example, the above "alkoxycarbonyl" substituted with the above "aromatic hydrocarbon group" can be mentioned, and specifically benzyloxycarbonyl, phenethyloxycarbonyl, 1-naphthylmethoxycarbonyl, 2-naphthylmethoxycarbonyl, and the like can be mentioned.

As "alkyl substituted with non-aromatic heterocycle", for example, the above "alkyl" substituted with the above "non-aromatic heterocyclic group" can be mentioned, and specifically, pyrrolidinomethyl, piperidinoethyl, morpholinomethyl, morpholinoethyl, piperidinomethyl, piperidinoethyl, and the like can be mentioned.

As "carbonyl substituted with non-aromatic heterocycle", for example, carbonyl substituted with the above "non-aromatic heterocyclic group" can be mentioned, and specifically, piperidinocarbonyl, morpholinocarbonyl, piperidinocarbonyl, and the like can be mentioned.

As "6-membered monocyclic aromatic heterocyclic ring" in ring A, for example, 6-membered monocyclic aromatic heterocyclic ring containing 1 to 4 nitrogen atoms other than carbon atom as an annular atom can be mentioned, and specifically, pyridine, pyrazine, pyrimidine, pyridazine, triazine, and tetrazine can be mentioned. Among them, 6-membered monocyclic aromatic heterocyclic ring containing 1 to 2 nitrogen atoms other than carbon atom as an annular atom can be preferably mentioned. Of these, pyridine, pyrazine, pyrimidine, and pyridazine are preferred, pyridine and pyrazine are more preferred, and pyridine is particularly preferred.

As a substituent group of "benzene which may be substituted" and "6-membered monocyclic aromatic heterocycle which may be substituted" in Ring A, for example, 1 to 3 alkyls can be mentioned, and when 2 or more alkyls are present, the substituent groups may be same or different. As a particularly preferred substituent group, methyl can be mentioned.

As "6-membered monocyclic aromatic heterocycle" in ring B, B$^1$, B$^2$ and B$^3$, for example, 6-membered monocyclic aromatic heterocycle containing 1 to 4 nitrogen atoms other than carbon atom as an annular atom can be mentioned, and specifically, pyridine, pyrazine, pyrimidine, pyridazine, triazine, and tetrazine can be mentioned. Among them, 6-membered monocyclic aromatic heterocycle containing 1 to 2 nitrogen atoms other than carbon atom as an annular atom can be preferably mentioned. Of these, pyridine, pyrazine, pyrimidine and pyridazine are preferred, and pyridine and pyrimidine are particularly preferred.

As a substituent group of "benzene which may be substituted" and "6-membered monocyclic aromatic heterocycle which may be substituted" in ring B and ring B$^1$, for example, alkyl, halogen atom, and cyano can be mentioned, and 1 to 3 of these substituent groups may be present. When 2 or more substituent groups are present, the substituent groups may be same or different. As a particularly preferred substituent group, methyl, fluorine atom, chlorine atom, and cyano can be mentioned.

As a substituent group of "benzene which may be substituted" and "6-membered monocyclic aromatic heterocycle which may be substituted" in ring B$^2$, for example, a group selected from halogen atom and cyano can be mentioned. 1 to 3 of these substituent groups may be present, and when 2 or more substituent groups are present, the substituent groups may be same or different. As a particularly preferred substituent group, fluorine atom, chlorine atom, and cyano can be mentioned.

As a preferred embodiment of ring A-ring B, ring A-ring B$^1$, and ring A-ring B$^2$, groups represented by the formula as below can be mentioned:

[Chemical Formula 11]

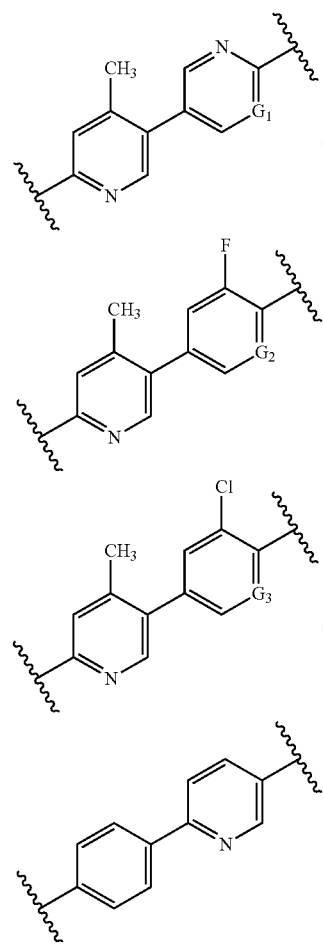

(wherein G$_1$, G$_2$ and G$_3$ represents CH or nitrogen atom.)

As "aromatic heterocyclic group" in ring C, the above "aromatic heterocyclic group" can be mentioned, and 5 to 6-membered monocyclic aromatic heterocyclic group containing 1 to 3 heteroatoms selected from nitrogen atom, sulfur atom and oxygen atom other than carbon atom as an annular atom can be preferably mentioned. Of these, pyridyl, pyrimidinyl, pyrazolyl, thienyl, isoxazolyl, oxazolyl, thiazolyl, oxadiazolyl, and triazolyl are preferred, pyridyl, pyrimidinyl, thienyl, thiazolyl, oxadiazolyl, and oxazolyl are more preferred, and thienyl is particularly preferred.

As ring C, "aromatic hydrocarbon group" is preferred.

As "alkyl" in Y, $Y^a$, $Y^b$, $Y^A$, $Y^B$, $Y^C$, and $Y^D$, a group which has 2 substituent groups ($R^5$ and $R^6$) on the same carbon atom of alkyl, and wherein the 2 substituent groups forms a ring together with the adjacent carbon atom is included. As such a group, for example, a group represented by the formula as below can be mentioned:

[Chemical Formula 12]

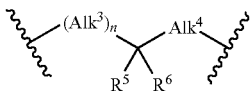

(wherein $Alk^3$ and $Alk^4$ are same or different, and each represent alkylene, n represents an integer from 0 to 1, and $R^5$ and $R^6$ each represent hydrogen or alkyl, or $R^5$ and $R^6$ represent a group which forms cycloalkane together with the adjacent carbon atom. Further, a bond at the right end represents a bond to X, $X^A$, $X^B$, $X^C$, and $X^D$.)

As a preferred specific example of "alkyl" in Y, $Y^a$, $Y^b$, $Y^A$, $Y^B$, $Y^C$, and $Y^D$, following groups can be mentioned:

[Chemical Formula 13]

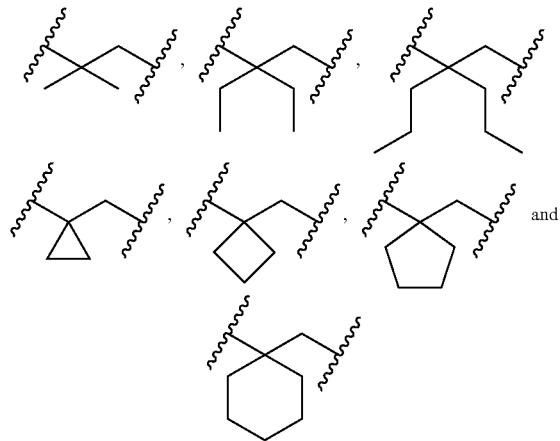

and (wherein a bond at the right end represents a bond to X, $X^A$, $X^B$, $X^C$, and $X^D$.)

In particular, following groups are preferred:

[Chemical Formula 14]

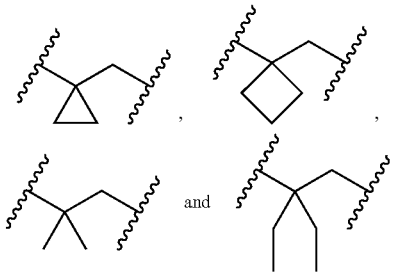

and (wherein a bond at the right end represents a bond to X, $X^A$, $X^B$, $X^C$, and $X^D$.)

As a substituent group of "alkyl which may be substituted" in Y and $Y^a$, for example, aminocarbonyl which may be substituted with alkyl which may be substituted with 1 to 3 hydroxys, and carboxy can be mentioned, and 1 to 3 of these substituent groups may be present. When 2 or more substituent groups are present, the substituent groups may be same or different. Among these, as a preferred substituent group, carboxy can be mentioned.

As a substituent group of "alkyl which may be substituted" in $Y^b$, for example, carboxy can be mentioned.

As a substituent group of "cycloalkyl which may be substituted" in $Y^a$, for example, carboxyalkyl can be mentioned, and 1 to 3 of the substituent groups may be present. As a specific example of the substituent group, carboxymethyl and the like can be mentioned.

As a substituent group of "cycloalkyl which may be substituted" in Y and $Y^b$, for example, carboxyalkyl, carboxy, alkoxyalkyl, and aminocarbonyl can be mentioned, and 1 to 3 of these substituent groups may be present. When 2 or more substituent groups are present, the substituent groups may be same or different. As a preferred substituent group, carboxyalkyl, carboxy, and alkoxyalkyl can be mentioned.

As "cycloalkyl" in $Y^b$, cycloalkyl containing 3 to 6 carbon atoms is preferred, and in particular, cyclohexyl is preferred.

As $Y^b$, "alkyl which may be substituted" is preferred.

As a substituent group of "alkyl which may be substituted" in $R^1$, for example, 1 to 6 halogen atoms can be mentioned, and when 2 or more substituent groups are present, the substituent groups may be same or different. As a particularly preferred substituent group, fluorine atom can be mentioned. As a specific example of "alkyl which may be substituted", difluoromethyl, trifluoromethyl, 2,2,2-trifluoroethyl, 2,2,3,3,3-pentafluoropropyl, and the like can be mentioned, and in particular, trifluoromethyl is preferred.

As "halogen atom" represented by $R^1$, chlorine atom is particularly preferred.

As "alkyl" represented by $R^1$, alkyl containing 1 to 3 carbon atoms is preferred, and in particular, methyl is preferred.

As "alkoxy" represented by $R^1$, alkoxy containing 1 to 3 carbon atoms is preferred, and in particular, methoxy is preferred.

As a substituent group of "alkyl which may be substituted" in $R^3$ and $R^4$, 1 to 6 halogen atoms can be mentioned, respectively, and when 2 or more substituent groups are present, the substituent groups may be same or different. In particular, fluorine atom is preferred. As a specific example of "alkyl which may be substituted", difluoromethyl, trifluoromethyl, 2,2,2-trifluoroethyl, 2,2,3,3,3-pentafluoropropyl, and the like can be mentioned, and in particular, trifluoromethyl is preferred.

As a substituent group of "alkoxy which may be substituted" in $R^3$ and $R^4$, alkoxy and 1 to 6 halogen atoms can be mentioned, respectively, and when 2 or more substituent groups are present, the substituent groups may be same or different. In particular, fluorine atom is preferred. As a specific example of "alkoxy which may be substituted", difluoromethoxy, trifluoromethoxy, 2,2,2-trifluoroethoxy, 2,2,3,3,3-pentafluoropropoxy, and the like can be mentioned, and in particular, difluoromethoxy and trifluoromethoxy are preferred.

As a substituent group of "alkyl which may be substituted" in $R^2$ and $R^{2b}$, for example, 1 to 6 halogen atoms can be mentioned, and when 2 or more substituent groups are present, the substituent groups may be same or different. As a particularly preferred substituent group, fluorine atom can be mentioned. As a specific example of the group, trifluoromethyl, 2,2,2-trifluoroethyl, 2,2,3,3,3-pentafluoropropyl, and the like can be mentioned.

As a substituent group of "alkoxy which may be substituted" in $R^2$ and $R^{2b}$, for example, 1 to 6 halogen atoms can be mentioned, and when 2 or more substituent groups are present, the substituent groups may be same or different. In particular, fluorine atom is preferred. As a specific example of the group, trifluoromethoxy, 2,2,2-trifluoroethoxy, 2,2,3,3,3-pentafluoropropoxy, and the like can be mentioned.

As a substituent group of "cycloalkyl which may be substituted" in $R^2$ and $R^{2b}$, for example, alkyl which may be substituted with 1 to 7 halogens can be mentioned, and when 2 or more substituent groups are present, the substituent groups may be same or different. As a specific example of the group, 1-trifluoromethylcyclopropyl, 1-trifluoromethylcyclobutyl, 1-trifluoromethylcyclohexyl, 1-trifluoromethylcyclohexyl, and the like can be mentioned.

As a substituent group of "aromatic hydrocarbon group which may be substituted" in $R^2$ and $R^{2b}$, for example, 1 to 3 alkoxys can be mentioned, and when 2 or more substituent groups are present, the substituent groups may be same or different. As a specific example of the group, 4-methoxyphenyl, 3-methoxyphenyl, 2-methoxyphenyl, 3,4-dimethoxyphenyl, and the like can be mentioned.

As a substituent group of "non-aromatic heterocyclic group which may be substituted" in $R^2$ and $R^{2b}$, for example, 1 to 3 halogen atoms can be mentioned, and when 2 or more substituent groups are present, the substituent groups may be same or different. As a specific example of the group, 4-fluoropiperidino, 4,4-difluoropiperidino, and the like can be mentioned.

As a substituent group of "aryloxy which may be substituted" in $R^2$ and $R^{2b}$, for example, a group selected from halogen atom and cyano can be mentioned. 1 to 3 of the substituent groups may be present, and when 2 or more groups are present, the substituent groups may be same or different. As a specific example of the group, 4-fluorophenyloxy, 2,4-difluorophenyloxy, 3,4-difluorophenyloxy, 4-cyanophenyloxy, and the like can be mentioned.

As a substituent group of "heteroaryloxy which may be substituted" in $R^2$ and $R^{2b}$, for example, 1 to 3 alkyls can be mentioned, and when 2 or more substituent groups are present, the substituent groups may be same or different. As a specific example of the group, 6-methylpyridin-2-yloxy, 6-methylpyrimidin-2-yloxy, and the like can be mentioned.

Since the compound of the present invention has a basic group and an acidic group in the molecule, as a pharmaceutically acceptable salt thereof, an acid addition salt (for example, inorganic acid salt such as hydrochloride, sulfate, phosphate, hydrobromide; and organic acid salt such as acetate, fumarate, maleate, oxalate, citrate, methanesulfonate, benzenesulfonate, toluenesulfonate), and a salt with a base (for example, alkali metal salt such as sodium salt, potassium salt; alkali earth metal salt such as calcium salt; organic base salt such as triethylamine salt; and amino acid salt such as lysine salt; and the like) can be mentioned.

In the compound of the present invention, an optical isomer based on asymmetric carbon may exist, and the compound of the present includes any isomer thereof and a mixture thereof. Further, if the compound of the present invention has a cycloalkanediyl, a cis form and a trans form may be present, and in the compound of the present invention, a tautomer based on an unsaturated bond such as carbonyl may be present. The compound of the present invention includes any isomer thereof and any mixture thereof.

Further, in the compound of the present invention a tautomer may exist as shown by formulae as below due to hydrogen ion transfer in an aromatic heterocyclic ring. Even when the compound of the present invention is represented by one of chemical structure, any tautomer thereof and any mixture thereof are included.

[Chemical Formula 15]

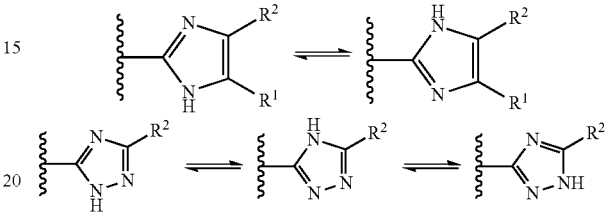

Although the compound of the present invention or a pharmaceutically acceptable salt thereof can be also prepared by the process as below.

A process for preparing Compound (1) of the invention is explained below by using Compound (1-A) and Compound (1-B) included in the Compound (1), and Compound (1) can be prepared in a manner similar to these processes.

[Method A]

Compound (1-A) can be prepared by the process as below:

[Chemical Formula 16]

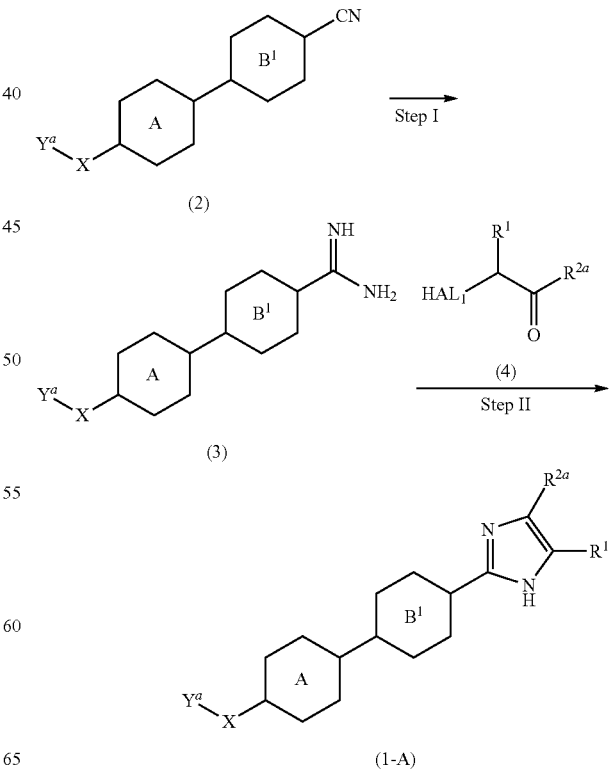

(wherein HAL₁ represents halogen atom (such as chlorine atom and bromine atom), and the other symbols have the same meaning as above.)

Step I:

The reaction of Compound (2) with hydroxylamine can be carried out, for example, in an appropriate solvent, according to the process as described in U.S. Pat. No. 5,576,447 and the like.

As the solvent, alcohols such as methanol and ethanol, ethers such as tetrahydrofuran and 1,4-dioxane, water, or a mixture thereof can be used.

The reaction time is usually 3 to 16 hours, preferably 4 to 6 hours. The reaction temperature is usually 5 to 100° C., preferably 25 to 80° C.

According to an ordinary method, the obtained product is treated with acetic acid-acetic anhydride, and subjected to a hydrogenation reaction in an appropriate solvent in the presence of palladium catalyst under hydrogen atmosphere to obtain Compound (3) as an acetate salt.

As the solvent, for example, alcohols such as methanol and ethanol, ethers such as tetrahydrofuran and 1,4-dioxane, acetic acid, or a solvent mixture thereof can be used.

As the palladium catalyst, for example, a catalyst such as palladium carbon, palladium black and palladium chloride can be used.

The reaction time differs depending on the catalyst, the solvent, and the like to be used, and is usually 30 minutes to 18 hours, preferably 30 minutes to 8 hours. The reaction temperature is usually 10 to 100° C., preferably 25 to 75° C.

Meanwhile, trialkylsilane such as triethylsilane can be used as a hydrogen source instead of hydrogen in the above hydrogenation reaction.

Further, Compound (3) can be prepared by reacting Compound (2) with an alkoxy alkali metal in an appropriate solvent, followed by reacting with ammonia source.

As the solvent, alcohols such as methanol and ethanol can be used.

As the alkoxy alkali metal, sodium methylate, sodium ethylate, potassium methylate, and the like can be used.

As the ammonia source, an ammonium halide such as ammonium chloride and ammonium bromide, an organic ammonium salt such as ammonium acetate and ammonium propionate, ammonia and the like can be used.

Step II:

Compound (1-A) can be prepared, for example, by subjecting Compound (3) and Compound (4) to a cyclization reaction in an appropriate solvent in the presence of base according to a method as described in I. M. Mallick et al., Journal of the American Chemical Society, 106(23), 7252-7254, 1984, and the like.

As the solvent, alcohols such as methanol and ethanol, amides such as N, N-dimethyformamide and N-methylpyrrolidone, halogenated hydrocarbons such as methylene chloride and chloroform, tetrahydrofuran, acetonitrile, water, or a solvent mixture thereof can be used.

As the base, potassium hydrogen carbonate, potassium carbonate, sodium ethylate, and the like can be used.

The reaction time differs depending on the base, the solvent, and the like to be used, and is usually 40 minutes to 18 hours, preferably 5 hour to 12 hours. The reaction temperature is usually 18 to 100° C., preferably 50 to 80° C.

Compound (1-A) can also be prepared by reacting, in an appropriate solvent in the presence of acid, a product obtained by reacting Compound (3) and Compound (4) in the above method.

As the acid, for example, hydrochloric acid, sulfuric acid, acetic acid, trifluoroacetic acid, p-toluenesulfonic acid, camphorsulfonic acid, and the like can be used.

As the solvent, for example, aromatic hydrocarbons such as benzene and toluene, halogenated hydrocarbons such as chloroform and 1,2-dichloroethane, ethers such as tetrahydrofuran and 1,2-dimethoxyethane, organic acids such as formic acid and acetic acid, or a solvent mixture thereof can be used.

The reaction time differs depending on the acid, the solvent, and the like to be used, and is usually 1 hour to 48 hours, preferably 4 hours to 8 hours. The reaction temperature is usually 50 to 100° C., preferably 70 to 90° C.

[Method B]

Compound (1-A) can also be prepared by the process as below:

[Chemical Formula 17]

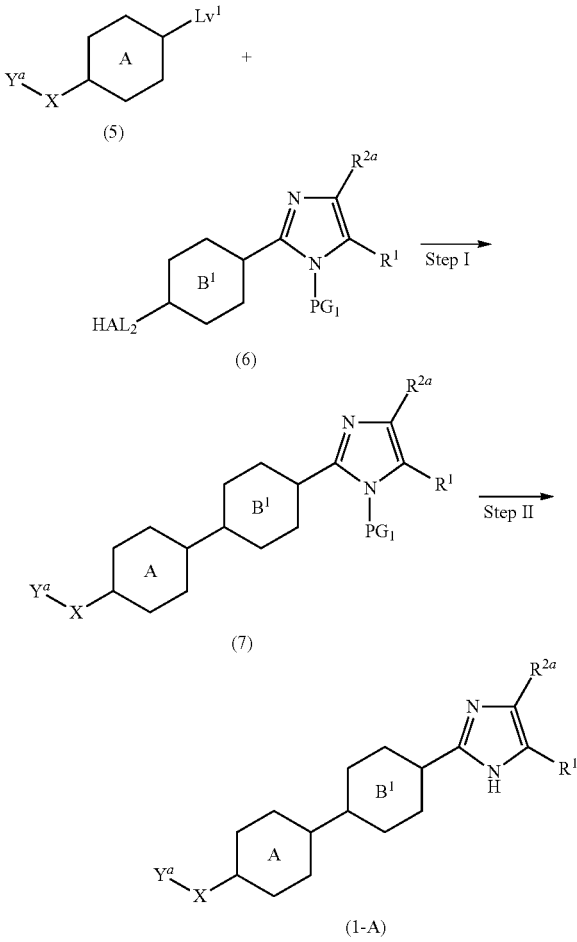

(wherein Lv¹ represents B(OH)₂, or

[Chemical Formula 18]

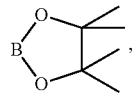

HAL₂ represents halogen atom (such as chlorine atom and bromine atom), PG₁ represents amino protective group (preferably, substituted alkyl (such as 2-(trimethylsilyl)ethoxymethyl and benzyl)), and the other symbols have the same meanings as the above.)

Step I;

Compound (7) can be prepared by subjecting Compound (5) and Compound (6) to Suzuki coupling reaction (for example, a reaction as described in Advanced Organic Chemistry Part B (F. A. Carey & R. J. Sundberg, Springer) and the like) in an appropriate solvent in the presence of a catalyst and a base.

As the catalyst, palladium chloride, palladium acetate, dichloro[1,1'-bis(diphenylphosphino)ferrocene]palladium (PdCl₂(dppf)), tetrakistriphenylphosphine palladium and the like can be used, and if necessary, a ligand such as 1,1'-bis(diphenylphosphino)ferrocene, 2-dicyclohexylphosphino-2',6'-dimethoxybiphenyl (S-PHOS), 2-dicyclohexylphosphino-2',4',6'-triisopropyl-1,1'-biphenyl (X-PHOS) and 4,5-bis(diphenylphosphino)-9,9-dimethylxanthene (Xantphos) can also be added.

As the base, an alkali metal such as sodium carbonate, potassium carbonate, potassium acetate, potassium phosphate, sodium hydroxide, and cesium carbonate, and the like can be used.

As the solvent, amides such as N, N-dimethyformamide, ethers such as tetrahydrofuran, 1,4-dioxane and dimethoxyethane, aromatic hydrocarbons such as benzene and toluene, water, and a solvent mixture thereof can be used.

The reaction time differs depending on the amount or the kind of the reagent, the catalyst, the base, or the reaction solvent to be used, and the reaction temperature, and is usually 2 to 48 hours, preferably 5 to 12 hours.

The reaction temperature is from room temperature to 150° C., preferably 60 to 120° C.

Step II:

Compound (1-A) can be prepared by deprotecting Compound (7).

The deprotection reaction of Compound (7) can be carried out, for example, when PG₁ is 2-(trimethylsilyl)ethoxymethyl, by treating Compound (7) with an acid (such as hydrochloric acid, trifluoroacetic acid and methanesulfonic acid) in an appropriate solvent (alcohols such as methanol and ethanol, water, a solvent mixture thereof, and the like), or by reacting Compound (7) with tetra-n-butylammonium fluoride in an appropriate solvent (ethers such as tetrahydrofuran, halogenated hydrocarbons such as methylene chloride, and the like) to yield Compound (1-A). Further, for example, when PG₁ is benzyl, Compound (7) is subjected to a hydrogenation reaction in an appropriate solvent (alcohols such as methanol and ethanol, and the like) in the presence of palladium catalyst (such as palladium carbon and palladium hydroxide) under hydrogen atmosphere to prepare Compound (1-A).

Further, Compound (1-A) can also be prepared by carrying out a similar method to the above using the compounds represented by formulae as below:

[Chemical Formula 19]

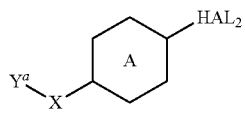

and

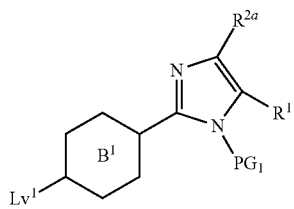

(wherein each symbol has the meaning as the above), (hereinafter, referred to as Compound (5a) and Compound (6a)) instead of Compound (5) and Compound (6), respectively.

[Method C]

Compound (1-A) wherein X is —O— (hereinafter referred to as Compound (1-A-a)) can be prepared by the process as below:

[Chemical Formula 20]

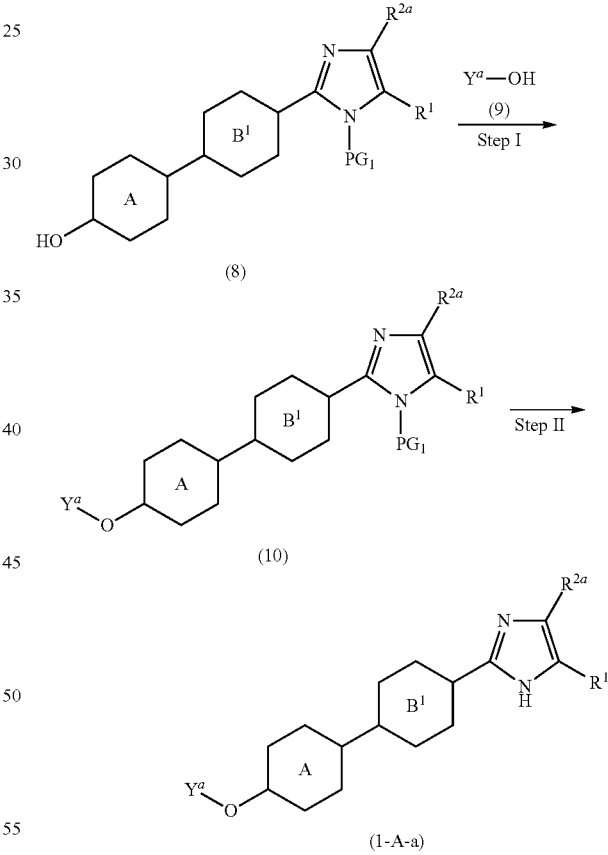

(wherein each symbol has the same meaning as the above.)

Step I:

Compound (10) can be prepared by subjecting Compound (8) and Compound (9) to Mitsunobu reaction (for example, a reaction as described in Advanced Organic Chemistry Part B (F. A. Carey & R. J. Sundberg, Springer), Okuda, M.; Tomioka, K.; Tetrahedron Lett [TELEAY] 1994, 35 (26), 4585-4586, and the like) in an appropriate solvent in the presence of azodicarboxylates and phosphines.

As the azodicarboxylates, diethyl azodicarboxylate, di-t-butyl azodicarboxylate, 1,1'-(azodicarbonyl)dipiperidine, and the like can be used.

As the phosphines, tri-aryl phosphines such as triphenylphosphine, tri-alkylphosphines such as tri-n-butylphosphine, and the like can be used.

As the solvent, for example, ethers such as tetrahydrofuran, 1,4-dioxane and diethylether, aromatic hydrocarbons such as benzene, toluene and xylene, halogenated hydrocarbons such as methylene chloride, 1,2-dichloroethane and chloroform, or a solvent mixture thereof can be used.

The reaction time differs depending on the reagent, the solvent, and the like to be used, and is usually 30 minutes to 24 hours, preferably 3 to 12 hours. The reaction temperature is usually 5° C. to 150° C., preferably room temperature to 80° C.

Step II:

The deprotection reaction of Compound (10) can be carried out in a manner similar to Step II of Method B.

[Method D]

Compound (1-A) wherein X is a single bond and $Y^a$ is cycloalkyl which may be substituted (hereinafter, referred to as Compound (1-A-b)) can be prepared by the process as below:

[Chemical Formula 21]

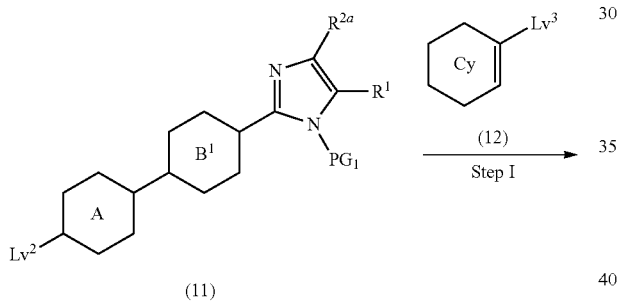

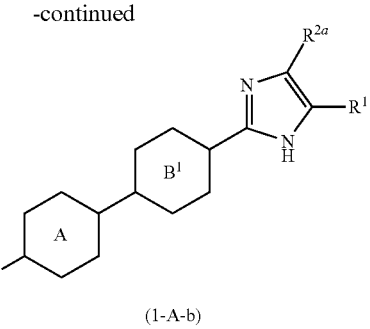

(1-A-b)

(wherein a group:

[Chemical Formula 22]

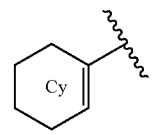

represents cycloalkenyl which may be substituted, $Y^2$ represents cycloalkyl which may be substituted, $Lv^2$ represents halogen atom (such as chlorine atom and bromine atom) or trifluoromethanesulfonyloxy group, and $Lv^3$ represents $B(OH)_2$ or

[Chemical Formula 23]

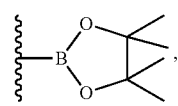

and the other symbols have the same meanings as the above.)

Step I:

Compound (13) can be prepared by a coupling reaction of Compound (11) with Compound (12), which can be carried out in a manner similar to Step I of Method B.

Step II:

Compound (14) can be prepared by subjecting Compound (13) to a hydrogenation reaction in an appropriate solvent in the presence of a palladium catalyst under hydrogen atmosphere.

As the solvent, alcohols such as methanol and ethanol, ethers such as tetrahydrofuran and 1,4-dioxane, or a solvent mixture thereof can be used.

As the palladium catalyst, a catalyst such as palladium carbon and palladium black can be used.

The reaction time differs depending on the catalyst, the solvent, and the like to be used, and is usually 1 hour to 24 hours, preferably 1 hour to 12 hours. The reaction temperature is usually 50 to 100° C., preferably 60 to 100° C.

Step III:

The deprotection reaction of Compound (14) can be carried out in a manner similar to Step II of Method B.

[Method E]

Compound (1-A) wherein $R^1$ is halogen (hereinafter, referred to as Compound (1-A-d)) and Compound (1-A) wherein $R^1$ is alkyl (hereinafter, referred to as Compound (1-A-e)) can be prepared by the process as below:

[Chemical Formula 24]

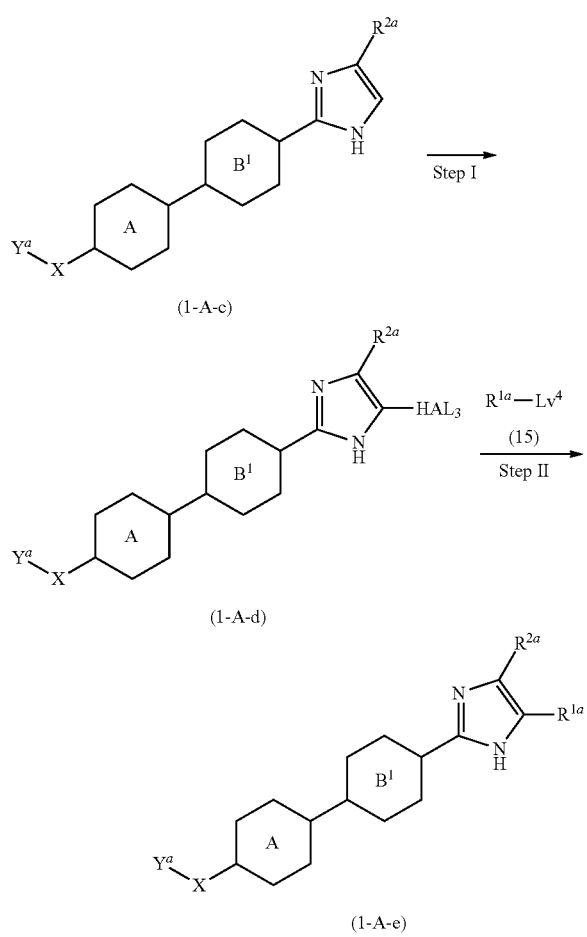

(wherein $HAL_3$ represents halogen atom (such as chlorine atom and bromine atom), and $R^{1a}$ represents alkyl, and $Lv^4$ represents $B(OH)_2$ or

[Chemical Formula 25]

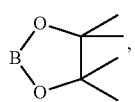

and the other symbols have the same meaning as above.)

Step I:
Compound (1-A-d) can be prepared by reacting Compound (1-A-c) with a halogenating agent in an appropriate solvent, if necessary, in the presence of base.

As the halogenating agent, N-chlorosuccinimide, N-bromosuccinimide, and the like can be used.

As the solvent, a halogenated hydrocarbon such as chloroform and methylene chloride, N, N-dimethyformamide, acetonitrile, ethanol, and the like can be used.

As the base, imidazole, triethylamine, and the like can be used.

The reaction time differs depending on the reagent, the solvent, and the like to be used, and is usually 1 hour to 22 hours, preferably 2 hours to 15 hours. The reaction temperature is usually 0° C. to 60° C., preferably room temperature to 50° C.

Step II:
The reaction of Compound (1-A-d) with Compound (15) can be carried out in a manner similar to Step I of Method B.

[Method F]
Compound (2) wherein X is —O— (hereinafter, referred to as Compound (2a)) can also be prepared by the process as below:

[Chemical Formula 26]

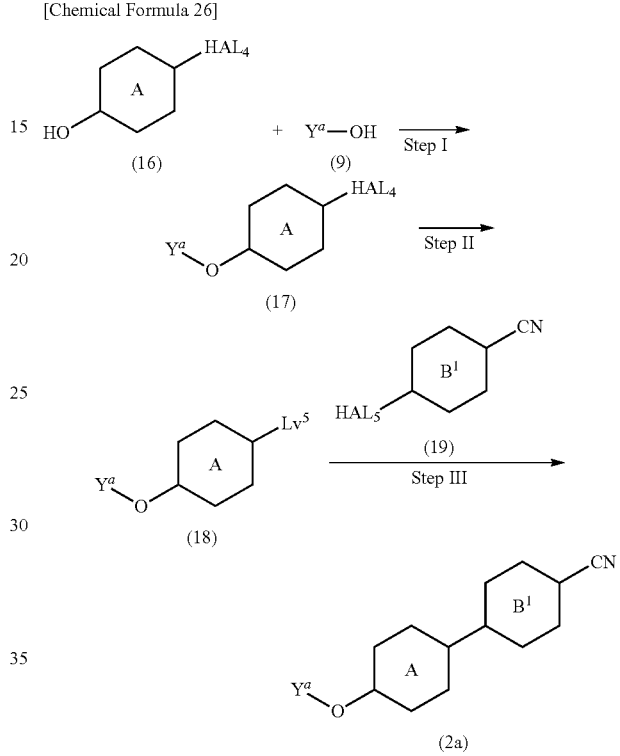

(wherein $HAL_4$ and $HAL_5$ represent halogen atom (such as chlorine atom and bromine atom), and $Lv^5$ represents $B(OH)_2$ or

[Chemical Formula 27]

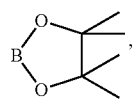

and the other symbols have the same meanings as the above.)

Step I:
The coupling reaction of Compound (16) with Compound (9) can be carried out in a manner similar to Step I of Method C.

Step II:
Compound (18) can be prepared by reacting Compound (17) with a boronic acid ester in an appropriate solvent in the presence of a palladium catalyst, a ligand and a base.

As the solvent, ethers such as 1,4-dioxane, dimethyl sulfoxide, aromatic hydrocarbons such as toluene, and the like can be used.

As the palladium catalyst, palladium acetate, dichloro[1, 1'-bis(di phenylphosphino)ferrocene]palladium ($PdCl_2$(dppf)) and the like can be used.

As the ligand, 2-dicyclohexylphosphino-2',6'-dimethoxybiphenyl (S-PHOS), 2-dicyclohexylphosphino-2',4',6'-triisopropyl-1,1'-biphenyl (X-PHOS), 4,5-bis(diphenylphosphino)-9,9-dimethylxanthene (Xantphos), and the like can be used.

As the base, potassium acetate, potassium phosphate, and the like can be used.

As the boronic acid ester, bis(pinacolato)diboron, trialkoxyboron, and the like can be used.

The reaction time differs depending on the catalyst, the solvent, and the like to be used, and is usually 1 hour to 24 hours, preferably 2 hours to 12 hours. The reaction temperature is usually 50 to 130° C., preferably 60 to 100° C.

Step III:

The coupling reaction of Compound (18) with Compound (19) can be carried out in a manner similar to Step I of Method B.

[Method G]

Compound (8), and Compound (11a) which is Compound (11) wherein $Lv^2$ is trifluoromethanesulfonyloxy can be prepared by the process as below:

[Chemical Formula 28]

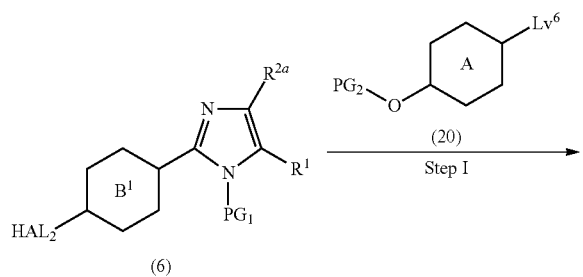

(6)

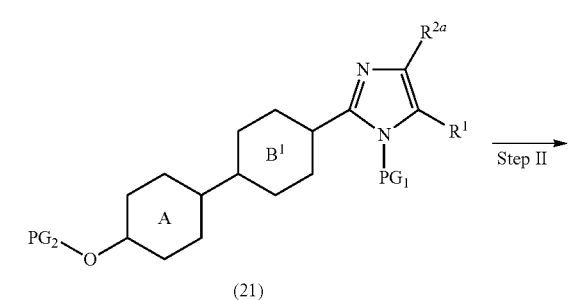

(21)

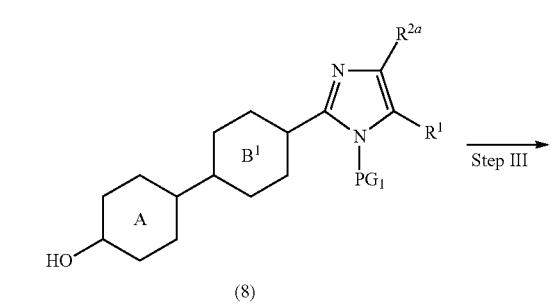

(8)

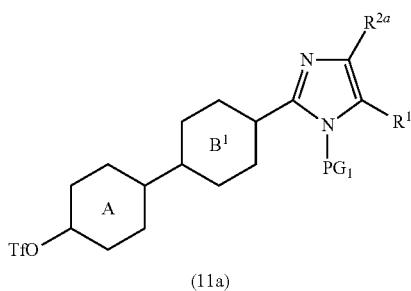

(11a)

(wherein $PG_2$ represents a hydroxyl group-protective group (preferably, substituted alkyl (such as benzyl)), $Lv^6$ represents $B(OH)_2$, or

[Chemical Formula 29]

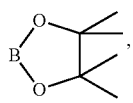

and each symbol has the same meaning as above.)

Step I:

The coupling reaction of Compound (6) with Compound (20) can be carried out in a manner similar to Step I of Method B.

Step II:

Compound (8) can be prepared by deprotecting $PG_2$ of Compound (21).

The deprotecting reaction of $PG_2$ can be carried out, for example, when $PG_2$ is a benzyl group, by subjecting Compound (21) to a hydrogenation reaction in an appropriate solvent (alcohols such as methanol and ethanol) in the presence of a palladium catalyst (such as palladium carbon and palladium hydroxide) under hydrogen atmosphere to prepare Compound (8).

Step III:

Compound (11a) can be prepared by reacting Compound (8) with trifluoromethanesulfonic anhydride in an appropriate solvent (halogenated hydrocarbons such as methylene chloride and chloroform, ethers such as tetrahydrofuran and diethylether, and the like) in the presence of a base (such as triethylamine, N,N-diisopropylethylamine and 2,6-lutidine) at 0° C. to 25° C. for 1 hour to 8 hours.

[Method H]

Compound (6) can also be prepared by the process as below:

[Chemical Formula 30]

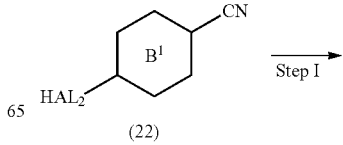

(22)

-continued

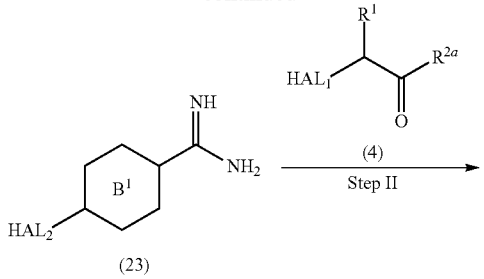

(23)

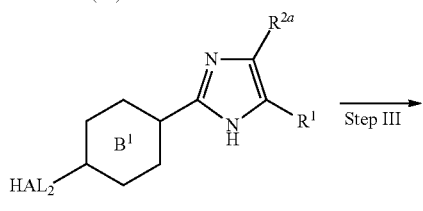

(24)

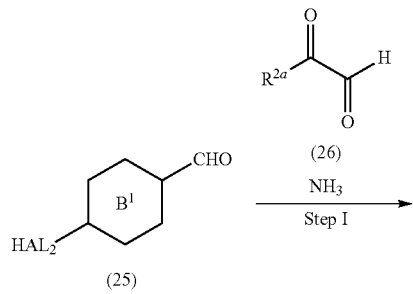

(6)

(wherein each symbol has the same meaning as above.)

Step I and Step II in the present reaction can be carried out in a manner similar to Step I and Step II of Method A.

Step III:

Compound (6) can be prepared by protecting the amino group of Compound (24). For example, when $PG_1$ is 2-(trimethylsilyl)ethoxymethyl group, Compound (6) can be prepared by reacting Compound (24) with 2-(trimethylsilyl)ethoxymethyl chloride in an appropriate solvent in the presence of a base.

As the solvent, for example, an aprotic polar solvent such as N,N-dimethyformamide, N,N-dimethylacetamide and N-methylpyrrolidone can be used.

As the base, for example, an alkali metal hydride (such as sodium hydride and lithium hydride), an alkali metal carbonate (such as potassium carbonate) can be used.

[Method I]

Compound (6) wherein $R^1$ is hydrogen (hereinafter, referred to as Compound (6a)) can be prepared by the process as below:

[Chemical Formula 31]

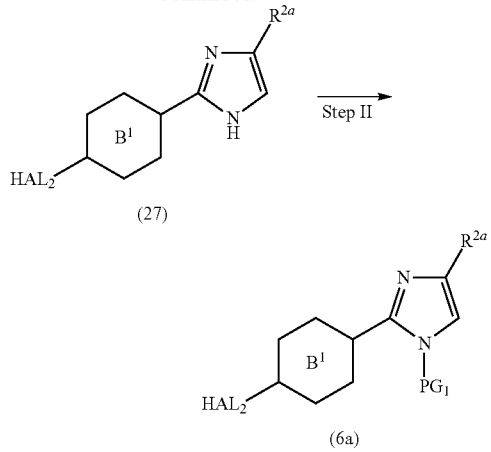

(wherein each symbol has the same meaning as above.)

Step I:

Compound (27) can be prepared by reacting Compound (25) with Compound (26) and ammonia in an appropriate solvent.

As the solvent, an alcoholic solvent such as methanol and ethanol, water, and the like can be used.

The reaction time is usually 1 hour to 24 hours, preferably 5 hours to 12 hours. The reaction temperature is usually 5° C. to 60° C., preferably room temperature to 40° C.

Step II:

The present reaction can be carried out in a manner similar to Step III of Method H.

[Method J]

Compound (27) can also be prepared by the process as below:

[Chemical Formula 32]

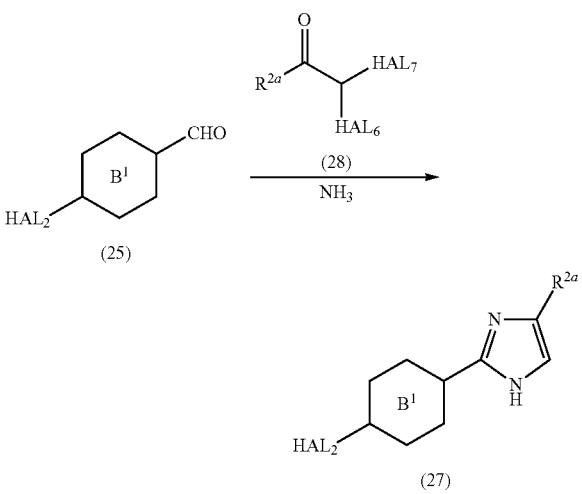

(wherein $HAL_6$ and $HAL_7$ are the same or different and represent a halogen atom (such as chlorine atom, bromine atom and iodine atom).)

Compound (27) can be prepared by reacting Compound (25) with Compound (28) and ammonia in an appropriate solvent in the presence of a base according to a method as described in J. J. Baldwin et al., Journal of Medicinal Chemistry, 29(6), 1065-1080, 1986 and the like.

As the solvent, alcohols such as methanol and ethanol, water, and the like can be used.

As the base, alkali metal acetate (for example, sodium acetate) and the like can be used.

The present reaction can be carried out by stirring Compound (28) in an aqueous solvent in the presence of a base at 90 to 100° C. for 30 minutes to 1 hour, and then adding Compound (25) and ammonia water to the reaction system under cooling, and further stirring under ice-cooling to 50° C. for 1 day to 2 days. The reaction is preferably carried out at room temperature to 40° C.

[Method K]

Compound (4) can also be prepared by the process as below:

[Chemical Formula 33]

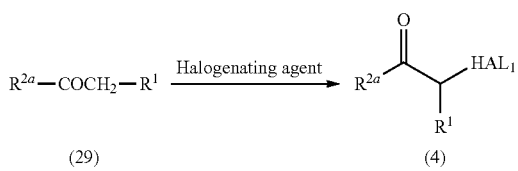

(wherein each symbol has the same meaning as above.)

Compound (4) can be prepared by reacting Compound (29) with a halogenating agent in an appropriate solvent (for example, halogenated hydrocarbons such as methylene chloride).

As the halogenating agent, for example, N-bromosuccinimide, N-chlorosuccinimide, copper bromide, hydrobromic acid, benzyltrimethylammonium tribromide, and the like can be mentioned.

[Method L]

Compound (4) wherein $R^1$ is hydrogen (hereinafter, referred to as Compound (4a)) can also be prepared by the process as below:

[Chemical Formula 34]

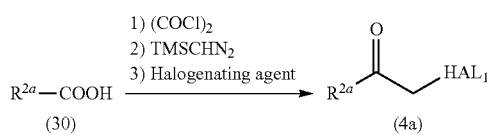

(wherein each symbol has the same meaning as above.)

Compound (4a) can be prepared by reacting Compound (30) with oxalyl chloride in an appropriate solvent, and reacting with trimethylsilyldiazomethane, then by subjecting to a halogenation in an appropriate solvent.

As the solvent for the reaction of Compound (30) with oxalyl chloride, halogenated hydrocarbon such as chloroform and methylene chloride, ethers such as tetrahydrofuran, and the like can be used.

The present reaction can be carried out by adding a catalystic amount of N, N-dimethyformamide at −20 to 40° C., preferably under ice-cooling to room temperature.

As the solvent for the reaction with trimethylsilyldiazomethane, acetonitrile, ethers such as tetrahydrofuran, and halogenated hydrocarbon such as chloroform and methylene chloride and the like can be used.

The present reaction can be carried out at −20 to 40° C., preferably under ice-cooling to room temperature.

The halogenation can be carried out in a manner similar to the halogenation of Method K.

[Method M]

A compound of the general formula (B) wherein $X^B$ is a single bond, and $Y^B$ is phenyl which may be substituted (hereinafter, referred to as Compound (B1)) can be prepared by the process as below:

[Chemical Formula 35]

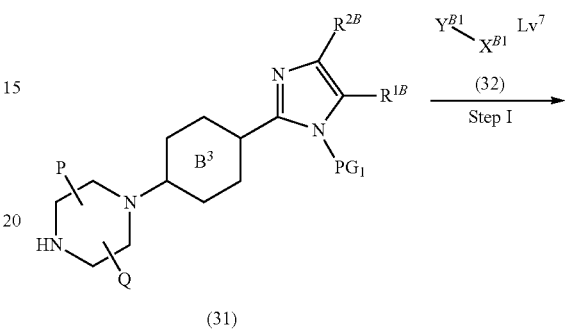

(wherein $X^{B1}$ represents a single bond, $Y^{B1}$ represents phenyl which may be substituted, $Lv^7$ represents a halogen atom (such as chlorine atom and bromine atom), $B(OH)_2$ or

[Chemical Formula 36]

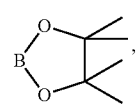

and the other symbols have the same meanings as above.

Step I:
(1) When Lv⁷ represents B(OH)₂ or

[Chemical Formula 37]

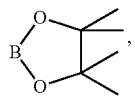,

Compound (33) can be prepared by reacting Compound (31) with Compound (32) in an appropriate solvent in the presence of a catalyst such as a copper catalyst, and a base.

As the solvent, halogenated hydrocarbons such as methylene chloride and 1,2-dichloroethane, aromatic hydrocarbons such as toluene, polar solvent such as acetonitrile, dimethylformamide and dimethylsulfoxide, and the like can be used.

As the catalyst, a copper catalyst such as copper acetate, and the like can be used.

As the base, organic base such as triethylamine and pyridine, and the like can be used.

Further, if necessary, a dehydrating agent such as molecular sieve can be used.

The reaction time differs depending on the reagent, the solvent, and the like to be used, and is usually 12 hours to 144 hours, preferably 24 hours to 48 hours. The reaction temperature is usually 20° C. to 90° C., preferably 20° C. to 40° C.

(2) When Lv⁷ is halogen, Compound (33) can be prepared by reacting Compound (31) with Compound (32) in an appropriate solvent in the presence of a base, and if necessary in the presence of a palladium catalyst and a ligand.

As the solvent, ethers such as tetrahydrofuran, 1 4-dioxane and dimethoxyethane, aromatic hydrocarbons such as benzene and toluene, halogenated hydrocarbons such as methylene chloride and 1,2-dichloroethane, water, N, N-dimethyformamide, dimethylsulfoxide, or a solvent mixture thereof can be used.

As the base, an inorganic base such as sodium carbonate, potassium carbonate, potassium acetate, potassium phosphate, sodium hydroxide and cesium carbonate, an organic base such as triethylamine, N,N-diisopropylethylamine, 1,8-diazabicyclo[5.4.0]undeca-7-en (DBU) and N-methylmorpholine, sodium tert-butoxide, and the like can be used.

As the catalyst, palladium chloride, palladium acetate, dichloro[1,1'-bis(diphenylphosphino)ferrocene]palladium (PdCl₂(dppf)), tetrakistriphenylphosphinepalladium and the like can be used, and if necessary, a ligand such as 1,1'-bis (diphenylphosphino)ferrocene, 2-dicyclohexylphosphino-2', 6'-dimethoxybiphenyl (S-PHOS), 2-dicyclohexylphosphino-2',4',6'-triisopropyl-1,1'-biphenyl (X-PHOS), 4,5-bis (diphenylphosphino)-9,9-dimethylxanthene (Xantphos), 2-dicyclohexylphosphino-2',6'-di-isopropoxy-1,1'-biphenyl (RuPhos) and the like can be added.

The reaction time differs depending on the reagent, the solvent, and the like to be used, and is usually 1 hour to 24 hours, preferably 3 hours to 15 hours. The reaction temperature is usually 70° C. to 120° C., preferably 80° C. to 100° C.

In the present reaction, the reaction can be accelerated by microwave irradiation.

Step II:

Compound (B1) can be prepared by deprotecting Compound (33), which can be carried out in a manner similar to Step II of Method B.

[Method N]

The compound of the general formula (B) or the general formula (C) (hereinafter, referred to as Compound (X)) can also be prepared by the process as below:

[Chemical Formula 38]

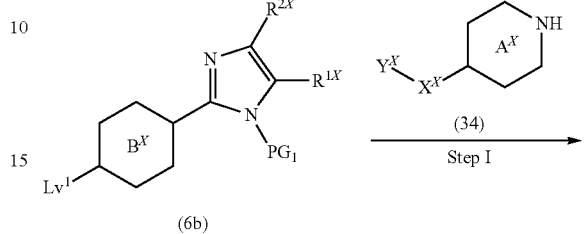

(wherein a group:

[Chemical Formula 39]

represents piperidine, or piperazine which may be substituted with P and/or Q; $B^X$, $X^X$, $Y^X$, $R^{1X}$ and $R^{2X}$ represent a group comprising $B^1$ and $B^3$, $X^B$ and $X^C$, $Y^B$ and $Y^C$, $R^{1B}$ and hydrogen atom, and $R^{2B}$ and $R^{2C}$, respectively, and the other symbols have the same meanings as above.)

Step I and Step II in the present reaction can be carried out in a manner similar to Step I and Step II of Method M.

[Method O]

The compound of the general formula (C) wherein $X^C$ is —O— or —OCH₂— and $Y^C$ is phenyl which may be substituted (hereinafter, referred to as Compound (C1)) can be prepared by the process as below:

[Chemical Formula 40]

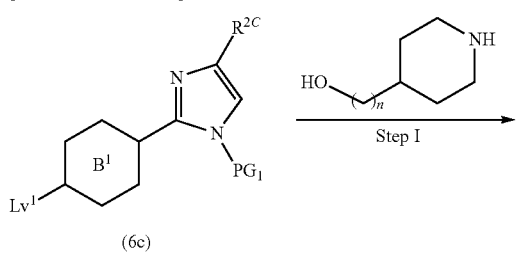

(wherein $Y^{C1}$ represents phenyl which may be substituted, n represents an integer from 0 to 1, and the other symbols have the same meanings as above.)

Step I and Step II of the present reaction can be carried out in a manner similar to Step I of Method N and Step I of Method C, and further $PG_1$ is deprotected to prepare Compound (C1).

[Method P]

Compound (34) wherein a group:

[Chemical Formula 41]

is piperidine, and X is —O— (hereinafter, referred to as Compound (34a)) can be prepared by the process as below:

[Chemical Formula 42]

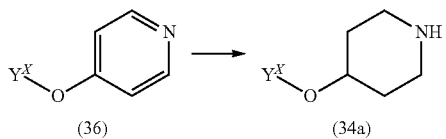

(wherein each symbol has the same meaning as above.)

Compound (34) can be prepared by subjecting Compound (36) to a reduction reaction.

The present reaction can be carried out by reacting Compound (36) with a reducing agent (such as sodium borohydride) in an appropriate solvent (for example, alcohols such as methanol and ethanol, and the like), and then subjecting to a hydrogenation reaction in the presence of a catalyst (such as palladium carbon) to prepare Compound (34a).

[Method Q]

The compound represented by the general formula (D) can be prepared by the process as below:

[Chemical Formula 43]

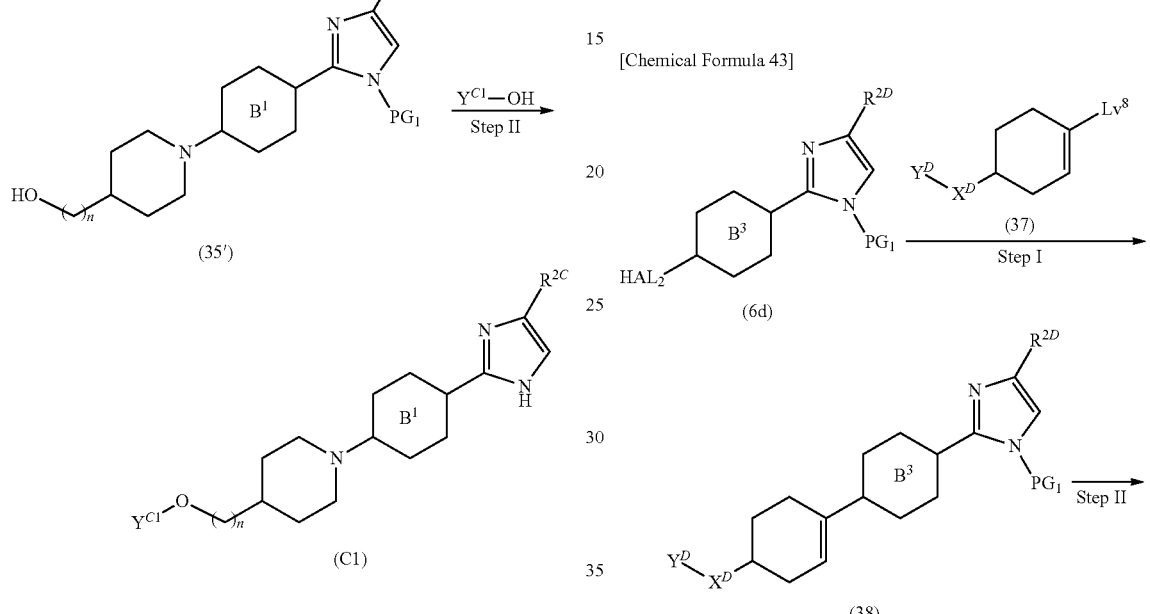

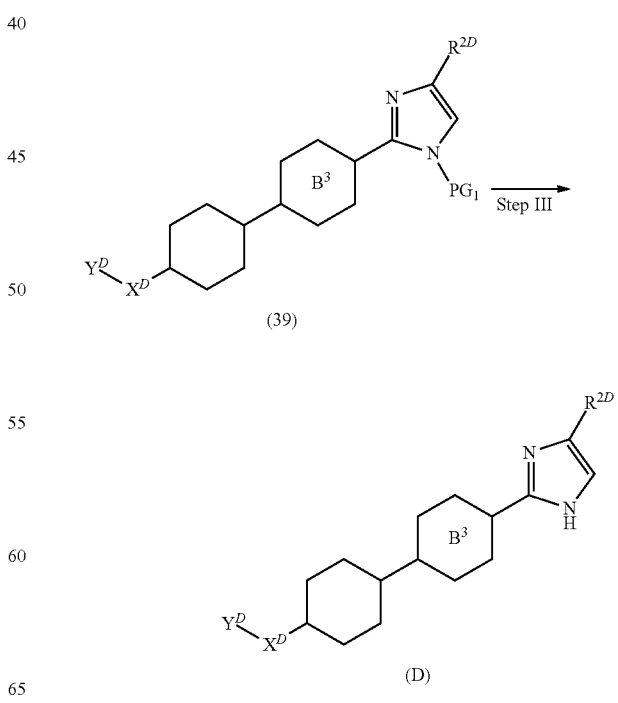

(wherein $Lv^8$ represents $B(OH)_2$, or

[Chemical Formula 44]

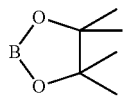

and the other symbols have the same meanings as above.)

Step I to Step III of the present reaction can be carried out in a manner similar to Step I to Step III of Method D.

[Method R]

Compound (1-B) can be prepared by the process as below:

[Chemical Formula 45]

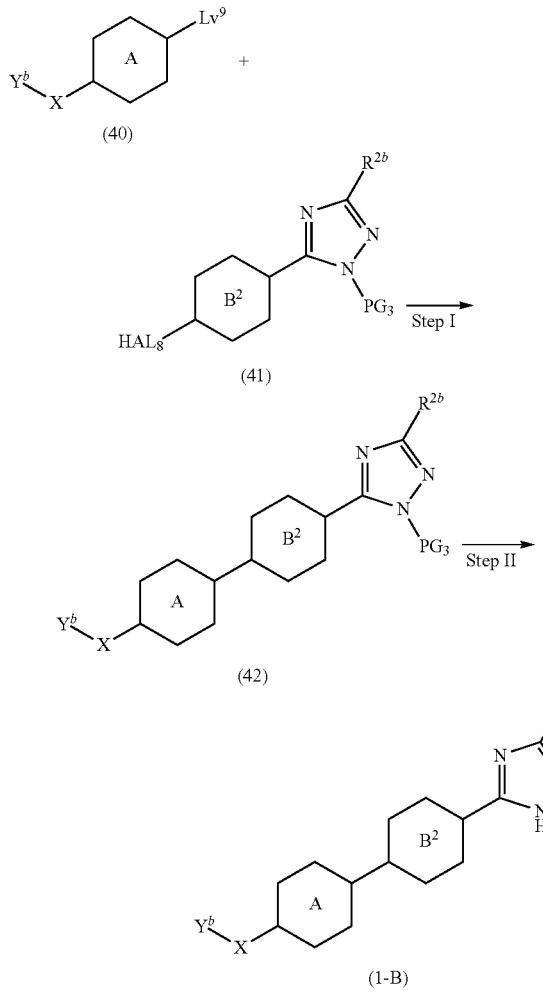

(wherein $Lv^9$ represents $B(OH)_2$ or

[Chemical Formula 46]

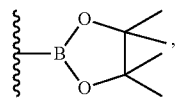

$HAL_8$ represents a halogen atom (such as chlorine atom and bromine atom), $PG_3$ represents an amino-protective group (preferably, substituted alkyl (2-(trimethylsilyl) ethoxymethyl, benzyl, and the like), and the other symbols have the same meanings as above.)

Step I:

Compound (42) can be prepared by subjecting Compound (40) and Compound (41) to Suzuki coupling reaction (for example, a reaction as described in Advanced Organic Chemistry Part B (F. A. Carey & R. J. Sundberg, Springer), and the like) in an appropriate solvent in the presence of a catalyst and a base.

As the catalyst, palladium chloride, palladium acetate, [1,1'-bis(diphenylphosphino)ferrocene]palladium (II) dichloride dichloromethane complex ($PdCl_2(dppf)CH_2Cl_2$), tetrakistriphenylphosphinepalladium, and the like can be used, and if necessary a ligand such as 1,1'-bis(diphenylphosphino)ferrocene, 2-dicyclohexylphosphino-2',6'-dimethoxybiphenyl (S-PHOS), 2-dicyclohexylphosphino-2',4',6'-triisopropyl-1,1'-biphenyl (X-PHOS), 4,5-bis (diphenylphosphino)-9,9-dimethylxanthene (Xantphos) and the like can be added.

As the base, an alkali metal such as sodium carbonate, potassium carbonate, potassium acetate, potassium phosphate, sodium hydroxide, and cesium carbonate, and the like can be used.

As the solvent, amides such as N, N-dimethyformamide, ethers such as tetrahydrofuran, 1,4-dioxane and dimethoxyethane, aromatic hydrocarbons such as benzene and toluene, water, or a solvent mixture thereof can be used.

The reaction time differs depending on the amount or the kind of the reagent, the catalyst, the base, or the reaction solvent to be used and the reaction temperature, and is usually 2 to 48 hours, preferably 5 to 12 hours.

The reaction temperature is room temperature to 150° C., preferably 60 to 120° C.

Step II:

Compound (1-B) can be prepared by deprotecting Compound (42).

The deprotection reaction of Compound (42) can be carried out, for example, when $PG_3$ is 2-(trimethylsilyl) ethoxymethyl, by treating Compound (42) with an acid (such as hydrochloric acid, trifluoroacetic acid and methanesulfonic acid) in an appropriate solvent (such as alcohols such as methanol and ethanol, water, or solvent mixture thereof) to prepare Compound (1-B). Further, Compound (1-B) can also be prepared by reacting Compound (42) with tetra-n-butylammonium fluoride in an appropriate solvent (ethers such as tetrahydrofuran, or halogenated hydrocarbons such as methylene chloride and the like).

Compound (1-B) can also be prepared by carrying out a similar method to the above using the compounds represented by following formulae:

[Chemical Formula 47]

-continued

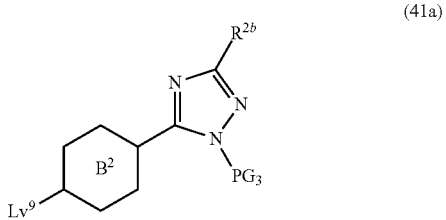
(41a)

(wherein each symbol has the same meaning as above,) (hereinafter, referred to as Compound (40a) and Compound (41a)), instead of Compound (40) and Compound (41).

[Method S]

Compound (1-B) wherein $R^{2b}$ is alkyl which may be substituted, an aromatic hydrocarbon group which may be substituted, or cycloalkyl which may be substituted (hereinafter, referred to as Compound (1-B-a)) can be prepared by the process as below:

[Chemical Formula 48]

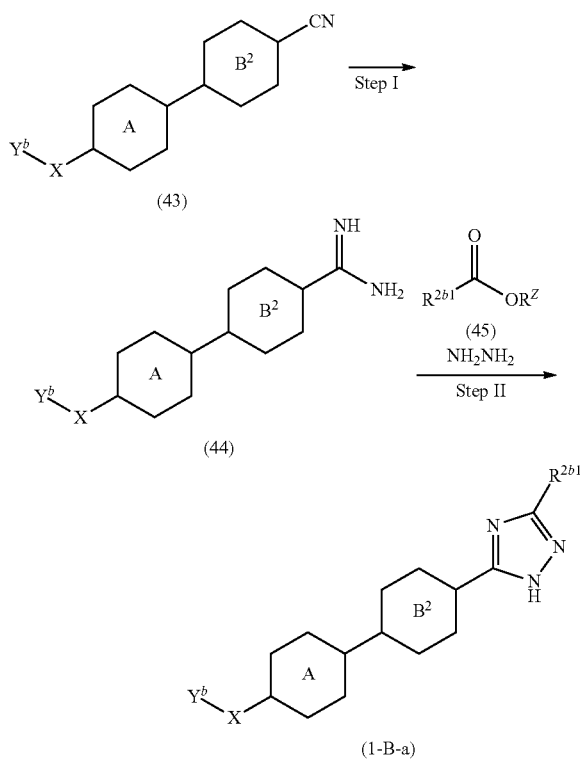

(wherein $R^{2b1}$ represents alkyl which may be substituted, an aromatic hydrocarbon group which may be substituted, or cycloalkyl which may be substituted, $R^z$ represents alkyl, and the other symbols have the same meanings as above.)

Step I:

Compound (44) can be prepared by (i) reacting Compound (43) with hydroxylamine followed by treatment with acetic acid-acetic anhydride and then a hydrogenation, or (ii) reacting Compound (43) with an alcohol in the presence of an acid, followed by reaction with ammonia or (iii) by reacting Compound (43) with lithium hexamethyldisilazane followed by treatment with an acid.

Reaction (i)

The reaction of Compound (43) with hydroxylamine can be carried out, for example, in an appropriate solvent, according to a method as described in U.S. Pat. No. 5,576,447 and the like.

As the solvent, alcohols such as methanol and ethanol, ethers such as tetrahydrofuran and 1,4-dioxane, water, and a solvent mixture thereof can be used.

The reaction time is usually 3 to 24 hours, preferably 4 to 18 hours. The reaction temperature is usually 5 to 100° C., preferably 25 to 80° C.

Thus obtained product is treated with acetic acid-acetic anhydride, and subjected to a hydrogenation reaction in an appropriate solvent in the presence of a palladium catalyst under hydrogen atmosphere according to an ordinary method to prepare Compound (44).

As the solvent, alcohols such as methanol and ethanol, ethers such as tetrahydrofuran and 1,4-dioxane, and a solvent mixture thereof can be used.

As the palladium catalyst, a catalyst such as palladium carbon and palladium black can be used.

The reaction time differs depending on the catalyst, the solvent, and the like to be used, and is usually 30 minutes to 18 hours, preferably 2 hours to 8 hours. The reaction temperature is usually 10 to 100° C., preferably 25 to 50° C.

In the hydrogenation reaction, trialkylsilane such as triethylsilane can be used as the hydrogen source instead of hydrogen.

Reaction (ii)

The reaction of Compound (43) with an alcohol can be carried out according to a method as described in Chemische Berichte, 1878, 11, 9.

As the acid, hydrochloric acid, sulfuric acid, and the like can be used.

As the alcohol, methanol, ethanol, propanol, butanol, and the like can be used.

The reaction time in the reaction of Compound (43) and an alcohol is usually 2 hours to 24 hours, preferably 5 hours to 20 hours. The reaction temperature is usually 5 to 50° C., preferably 25 to 50° C.

In the reaction with ammonia, a solvent may be used, and as the solvent, alcohols such as methanol and ethanol, ethers such as tetrahydrofuran, a solvent mixture thereof, and the like can be used.

The reaction time in the reaction with ammonia is usually 3 hours to 24 hours, preferably 8 hours to 20 hours. The reaction temperature is usually 5 to 50° C., preferably 25 to 50° C.

Reaction (iii)

The reaction of Compound (43) with lithium hexamethyldisilazane can be carried out according to a method as described in J. Organomet. Chem., 1987, 331, 21, 161-167.

As the solvent, ethers such as tetrahydrofuran, and the like can be used.

The reaction time in the reaction with lithium hexamethyldisilazane is usually 1 hour to 24 hours, preferably 2 hours to 18 hours. The reaction temperature is usually 0 to 50° C., preferably 5 to 30° C.

As the acid in the treatment with an acid, hydrochloric acid, hydrobromic acid, and the like can be used.

In the treatment with an acid, a solvent may be used, and as the solvent, ethers such as tetrahydrofuran and dioxane and the like can be used.

The reaction time in the treatment with an acid differs depending on the acid, the solvent and the like to be used, and is usually 30 minutes to 24 hours, preferably 1 hour to 18 hours. The reaction temperature is usually 0 to 50° C., preferably 5 to 30° C.

Step II:

Compound (1-B-a) can be prepared by reacting Compound (44) with Compound (45) and hydrazine in an appropriate solvent in the presence or absence of a base.

As the solvent, ethers such as tetrahydrofuran and 1,4-dioxane, halogenated hydrocarbons such as 1,2-dichloroethane and carbon tetrachloride, alcohols such as methanol and ethanol, a solvent mixture thereof, and the like can be used.

As the base, an alkali metal carbonate such as potassium carbonate and sodium hydrogencarbonate, alkali metal alkoxide such as sodium methoxide, alkali metal hydroxide such as sodium hydroxide and potassium hydroxide, and the like can be used.

Hydrazine used in the present reaction may be in a form of salt (for example, hydrochloride salt) and/or may be a hydrate.

The reaction time in the reaction with hydrazine is usually 30 minutes to 12 hours, preferably 30 minutes to 8 hours. The reaction temperature is usually 25 to 100° C., preferably 50 to 80° C.

Further, a hydrazide compound (45a) represented by the formula as below:

[Chemical Formula 49]

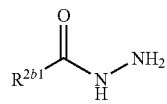

(45a)

(wherein each symbol has the same meaning as above) may be used instead of Compound (45) and hydrazine to obtain Compound (1-B-a) according to a method as described in Tetrahedron Letters, 1987, 28, 5133-5136.

[Method T]

Compound (1-B) wherein X is —O— (hereinafter, referred to as Compound (1-B-b) can be prepared by the process as below:

[Chemical Formula 50]

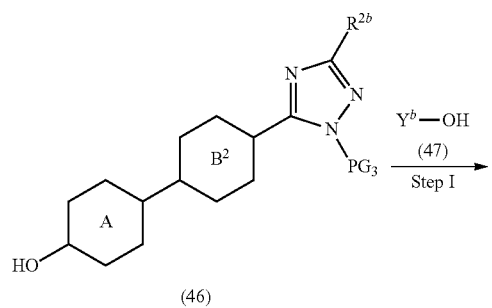

(46)

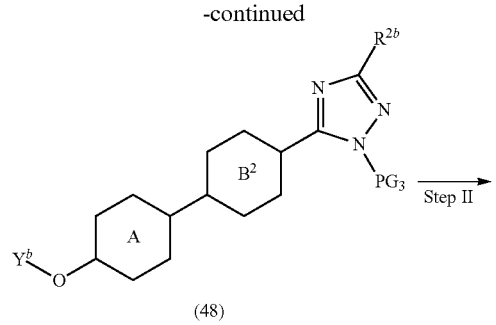

(48)

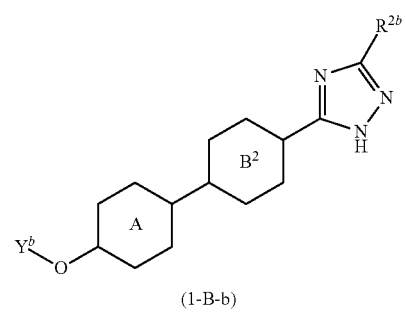

(1-B-b)

(wherein each symbol has the same meaning as above.)

Step I:

Compound (48) can be prepared by subjecting Compound (46) and Compound (47) to Mitsunobu reaction (for example, a reaction as described in Advanced Organic Chemistry Part B (F. A. Carey & R. J. Sundberg, Springer), Okuda, M.; Tomioka, K.; Tetrahedron Lett [TELEAY] 1994, 35 (26), 4585-4586, and the like) in an appropriate solvent in the presence of azodicarboxylates and phosphines.

As the azodicarboxylates, diethyl azodicarboxylate, di-t-butyl azodicarboxylate, 1,1'-(azodicarbonyl)dipiperidine, and the like can be used.

As the phosphines, triarylphosphines such as triphenylphosphine, trialkylphosphines such as tri-n-butylphosphine, and the like can be used.

As the solvent, ethers such as tetrahydrofuran, 1,4-dioxane and diethylether, aromatic hydrocarbons such as benzene, toluene and xylene, halogenated hydrocarbons such as methylene chloride, 1,2-dichloroethane and chloroform, or a solvent mixture thereof can be used.

The reaction time differs depending on the reagent, the solvent, and the like to be used, and is usually 30 minutes to 24 hours, preferably 1 hour to 12 hours. The reaction temperature is usually 0° C. to 100° C., preferably 25° C. to 80° C.

Step II:

The deprotection reaction of Compound (48) can be carried out in a manner similar to Step II of Method R.

[Method U]

Compound (1-B) wherein X is a single bond and $Y^b$ is cycloalkyl which may be substituted (hereinafter, referred to as Compound (1-B-c) can be prepared by the process as below:

[Chemical Formula 51]

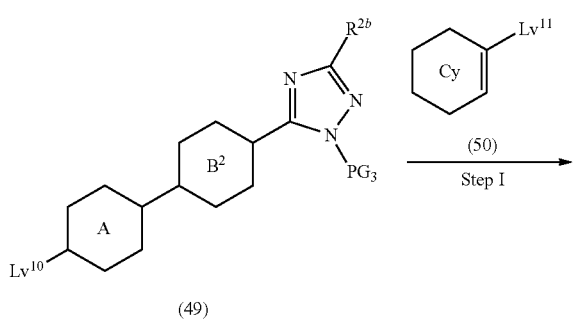

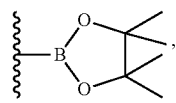

a halogen atom (such as chlorine atom and bromine atom), or trifluoromethanesulfonyloxy group, $Lv^{11}$ represents $B(OH)_2$ or

[Chemical Formula 53]

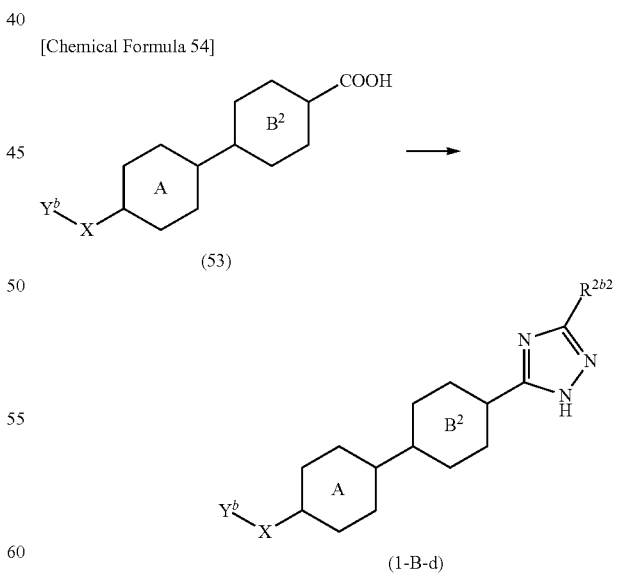

and the other symbols have the same meanings as above.)

Step I:
Compound (51) can be prepared by a coupling reaction of Compound (49) with Compound (50), which can be carried out in a manner similar to Step I of Method R.

Step II:
Compound (52) can be prepared by subjecting Compound (51) to a hydrogenation reaction in an appropriate solvent in the presence of a palladium catalyst under hydrogen atmosphere.

As the solvent, alcohols such as methanol and ethanol, ethers such as tetrahydrofuran and 1,4-dioxane, or a solvent mixture thereof can be used.

As the palladium catalyst, a catalyst such as palladium carbon and palladium black can be used.

The reaction time differs depending on the catalyst, the solvent, and the like to be used, and is usually 1 hour to 24 hours, preferably 1 hour to 12 hours. The reaction temperature is usually 20 to 50° C., preferably 20 to 40° C.

Step III:
The deprotection reaction of Compound (52) can be carried out in a manner similar to Step II of Method R.

[Method V]
Compound (1-B) wherein $R^{2b}$ is alkoxy (hereinafter, referred to as Compound (1-B-d)) can be prepared by the process as below:

[Chemical Formula 54]

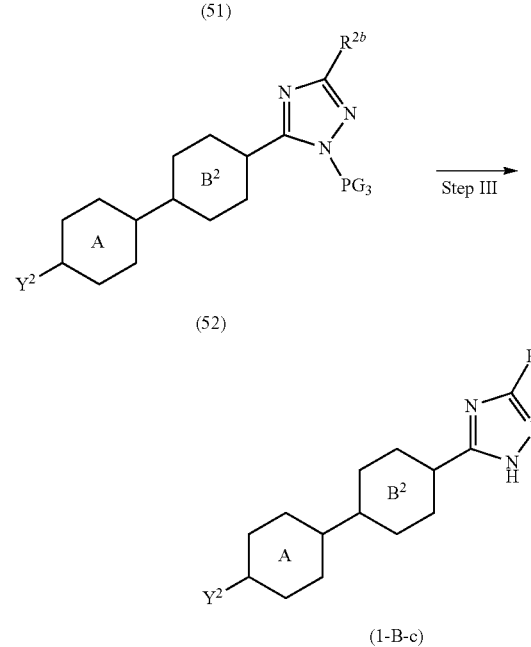

(wherein a group

[Chemical Formula 52]

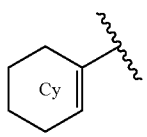

represents cycloalkenyl which may be substituted, $Y^2$ represents cycloalkyl which may be substituted, $Lv^{10}$ represents (wherein $R^{2b2}$ represents alkoxy, and the other symbols have the same meanings as above.)

Compound (1-B-d) can be prepared by reacting Compound (53) with oxalyl chloride or thionyl chloride in an appropriate solvent in the presence or absence of N, N-dimethyformamide, then reacting with potassium thiocyanate, and reacting with an alcohol and hydrazine.

As the solvent in the reaction with oxalyl chloride or thionyl chloride, halogenated hydrocarbons such as methylene chloride, ethers such as tetrahydrofuran, and the like can be used.

The reaction time in the reaction with oxalyl chloride or thionyl chloride is usually 30 minutes to 5 hours, preferably 1 hour to 3 hours. The reaction temperature is usually 0 to 60° C., preferably 20 to 40° C.

As the solvent in the reaction with potassium thiocyanate, aromatic hydrocarbons such as toluene, halogenated hydrocarbons such as methylene chloride, and the like can be used.

The reaction time in the reaction with potassium thiocyanate is usually 2 hours to 24 hours, preferably 1 hour to 3 hours. The reaction temperature is usually 0 to 60° C., preferably 20 to 40° C.

As the alcohol in the present reaction, methanol, ethanol, propanol, isopropanol, butanol, t-butanol, and the like can be used.

The reaction time in the reaction with alcohol is usually 30 minutes to 5 hours, preferably 1 hour to 3 hours. The reaction temperature is usually 0 to 100° C., preferably 20 to 40° C.

The reaction time in the reaction with hydrazine is usually 2 hours to 24 hours, preferably 1 hour to 3 hours. The reaction temperature is usually 0 to 100° C., preferably 50 to 80° C.

Hydrazine used in the present reaction may be in a form of salt (for example, hydrochloride salt), and/or may be in a hydrate.

[Method W]

Compound (43) wherein X is —O— (hereinafter, referred to as Compound (43a) can be prepared by the process as below:

[Chemical Formula 55]

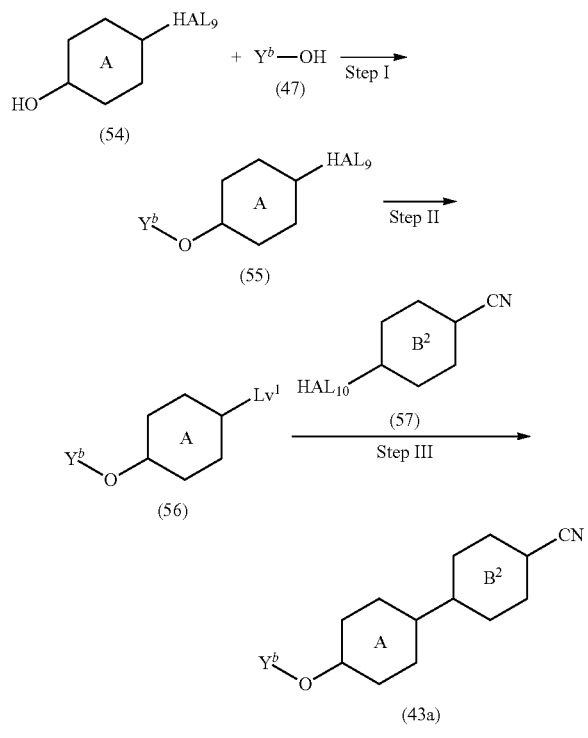

(wherein $HAL_9$ and $HAL_{10}$ represent a halogen atom (such as chlorine atom and bromine atom), and the other symbols have the same meanings as above.)

Step I:

The coupling reaction of Compound (54) with Compound (47) can be carried out in a manner similar to Step I of Method T.

Step II:

Compound (56) can be prepared by reacting Compound (55) with a boronic acid ester in an appropriate solvent in the presence of a palladium catalyst, a ligand and a base.

As the solvent, ethers such as 1,4-dioxane, dimethylsulfoxide, aromatic hydrocarbons such as toluene, and the like can be used.

As the palladium catalyst, palladium acetate, [1,1'-bis(diphenylphosphino)ferrocene]palladium (II) dichloride dichloromethane complex ($PdCl_2(dppf)CH_2Cl_2$) and the like can be used.

As the ligand, 2-dicyclohexylphosphino-2',6'-dimethoxybiphenyl (S-PHOS), 2-dicyclohexylphosphino-2',4',6'-triisopropyl-1,1'-biphenyl (X-PHOS), 4,5-bis(diphenylphosphino)-9,9-dimethylxanthene (Xantphos), and the like can be used.

As the base, potassium acetate, potassium phosphate, and the like can be used.

As the boronic acid ester, bis(pinacolato)diboron, trialkoxyboron, and the like can be used.

The reaction time differs depending on the catalyst, the solvent, and the like to be used, and is usually 1 hour to 24 hours, preferably 2 hours to 12 hours. The reaction temperature is usually 50 to 130° C., preferably 60 to 100° C.

Step III:

The coupling reaction of Compound (56) with Compound (57) can be carried out in a manner similar to Step I of Method R.

[Method X]

Compound (41) wherein $R^{2b}$ is alkyl which may be substituted, aromatic hydrocarbon group which may be substituted, or cycloalkyl which may be substituted (hereinafter, referred to as Compound (41b)) can be prepared by the process as below:

[Chemical Formula 56]

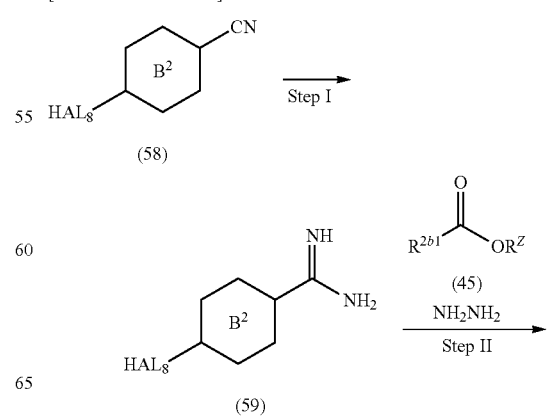

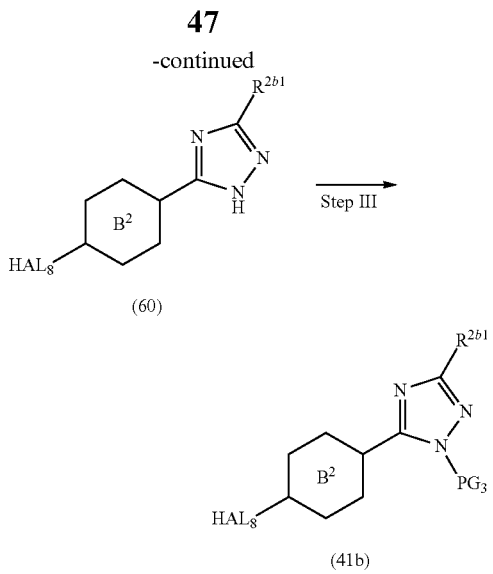

(wherein each symbol has the same meaning as above.)

Steps I and II:

Compound (60) can be prepared in a manner similar to Step I and Step II of Method S.

Step III:

Compound (41b) can be prepared by protecting the amino group of Compound (60). For example, when $PG_3$ is 2-(trimethylsilyl)ethoxymethyl group, it can be prepared by reacting Compound (60) with 2-(trimethylsilyl)ethoxymethyl chloride in an appropriate solvent in the presence of a base.

As the solvent, an aprotic polar solvent such as N,N-dimethylformamide, N,N-dimethylacetamide and N-methylpyrrolidone can be used.

As the base, an alkali metal hydride such as sodium hydride and potassium hydride, or an alkali metal carbonate such as potassium carbonate and sodium carbonate can be used.

[Method Y]

Compound (41) wherein $R^{2b}$ is alkylthio (hereinafter, referred to as Compound (41c)) can be prepared by the process as below:

[Chemical Formula 57]

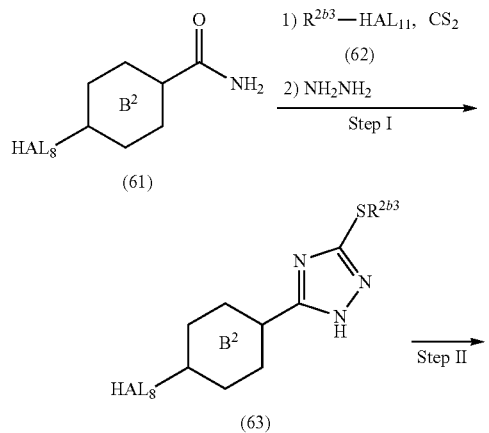

wherein $HAL_{11}$ represents a halogen atom such as chlorine atom, bromine atom and iodine atom), $R^{2b3}$ represents alkyl, and the other symbols have the same meanings as above.

Step I:

Compound (63) can be prepared by reacting Compound (61) with Compound (62) in an appropriate solvent in the presence of methyl iodide, carbon disulfide and a base, and by reacting the obtained product with hydrazine in an appropriate solvent.

As the solvent in the reaction of Compound (61) with Compound (62), amides such as N,N-dimethyformamide, ethers such as tetrahydrofuran, and the like can be used.

As the base in the reaction of Compound (61) with Compound (62), alkyl metal hydride such as sodium hydride and potassium hydride, and the like can be used.

The reaction time in the reaction of Compound (61) with Compound (62) is usually 1 hour to 24 hours, preferably 2 hours to 12 hours. The reaction temperature is usually −10 to 40° C., preferably −10 to 25° C.

As the solvent in the reaction with hydrazine, ethers such as tetrahydrofuran, alcohols such as methanol and ethanol, a solvent mixture thereof, and the like can be used.

Hydrazine used in the present reaction may be in a form of salt and/or may be a hydrate.

The reaction time in the reaction with hydrazine is usually 30 minutes to 8 hours, preferably 1 hour to 5 hours. The reaction temperature is usually 0 to 40° C., preferably 0 to 25° C.

Step II:

The reaction from Compound (63) to Compound (41c) can be carried out in a manner similar to Step III of Method X.

[Method Z]

Compound (63) can also be prepared by the process as below:

[Chemical Formula 58]

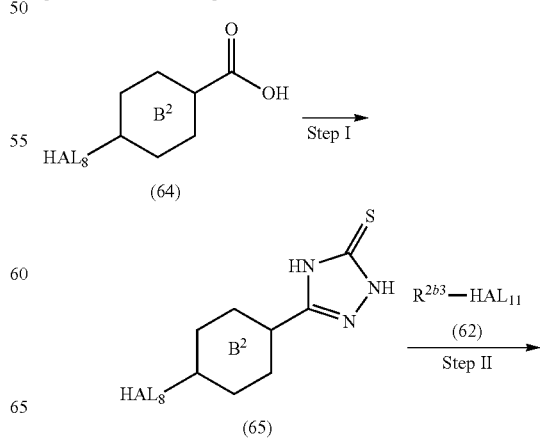

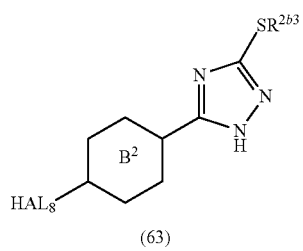

(63)

[Chemical Formula 59]

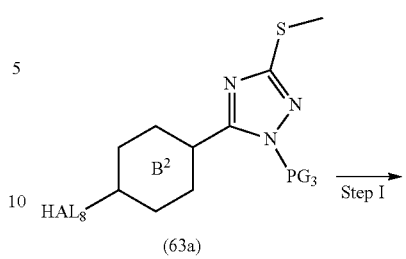

(63a)

(wherein each symbol has the same meaning as above.)

Step I:

Compound (65) can be prepared by reacting Compound (64) with oxalyl chloride or thionyl chloride in an appropriate solvent in the presence or absence of N,N-dimethylformamide, followed by reaction with thiosemicarbazide in an appropriate solvent in the presence of a base.

As the solvent in the reaction with oxalyl chloride or thionyl chloride, halogenated hydrocarbons such as methylene chloride, ethers such as tetrahydrofuran, and the like can be used.

The reaction time in the reaction with oxalyl chloride or thionyl chloride is usually 30 minutes to 5 hours, preferably 1 hour to 3 hours. The reaction temperature is usually 0 to 60° C., preferably 20 to 40° C.

As the solvent in the reaction with thiosemicarbazide, ethers such as tetrahydrofuran, halogenated hydrocarbons such as methylene chloride, and the like can be used.

As the base in the reaction with thiosemicarbazide, pyridine, triethylamine, and the like can be used.

The reaction time in the reaction with thiosemicarbazide is usually 2 hours to 24 hours, preferably 1 hour to 3 hours. The reaction temperature is usually 25 to 100° C., preferably 80 to 100° C.

Step II:

Compound (63) can be prepared by reacting Compound (65) with Compound (62) in an appropriate solvent in the presence of an alkali metal base such as an alkali metal hydroxide and potassium carbonate.

As the solvent, a mixed solvent of alcohol such as methanol and ethanol, and water, and the like can be used.

As the alkali metal hydroxide base, sodium hydroxide, potassium hydroxide, and the like can be used.

The reaction time is usually 30 minutes to 5 hours, preferably 1 hour to 3 hours. The reaction temperature is usually 0 to 40° C., preferably 0 to 25° C.

[Method AA]

Compound (41) wherein $R^{2b}$ is alkoxy which may be substituted, aryloxy which may be substituted, heteroaryloxy which may be substituted, cycloalkyloxy, cycloalkylalkoxy, or non-aromatic heterocycle having a bond at the nitrogen atom which may be substituted (hereinafter, referred to as Compound (41d)) can be prepared by the process as below:

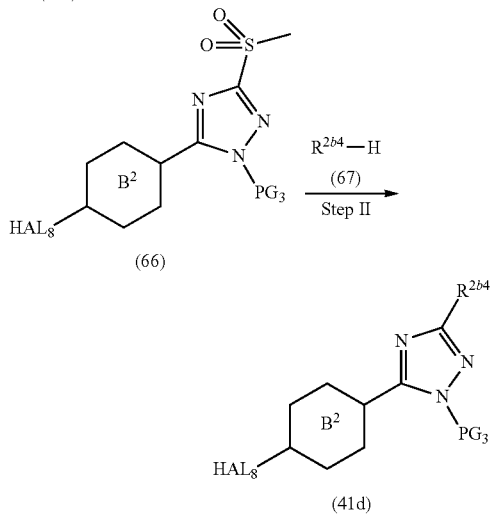

(wherein $R^{2b4}$ represents alkoxy which may be substituted, aryloxy which may be substituted, heteroaryloxy which may be substituted, cycloalkyloxy, cycloalkylalkoxy, or non-aromatic heterocycle having a bond at the nitrogen atom which may be substituted (preferably, piperidino, 1-piperazinyl, morpholino, and the like), and the other symbols have the same meanings as above.)

Step I:

Compound (66) can be prepared by reacting Compound (63a) with an oxidizing agent in an appropriating solvent.

As the solvent, halogenated hydrocarbons such as methylene chloride and chloroform, ethers such as tetrahydrofuran, and the like can be used.

As the oxidizing agent, m-chloroperoxybenzoic acid and the like can be used.

The reaction time is usually 30 minutes to 24 hours, preferably 1 hour to 12 hours. The reaction temperature is usually 0 to 40° C., preferably 0 to 25° C.

Step II:

Compound (41d) can be prepared by reacting Compound (66) with Compound (67) in an appropriate solvent in the presence of a base.

As the solvent, amides such as N, N-dimethyformamide and N-methylpyrrolidone, ethers such as tetrahydrofuran and 1,4-dioxane, a solvent mixture thereof, and the like can be used.

As the base, an alkali metal hydride such as sodium hydride and potassium hydride, an alkali metal carbonate such as potassium carbonate and sodium carbonate, an organic bases such as triethylamine and N,N-diisopropylethylamine, and the like can be used.

The reaction time is usually 10 minutes to 24 hours, preferably 10 minutes to 12 hours. The reaction temperature is usually 0 to 150° C., preferably 0 to 120° C.

[Method AB]

Compound (41) wherein $R^{2b}$ is alkoxy which may be substituted (hereinafter, referred to as Compound (41e)) can be prepared by the process as below:

[Chemical Formula 60]

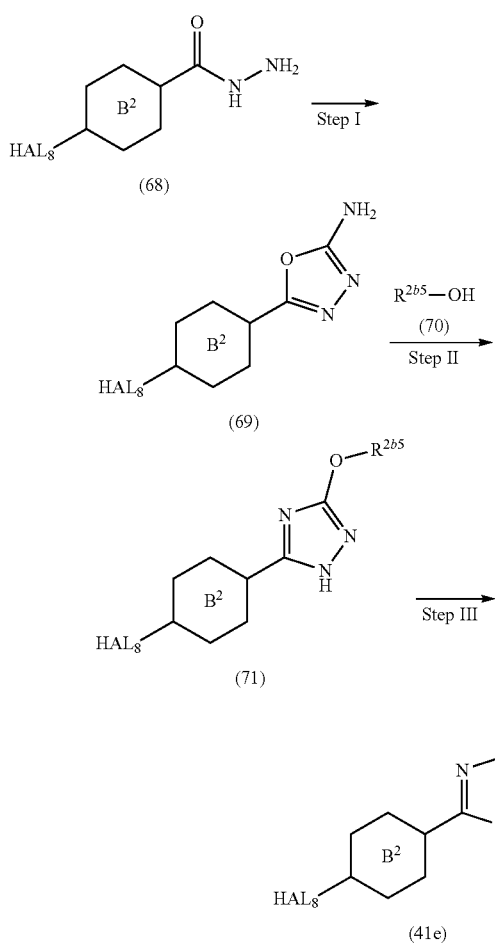

(wherein $R^{2b5}$ represents alkyl which may be substituted, and the other symbols have the same meanings as above.)

Step I:

Compound (69) can be prepared by reacting Compound (68) with a cyanogen halide (such as bromo cyanide) in an appropriate solvent in the presence of a base, according to a process as described in Justus Liebigs Annalen der Chemie, 1955, 597, 157-165 and the like.

As the solvent, ethers such as 1,4-dioxane, halogenated hydrocarbons such as methylene chloride, acetonitrile, and the like can be used.

As the base, an alkali metal carbonate such as sodium hydrogencarbonate, an alkali metal hydroxide such as sodium hydroxide, and the like can be used.

The reaction time is usually 1 hour to 48 hours, preferably 2 hours to 24 hours. The reaction temperature is usually 0 to 100° C., preferably 25 to 80° C.

Step II:

Compound (71) can be prepared by reacting Compound (69) with Compound (70) in the present of an alkali metal hydroxide base.

As the alkali metal hydroxide base, sodium hydroxide, potassium hydroxide, and the like can be used.

The reaction time is usually 1 hour to 24 hours, preferably 3 hours to 12 hours. The reaction temperature is usually 50 to 100° C., preferably 60 to 90° C.

Step III:

Compound (41e) can be prepared by protecting Compound (71) in a manner similar to Step III of Method X.

[Method AC]

Compound (41) wherein $R^{2b}$ is non-aromatic heterocyclic group having a bond at the nitrogen atom which may be substituted (preferably, piperidino, 1-piperazinyl, morpholino, and the like) (hereinafter, referred to as Compound (41o) can be prepared by the process as below:

[Chemical Formula 61]

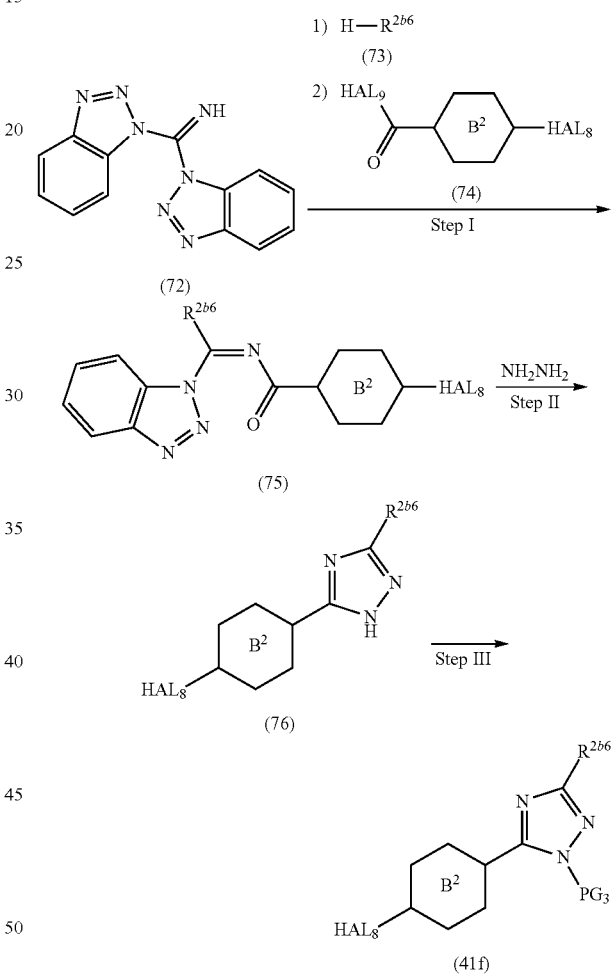

(wherein $R^{2b6}$ represents non-aromatic heterocyclic group having a bond at the nitrogen atom which may be substituted (preferably, piperidino, 1-piperazinyl, morpholino, and the like), and the other symbols have the same meanings as above.)

Step I:

Compound (75) can be prepared by reacting Compound (72), which can be obtained by reacting benzotriazole with a cyanogen halide (such as cyanogen bromide), with Compound (73) in an appropriate solvent in the presence of a base, followed by reaction with Compound (74) in an appropriate solvent in the presence of a base.

As the solvent in the reaction of Compound (72) with Compound (73), ethers such as tetrahydrofuran and dioxane, halogenated hydrocarbons such as methylene chloride, acetonitrile, and the like can be used.

As the base in the reaction of Compound (72) with Compound (73), an organic base such as triethylamine, diisopropylethylamine and pyridine can be used.

The reaction time in the reaction of Compound (72) with Compound (73) is usually 1 hour to 24 hours, preferably 3 hours to 12 hours. The reaction temperature is usually 0 to 40° C., preferably 0 to 25° C.

As the solvent in the reaction with Compound (74), halogenated hydrocarbons such as chloroform and methylene chloride, ethers such as tetrahydrofuran and dioxane, halogenated hydrocarbons such as methylene chloride, acetonitrile, and the like can be used.

As the base in the reaction with Compound (74), an organic base such as triethylamine, diisopropylethylamine and pyridine can be used.

The reaction time in the reaction with Compound (74) is usually 1 hour to 24 hours, preferably 1 hour to 12 hours. The reaction temperature is usually 0 to 60° C., preferably 0 to 40° C.

Step II:

Compound (76) can be prepared by reacting Compound (75) with hydrazine in an appropriate solvent according to a method as described in Synthesis, 2001, 6, 897-903.

As the solvent, halogenated hydrocarbons such as chloroform and methylene chloride, and the like can be used.

The reaction time is usually 1 hour to 24 hours, preferably 3 hour to 12 hours. The reaction temperature is usually 0 to 60° C., preferably 0 to 40° C.

Step III:

Compound (41f) can be prepared by protecting Compound (76) in a manner similar to Step III of Method X.

[Method AD]

Compound (41) wherein $R^{2b}$ is aromatic hydrocarbon group which may be substituted (hereinafter, referred to as Compound (41g)) can be prepared by the process as below:

[Chemical Formula 62]

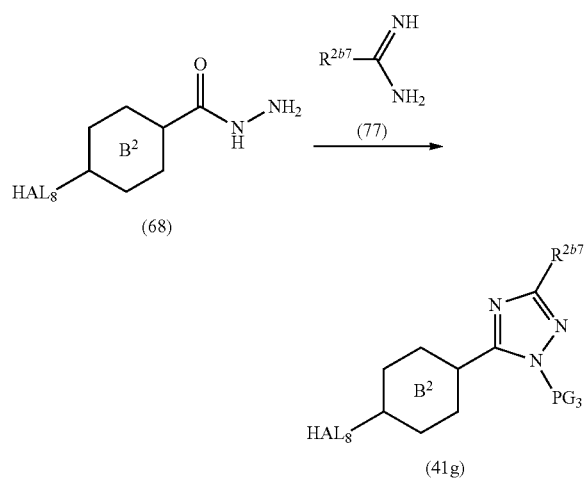

(wherein $R^{2b7}$ represents aromatic hydrocarbon group which may be substituted, and the other symbols have the same meanings as above.)

Compound (41g) can be prepared by reacting Compound (68) with Compound (77) in an appropriate solvent in the presence of a base, and by protecting the amino group with $PG_3$.

As the solvent, alcohols such as methanol, ethanol and isopropylalcohol, and the like can be used.

As the base, an alkali metal alkoxide such as sodium methoxide and potassium methoxide, and the like can be used.

The reaction time is usually 12 hours to 72 hours, preferably 24 hours to 48 hours. The reaction temperature is usually 25 to 100° C., preferably 50 to 90° C.

[Method AE]

Compound (41) wherein $R^{2b}$ is alkyl which may be substituted, cycloalkyl which may be substituted, or aromatic hydrocarbon group which may be substituted (hereinafter, referred to as Compound (41h)) can be prepared by the process as below:

[Chemical Formula 63]

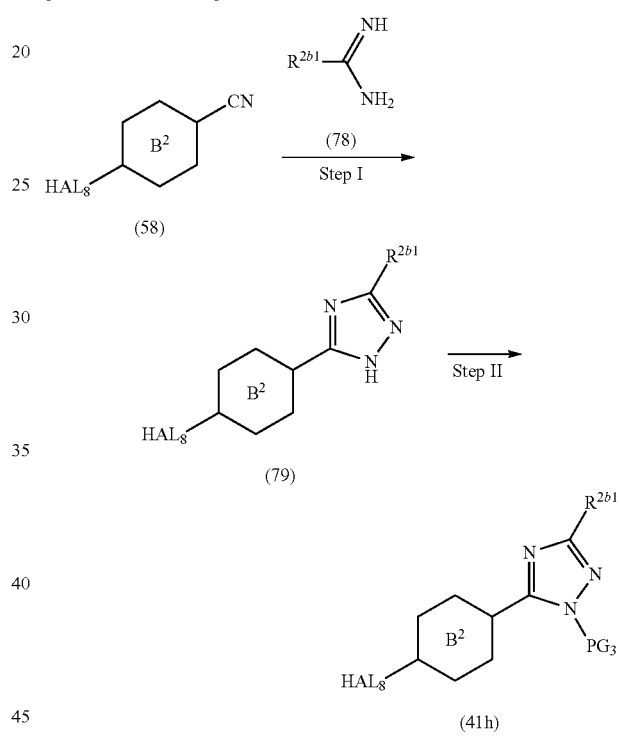

(wherein each symbol has the same meaning as above.)

Compound (79) can be prepared by reacting Compound (58) with Compound (78) in an appropriate solvent under oxygen atmosphere in the presence of a base and a catalyst according to a method as described in J. Am. Chem. Soc. 2009, 131, p. 15080-15081.

As the solvent, dimethylsulfoxide, N, N-dimethyformamide, dichlorobenzene, toluene, and the like can be used.

As the base, an alkali metal carbonate such as sodium carbonate, potassium carbonate and cesium carbonate, and the like can be used.

As the catalyst, a catalyst such as copper (I) chloride, copper (I) bromide, copper (II) bromide, copper (II) acetate can be used. Depending on the reactive group, 1,10-phenanthroline and zinc (II) halide is effective as an additive.

The reaction time is usually 12 hours to 48 hours, preferably 12 hours to 24 hours. The reaction temperature is usually room temperature to the reflux temperature of the solvent, preferably 80 to 150° C.

Step II:

A reaction from Compound (79) to Compound (41h) can be carried out in a manner similar to Step III of Method X.
[Method AF]

Compound (46) and Compound (49a) which is Compound (49) wherein $LV^{10}$ is trifluoromethanesulfonyloxy can be prepared by the process as below:

[Chemical Formula 64]

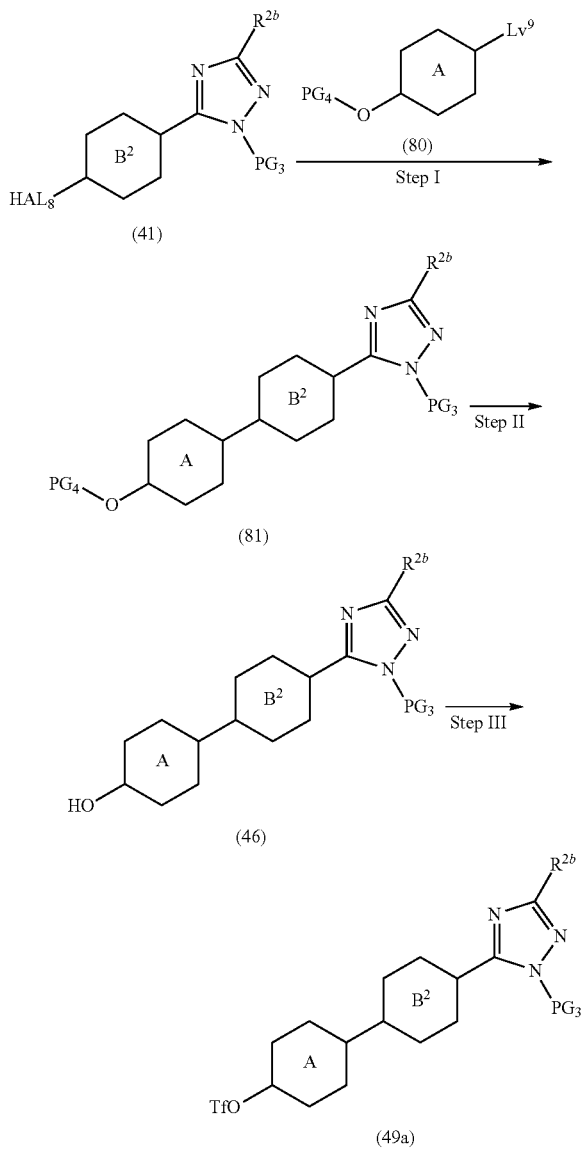

(wherein $PG_4$ represents a hydroxyl group-protective group (preferably, benzyl and the like), and the other symbols have the same meanings as above.)

Step I:

The coupling reaction of Compound (41) with Compound (80) can be carried out in a manner similar to Step I of Method R.

Step II:

Compound (46) can be prepared by deprotecting $PG_4$ of Compound (81).

The deprotection reaction of $PG_4$ can be carried, for example when $PG_4$ is benzyl group, by subjecting Compound (81) to a hydrogenation reaction in an appropriate solvent (alcohols such as methanol and ethanol, and the like) in the presence of palladium catalyst (such as palladium carbon and palladium hydroxide) under hydrogen atmosphere to prepare Compound (46).

Step III:

Compound (49a) can be prepared by reacting Compound (46) with trifluoromethanesulfonic anhydride in an appropriate solvent (halogenated hydrocarbons such as methylene chloride and chloroform, ethers such as tetrahydrofuran and dimethyl ether, and the like) in the presence of a base (such as triethylamine and N,N-diisopropylethylamine) at 0° C. to 25° C. for 1 hour to 8 hours.

The compound represented by the general formula (A) can be prepared by the above Method A to Method AF, or according to a method as described in PCT/JP2011/079958.

When the compound of the present invention, the intermediate compound, the starting compound, and the like have a functional group (such as hydroxyl, amino and carboxy), the functional group can be protected with a protective group which is usually used in the organic synthetic chemistry and after a reaction, the protective group can be removed to obtain an intended compound, according to a method as described in Theodora W. Greene, Peter G. M. Wuts, "Protective Groups in Organic Synthesis" 3rd. ed., John Wiley & Sons, Inc., 1999. As the protective group, a protective group which is usually used in the organic synthetic chemistry described in the above book can be mentioned, and as a protective group of hydroxyl group, for example, tetrahydropyranyl, trimethylsilyl, t-butyldimethylsilyl, benzyl, 4-methoxybenzyl, methoxymethyl, acetyl, and the like can be mentioned. As a protective group of amino group, for example, t-butoxycarbonyl, benzyloxycarbonyl, 9-fluorenylmethoxycarbonyl, 2,2,2-trichloroethoxycarbonyl, t-amyloxycarbonyl, 4-methoxybenzyl, 2-nitrobenzenesulfonyl, 2,4-dinitrobenzenesulfonyl, 2-(trimethylsilyl)ethoxymethyl, and the like can be mentioned, and as a protective group of carboxy, for example, alkyl such as methyl, ethyl and t-butyl, benzyl, and the like can be mentioned.

Further, after the compound of the present invention or the intermediate compound is prepared by the above method, the functional group can be converted or modified according to an ordinary method. The specific methods can be mentioned as follows.

(1) Conversion of Carboxy or Ester Thereof to Aminocarbonyl

By converting a carboxy or a salt thereof to an acyl halide and reacting it with an amine; by reacting a carboxy or a salt thereof with an amine in the presence of a condensation agent; or by reacting an ester thereof with an amine, a carboxy or ester thereof can be converted to a corresponding aminocarbonyl.

(2) Conversion of Amine to Amide

By reacting an amine or a salt thereof with a carboxy or a corresponding acyl halide; by reacting an amine or a salt thereof with a carboxy in the presence of a condensing agent; or by reacting an amine with an ester of carboxy, an amine can be converted to a corresponding amide.

(3) Conversion of Ester to Carboxy

By hydrolyzing an ester with an alkali metal hydroxide base (such as sodium hydroxide and potassium hydroxide) or an acid (such as hydrochloric acid and sulfuric acid); or by hydrogenating using a metal catalyst, an ester can be converted to a corresponding carboxy or a salt thereof can be obtained.

(4) Conversion of Ester to Hydroxymethyl

By reacting an ester with a reducing agent (such as metal reducing agent including sodium borohydride, lithium borohydride, lithium aluminium hydride and sodium triacetoxyborohydride), an ester can be converted to a corresponding hydroxymethyl.

(5) Conversion of Alcohol to Ether

By reacting an alcohol with an alkyl halide in the presence of a base, an alcohol can be converted to a corresponding ether.

(6) Conversion of Alcohol to Aldehyde

By reacting an alcohol with an oxidizing agent (such as manganese dioxide), an alcohol can be converted to a corresponding aldehyde.

(7) Conversion of Aldehyde to Aminomethyl or Cyclic Aminomethyl

By reacting an aldehyde with an amine or a cyclic amine (such as piperidine, piperazine and morpholine) in the presence of a reducing agent (such as metal reducing agent including sodium borohydride, lithium borohydride, lithium aluminium hydride and sodium triacetoxyborohydride), an aldehyde can be converted to a corresponding aminomethyl or cyclic aminomethyl.

(8) Conversion of Halogen to Cyano

By reacting a halogen with a cyanating agent (such as potassium hexacyanoferrate (II) trihydrate, copper (I) cyanide and zinc cyanide) a palladium catalyst (such as palladium acetate and $PdCl_2(dppf)$), a ligand (such as butyl di-1-adamantylphosphine, X-PHOS, S-PHOS and Xantphos), and in the presence or absence of a base (such as sodium carbonate and potassium carbonate), a halogen can be converted to a corresponding cyano.

(9) Conversion of Haloalkyl to Carboxy

By hydrolyzing a haloalkyl with a base (such as an alkali metal hydroxide base including sodium hydroxide and potassium hydroxide), a haloalkyl can be converted to a corresponding carboxy or a salt thereof.

(10) Conversion of Haloalkyl to Cyano

By treating a haloalkyl with ammonia, a haloalkyl can be converted to a corresponding cyano or a salt thereof.

(11) Conversion of Alkylthio to Alkylsulfonyl

By treating an alkylthio with an oxidizing agent (such as m-chloro-perbenzoic acid), an alkylthio can be converted to a corresponding alkylsulfonyl.

(12) Conversion of Alkylsulfonyl to Alkoxy, Aryloxy or Heteroaryloxy

By reacting an alkylsulfonyl with an alcohol, a hydroxyaryl or a hydroxyheteroaryl in the presence of a base (such as potassium carbonate, sodium carbonate and sodium hydride), an alkylsulfonyl can be converted to a corresponding alkoxy, aryloxy, or heteroaryloxy.

Further, the prepared compound of the present invention and each intermediate compound in the above preparation can be purified by an ordinary method, for example, chromatography, distillation, recrystallization, and the like. As the solvent for recrystallization, for example, an alcohol solvent such as methanol, ethanol and 2-propanol; an ether solvent such as diethylether, diisopropylether and THF; an ester solvent such as ethyl acetate; an aromatic solvent such as toluene; a ketone solvent such as acetone; a hydrocarbon solvent such as hexane; water, and the like; or a solvent mixture thereof; and the like can be mentioned. Further, the compound of the present invention can be converted to a pharmaceutically acceptable salt thereof according to an ordinary method, and then, recrystallization and the like can be carried out.

If the compound of the present invention or a pharmaceutically acceptable salt thereof has an optical isomer based on an asymmetric carbon, they can be separated to each optical isomer by an ordinary optical resolution method (fractional crystallization method or separation method using a chiral column) Further, an optically pure starting compound can be used to synthesize an optical isomer.

Effect of the Invention

The compound of the present invention or a pharmaceutically acceptable salt thereof has an excellent DGAT1 inhibitory activity, and is useful as a medicament for the prevention and/or treatment of the following diseases in warm-blooded animals, preferably, mammals including human being:

(1) diseases relating to adiposity (obesity): hyperlipidemia, hypertriglyceridemia, lipid metabolism disorder, fatty liver, and the like, (2) diseases considered to be caused by adiposity (obesity); type 2 diabetes mellitus, diabetic complication (including diabetic peripheral neuropathy, diabetic nephropathy, diabetic retinopathy and diabetic macroangiopathy); arteriosclerosis, hypertension, cerebrovascular disorder, coronary artery disease; dyspnoea, lumbago, gonarthrosis, and the like, and (3) familial hyperchylomicronemia.

Further, since the compound of the present invention or a pharmaceutically acceptable salt thereof has GLP-1 secretion promoting activity based on DGAT1 inhibitory activity, it is expected to have insulin secretion promoting activity, and/or a pancreas-protecting activity.

Thus obtained compound of the present invention or a pharmaceutically acceptable salt thereof can be formulated as a pharmaceutically composition comprising a therapeutically effective amount of the compound and a pharmaceutically acceptable carrier. As the pharmaceutically acceptable carrier, a binder (for example, hydroxypropylcellulose, polyvinylalcohol, polyvinylpyrrolidone, or polyethyleneglycol), excipient (for example, lactose, sucrose, mannitol, sorbitol, cornstarch, potato starch, crystalline cellulose or calcium carbonate), a lubricant (for example, magnesium stearate, calcium stearate or talc), a disintegrating agent (for example, low substituted hydroxypropylcellulose, or cross-linked carboxymethylcellulose), a humectant (for example, sodium lauryl sulfate), and the like can be mentioned.

The compound of the present invention or a pharmaceutically acceptable salt thereof can be orally or parenterally administered, and can be used as an appropriate pharmaceutical preparation. As an appropriate pharmaceutical preparation for oral administration, for example, a solid preparation such as tablet, granule, capsule, or powder; a solution preparation, a suspension preparation, and an emulsion preparation can be mentioned. As an appropriate pharmaceutical preparation for parenteral administration, suppository, injection or drip infusion preparation using distilled water for injection, physiological saline, glucose aqueous solution, and the like; inhalant, and the like can be mentioned.

The dose of the compound of the present invention or a pharmaceutically acceptable salt thereof, differs depending on the administration method; the age, the body weight and the condition of patient, and it is 0.001 to 100 mg/kg/day, preferably 0.1 to 30 mg/kg/day, more preferably 0.1 to 10 mg/kg/day for usual oral administration, which is administered in one dose or in 2 to 4 doses. For parenteral administration, 0.0001 to 10 mg/kg/day is preferable, which is administered in one dose or several doses. Further, for transmucosal administration, 0.001 to 100 mg/kg/day is administered once a day or in several doses.

BEST MODE FOR CARRYING OUT THE INVENTION

The present invention is explained in detail hereinafter with examples, reference examples and experimental examples, but, the present invention is not limited thereby.

EXAMPLE

Example 1-1

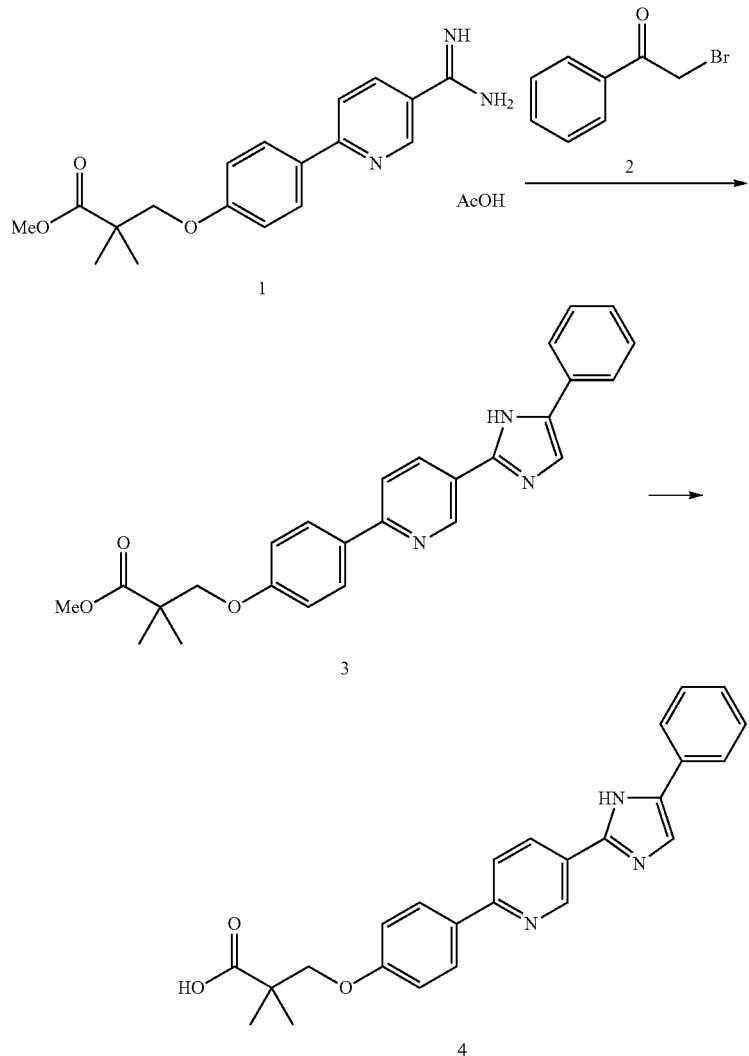

(1) An acetate of Compound 1 (1.94 g) and potassium carbonate (1.73 g) were dissolved in dichloromethane (50 mL) and saturated brine (50 mL), to this was added Compound 2 (phenacyl bromide) (1.49 g), and then the mixture was heated at reflux for 4 hours. After the temperature of the reaction solution was brought back to room temperature, dichloromethane was added to carry out a liquid separation. The organic layer was separated and dried over anhydrous sodium sulfate, and the solvent was distilled off under reduced pressure. The obtained residue was purified by silica gel column chromatography (chloroform:methanol=99:1 to 95:5), to the obtained residue was added diethyl ether, the solid was collected by filtration, washed with diethyl ether and dried to obtain Compound 3 (1.93 g).

MS (m/z): 428 [M+H]$^+$ (2) Compound 3 (0.31 g) was dissolved in methanol (7 mL) and tetrahydrofuran (7 mL), and an 8N aqueous sodium hydroxide solution (0.92 mL) was added dropwise, and the mixture was stirred at 50° C. overnight. After the temperature of the reaction solution was brought back to room temperature, the solvent was distilled off under reduced pressure, and to the obtained residue was added water, and the mixture was neutralized with acetic acid. After the solvent was distilled under reduced pressure, water was added, and the obtained solid residue was collected by filtration, washed with water and subsequently dried. To the obtained residue was added diethyl ether, and the solid was collected by filtration, washed with diethyl ether and dried to obtain Compound 4 (0.29 g).

MS (m/z): 414 [M+H]$^+$

Examples 1-2 to 1-69
A treatment was carried out in a manner similar to the Example 1-1 to obtain compounds of Examples 1-2 to 1-69 in Table 1 below.
TABLE 1
| Example | Starting material 1 | Starting material 2 |
|---------|---------------------|---------------------|
| 1-2 | 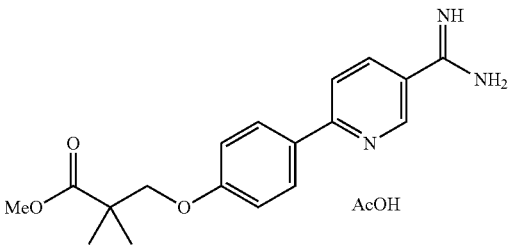 [SMILES: "AcOH" ; COC(=O)C(C)(C)COc1ccc(-c2ccc(C(=N)N)cn2)cc1] AcOH | 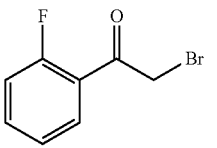 [SMILES: O=C(CBr)c1ccccc1F] |
| 1-3 | 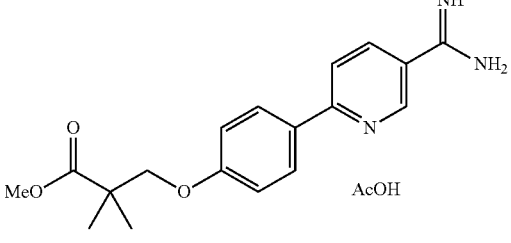 AcOH | 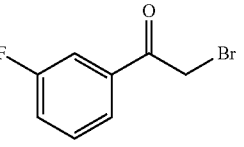 |
| 1-4 | 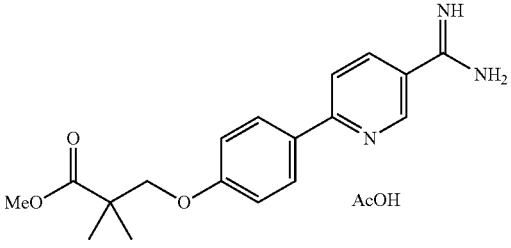 [SMILES: "AcOH" ; COC(=O)C(C)(C)COc1ccc(-c2ccc(C(=N)N)cn2)cc1] AcOH | 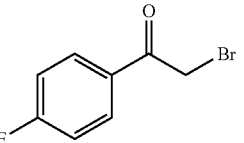 |
| 1-5 | 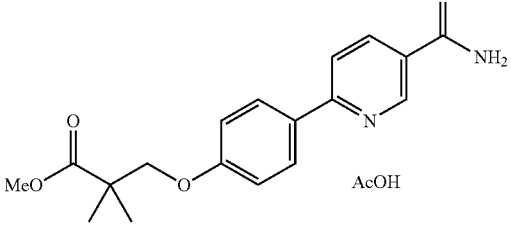 AcOH | 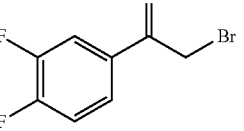 |
| 1-6 | 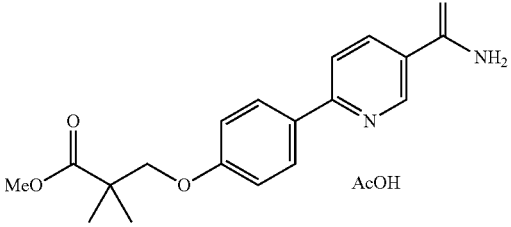 AcOH | 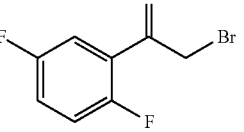 |

TABLE 1-continued
1-7 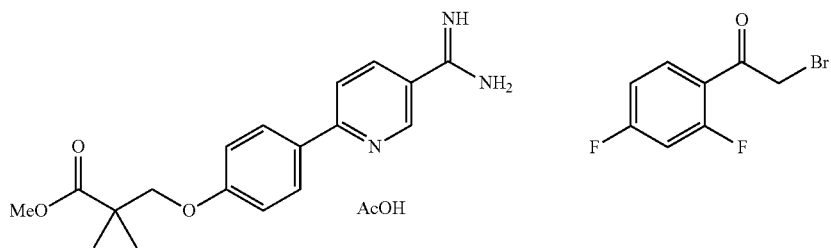
1-8 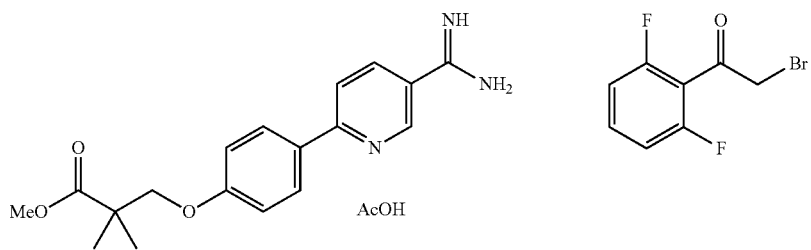
1-9 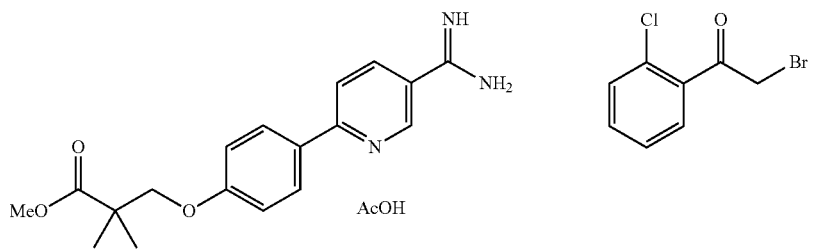
1-10 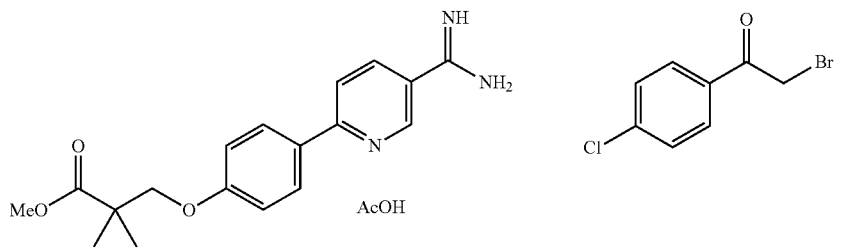
1-11 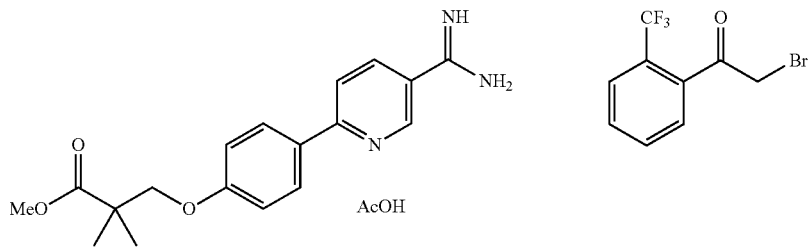
1-12 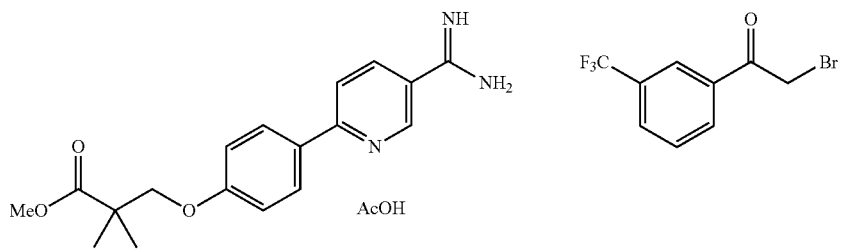

TABLE 1-continued
1-13 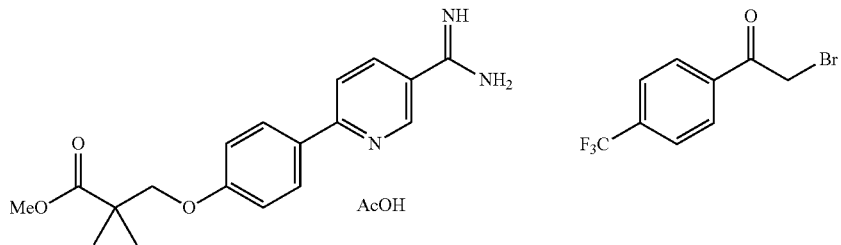
1-14 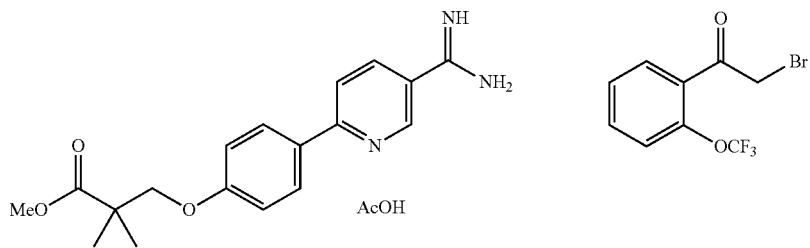
1-15 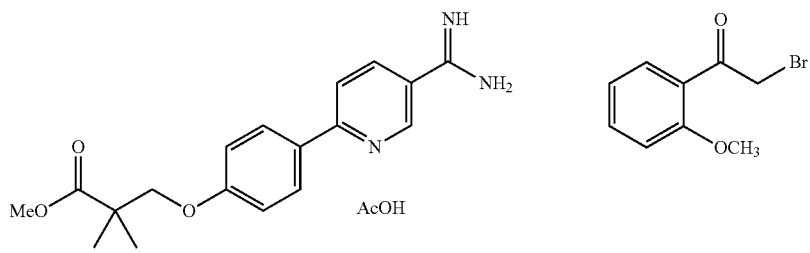
1-16 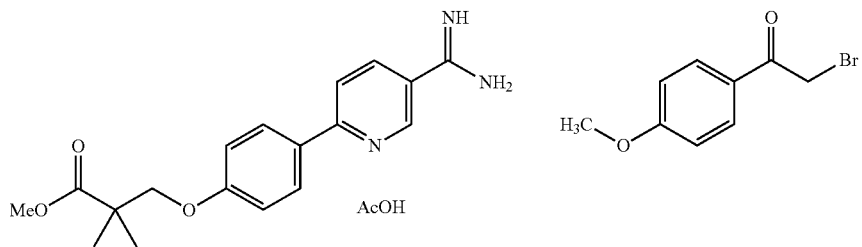
1-17 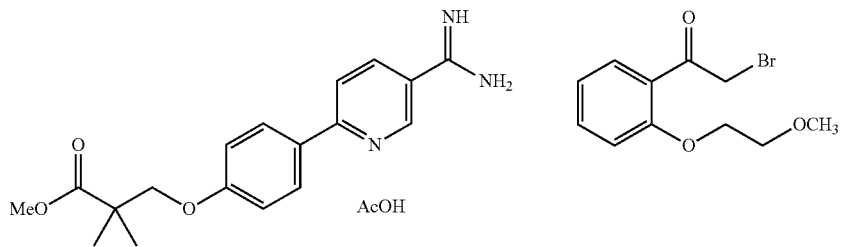
1-18 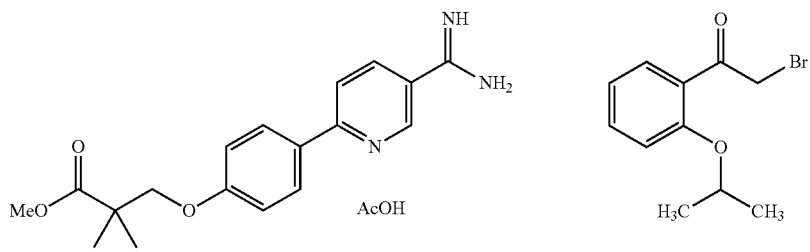

TABLE 1-continued
| 1-19 | 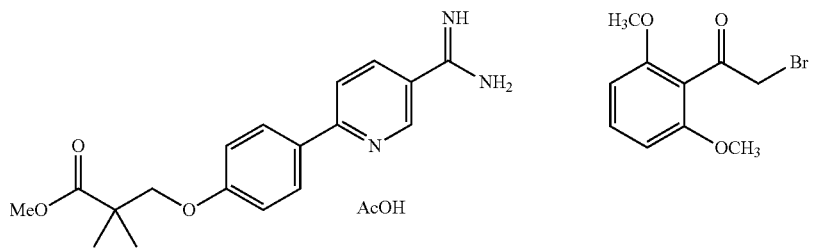 |
| 1-20 | 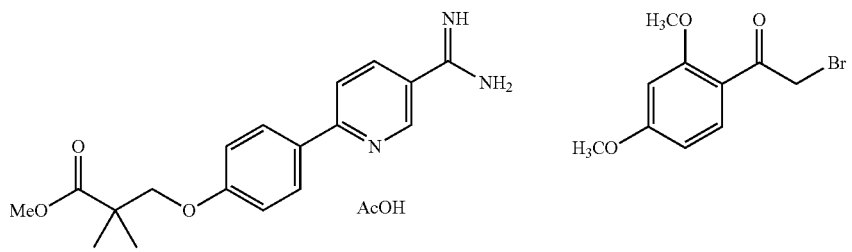 |
| 1-21 | 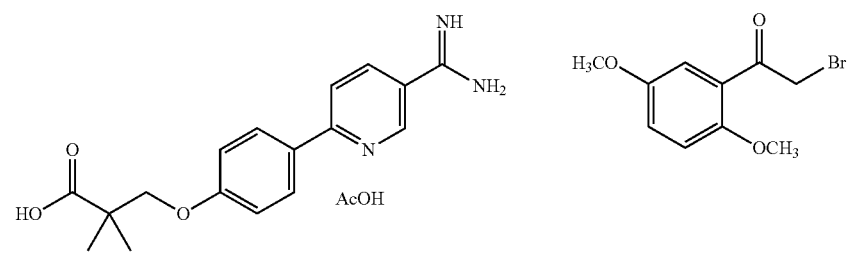 |
| 1-22 | 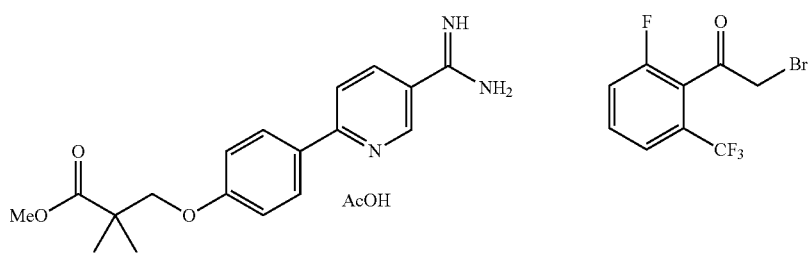 |
| 1-23 | 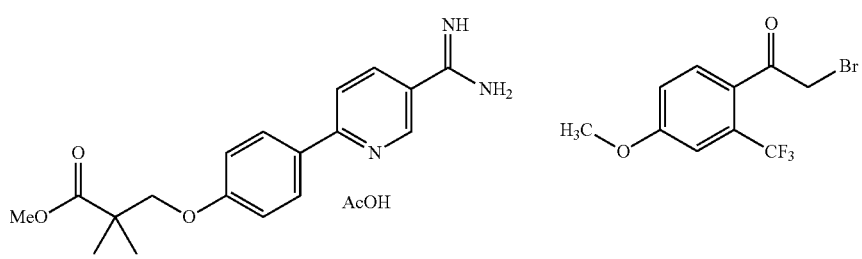 |
| 1-24 | 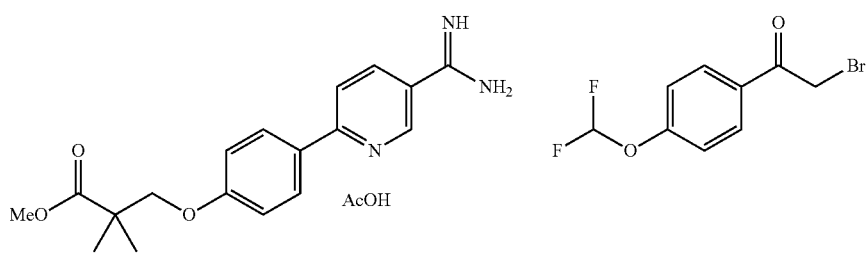 |

TABLE 1-continued
1-25 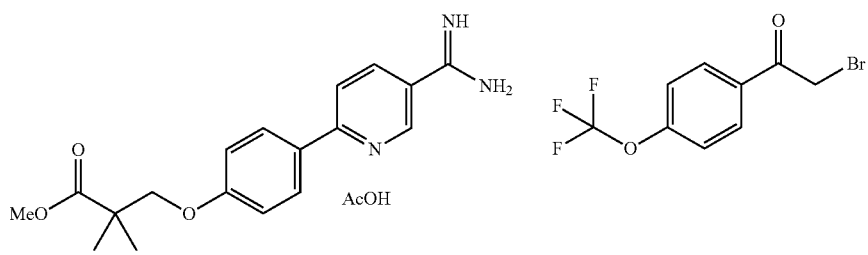
1-26 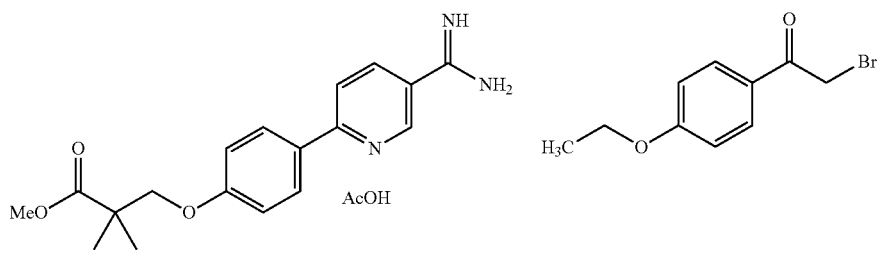
1-27 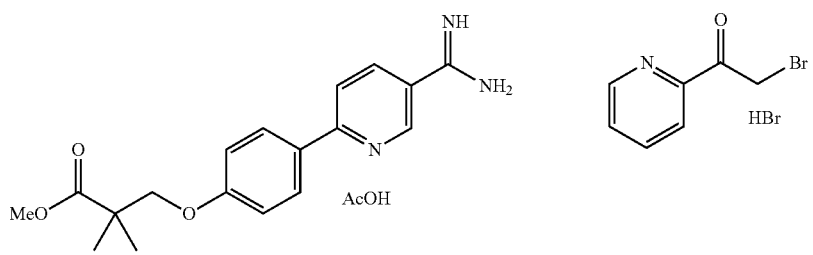
1-28 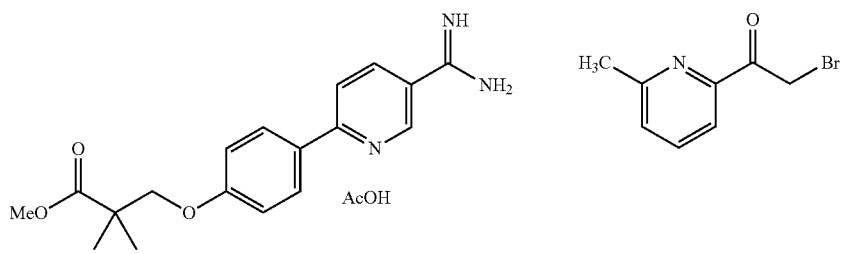
1-29 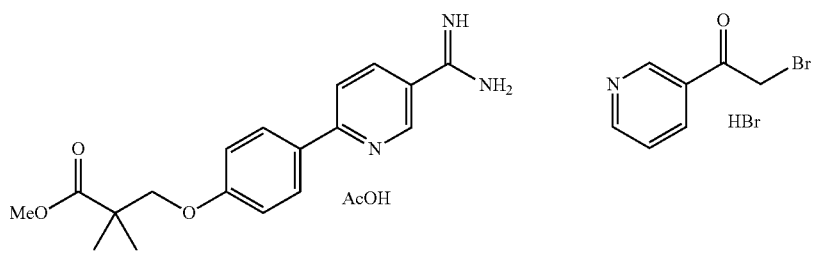
1-30 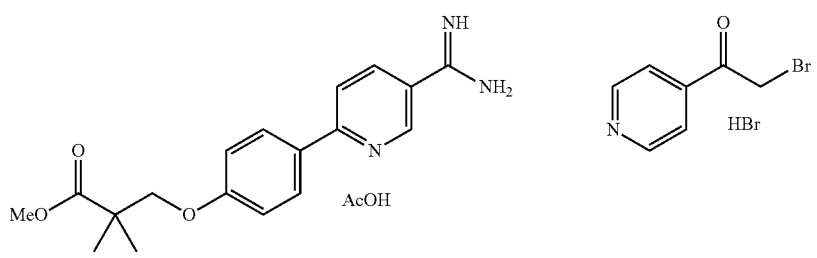

TABLE 1-continued
1-31 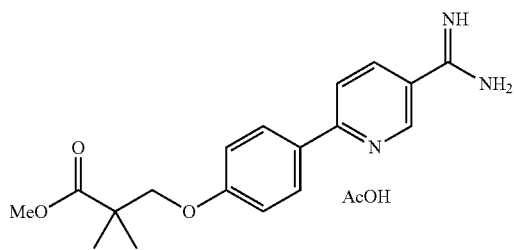 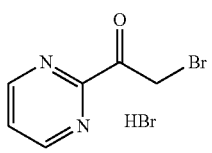
1-32 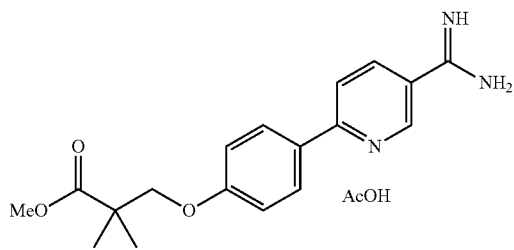 [SMILES: "AcOH" ; COC(=O)C(C)(C)COc1ccc(-c2ccc(C(=N)N)cn2)cc1] 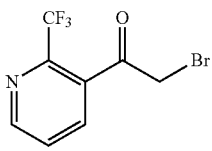
1-33 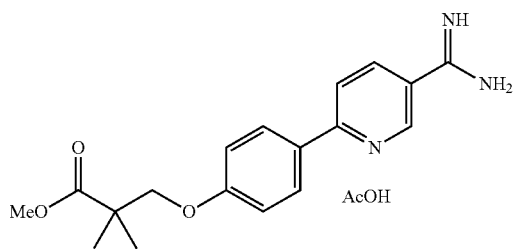 [SMILES: "AcOH" ; COC(=O)C(C)(C)COc1ccc(-c2ccc(C(=N)N)cn2)cc1] 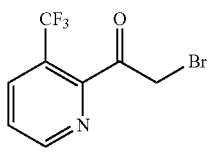 [SMILES: O=C(CBr)c1ncccc1C(F)(F)F]
1-34 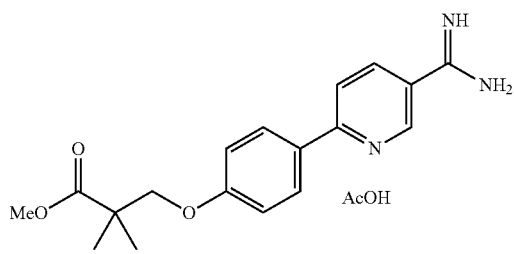 [SMILES: "AcOH" ; COC(=O)C(C)(C)COc1ccc(-c2ccc(C(=N)N)cn2)cc1] 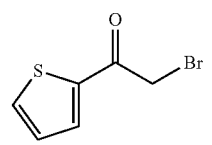
1-35 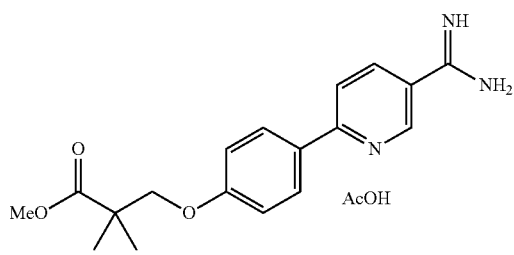 [SMILES: "AcOH" ; COC(=O)C(C)(C)COc1ccc(-c2ccc(C(=N)N)cn2)cc1] 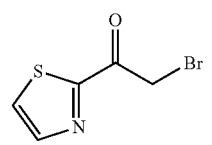
1-36 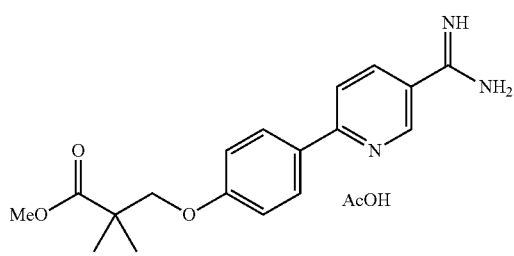 [SMILES: "AcOH" ; COC(=O)C(C)(C)COc1ccc(-c2ccc(C(=N)N)cn2)cc1] 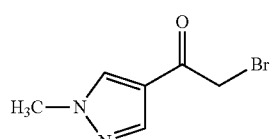

TABLE 1-continued
1-37 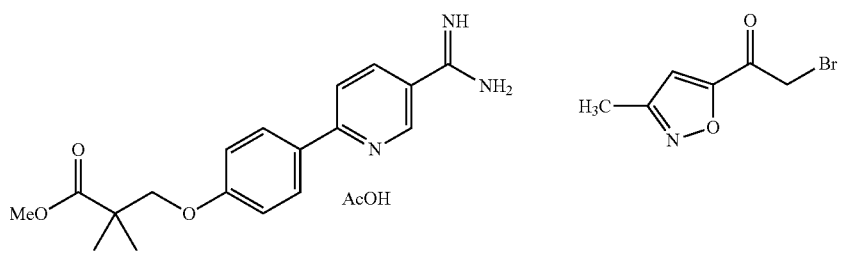
1-38 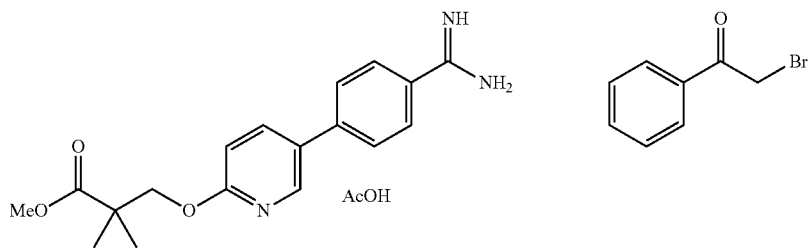
1-39 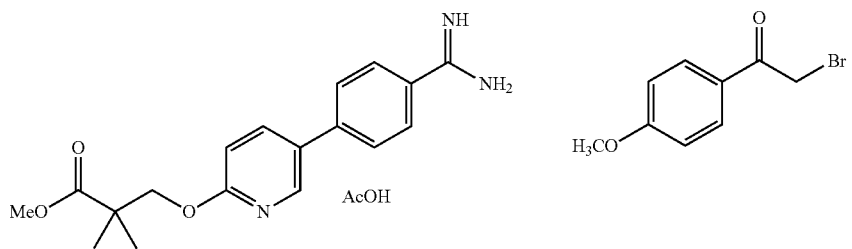
1-40 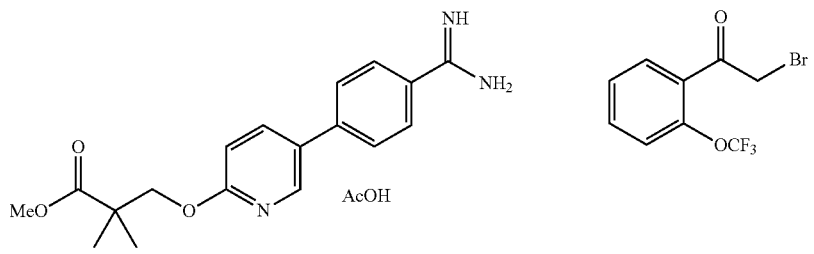
1-41 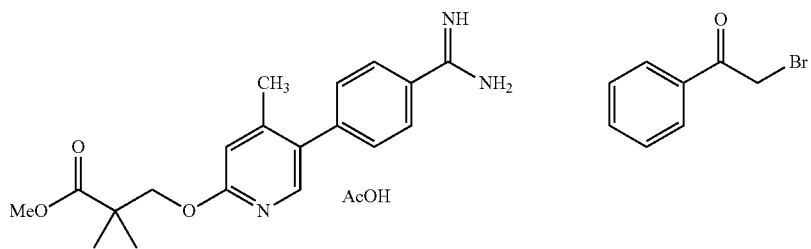
1-42 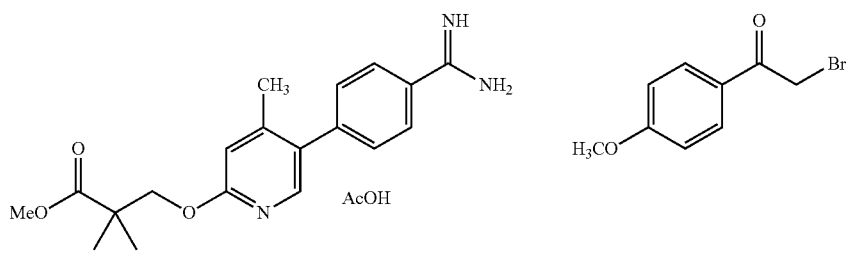

TABLE 1-continued
| | | |
|---|---|---|
| 1-43 | 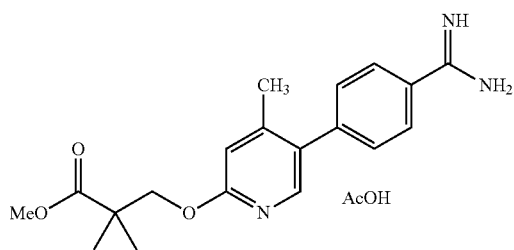 [SMILES: "AcOH" ; COC(=O)C(C)(C)COc1cc(C)c(-c2ccc(C(=N)N)cc2)cn1] | 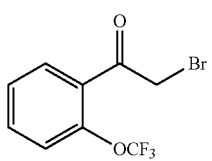 |
| 1-44 | 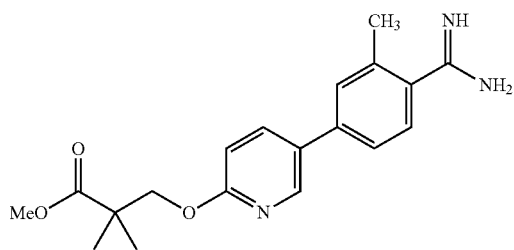 [SMILES: COC(=O)C(C)(C)COc1ccc(-c2ccc(C(=N)N)c(C)c2)cn1] | 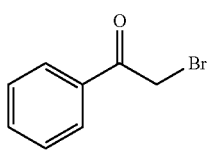 |
| 1-45 | 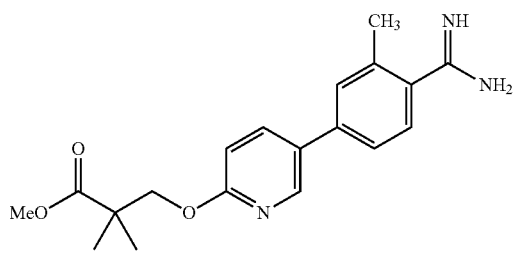 [SMILES: COC(=O)C(C)(C)COc1ccc(-c2ccc(C(=N)N)c(C)c2)cn1] | 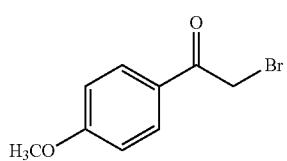 [SMILES: COc1ccc(C(=O)CBr)cc1] |
| 1-46 | 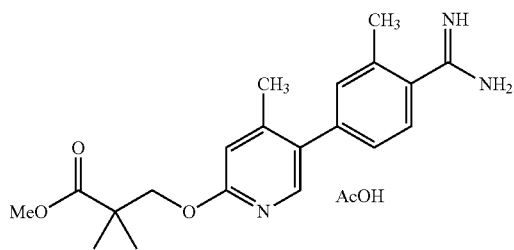 [SMILES: "AcOH" ; COC(=O)C(C)(C)COc1cc(C)c(-c2ccc(C(=N)N)c(C)c2)cn1] | 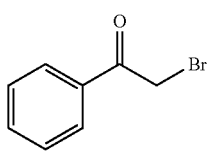 |
| 1-47 | 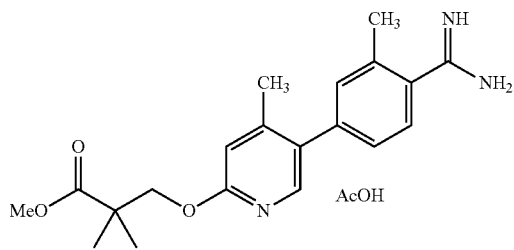 [SMILES: "AcOH" ; COC(=O)C(C)(C)COc1cc(C)c(-c2ccc(C(=N)N)c(C)c2)cn1] | 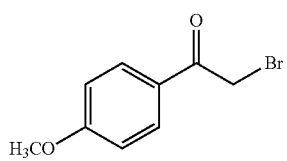 [SMILES: COc1ccc(C(=O)CBr)cc1] |
| 1-48 | 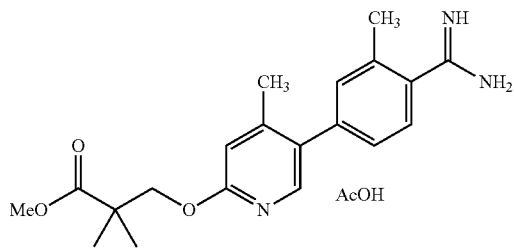 [SMILES: "AcOH" ; COC(=O)C(C)(C)COc1cc(C)c(-c2ccc(C(=N)N)c(C)c2)cn1] | 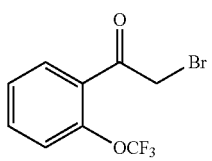 |

TABLE 1-continued
| 1-49 | 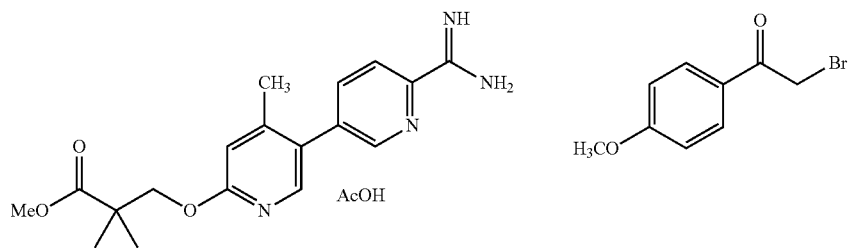 | | |
| 1-50 | 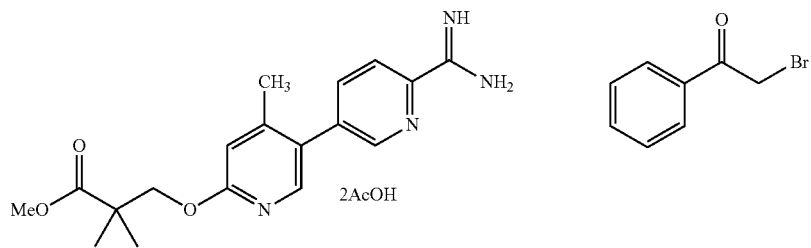 | | |
| 1-51 | 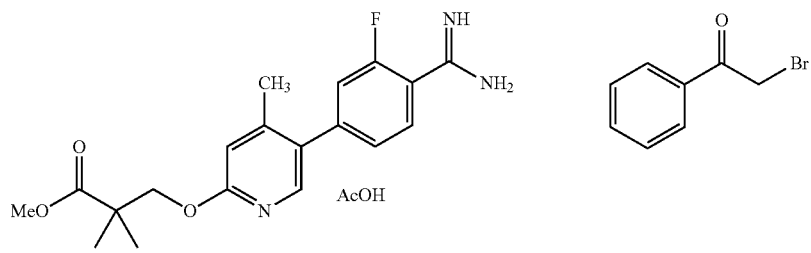 | | |
| 1-52 | 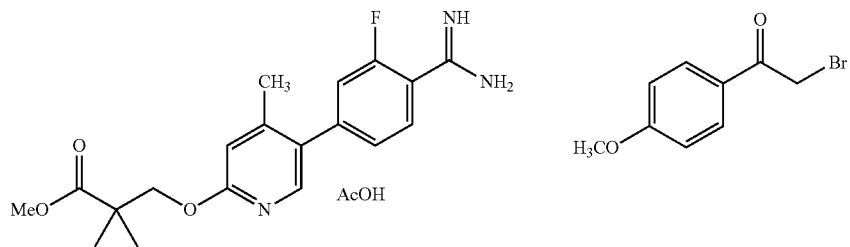 | | |
| 1-53 | 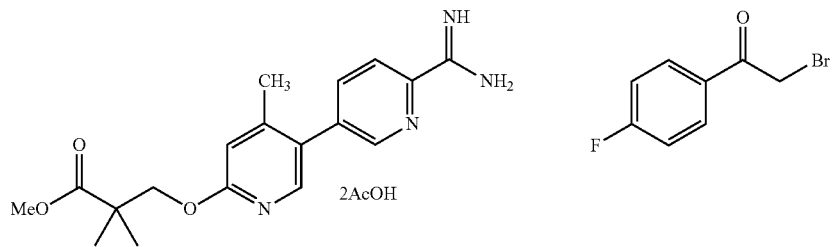 | | |
| 1-54 | 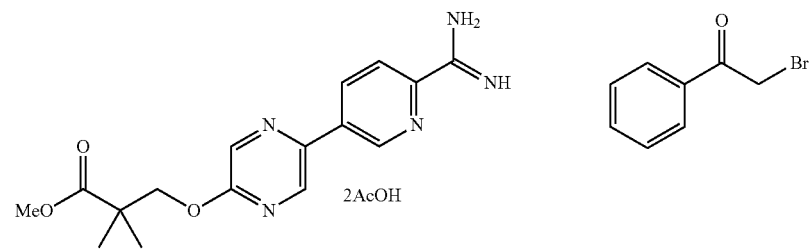 | | |

TABLE 1-continued
| | | |
|---|---|---|
| 1-55 | 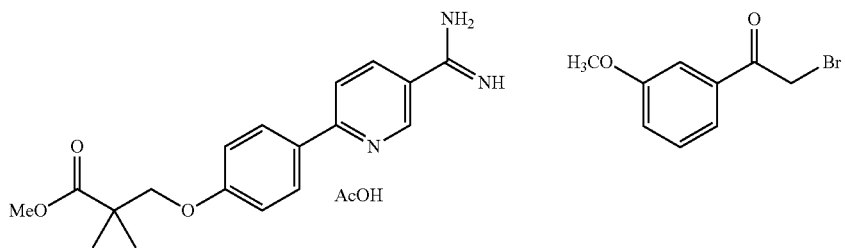 | |
| 1-56 | 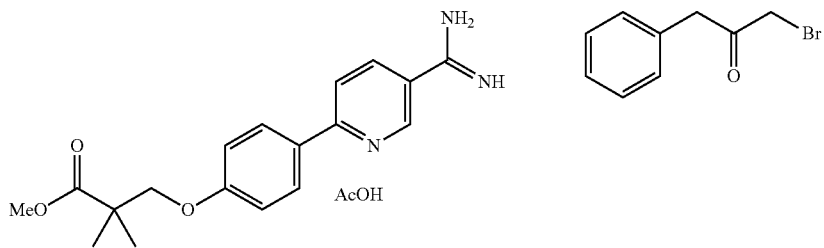 | |
| 1-57 | 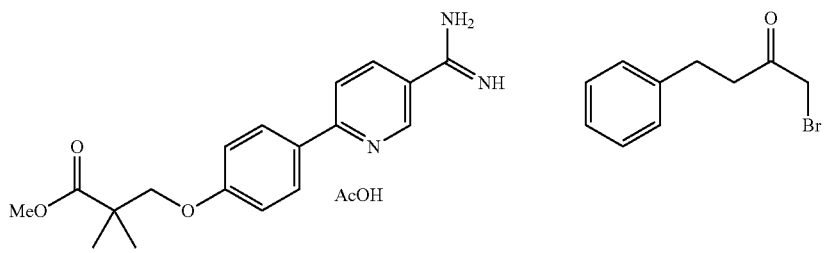 | |
| 1-58 | 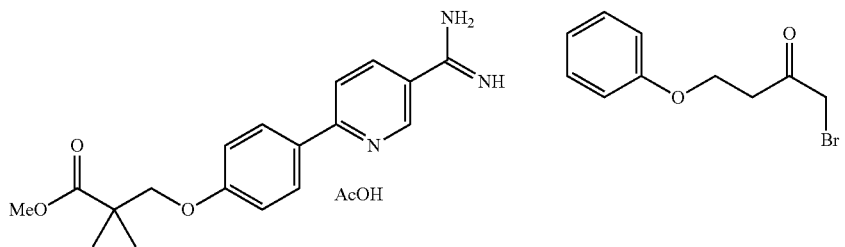 | |
| 1-59 | 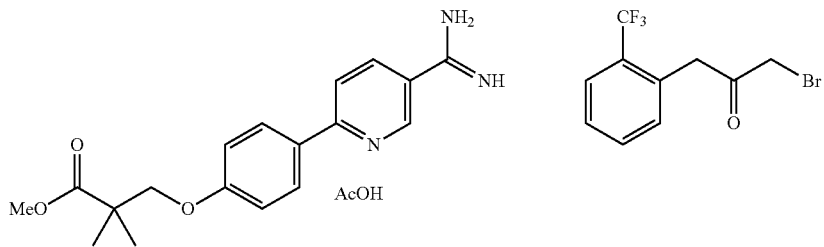 | |
| 1-60 | 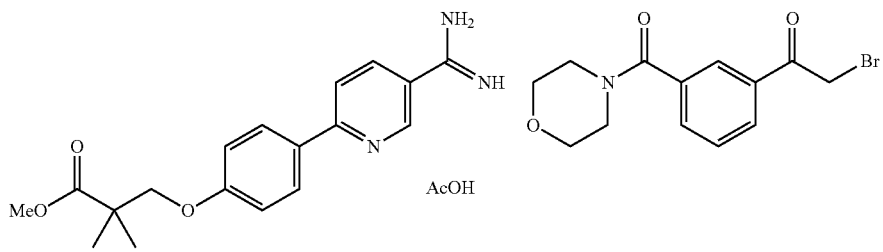 | |

TABLE 1-continued
| | | |
|---|---|---|
| 1-61 |  AcOH | 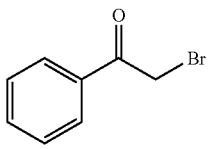 |
| 1-62 | 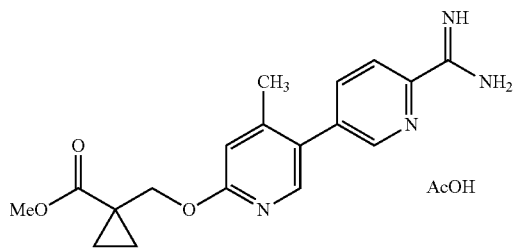 [SMILES: "AcOH" ; COC(=O)C1(COc2cc(C)c(-c3ccc(C(=N)N)nc3)cn2)CC1] AcOH | 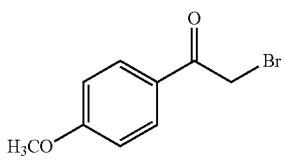 [SMILES: COc1ccc(C(=O)CBr)cc1] |
| 1-63 | 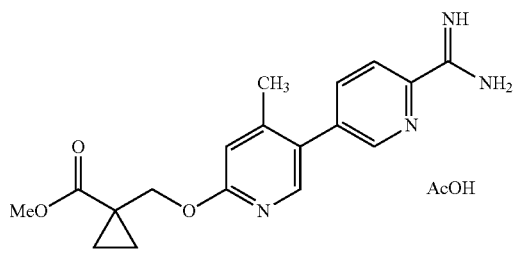 [SMILES: "AcOH" ; COC(=O)C1(COc2cc(C)c(-c3ccc(C(=N)N)nc3)cn2)CC1] AcOH | 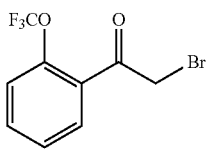 [SMILES: O=C(CBr)c1ccccc1OC(F)(F)F] |
| 1-64 | 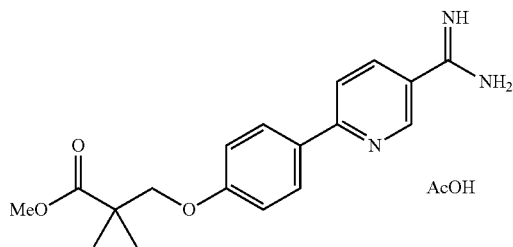 [SMILES: "AcOH" ; COC(=O)C(C)(C)COc1ccc(-c2ccc(C(=N)N)cn2)cc1] AcOH | 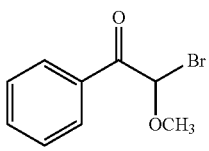 [SMILES: COC(Br)C(=O)c1ccccc1] |
| 1-65 | 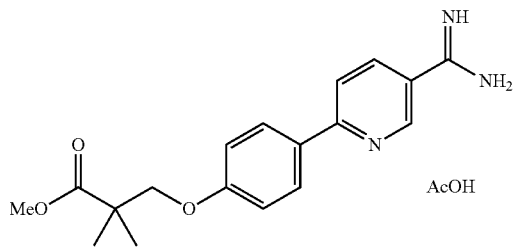 [SMILES: "AcOH" ; COC(=O)C(C)(C)COc1ccc(-c2ccc(C(=N)N)cn2)cc1] AcOH | 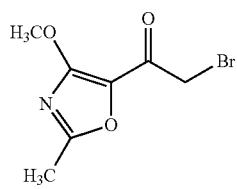 |
| 1-66 |  AcOH | 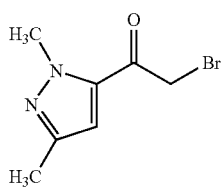 |

TABLE 1-continued
| 1-67 | 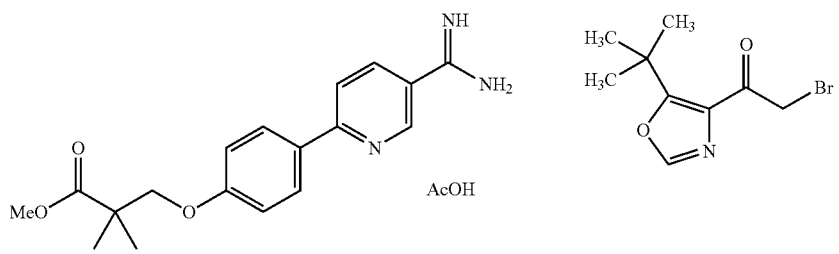 |
| 1-68 | 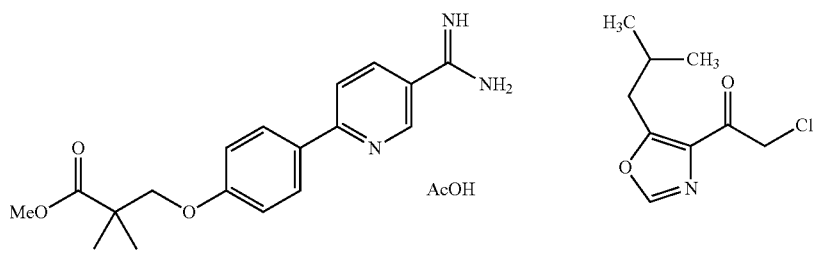 |
| 1-69 | 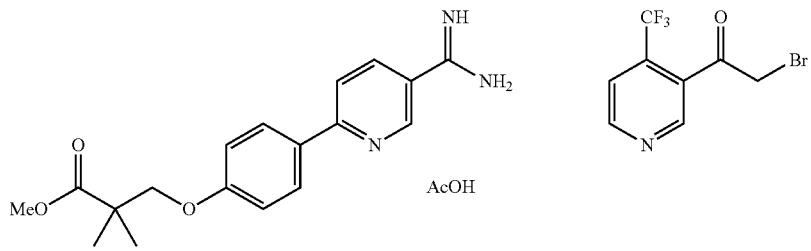 |
| Example | Product | MS (m/z) |
| --- | --- | --- |
| 1-2 | 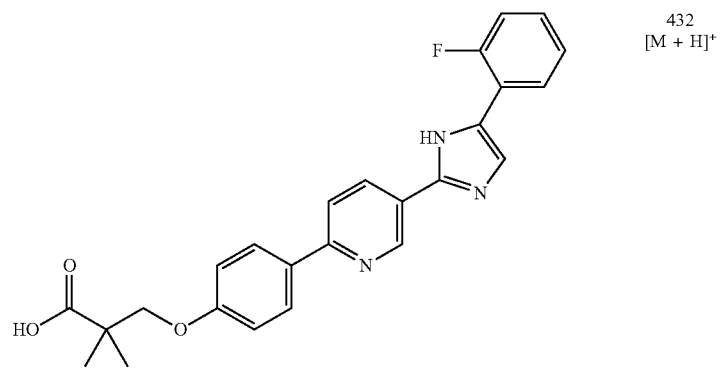 | 432 [M + H]⁺ |
| 1-3 | 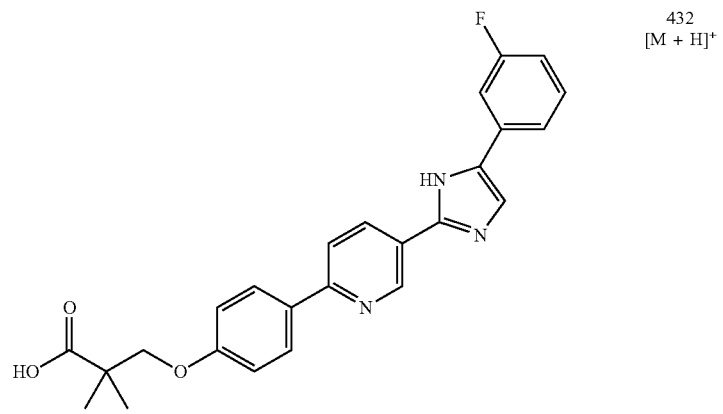 | 432 [M + H]⁺ |

TABLE 1-continued
| | | |
|---|---|---|
| 1-4 | 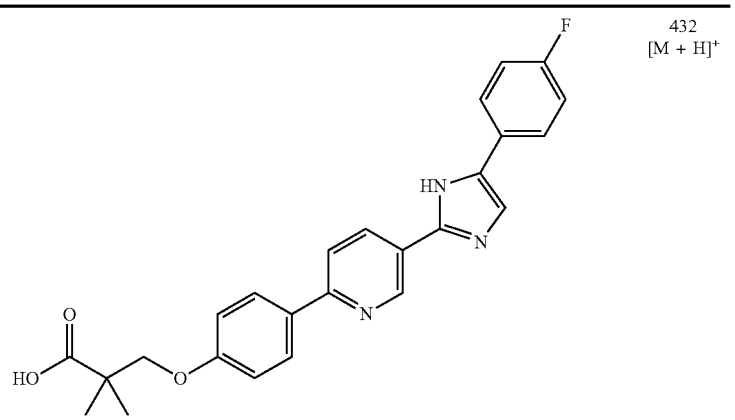 | 432 [M + H]+ |
| 1-5 | 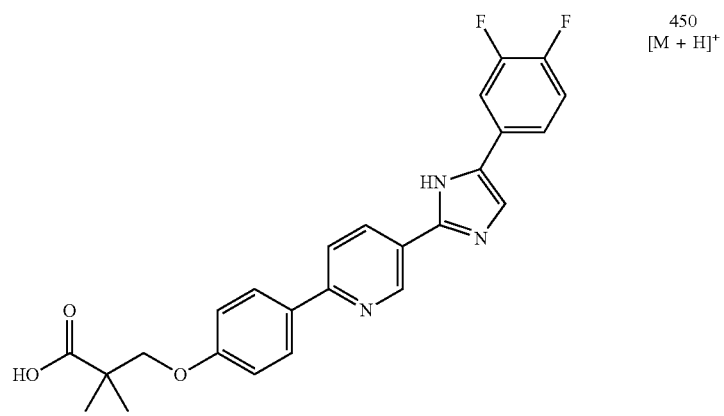 | 450 [M + H]+ |
| 1-6 | 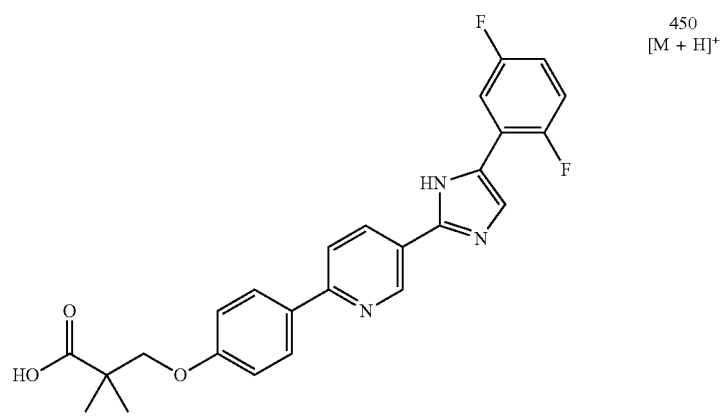 | 450 [M + H]+ |
| 1-7 | 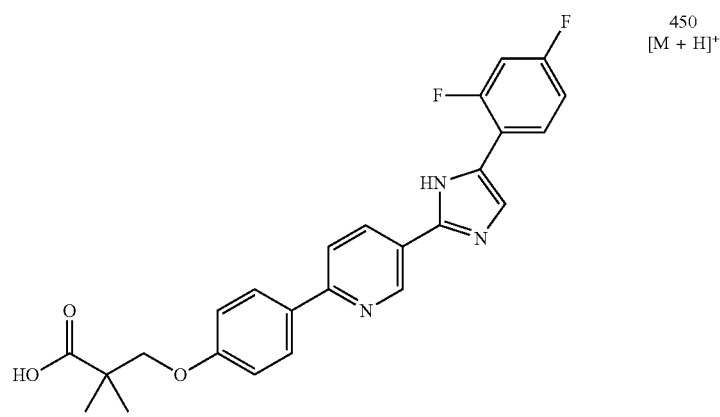 | 450 [M + H]+ |

TABLE 1-continued
| 1-8 | 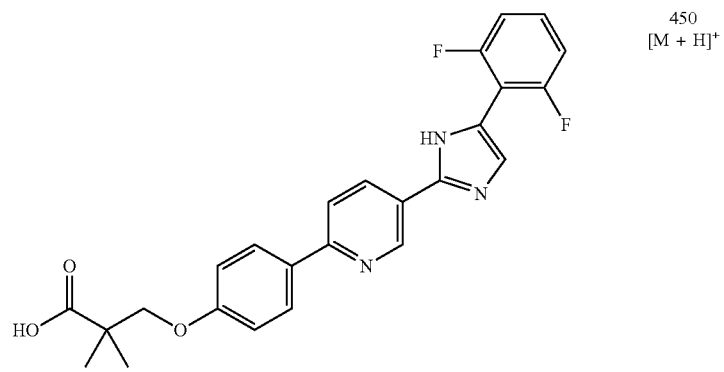 | 450 [M + H]+ |
| --- | --- | --- |
| 1-9 | 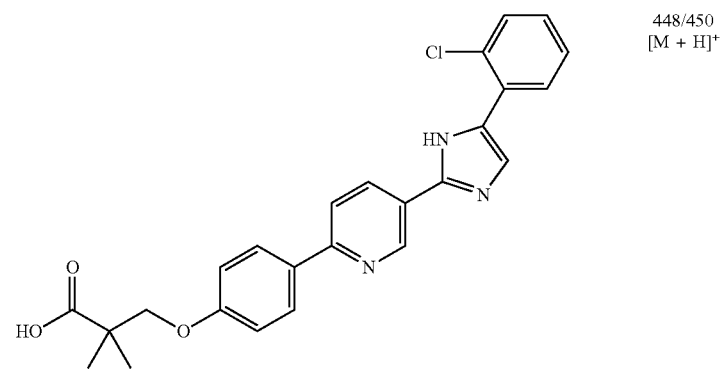 | 448/450 [M + H]+ |
| 1-10 | 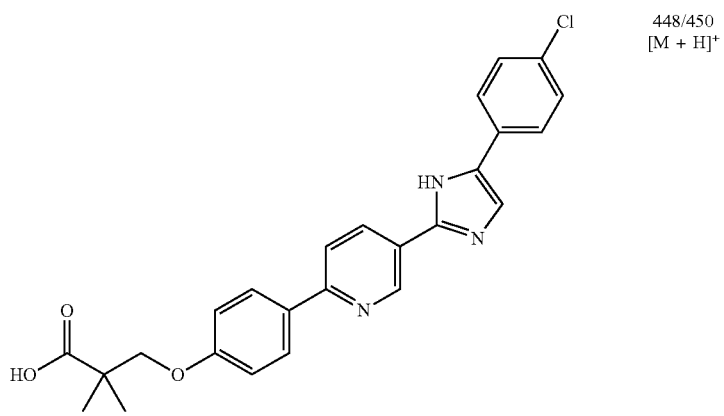 | 448/450 [M + H]+ |
| 1-11 | 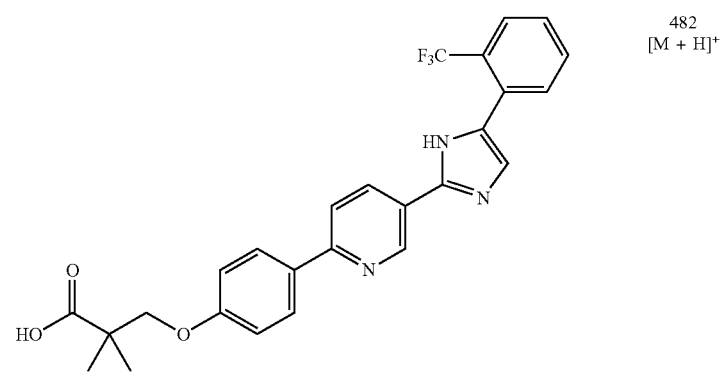 | 482 [M + H]+ |

TABLE 1-continued
| 1-12 | 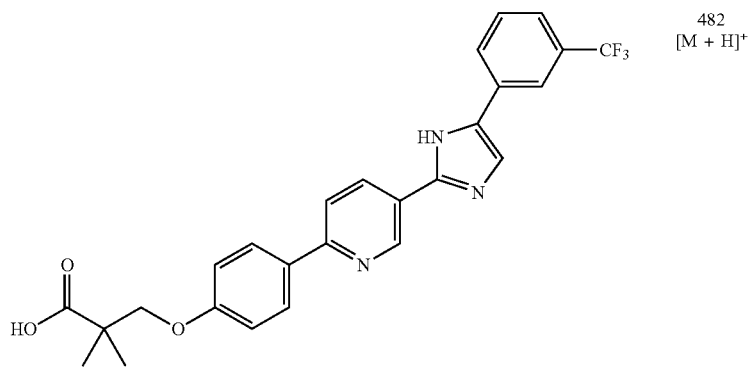 | 482 [M + H]+ |
| 1-13 | 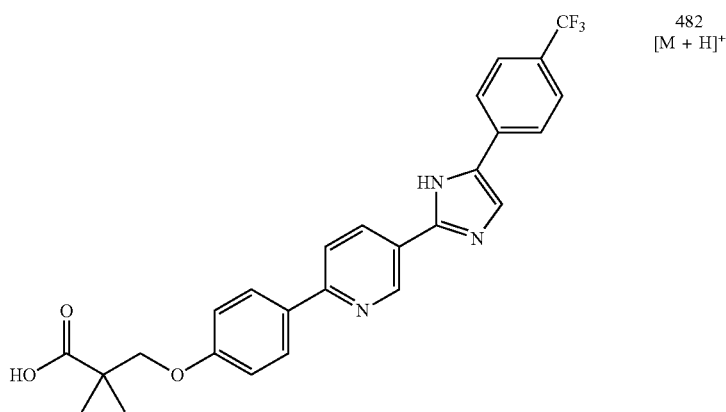 | 482 [M + H]+ |
| 1-14 | 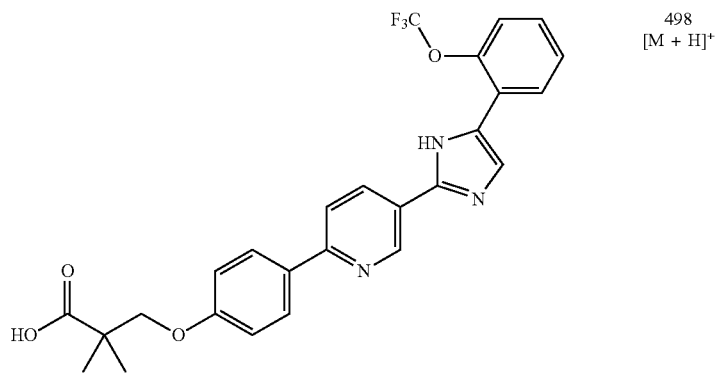 | 498 [M + H]+ |
| 1-15 | 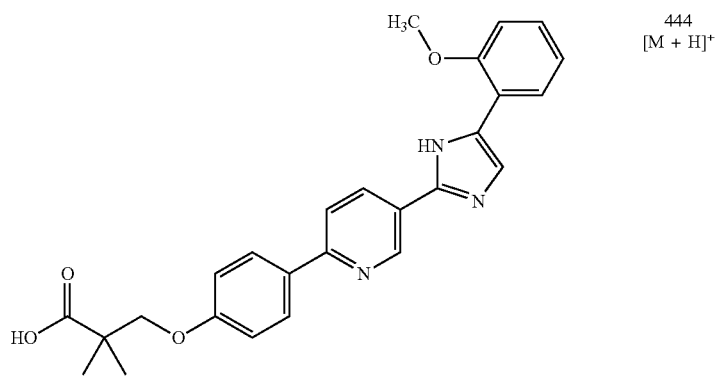 | 444 [M + H]+ |

TABLE 1-continued
| | | |
|---|---|---|
| 1-16 | 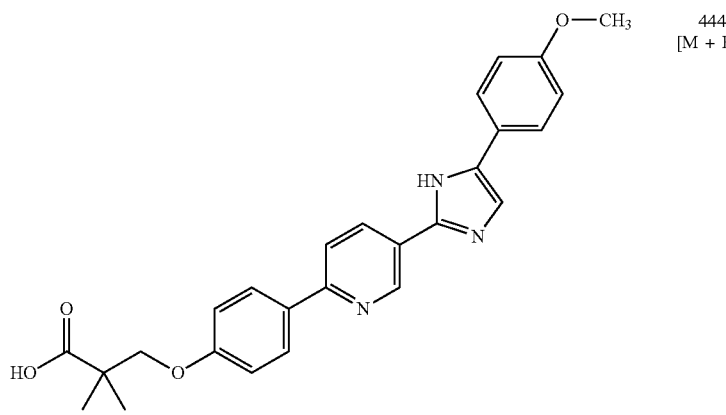 | 444 [M + H]+ |
| 1-17 | 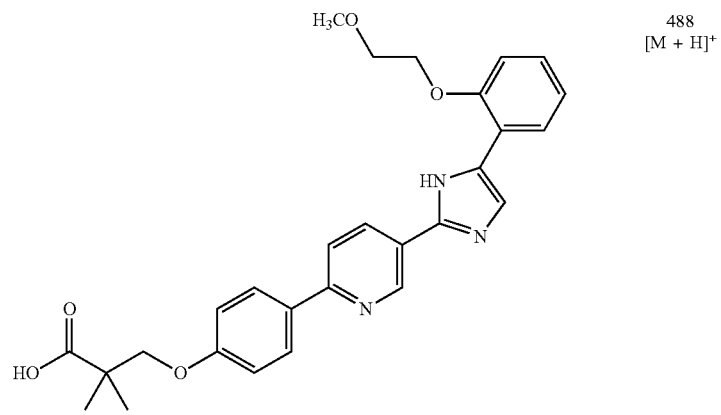 | 488 [M + H]+ |
| 1-18 | 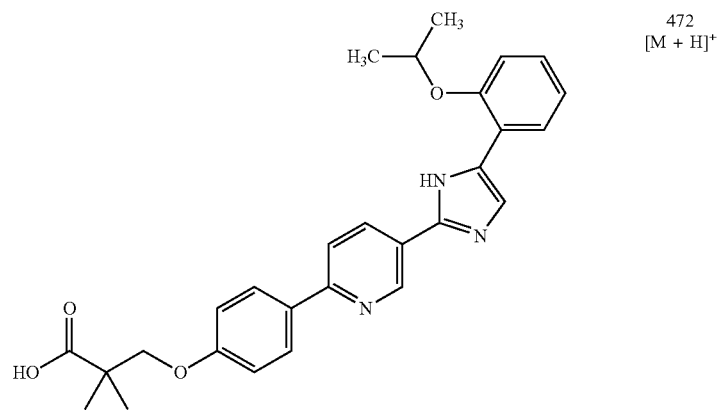 | 472 [M + H]+ |
| 1-19 | 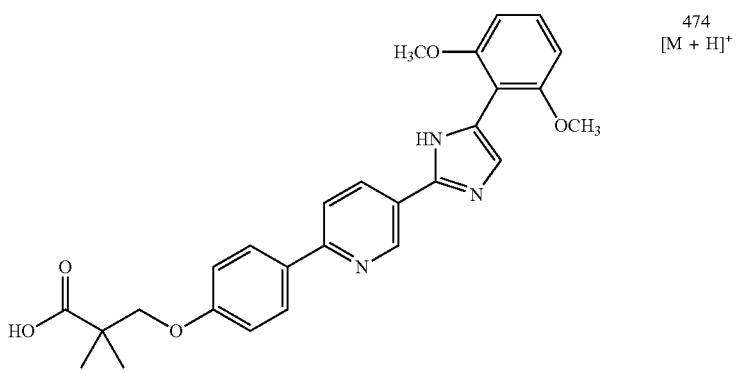 | 474 [M + H]+ |

TABLE 1-continued
| 1-20 | 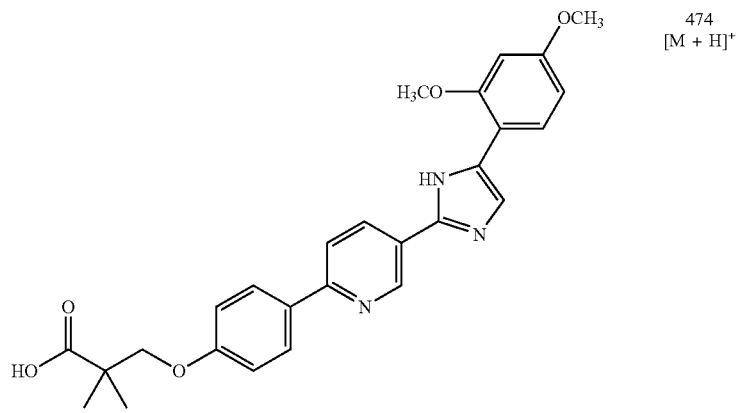 | 474 [M + H]⁺ |
| 1-21 | 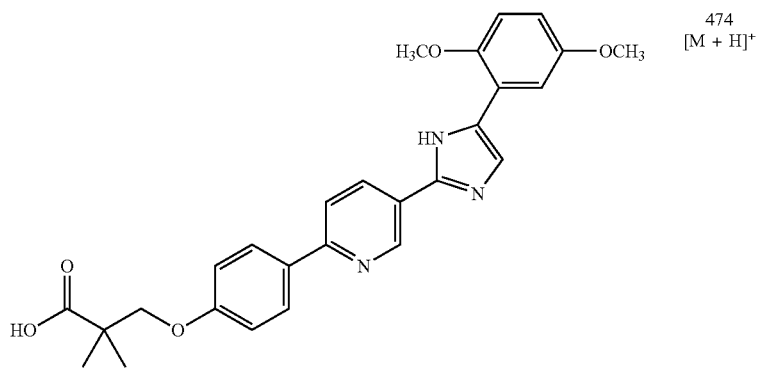 | 474 [M + H]⁺ |
| 1-22 | 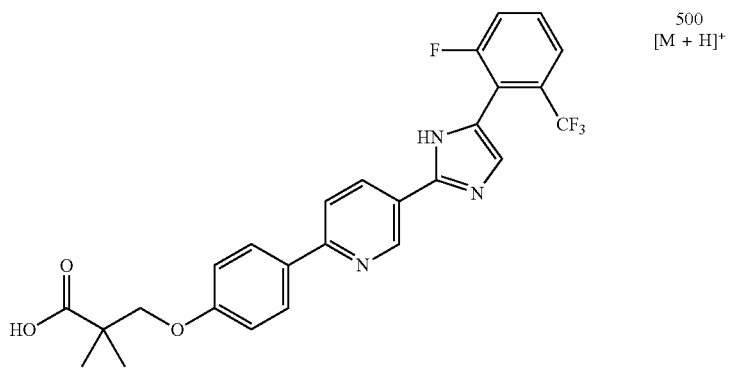 | 500 [M + H]⁺ |
| 1-23 | 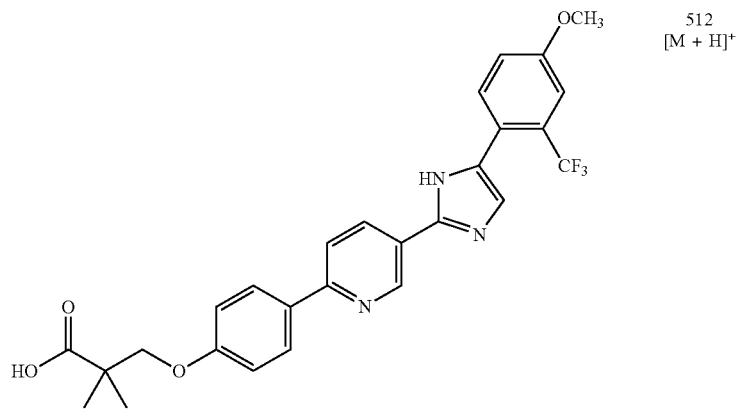 | 512 [M + H]⁺ |

TABLE 1-continued
| 1-24 | 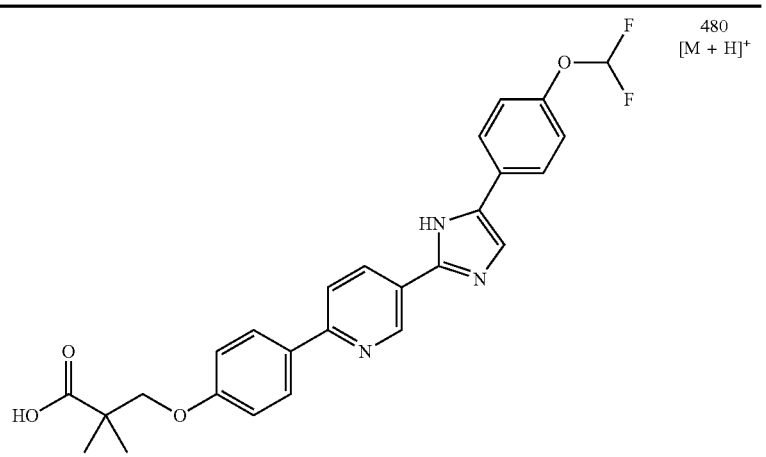 | 480 [M + H]+ |
| 1-25 | 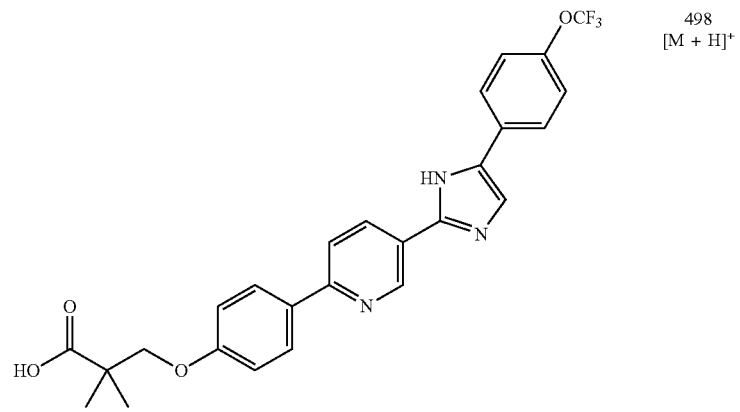 | 498 [M + H]+ |
| 1-26 | 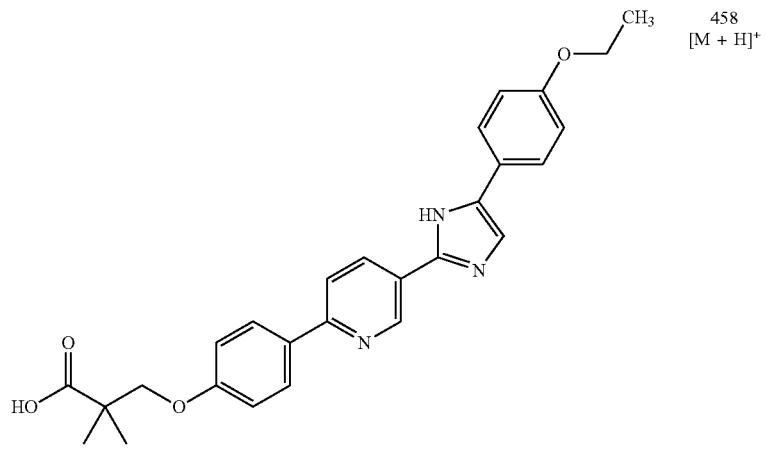 | 458 [M + H]+ |
| 1-27 | 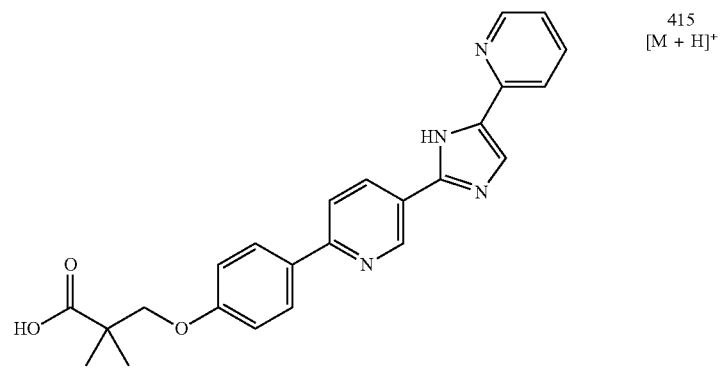 | 415 [M + H]+ |

| | | |
|---|---|---|
| 1-28 | 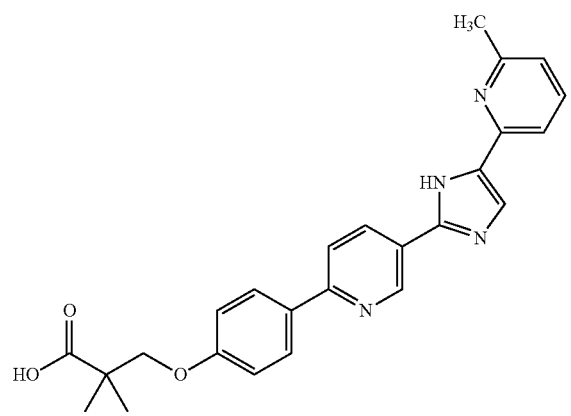 [SMILES: Cc1cccc(-c2cnc(-c3ccc(-c4ccc(OCC(C)(C)C(=O)O)cc4)nc3)[nH]2)n1] | 429 [M + H]+ |
| 1-29 | 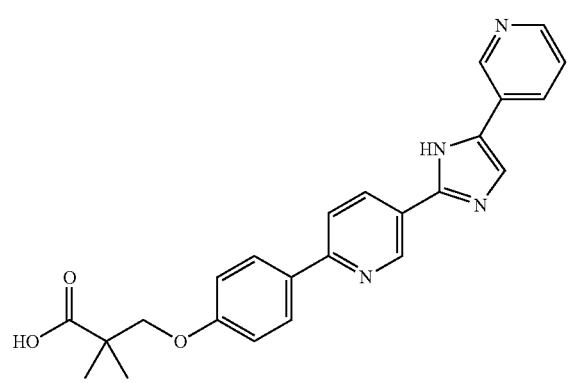 [SMILES: CC(C)(COc1ccc(-c2ccc(-c3ncc(-c4cccnc4)[nH]3)cn2)cc1)C(=O)O] | 415 [M + H]+ |
| 1-30 | 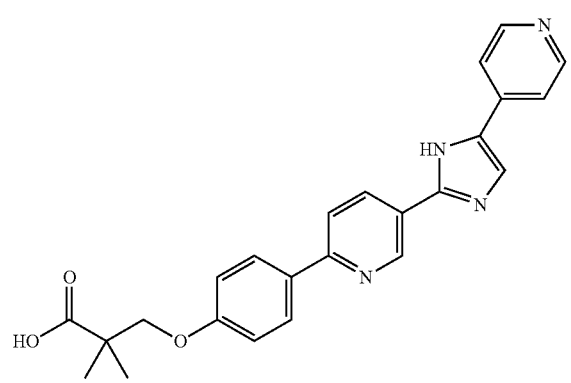 [SMILES: CC(C)(COc1ccc(-c2ccc(-c3ncc(-c4ccncc4)[nH]3)cn2)cc1)C(=O)O] | 415 [M + H]+ |
| 1-31 | 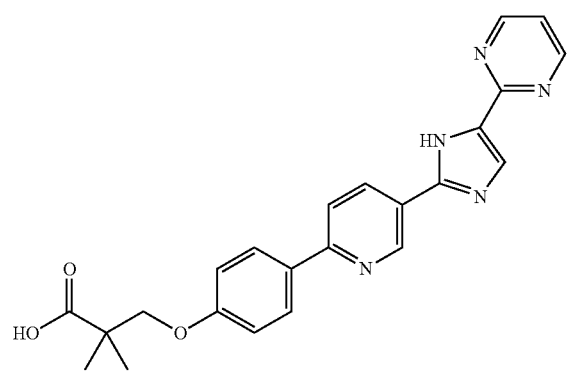 [SMILES: CC(C)(COc1ccc(-c2ccc(-c3ncc(-c4ncccn4)[nH]3)cn2)cc1)C(=O)O] | 416 [M + H]+ |

TABLE 1-continued
| 1-32 | 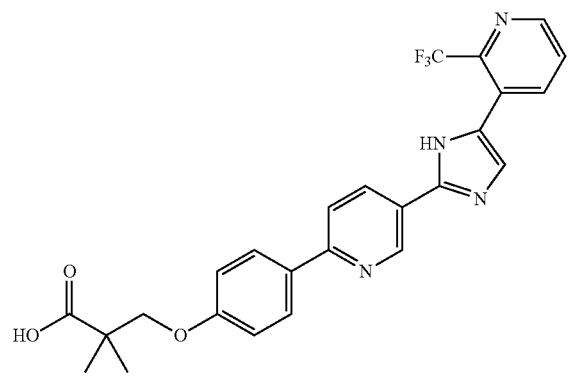 [SMILES: CC(C)(COc1ccc(-c2ccc(-c3ncc(-c4cccnc4C(F)(F)F)[nH]3)cn2)cc1)C(=O)O] | 483 [M + H]+ |
| 1-33 | 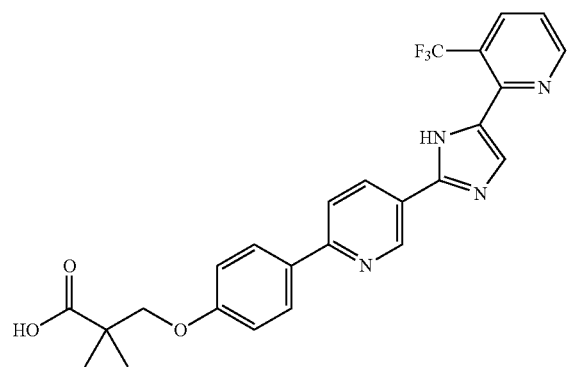 | 483 [M + H]+ |
| 1-34 | 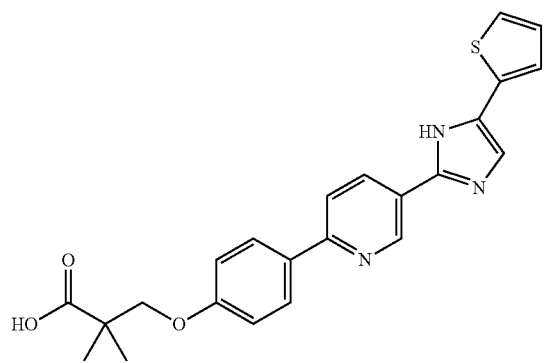 [SMILES: CC(C)(COc1ccc(-c2ccc(-c3ncc(-c4cccs4)[nH]3)cn2)cc1)C(=O)O] | 420 [M + H]+ |
| 1-35 | 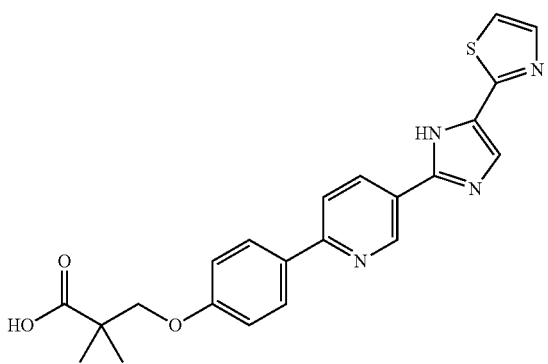 [SMILES: CC(C)(COc1ccc(-c2ccc(-c3ncc(-c4nccs4)[nH]3)cn2)cc1)C(=O)O] | 421 [M + H]+ |

TABLE 1-continued
| 1-36 | 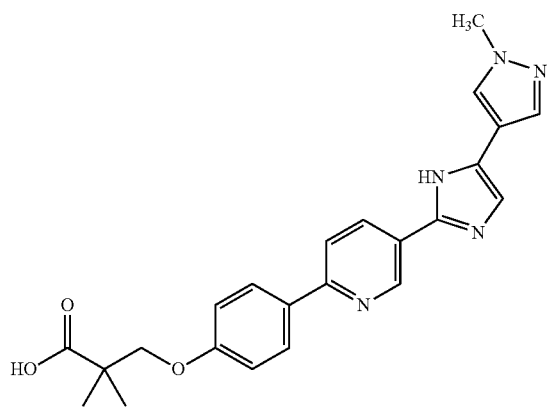 [SMILES: Cn1cc(-c2cnc(-c3ccc(-c4ccc(OCC(C)(C)C(=O)O)cc4)nc3)[nH]2)cn1] | 418 [M + H]+ |
| 1-37 | 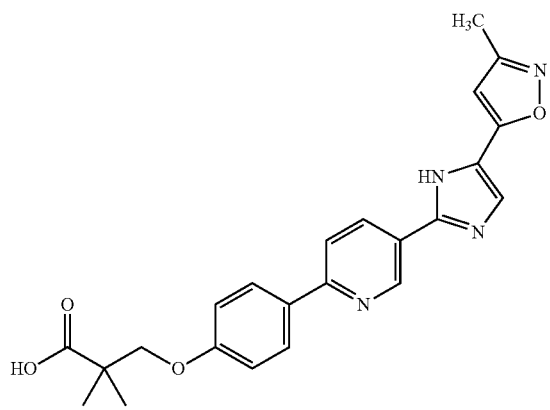 [SMILES: Cc1cc(-c2cnc(-c3ccc(-c4ccc(OCC(C)(C)C(=O)O)cc4)nc3)[nH]2)on1] | 419 [M + H]+ |
| 1-38 | 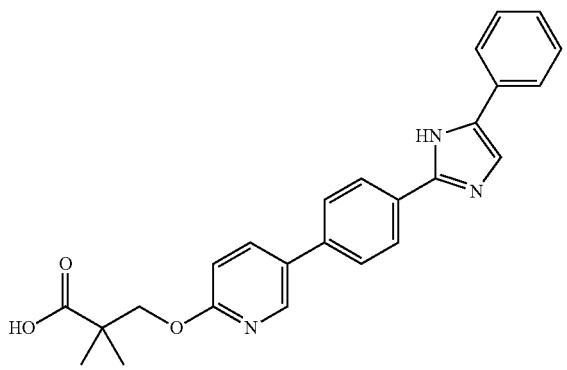 [SMILES: CC(C)(COc1ccc(-c2ccc(-c3ncc(-c4ccccc4)[nH]3)cc2)cn1)C(=O)O] | 414 [M + H]+ |
| 1-39 | 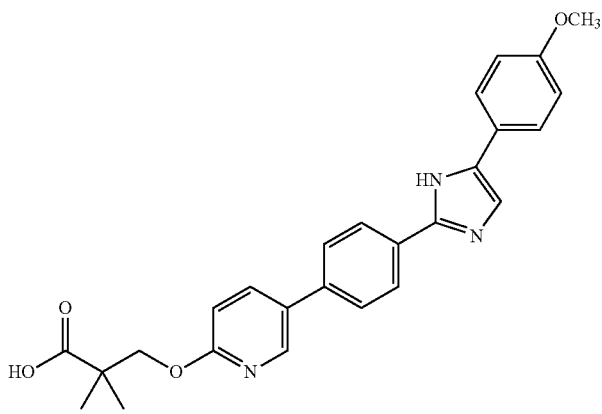 [SMILES: COc1ccc(-c2cnc(-c3ccc(-c4ccc(OCC(C)(C)C(=O)O)nc4)cc3)[nH]2)cc1] | 444 [M + H]+ |

TABLE 1-continued
| | | |
|---|---|---|
| 1-40 | 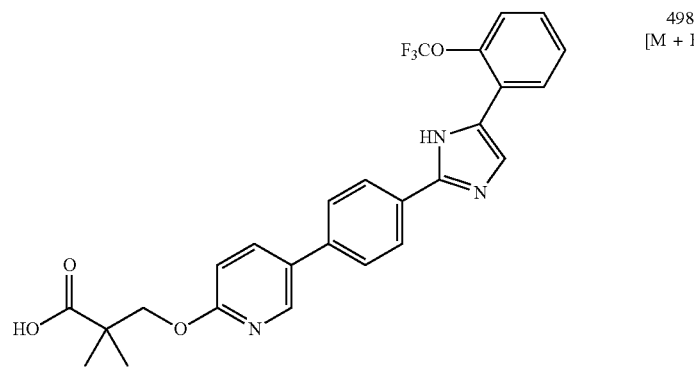 | 498 [M + H]+ |
| 1-41 | 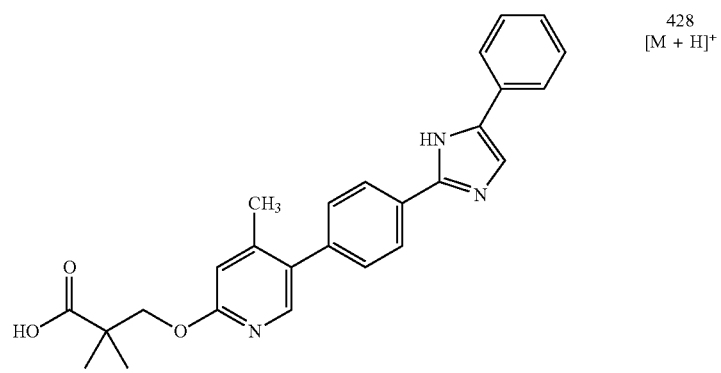 | 428 [M + H]+ |
| 1-42 | 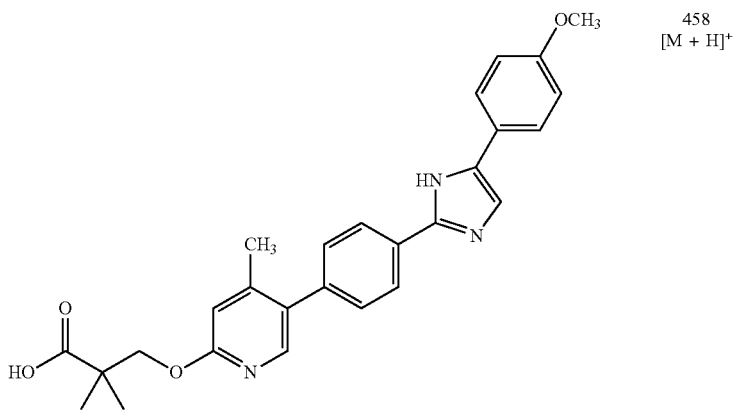 | 458 [M + H]+ |
| 1-43 | 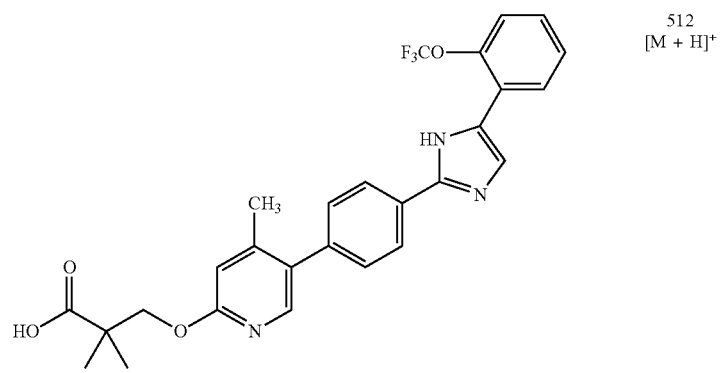 | 512 [M + H]+ |

TABLE 1-continued
| 1-44 | 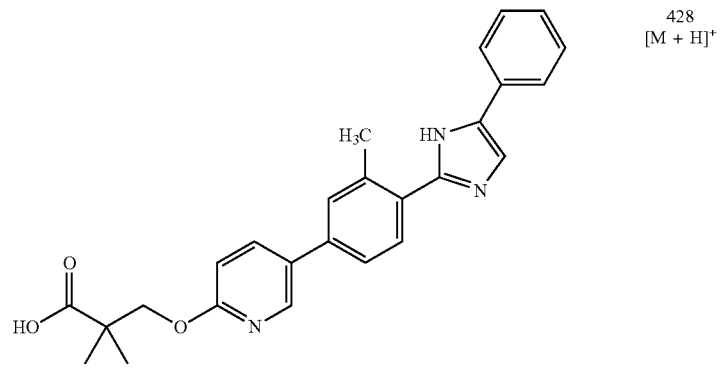 | 428 [M + H]+ |
| 1-45 | 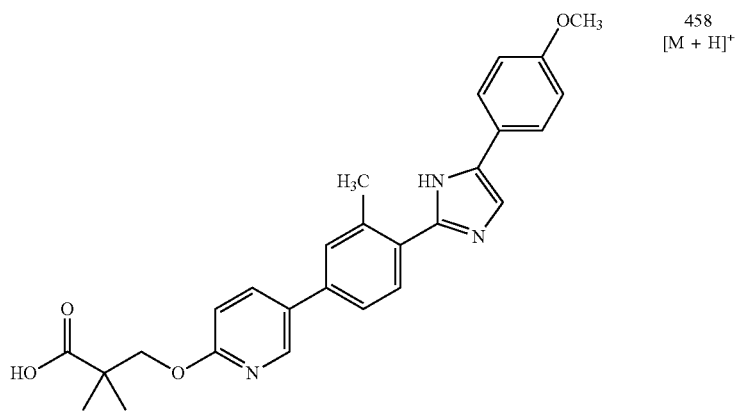 | 458 [M + H]+ |
| 1-46 | 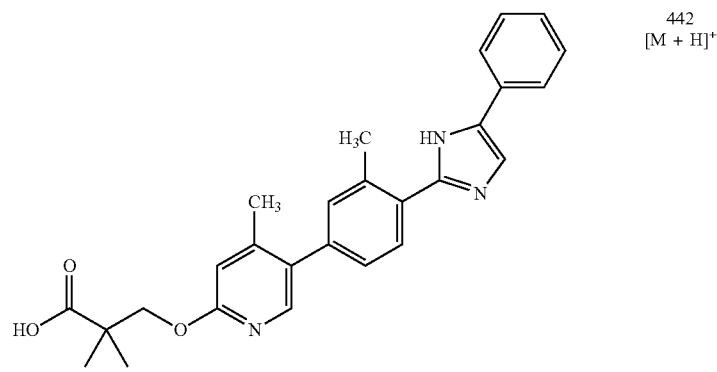 | 442 [M + H]+ |
| 1-47 | 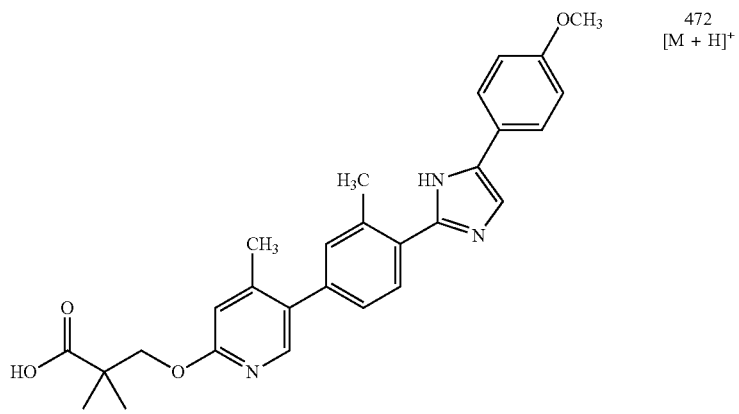 | 472 [M + H]+ |

TABLE 1-continued
| 1-48 | 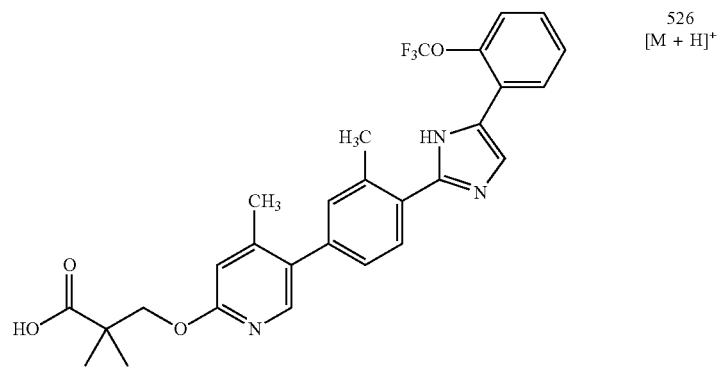 | 526 [M + H]+ |
| 1-49 | 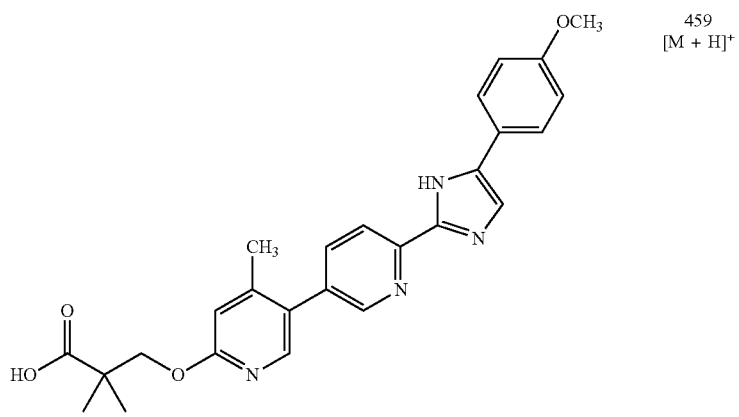 | 459 [M + H]+ |
| 1-50 | 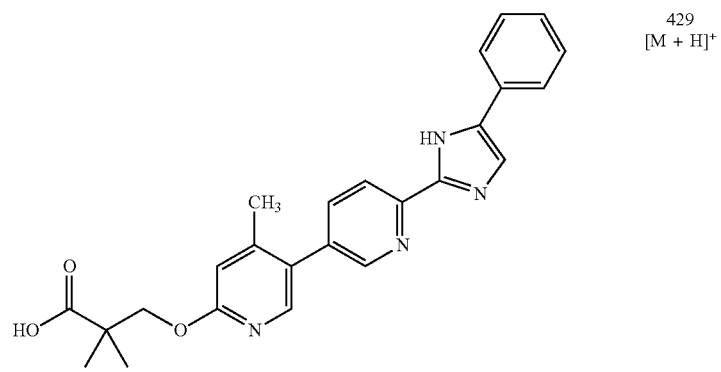 | 429 [M + H]+ |
| 1-51 | 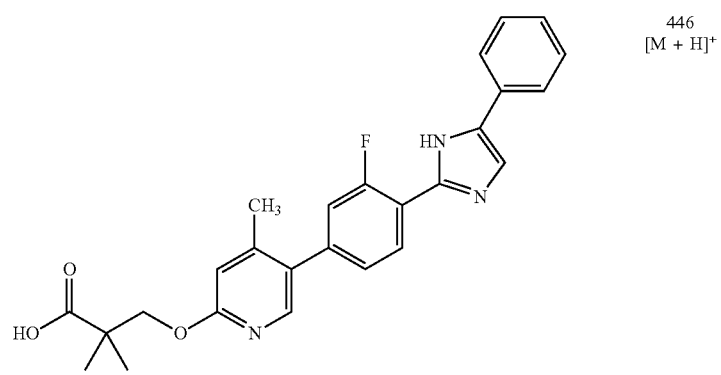 | 446 [M + H]+ |

TABLE 1-continued
| | | |
|---|---|---|
| 1-52 | 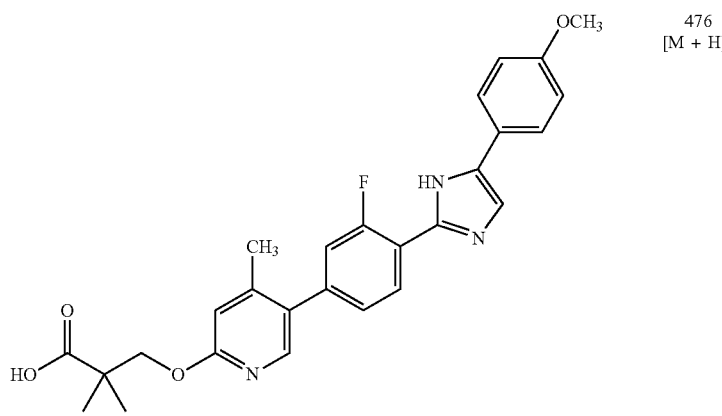 | 476 [M + H]+ |
| 1-53 | 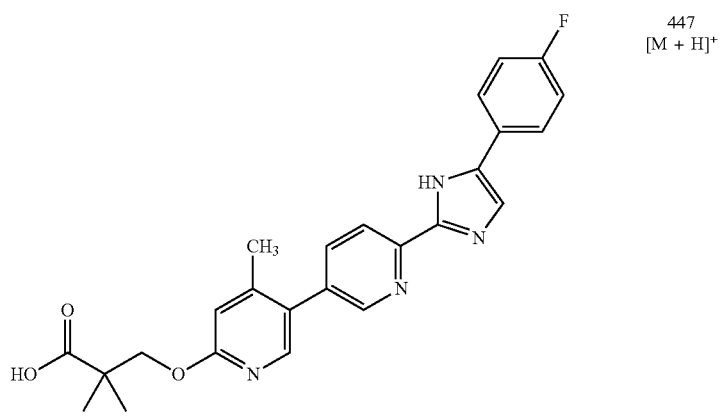 | 447 [M + H]+ |
| 1-54 | 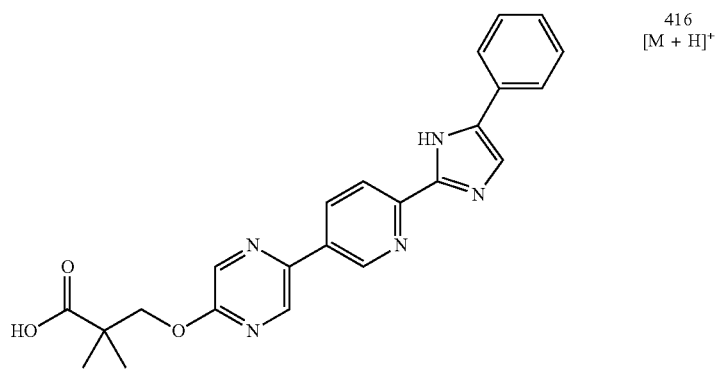 | 416 [M + H]+ |
| 1-55 | 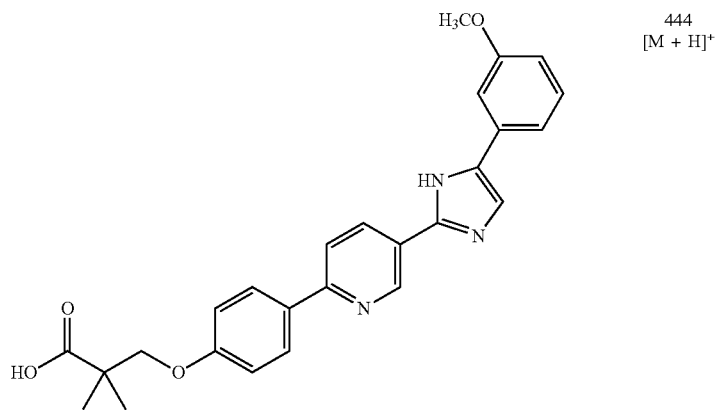 | 444 [M + H]+ |

TABLE 1-continued
1-56 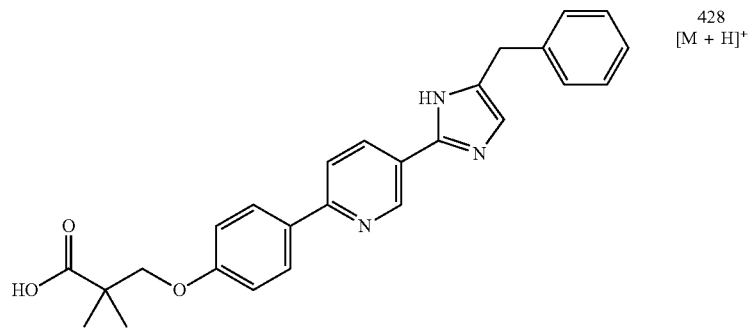 428 [M + H]+
1-57 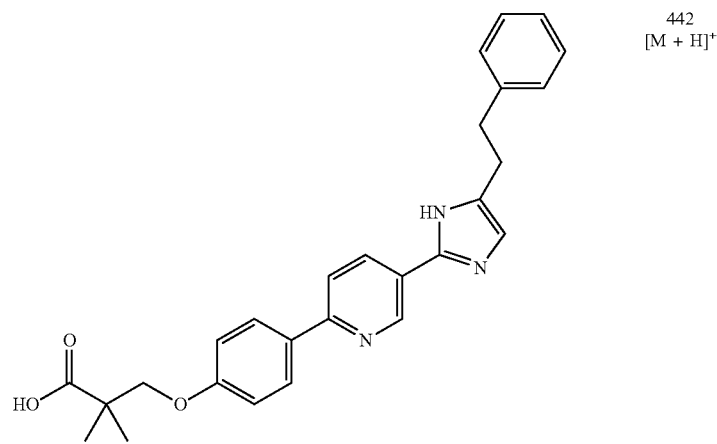 442 [M + H]+
1-58 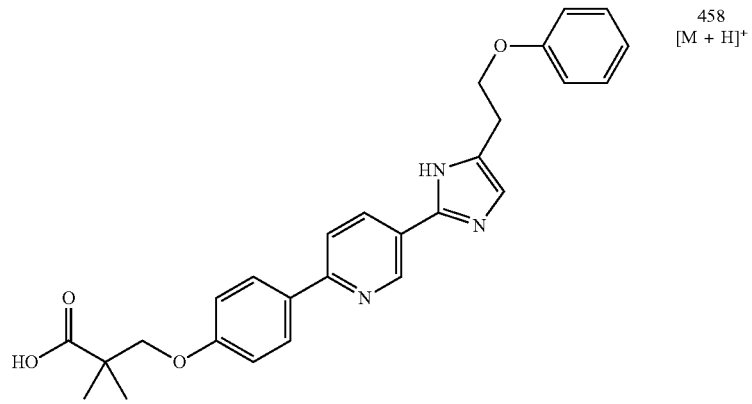 458 [M + H]+
1-59 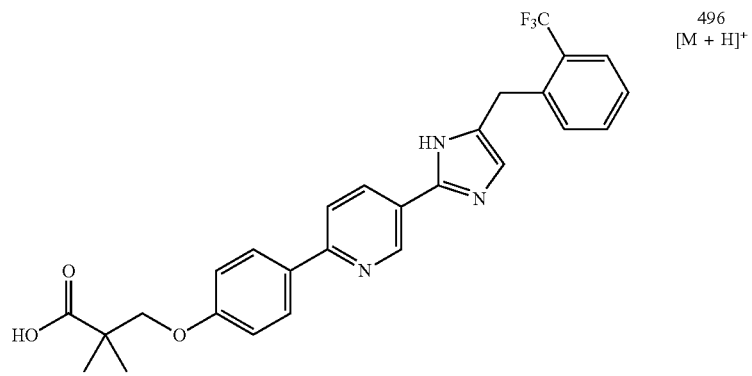 496 [M + H]+

TABLE 1-continued
1-60 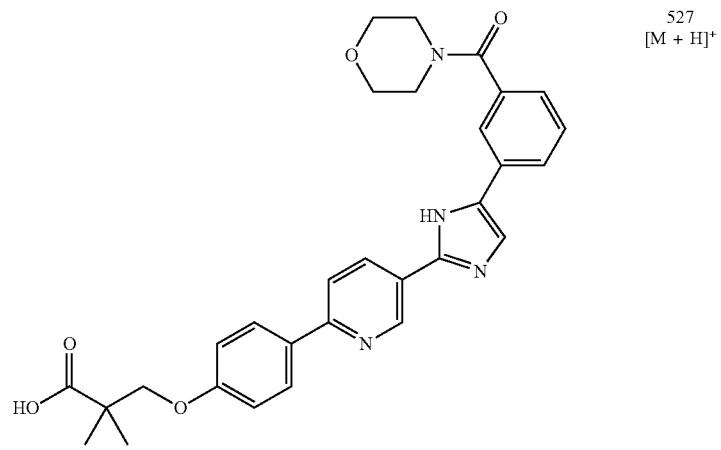 527 [M + H]⁺
1-61 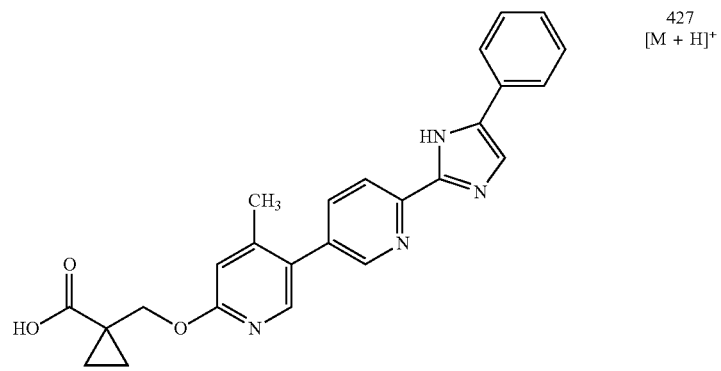 427 [M + H]⁺
1-62 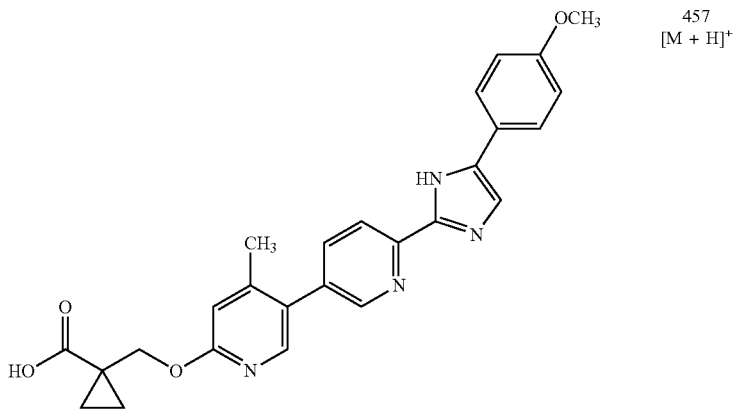 457 [M + H]⁺
1-63 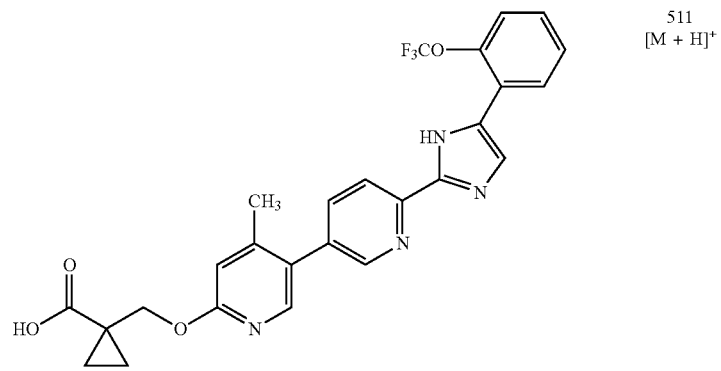 511 [M + H]⁺

TABLE 1-continued
| | | |
|---|---|---|
| 1-64 | 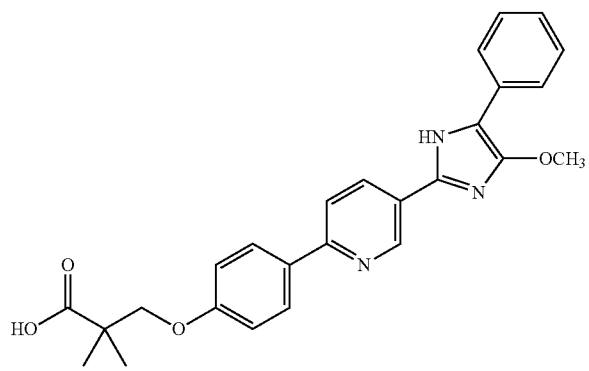 [SMILES: COc1nc(-c2ccc(-c3ccc(OCC(C)(C)C(=O)O)cc3)nc2)[nH]c1-c1ccccc1] | 444 [M + H]+ |
| 1-65 | 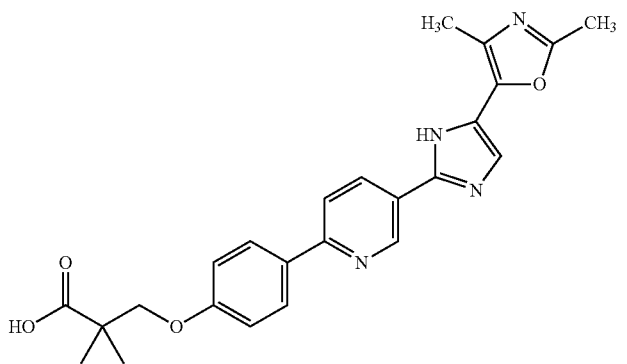 [SMILES: Cc1nc(C)c(-c2cnc(-c3ccc(-c4ccc(OCC(C)(C)C(=O)O)cc4)nc3)[nH]2)o1] | 433 [M + H]+ |
| 1-66 | 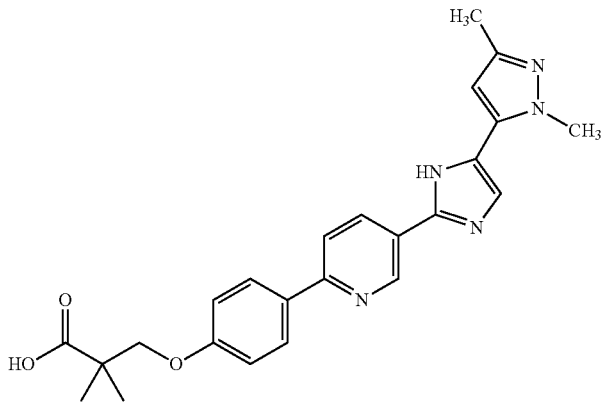 [SMILES: Cc1cc(-c2cnc(-c3ccc(-c4ccc(OCC(C)(C)C(=O)O)cc4)nc3)[nH]2)n(C)n1] | 432 [M + H]+ |
| 1-67 | 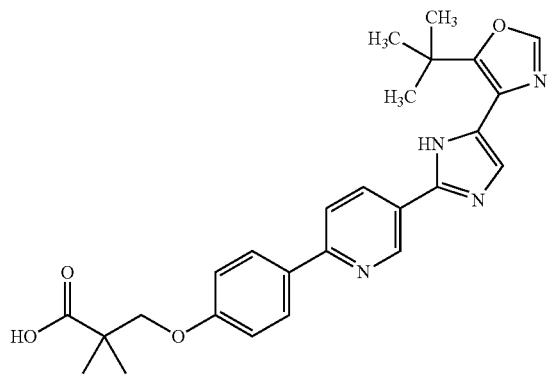 [SMILES: CC(C)(COc1ccc(-c2ccc(-c3ncc(-c4ncoc4C(C)(C)C)[nH]3)cn2)cc1)C(=O)O] | 461 [M + H]+ |

TABLE 1-continued
| 1-68 | 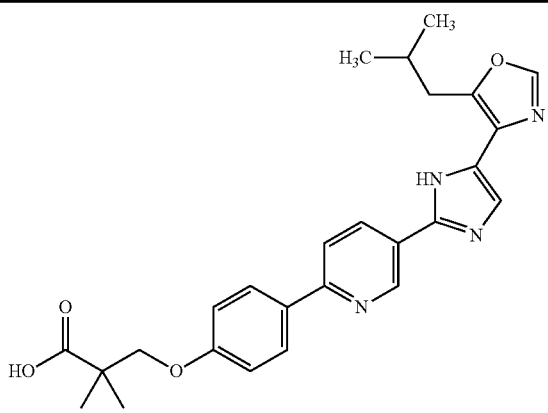 | 461 [M + H]⁺ |
| 1-69 | 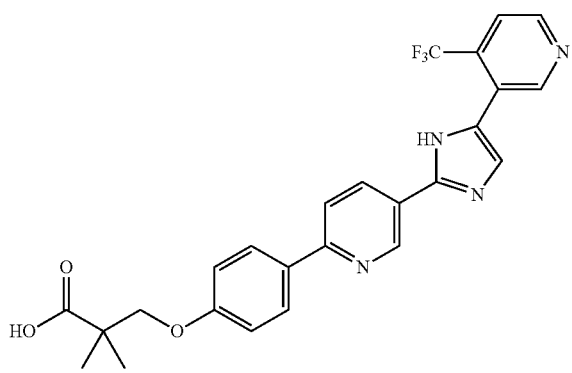 [SMILES: CC(C)(COc1ccc(-c2ccc(-c3ncc(-c4cnccc4C(F)(F)F)[nH]3)cn2)cc1)C(=O)O] | 483 [M + H]⁺ |
Example 2-1
[Chemical Formula 66]
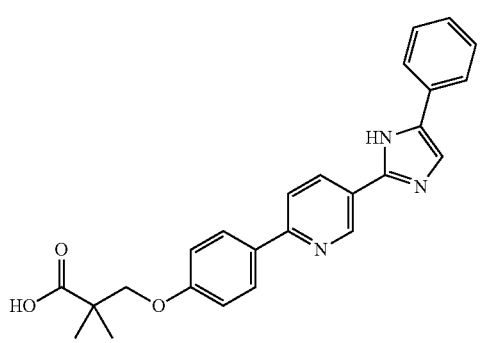
1
→
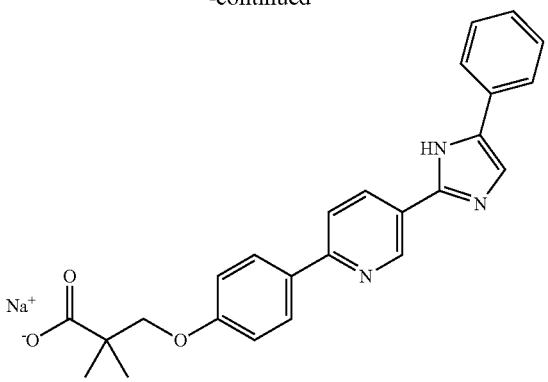
2
Compound 1 (4.40 g) was suspended in acetonitrile (100 mL), and a 1N aqueous sodium hydroxide solution (10.6 mL) was added dropwise, and the mixture was stirred at room temperature overnight. The obtained solid was collected by filtration, washed with acetonitrile and subsequently dried to obtain Compound 2 (4.55 g).
MS (m/z): 412 [M–Na]⁻

Examples 2-2 to 2-16

A treatment was carried out in a manner similar to the Example 2-1 to obtain compounds of Examples 2-2 to 2-16 in Table 2 below.

TABLE 2

| Example | Starting material | Product | MS (m/z) |
|---|---|---|---|
| 2-2 | | | 496 [M − Na]⁻ |
| 2-3 | | | 478/480 [M − Na + Cl]⁻ |
| 2-4 | | | 478 [M − Na]⁻ |
| 2-5 | | | 496 [M − Na]⁻ |

TABLE 2-continued

| Example | Starting material | Product | MS (m/z) |
|---|---|---|---|
| 2-6 | | | 456 [M − Na]⁻ |
| 2-7 | | | 412 [M − Na]⁻ |
| 2-8 | | | 442 [M − Na]⁻ |
| 2-9 | | | 496 [M − Na]⁻ |
| 2-10 | | | 426 [M − Na]⁻ |

TABLE 2-continued

| Example | Starting material | Product | MS (m/z) |
|---|---|---|---|
| 2-11 | | | 456 [M − Na]− |
| 2-12 | | | 508/510 [M + Cl − Na]− |
| 2-13 | | | 486 [M − Na]− |
| 2-14 | | | 480 [M − Na]− |
| 2-15 | | | 508/510 [M + Cl − Na]− |

TABLE 2-continued

| Example | Starting material | Product | MS (m/z) |
|---|---|---|---|
| 2-16 | 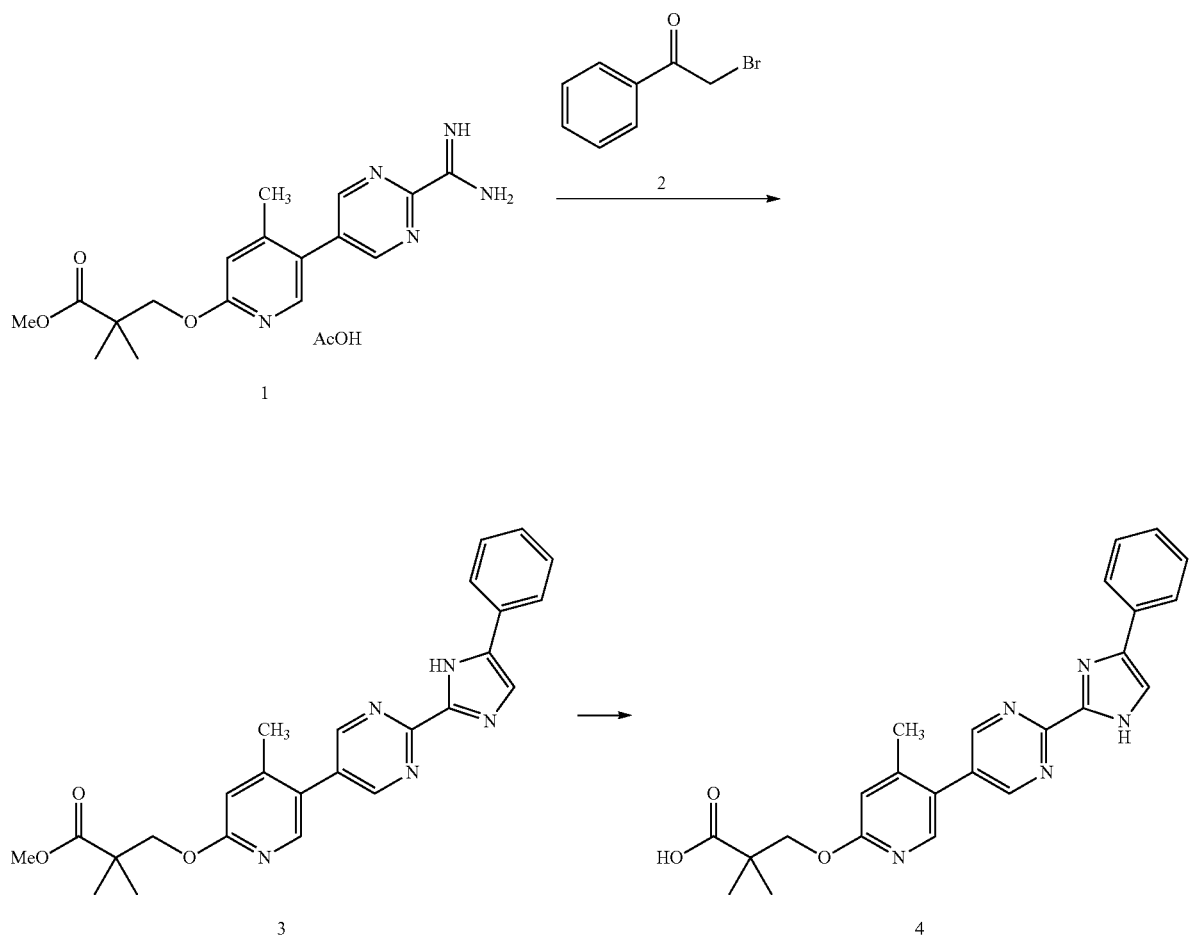 | | 442 [M − Na]⁻ |

Example 3-1

[Chemical Formula 67]

(1) Compound 1 (300 mg), Compound 2 (163 mg) and potassium carbonate (308 mg) were added into tetrahydrofuran (8 mL), and additionally saturated brine (8 mL) was added, and the mixture was stirred at 80° C. for 3 hours. After the reaction solution was cooled to room temperature, ethyl acetate and saturated brine were added to carry out a liquid separation. The organic layer was separated and subsequently dried over anhydrous sodium sulfate, and the solvent was distilled off under reduced pressure. To the obtained residue was added acetic acid (8 mL), and the mixture was stirred at 80° C. for 2 hours. After the temperature of the reaction solution was brought back to room temperature, the solvent was distilled off under reduced pressure, and ethyl acetate and saturated brine were added to carry out a liquid separation. The organic layer was separated and subsequently dried over anhydrous sodium sulfate, and the solvent was distilled off under reduced pressure. The obtained residue was purified by silica gel column chromatography (chloroform:methanol=100:0 to 97:3) to obtain Compound 3 (144 mg).

MS (m/z) 444 [M+H]+

(2) Compound 3 (142 mg) was treated in a manner similar to the Example 1-1 (2) to obtain Compound 4 (115 mg).

MS (m/z): 430 [M+H]+

Examples 3-2 to 3-13

A treatment was carried out in a manner similar to the Example 3-1 to obtain compounds of Examples 3-2 to 3-13 in Table 3 below.

TABLE 3

| Example | Starting material 1 | Starting material 2 |
|---|---|---|
| 3-2 | 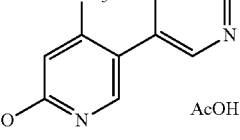 AcOH | 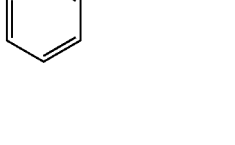 |
| 3-3 | 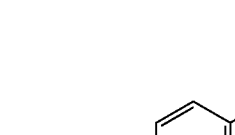 AcOH | 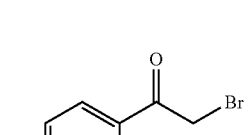 |
| 3-4 | 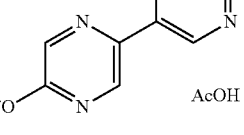 AcOH | 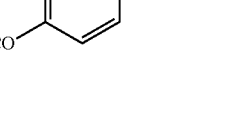 |
| 3-5 | 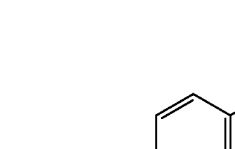 | 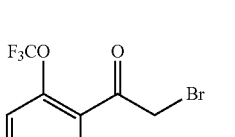 |
| 3-6 | 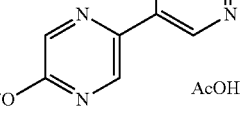 | 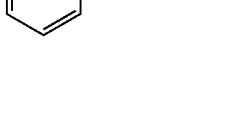 |

TABLE 3-continued
| | | |
|---|---|---|
| 3-7 | 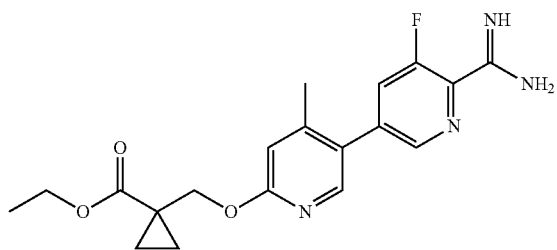 [SMILES: CCOC(=O)C1(COc2cc(C)c(-c3cnc(C(=N)N)c(F)c3)cn2)CC1] | 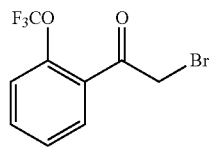 [SMILES: O=C(CBr)c1ccccc1OC(F)(F)F] |
| 3-8 | 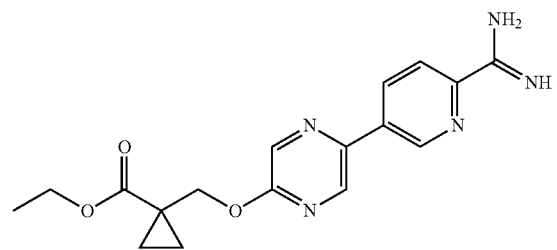 [SMILES: CCOC(=O)C1(COc2cnc(-c3ccc(C(=N)N)nc3)cn2)CC1] | 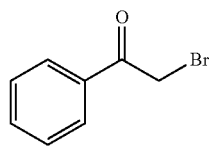 |
| 3-9 | 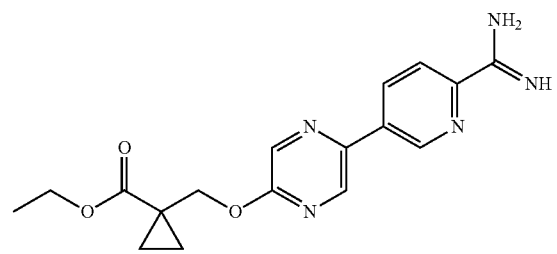 [SMILES: CCOC(=O)C1(COc2cnc(-c3ccc(C(=N)N)nc3)cn2)CC1] | 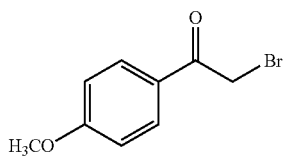 [SMILES: COc1ccc(C(=O)CBr)cc1] |
| 3-10 | 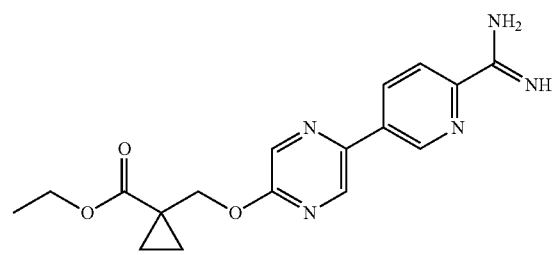 [SMILES: CCOC(=O)C1(COc2cnc(-c3ccc(C(=N)N)nc3)cn2)CC1] | 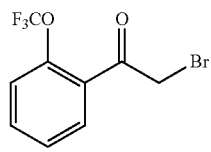 [SMILES: O=C(CBr)c1ccccc1OC(F)(F)F] |
| 3-11 | 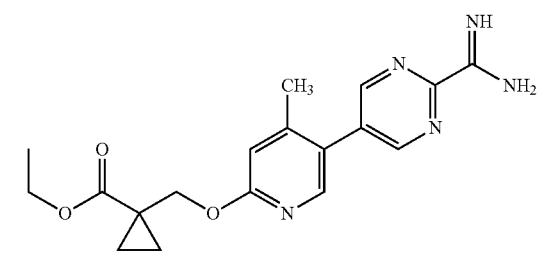 [SMILES: CCOC(=O)C1(COc2cc(C)c(-c3cnc(C(=N)N)nc3)cn2)CC1] | 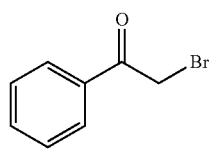 |
| 3-12 | 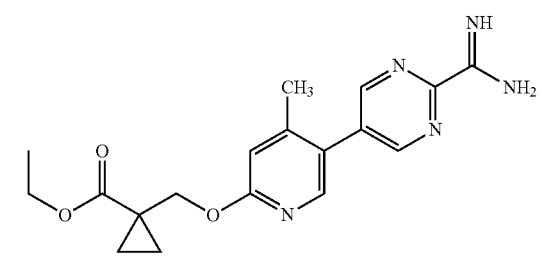 [SMILES: CCOC(=O)C1(COc2cc(C)c(-c3cnc(C(=N)N)nc3)cn2)CC1] | 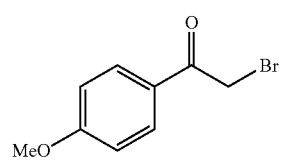 |

TABLE 3-continued
| 3-13 | 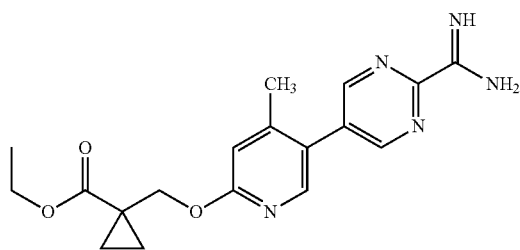 [SMILES: CCOC(=O)C1(COc2cc(C)c(-c3cnc(C(=N)N)nc3)cn2)CC1] | 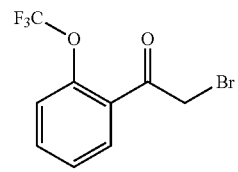 [SMILES: O=C(CBr)c1ccccc1OC(F)(F)F] |
| Example | Product | MS (m/z) |
| --- | --- | --- |
| 3-2 | 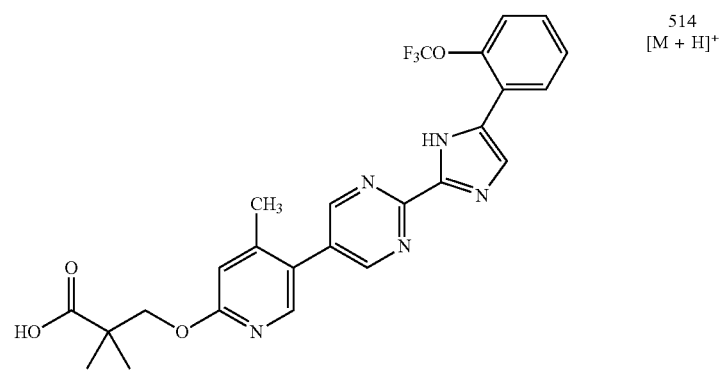 | 514 [M + H]+ |
| 3-3 | 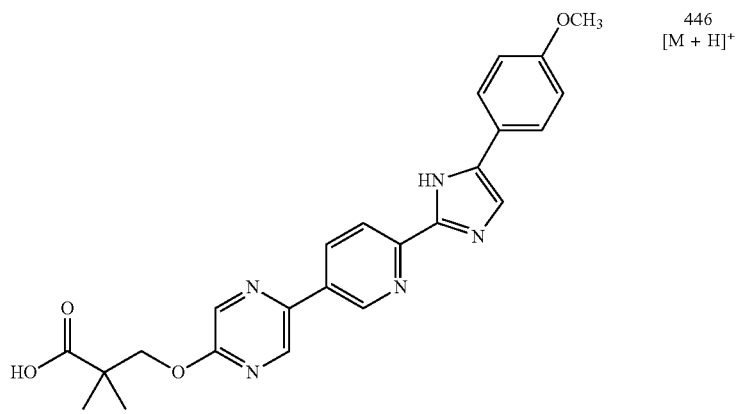 | 446 [M + H]+ |
| 3-4 | 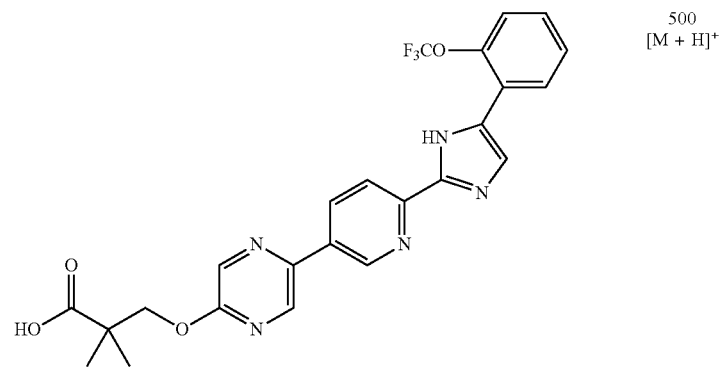 | 500 [M + H]+ |

TABLE 3-continued
3-5 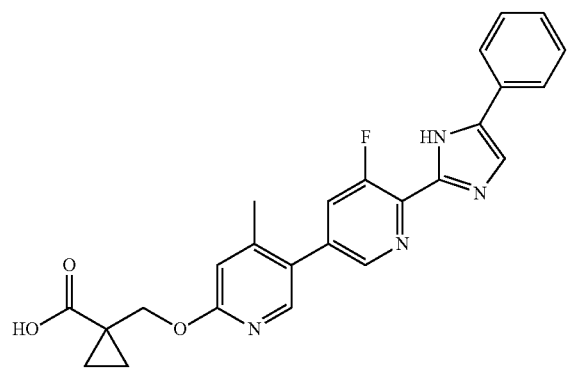 [SMILES: Cc1cc(OCC2(C(=O)O)CC2)ncc1-c1cnc(-c2ncc(-c3ccccc3)[nH]2)c(F)c1] 445 [M + H]+
3-6 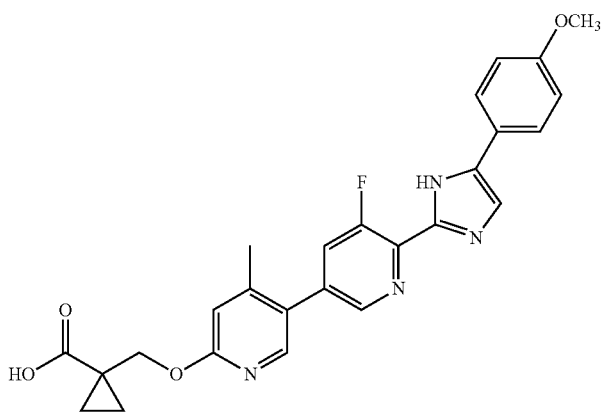 [SMILES: COc1ccc(-c2cnc(-c3ncc(-c4cnc(OCC5(C(=O)O)CC5)cc4C)cc3F)[nH]2)cc1] 475 [M + H]+
3-7 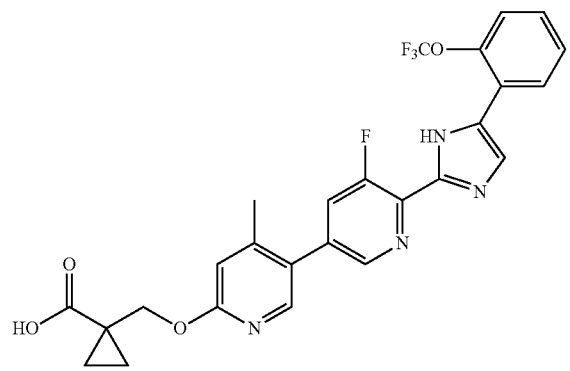 [SMILES: Cc1cc(OCC2(C(=O)O)CC2)ncc1-c1cnc(-c2ncc(-c3ccccc3OC(F)(F)F)[nH]2)c(F)c1] 529 [M + H]+
3-8 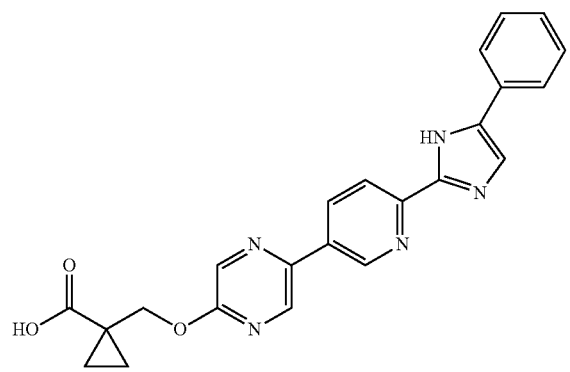 [SMILES: O=C(O)C1(COc2cnc(-c3ccc(-c4ncc(-c5ccccc5)[nH]4)nc3)cn2)CC1] 414 [M + H]+

TABLE 3-continued
| | | |
|---|---|---|
| 3-9 | 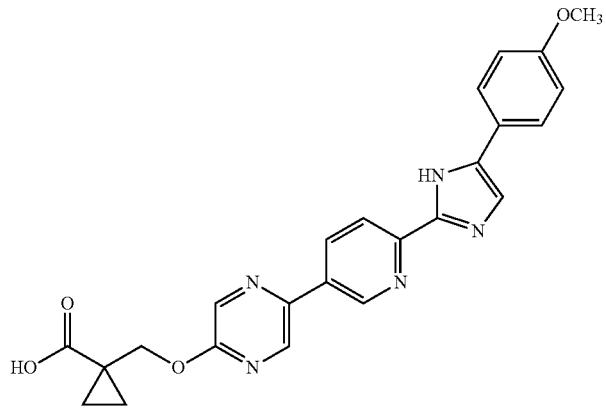 [SMILES: COc1ccc(-c2cnc(-c3ccc(-c4cnc(OCC5(C(=O)O)CC5)cn4)cn3)[nH]2)cc1] | 444 [M + H]+ |
| 3-10 | 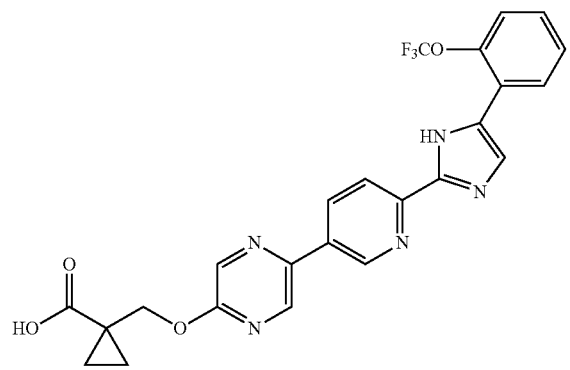 [SMILES: O=C(O)C1(COc2cnc(-c3ccc(-c4ncc(-c5ccccc5OC(F)(F)F)[nH]4)nc3)cn2)CC1] | 498 [M + H]+ |
| 3-11 | 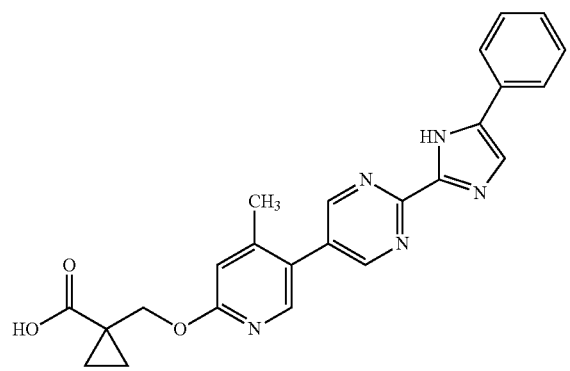 [SMILES: Cc1cc(OCC2(C(=O)O)CC2)ncc1-c1cnc(-c2ncc(-c3ccccc3)[nH]2)nc1] | 428 [M + H]+ |
| 3-12 | 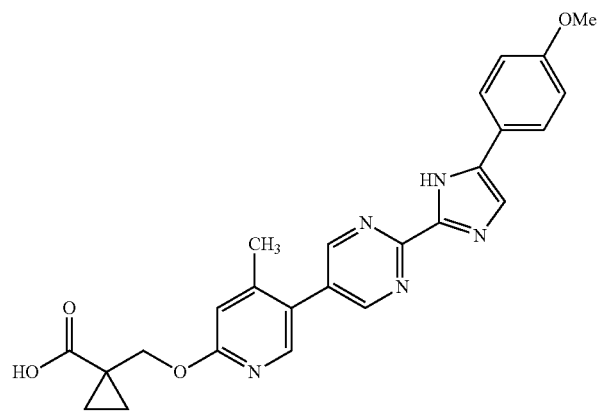 [SMILES: COc1ccc(-c2cnc(-c3ncc(-c4cnc(OCC5(C(=O)O)CC5)cc4C)cn3)[nH]2)cc1] | 458 [M + H]+ |

TABLE 3-continued
| | | |
|---|---|---|
| 3-13 | 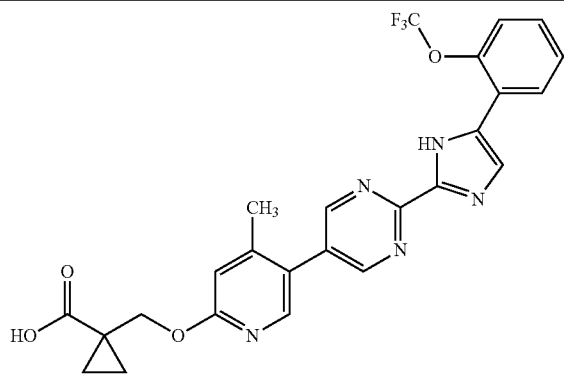 | 512 [M + H]+ |
Example 4-1
[Chemical Formula 68]
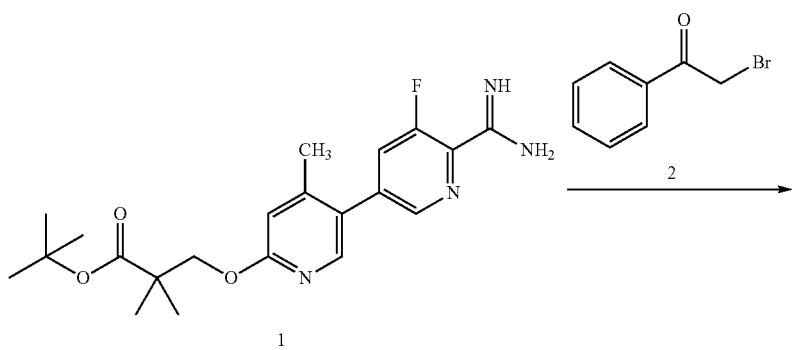
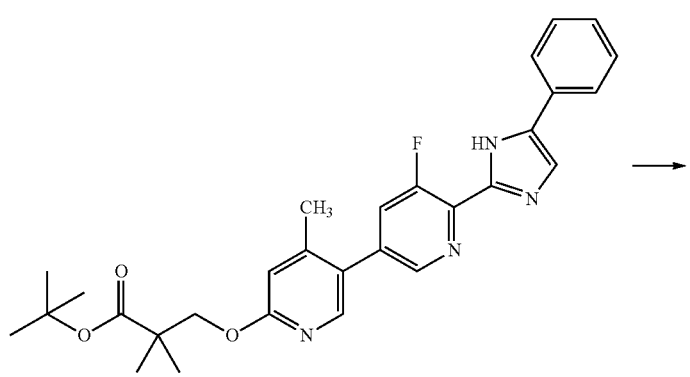

-continued

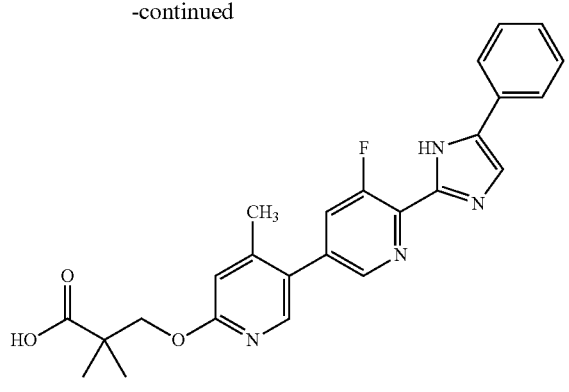

4

(1) Compound 1 (250 mg) and Compound 2 (105 mg) were treated in a manner similar to the Example 1-1 (1) to obtain Compound 3 (131.9 mg).
MS (m/z): 503 [M+H]$^+$
(2) Compound 3 (130 mg) was dissolved in trifluoroacetic acid (3 mL) and water (0.3 mL), and the mixture was stirred at room temperature for 3 hours. The residue obtained by concentration under reduced pressure was dissolved in tetrahydrofuran, and the mixture was neutralized with a 1N aqueous sodium hydroxide solution. After a few drops of acetic acid was added, ethyl acetate and water were added to carry out a liquid separation. The organic layer was separated and subsequently dried over anhydrous sodium sulfate, and the solvent was distilled off under reduced pressure. To the obtained residue were added diethyl ether, diisopropyl ether and ethyl acetate, the mixture was powderized and the solvent was distilled off under reduced pressure. To the obtained residue was added diisopropyl ether, and the powder was collected by filtration and dried to obtain Compound 4 (94.5 mg).
MS (m/z) 447 [M+H]$^+$ Examples 4-2 to 4-16

A treatment was carried out in a manner similar to the Example 4-1 to obtain compounds of Examples 4-2 to 4-16 in Table 4 below.

TABLE 4

| Example | Starting material 1 | Starting material 2 |
|---|---|---|
| 4-2 | 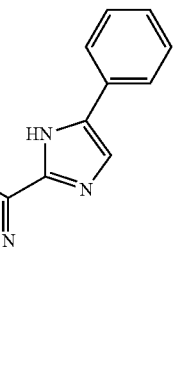 | |
| 4-3 | | |

TABLE 4-continued
| 4-4 | 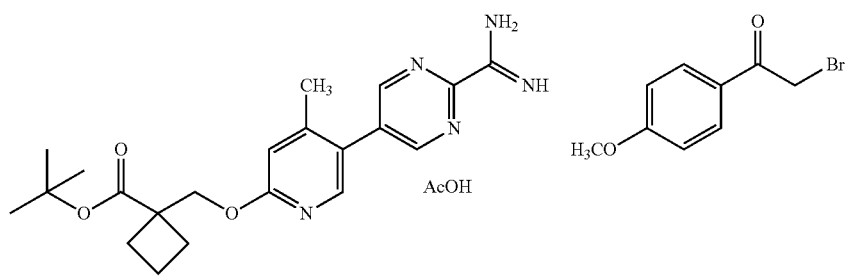 |
| --- | --- |
| 4-5 | 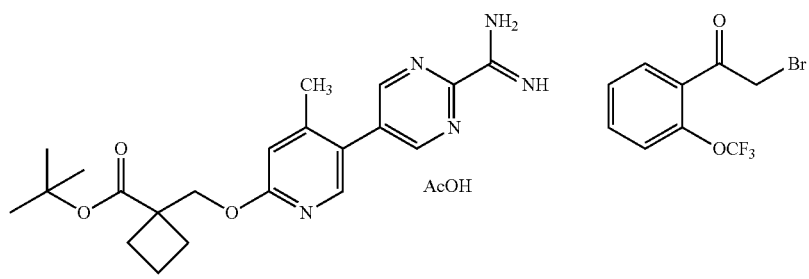 |
| 4-6 | 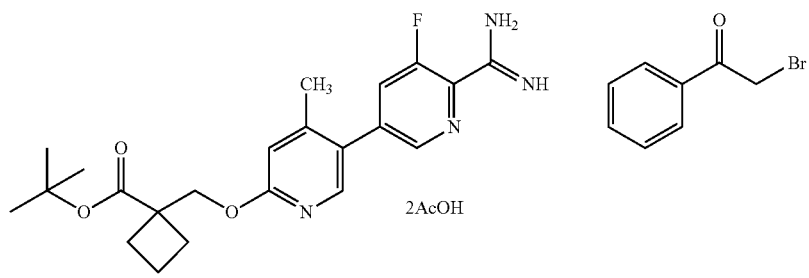 |
| 4-7 | 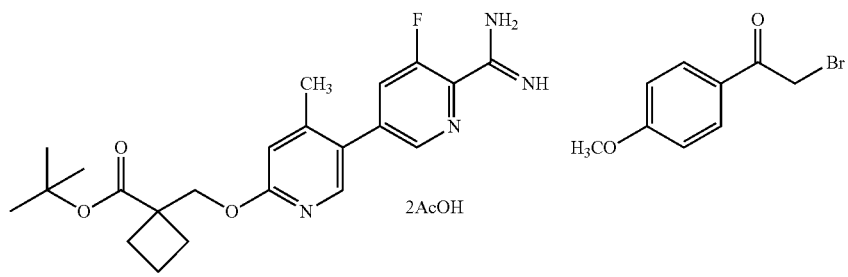 |
| 4-8 | 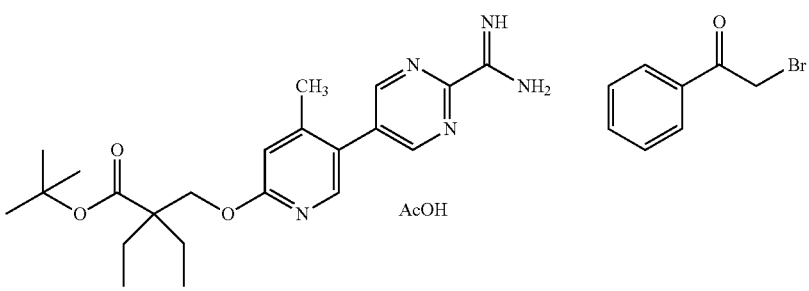 |

TABLE 4-continued
| 4-9 | 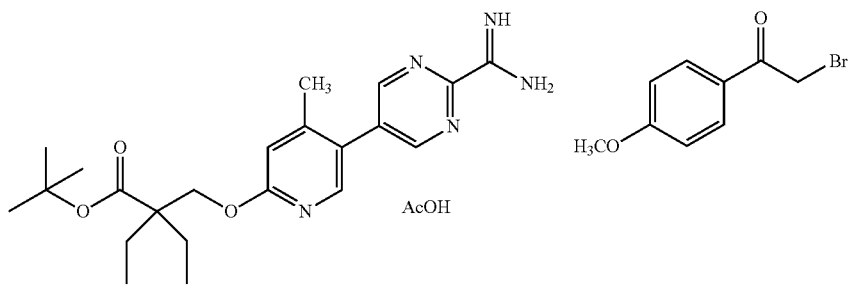 |
| --- | --- |
| 4-10 | 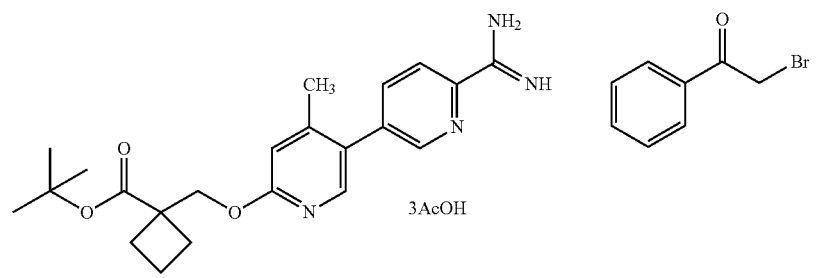 |
| 4-11 | 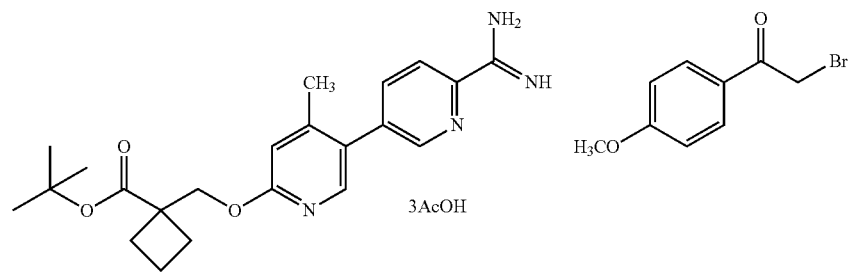 |
| 4-12 | 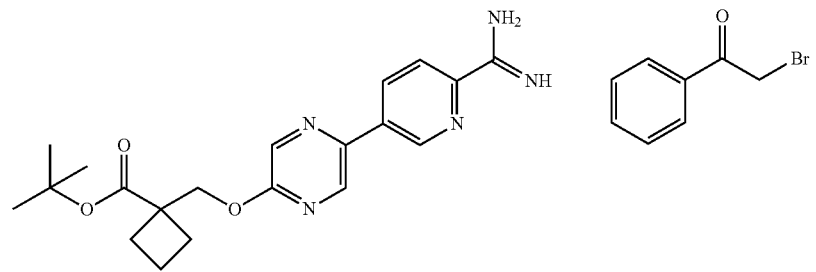 |
| 4-13 | 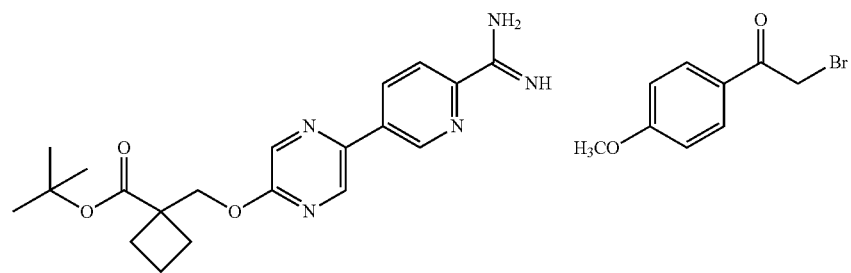 |

TABLE 4-continued
| | | |
|---|---|---|
| 4-14 | 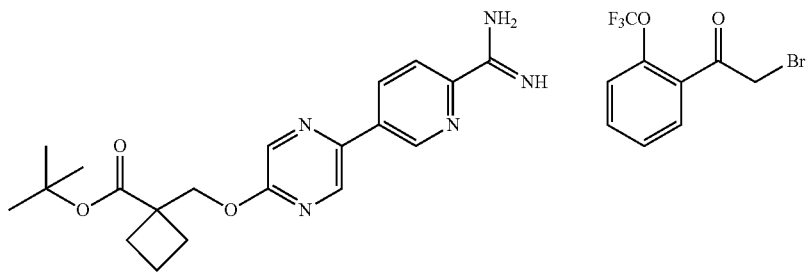 | |
| 4-15 | 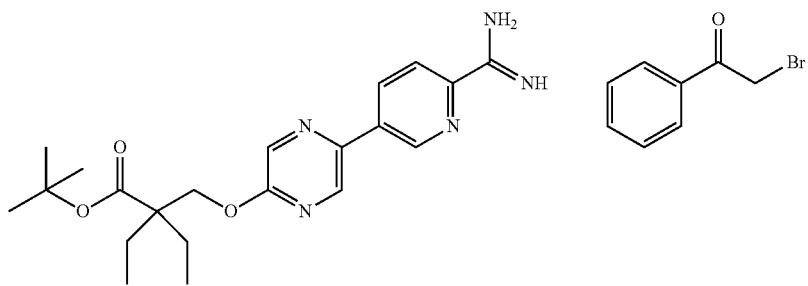 | |
| 4-16 | 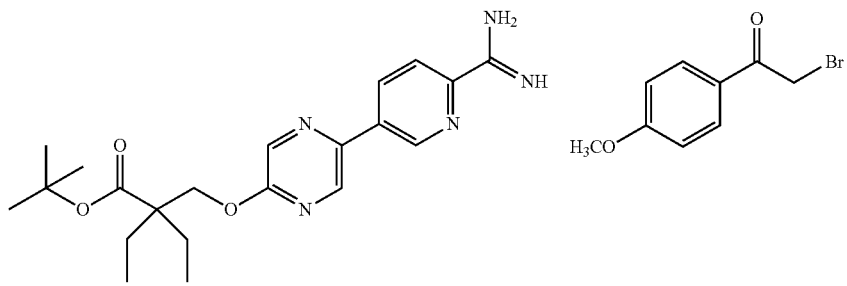 | |
| Example | Product | MS (m/z) |
|---|---|---|
| 4-2 | ![product structure] | 477 [M + H]⁺ |

TABLE 4-continued
| | | |
|---|---|---|
| 4-3 | 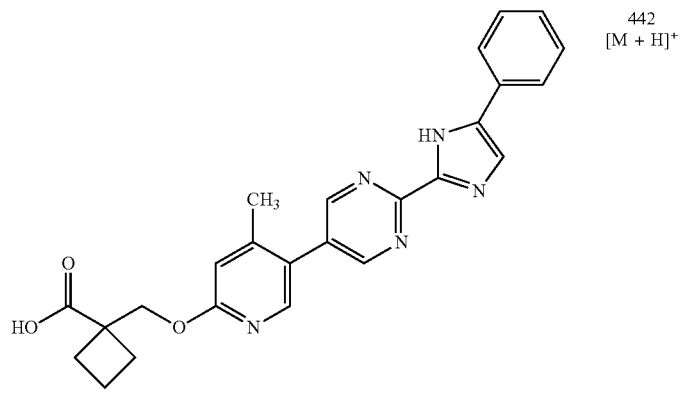 | 442 [M + H]+ |
| 4-4 | 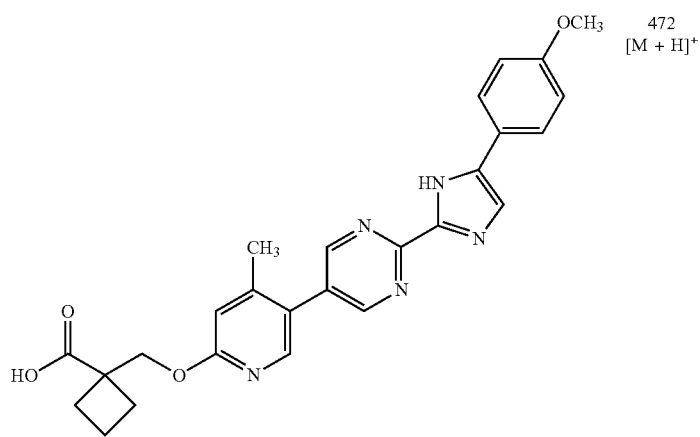 | 472 [M + H]+ |
| 4-5 |  | 526 [M + H]+ |
| 4-6 | 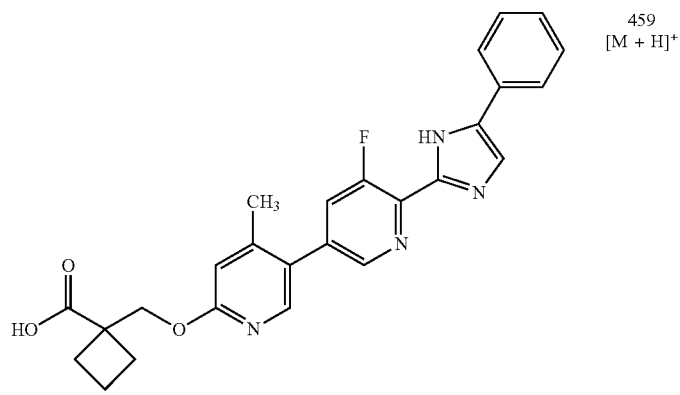 | 459 [M + H]+ |

TABLE 4-continued
| | | |
|---|---|---|
| 4-7 | 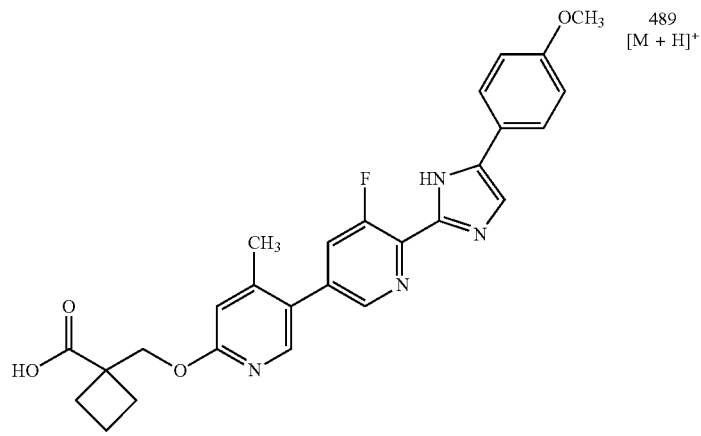 | 489 [M + H]+ |
| 4-8 | 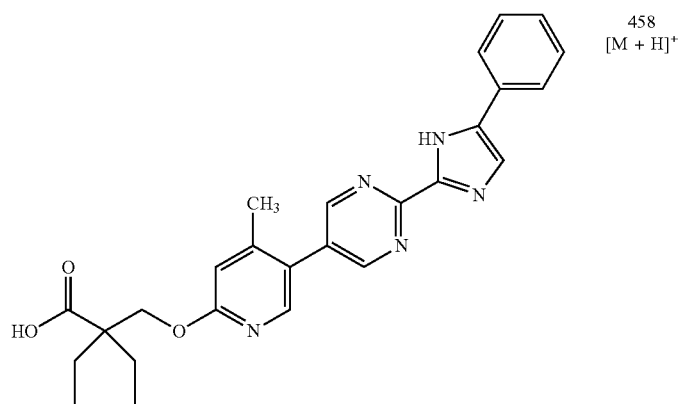 | 458 [M + H]+ |
| 4-9 | 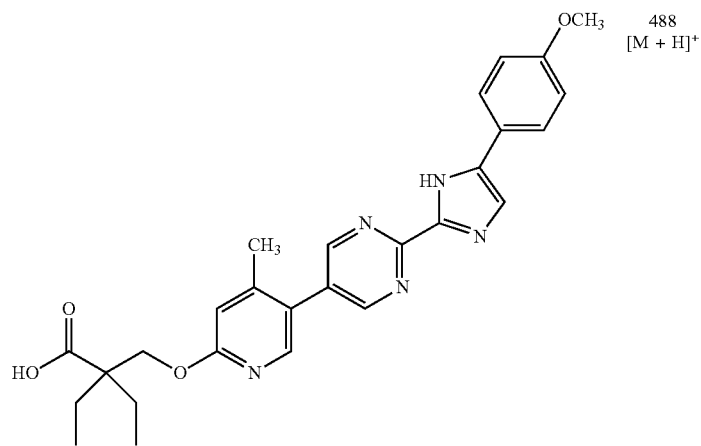 | 488 [M + H]+ |

TABLE 4-continued
| 4-10 | 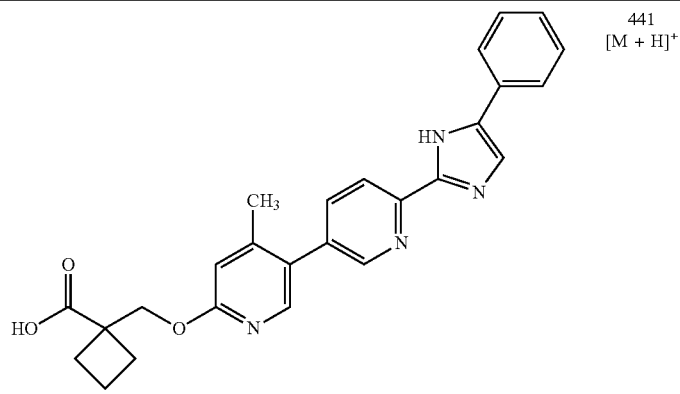 | 441 [M + H]+ |
| 4-11 | 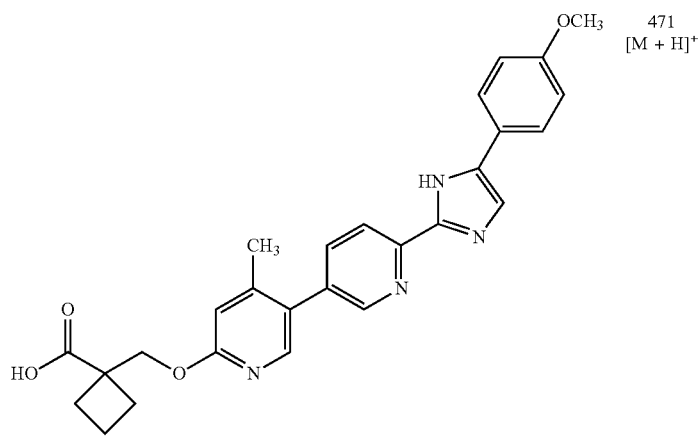 | 471 [M + H]+ |
| 4-12 | 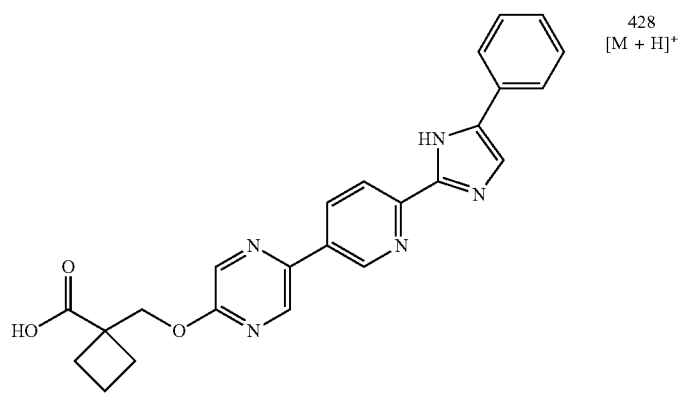 | 428 [M + H]+ |
| 4-13 | 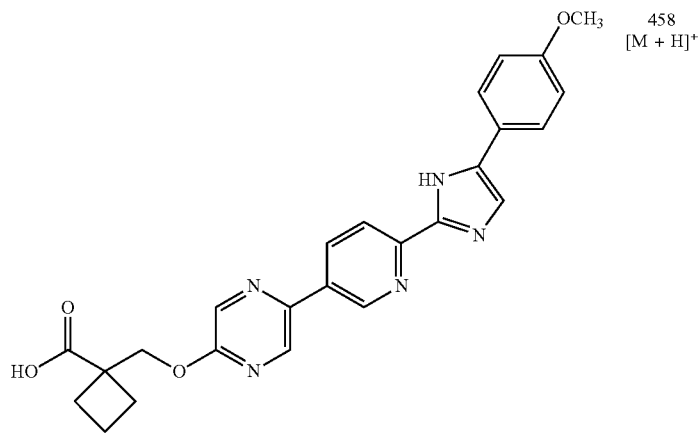 | 458 [M + H]+ |

TABLE 4-continued
| 4-14 | 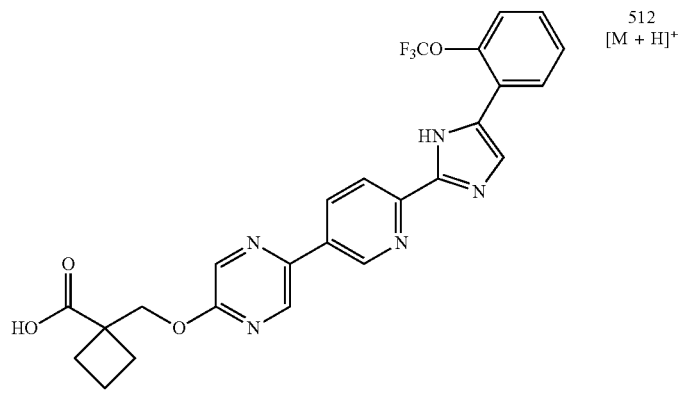 | 512 [M + H]+ |
| 4-15 | 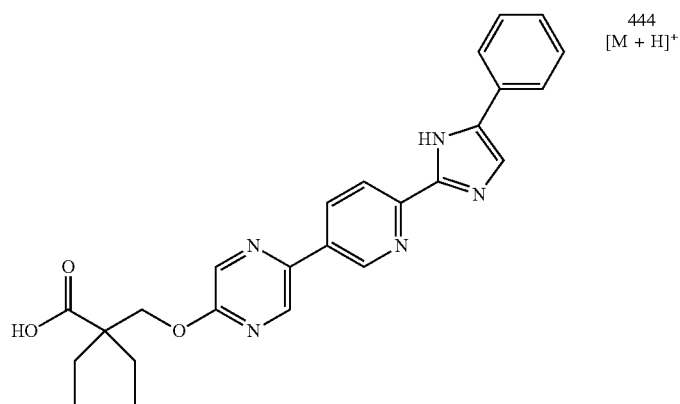 | 444 [M + H]+ |
| 4-16 | 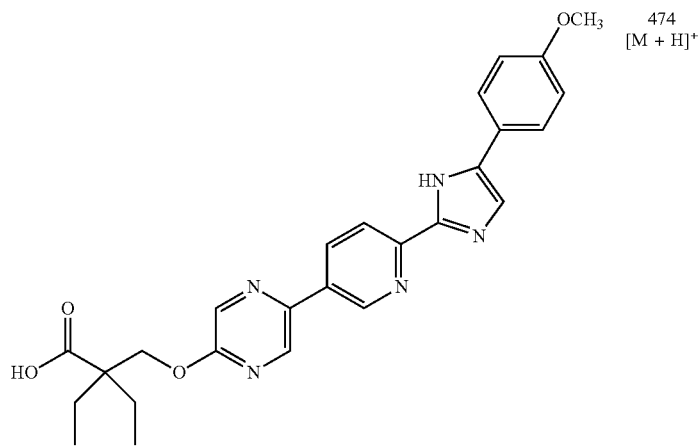 | 474 [M + H]+ |

Example 5-1

[Chemical Formula 69]

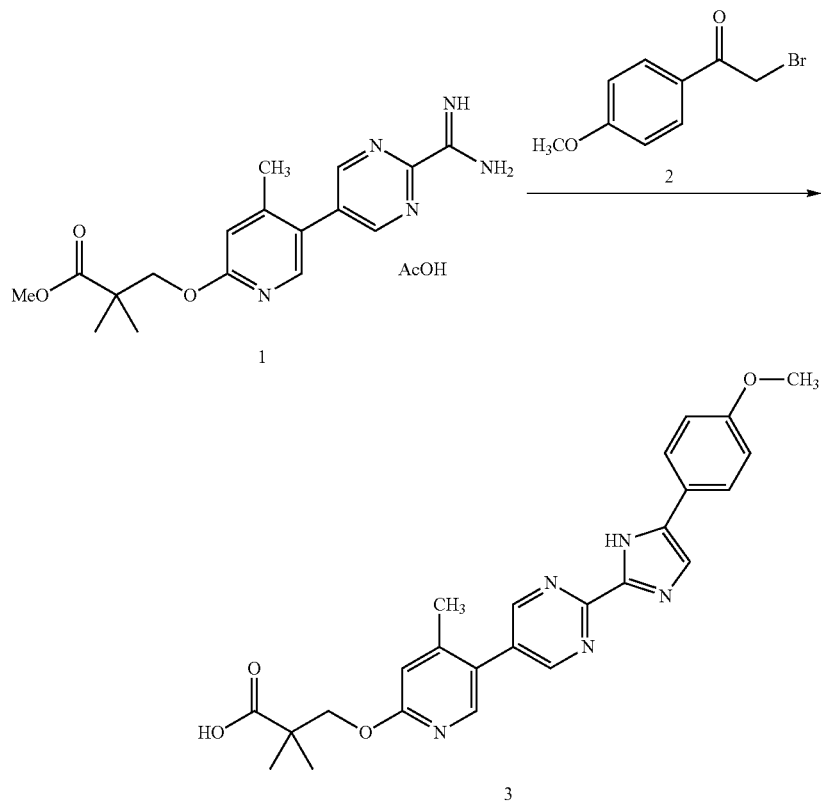

Compound 1 (300 mg), Compound 2 (187 mg) and potassium carbonate (308 mg) were added to tetrahydrofuran (8 mL), and additionally saturated brine (8 mL) was added, and the mixture was stirred at 80° C. for 5 hours. After the reaction solution was cooled to room temperature, ethyl acetate and saturated brine were added to carry out a liquid separation. The organic layer was separated and dried over anhydrous sodium sulfate, and subsequently the solvent was distilled off under reduced pressure. The obtained residue was purified by silica gel column chromatography (chloroform:methanol=100:0 to 94:6). The obtained solid was dissolved in methanol (5 mL) and tetrahydrofuran (5 mL), and a 2N aqueous sodium hydroxide solution (1.52 mL) was added, and the mixture was stirred at 50° C. for 3 hours. To the residue obtained by concentration under reduced pressure were added water and acetic acid, and the deposited solid was washed with water and dried to obtain Compound 3 (117.2 mg).

MS (m/z) 460 $[M+H]^+$

Example 5-2

A treatment was carried out in a manner similar to the Example 5-1 to obtain a compound of Example 5-2 in Table 5 below.

TABLE 5

| Example | Starting material 1 | Starting material 2 |
|---|---|---|
| 5-2 | 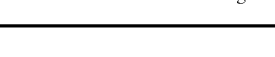 | 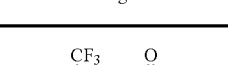 |

TABLE 5-continued
| Example | Product | MS (m/z) |
|---|---|---|
| 5-2 | 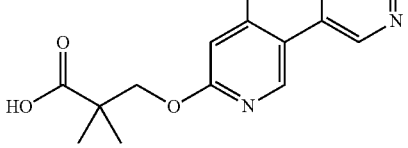 | 498 [M + H]+ |
Example 6
[Chemical Formula 70]
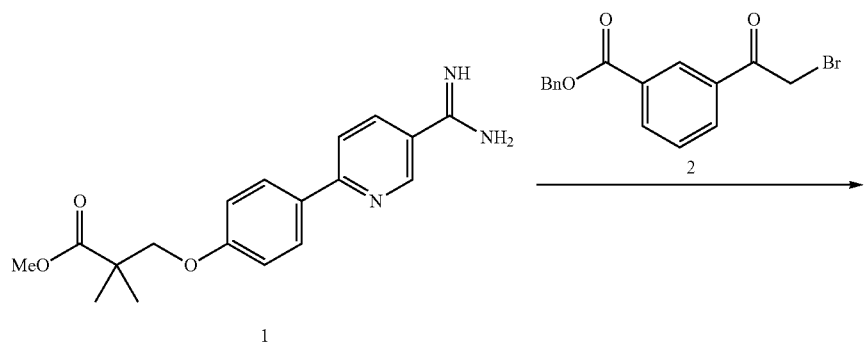

-continued
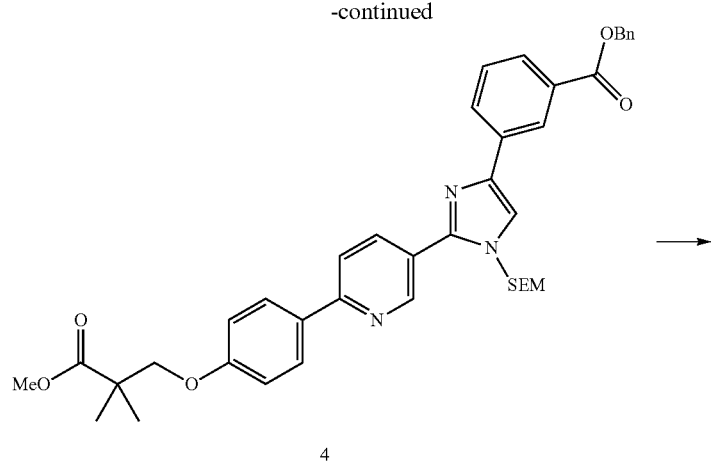
4
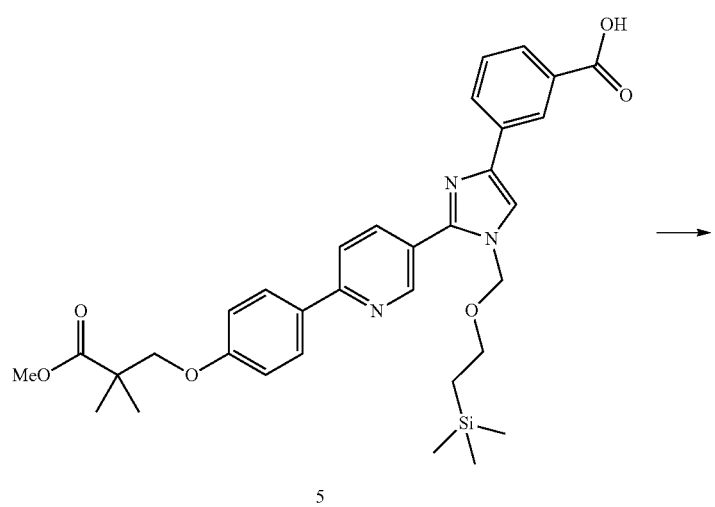
5
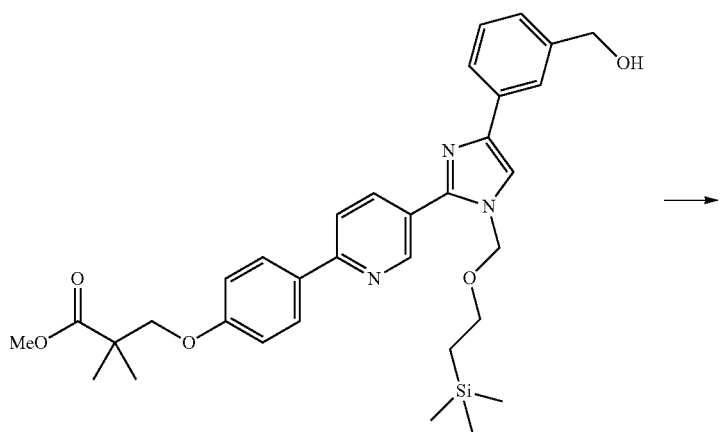
6

-continued
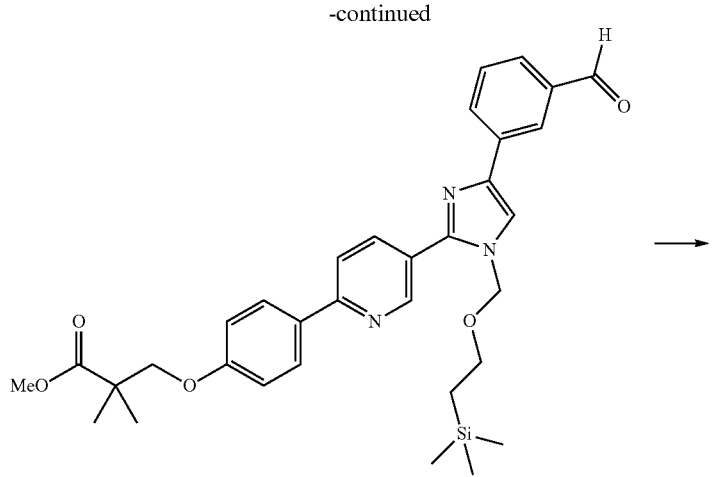
7
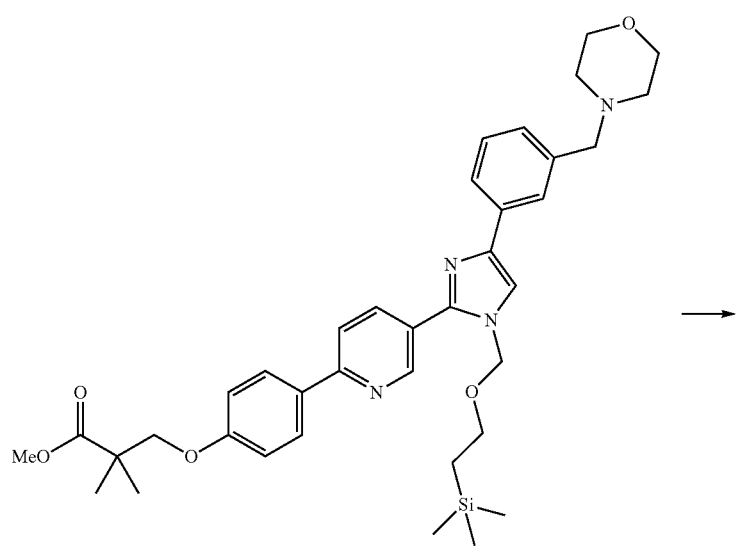
8
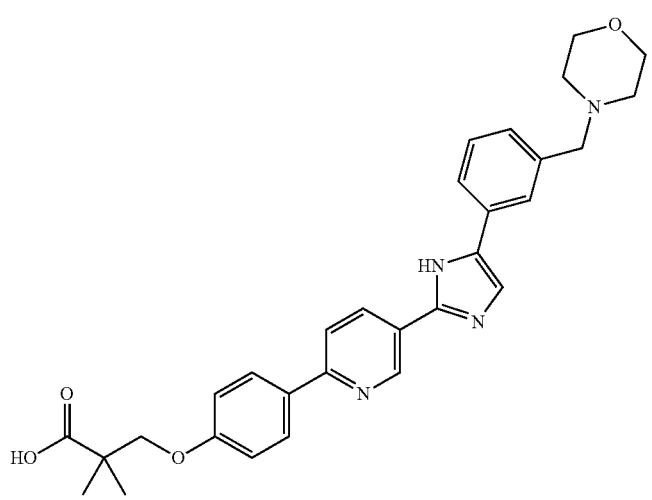
9

(1) Compound 1 (696 mg) and Compound 2 (665 mg) were treated in a manner similar to Example 1-1 (1) to obtain Compound 3 (938 mg).

MS (m/z): 562 [M+H]$^+$ (2) Compound 3 (936 mg) was dissolved in N,N-dimethylformamide (9 mL), and 60% sodium hydride (87 mg) was added under a nitrogen atmosphere under ice cooling, and the mixture was stirred. After 1 hour, 2-(trimethylsilyl)ethoxymethyl chloride (442 µL) was added under ice cooling, and the mixture was stirred overnight while the temperature gradually brought back to room temperature. To the reaction solution was added a saturated aqueous ammonium chloride solution, and a liquid separation was carried out between ethyl acetate and water. The organic layer was dried over anhydrous sodium sulfate and subsequently the solvent was distilled off under reduced pressure. The obtained residue was purified by silica gel column chromatography (n-hexane:ethyl acetate=85:15 to 65:35) to obtain Compound 4 (782 mg).

MS (m/z): 692 [M+H]$^+$ (3) Compound 4 (782 mg) was dissolved in methanol (15 mL) and tetrahydrofuran (15 mL), 10% palladium carbon (300 mg) was added under a nitrogen atmosphere and subsequently a hydrogen atmosphere was substituted therefor, and the mixture was stirred at room temperature for 3 hours. The insoluble substance was filtered through a membrane-filter and the filtrate was concentrated under reduced pressure to obtain Compound 5 (658 mg).

MS (m/z): 602 [M+H]$^+$ (4) Compound 5 (655 mg) was dissolved in tetrahydrofuran (13 mL) and triethylamine (182 µL) and isobutyl chloroformate (169 µL) were added under ice cooling, and the mixture was stirred for 30 minutes. The obtained solid was filtered and washed with tetrahydrofuran, and subsequently to the filtrate was added sodium borohydride (62 mg) under ice cooling, and the mixture was stirred for two days while the temperature brought back to room temperature. To the reaction solution was added a saturated aqueous ammonium chloride solution and a liquid separation was carried out between ethyl acetate and water. The organic layer was separated and dried over anhydrous sodium sulfate, and subsequently the solvent was distilled off under reduced pressure. The obtained residue was purified by silica gel column chromatography (chloroform:methanol=100:0 to 95:5) to obtain Compound 6 (553 mg).

MS (m/z): 588 [M+H]$^+$ (5) Compound 6 (551 mg) was dissolved in dichloromethane (11 mL) and manganese dioxide (815 mg) was added, and the mixture was stirred at room temperature overnight. The insoluble substance was filtered through a membrane-filter, and the filtrate was concentrated under reduced pressure to obtain Compound 7 (443 mg).

MS (m/z): 586 [M+H]$^+$ (6) Compound 7 (441 mg) was dissolved in tetrahydrofuran (9 mL) and morpholine (132 µL) was added, and the mixture was stirred. After 1 hour, sodium triacetoxyborohydride (479 mg) and acetic acid (43 µL) were added, and the mixture was further stirred at room temperature overnight. Dichloromethane and a saturated aqueous sodium hydrogen carbonate solution were added to the reaction solution to carry out a liquid separation. The organic layer was washed with water, and dried over anhydrous sodium sulfate. The solvent was distilled off under reduced pressure. The obtained residue was purified by silica gel column chromatography (n-hexane:ethyl acetate=50:50 to 0:100) to obtain Compound 8 (477 mg).

MS (m/z): 657 [M+H]$^+$ (7) Compound 8 (475 mg) was dissolved in trifluoroacetic acid (10 mL) and water (1 mL), and the mixture was stirred at room temperature overnight. After the solvent was distilled off under reduced pressure, ethyl acetate and a saturated aqueous sodium hydrogen carbonate solution were added to the residue to carry out a liquid separation. The organic layer was washed with water, and dried over anhydrous sodium sulfate. The solvent was distilled off under reduced pressure. The obtained residue was dissolved in methanol (5 mL) and tetrahydrofuran (5 mL) and a 2N aqueous sodium hydroxide solution (1.8 mL) was added under ice cooling, and the mixture was stirred at room temperature overnight. To the reaction solution was added 2N hydrochloric acid (1.8 mL), and the solvent was distilled off under reduced pressure. The obtained residue was purified by preparative LC-MS to obtain Compound 9 (264 mg).

MS (m/z): 513 [M+H]$^+$

Example 7

[Chemical Formula 71]

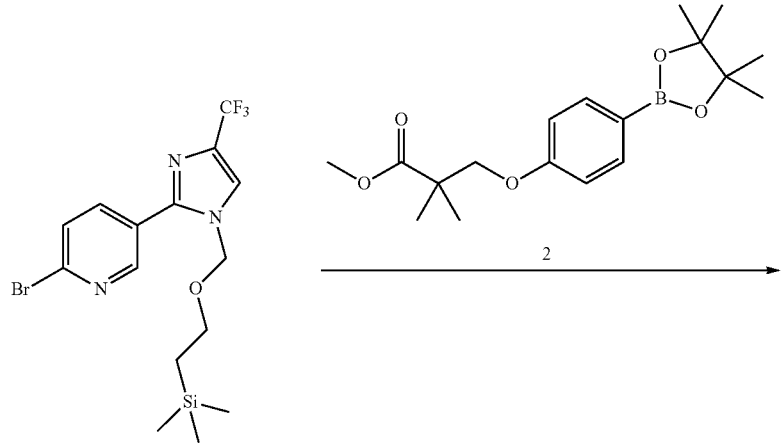

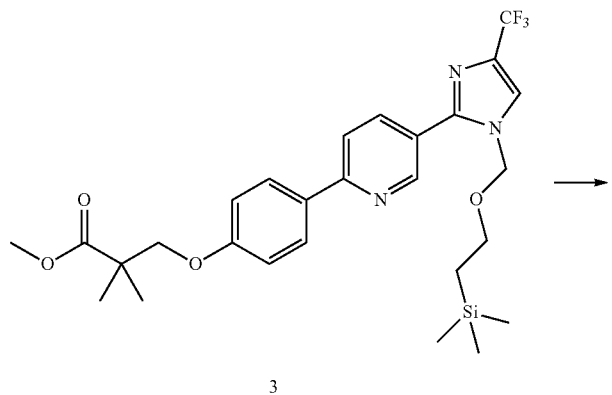
3
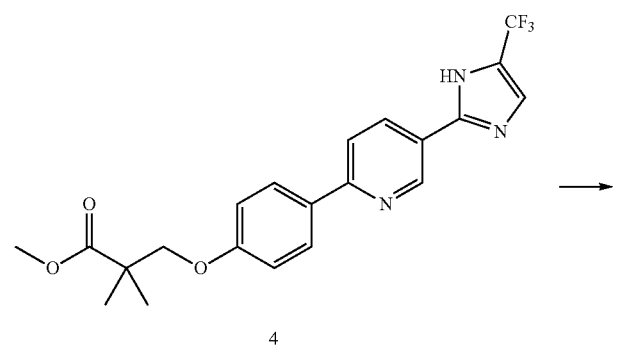
4
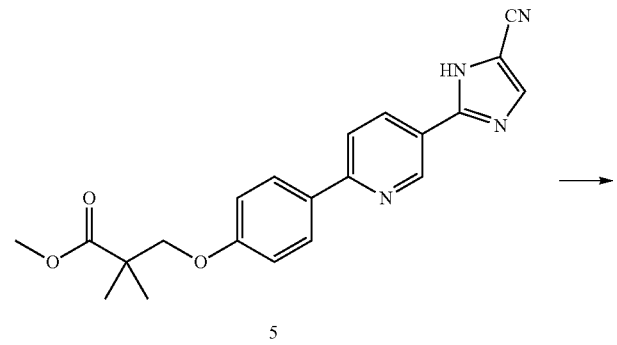
5
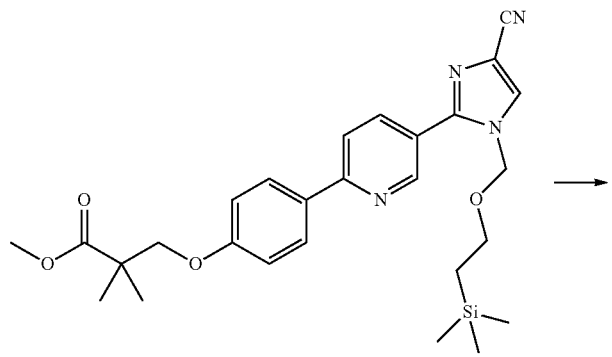
6

-continued

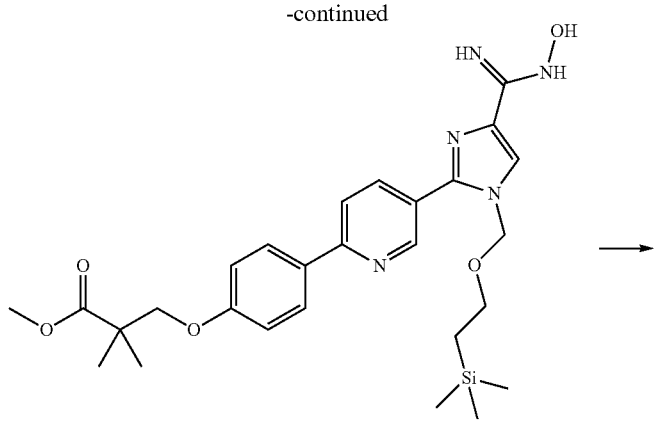

7

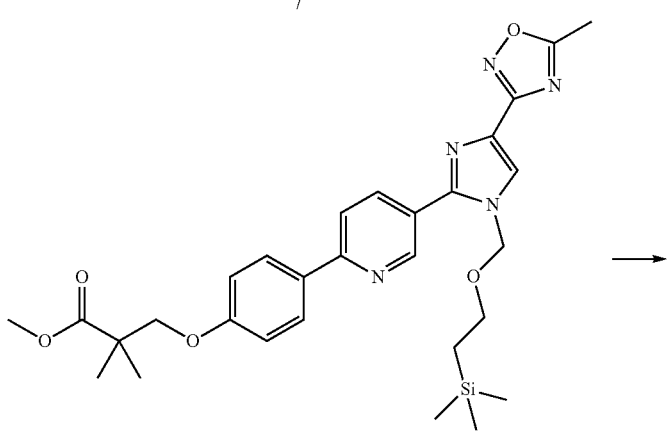

8

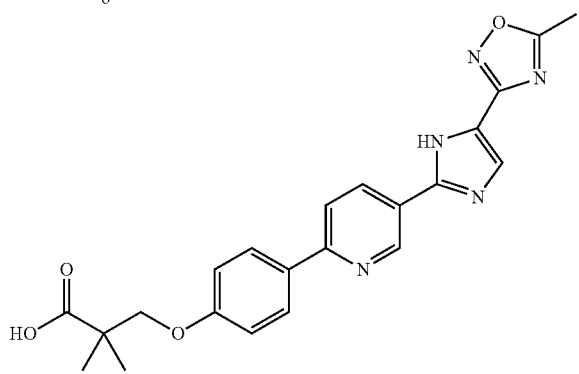

9

(1) Compound 1 (1000 mg), Compound 2 (986 mg) and a [1,1'-bis(diphenylphosphino)ferrocene]palladium dichloride-dichloromethane complex (193 mg) were dissolved in N,N-dimethylformamide (12 mL), and a 2M aqueous sodium carbonate solution (3.55 mL) was added, and the mixture was stirred under a nitrogen atmosphere at 65° C. for 6 hours. After the reaction solution was cooled to room temperature, brine and ethyl acetate were added to carry out a liquid separation. After the organic layer was separated, anhydrous magnesium sulfate and activated charcoal were added and filtered through Celite. The filtrate was concentrated under reduce pressure. The obtained residue was purified by silica gel column chromatography (n-hexane:ethyl acetate=88:12, 80:20 and to 75:25) to obtain Compound 3 (1.14 g).

MS (m/z): 550 [M+H]$^+$ (2) Compound 3 (2.56 g) was dissolved in trifluoroacetic acid (40 mL) and water (6 mL), and the mixture was stirred at room temperature overnight. To the residue obtained by concentration under reduce pressure was added a saturated aqueous sodium hydrogen carbonate solution, and the mixture was extracted with ethyl acetate and tetrahydrofuran. The organic layer was washed with saturated brine and subsequently dried over anhydrous sodium sulfate, and the solvent was distilled off under reduced pressure. The obtained residue was purified by silica gel column chromatography (chloroform:methanol=100:0 to 95:5) to obtain Compound 4 (1.90 g).

MS (m/z): 420 [M+H]$^+$ (3) Compound 4 (1.88 g) was dissolved in methanol (20 mL) and tetrahydrofuran (20 mL), and 28% aqueous ammonia (40 mL) was added, and the mixture was stirred at 40° C. overnight. Further, 28% aqueous ammonia (10 mL) was added in two parts, and the mixture was stirred at 40° C. overnight. After the temperature of the reaction solution brought back to room temperature, the solvent was distilled off under reduced pressure, and ethyl acetate, tetrahydrofuran and water were added to the obtained residue to carry out a liquid separation. The organic layer was washed with saturated brine and subsequently dried over anhydrous magnesium sulfate, and the solvent was distilled off under reduced pressure. The obtained residue was purified with silica gel column chromatography (chloroform:methanol=100:0 to 96:4) to obtain Compound 5 (1.16 g).

MS (m/z): 377 [M+H]$^+$ (4) A treatment was carried out in a manner similar to Example 6 (2) using Compound 5 (854 mg) to obtain Compound 6 (1.09 g).

MS (m/z): 507 [M+H]$^+$ (5) A treatment was carried out in a manner similar to Reference Example 7-1 (4) using Compound 6 (1.08 g) to obtain Compound 7 (1.14 g).

MS (m/z): 540 [M+H]$^+$ (6) To Compound 7 (1.14 g) was added acetic anhydride (15 mL), and the mixture was stirred at 120° C. for 2 hours. After the temperature of the reaction solution brought back to room temperature, the solvent was distilled off under reduced pressure (including an azeotropic procedure using toluene (three times)), to the obtained residue added a saturated aqueous sodium hydrogen carbonate solution, and the mixture was extracted with ethyl acetate. The organic layer was washed with saturated brine, and the aqueous layer thus obtained was further extracted with ethyl acetate. After the organic layers were combined and dried over anhydrous sodium sulfate, the solvent was distilled off under reduced pressure. The obtained residue was purified by silica gel column chromatography (n-hexane:ethyl acetate) to obtain Compound 8 (679 mg).

MS (m/z): 564 [M+H]$^+$ (7) A treatment was carried out in a manner similar to the Example 6 (7) using Compound 8 (672 mg) to obtain Compound 9 (389 mg).

MS (m/z): 420 [M+H]$^+$

Example 8

[Chemical Formula 72]

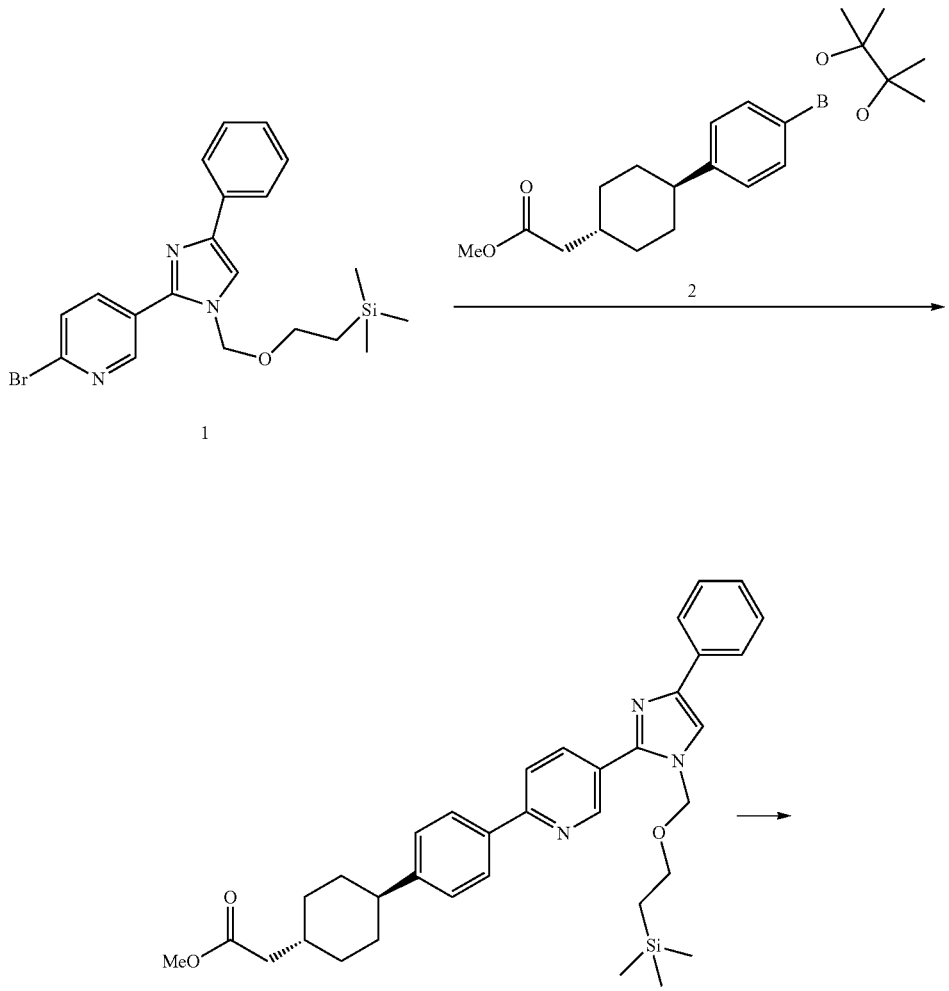

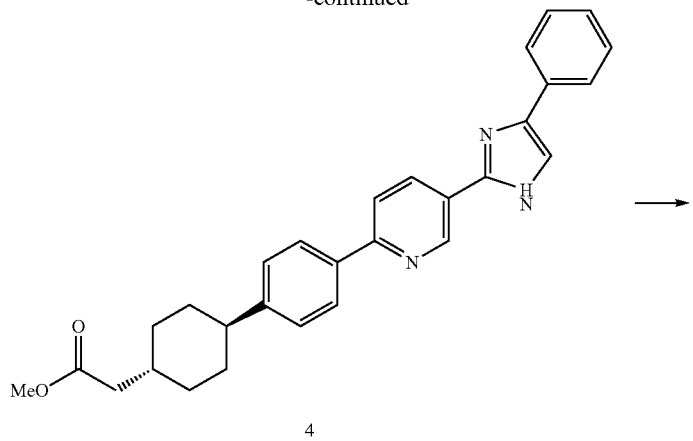

4

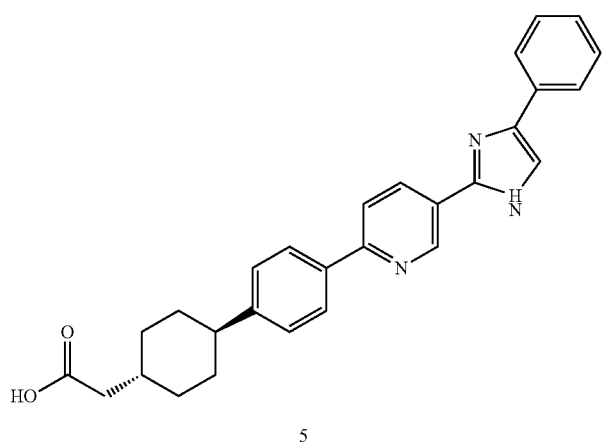

5

(1) Compound 1 (102 mg) and Compound 2 (119 mg) were dissolved in dimethylformamide (2.5 mL), and a palladium chloride (dppf)-methylene chloride complex (10 mg) and a 2M aqueous sodium carbonate solution (0.5 mL) were added, and the mixture was stirred under a nitrogen atmosphere at 70° C. for 8 hours. Water and ethyl acetate were added to the reaction mixture to carry out a liquid separation, to the organic layer was added hexane, and the solution was washed with water and saturated brine. After the organic layer was dried over anhydrous sodium sulfate, the solvent was distilled off under reduced pressure, and the obtained residue was purified by silica gel column chromatography (hexane:ethyl acetate=90:10 to 67:33) to obtain Compound 3 (81 mg).

MS (m/z): 582 [M+H]$^+$ (2) A treatment was carried out in a manner similar to the Example 7 (2) using Compound 3 (80 mg) to obtain Compound 4 (51 mg)

MS (m/z): 452 [M+H]$^+$ (3) A treatment was carried out in a manner similar to the Example 1-1 (2) using Compound 4 (43 mg) to obtain Compound 5 (36 mg).

MS (m/z): 438 [M+H]$^+$

Example 9

[Chemical Formula 73]

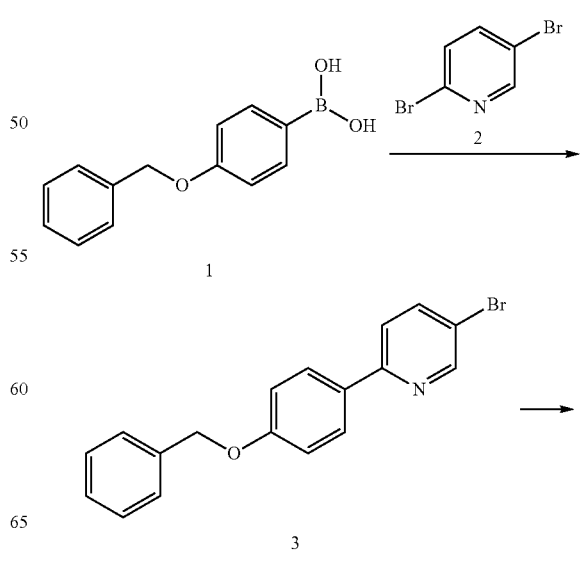

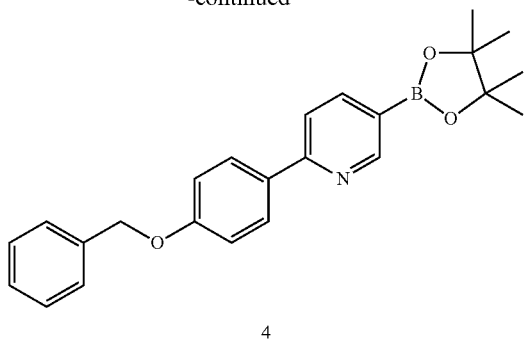

4

(1) Compound 1 (9.43 g), Compound 2 (10 g) and sodium carbonate (8.77 g) were added to a mixed solvent of toluene (285 mL), ethanol (143 mL) and water (143 mL), and the atmosphere was replaced with a nitrogen atmosphere. To this was added tetrakistriphenylphosphine palladium (0.48 g), and the mixture was heated at reflux for 16 hours. After the reaction solution was cooled to room temperature, ethyl acetate and water were added to carry out a liquid separation. The organic layer was separated and dried over anhydrous magnesium sulfate, and subsequently the solvent was distilled off under reduced pressure. The obtained solid was crystallized from ethyl acetate to obtain Compound 3 (10.55 g).

MS (m/z): 340/342 [M+H]$^+$ (2) Compound 3 (1000 mg), bis(pinacolato)diborane (933 mg) and potassium acetate (865 mg) were added to 1,4-dioxane (29 mL), and the mixture was subjected to nitrogen substitution. To this were added a palladium chloride (dppf)-methylene chloride complex (72 mg) and dppf (49 mg) and then nitrogen substitution was carried out, and the mixture was stirred at 80° C. overnight. To the reaction solution were added water and ethyl acetate, and the mixture was stirred, and filtered through Celite. The organic layer was separated, and anhydrous magnesium sulfate and activated charcoal were added, and the mixture was filtered through Celite. The solvent was distilled off under reduced pressure. To the obtained residue was added methanol, and the solid was collected by filtration to obtain Compound 4 (803 mg).

MS (m/z): 388 [M+H]$^+$

[Chemical Formula 74]

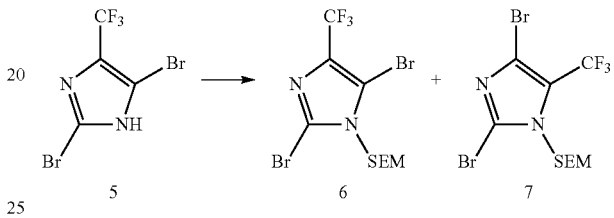

(3) A treatment was carried out in a manner similar to the Example 6 (2) using Compound 5 (10 g) to obtain a mixture of Compound 6 and Compound 7 (13.27 g).

MS (m/z): 423/425 [M+H]$^+$

[Chemical Formula 75]

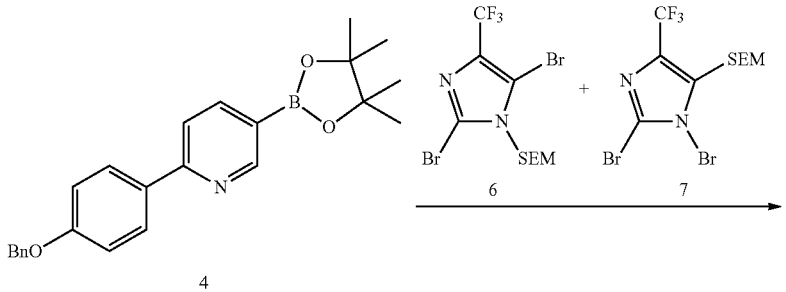

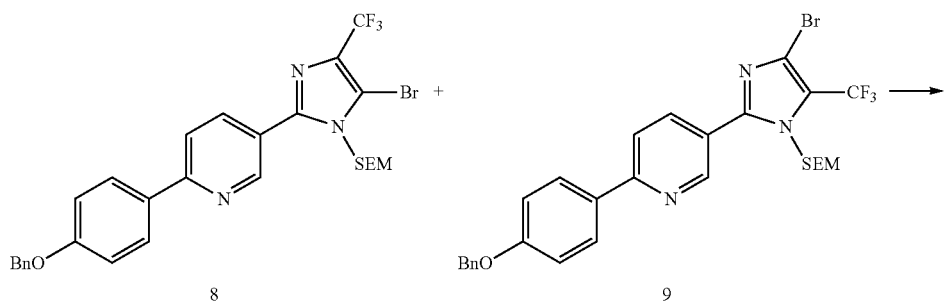

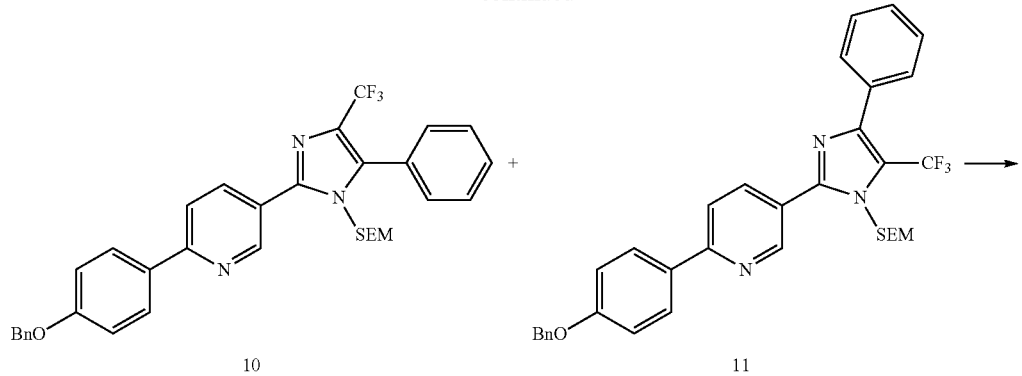

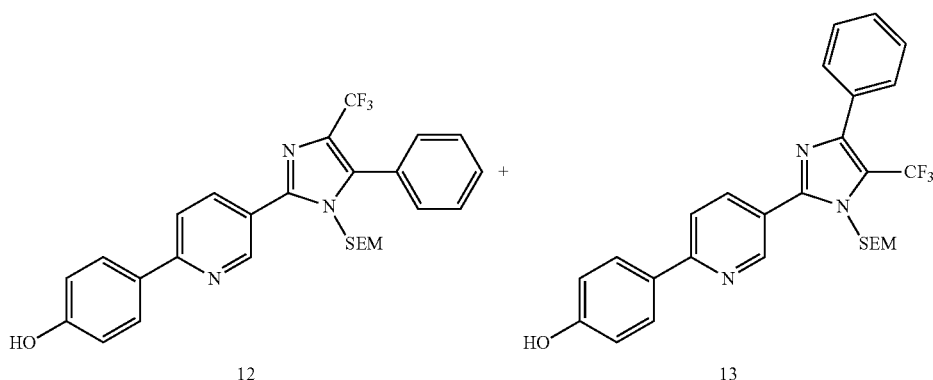

(4) Compound 4 (800 mg) and the mixture of Compound 6 and Compound 7 (1139 mg) were added to a mixed solvent of a 2M aqueous sodium carbonate solution (4131 µL) and dimethoxyethane (17 mL), and the mixture was subjected to nitrogen substitution. To this was added tetrakis(triphenylphosphine)palladium (24 mg), and the mixture was stirred at 80° C. for 12 hours. To the reaction solution were added ethyl acetate and water, and the mixture was stirred. The insoluble substance was filtered out. The organic layer was separated, washed with saturated brine, and dried over anhydrous magnesium sulfate. The solvent was distilled off under reduced pressure. The obtained residue was purified by silica gel column chromatography (n-hexane:ethyl acetate=91:9 to 67:33) to obtain a mixture of Compound 8 and Compound 9 (749 mg).

MS (m/z): 604/606 [M+H]$^+$ (5) A mixture of Compound 8 and Compound 9 (500 mg), phenylboronic acid (151 mg) and a 2M aqueous sodium carbonate solution (1654 µL) were added to a mixed solvent of dimethoxyethane (5 mL) and ethanol (5 mL), and the mixture was subjected to nitrogen substitution. To this was added a palladium chloride (dppf)-methylene chloride complex (68 mg), and the mixture was stirred at 80° C. overnight. Ethyl acetate and water were added to the reaction solution to carry out a liquid separation. The organic layer was separated and washed with saturated brine, and dried over anhydrous magnesium sulfate. The solvent was distilled off under reduced pressure. The obtained residue was purified by silica gel column chromatography (n-hexane: ethyl acetate=90:10 to 85:15) to obtain a mixture of Compound 10 and Compound 11 (403 mg).

MS (m/z): 602 [M+H]$^+$ (6) The mixture of Compound 10 and Compound 11 (400 mg) was dissolved in methanol (8 mL), and palladium-carbon (80 mg) was added, and the mixture was stirred under a hydrogen atmosphere at room temperature for 5 hours. The insoluble matter was filtered through a membrane-filter, and the filtrate was concentrated under reduced pressure to obtain a mixture of Compound 12 and Compound 13 (300 mg).

MS (m/z): 512 [M+H]$^+$

[Chemical Formula 76]

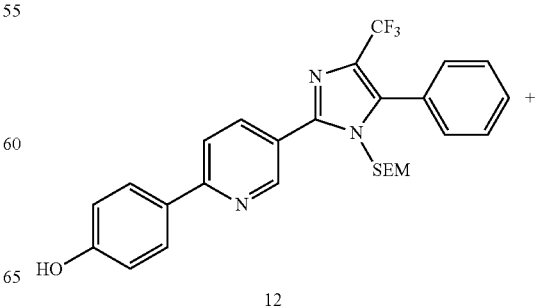

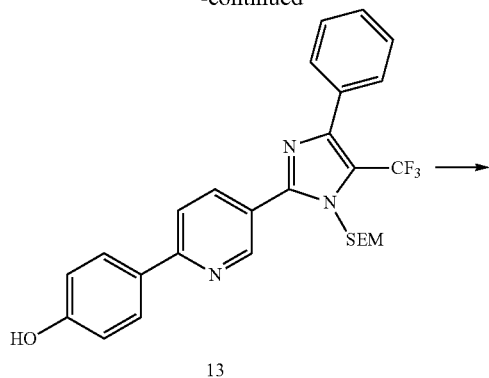

13

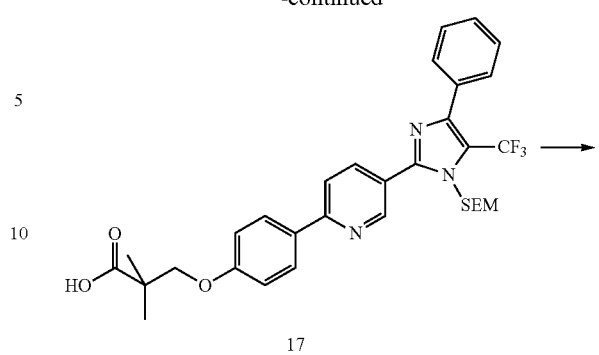

17

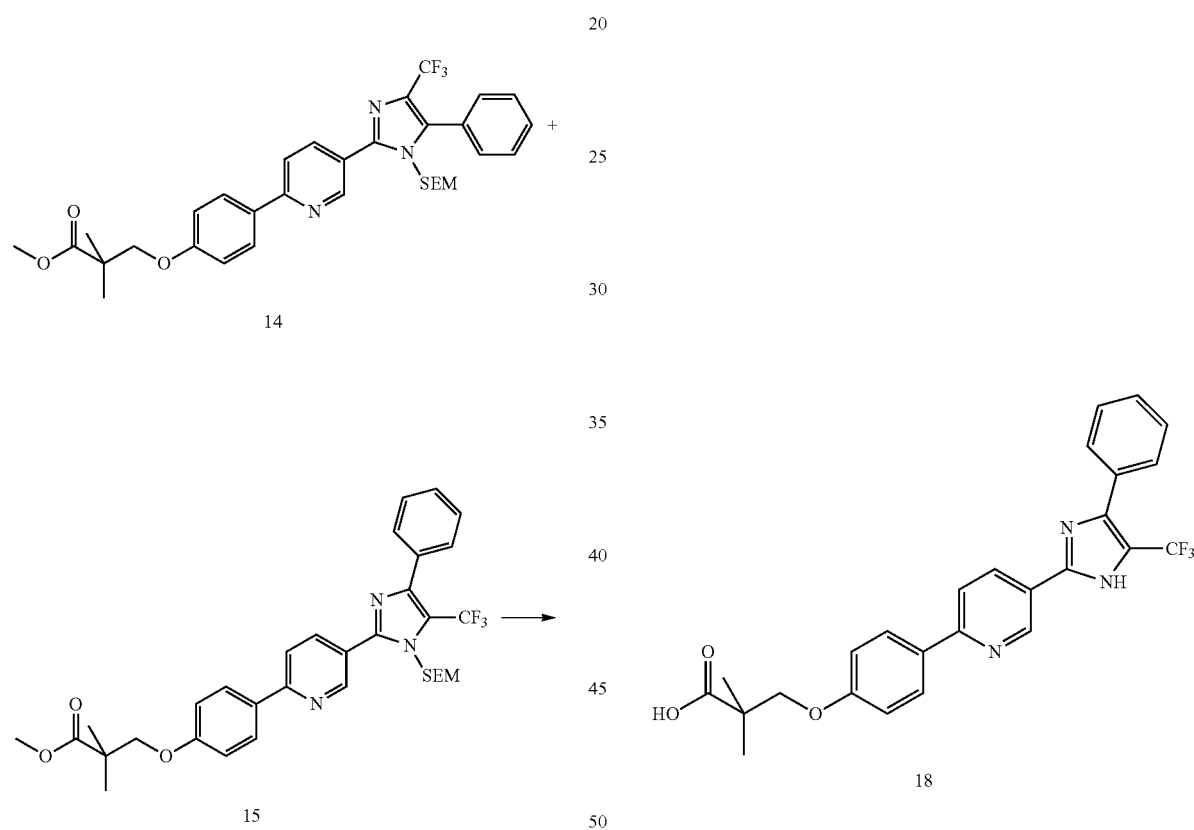

14

15

16

18

(7) A treatment was carried out in a manner similar to Reference Example 7-1 (1) using the mixture of Compound 12 and Compound 13 (300 mg) to obtain a mixture of Compound 14 and Compound 15 (58 mg).

MS (m/z): 626 [M+H]+

(8) A treatment was carried out in a manner similar to the Example 1-1 (2) using the mixture of Compound 14 and Compound 15 (58 mg) to obtain a mixture of Compound 16 and Compound 17 (57 mg).

MS (m/z): 612 [M+H]+

(9) A treatment was carried out in a manner similar to the Example 7 (2) using the mixture of Compound 16 and Compound 17 (57 mg) to obtain Compound 18 (34 mg).

MS (m/z): 482 [M+H]+

Example 10
[Chemical Formula 77]
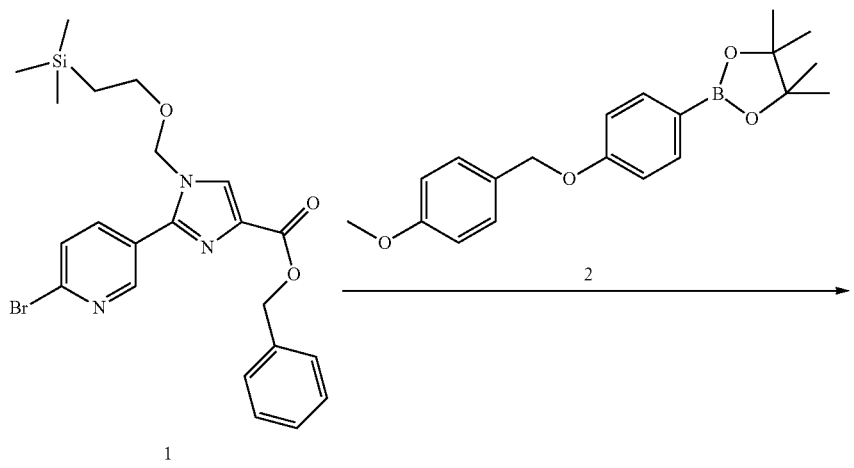
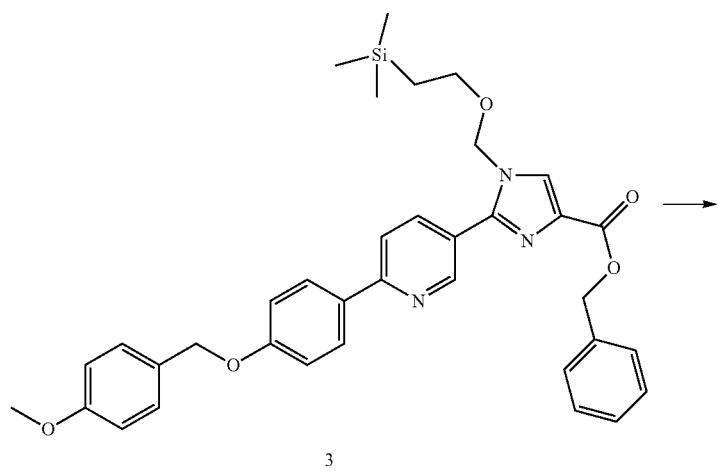
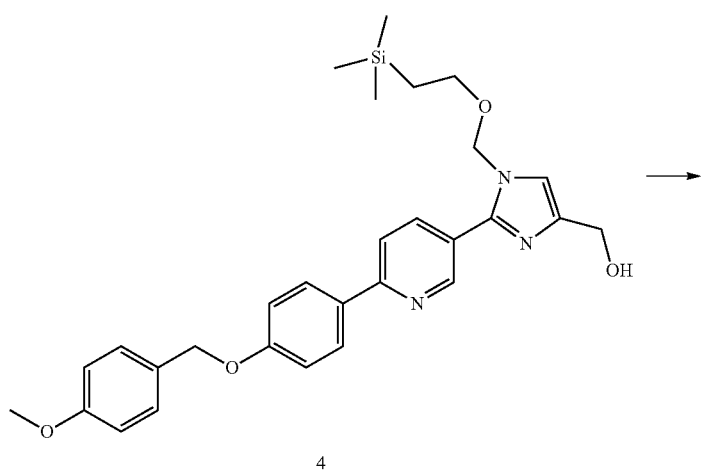

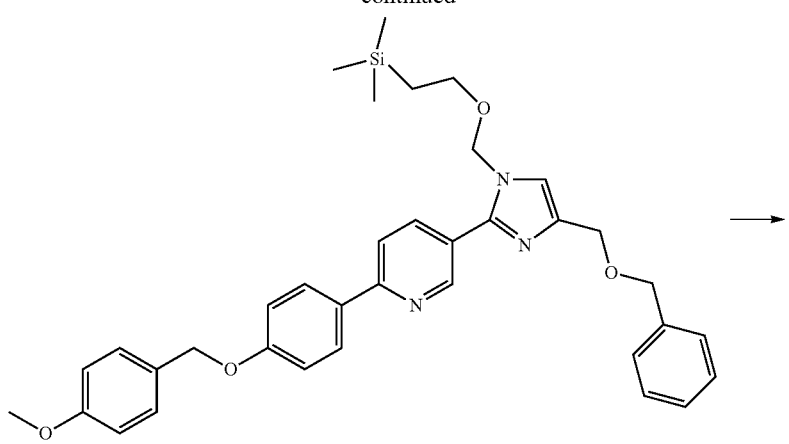
5
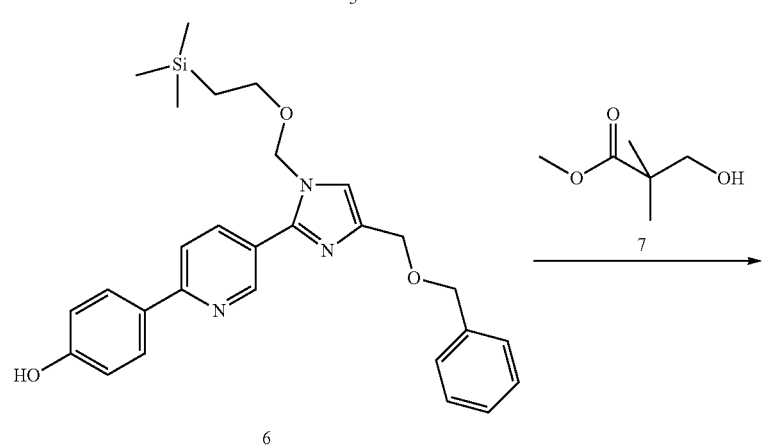
6
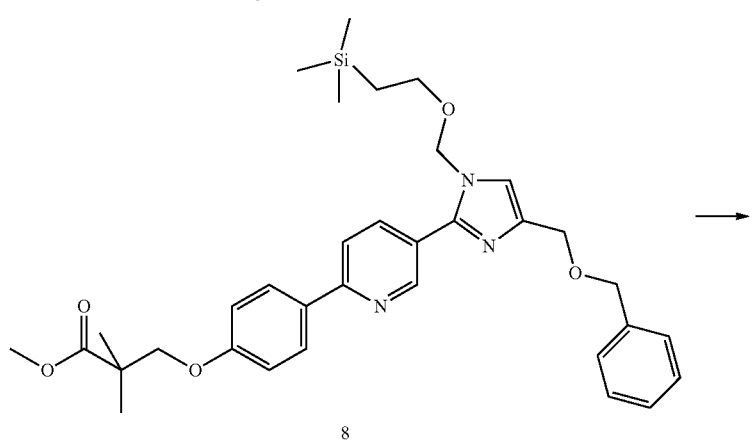
8
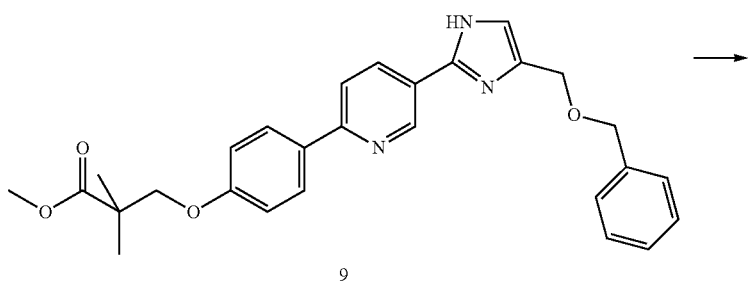
9

-continued

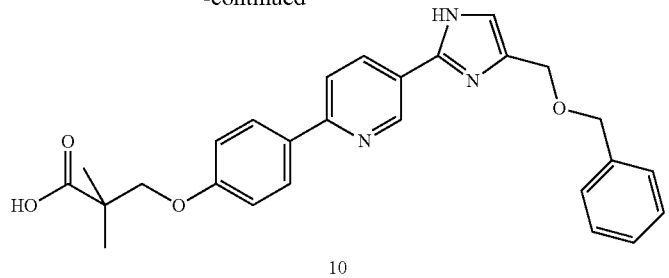

10

(1) A treatment was carried out in a manner similar to Example 7 (1) using Compound 1 (6.69 g) and Compound 2 (6.04 g) to obtain Compound 3 (6.54 g).
MS (m/z): 622 [M+H]$^+$ (2) Compound 3 (1.14 g) was dissolved in tetrahydrofuran (30 mL), and lithium aluminum hydride (104 mg) was added under ice cooling, and the mixture was stirred at 0° C. for 20 minutes. To the reaction solution were added sequentially water (1 mL), a 15% aqueous sodium hydroxide solution (1 mL) and water (2 mL), and the mixture was stirred under ice cooling for 30 minutes. The reaction solution was filtered through Celite, and the filtrate was concentrated under reduced pressure. The obtained residue was dissolved in tetrahydrofuran, the pH was adjusted to below 4 with a 10% aqueous citric acid solution, and ethyl acetate was added to carry out a liquid separation. The organic layer was separated and washed with water and saturated brine, and dried over anhydrous sodium sulfate. The solvent was distilled off under reduced pressure. The obtained residue was purified by silica gel column chromatography (chloroform:methanol=100:0 to 85:15), to the obtained solid were added ice-cold ethyl acetate and n-hexane, and the solid was collected by filtration to obtain Compound 4 (872 mg).
MS (m/z): 518 [M+H]$^+$ (3) Compound 4 (290 mg) was dissolved in tetrahydrofuran (10 mL) and N,N-dimethylformamide (10 mL), and 60% sodium hydride (34 mg) was added, and the mixture was sonicated for 1 minute. To this was added benzyl bromide (125 mg) at room temperature, and the mixture was further stirred at room temperature for 6 hours. Diethyl ether, n-hexane, ethyl acetate and water were added to the reaction solution to carry out a liquid separation. The organic layer was separated and washed with water and saturated brine, and dried over anhydrous sodium sulfate. The solvent was distilled off under reduced pressure. To the obtained residue were added diisopropyl ether and n-hexane, and the solid was collected by filtration to obtain Compound 5 (293 mg).
MS (m/z): 608 [M+H]$^+$ (4) Compound 5 (290 mg) was dissolved in methylene chloride (8 mL), and trifluoroacetic acid (4 mL) was added under ice cooling, and the mixture was stirred for 1 hour under the same conditions. To the reaction mixture was added an aqueous saturated sodium bicarbonate solution to make it basic (>pH 8), and a liquid separation was carried out by addition of ethyl acetate. The organic layer was separated and washed with water and saturated brine, and dried over anhydrous sodium sulfate. The solvent was distilled off under reduced pressure. The obtained residue was purified by silica gel column chromatography (chloroform:methanol=100:0 to 90:10), to the obtained residue were added diisopropyl ether and n-hexane, and the solid was collected by filtration to obtain Compound 6 (209 mg).
MS (m/z): 488 [M+H]$^+$ (5) A treatment was carried out in a manner similar to Reference Example 7-1 (1) using Compound 6 (208 mg) and Compound 7 (113 mg) to obtain Compound 8 (127 mg).
MS (m/z): 602 [M+H]$^+$ (6) A treatment was carried out in a manner similar to Example 7 (2) using Compound 8 (127 mg) to obtain Compound 9 (67 mg).
MS (m/z): 472 [M+H]$^+$ (7) A treatment was carried out in a manner similar to Example 1-1 (2) using Compound 9 (67 mg) to obtain Compound 10 (34 mg).
MS (m/z): 458 [M+H]$^+$ Example 11

[Chemical Formula 78]

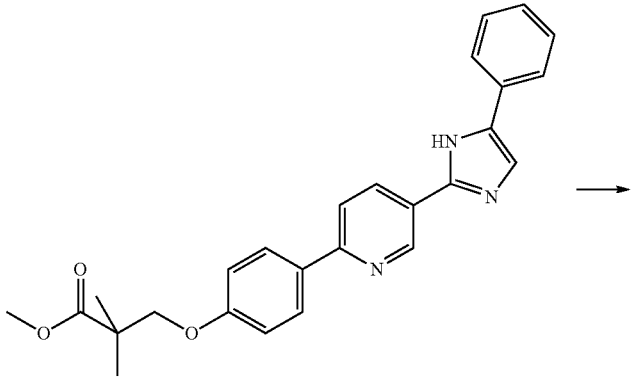

1

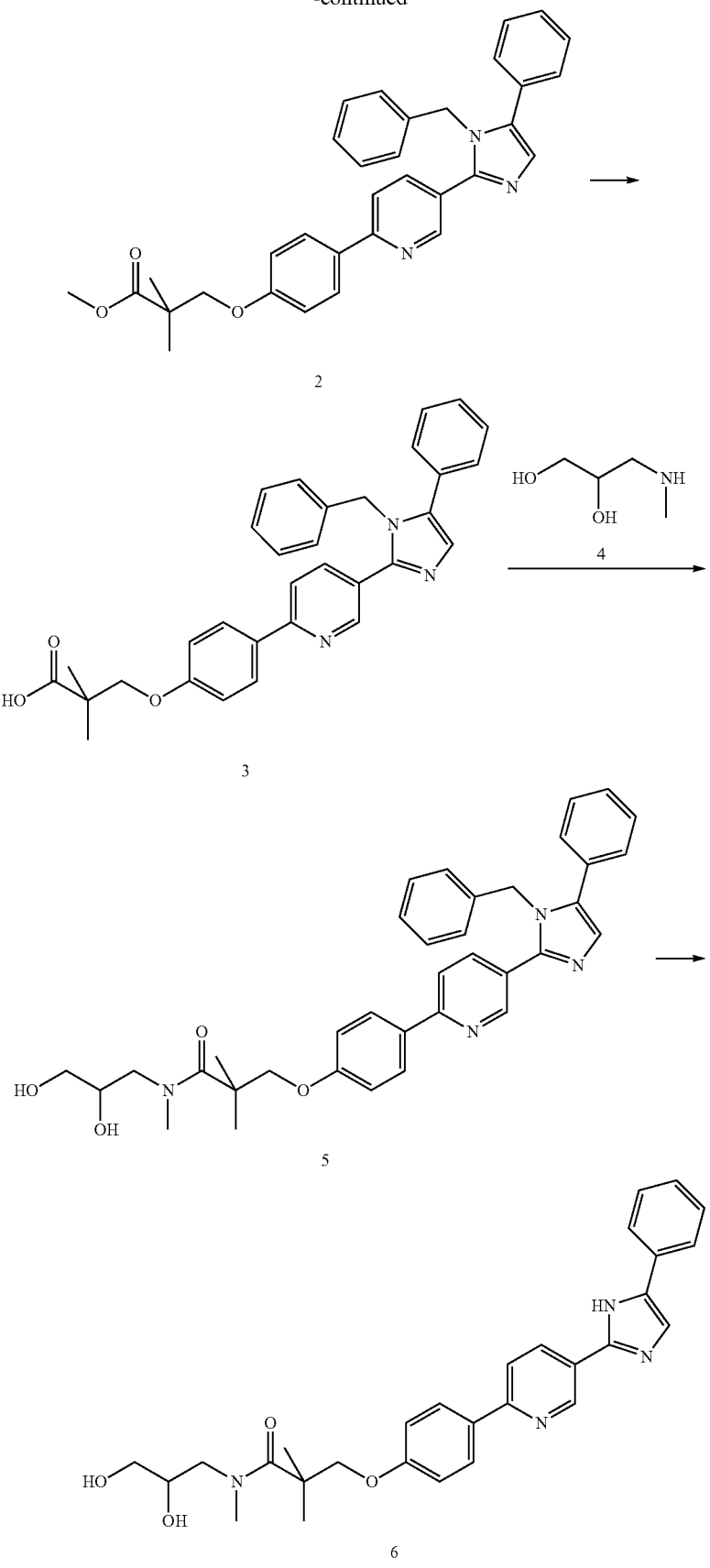

(1) Compound 1 (2.46 g) was dissolved in a mixed solvent of N,N-dimethylformamide (10 mL) and tetrahydrofuran (20 mL), and 60% sodium hydride (276 mg) was added under ice cooling. After the reaction solution was stirred for 5 minutes, to this solution was added benzyl bromide (1.18 g), and the solution was further stirred under ice cooling for 2 hours. To the reaction solution was added a 10% aqueous citric acid solution to adjust the pH to 4, and diethyl ether was added to carry out a liquid separation. The organic layer was separated and washed with water and saturated brine, and dried over anhydrous sodium sulfate. The solvent was distilled off under reduced pressure. The obtained residue was purified by silica gel column chromatography (chloroform:ethyl acetate=100:0 to 85:15) to obtain Compound 2 (2.82 g).

MS (m/z): 518 [M+H]$^+$ (2) A treatment was carried out in a manner similar to the Example 1-1 (2) using Compound 2 (2.82 g) to obtain Compound 3 (2.58 g).

MS (m/z): 504 [M+H]$^+$ (3) Compound 3 (200 mg), Compound 4 (83 mg), 1-hydroxybenzotriazole (107 mg), and 1-(3-dimethylaminopropyl)-3-ethyl carbodiimide hydrochloride (152 mg) were added to N,N-dimethylformamide, and the mixture was stirred at room temperature for two days. The solvent was distilled off under reduced pressure, and ethyl acetate and a saturated aqueous sodium hydrogen carbonate solution were added to the obtained residue to carry out a liquid separation. The organic layer was separated, and washed with a 10% aqueous citric acid solution, water and saturated brine, and dried over anhydrous sodium sulfate. The solvent was distilled off under reduced pressure. The obtained residue was purified by silica gel column chromatography (chloroform:methanol=100:0 to 85:15) to obtain Compound 5 (119 mg).

MS (m/z): 591 [M+H]$^+$ (4) Compound 5 (115 mg) was dissolved in tetrahydrofuran (10 mL), and 20% palladium hydroxide-carbon (130 mg) was added, and the mixture was stirred under a hydrogen atmosphere at room temperature for 8 hours. The solvent was substituted with ethanol (10 mL), and the mixture was stirred under a hydrogen atmosphere at 75° C. for 4 hours. The reaction solution was subject to nitrogen gas substitution, subsequently diluted with chloroform and methanol, and filtered. The solvent was distilled off under reduced pressure, the obtained residue was purified by silica gel column chromatography (chloroform:methanol=100:0 to 85:15), the obtained oil was solidified with diethyl ether and diisopropyl ether, and the obtained solid was collected by filtration to obtain Compound 6 (36 mg).

MS (m/z): 501 [M+H]$^+$

Example 12

[Chemical Formula 79]

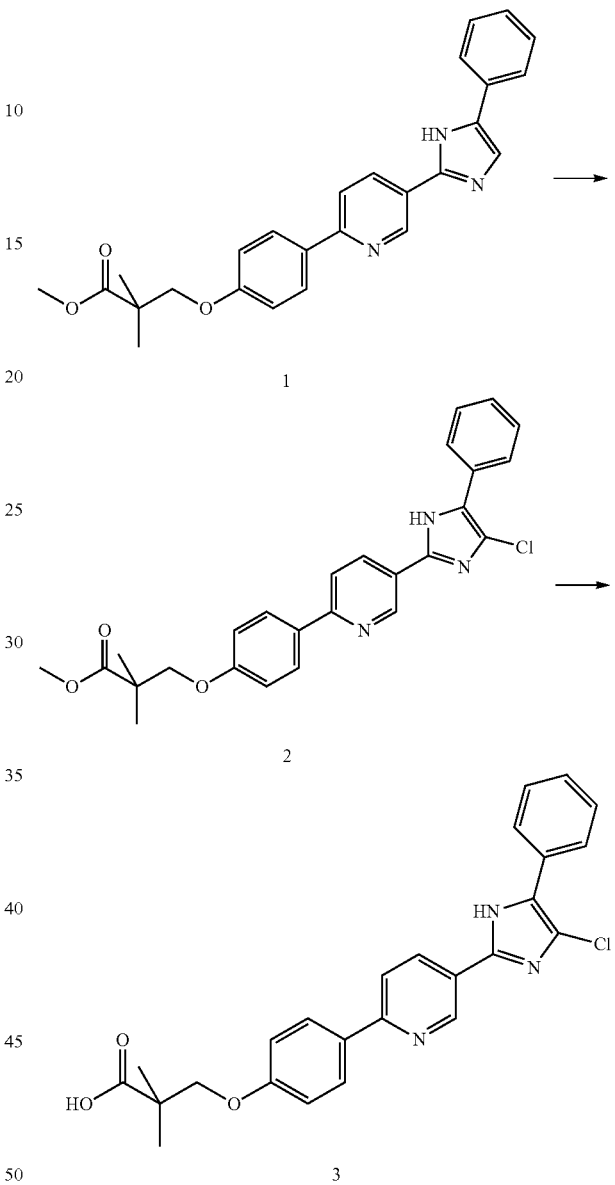

(1) Compound 1 (see Compound 3 in Example 1-1) (200 mg) and N-chlorosuccinimide (102 mg) were added to chloroform (30 mL), and the mixture was stirred at room temperature overnight. Additional N-chlorosuccinimide (102 mg) was added, and the mixture was further stirred for 4 hours. The reaction solution was purified by silica gel column chromatography (chloroform:ethyl acetate=100:0 to 50:50), and the obtained oil was solidified with diisopropyl ether, and diluted with n-hexane. Subsequently, the solid was collected by filtration to obtain Compound 2 (207 mg).

MS (m/z): 462/464 [M+H]$^+$ (2) Compound 2 (100 mg), methanol (500 μL), and 60% sodium hydride (26 mg) were added to 1,4-dioxane (5 mL), and the mixture was stirred at 95° C. for 1 hour. N,N-Dimethylacetamide (5 mL) was added, and the mixture was stirred at 95° C. overnight. A 10% aqueous citric acid solution, n-hexane and ethyl acetate were added to the reaction mixture to carry out a liquid separation. The organic layer was separated, washed with water and saturated brine, dried over sodium sulfate and concentrated under reduced pressure. The residue was purified by silica gel column chromatography (chloroform:ethyl acetate=100:0 to 50:50), and to the obtained solid were added diisopropyl ether and isopropyl alcohol, and filtered to obtain Compound 3 (51 mg).

MS (m/z): 448/450 [M+H]$^+$

Example 13

[Chemical Formula 80]

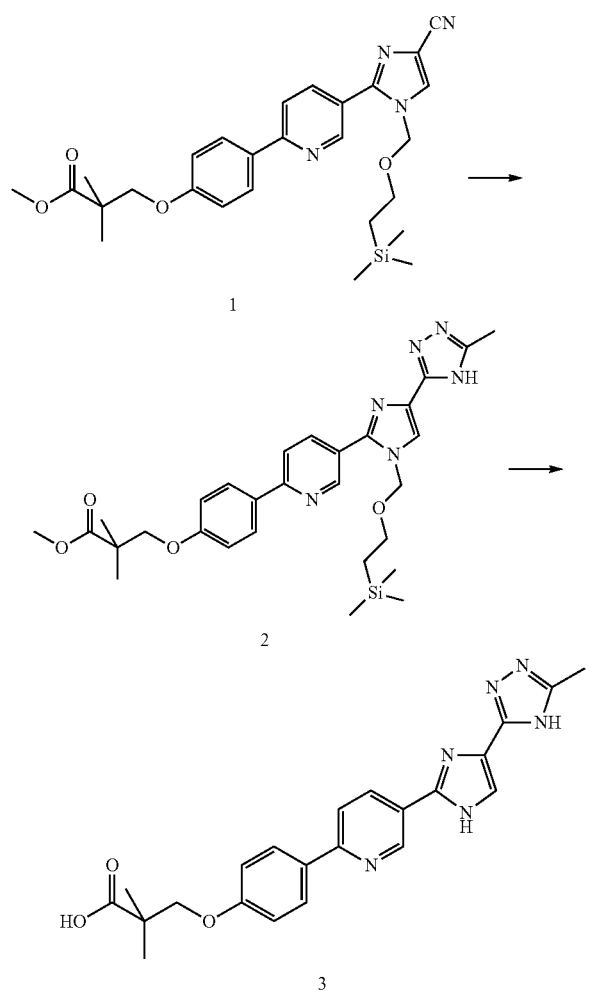

(1) Compound 1 (250 mg), acetamidine hydrochloride (70 mg), copper bromide (4 mg), and cesium carbonate (482 mg) were added to dimethylsulfoxide (4 mL), and the mixture was stirred at 120° C. overnight. To the reaction solution were added water and ethyl acetate, and the mixture was stirred. The insoluble substance was filtered. The organic layer of the filtrate was separated, washed with saturated brine, and dried over anhydrous sodium sulfate. The solvent was distilled off under reduced pressure. The obtained residue was purified by silica gel column chromatography (chloroform:methanol=100:0 to 90:10), LC-MS preparative, and diol silica gel column chromatography (n-hexane:ethyl acetate=50:50 to 0:100) to obtain Compound 2 (20.4 mg).

MS (m/z): 563 [M+H]$^+$ (2) A treatment was carried out in a manner similar to the Example 6 (7) using Compound 2 (19 mg) to obtain Compound 3 (11.5 mg).

MS (m/z): 419 [M+H]$^+$

Example 14

[Chemical Formula 81]

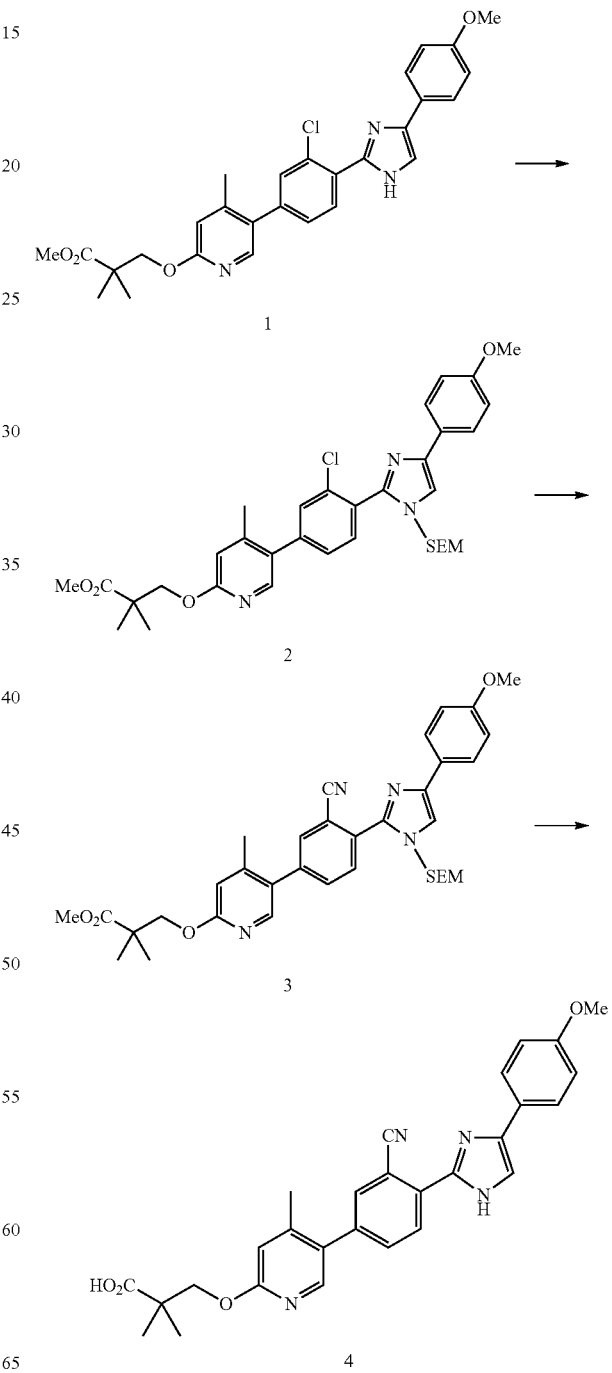

(1) A treatment was carried out in a manner similar to Example 6 (2) using Compound 1 (120 mg) to obtain Compound 2 (112 mg).

MS (m/z): 636/638 [M+H]$^+$ (2) Compound 2 (110 mg), $K_4[Fe(CN)_6]3H_2O$ (37 mg), palladium acetate (4 mg), butyl di-1-adamantylphosphine (19 mg) and sodium carbonate (4 mg) were added to N-methylpyrrolidone (2 mL), and the mixture was stirred under a nitrogen atmosphere at 140° C. for 2.5 hours and then at 160° C. for 3 hours. After the reaction solution was cooled to room temperature, ethyl acetate and water were added thereto to carry out a liquid separation. The organic layer was separated, washed with water and saturated brine, and dried over magnesium sulfate. The solvent was distilled off under reduced pressure. The obtained residue was purified by silica gel column chromatography (n-hexane:ethyl acetate=90:10 to 50:50) to obtain Compound 3 (32 mg).

MS (m/z): 627 [M+H]$^+$ (3) To Compound 3 (30 mg) was added a 1M tetrabutylammonium fluoride-tetrahydrofuran solution (239 μL), and the mixture was stirred at room temperature for 2.5 hours and further 60° C. for 4 hours. A saturated aqueous sodium hydrogen carbonate solution and ethyl acetate were added to the reaction solution to carry out a liquid separation. The organic layer was separated, washed with saturated brine, and dried over anhydrous magnesium sulfate. The solvent was distilled off under reduced pressure. The obtained residue was dissolved in methanol (1 mL) a 1N aqueous sodium hydroxide solution (479 μL) was added, and the mixture was stirred at room temperature for 17 hours. After 1N hydrochloric acid (479 μL) was added to the reaction solution, ethyl acetate was added to carry out a liquid separation. The organic layer was separated, washed with saturated brine, and dried over anhydrous magnesium sulfate. The solvent was distilled off under reduced pressure. After the obtained residue was purified by silica gel column chromatography (n-hexane:ethyl acetate=100:0 to 90:10), diethyl ether was added. The solid was collected by filtration and dried to obtain Compound 4 (13.8 mg).

MS (m/z): 483 [M+H]$^+$

Example 15-1

[Chemical Formula 82]

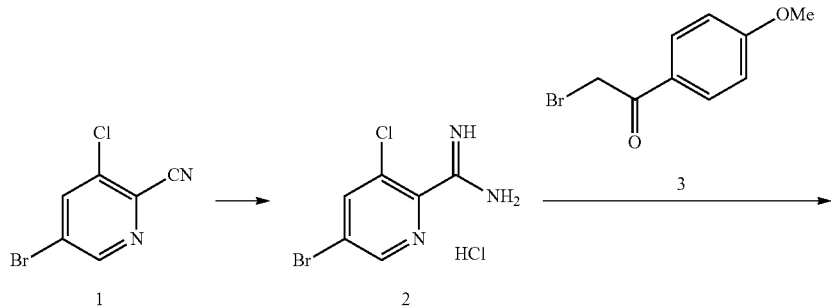

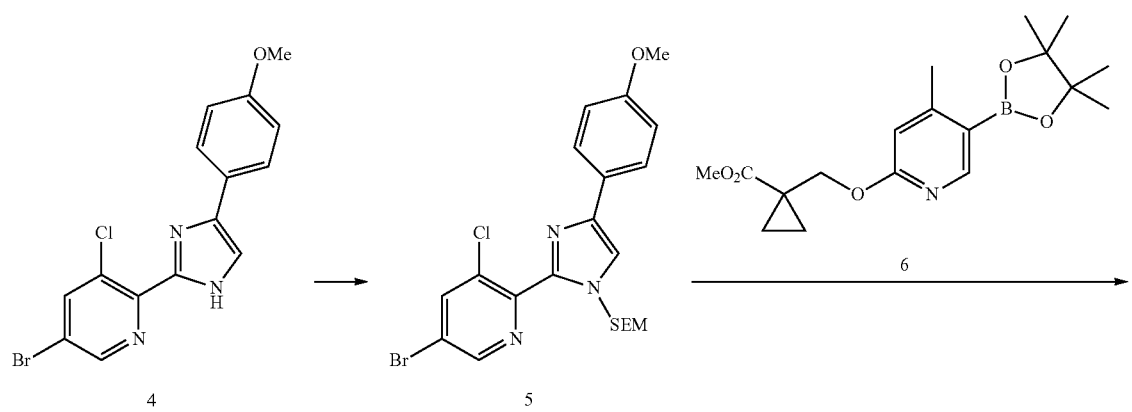

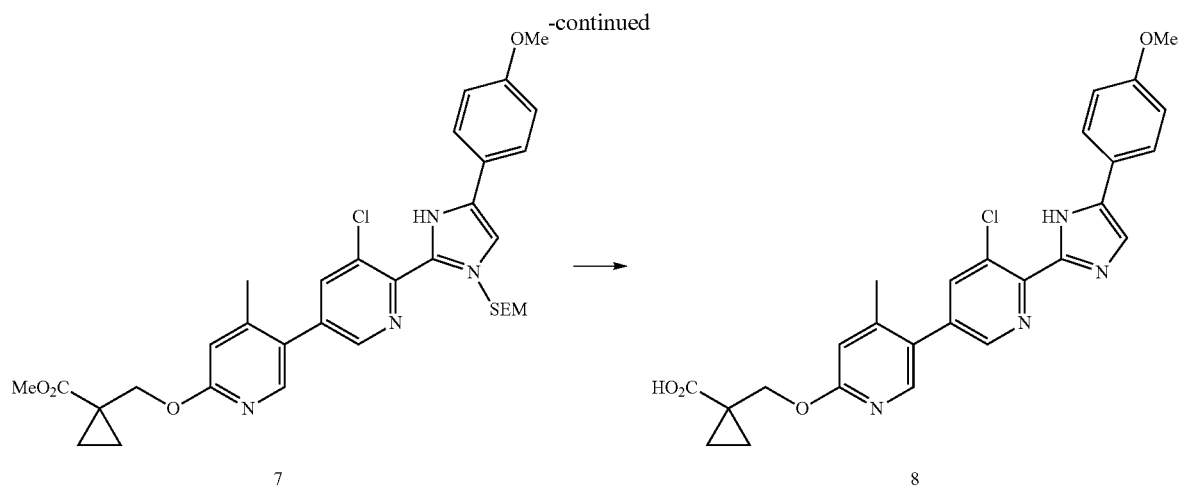

(1) Compound 1 (1394 mg) was dissolved in methanol (14 mL), and sodium methylate (35 mg) was added, and the mixture was stirred at room temperature overnight. To the reaction solution was added ammonium chloride (377 mg), and the mixture was stirred at room temperature for 1 hour and then heated at reflux for 7 hours. The reaction solution was concentrated under reduced pressure, to the obtained residue was added ethyl acetate, and the solid was collected by filtration and dried to obtain Compound 2 (1268 mg) as a hydrochloride salt.

MS (m/z): 234/236 [M+H]$^+$ (2) A treatment was carried out in a manner similar to the Example 3-1 (1) using Compound 2 (600 mg) and Compound 3 (533 mg) to obtain Compound 4 (465 mg).

MS (m/z): 364/366 [M+H]$^+$ (3) A treatment was carried out in a manner similar to Example 6 (2) using Compound 4 (450 mg) to obtain Compound 5 (605 mg).

MS (m/z): 494/496 [M+H]$^+$ (4) A treatment was carried out in a manner similar to Example 7 (1) using Compound 5 (300 mg) and Compound 6 (253 mg) to obtain Compound 7 (88 mg).

MS (m/z): 634/635 [M+H]$^+$ (5) A treatment was carried out in a manner similar to Example 6 (7) using Compound 7 (85 mg) to obtain Compound 8 (59 mg).

MS (m/z): 491/493 [M+H]$^+$

Example 15-2

A treatment was carried out in a manner similar to the Example 15-1 to obtain a compound of Example 15-2 in Table 6 below.

TABLE 6

| Example | Starting material | Bromoketone | Product | MS (m/z) |
|---|---|---|---|---|
| 15-2 | (structure) | (structure) | (structure) | 461/463 [M + H]$^+$ |

Example 16

[Chemical Formula 83]

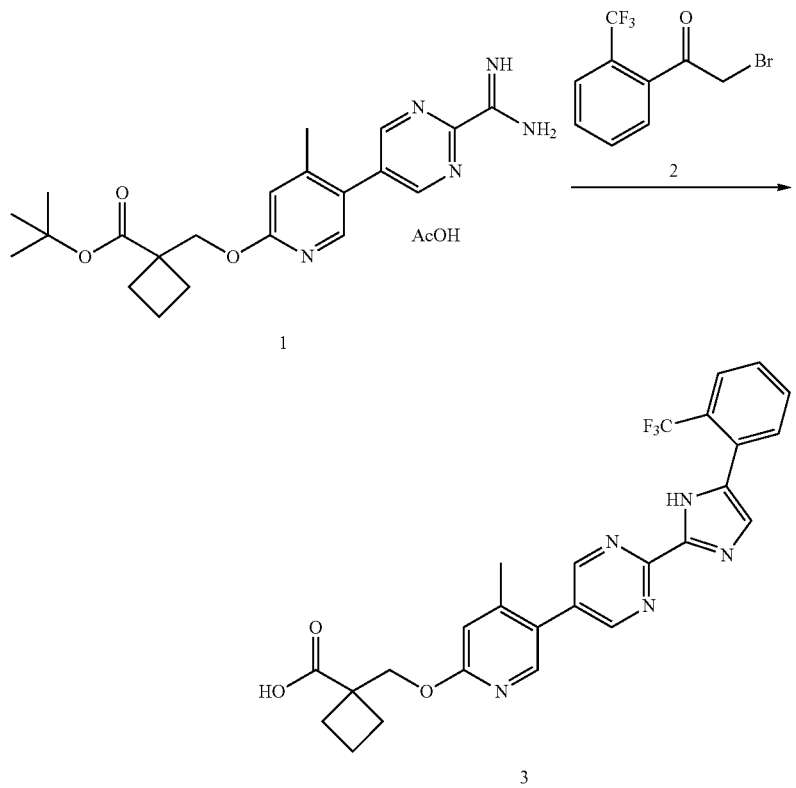

Compound 1 (see Reference Example 7-11) (200 mg), Compound 2 (175 mg) and potassium carbonate (242 mg) were added to a mixed solvent of chloroform (5 mL) and saturated brine (5 mL), and the mixture was stirred at 70° C. for 7 hours. The organic layer was separated from the reaction solution and dried over anhydrous sodium sulfate, and subsequently the solvent was distilled off under reduced pressure. The obtained residue was dissolved in methanol (7 mL) and tetrahydrofuran (7 mL), a 2N aqueous sodium hydroxide solution (2186 μL) was added, and the mixture was stirred at 50° C. for 5 hours. The reaction solution was concentrated under reduced pressure, and to the obtained residue was added trifluoroacetic acid (5 mL), and the mixture was stirred at room temperature for 7 hours. The reaction solution was concentrated under reduced pressure, and to the obtained residue was added a small amount of tetrahydrofuran, and neutralized with a 1N aqueous sodium hydroxide solution. After a few drops of acetic acid was added to the reaction solution, ethyl acetate was added thereto to carry out a liquid separation. The organic layer was separated and dried over anhydrous sodium sulfate, and subsequently the solvent was distilled off under reduced pressure. The obtained residue was purified by silica gel column chromatography (chloroform:methanol=100:0 to 94:6), solidified from diethyl ether and collected by filtration to obtain Compound 3 (12.3 mg).

MS (m/z): 510 [M+H]$^+$

Example 17

[Chemical Formula 84]

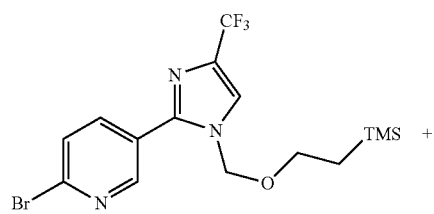 TMS +

-continued
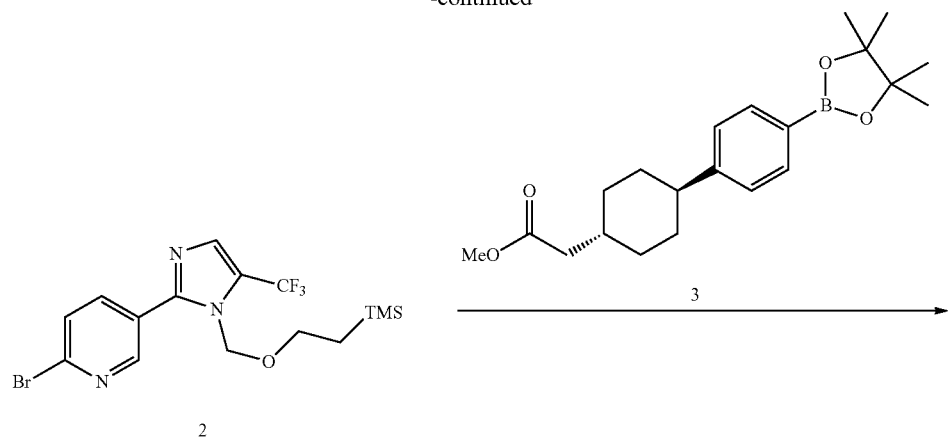
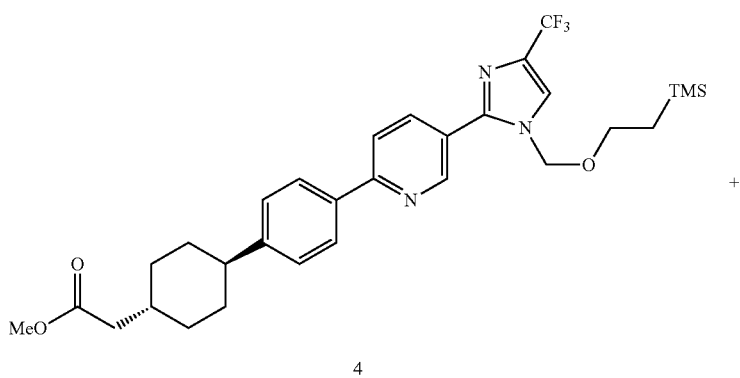
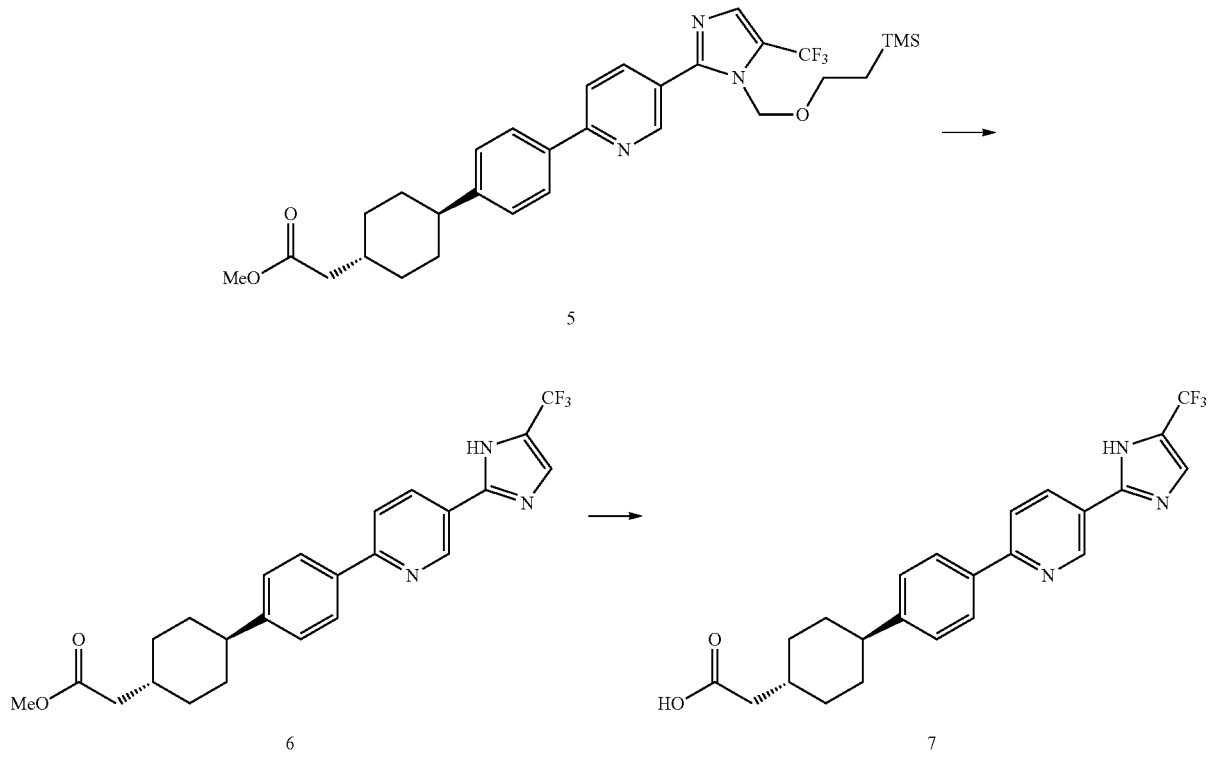

(1) A treatment was carried out in a manner similar to the Example 7 (1) using a mixture of Compound 1 and Compound 2 (300 mg) and Compound 3 (357 mg) to obtain a mixture of Compound 4 and Compound 5 (317 mg).

MS (m/z): 574 [M+H]$^+$ (2) A treatment was carried out in a manner similar to the Example 7 (2) using the mixture of Compound 4 and Compound 5(369 mg) to obtain Compound 6 (235 mg).

MS (m/z): 444 [M+H]$^+$ (3) A treatment was carried out in a manner similar to the Example 1-1 (2) using Compound 6 (195 mg) to obtain Compound 7 (160 mg).

MS (m/z): 430 [M+H]$^+$

Example 18-1

[Chemical Formula 85]

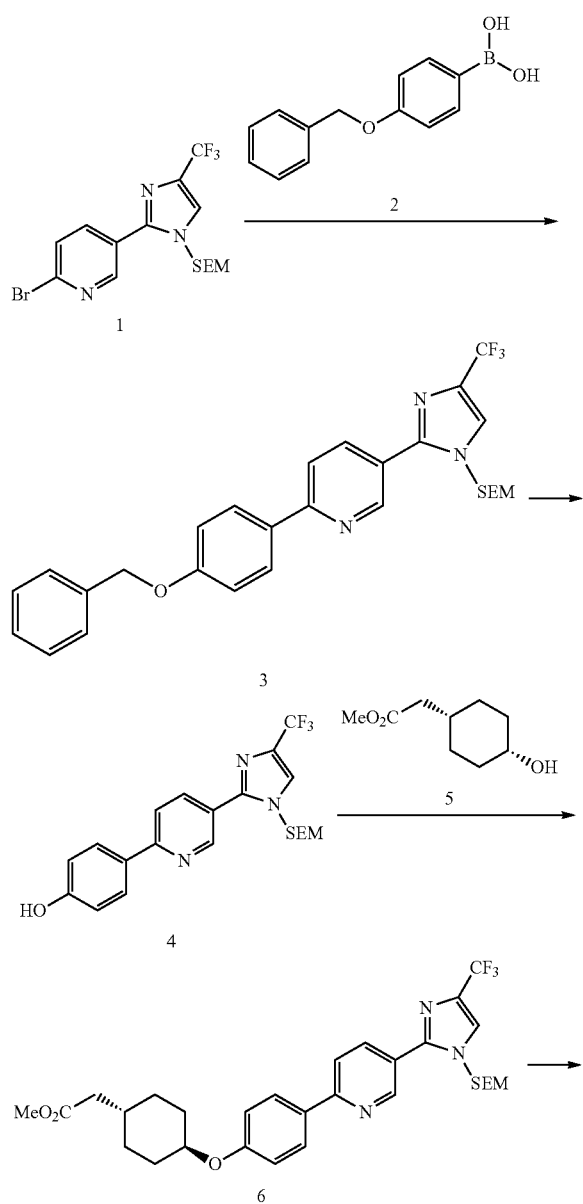

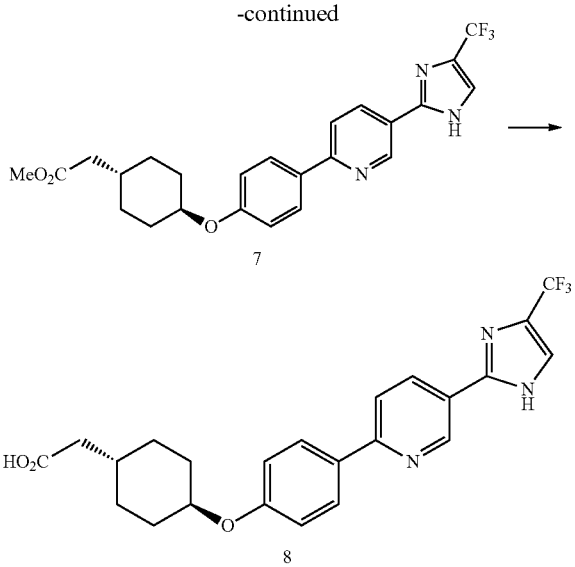

(1) A treatment was carried out in a manner similar to the Example 7 (1) using Compound 1 (1.0 g) and Compound 2 (1.08 g) to obtain Compound 3 (1.04 g).

MS (m/z): 525 [M+H]$^+$ (2) Compound 3 (770 mg) was dissolved in methanol (8 mL) and tetrahydrofuran (6 mL), 10% palladium-carbon (154 mg) was added under a nitrogen atmosphere, a hydrogen atmosphere was substituted therefor, and the mixture was stirred at room temperature for 5 hours. The reaction mixture was filtered through a membrane-filter, and the filtrate was concentrated under reduced pressure. The obtained residue was diluted with methanol, to this was added activated charcoal, the mixture was filtered through Celite, and the filtrate was concentrated under reduced pressure. The residue was crystallized by sonication to obtain Compound 4 (612 mg).

MS (m/z): 436 [M+H]$^+$ (3) Compound 4 (150 mg), Compound 5 (119 mg) and 1,1'-(azodicarbonyl)dipiperidine (ADDP) (217 mg) were mixed in tetrahydrofuran (3 mL), to this was added tributylphosphine (213 μL), and the mixture was stirred at 70° C. for 8 hours. Compound 5 (119 mg), 1,1'-(azodicarbonyl) dipiperidine (217 mg) and tributylphosphine (213 μL) were additionally added, and the mixture was stirred at 70° C. for further 2.5 hours. To the reaction solution was added diethyl ether, and the insoluble matter was filtered. The filtrate was concentrated under reduced pressure, and purificated by silica gel column chromatography (n-hexane:ethyl acetate=85:15 to 67:33) to obtain Compound 6 (117 mg).

MS (m/z): 590 [M+H]$^+$ (4) A treatment was carried out in a manner similar to the Example 7 (2) using Compound 6 (117 mg) to obtain Compound 7 (74 mg).

MS (m/z): 460 [M+H]$^+$ (5) A treatment was carried out in a manner similar to the Example 1-1 (2) using Compound 7 (73 mg) to obtain Compound 8 (27.5 mg).

MS (m/z): 446 [M+H]$^+$

Example 18-2

A treatment was carried out in a manner similar to the Example 18-1 to obtain a compound of Example 18-2 in Table 7 below.

TABLE 7

| Example | Intermediate 1 | Intermediate 2 |
|---|---|---|
| 18-2 | (structure) | (structure) |

| Example | Product | MS (m/z) |
|---|---|---|
| 18-2 | (structure) | 446 [M + H]⁺ |

Example 19-1

[Chemical Formula 86]

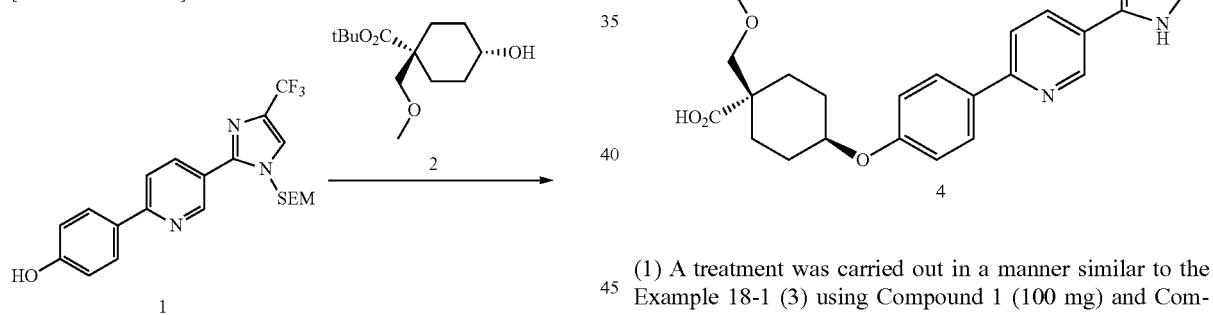

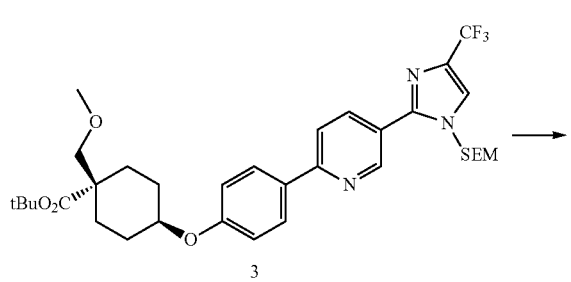

(1) A treatment was carried out in a manner similar to the Example 18-1 (3) using Compound 1 (100 mg) and Compound 2 (168 mg) to obtain Compound 3 (152 mg).

MS (m/z): 662 [M+H]⁺

(2) Compound 3 (151 mg) was dissolved in trifluoroacetic acid (3 mL) and water (0.3 mL), and the mixture was stirred at room temperature overnight. The reaction solution was concentrated under reduced pressure, the obtained residue was dissolved in tetrahydrofuran, and 0.1N phosphate buffer (pH 7) and ethyl acetate were added to be mixed. The organic layer was separated and concentrated under reduced pressure. To the obtained residue was added cooled methanol, and the solid was collected by filtration to obtain Compound 4 (89.7 mg).

MS (m/z): 476 [M+H]⁺

Examples 19-2 to 19-4

A treatment was carried out in a manner similar to the Example 19-1 to obtain compounds of Examples 19-2 to 19-4 in Table 8 below.

TABLE 8

| Example | Intermediate 1 | Intermediate 2 |
|---|---|---|
| 19-2 | (structure: 4-hydroxyphenyl-pyridine-imidazole-CF₃ with SEM protecting group) | (structure: tBuO₂C, methoxymethyl cyclohexanol) |
| 19-3 | (structure: 4-hydroxy-2-methylphenyl-pyridine-imidazole-CF₃ with SEM) | (structure: tBuO₂C, methoxymethyl cyclohexanol) |
| 19-4 | (structure: 6-hydroxypyridyl-pyridine-imidazole-CF₃ with SEM) | (structure: tBuO₂C, methoxymethyl cyclohexanol) |

| Example | Product | MS (m/z) |
|---|---|---|
| 19-2 | (structure) | 476 [M + H]⁺ |

TABLE 8-continued

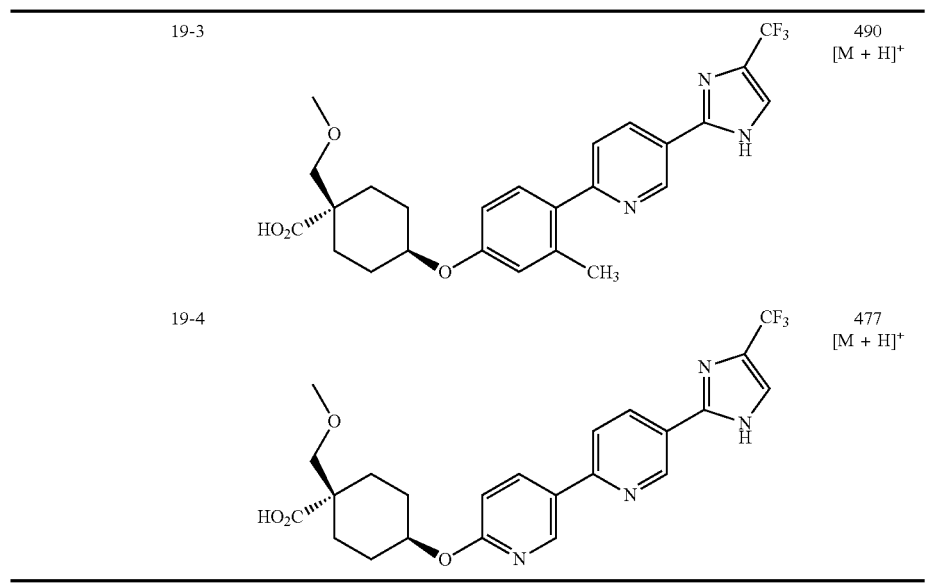

| | | | |
|---|---|---|---|
| 19-3 | | CF$_3$ | 490 [M + H]$^+$ |
| 19-4 | | CF$_3$ | 477 [M + H]$^+$ |

Example 20-1

[Chemical Formula 87]

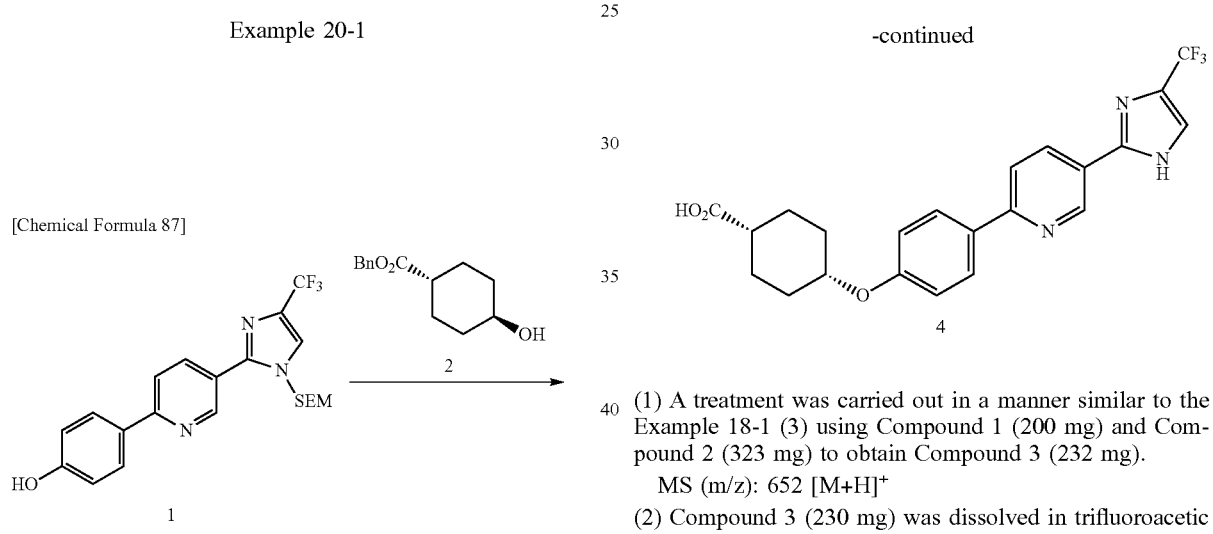

-continued

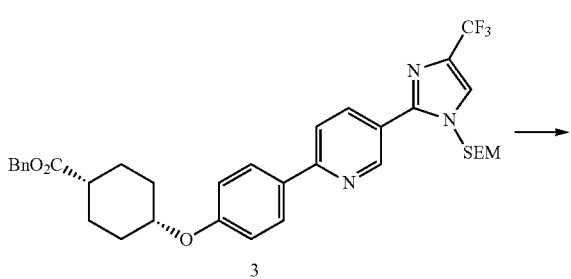

(1) A treatment was carried out in a manner similar to the Example 18-1 (3) using Compound 1 (200 mg) and Compound 2 (323 mg) to obtain Compound 3 (232 mg).

MS (m/z): 652 [M+H]$^+$ (2) Compound 3 (230 mg) was dissolved in trifluoroacetic acid (2.3 mL) and water (0.2 mL), and the mixture was stood at room temperature for one day. The reaction solution was concentrated under reduced pressure, and ethyl acetate and a saturated aqueous sodium hydrogen carbonate solution were added to carry out a liquid separation. The organic layer was separated, washed with saturated brine, and dried over anhydrous magnesium sulfate. The solvent was distilled off under reduced pressure. The obtained residue was dissolved in methanol (4.6 mL) and tetrahydrofuran (2.3 mL), 10% palladium-carbon (46 mg) was added, and the mixture was stirred under a hydrogen atmosphere for 7 hours. The reaction solution was filtered, the filtrate was concentrated under reduced pressure, and the obtained solid was collected by filtration and dried to obtain Compound 4 (145 mg).

MS (m/z): 432 [M+H]$^+$

Example 20-2

A treatment was carried out in a manner similar to the Example 20-1 to obtain a compound of Example 20-2 in Table 9 below.

TABLE 9

| Example | Intermediate 1 | Intermediate 2 |
|---|---|---|
| 20-2 | | |

| Example | Product | MS (m/z) |
|---|---|---|
| 20-2 | | 432 [M + H]+ |

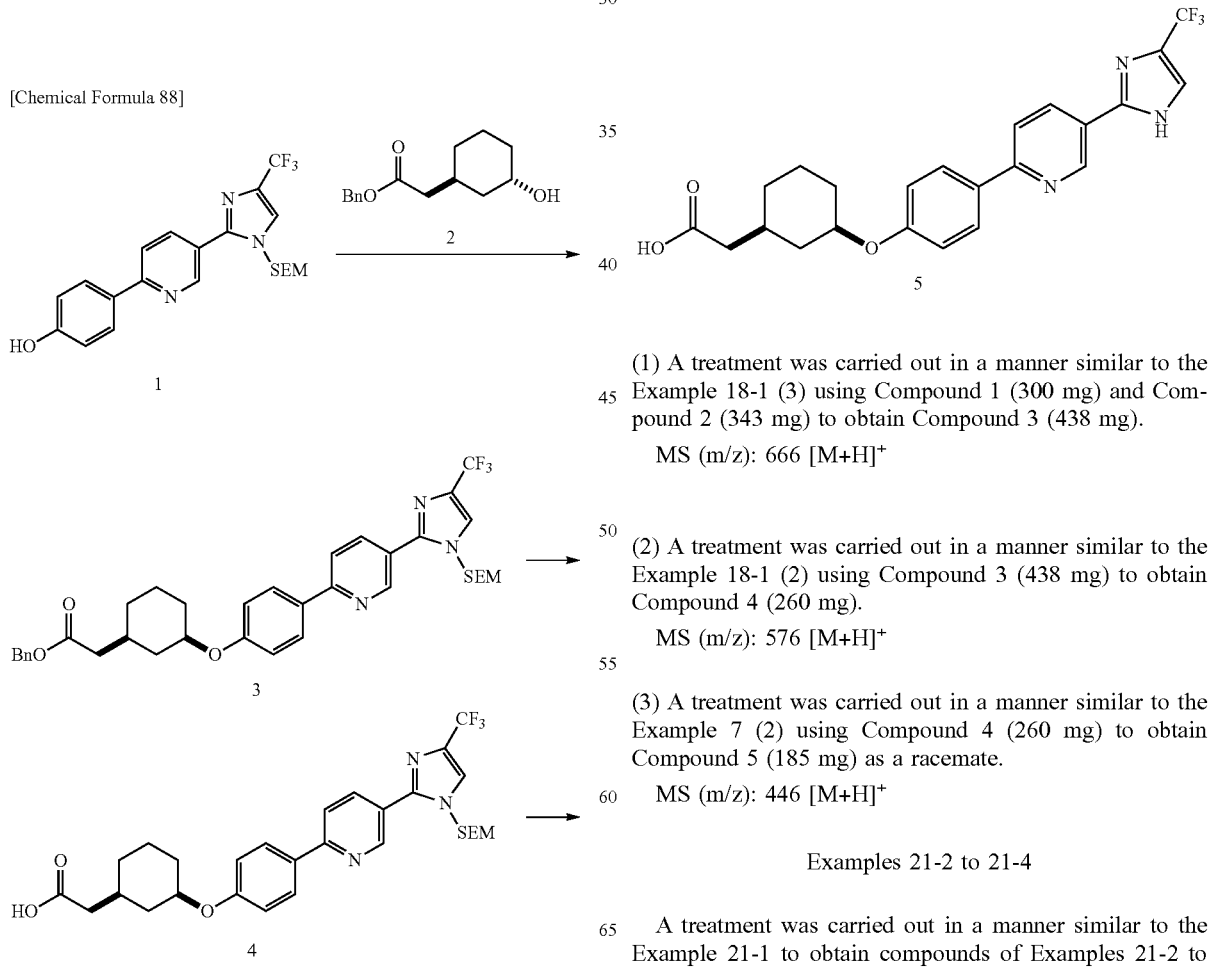

Example 21-1

[Chemical Formula 88]

(1) A treatment was carried out in a manner similar to the Example 18-1 (3) using Compound 1 (300 mg) and Compound 2 (343 mg) to obtain Compound 3 (438 mg).

MS (m/z): 666 [M+H]+

(2) A treatment was carried out in a manner similar to the Example 18-1 (2) using Compound 3 (438 mg) to obtain Compound 4 (260 mg).

MS (m/z): 576 [M+H]+

(3) A treatment was carried out in a manner similar to the Example 7 (2) using Compound 4 (260 mg) to obtain Compound 5 (185 mg) as a racemate.

MS (m/z): 446 [M+H]+

Examples 21-2 to 21-4

A treatment was carried out in a manner similar to the Example 21-1 to obtain compounds of Examples 21-2 to 21-4 in Table 10 below.

TABLE 10
| Example | Intermediate 1 | Intermediate 2 |
|---|---|---|
| 21-2 | 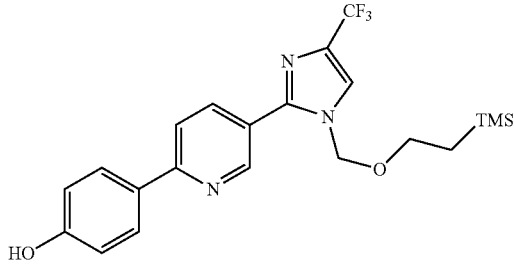 | 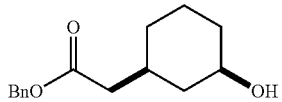 [SMILES: O=C(C[C@H]1CCC[C@@H](O)C1)OCc1ccccc1] |
| 21-3 | 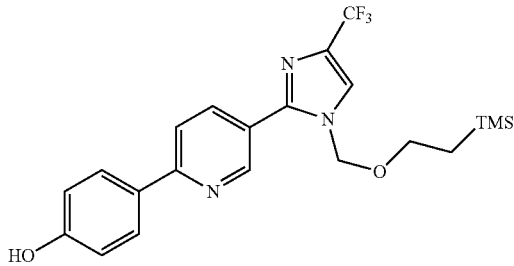 [SMILES: C[Si](C)(C)CCOCn1cc(C(F)(F)F)nc1-c1ccc(-c2ccc(O)cc2)nc1] | 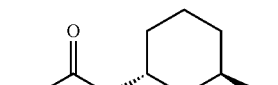 |
| 21-4 | 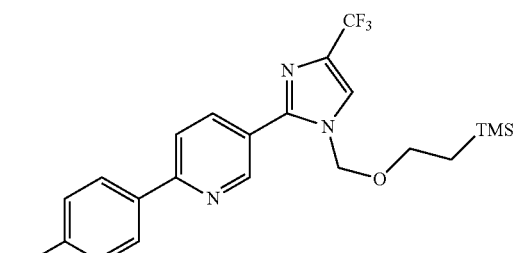 | 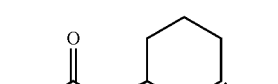 |
| Example | Product | MS (m/z) |
|---|---|---|
| 21-2 | 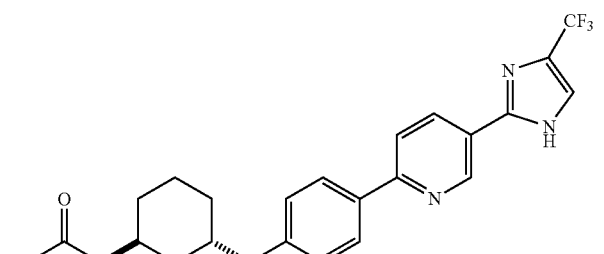 | 446 [M + H]+ |
| 21-3 | 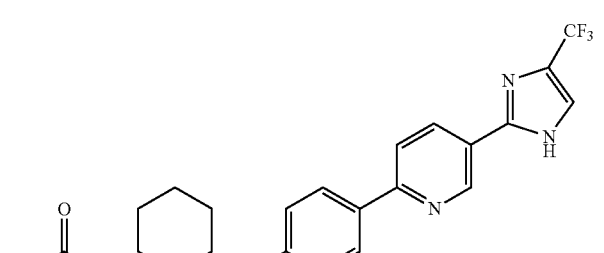 | 446 [M + H]+ |

TABLE 10-continued
| | | | |
|---|---|---|---|
| 21-4 | 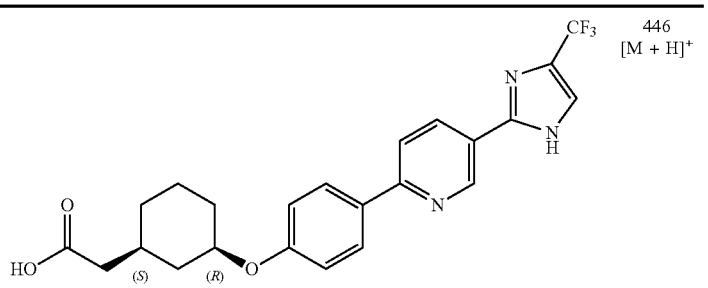 | 15 | 446 [M + H]⁺ |
Example 22
[Chemical Formula 89]
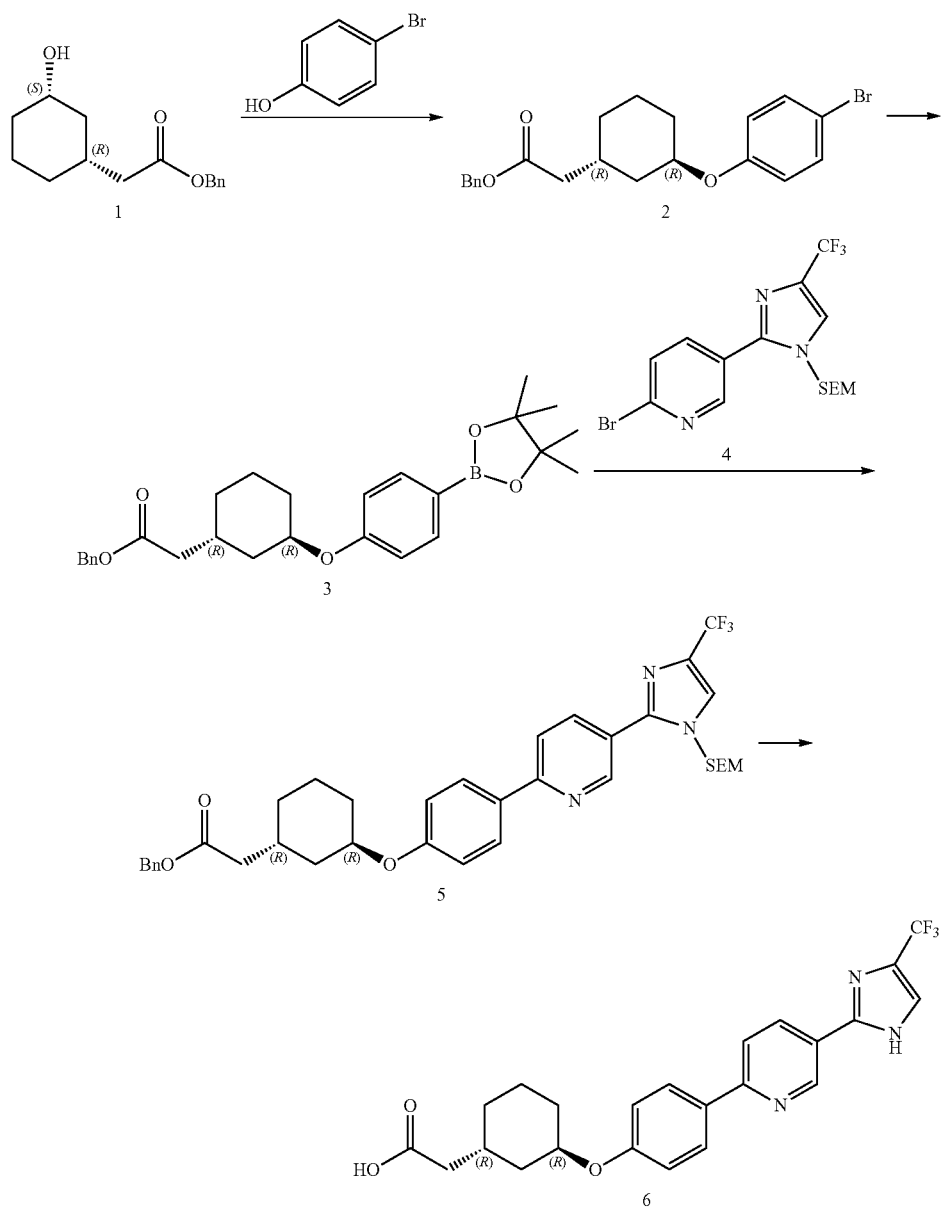

(1) A treatment was carried out in a manner similar to the Example 18-1 (3) using Compound 1 (1.55 g) and 4-bromophenol (1.62 g) to obtain Compound 2 (0.408 g).

MS (m/z): 420/422 [M+NH$_4$]$^+$ (2) Compound 2 (400 mg), tris(dibenzylideneacetone)dipalladium(0) (18 mg), 2-dicyclohexylphosphino-2',4',6'-triisopropyl-1,1'-biphenyl (X-PHOS) (19 mg), potassium acetate (292 mg) and bis pinacolato diboron (504 mg) were added to 1,4-dioxane (20 mL), and the mixture was heated at reflux under a nitrogen atmosphere overnight. The reaction solution was cooled to room temperature and subsequently filtered through Celite, and the filtrate was concentrated under reduced pressure. The obtained residue was purified by silica gel column chromatography (n-hexane:ethyl acetate=99:1 to 93:7) to obtain Compound 3 (461 mg).

MS (m/z): 468 [M+NH4]$^+$ (3) A treatment was carried out in a manner similar to the Example 7 (1) using Compound 3 (460 mg) and Compound 4 (287 mg) to obtain Compound 5 (521 mg).

MS (m/z): 666 [M+H]$^+$ (4) A treatment was carried out in a manner similar to the Example 18-1 (2) and Example 7 (2) using Compound 5 (520 mg) to obtain Compound 6 (203 mg).

MS (m/z): 446 [M+H]$^+$

Example 23-1

[Chemical Formula 90]

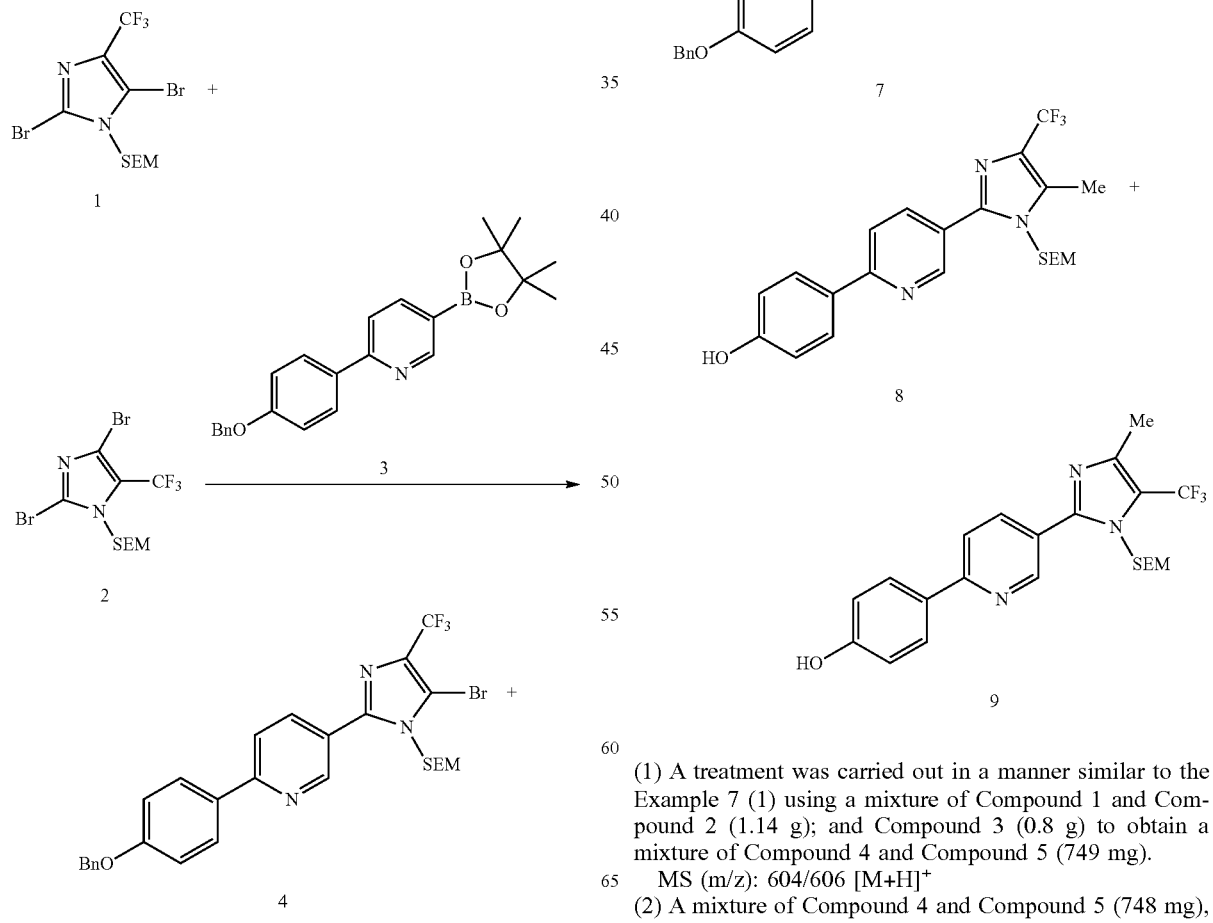

(1) A treatment was carried out in a manner similar to the Example 7 (1) using a mixture of Compound 1 and Compound 2 (1.14 g); and Compound 3 (0.8 g) to obtain a mixture of Compound 4 and Compound 5 (749 mg).

MS (m/z): 604/606 [M+H]$^+$ (2) A mixture of Compound 4 and Compound 5 (748 mg), methylboronic acid (148 mg) and cesium carbonate (806 mg) were added to 1,4-dioxane (15 mL). Under a nitrogen atmosphere, a palladium chloride (dppf)-methylene chloride complex (101 mg) was added, and the mixture was stirred at 80° C. overnight. The reaction solution was cooled to room temperature, subsequently treated with NH-silica gel, and eluted with ethyl acetate. The eluate was concentrated, the obtained residue, methylboronic acid (148 mg) and cesium carbonate (806 mg) were added to 1,4-dioxane (15 mL). Under a nitrogen atmosphere, a palladium chloride (dppf)-methylene chloride complex (101 mg) was added, and the mixture was stirred at 80° C. for 2.5 hours. The reaction solution was cooled to room temperature, subsequently treated with NH-silica gel, and eluted with ethyl acetate. The eluate was concentrated, and the obtained residue was purified by silica gel column chromatography (n-hexane: ethyl acetate=90:10 to 70:30) to obtain a mixture of Compound 6 and Compound 7 (579 mg).

MS (m/z): 540 [M+H]$^+$ (3) A treatment was carried out in a manner similar to the Example 18-1 (2) using the mixture of Compound 6 and Compound 7 (579 mg) to obtain a mixture of Compound 8 and Compound 9 (476 mg).

MS (m/z): 450 [M+H]$^+$

[Chemical Formula 91]

(4) A treatment was carried out in a manner similar to the Example 18-1 (3) using the mixture of Compound 8 and Compound 9 (161 mg); and Compound 10 (231 mg) to obtain a mixture of Compound 11 and Compound 12 (131 mg).

MS (m/z): 676 [M+H]$^+$ (5) A treatment was carried out in a manner similar to the Example 19-1 (2) using the mixture of Compound 11 and Compound 12 (109 mg) to obtain Compound 13 (39.9 mg).

MS (m/z): 490 [M+H]$^+$

Example 23-2

A treatment was carried out in a manner similar to the Example 23-1 to obtain a compound of Example 23-2 in Table 11 below.

TABLE 11
| Example | Intermediate 1 | Intermediate 2 |
|---|---|---|
| 23-2 | 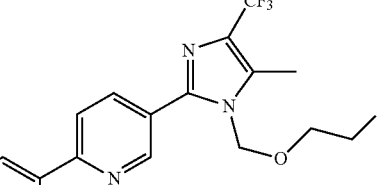 | 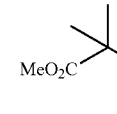 |
| Example | Product | MS (m/z) |
|---|---|---|
| 23-2 | 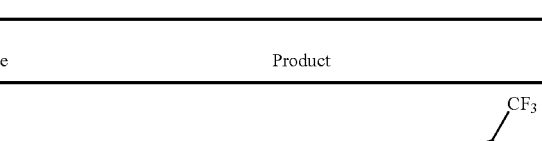 | 420 [M + H]+ |
Example 24-1
[Chemical Formula 92]
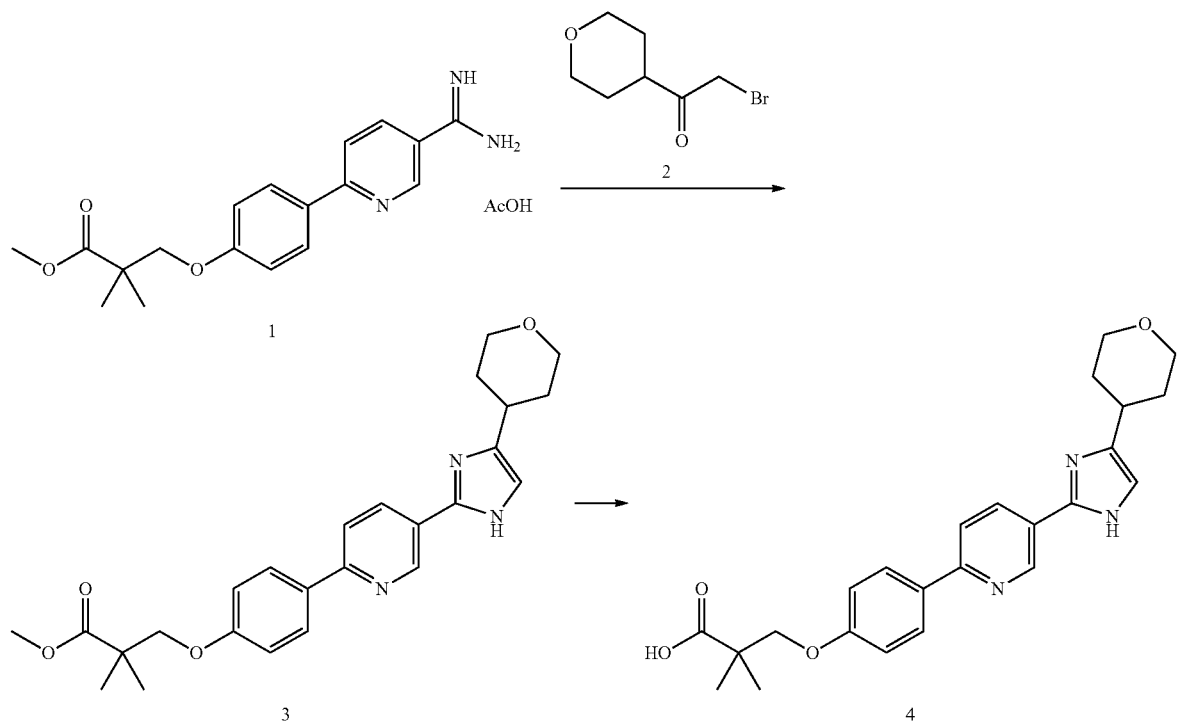
(1) A treatment was carried out in a manner similar to the Example 1-1 (1) using Compound 1 (100 mg) and Compound 2 (64 mg) to obtain Compound 3 (96 mg).
MS (m/z): 436 [M+H]+
(2) A treatment was carried out in a manner similar to the Example 1-1 (2) using Compound 3 (128 mg) to obtain Compound 4 (102 mg).
MS (m/z): 422 [M+H]+

Example 24-2
A treatment was carried out in a manner similar to the Example 24-1 to obtain a compound of Example 24-2 in Table 12 below.
TABLE 12
| Example | Intermediate 1 | Intermediate 2 |
|---|---|---|
| 24-2 | 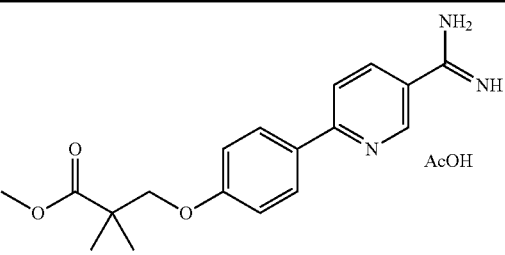 AcOH | 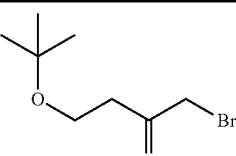 |
| Example | Product | MS (m/z) |
|---|---|---|
| 24-2 | 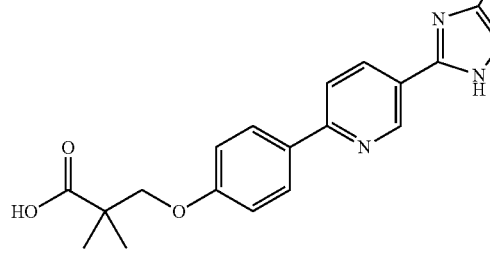 | 438 [M + H]$^+$ |
Example 25
[Chemical Formula 93]
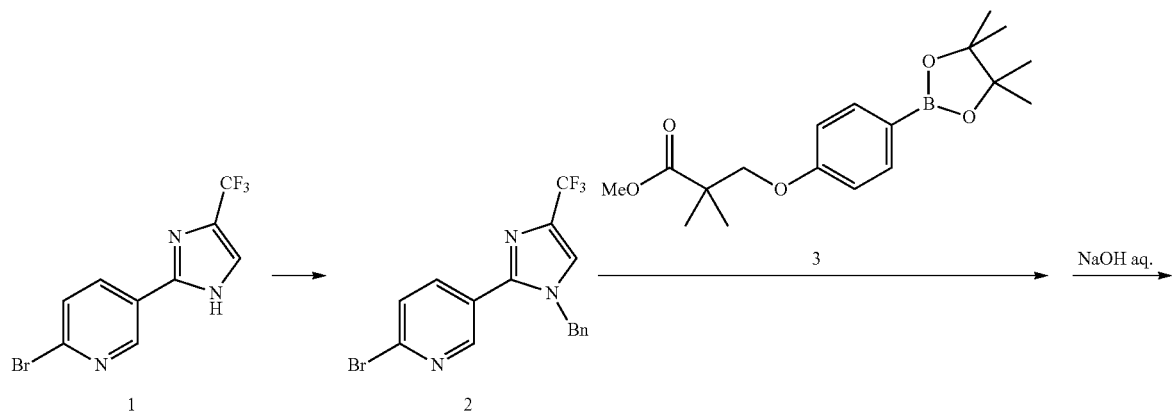

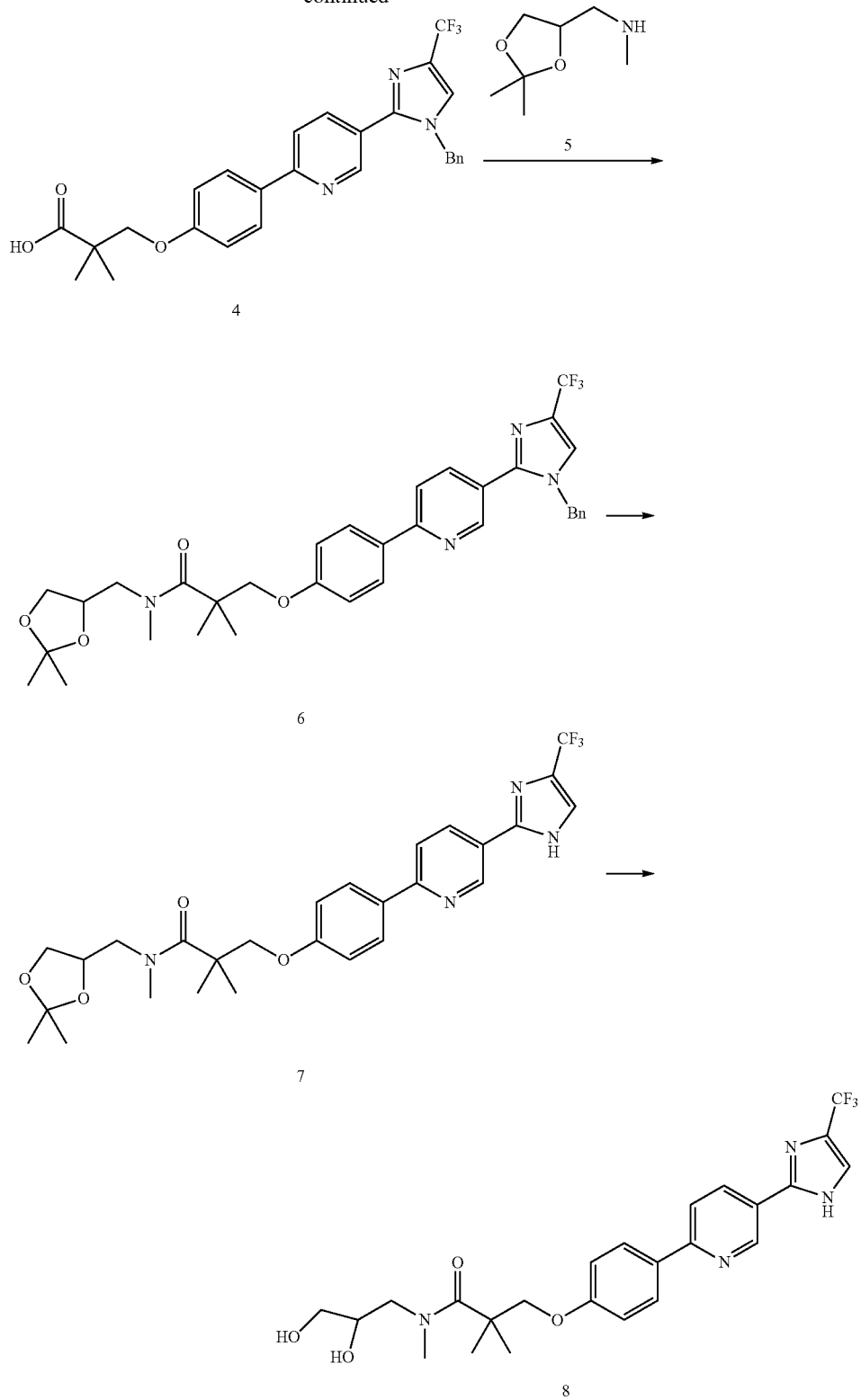
(1) A treatment was carried out in a manner similar to the Example 11 (1) using Compound 1 (1.0 g) to obtain Compound 2 (2.68 g).
MS (m/z): 382/384 [M+H]⁺
(2) A treatment was carried out in a manner similar to the Example 7 (1) and the Example 1-1 (2) using Compound 2 (1.28 g) and Compound 3 (2.24 g) to obtain Compound 4 (1.51 g).
MS (m/z): 496 [M+H]⁺

(3) A treatment was carried out in a manner similar to the Example 11 (3) using Compound 4 (600 mg) and Compound 5 (351 mg) to obtain Compound 6 (531 mg).

MS (m/z): 623 [M+H]$^+$ (4) A treatment was carried out in a manner similar to the Example 11 (4) using Compound 6 (530 mg) to obtain Compound 7 (161 mg).

MS (m/z): 533 [M+H]$^+$ (5) Compound 7 (140 mg) was dissolved in acetic acid (2 mL) and water (400 µL), and the mixture was stirred at room temperature for 6 hours. Water, ethyl acetate and tetrahydrofuran were added to the reaction solution to carry out a liquid separation. The organic layer was separated, washed with water, a saturated aqueous sodium hydrogen carbonate solution and saturated brine, and dried over anhydrous sodium sulfate. The solvent was distilled off under reduced pressure. After the obtained residue was purified by thin-layer silica gel chromatography (chloroform:methanol=5:1), the residue were solidified with addition of t-butyl alcohol and n-hexane, and subsequently the solid was collected by filtration to obtain Compound 8 (38 mg).

MS (m/z): 493 [M+H]$^+$

Example 26-1

[Chemical Formula 94]

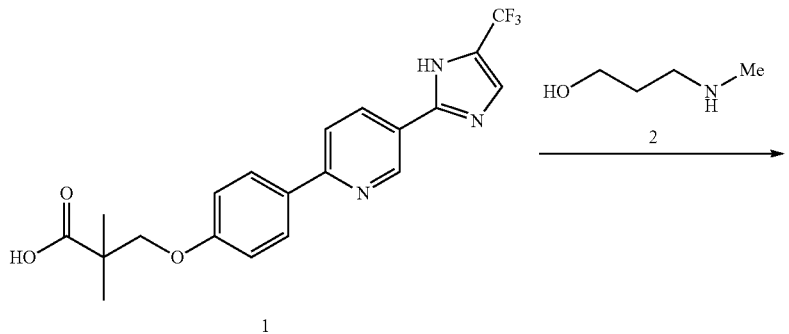

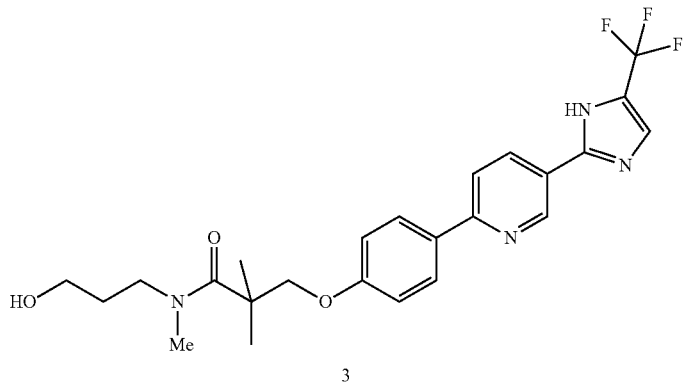

A treatment was carried out in a manner similar to the Example 11 (3) using Compound 1 (300 mg) and Compound 2 (99 mg) to obtain Compound 3 (161 mg).

MS (m/z): 477 [M+H]$^+$

Example 26-2

A treatment was carried out in a manner similar to the Example 26-1 to obtain a compound of Example 26-2 in Table 13 below.

TABLE 13

| Example | Starting material 1 | Product | MS (m/z) |
|---|---|---|---|
| 26-2 | 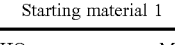 |  | 463 [M + H]+ |

Example 27

[Chemical Formula 95]

Example 28

[Chemical Formula 96]

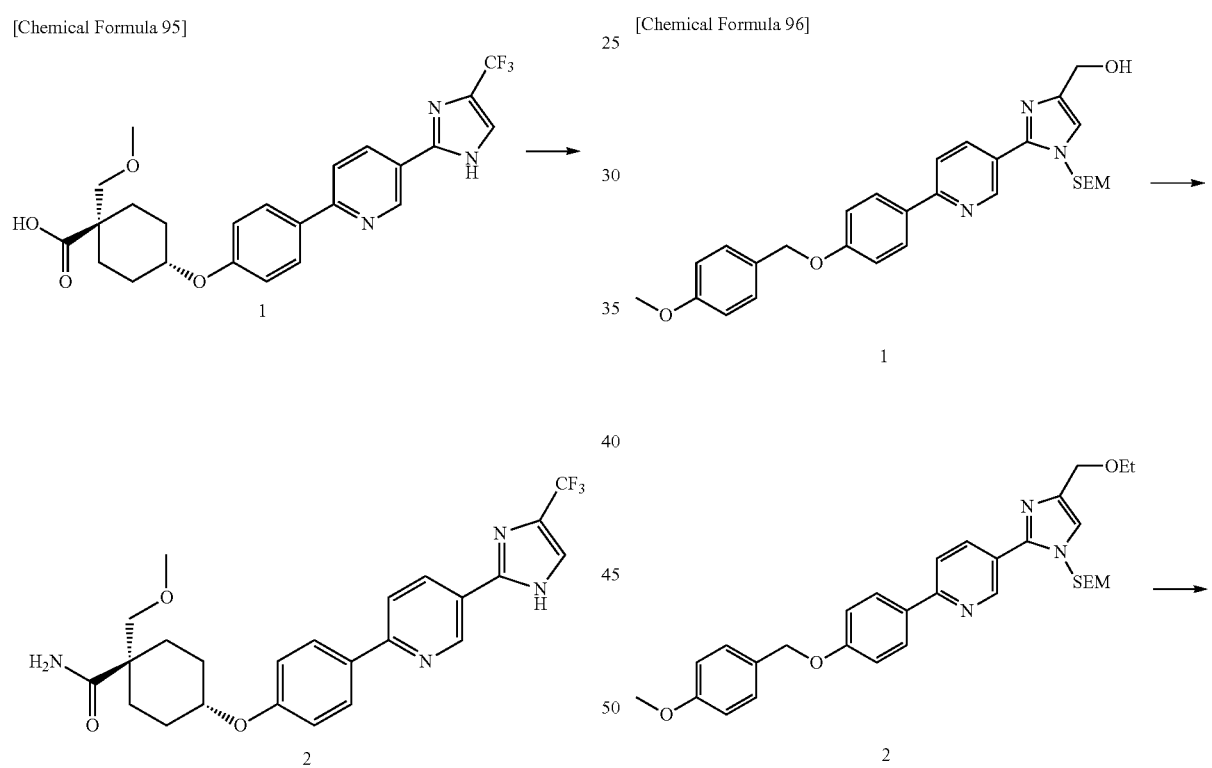

Compound 1 (60 mg), triethylamine (176 μL), ammonium chloride (68 mL), 1-(3-dimethylaminopropyl)-3-ethylcarbodiimide hydrochloride (EDC.HCl) (173 mg) and 1-hydroxybenzotriazole (HOBt) (51 mg) were added to dimethylsulfoxide (1 mL), and the mixture was stirred at room temperature overnight. Ethyl acetate and water were added to the reaction solution to carry out a liquid separation. The organic layer was separated, washed with water, and dried over anhydrous sodium sulfate. The solvent was distilled off under reduced pressure. The obtained residue was purified by thin layer silica gel column chromatography (chloroform: methanol=99:1) to obtain Compound 2 (51 mg).

MS (m/z): 475 [M+H]+

-continued

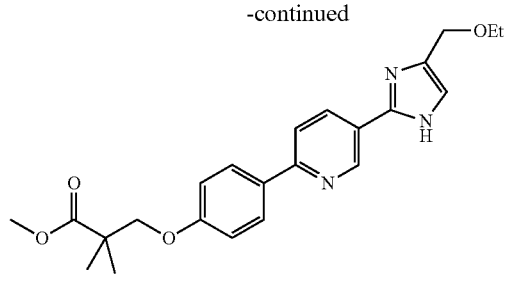

4

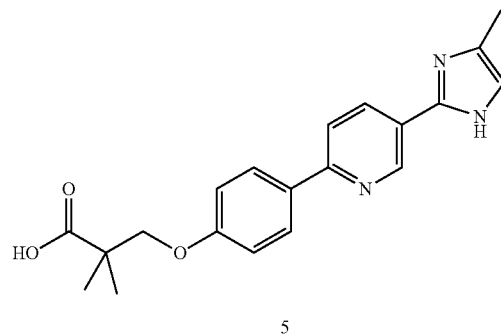

5

(1) A treatment was carried out in a manner similar to Example 31-1 (3) using Compound 1 (300 mg) and ethyl iodide (70 μL) to obtain Compound 2 (270 mg).

MS (m/z): 546 [M+H]⁺

(2) A treatment was carried out in a manner similar to the Example 10-(4) using Compound 2 (268 mg) to obtain Compound 3 (180 mg).

MS (m/z): 426 [M+H]⁺

(3) A treatment was carried out in a manner similar to Reference Example 7-1 (1) and the Example 7 (2) using Compound 3 (179 mg) to obtain Compound 4 (20 mg).

MS (m/z): 410 [M+H]⁺

(4) A treatment was carried out in a manner similar to the Example 1-1 (2) using Compound 4 (19 mg) to obtain Compound 5 (10 mg).

MS (m/z): 396 [M+H]⁺

Example 29-1

[Chemical Formula 97]

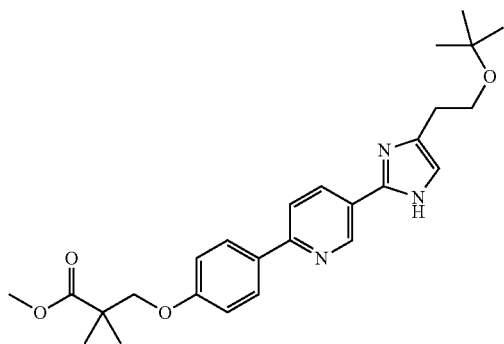

1

-continued

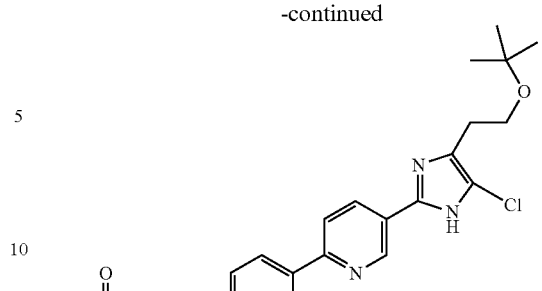

2

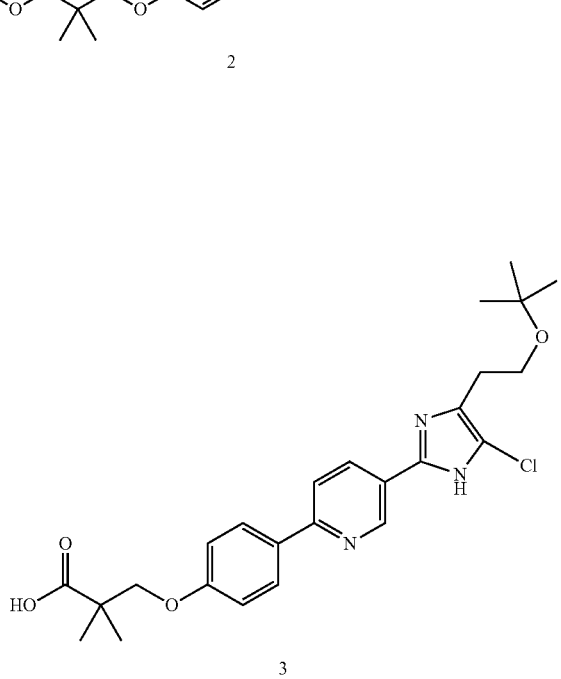

3

(1) Compound 1 (see Example 24-2) (50 mg) and N-chlorosuccinimide (16.3 mg) were added to N,N-dimethylformamide (0.6 mL), and the mixture was stirred at room temperature overnight. The separately prepared Compound 1 (250 mg) and N-chlorosuccinimide (81.3 mg) were added to N,N-dimethylformamide (3.1 mL), and the mixture was stirred at room temperature overnight. The above reaction solutions are combined, and ethyl acetate and an aqueous saturated sodium hydrogen carbonate solution were added to carry out a liquid separation. The organic layer was separated and washed with saturated brine and water, and subsequently the solvent was distilled off under reduced pressure. The obtained residue was purified by silica gel column chromatography (n-hexane:ethyl acetate=80:20 to 67:33) to obtain Compound 2 (236 mg).

MS (m/z): 486/488 [M+H]⁺

(2) A treatment was carried out in a manner similar to the Example 1-1 (2) using Compound 2 (235 mg) to obtain Compound 3 (237 mg).

MS (m/z): 472/474 [M+H]⁺

Examples 29-2 to 29-3

A treatment was carried out in a manner similar to the Example 29-1 to obtain compounds of Examples 29-2 and 29-3 in Table 14 below.

TABLE 14

| Example | Intermediate |
|---|---|
| 29-2 | (methyl 3-(4-(5-(4-cyano-1H-imidazol-2-yl)pyridin-2-yl)phenoxy)-2,2-dimethylpropanoate) |
| 29-3 | (methyl 3-(4-(5-(4-chloro-1H-imidazol-2-yl)pyridin-2-yl)phenoxy)-2,2-dimethylpropanoate) |

| Example | Product | MS (m/z) |
|---|---|---|
| 29-2 | (3-(4-(5-(4-chloro-5-cyano-1H-imidazol-2-yl)pyridin-2-yl)phenoxy)-2,2-dimethylpropanoic acid) | 397/399 [M + H]$^+$ |
| 29-3 | (3-(4-(5-(4,5-dichloro-1H-imidazol-2-yl)pyridin-2-yl)phenoxy)-2,2-dimethylpropanoic acid) | 406/408/410 [M + H]$^+$ |

Example 30
[Chemical Formula 98]
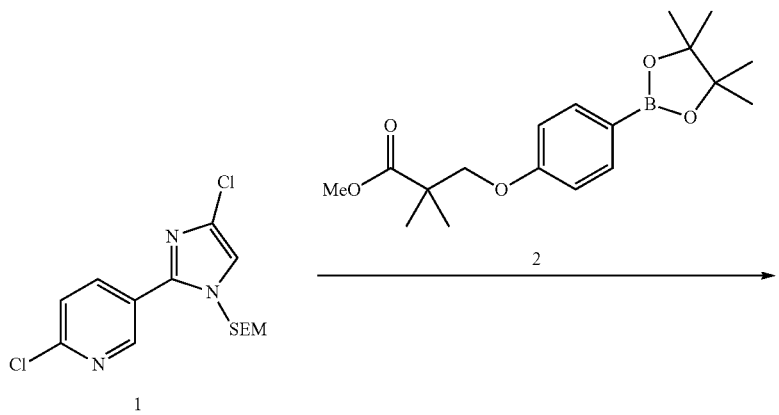
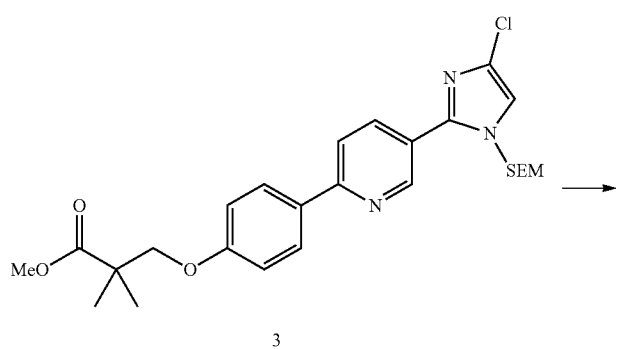
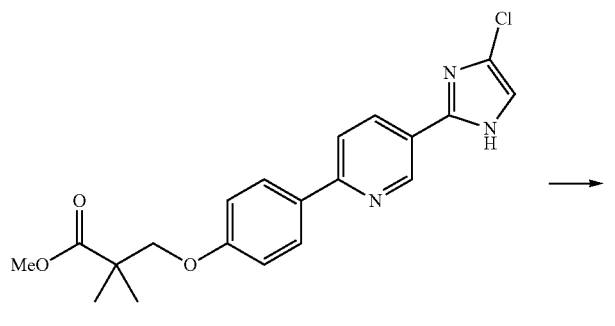
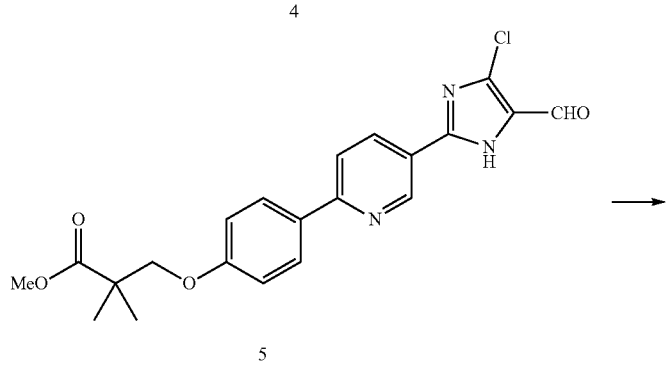

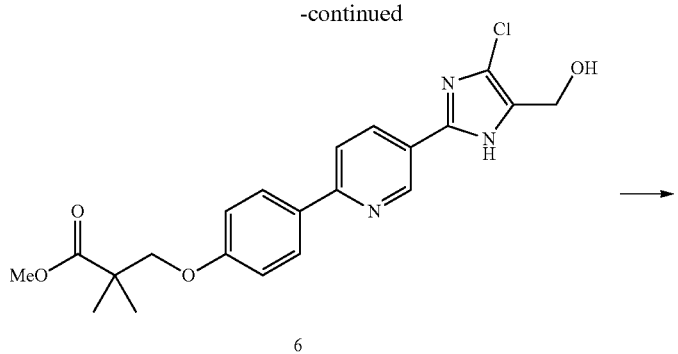

6

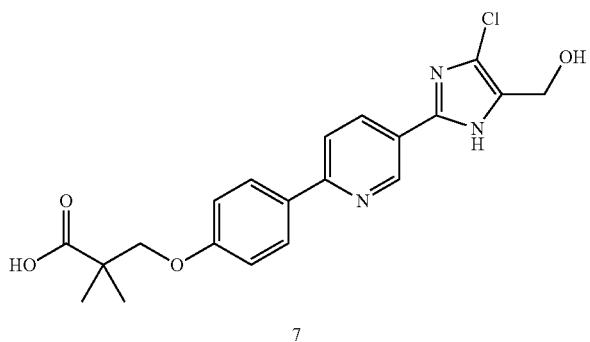 [SMILES: CC(C)(COc1ccc(-c2ccc(-c3nc(Cl)c(CO)[nH]3)cn2)cc1)C(=O)O]

7

(1) A treatment was carried out in a manner similar to the Example 7 (1) using Compound 1 (2.0 g) and Compound 2 (2.42 g) to obtain Compound 3 (2.00 g).

MS (m/z): 516/518 [M+H]$^+$ (2) A treatment was carried out in a manner similar to the Example 7 (2) using Compound 3 (950 mg) to obtain Compound 4 (665 mg).

MS (m/z): 386/388 [M+H]$^+$ (3) Compound 4 (50 mg), N,N-dimethylformamide diethyl acetal (33 μL) and triethylamine (1.8 μL) were added to toluene (1 mL), and the mixture was stirred at 110° C. overnight. After the reaction solution was cooled to room temperature, 1N hydrochloric acid (1.3 mL) was added, and the mixture was stirred for 30 minutes. A 1N aqueous sodium hydroxide solution (1.3 mL) and ethyl acetate were added to the reaction solution to carry out a liquid separation. The organic layer was separated and washed with 0.1N phosphate buffer (pH 7), and subsequently the solvent was distilled off under reduced pressure. The obtained residue was purified by silica gel column chromatography (n-hexane:ethyl acetate=80:20 to 70:30) to obtain Compound 5 (34 mg).

MS (m/z): 414/416 [M+H]$^+$ (4) Compound 5 (34 mg) was mixed with sodium borohydride (31.1 mg) in methanol (1.4 mL), to this was added tetrahydrofuran (2 mL), and the mixture was stirred at 65° C. for 1 minute and then at room temperature for 15 minutes. The reaction solution was concentrated under reduced pressure, and ethyl acetate and water were added to the residue to carry out a liquid separation. The organic layer was separated, and the solvent was distilled off under reduced pressure. To the obtained solid was added acetonitrile, and the solid was collected by filtration and dried to obtain Compound 6 (30.5 mg).

MS (m/z): 416/418 [M+H]$^+$ (5) A treatment was carried out in a manner similar to the Example 1-1 (2) using Compound 6 (30.5 mg) to obtain Compound 7 (20 mg).

MS (m/z): 402/404 [M+H]$^+$

Example 31-1

[Chemical Formula 99]

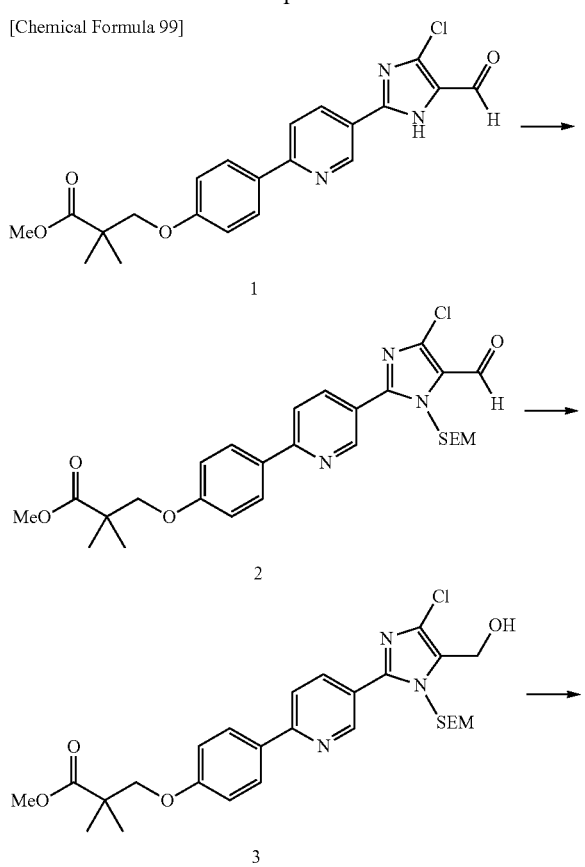

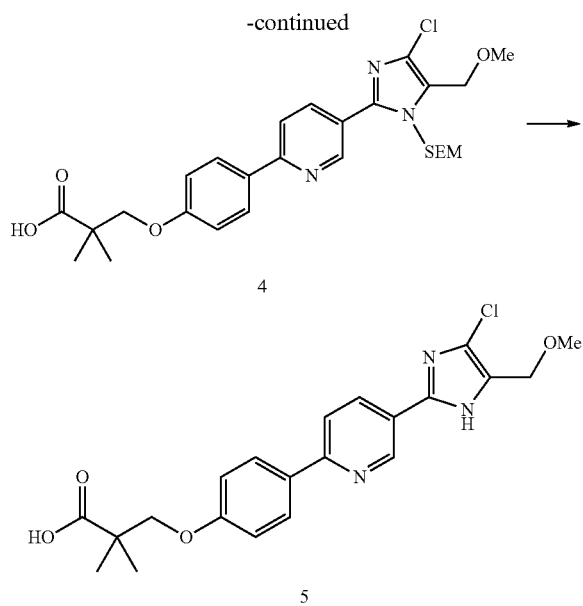

(1) A treatment was carried out in a manner similar to the Example 6 (2) using Compound 1 (409 mg) to obtain Compound 2 (411 mg).
MS (m/z): 544/546 [M+H]+

(2) A treatment was carried out in a manner similar to the Example 30 (4) using Compound 2 (408 mg) to obtain Compound 3 (357 mg).
MS (m/z): 546/548 [M+H]+

(3) Compound 3 (177 mg) was dissolved in N,N-dimethylformamide (1.8 mL) and tetrahydrofuran (1.8 mL), 60% sodium hydride (19.4 mg) was added under ice cooling, and the mixture was stirred for 5 minutes. Methyl iodide (40 μL) was added, and the mixture was stirred under ice cooling for 10 minutes and then at room temperature for 2 hours. Water, a saturated aqueous sodium hydrogen carbonate solution and ethyl acetate were added to the reaction solution to carry out a liquid separation. The organic layer was separated and washed with brine, and subsequently the solvent was distilled off under reduced pressure. The obtained solid was dissolved in methanol (1.8 mL) and tetrahydrofuran (1.8 mL), a 2N aqueous sodium hydroxide solution (1.29 mL) was added, and the mixture was stirred at room temperature overnight. After acetic acid was added to the reaction solution, then brine and ethyl acetate were added to carry out a liquid separation. The organic layer was separated and washed with 0.1N phosphate buffer (pH 7), and subsequently the solvent was distilled off under reduced pressure to obtain Compound 4 (199 mg).
MS (m/z): 546/548 [M+H]+

(4) A treatment was carried out in a manner similar to the Example 7 (2) using Compound 4 (199 mg) to obtain Compound 5 (63 mg).
MS (m/z): 416/418 [M+H]+

Example 31-2

A treatment was carried out in a manner similar to the Example 31-1 to obtain a compound of Example 31-2 in Table 15 below.

TABLE 15

| Example | Intermediate | Alkylating agent |
|---|---|---|
| 31-2 | (structure with —OH) | Et—I |

| Example | Product | MS (m/z) |
|---|---|---|
| 31-2 | (structure with —OEt) | 430/432 [M + H]+ |

Example 32-1

[Chemical Formula 100]

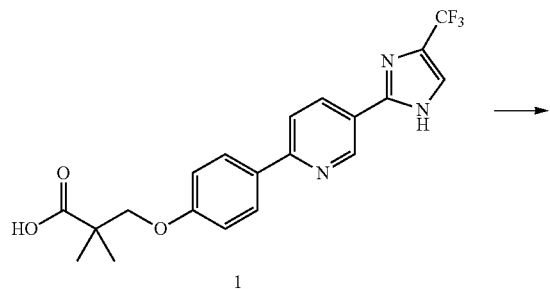

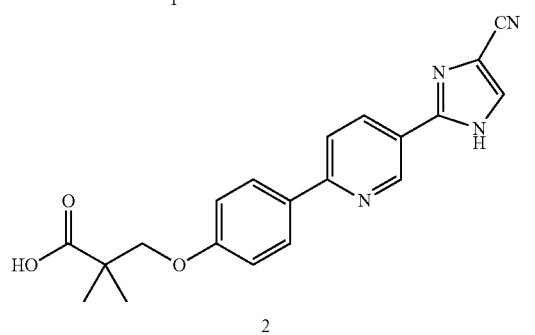

Compound 1 (see PCT/JP2011/079958) (470 mg) was dissolved in 28% aqueous ammonia (20 mL), and the mixture was stirred at room temperature for 4 days and at 40° C. overnight. After the reaction solution was concentrated under reduced pressure, the obtained residue was purified by silica gel column chromatography (chloroform:methanol=100:0 to 85:15), subsequently to the obtained solid were added isopropyl alcohol and diisopropyl ether, and the solid was collected by filtration to obtain Compound 2 (300 mg).

MS (m/z): 363 [M+H]$^+$

Examples 32-2 to 32-4

A treatment was carried out in a manner similar to the Example 32-1 to obtain compounds of Examples 32-2 to 32-4 in Table 16 below.

TABLE 16

| Example | Intermediate |
| --- | --- |
| 32-2 | 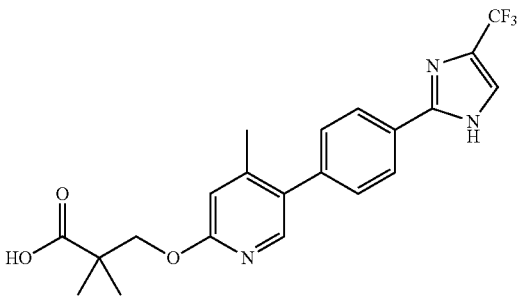 [SMILES: Cc1cc(OCC(C)(C)C(=O)O)ncc1-c1ccc(-c2nc(C(F)(F)F)c[nH]2)cc1] |
| 32-3 | 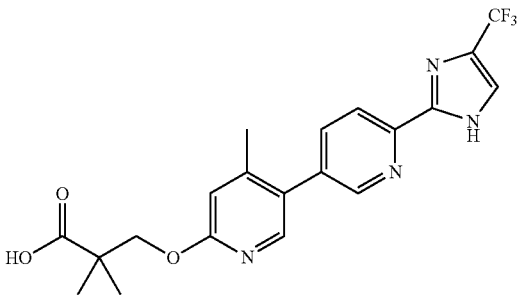 [SMILES: Cc1cc(OCC(C)(C)C(=O)O)ncc1-c1ccc(-c2nc(C(F)(F)F)c[nH]2)nc1] |

TABLE 16-continued
| Example | Product | MS (m/z) |
|---|---|---|
| 32-4 | 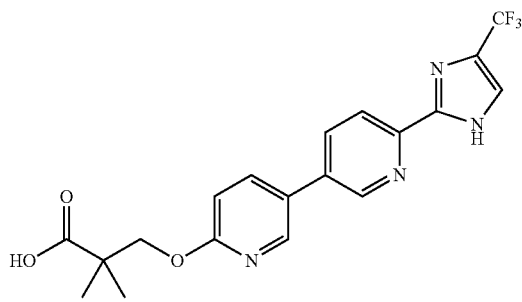 [SMILES: CC(C)(COc1ccc(-c2ccc(-c3nc(C(F)(F)F)c[nH]3)nc2)cn1)C(=O)O] | |
| 32-2 | | 377 [M + H]+ |
| 32-3 | | 378 [M + H]+ |
| 32-4 | | 364 [M + H]+ |

Example 33
[Chemical Formula 101]
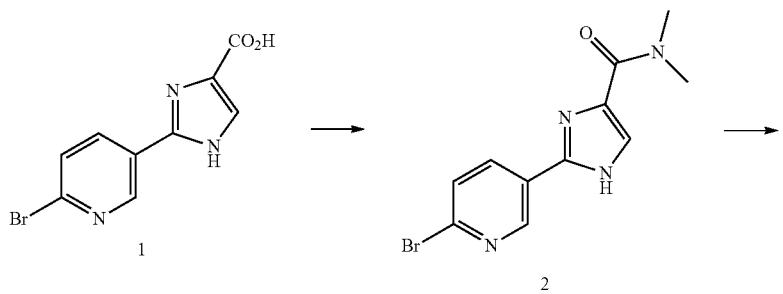
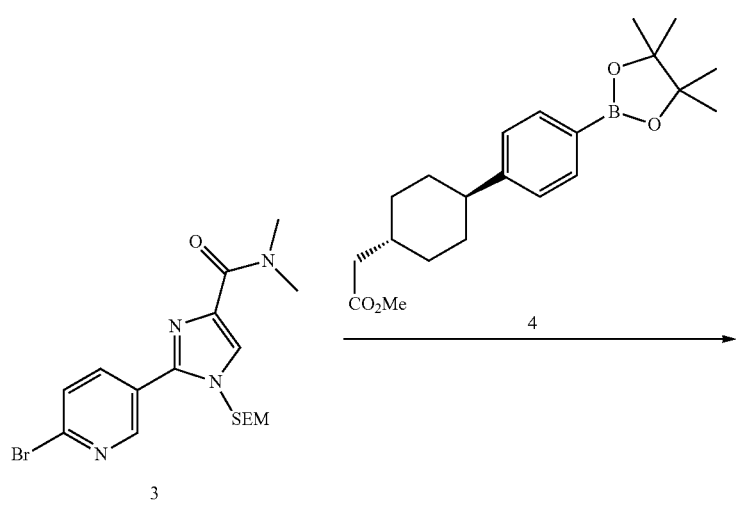
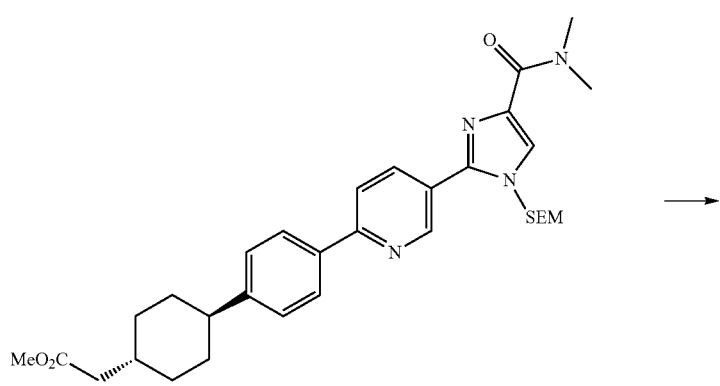

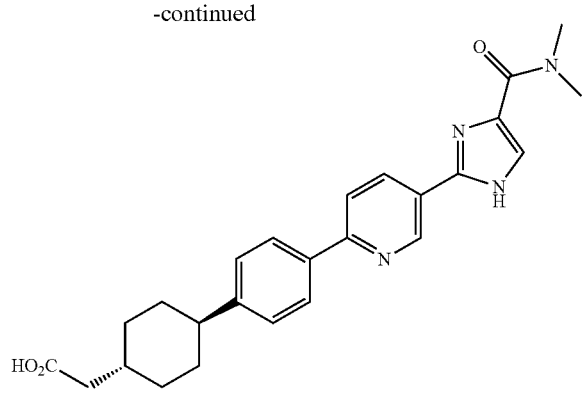

6

(1) A treatment was carried out in a manner similar to the Example 11 (3) using Compound 1 (570 mg) and a 2M dimethyl amine-tetrahydrofuran solution (3.2 mL) to obtain Compound 2 (139 mg).

MS (m/z): 295/297 [M+H]$^+$ (2) A treatment was carried out in a manner similar to the Example 6 (2) using Compound 2 (260 mg) to obtain Compound 3 (292 mg).

MS (m/z): 425/427 [M+H]$^+$ (3) A treatment was carried out in a manner similar to the Example 7 (1) using Compound 3 (292 mg) and Compound 4 (344 mg) to obtain Compound 5 (350 mg).

MS (m/z): 577 [M+H]$^+$ (4) A treatment was carried out in a manner similar to the Example 6 (7) using Compound 5 (350 mg) to obtain Compound 6 (178 mg).

MS (m/z): 433 [M+H]$^+$

Example 34

[Chemical Formula 102]

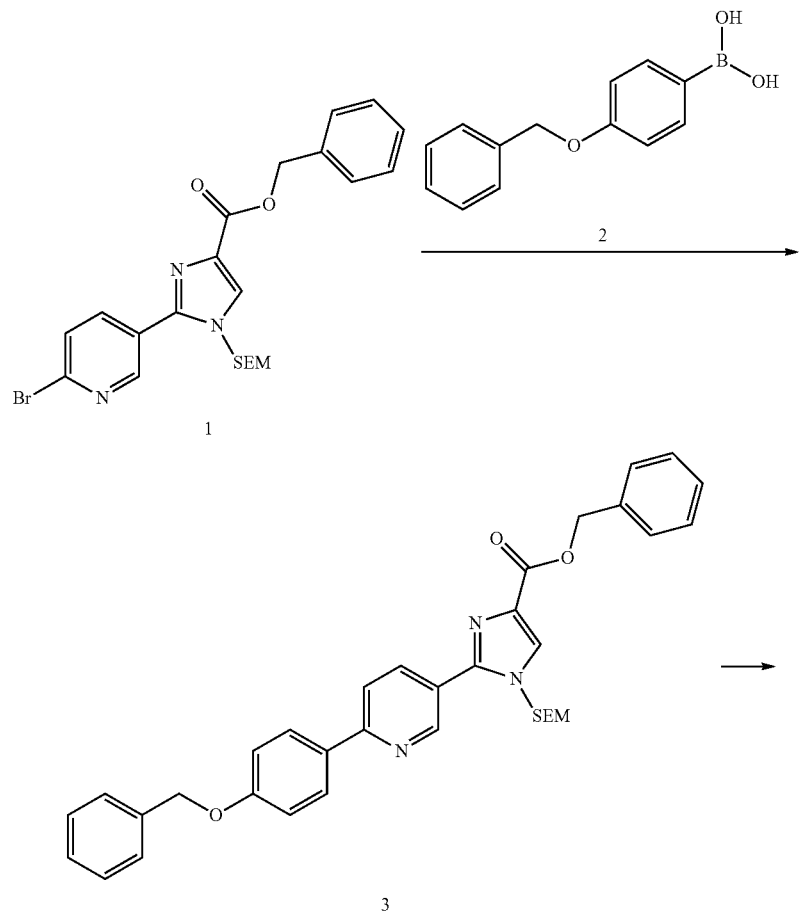

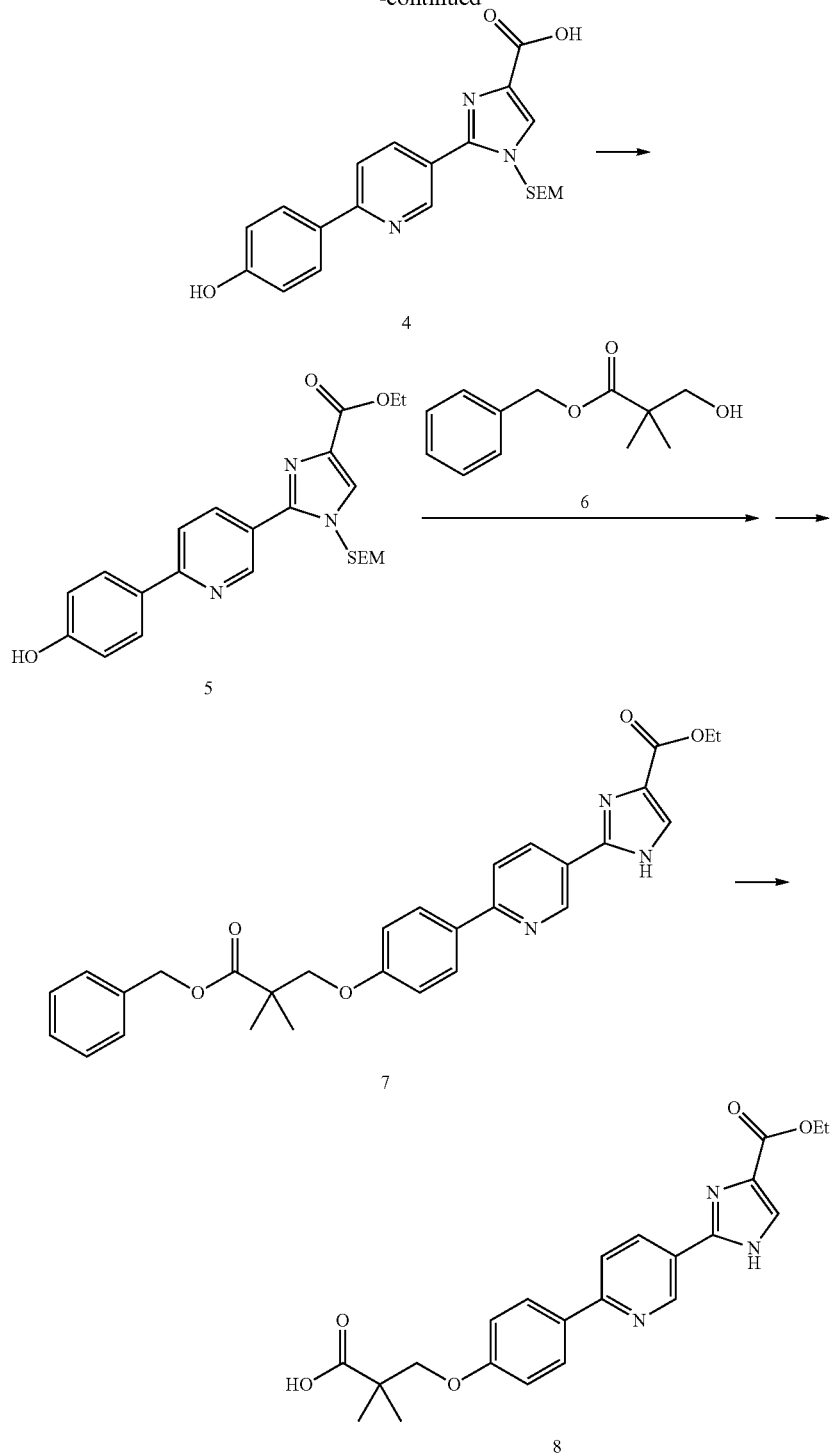

(1) A treatment was carried out in a manner similar to the Example 7 (1) using Compound 1 (see Reference Example 15-1) (1.5 g) and Compound 2 (1.4 g) to obtain Compound 3 (1.35 g).
MS (m/z): 592 [M+H]+

(2) A treatment was carried out in a manner similar to the Example 18-1 (2) using Compound 3 (1.30 g) to obtain Compound 4 (860 mg).
MS (m/z): 412 [M+H]+

(3) Compound 4 (480 mg), N,N-diisopropylethylamine (408 µL) and ethyl iodide (187 µL) were added to N,N-dimethylacetamide (5 mL), and the mixture was stirred at room temperature for 4 hours. To the reaction mixture was added water, the supernatant was discarded, the obtained oily deposit was washed with water and n-hexane, and subsequently ethyl acetate and a 10% aqueous citric acid solution were added to carry out a liquid separation. The organic layer was separated, washed with water and saturated brine, and dried over magnesium sulfate. The solvent was distilled off under reduced pressure. The obtained residue was purified by silica gel column chromatography (ethyl acetate:chloroform=0:100 to 40:60) to obtain Compound 5 (359 mg).

MS (m/z): 440 [M+H]+

(4) A treatment was carried out in a manner similar to Reference Example 7-1 (1) and the Example 7 (2) using Compound 5 (359 mg) and Compound 6 (340 mg) to obtain Compound 7 (228 mg).

MS (m/z): 500 [M+H]+

(5) A treatment was carried out in a manner similar to the Example 18-1 (2) using Compound 7 (225 mg) to obtain Compound 8 (165 mg).

MS (m/z): 410 [M+H]+

Example 35-1

[Chemical Formula 103]

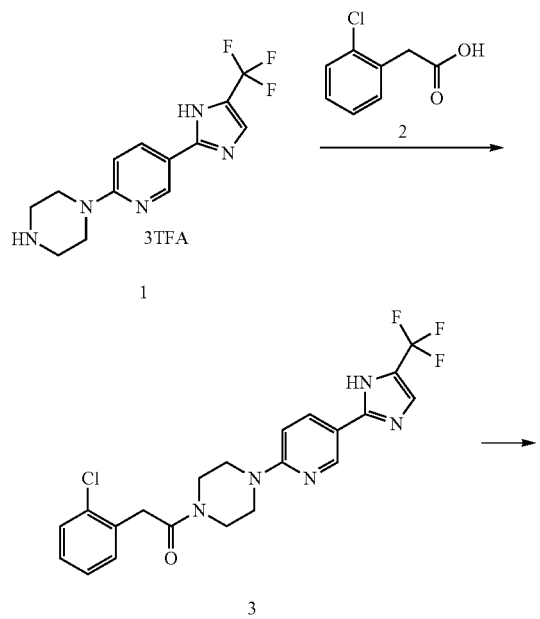

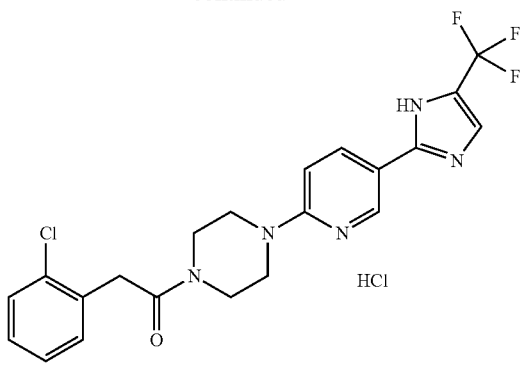

(1) Compound 1 (80 mg), Compound 2 (26 mg), 1-hydroxybenzotriazole (25 mg), and 1-(3-dimethylaminopropyl)-3-ethylcarbodiimide hydrochloride (36 mg) were added to N,N-dimethylformamide (1 mL), and the mixture was stirred at room temperature overnight. The solvent was distilled off under reduced pressure, and the obtained residue was purified by thin layer silica gel chromatography (chloroform:methanol) to obtain Compound 3 (40 mg).

MS (m/z): 450/452 [M+H]+

(2) Compound 3 (40 mg) was dissolved in a mixed solvent of ethanol and dichloromethane, and a 4N hydrochloric acid-1,4-dioxane solution (23 µL) was added. The reaction solution was concentrated under reduced pressure, and to the obtained solid residue was added diethyl ether, and the mixture was triturated, filtered and dried to obtain Compound 4 (42.8 mg) as a hydrochloride salt.

MS (m/z): 450/452 [M+H]+

Example 35-2

A treatment was carried out in a manner similar to the Example 35-1 to obtain a compound of Example 35-2 in Table 17 below.

TABLE 17

| Example | Intermediate 1 | Intermediate 2 |
|---|---|---|
| 35-2 | | |

TABLE 17-continued

| Example | Product | MS (m/z) |
|---|---|---|
| 35-2 | | 431 [M + H]+ |

Example 36

[Chemical Formula 104]

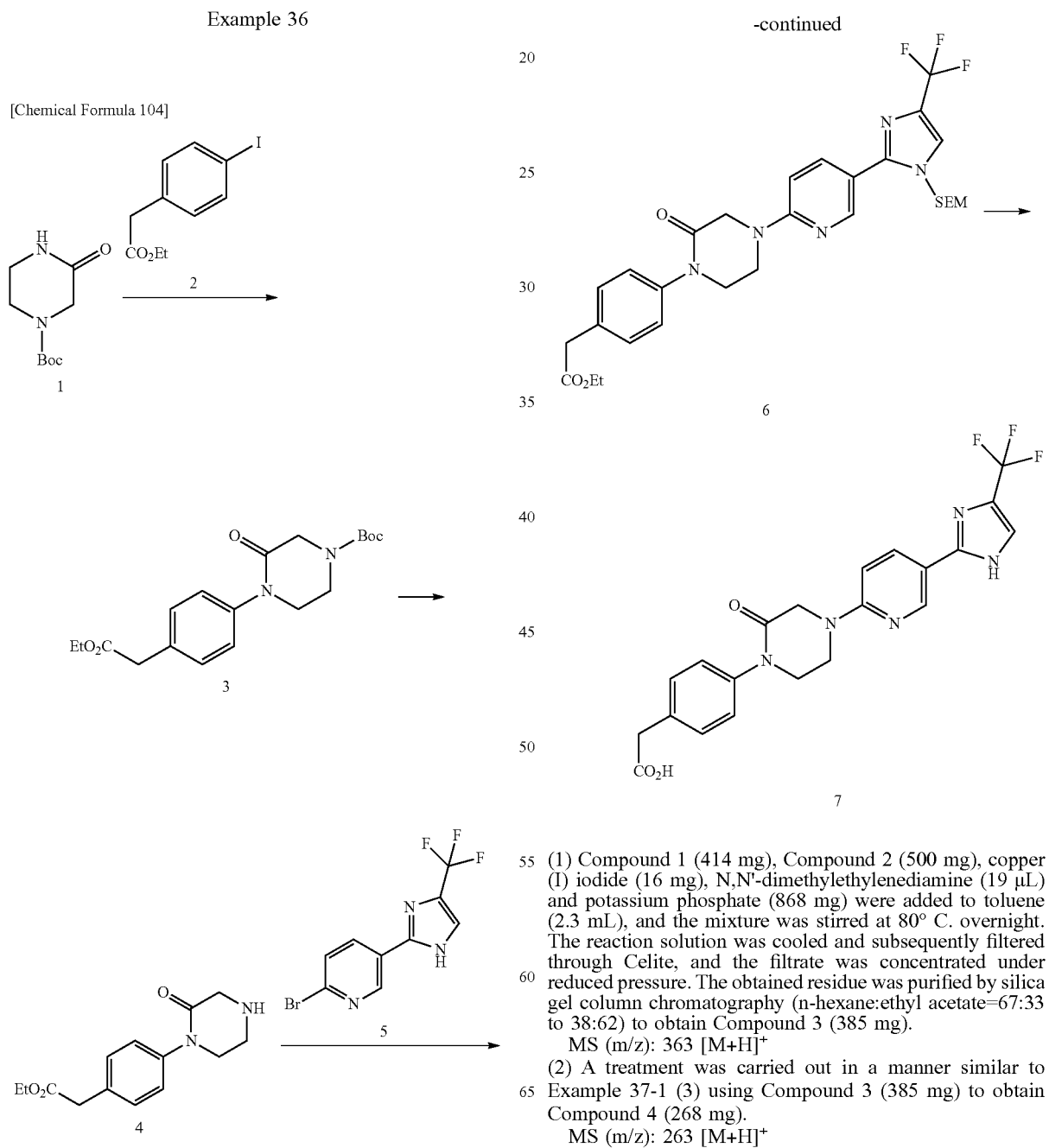

(1) Compound 1 (414 mg), Compound 2 (500 mg), copper (I) iodide (16 mg), N,N'-dimethylethylenediamine (19 μL) and potassium phosphate (868 mg) were added to toluene (2.3 mL), and the mixture was stirred at 80° C. overnight. The reaction solution was cooled and subsequently filtered through Celite, and the filtrate was concentrated under reduced pressure. The obtained residue was purified by silica gel column chromatography (n-hexane:ethyl acetate=67:33 to 38:62) to obtain Compound 3 (385 mg).
MS (m/z): 363 [M+H]+

(2) A treatment was carried out in a manner similar to Example 37-1 (3) using Compound 3 (385 mg) to obtain Compound 4 (268 mg).
MS (m/z): 263 [M+H]+

(3) A treatment was carried out in a manner similar to Example 39 (1) using Compound 4 (268 mg) and Compound 5 (400 mg) to obtain Compound 6 (80 mg).

MS (m/z): 604 [M+H]+

(4) A treatment was carried out in a manner similar to Example 6 (7) using Compound 6 (79 mg) to obtain Compound 7 (28 mg).

MS (m/z): 446 [M+H]+

Example 37-1

[Chemical Formula 105]

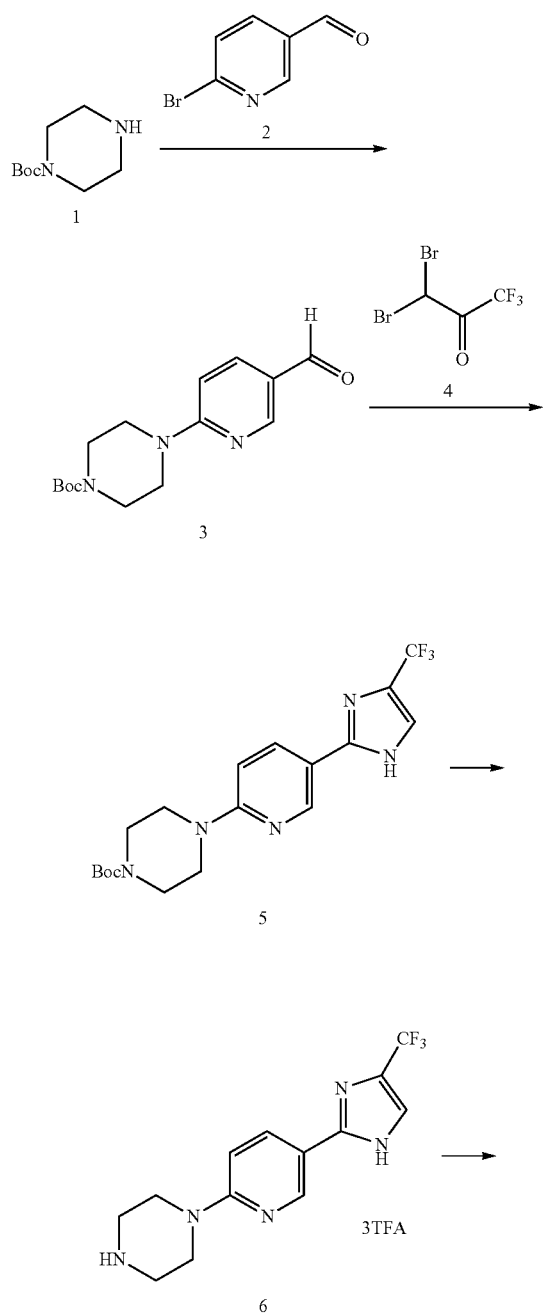
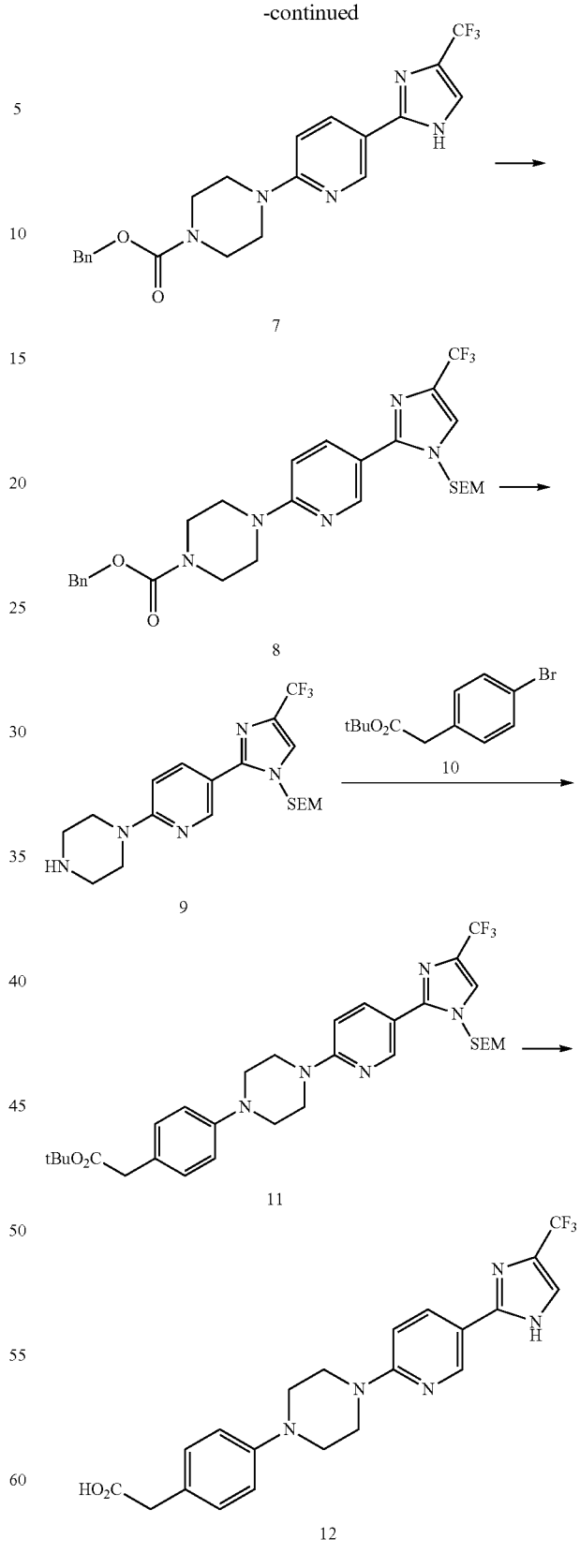

(1) Compound 1 (18.5 g), Compound 2 (20 g) and potassium carbonate (16.35 g) were added to dimethylsulfoxide (280 mL), and the mixture was stirred at 90° C. overnight. After the reaction solution was cooled, water and ethyl acetate were added to carry out a liquid separation. The organic layer was separated, washed with saturated brine, and dried over anhydrous magnesium sulfate. The solvent was distilled off under reduced pressure. To the obtained residue were added n-hexane and ethyl acetate, and the mixture was stirred, and subsequently, the solid was collected by filtration to obtain Compound 3 (23.21 g).

MS (m/z): 292 [M+H]$^+$ (2) Compound 4 (7.44 g) and sodium acetate (4.48 g) were mixed in water (15.2 mL), and the mixture was stirred at 95° C. for 30 minutes and then cooled. Compound 3 (4 g) was dissolved in 28% aqueous ammonia and methanol (200 mL), and the above-prepared reaction solution was added, and the mixture was stirred at room temperature overnight. The reaction solution was concentrated under reduced pressure, and ethyl acetate and water were added to carry out a liquid separation. The organic layer was separated, washed with saturated brine, and dried over anhydrous magnesium sulfate. The solvent was distilled off under reduced pressure. After the obtained residue was purified by NH-silica gel column chromatography (chloroform:methanol=20:1), the obtained solid was washed with diisopropyl ether, filtered and dried to obtain Compound 5 (4.14 g).

MS (m/z): 398 [M+H]$^+$ (3) To Compound 5 (4.14 g) was added trifluoroacetic acid (21 mL), and the mixture was stirred at room temperature for 30 minutes. To the reaction solution was added diethyl ether (150 mL), and the mixture was stirred for 10 minutes. The deposited solid was collected by filtration, washed with diethyl ether and dried to obtain Compound 6 (6.33 g).

MS (m/z): 298 [M+H]$^+$ (4) Compound 6 (1.50 g) and triethylamine (1.47 mL) were mixed in tetrahydrofuran (15 mL), benzyl chloroformate (0.63 mL) was added under ice cooling, and the mixture was stirred at room temperature overnight. Water and ethyl acetate were added to the reaction solution to carry out a liquid separation. The organic layer was separated, washed with a saturated aqueous sodium hydrogen carbonate solution and water, and dried over anhydrous sodium sulfate. The solvent was distilled off under reduced pressure. To the obtained solid residue was added methanol, and the solid was collected by filtration to obtain Compound 7 (709 mg).

MS (m/z): 432 [M+H]$^+$ (5) A treatment was carried out in a manner similar to Example 6 (2) using Compound 7 (889 mg) to obtain Compound 8 (1.117 g).

MS (m/z): 562 [M+H]$^+$ (6) A treatment was carried out in a manner similar to Example 18-1 (2) using Compound 8 (1.11 g) to obtain Compound 9 (833 mg).

MS (m/z): 428 [M+H]$^+$ (7) Under a nitrogen atmosphere, palladium acetate (2.7 mg), 2-dicyclohexylphosphino-2',4',6'-triisopropyl-1,1'-biphenyl (X-PHOS) (17.3 mg) and water (1.1 μL) were added to 1,4-dioxane (1.7 mL), and the mixture was stirred at 80° C. for 2 minutes. Separately, Compound 9 (170 mg), Compound 10 (153 mg) and cesium carbonate (197 mg) were mixed under a nitrogen atmosphere, the above prepared solution was added at 80° C., and subsequently the mixture was stirred at 100° C. overnight. The reaction solution was filtered through Celite, and the filtrate was concentrated under reduced pressure. The obtained residue was purified by silica gel column chromatography (n-hexane:ethyl acetate=95:5 to 70:30) to obtain Compound 11 (163 mg).

MS (m/z): 618 [M+H]$^+$ (8) A treatment was carried out in a manner similar to the Example 19-1 (2) using Compound 11 (163 mg) to obtain Compound 12 (73 mg).

MS (m/z): 432 [M+H]$^+$

Examples 37-2 to 37-6

A treatment was carried out in a manner similar to the Example 37-1 to obtain compounds of Examples 37-2 to 37-6 in Table 18 below.

TABLE 18

| Example | Intermediate 1 | Intermediate 2 |
|---|---|---|
| 37-2 | 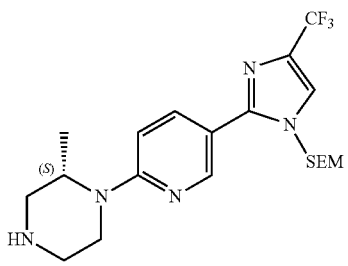 | 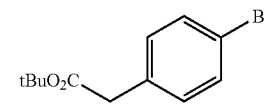 |
| 37-3 | 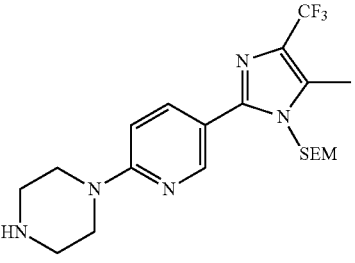 [SMILES: Cc1c(C(F)(F)F)nc(-c2ccc(N3CCNCC3)nc2)n1COCC[Si](C)(C)C] | 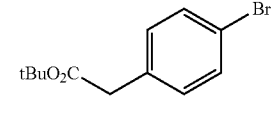 [SMILES: CC(C)(C)OC(=O)Cc1ccc(Br)cc1] |

TABLE 18-continued
| | | |
|---|---|---|
| 37-4 | 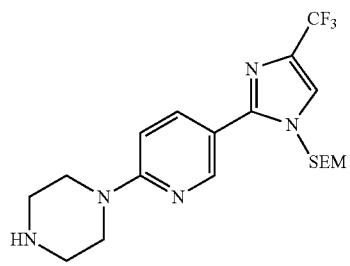 [SMILES: C[Si](C)(C)CCOCn1cc(C(F)(F)F)nc1-c1ccc(N2CCNCC2)nc1] | 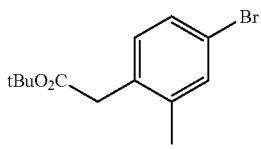 |
| 37-5 | 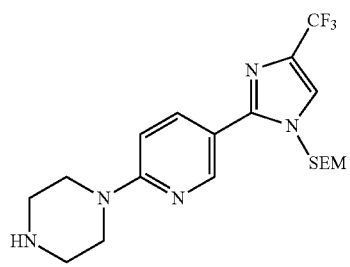 [SMILES: C[Si](C)(C)CCOCn1cc(C(F)(F)F)nc1-c1ccc(N2CCNCC2)nc1] | 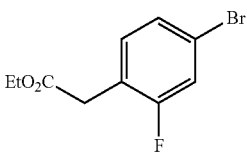 [SMILES: CCOC(=O)Cc1ccc(Br)cc1F] |
| 37-6 | 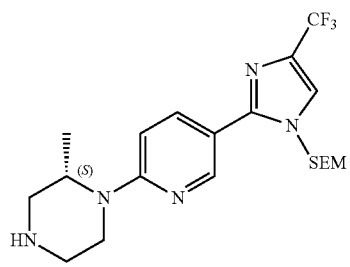 | 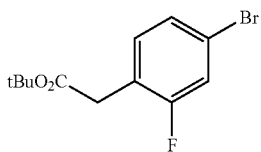 |
| Example | Product | MS (m/z) |
|---|---|---|
| 37-2 | 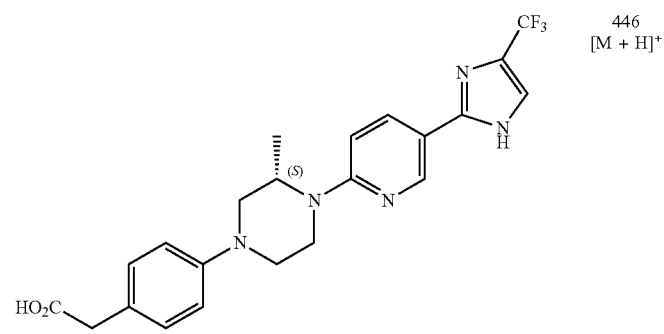 | 446 [M + H]+ |
| 37-3 | 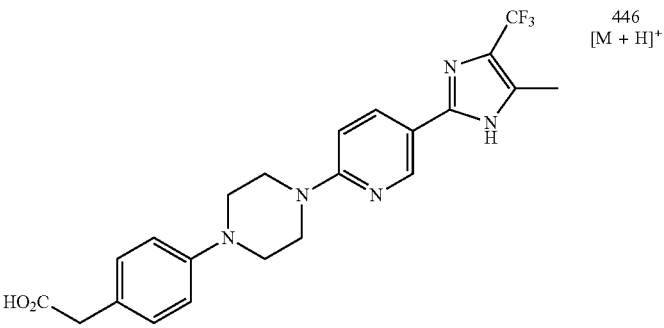 | 446 [M + H]+ |

TABLE 18-continued
| | | |
|---|---|---|
| 37-4 | 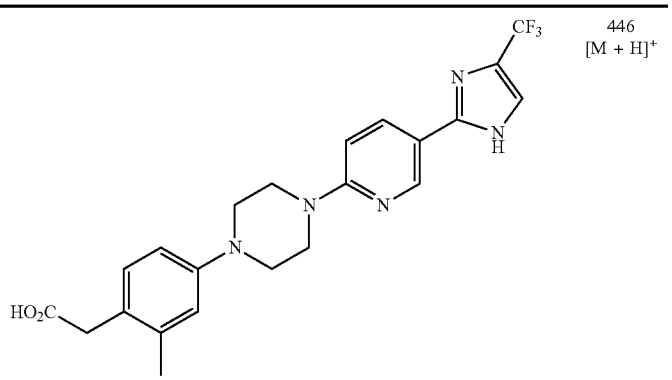 | 446 [M + H]+ |
| 37-5 | 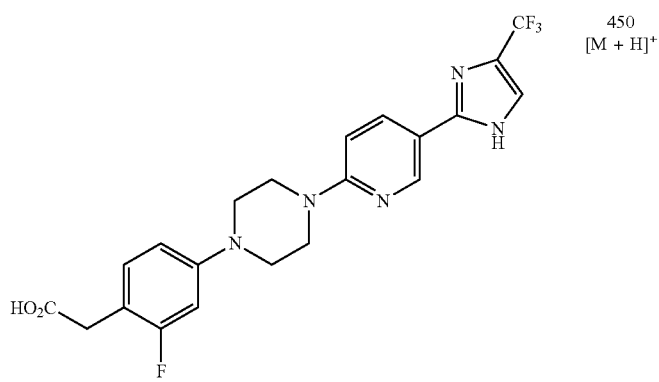 | 450 [M + H]+ |
| 37-6 | 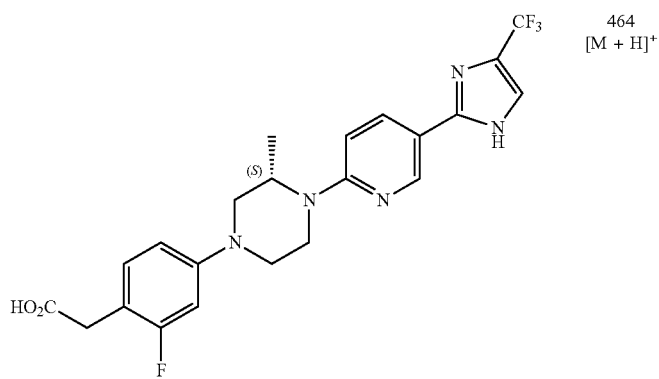 | 464 [M + H]+ |
Example 38-1
[Chemical Formula 106]
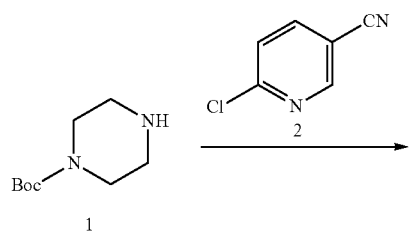
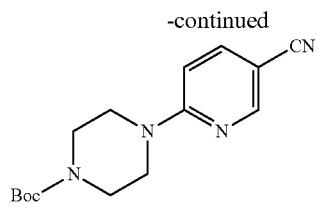
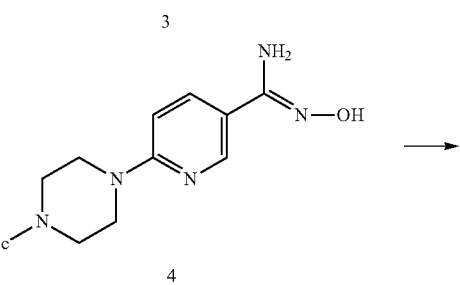

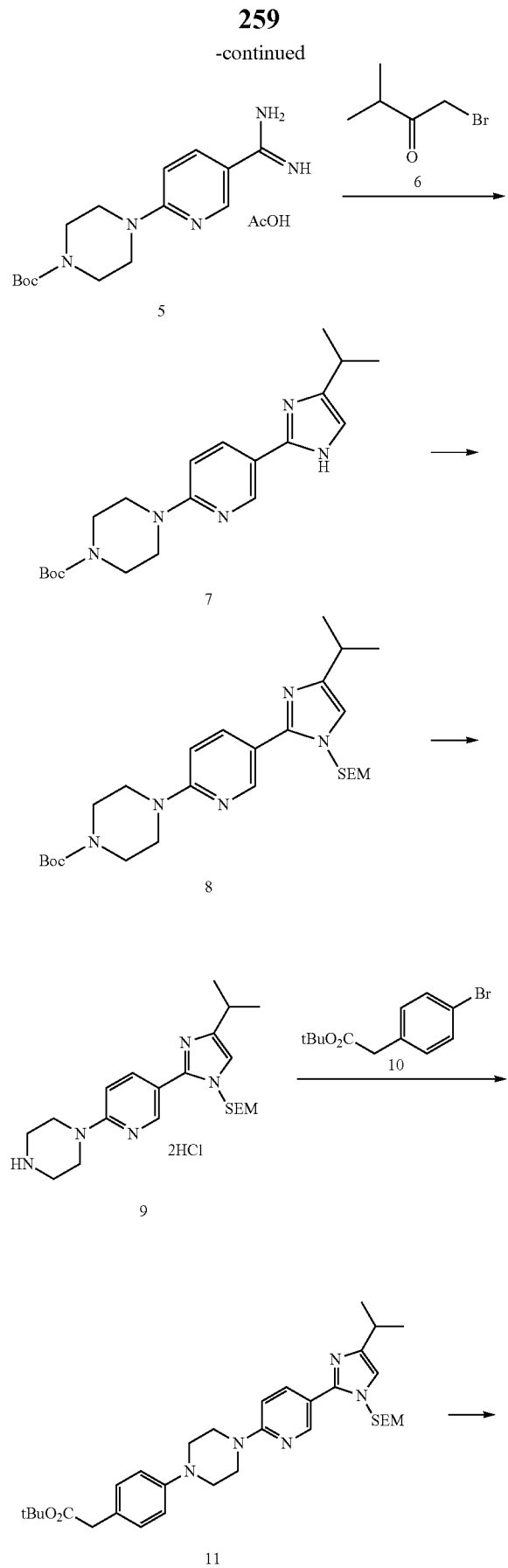

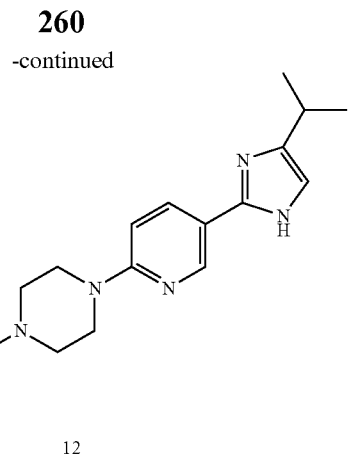

(1) A treatment was carried out in a manner similar to the Example 37-1 (1) using Compound 1 (1.0 g) and Compound 2 (818 mg) to obtain Compound 3 (1.457 g).
MS (m/z): 289 [M+H]$^+$ (2) A treatment was carried out in a manner similar to Reference Example 7-1 (4) using Compound 3 (4.0 g) to obtain Compound 4 (4.23 g).
MS (m/z): 322 [M+H]$^+$ (3) A treatment was carried out in a manner similar to Reference Example 7-1 (5) using Compound 4 (2.23 g) to obtain Compound 5 (2.51 g).
MS (m/z): 306 [M+H]$^+$ (4) A treatment was carried out in a manner similar to the Example 1-1 (1) using Compound 5 (2.94 g) and Compound 6 (1.99 g) to obtain Compound 7 (345 mg).
MS (m/z): 372 [M+H]$^+$ (5) A treatment was carried out in a manner similar to the Example 6 (2) using Compound 7 (337 mg) to obtain Compound 8 (422 mg).
MS (m/z): 502 [M+H]$^+$ (6) To Compound 8 (416 mg) was added a 4N hydrochloric acid-1,4-dioxane solution (4 mL), and the mixture was stirred at room temperature for 30 minutes. To the reaction solution was added diethyl ether, and the deposited solid was collected by filtration, washed with diethyl ether and then dried to obtain Compound 9 (345 mg).
MS (m/z): 402 [M+H]$^+$ (7) Compound 9 (338 mg), Compound 10 (290 mg), tris(dibenzylideneacetone)dipalladium(0) (33 mg), 2-dicyclohexylphosphino-2',4',6'-triisopropyl-1,1'-biphenyl (X-PHOS) (33 mg) and cesium carbonate (928 mg) were added to toluene (4 mL) under a nitrogen atmosphere, and the mixture was stirred at 80° C. overnight. The reaction solution was filtered using NH-silica gel, and the filtrate was purified by silica gel column chromatography (n-hexane:ethyl acetate=75:25 to 50:50) to obtain Compound 11 (156 mg).
MS (m/z): 592 [M+H]$^+$ (8) A treatment was carried out in a manner similar to the Example 19-1 (2) using Compound 11 (150 mg) to obtain Compound 12 (42 mg).
MS (m/z): 406 [M+H]$^+$ Examples 38-2 to 38-5

A treatment was carried out in a manner similar to the Example 38-1 to obtain compounds of Examples 38-2 to 38-5 in Table 19 below.

TABLE 19

| Example | Intermediate 1 | Intermediate 2 | Intermediate 3 |
|---|---|---|---|
| 38-2 | Boc-piperazinyl-pyridine-amidine | cyclopropyl-C(O)-CH2-Br | tBuO2C-CH2-C6H4-Br |
| 38-3 | Boc-piperazinyl-pyridine-amidine | CH3CH2CH2-C(O)-CH2-Br | tBuO2C-CH2-C6H4-Br |
| 38-4 | Boc-piperazinyl-pyridine-amidine | CH3CH2-C(O)-CH(CH3)-Br | tBuO2C-CH2-C6H4-Br |
| 38-5 | Boc-piperazinyl-pyridine-amidine | cyclobutyl-C(O)-CH2-Br | tBuO2C-CH2-C6H4-Br |

| Example | Product | MS (m/z) |
|---|---|---|
| 38-2 | 4-cyclopropyl-imidazolyl-pyridyl-piperazinyl-phenyl-CH2-CO2H | 404 [M + H]+ |

TABLE 19-continued
| | | |
|---|---|---|
| 38-3 | 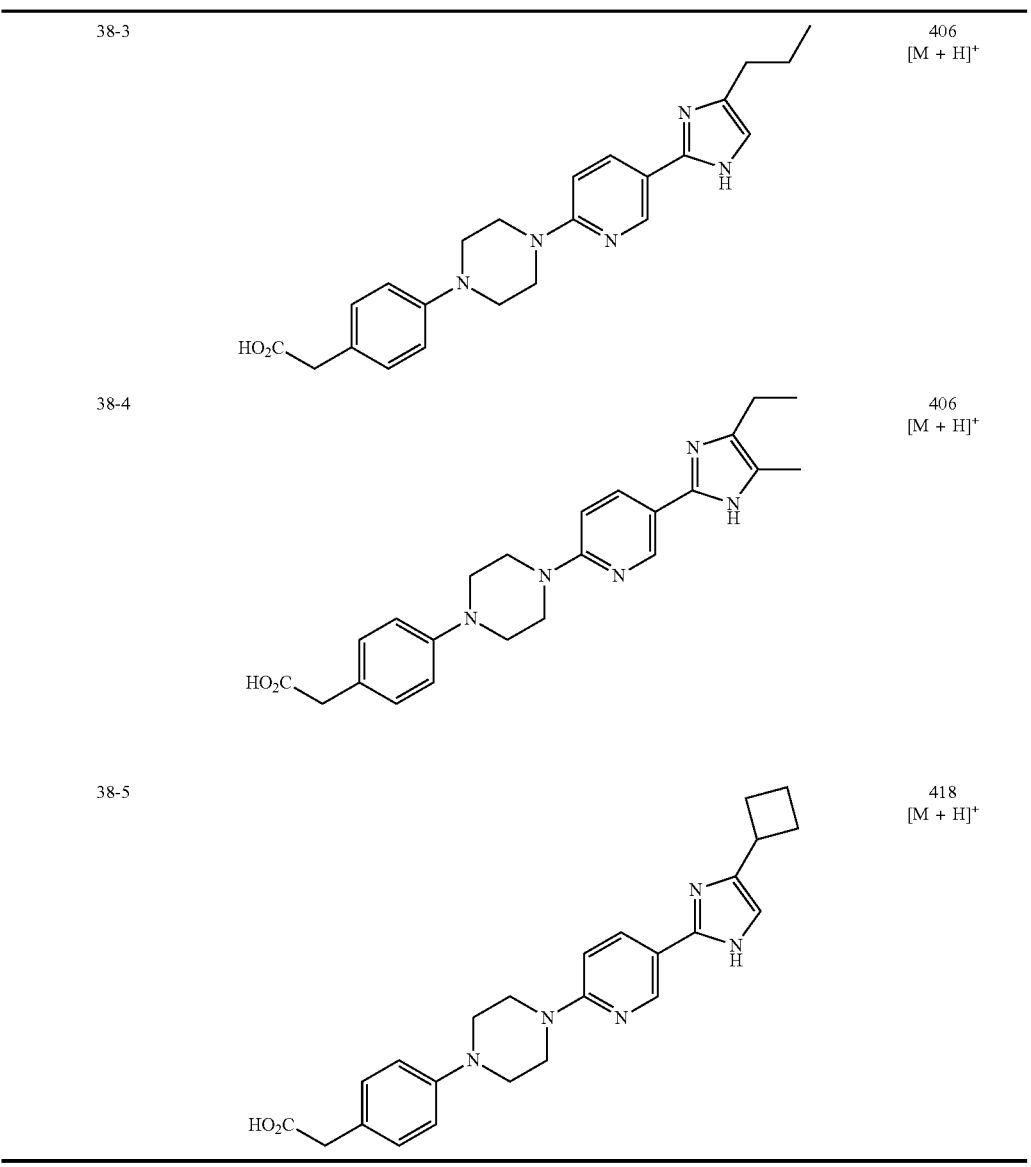 | 406 [M + H]+ |
| 38-4 | | 406 [M + H]+ |
| 38-5 | | 418 [M + H]+ |
Example 39
[Chemical Formula 107]
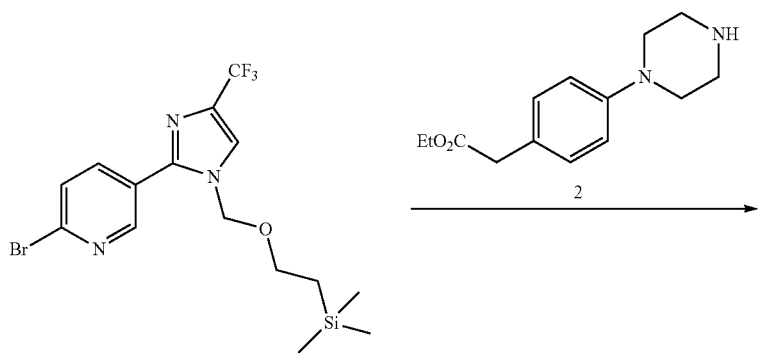

-continued

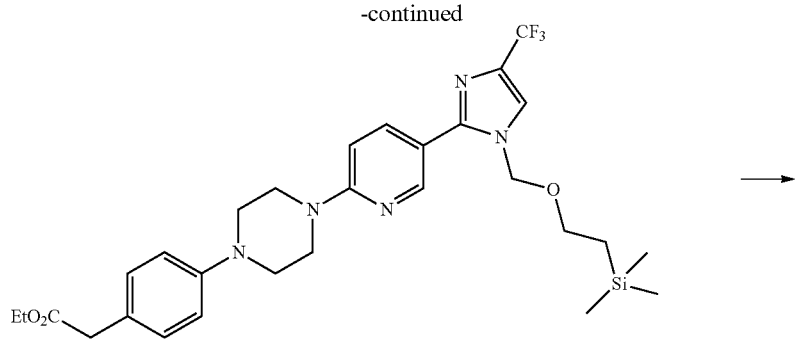

3

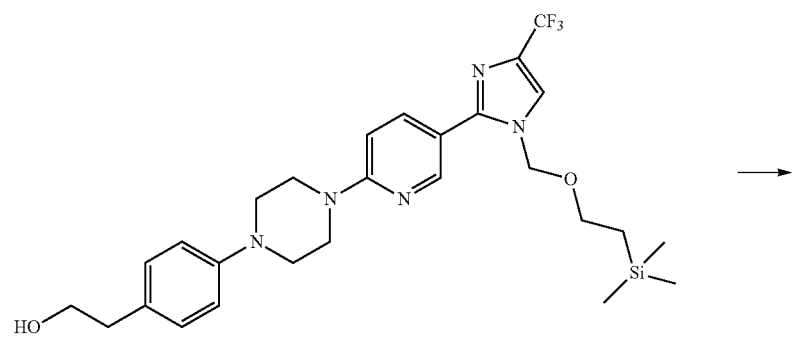

4

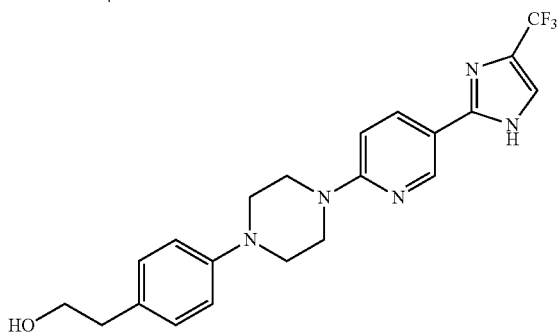

5

(1) Compound 1 (330 mg) was dissolved in dimethylsulfoxide (7 mL), and Compound 2 (290 mg) and potassium carbonate (140 mg) were added, and the mixture was stirred at 100° C. overnight. Water and ethyl acetate were added to the reaction solution to carry out a liquid separation. The organic layer was separated, washed with saturated brine, and dried over anhydrous magnesium sulfate. The solvent was distilled off under reduced pressure. The obtained residue was purified by silica gel column chromatography (n-hexane:ethyl acetate=78:22 to 63:37) to obtain Compound 3 (263 mg).

MS (m/z): 590 [M+H]$^+$ (2) Lithium aluminum hydride (16 mg) was suspended in tetrahydrofuran (2 mL), and a solution of Compound 3 (256 mg) in tetrahydrofuran (3 mL) was added dropwise at room temperature. After the mixture was stirred for 1 hour, additional lithium aluminum hydride (16 mg) was added portionwise, and the mixture was further stirred for 30 minutes. To the reaction solution were added sodium sulfate (0.2 g) and water (0.2 g) under ice cooling, and the mixture was stirred at room temperature for 30 minutes. The insoluble matter was filtered, and the filtrate was concentrated under reduced pressure. The obtained residue was purified by silica gel column chromatography (n-hexane: ethyl acetate=70:30 to 25:75) to obtain Compound 4 (218 mg).

MS (m/z): 548 [M+H]$^+$ (3) A treatment was carried out in a manner similar to Example 7 (2) using Compound 4 (214 mg) to obtain Compound 5 (54 mg).

MS (m/z): 418 [M+H]$^+$

Example 40-1
[Chemical Formula 108]
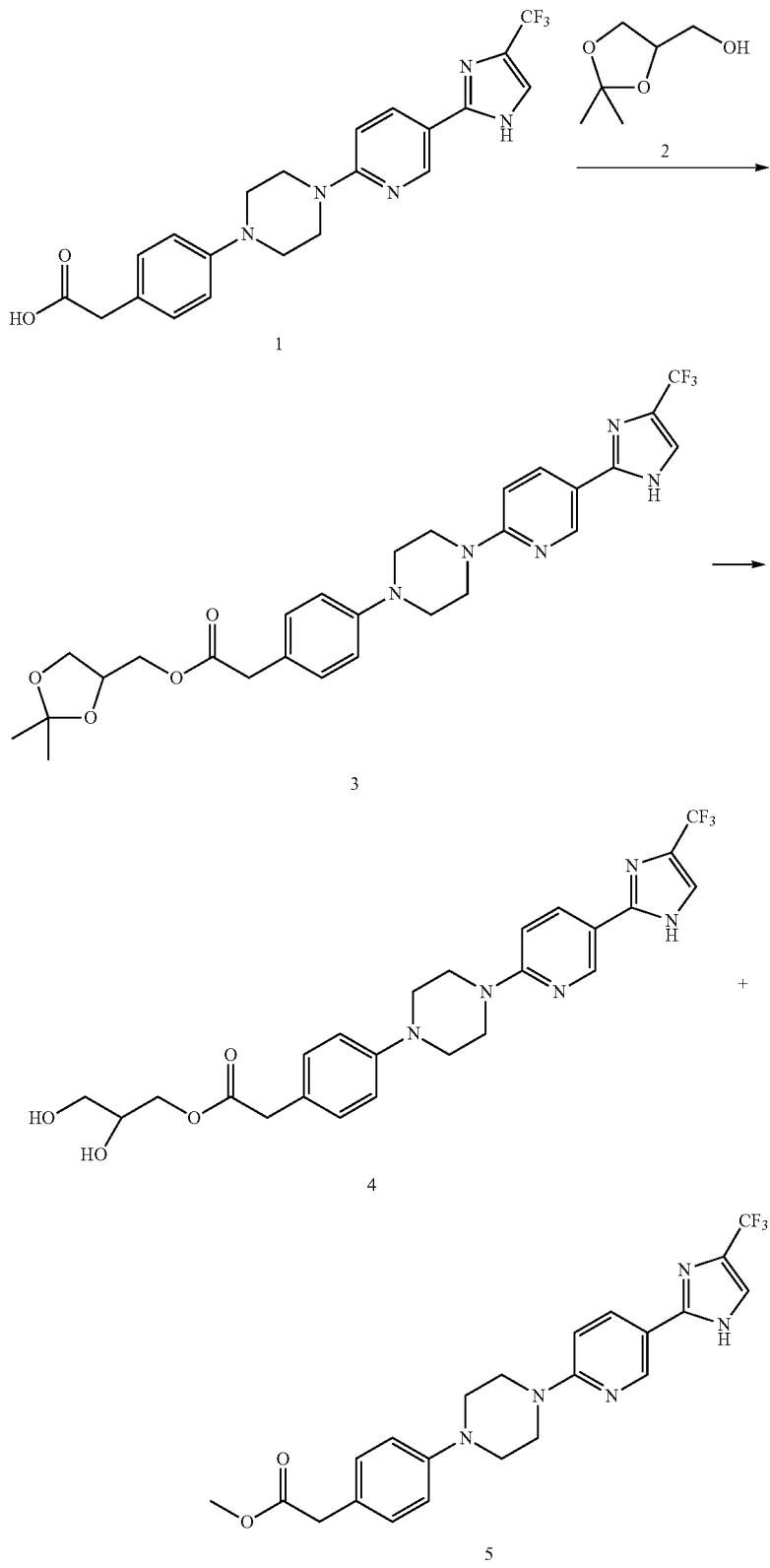

(1) Compound 1 (200 mg), Compound 2 (123 mg), 1-(3-dimethylaminopropyl)-3-ethylcarbodiimide hydrochloride (178 mg) and N,N-dimethylaminopyridine (DMAP) (6 mg) were added to dimethylacetamide (5 mL), and the mixture was stirred at room temperature for two days. Ethyl acetate and a 10% aqueous citric acid solution were added to the reaction solution to carry out a liquid separation. The organic layer was separated, washed with water and saturated brine, and dried over anhydrous sodium sulfate. The solvent was distilled off under reduced pressure. After the obtained residue was purified by silica gel column chromatography (n-hexane:ethyl acetate=100:0 to 30:70), diisopropyl ether and n-hexane were added, and the solid was collected by filtration to obtain Compound 3 (191 mg).

MS (m/z): 546 [M+H]$^+$ (2) Compound 3 (157 mg) was dissolved in methanol (6 mL) and to this was added 1N hydrochloric acid (2 mL), and the mixture was stirred at room temperature overnight. The reaction solution was concentrated under reduced pressure, and an aqueous saturated sodium hydrogen carbonate solution, ethyl acetate and tetrahydrofuran were added to the obtained residue under ice cooling to carry out a liquid separation. The organic layer was separated, washed with saturated brine, and dried over anhydrous sodium sulfate. The solvent was distilled off under reduced pressure. After the obtained residue was purified by silica gel column chromatography (n-hexane:ethyl acetate=100:0 to 80:20), isopropyl ether and n-hexane were added, and the solid was collected by filtration to obtain Compound 4 (75 mg) and Compound 5 (20 mg).

Compound 4 MS (m/z): 506 [M+H]$^+$
Compound 5 MS (m/z): 446 [M+H]$^+$

Example 40-2

A treatment was carried out in a manner similar to the Example 40-1 to obtain a compound of Example 40-2 in Table 20 below.

TABLE 20

| Example | Starting material 1 | Starting material 2 |
|---|---|---|
| 40-2 | 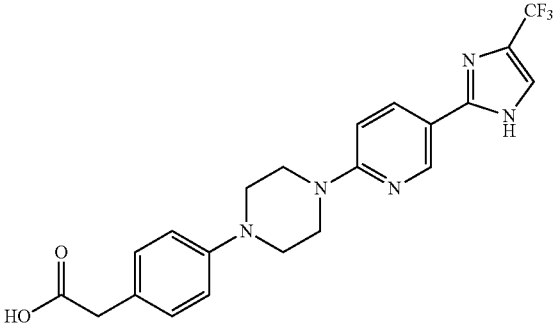 [SMILES: O=C(O)Cc1ccc(N2CCN(c3ccc(-c4nc(C(F)(F)F)c[nH]4)cn3)CC2)cc1] | 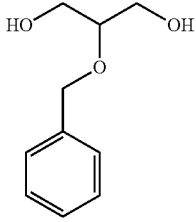 |

| Example | Product | MS (m/z) |
|---|---|---|
| 40-2 | 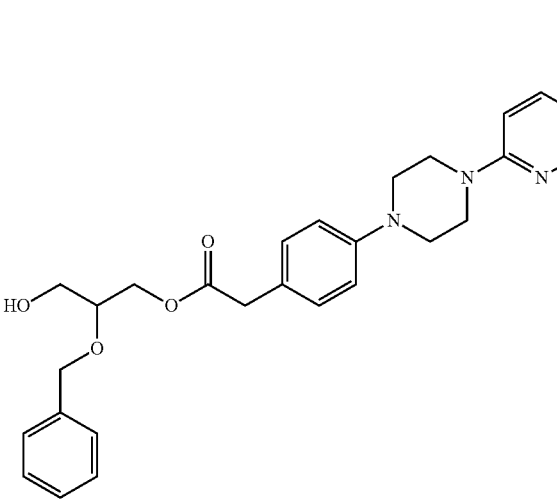 | 596 [M + H]$^+$ |

Example 41-1

[Chemical Formula 109]

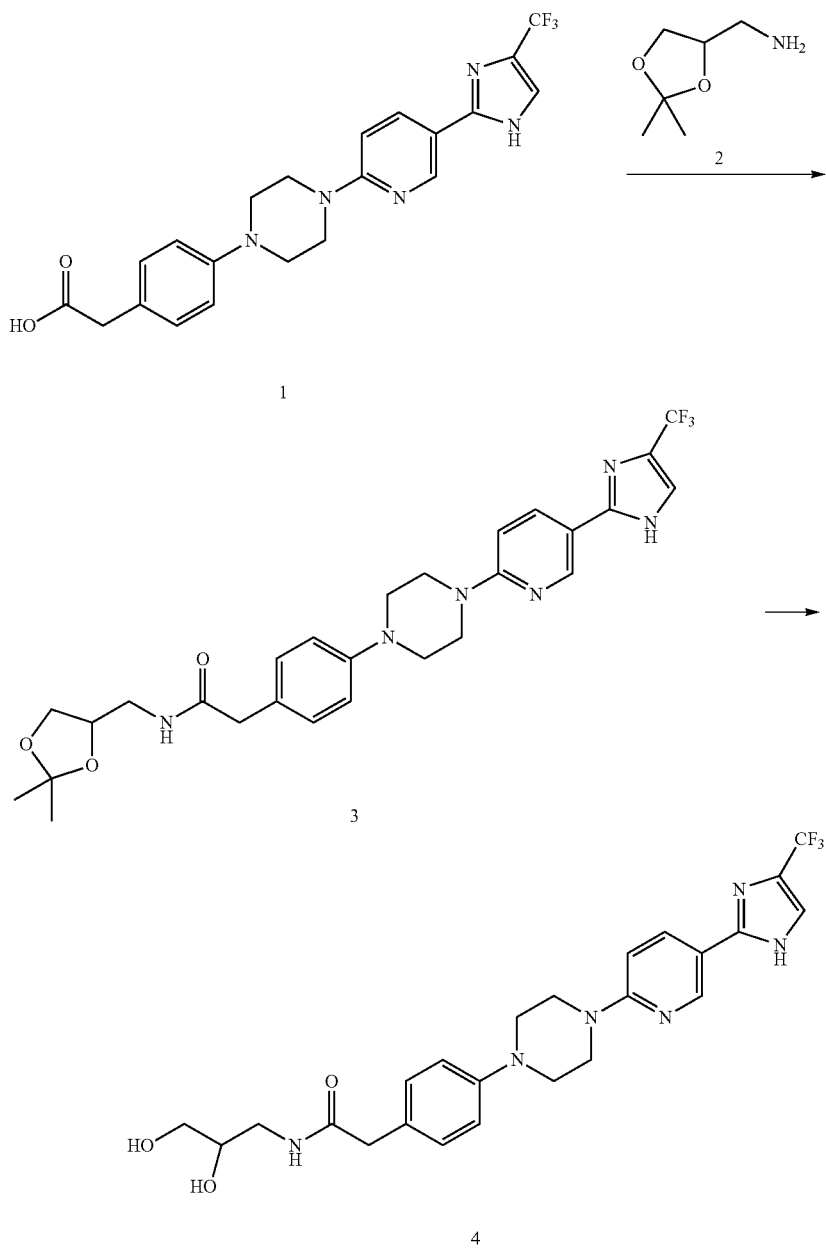

(1) Compound 1 (200 mg), Compound 2 (122 mg), 1-(3-dimethylaminopropyl)-3-ethylcarbodiimide hydrochloride (178 mg) and 1-hydroxybenzotriazole (125 mg) were added to dimethylformamide (5 mL), and the mixture was stirred at room temperature overnight. Ethyl acetate, n-hexane and water were added to the reaction solution to carry out a liquid separation. The organic layer was separated, washed with water and saturated brine, and dried over anhydrous sodium sulfate. The solvent was distilled off under reduced pressure. After the obtained residue was purified by silica gel column chromatography (n-hexane:ethyl acetate=100:0 to 90:10), diisopropyl ether and n-hexane were added, and the solid was collected by filtration to obtain Compound 3 (241 mg).
MS (m/z): 545 [M+H]$^+$ (2) Compound 3 (164 mg) was dissolved in 1,4-dioxane (5 mL) and concentrated hydrochloric acid (5 mL), and the mixture was stirred at room temperature for 6 hours. A saturated aqueous sodium hydrogen carbonate solution was added under ice cooling, and ethyl acetate and tetrahydrofuran were further added to carry out a liquid separation. The organic layer was separated, washed with saturated brine, and dried over anhydrous sodium sulfate. The solvent was distilled off under reduced pressure. To the obtained residue were added diisopropyl ether and isopropyl alcohol, and the solid was collected by filtration to obtain Compound 4 (58 mg).
MS (m/z): 505 [M+H]$^+$ Examples 41-2 to 41-3

A treatment was carried out in a manner similar to the Example 41-1 to obtain compounds of Examples 41-2 and 41-3 in Table 21 below.

TABLE 21

| Example | Starting material 1 | Starting material 2 |
|---|---|---|
| 41-2 | (structure: 4-[4-[5-(4-trifluoromethyl-1H-imidazol-2-yl)pyridin-2-yl]piperazin-1-yl]phenylacetic acid) | (S)-(2,2-dimethyl-1,3-dioxolan-4-yl)methyl-methylamine |
| 41-3 | (structure: 4-[4-[5-(4-trifluoromethyl-1H-imidazol-2-yl)pyridin-2-yl]piperazin-1-yl]phenylacetic acid) | (R)-(2,2-dimethyl-1,3-dioxolan-4-yl)methyl-methylamine |

| Example | Product | MS (m/z) |
|---|---|---|
| 41-2 | (S)-product structure | 519 [M + H]$^+$ |
| 41-3 | (R)-product structure | 519 [M + H]$^+$ |

Example 42
[Chemical Formula 110]
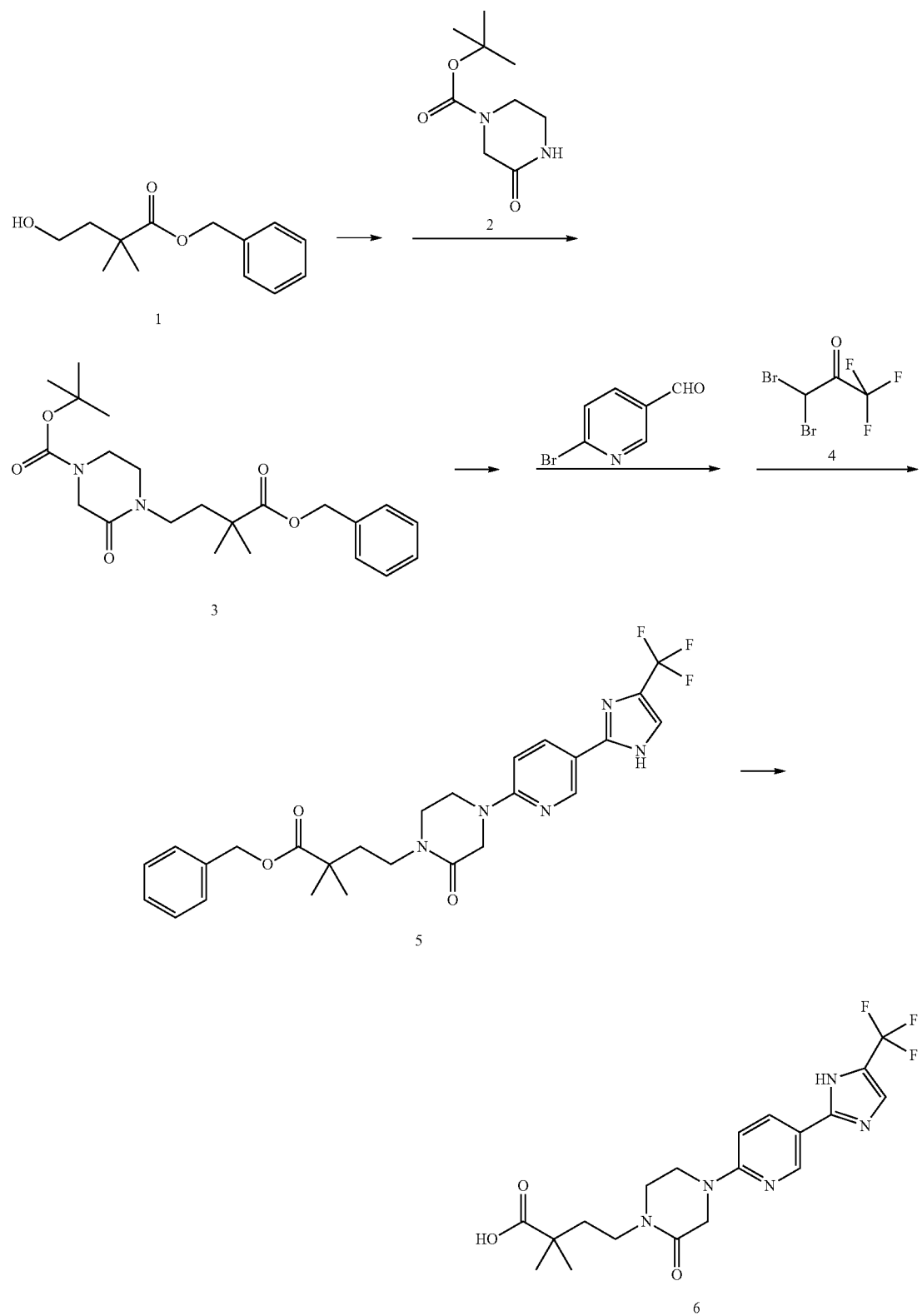

(1) To a solution of Compound 1 (200 mg) in toluene (10 mL) were added sequentially imidazole (153 mg), triphenylphosphine (590 mg) and iodine (457 mg), and the mixture was stirred at room temperature for 30 minutes. The reaction solution was diluted with ethyl acetate, to this was added an aqueous sodium sulfite solution, and the mixture was stirred. The organic layer was separated, washed with saturated brine, and dried over anhydrous sodium sulfate. The solvent was distilled off under reduced pressure.

To a solution of Compound 2 (180 mg) in N,N-dimethylformamide (4 mL) was added 60% sodium hydride (43 mg) under ice cooling, and the mixture was stirred at room temperature for 30 minutes. Then, a solution of the above residue in N,N-dimethylformamide (2 mL) was added, and the mixture was stirred at room temperature overnight. To the reaction solution was added a saturated aqueous ammonium chloride solution, and then ethyl acetate and water were added to carry out a liquid separation. The organic layer was separated, washed with water, and dried over anhydrous sodium sulfate. The solvent was distilled off under reduced pressure. The obtained residue was purified by silica gel column chromatography (n-hexane:ethyl acetate=67:33 to 40:60) to obtain Compound 3 (44 mg).

MS (m/z): 405 [M+H]$^+$ (2) Compound 3 (50 mg) was dissolved in 4N hydrochloric acid-1,4-dioxane solution (1 mL), and the mixture was stirred at room temperature overnight. The reaction solution was concentrated under reduced pressure, the obtained residue was dissolved in dimethylsulfoxide (1 mL), potassium carbonate (51 mg) and 6-bromonicotinaldehyde (30 mg) were added, and the mixture was stirred at 100° C. for 3 hours. After the reaction solution was cooled, ethyl acetate and water were added to carry out a liquid separation. The organic layer was separated, washed with water, and dried over anhydrous sodium sulfate. The solvent was distilled off under reduced pressure.

Compound 4 (100 mg) and sodium acetate (71 mg) were added to water (1 mL), and the mixture was stirred at 95° C. for 30 minutes. This was cooled to room temperature, to this were added a solution of the above residue in 25% aqueous ammonia (1 mL) and methanol (3 mL), and the mixture was stirred at room temperature overnight. Ethyl acetate and water to the reaction solution were added to carry out a liquid separation. The organic layer was separated, washed with water, and dried over anhydrous sodium sulfate. The solvent was distilled off under reduced pressure. The obtained residue was purified by thin layer silica gel chromatography (chloroform:methanol=9:1) to obtain Compound 5 (30 mg).

MS (m/z): 516 [M+H]$^+$ (3) A treatment was carried out in a manner similar to Example 18-1 (2) using Compound 5 (30 mg) to obtain Compound 6 (18.9 mg).

MS (m/z): 426 [M+H]$^+$

Example 43-1

[Chemical Formula 111]

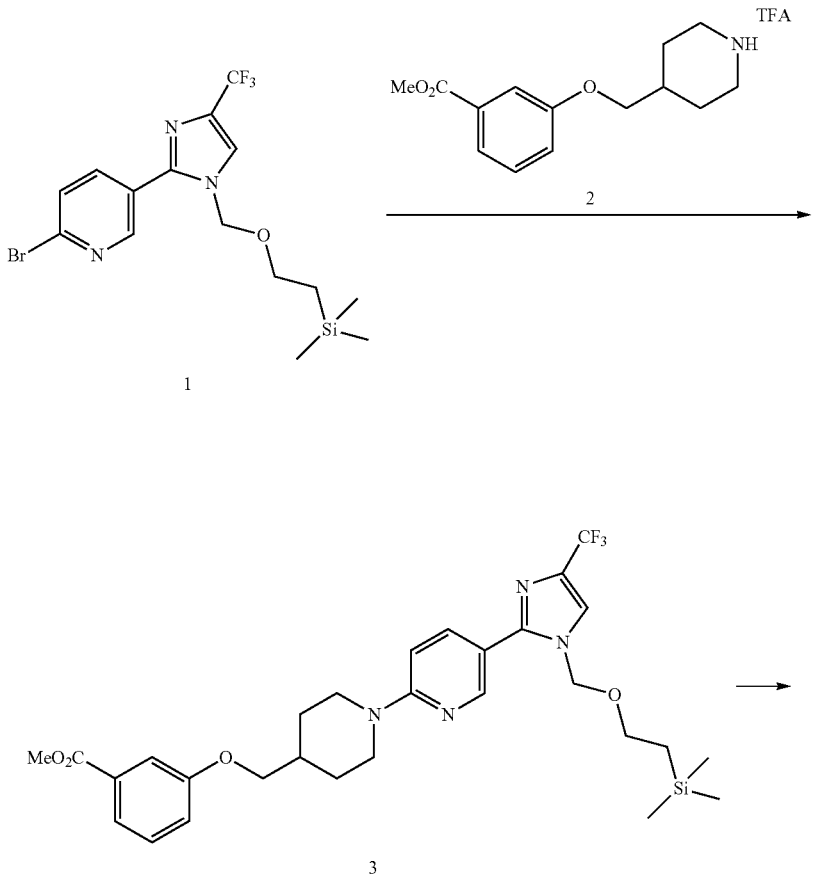

-continued

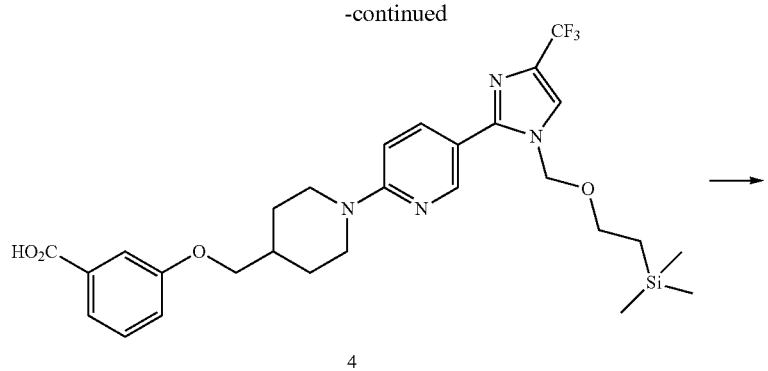

4

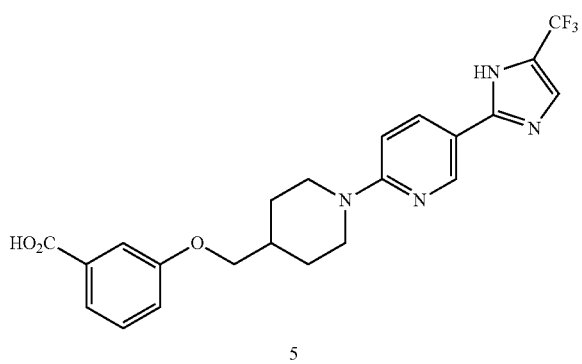

5

(1) Compound 1 (589 mg), Compound 2 (390 mg) and potassium carbonate (371 mg) were added to dimethylsulfoxide (8 mL), and the mixture was stirred at 100° C. overnight. Water and ethyl acetate were added to the reaction solution to carry out a liquid separation. The organic layer was separated, washed with saturated brine, and dried over anhydrous magnesium sulfate. The solvent was distilled off under reduced pressure. The residue was purified by silica gel column chromatography (n-hexane:ethyl acetate=85:15 to 70:30) to obtain Compound 3 (467 mg).

MS (m/z): 591 [M+H]$^+$ (2) A treatment was carried out in a manner similar to Example 1-1 (2) using Compound 3 (467 mg) to obtain Compound 4 (446 mg).

MS (m/z): 577 [M+H]$^+$ (3) A treatment was carried out in a manner similar to Example 7 (2) using Compound 4 (440 mg) to obtain Compound 5 (292 mg).

MS (m/z): 447 [M+H]$^+$

Examples 43-2 to 43-7

A treatment was carried out in a manner similar to the Example 43-1 to obtain compounds of Examples 43-2 to 43-7 in Table 22 below.

TABLE 22

| Example | Starting material 1 | Starting material 2 |
|---|---|---|
| 43-2 | ![structure with CF3, imidazole-SEM, bromopyridine] | ![4-(piperidin-4-yl)benzyl ester, TFA] |

TABLE 22-continued
| | | |
|---|---|---|
| 43-3 |  | 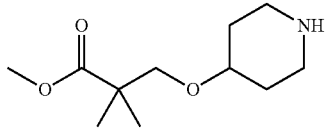 |
| 43-4 | 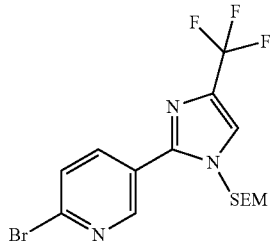 [SMILES: C[Si](C)(C)CCOCn1cc(C(F)(F)F)nc1-c1ccc(Br)nc1] | 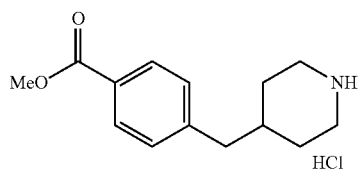 [SMILES: COC(=O)c1ccc(CC2CCNCC2)cc1 ; Cl] |
| 43-5 | 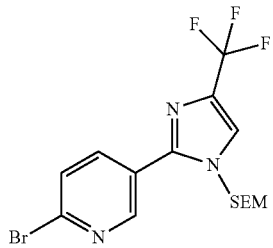 [SMILES: C[Si](C)(C)CCOCn1cc(C(F)(F)F)nc1-c1ccc(Br)nc1] | 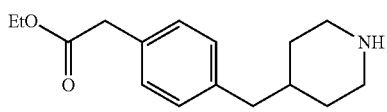 [SMILES: CCOC(=O)Cc1ccc(CC2CCNCC2)cc1] |
| 43-6 | 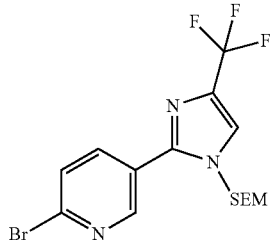 [SMILES: C[Si](C)(C)CCOCn1cc(C(F)(F)F)nc1-c1ccc(Br)nc1] | 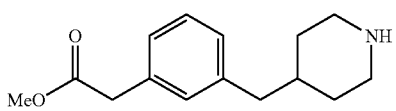 [SMILES: COC(=O)Cc1cccc(CC2CCNCC2)c1] |
| 43-7 | 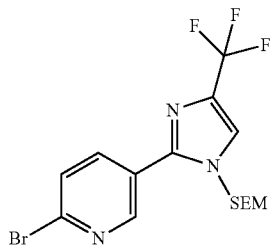 [SMILES: C[Si](C)(C)CCOCn1cc(C(F)(F)F)nc1-c1ccc(Br)nc1] | 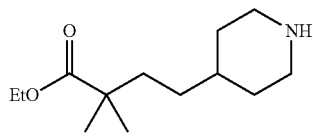 [SMILES: CCOC(=O)C(C)(C)CCC1CCNCC1] |

TABLE 22-continued
| Example | Product | MS (m/z) |
|---|---|---|
| 43-2 | 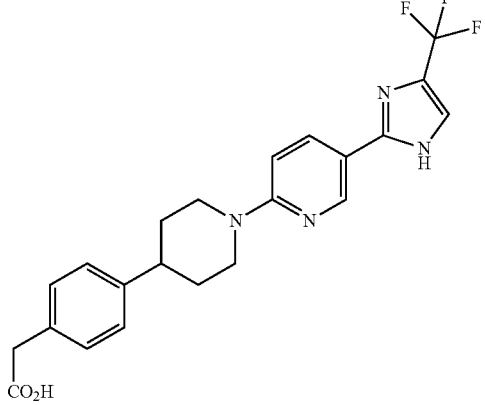 | 431 [M + H]⁺ |
| 43-3 | 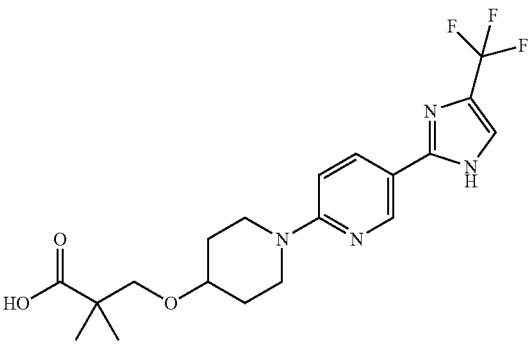 [SMILES: CC(C)(COC1CCN(c2ccc(-c3nc(C(F)(F)F)c[nH]3)cn2)CC1)C(=O)O] | 413 [M + H]⁺ |
| 43-4 | 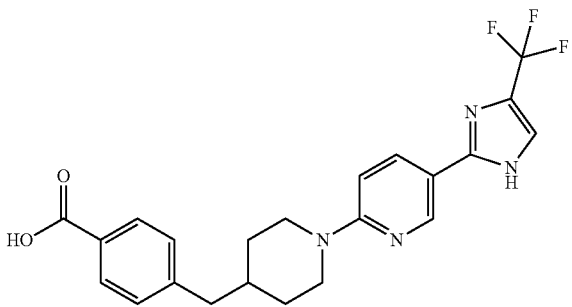 [SMILES: O=C(O)c1ccc(CC2CCN(c3ccc(-c4nc(C(F)(F)F)c[nH]4)cn3)CC2)cc1] | 431 [M + H]⁺ |
| 43-5 | 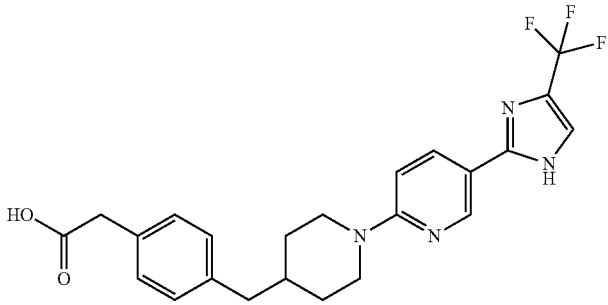 [SMILES: O=C(O)Cc1ccc(CC2CCN(c3ccc(-c4nc(C(F)(F)F)c[nH]4)cn3)CC2)cc1] | 445 [M + H]⁺ |

TABLE 22-continued
| | | |
|---|---|---|
| 43-6 | 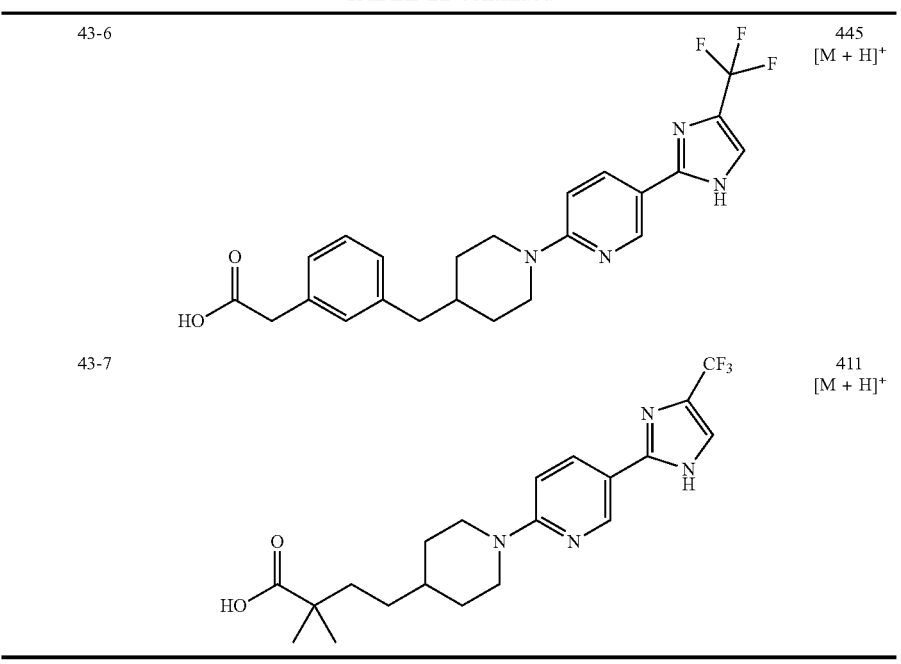 | 445 [M + H]+ |
| 43-7 | | 411 [M + H]+ |
Example 44-1
[Chemical Formula 112]
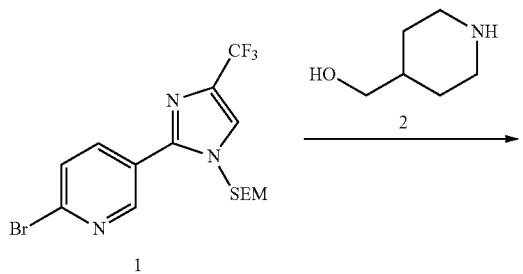
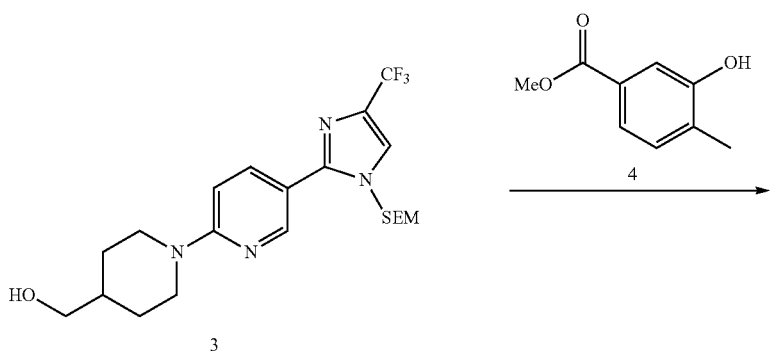

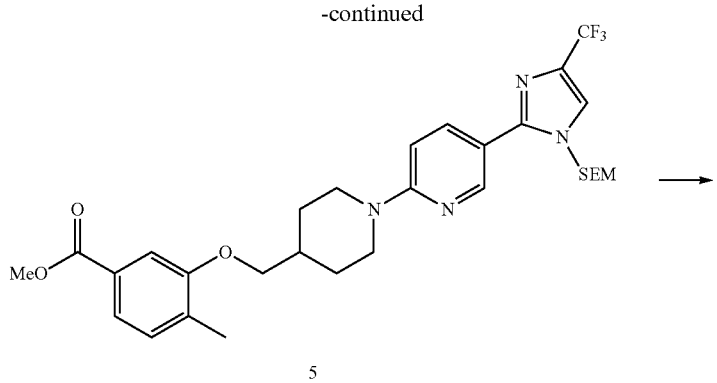

5

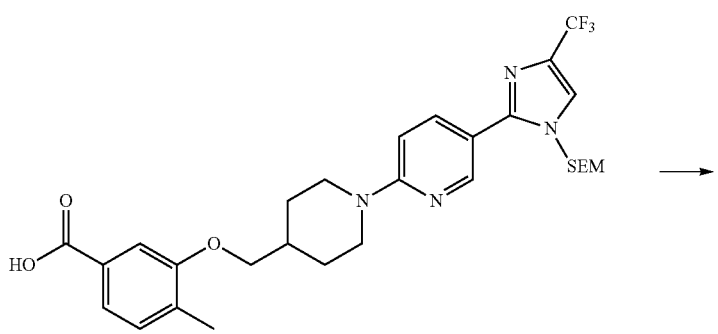

6

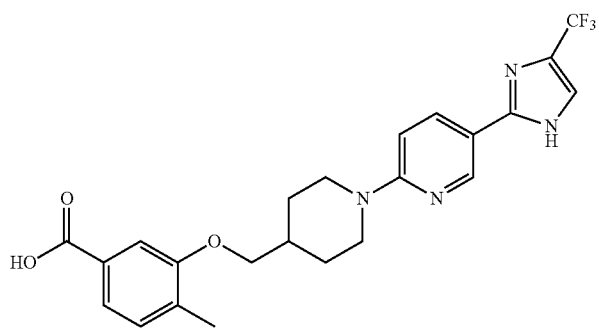 [SMILES: Cc1c(OCC2CCN(c3ccc(-c4nc(C(F)(F)F)c[nH]4)cn3)CC2)cccc1C(=O)O]

7

(1) A treatment was carried out in a manner similar to the Example 43-1 (1) using Compound 1 (1 g) and Compound 2 (0.545 g) to obtain Compound 3 (1.95 g).

MS (m/z): 457 [M+H]$^+$ (2) A treatment was carried out in a manner similar to the Example 18-1 (3) using Compound 3 (0.246 g) and Compound 4 (0.179 g) to obtain Compound 5 (0.253 g).

MS (m/z): 605 [M+H]$^+$ (3) A treatment was carried out in a manner similar to the Example 1-1 (2) using Compound 5 (0.252 g) to obtain Compound 6 (0.242 g).

MS (m/z): 591 [M+H]$^+$ (4) A treatment was carried out in a manner similar to the Example 7 (2) using Compound 6 (0.241 g) to obtain Compound 7 (0.164 g).

MS (m/z): 461 [M+H]$^+$

Examples 44-2 to 44-11

A treatment was carried out in a manner similar to the Example 44-1 to obtain compounds of Examples 44-2 to 44-11 in Table 23 below.

TABLE 23

| Example | Intermediate 1 | Intermediate 2 |
|---|---|---|
| 44-2 | (pyridine-piperidine-imidazole-CF3-SEM intermediate with HOCH2-piperidine) | methyl 3-hydroxy-5-methylbenzoate |
| 44-3 | (same intermediate 1) | methyl 3-hydroxy-2-methylbenzoate |
| 44-4 | (same intermediate 1) | methyl 5-hydroxy-2-methylbenzoate |
| 44-5 | (same intermediate 1) | ethyl 2-fluoro-3-hydroxybenzoate |
| 44-6 | (same intermediate 1) | methyl 2-chloro-3-hydroxybenzoate |
| 44-7 | (same intermediate 1) | methyl 4-hydroxybenzoate |

TABLE 23-continued
44-8
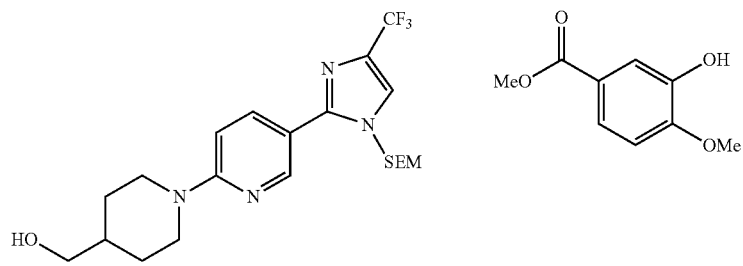
44-9
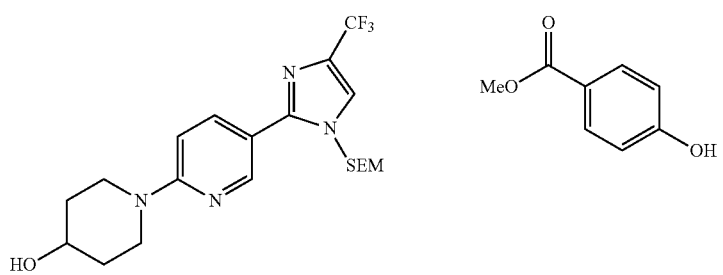
44-10
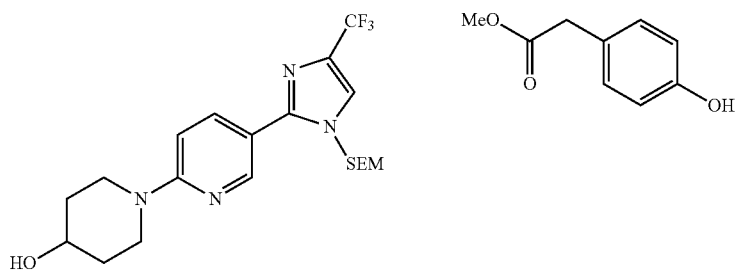
44-11
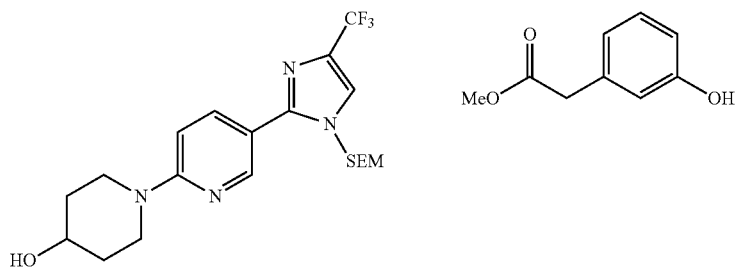
| Example | Product | MS (m/z) |
|---------|---------|----------|
| 44-2 | 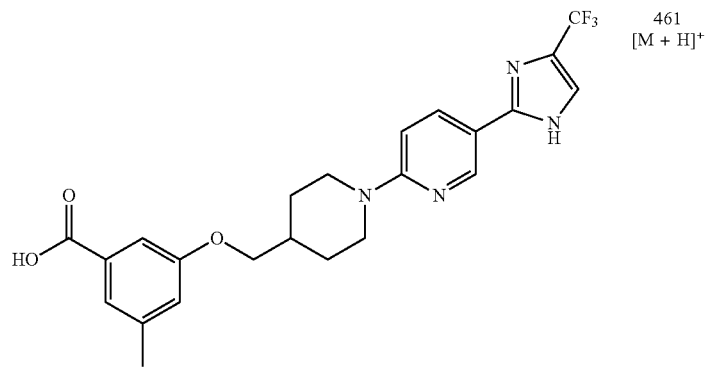 | 461 [M + H]+ |

TABLE 23-continued
| 44-3 | 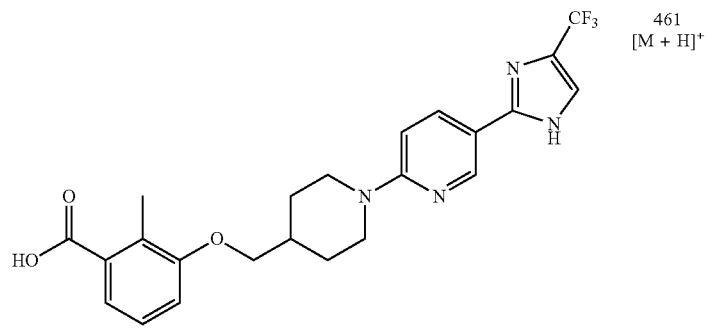 | 461 [M + H]+ |
| --- | --- | --- |
| 44-4 | 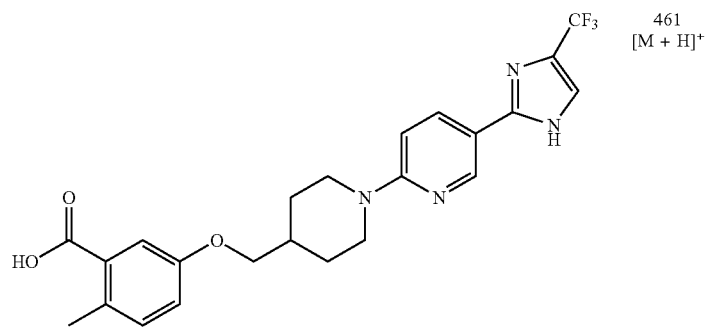 | 461 [M + H]+ |
| 44-5 | 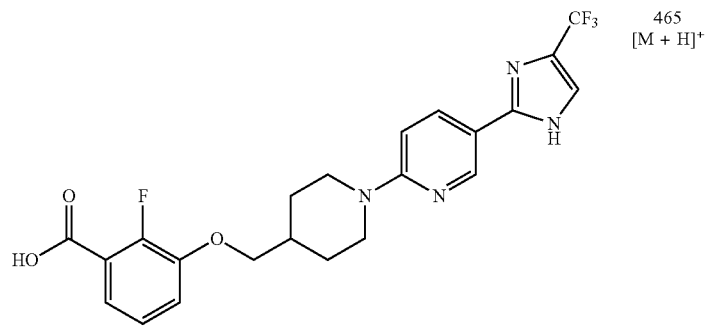 | 465 [M + H]+ |
| 44-6 |  | 481/483 [M + H]+ |

TABLE 23-continued
| 44-7 | 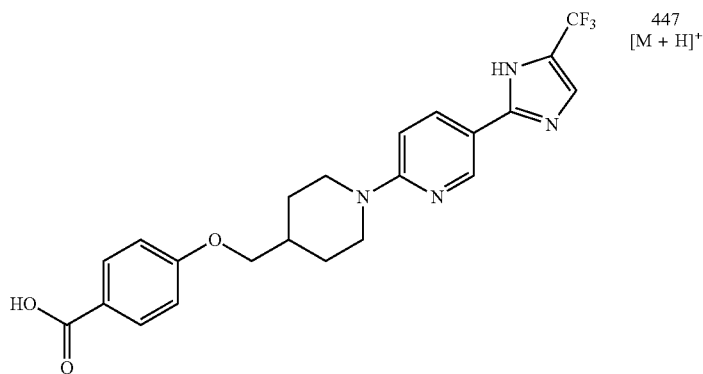 | 447 [M + H]+ |
| --- | --- | --- |
| 44-8 | 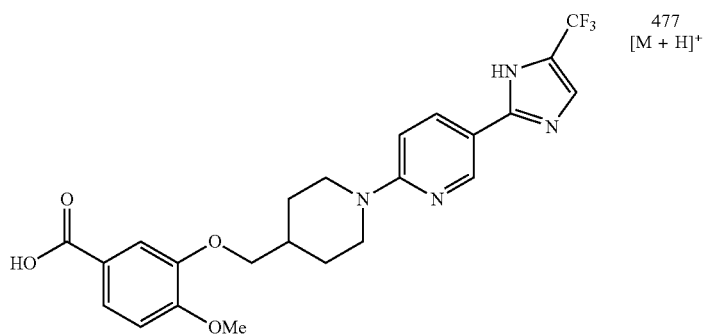 | 477 [M + H]+ |
| 44-9 | 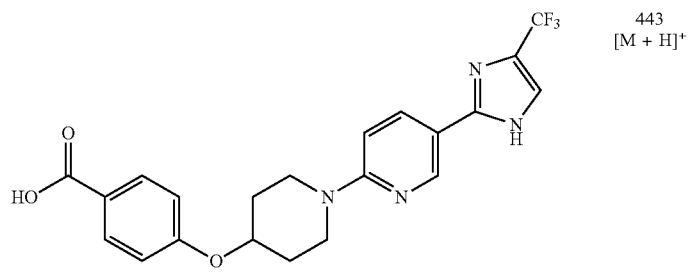 | 443 [M + H]+ |
| 44-10 |  | 447 [M + H]+ |
| 44-11 | 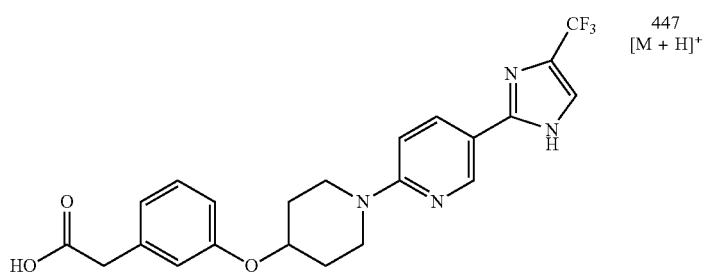 | 447 [M + H]+ |

Example 45-1

[Chemical Formula 113]

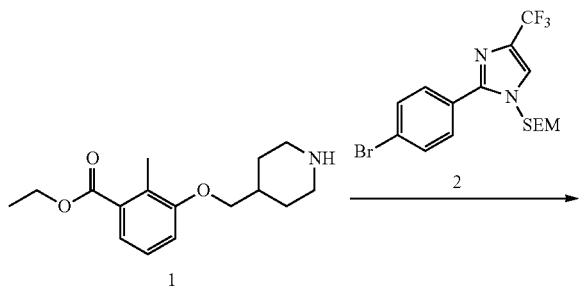

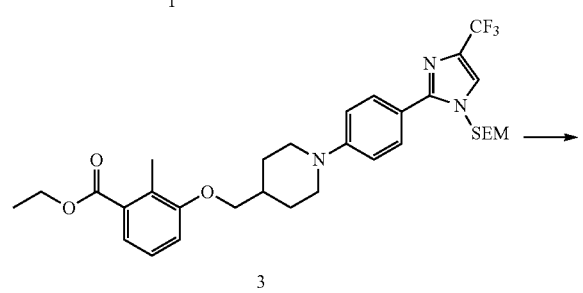

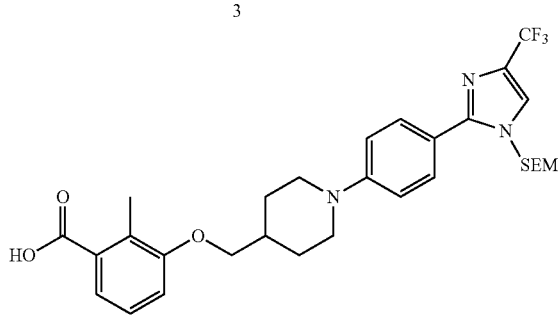

(1) Compound 1 (395 mg), Compound 2 (500 mg), tris(dibenzylideneacetone)dipalladium(0) (22 mg), 4,5-bis(diphenylphosphino)-9,9-dimethyl xanthene (Xantphos) (41 mg) and sodium t-butoxide (342 mg) were added to toluene (10 mL), and the mixture was stirred under a nitrogen atmosphere at 100° C. for 3 hours. Ethyl acetate and water were added to the reaction solution to carry out a liquid separation. The organic layer was separated, washed with saturated brine, and dried over anhydrous sodium sulfate. The solvent was distilled off under reduced pressure. The residue was purified by silica gel column chromatography (n-hexane:ethyl acetate=95:5 to 80:20) to obtain Compound 3 (121 mg).

MS (m/z): 618 [M+H]$^+$ (2) A treatment was carried out in a manner similar to the Example 6 (7) using Compound 3 (120 mg) to obtain Compound 4 (34 mg).

MS (m/z): 460 [M+H]$^+$

Examples 45-2 to 45-3

A treatment was carried out in a manner similar to the Example 45-1 to obtain compounds of Examples 45-2 and 45-3 in Table 24 below.

TABLE 24

| Example | Starting material 1 | Starting material 2 |
|---|---|---|
| 45-2 | 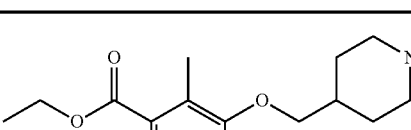 | 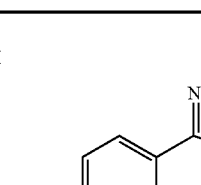 |
| 45-3 | 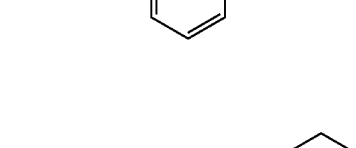 | 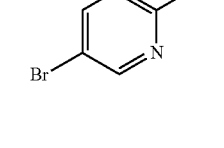 |

TABLE 24-continued
| Example | Product | MS (m/z) |
|---|---|---|
| 45-2 | 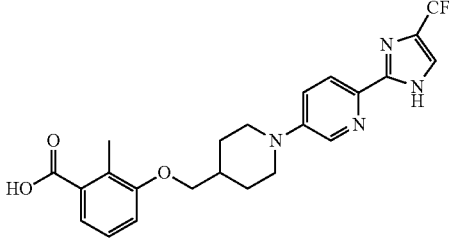 | 461 [M + H]+ |
| 45-3 | 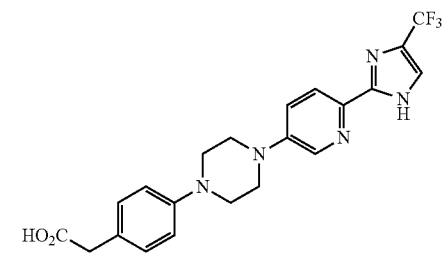 [SMILES: O=C(O)Cc1ccc(N2CCN(c3ccc(-c4nc(C(F)(F)F)c[nH]4)nc3)CC2)cc1] | 432 [M + H]+ |
Example 46-1
[Chemical Formula 114]
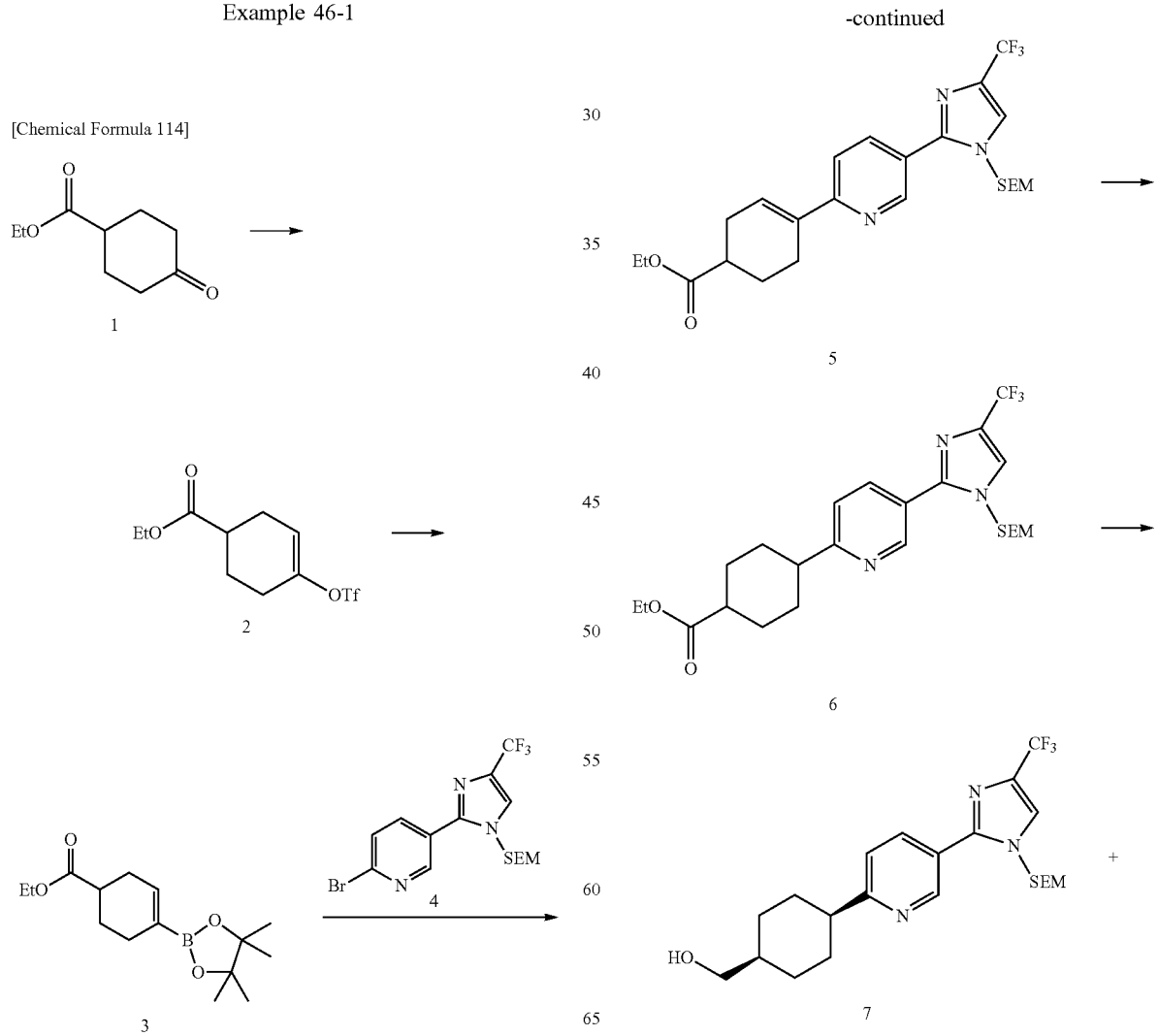

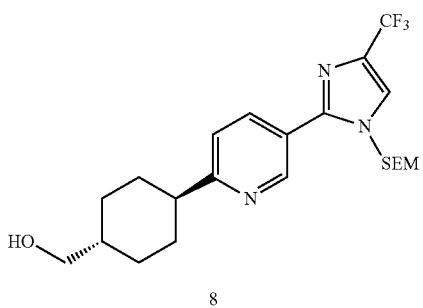

8

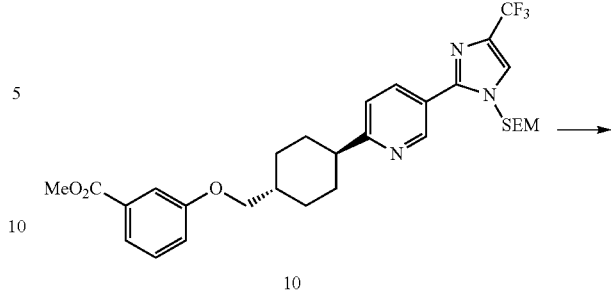

10

(1) Compound 1 (5 g) and 2,6-lutidine (5.13 mL) were dissolved in methylene chloride (50 mL), trifluoromethanesulfonic anhydride (9.88 mL) was added dropwise under ice cooling over 30 minutes, and the mixture was stirred at room temperature for 1 hour. Additional trifluoromethanesulfonic anhydride (2.4 mL) was added dropwise, and the mixture was stirred at room temperature for 3 hours. After the reaction solution was concentrated under reduced pressure, the obtained residue was purified by silica gel column chromatography (n-hexane:ethyl acetate=90:10) to obtain Compound 2 (5.44 g).

MS (m/z): 303 [M+H]$^+$ (2) A treatment was carried out in a manner similar to the Example 9 (2) using Compound 2 (5.4 g) to obtain Compound 3 (4.42 g).

MS (m/z): 281 [M+H]$^+$ (3) A treatment was carried out in a manner similar to the Example 7 (1) using Compound 3 (4.4 g) and Compound 4 (6.15 g) to obtain Compound 5 (6.06 g).

MS (m/z): 496 [M+H]$^+$ (4) Compound 5 (5.73 g) and 10% palladium-carbon (0.57 g) were mixed in ethanol (115 mL), and the mixture was stirred under a hydrogen atmosphere at room temperature for 6 hours. The reaction solution was filtered, and the filtrate was concentrated under reduced pressure. The obtained residue was purified by silica gel column chromatography (n-hexane:ethyl acetate=90:10 to 66:34) to obtain Compound 6 (5.35 g).

MS (m/z): 498 [M+H]$^+$ (5) A treatment was carried out in a manner similar to the Example 10 (2) using Compound 6 (0.906 g) to obtain Compound 7 (446 mg) and Compound 8 (176 mg).

MS (m/z): 456 [M+H]$^+$

[Chemical Formula 115]

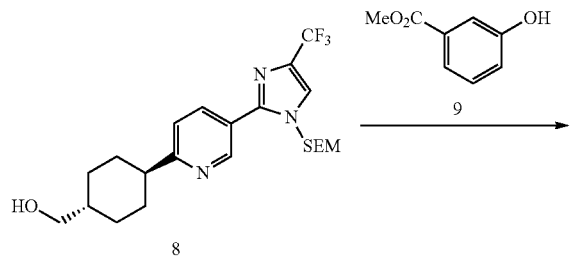

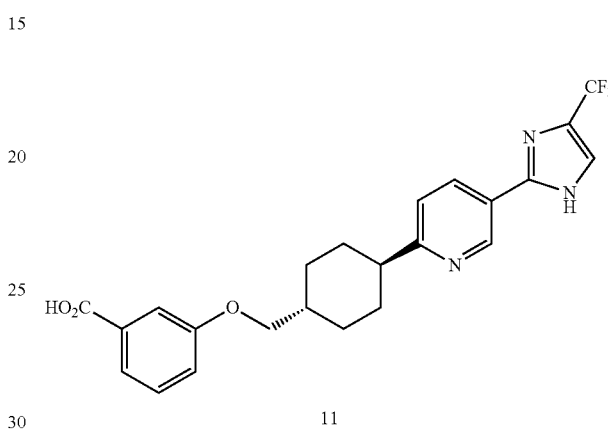

11

(6) Compound 8 (165 mg) was dissolved in methylene chloride (3.3 mL), then diisopropyl ethyl amine (126 μL) and methanesulfonyl chloride (42 μL) were added under ice cooling, and the mixture was stirred at room temperature for 50 minutes. Diethyl ether and water were added to the reaction solution to carry out a liquid separation. The organic layer was separated, washed with water, and dried over anhydrous magnesium sulfate. The solvent was distilled off under reduced pressure. Compound 9 (83 mg) was dissolved in N,N-dimethylformamide (1.6 mL), 60% sodium hydride (24.6 mg) was added under ice cooling, and the mixture was stirred at room temperature for 30 minutes. To this was added a solution of the above residue in N,N-dimethylformamide (1.6 mL), and the mixture was stirred at 70° C. for 3 hours. After the reaction solution was cooled, water and ethyl acetate were added to carry out a liquid separation. The organic layer was separated, washed with water and saturated brine, and dried over anhydrous magnesium sulfate. The solvent was distilled off under reduced pressure. The obtained residue was purified by silica gel column chromatography (n-hexane:ethyl acetate=95:5 to 80:20) to obtain Compound 10 (107 mg).

MS (m/z): 590 [M+H]$^+$ (7) A treatment was carried out in a manner similar to Example 1-1 (2) and Example 7 (2) using Compound 10 (97 mg) to obtain Compound 11 (79 mg).

MS (m/z): 446 [M+H]$^+$

Examples 46-2 to 46-7

A treatment was carried out in a manner similar to the Example 46-1 to obtain compounds of Examples 46-2 to 46-7 in Table 25 below.

TABLE 25

| Example | Intermediate 1 | Intermediate 2 |
| --- | --- | --- |
| 46-2 | [cyclohexyl(HOCH2)-pyridine-imidazole(CF3)(SEM)] | 3-hydroxy methyl benzoate (MeO2C, OH) |
| 46-3 | [cyclohexyl(HOCH2)-pyridine-imidazole(CF3)(SEM)] | methyl 3-hydroxy-2-methylbenzoate |
| 46-4 | [cyclohexyl(HOCH2)-pyridine-imidazole(CF3)(SEM)] | methyl 5-hydroxy-2-methylbenzoate |
| 46-5 | [cyclohexyl(HOCH2)-pyridine-imidazole(CF3)(SEM)] | methyl 2-fluoro-3-hydroxybenzoate |
| 46-6 | [cyclohexyl(HOCH2)-pyridine-imidazole(CF3)(SEM)] | methyl 2-chloro-3-hydroxybenzoate |

TABLE 25-continued
| | | |
|---|---|---|
| 46-7 | 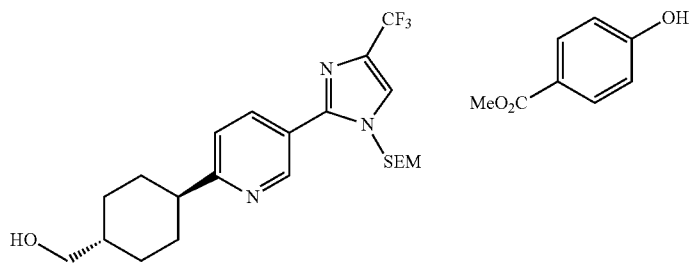 | |
| Example | Product | MS (m/z) |
|---|---|---|
| 46-2 | 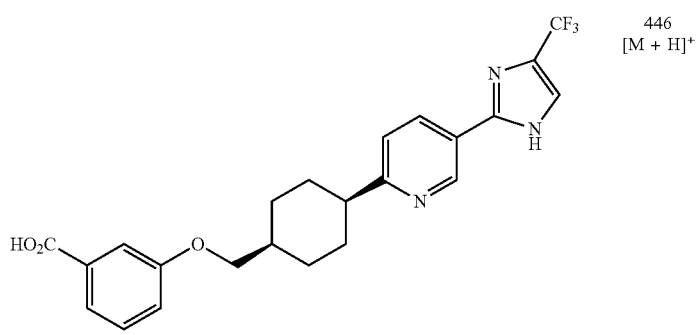 | 446 [M + H]+ |
| 46-3 | 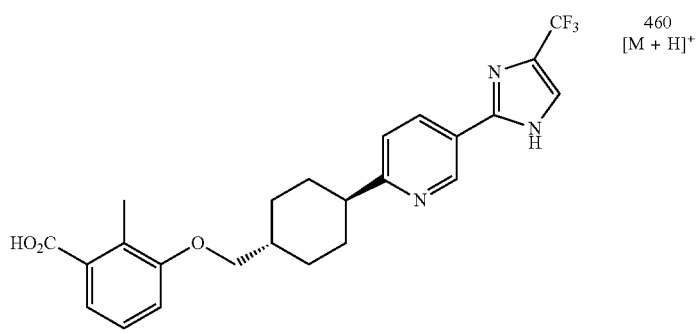 | 460 [M + H]+ |
| 46-4 |  | 460 [M + H]+ |

TABLE 25-continued
| 46-5 | 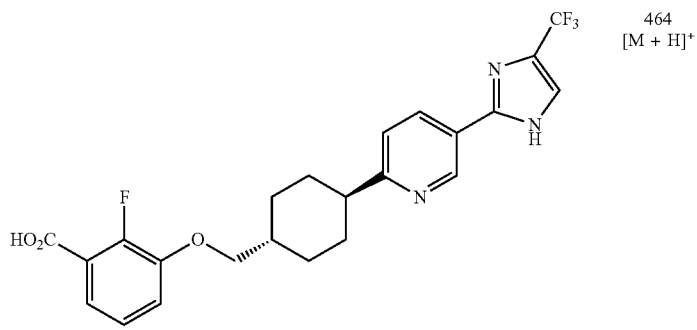 | 464 [M + H]+ |
| 46-6 | 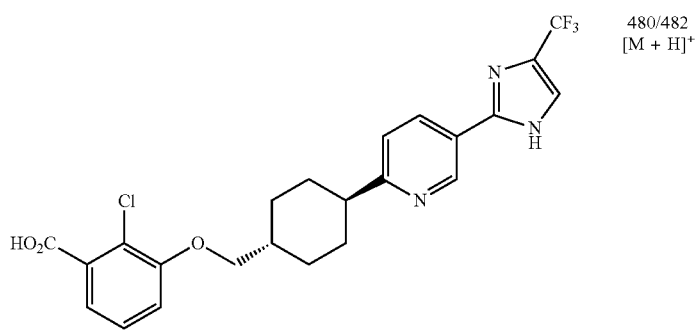 | 480/482 [M + H]+ |
| 46-7 | 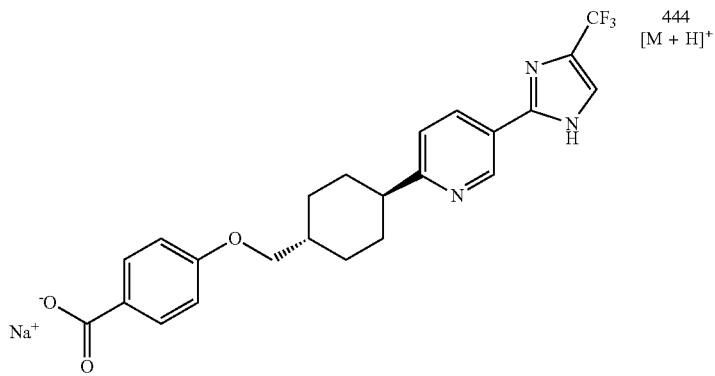 | 444 [M + H]+ |

Example 47-1

[Chemical Formula 116]

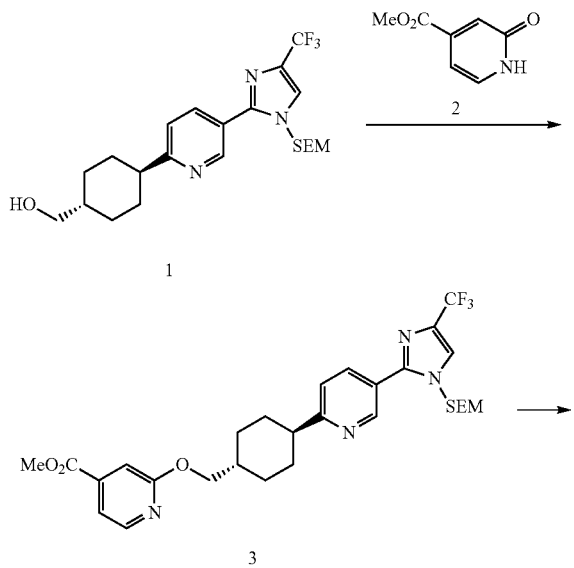

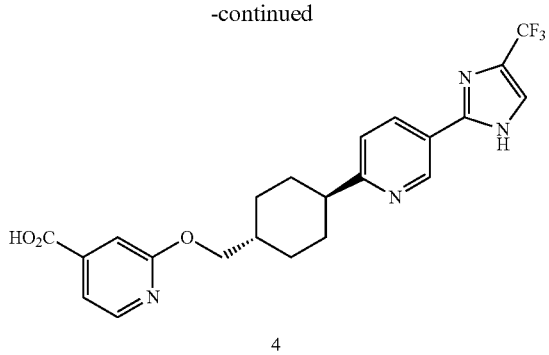

(1) A treatment was carried out in a manner similar to the Example 18-1 (3) using Compound 1 (91 mg) and Compound 2 (61 mg) to obtain Compound 3 (70 mg).
MS (m/z): 591 [M+H]$^+$ (2) A treatment was carried out in a manner similar to the Example 1-1 (2) and Example 7 (2) using Compound 3 (67 mg) to obtain Compound 4 (41 mg).
MS (m/z): 447 [M+H]$^+$

Example 47-2

A treatment was carried out in a manner similar to the Example 47-1 to obtain a compound of Example 47-2 in Table 26 below.

TABLE 26

| Example | Intermediate 1 | Intermediate 2 |
|---|---|---|
| 47-2 | (structure: cyclohexyl-pyridyl-imidazole-CF$_3$-SEM with HOCH$_2$-) | MeO$_2$C-pyridyl-OH |

| Example | Product | MS (m/z) |
|---|---|---|
| 47-2 | (structure: HO$_2$C-pyridyl-O-CH$_2$-cyclohexyl-pyridyl-imidazole-CF$_3$) | 447 [M + H]$^+$ |

Example 48
[Chemical Formula 117]
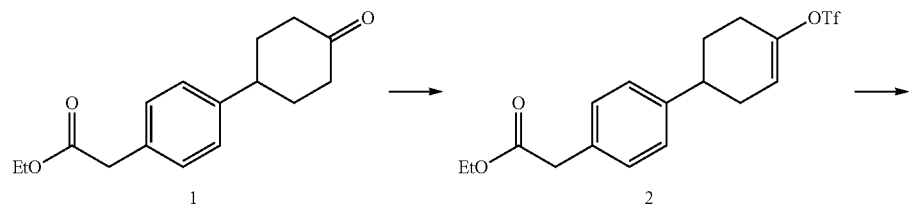
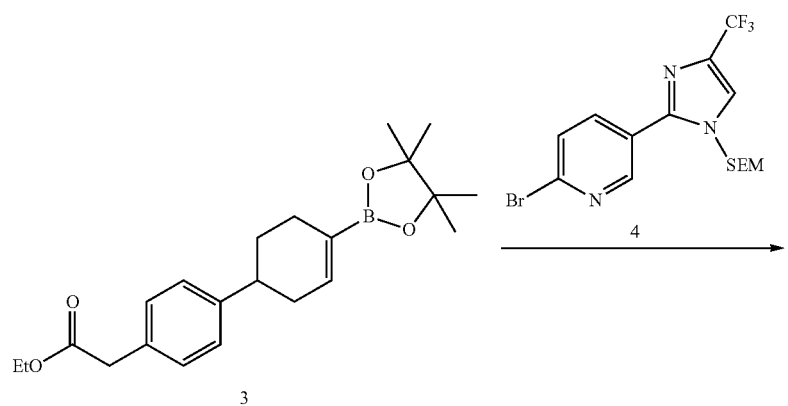
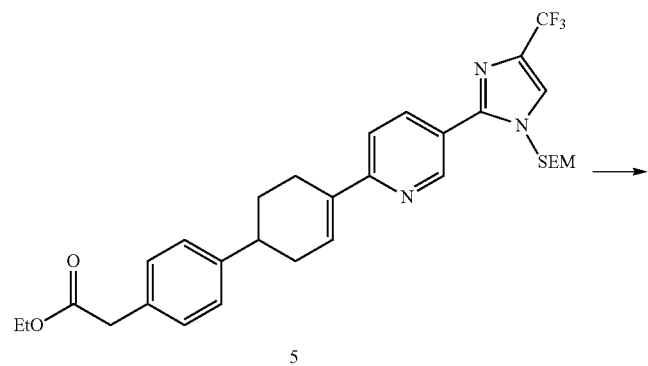
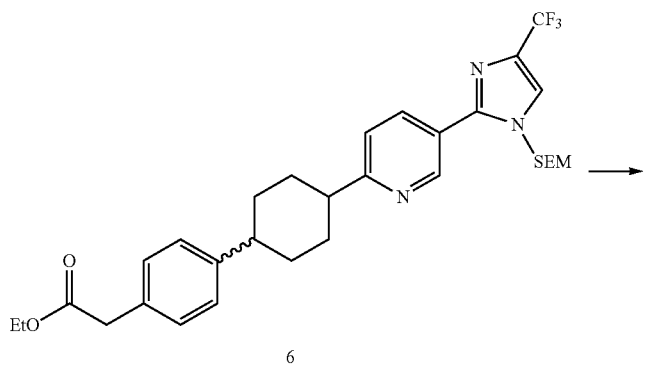

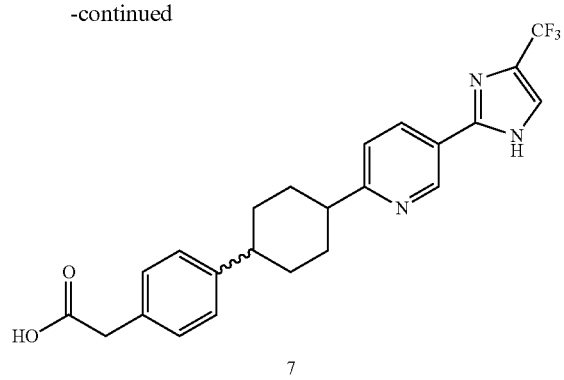

7

(1) Compound 1 (see US2010/267689) (320 mg) and 2,6-di-t-butyl-4-methylpyridine (197 μL) were dissolved in methylene chloride (8 mL), trifluoromethanesulfonic anhydride (238 μL) was added, and the mixture was stirred at room temperature overnight. Water was added to the reaction solution to carry out a liquid separation. The organic layer was separated, and the solvent was distilled off under reduced pressure. To the obtained residue was added diisopropyl ether to be mixed. The insoluble substance was filtered out. The filtrate was concentrated under reduced pressure, and the obtained residue was purified by silica gel column chromatography (n-hexane:ethyl acetate=95:5 to 85:15) to obtain Compound 2 (181 mg).

MS (m/z): 393 [M+H]$^+$ (2) A treatment was carried out in a manner similar to the Example 9 (2) using Compound 2 (180 mg) to obtain Compound 3 (202 mg).

MS (m/z): 388 [M+NH4]$^+$ (3) A treatment was carried out in a manner similar to the Example 7 (1) using Compound 3 (210 mg) and Compound 4 (150 mg) to obtain Compound 5 (56 mg).

MS (m/z): 586 [M+H]$^+$ (4) Compound 5 (56 mg) was dissolved in ethanol (2.2 mL) and ethyl acetate (0.56 mL), 10% palladium-carbon (11 mg) was added, and the mixture was stirred under a hydrogen atmosphere at room temperature for 6 hours. The reaction solution was filtered through a membrane-filter, and the filtrate was concentrated under reduced pressure to obtain Compound 6 (55 mg).

MS (m/z): 588 [M+H]$^+$ (5) A treatment was carried out in a manner similar to Example 1-1 (2) and Example 7 (2) using Compound 6 (54 mg) to obtain Compound 7 (28 mg).

MS (m/z): 430 [M+H]$^+$

Example 49

[Chemical Formula 118]

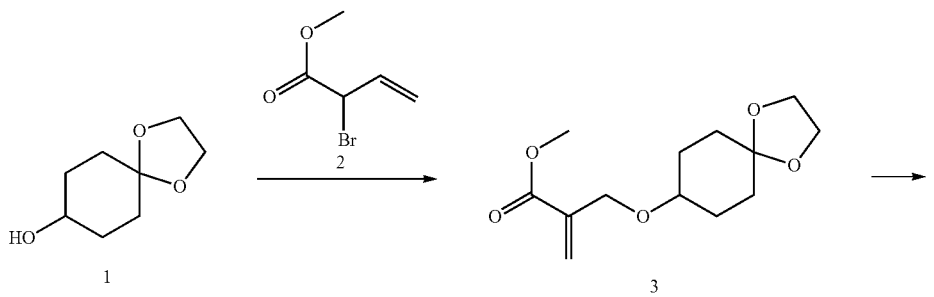

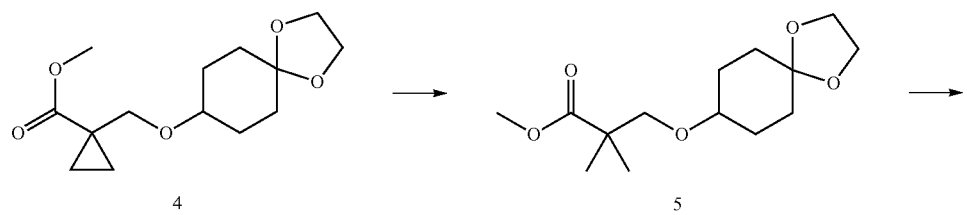

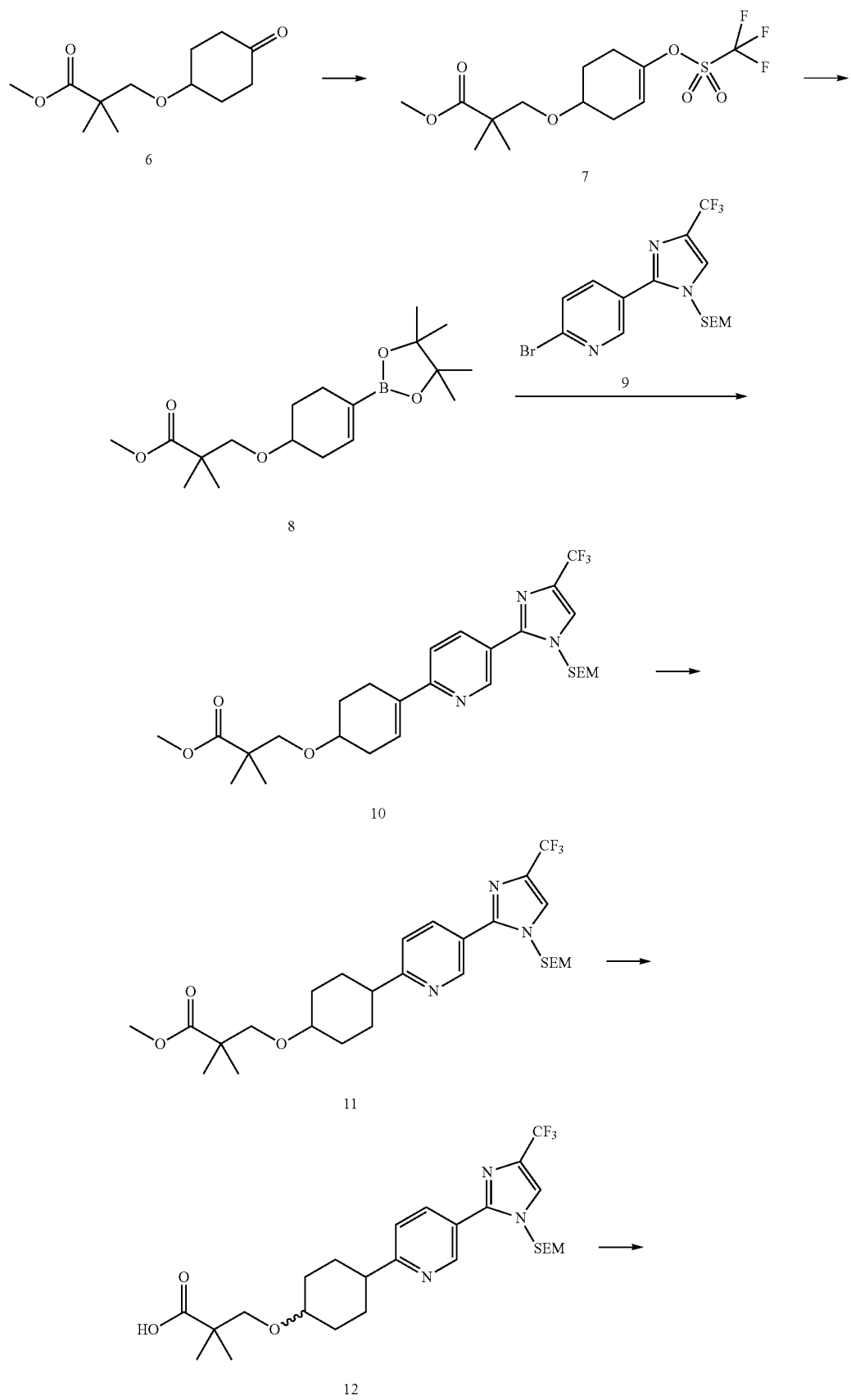

-continued

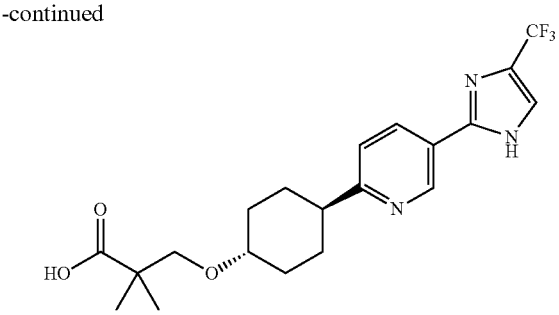

13

(1) Compound 1 (4.5 g) was dissolved in N,N-dimethylformamide (45 mL), to this was added sodium hydride (1.37 g) under ice cooling, and the mixture was stirred under a nitrogen stream for 30 minutes. To this was added dropwise Compound 2 (5.09 g), and the mixture was stirred at 0° C. for 30 minutes and then at room temperature for 1 hour. Water and ethyl acetate were added to the reaction solution to carry out a liquid separation. The organic layer was separated, washed with saturated brine, and dried over anhydrous magnesium sulfate. The solvent was distilled off under reduced pressure. The obtained residue was purified by silica gel column chromatography (n-hexane:ethyl acetate=95:5 to 65:35) to obtain Compound 3 (3.13 g).

MS (m/z): 257 [M+H]$^+$ (2) 60% Sodium hydride (537 mg) was suspended in dimethylsulfoxide (4 mL), and trimethylsulfonium iodide (2.95 g) was added, and the mixture was stirred at room temperature for 1 hour. To this was added dropwise a solution of Compound 3 (3.13 g) in dimethylsulfoxide (2 mL), and the mixture was stirred at room temperature for 3 days. Water and diethyl ether were added to the reaction solution to carry out a liquid separation. The organic layer was separated and washed with saturated brine, and then the solvent was distilled off under reduced pressure. The obtained residue was purified by silica gel column chromatography (n-hexane:ethyl acetate=90:10 to 65:35) to obtain Compound 4 (898 mg).

MS (m/z): 271 [M+H]$^+$ (3) Compound 4 (100 mg) was dissolved in acetic acid (2 mL), and platinum oxide (10 mg) was added under a nitrogen atmosphere, and the mixture was stirred under a hydrogen atmosphere at room temperature for 8 hours. The reaction solution was filtered through a membrane-filter, and the filtrate was concentrated under reduced pressure. The obtained residue was purified by silica gel column chromatography (n-hexane:ethyl acetate=90:10 to 35:65) to obtain Compound 5 (41 mg).

MS (m/z): 273 [M+H]$^+$ (4) Compound 5 (355 mg) was dissolved in trifluoroacetic acid (0.3 mL), water (1 mL) and tetrahydrofuran (3 mL), and the mixture was stirred at 65° C. for 3 hours. Water, an aqueous sodium hydrogen carbonate solution and ethyl acetate were added to the reaction solution to carry out a liquid separation. The organic layer was separated and washed with saturated brine, and then the solvent was distilled off under reduced pressure. The obtained residue was purified by silica gel column chromatography (n-hexane:ethyl acetate=90:10 to 65:35) to obtain Compound 6 (242 mg).

MS (m/z): 229 [M+H]$^+$ (5) Compound 6 (230 mg) and N-phenylbis(trifluoromethanesulfonamide) (719 mg) were dissolved in tetrahydrofuran (5 mL), 0.5N potassium hexamethyldisilazane (4.03 mL) was added dropwise under a nitrogen atmosphere at −78° C., and the mixture was stirred for 1 hour. Water, an aqueous saturated ammonium chloride solution and ethyl acetate were added to the reaction solution to carry out a liquid separation. The organic layer was separated and washed with saturated brine, and subsequently the solvent was distilled off under reduced pressure. The obtained residue was purified by silica gel column chromatography (n-hexane:ethyl acetate=96:4 to 80:20) and NH-silica gel column chromatography (n-hexane:ethyl acetate=98:2 to 92:8) to obtain Compound 7 (623 mg).

MS (m/z): 361 [M+H]$^+$ (6) A treatment was carried out in a manner similar to the Example 9 (2) using Compound 7 to obtain Compound 8.

MS (m/z): 339 [M+H]$^+$ (7) A treatment was carried out in a manner similar to the Example 7 (1) using Compound 8 to obtain Compound 10.

MS (m/z): 554 [M+H]$^+$ (8) Compound 10 (257 mg) was suspended in methanol (4 mL) and tetrahydrofuran (2 mL), 10% palladium-carbon (26 mg) was added under a nitrogen atmosphere, and the mixture was stirred under a hydrogen atmosphere at room temperature for 5 hours. The reaction solution was filtered through a membrane-filter, and the filtrate was concentrated under reduced pressure. The obtained residue was purified by silica gel column chromatography (n-hexane:ethyl acetate=80:20 to 60:40) to obtain Compound 11 (220 mg).

MS (m/z): 556 [M+H]$^+$ (9) A treatment was carried out in a manner similar to the Example 1-1 (2) using Compound 11 (218 mg) to obtain Compound 12 (131 mg).

MS (m/z): 542 [M+H]$^+$

(10) A treatment was carried out in a manner similar to the Example 7 (2) using Compound 12 (130 mg) to obtain Compound 13 (4.8 mg).

MS (m/z): 412 [M+H]$^+$

Example 50

(1)

[Chemical Formula 119]

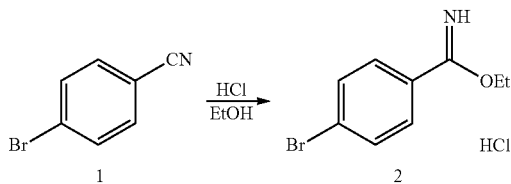

To ethanol (250 mL) was added Compound 1 (10 g), and the mixture was ice-cooled. Hydrochloric acid gas was blown for 10 minutes. The reaction solution was stirred at room temperature overnight and subsequently concentrated under reduced pressure to obtain Compound 2 (12.53 g) as a white powder.

MS (m/z): 228/230 [M+H]$^+$ (2)

[Chemical Formula 120]

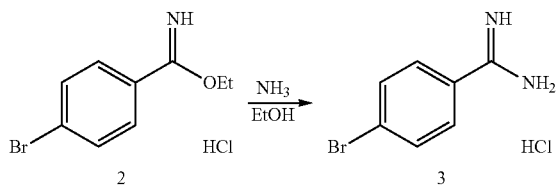

Compound 2 (12.53 g) was dissolved in ethanol (94 mL), and a 7N ammonia/methanol solution (31.5 mL) was added dropwise at room temperature over 5 minutes. After the reaction solution was stirred at room temperature for 3 hours, an additional 7N ammonia/methanol solution (15.7 mL) was added, and the mixture was stirred overnight. The reaction solution was concentrated under reduced pressure, to the obtained white solid was added diethyl ether, and the mixture was stirred. Subsequently, the solid was collected by filtration and dried to obtain Compound 3 (13.25 g) as a white powder.

MS (m/z): 199/201 [M+H]$^+$ (3)

[Chemical Formula 121]

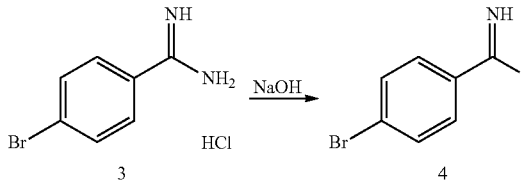

Compound 3 (13.25 g) was suspended in water (40 mL), and a 5N aqueous sodium hydroxide solution (40 mL) was added, and the mixture was stirred at room temperature for 3 hours. The deposit was collected by filtration and washed with water. The obtained white solid was dissolved in acetone, activated charcoal was added, and the mixture was stirred for 10 minutes, and subsequently, filtered through Celite. The filtrate was concentrated under reduced pressure, and the obtained powder was washed with diethyl ether, collected by filtration and dried to obtain Compound 4 (9.58 g) as a white powder.

(4)

[Chemical Formula 122]

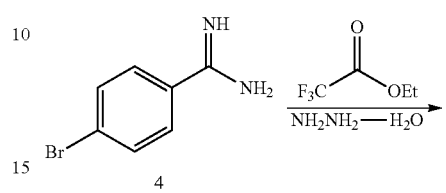

To tetrahydrofuran (6 mL) were added ethyl trifluoroacetate (598 μL) and hydrazine hydrate (232 μL), and the mixture was stirred at 65° C. for 1 hour. To the reaction solution was added Compound 4 (1 g), and the mixture was stirred at 65° C. for 4.5 hours. Water was added, and the mixture was extracted with ethyl acetate, washed with saturated brine, and dried over anhydrous magnesium sulfate. After the mixture was dried and concentrated under reduced pressure, the obtained solid was dissolved in ethyl acetate, activated charcoal was added, and the mixture was stirred. Subsequently, the mixture was filtered out through Celite. The filtrate was concentrated under reduced pressure, and the obtained residue was purified by silica gel column chromatography (n-hexane:ethyl acetate=90:10 to 80:20) to obtain Compound 5 (1.082 g) as a white solid.

MS (m/z): 292/294 [M+H]$^+$ (5)

[Chemical Formula 123]

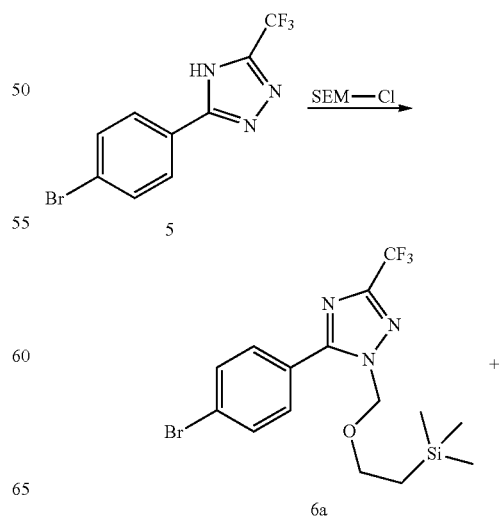

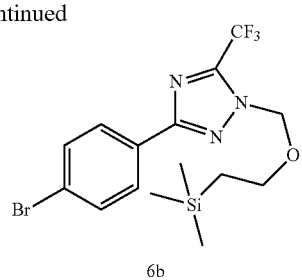

6b

Compound 5 (1 g) was dissolved in N,N-dimethylformamide (25 mL), sodium hydride (212 mg) was added under ice cooling, and the mixture was stirred for 40 minutes. At the same temperature, 2-(chloromethoxy)ethyltrimethylsilane (910 μL) was added, the temperature was elevated to room temperature, and the mixture was stirred for 5 hours. An aqueous saturated sodium hydrogen carbonate solution was added, and the mixture was extracted with ethyl acetate. The organic layer was washed with saturated brine, dried over anhydrous sodium sulfate and concentrated under reduced pressure. The obtained residue was purified by silica gel column chromatography (n-hexane:ethyl acetate=90:10 to 80:20) to obtain a mixture of Compounds 6a and 6b (10:9) as a colorless liquid.

MS (m/z): 422/424 [M+H]$^+$ (6)

[Chemical Formula 124]

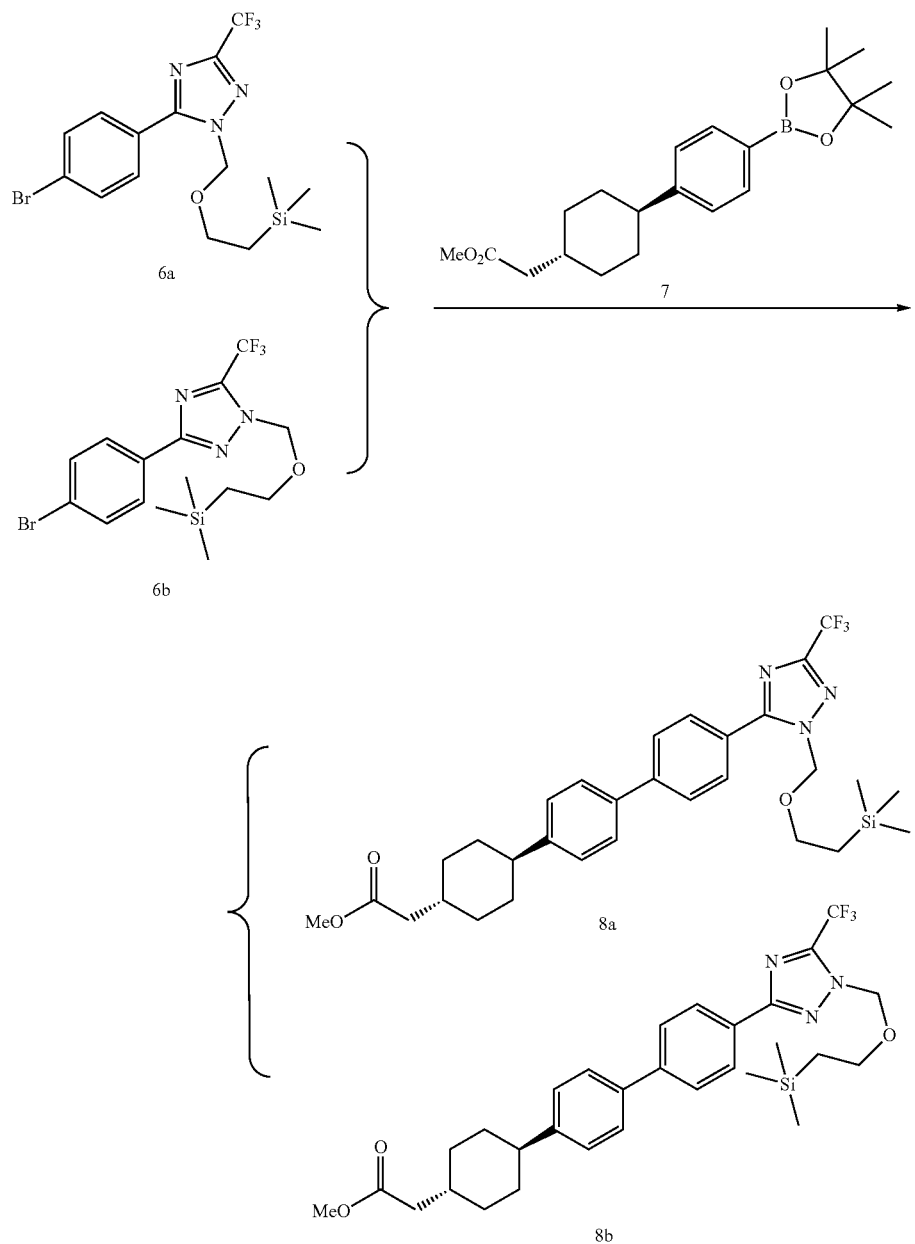

The mixed solution of the mixture of Compounds 6a and 6b (202 mg), Compound 7 (242 mg), a [1,1'-bis(diphenylphosphino)ferrocene]palladium(II) dichloride dichloromethane complex (20 mg), N,N-dimethylformamide (5 mL) and a 2N aqueous sodium carbonate solution (950 µL) was stirred at 80° C. for 19 hours. The reaction solution was filtered through Celite, and to the filtrate was added water, and the mixture was extracted with ethyl acetate. The extract was washed with saturated brine, and concentrated. The obtained residue was purified by silica gel column chromatography (n-hexane:ethyl acetate=90:10 to 85:15) to obtain a mixture of Compounds 8a and 8b (278 mg) as a pale yellow solid.

MS (m/z): 574 [M+H]$^+$ (7)

[Chemical Formula 125]

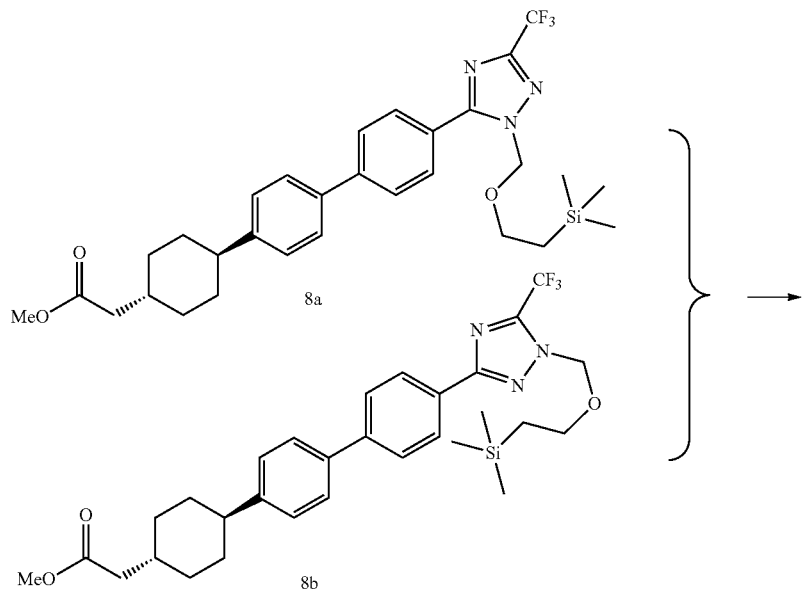

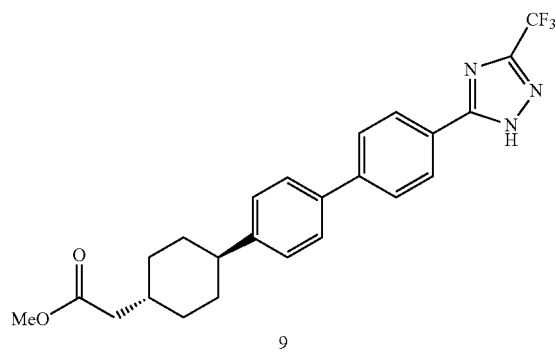

To the mixture of Compounds 8a and 8b (272 mg) were added trifluoroacetic acid (5.4 mL) and water (540 μL), and the mixture was stirred at room temperature for 7 hours. The reaction solution was concentrated under reduced pressure, and to the obtained solid was added cold methanol, and the mixture was sonicated. The obtained suspension was filtered and then washed with cold methanol to obtain Compound 9 (152 mg) as a white solid.

MS (m/z): 444 [M+H]$^+$ (8)

[Chemical Formula 126]

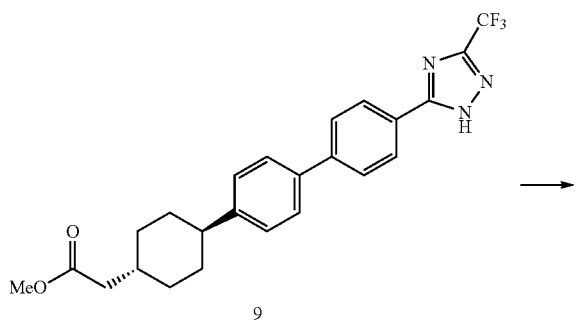

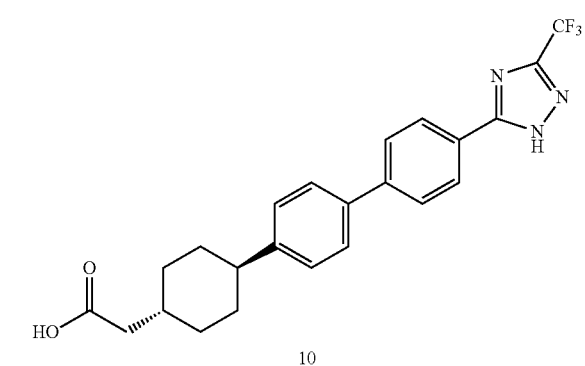

To Compound 9 (150 mg) were added tetrahydrofuran (6 mL), methanol (6 mL), and an 8N aqueous sodium hydroxide solution (0.175 mL), and the mixture was stirred at room temperature overnight. To the reaction solution were added acetic acid (2 mL) and water (2 mL), and the solution was concentrated under reduced pressure. The obtained solid was suspended in cold methanol, collected by filtration and washed with water and methanol. The obtained white powder was purified using LC-MS, the obtained fraction was concentrated, and water (3 mL) and methanol (0.5 mL) were added. Then, the mixture was suspended by sonification, acetic acid (200 μL) was added, and the mixture was stirred. The obtained powder was collected by filtration, washed with water and methanol and dried to obtain Compound 10 (27 mg).

MS (m/z): 430 [M+H]$^+$

Example 51

(1)

[Chemical Formula 127]

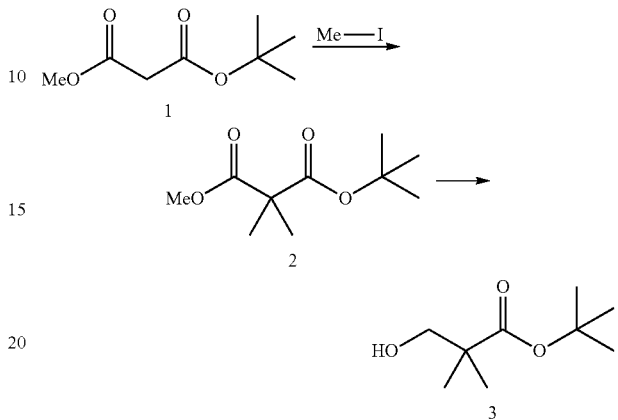

Sodium hydride (15.6 g) was suspended in 300 mL of tetrahydrofuran under a nitrogen stream, and Compound 1 (30 mL) was added dropwise over 30 minutes under ice cooling. After the mixture was stirred under ice cooling for 30 minutes, methyl iodide (24.3 mL) was added dropwise, and the mixture was stirred at room temperature for 16 hours. To the reaction solution was added water, and the mixture was extracted with ethyl acetate. The extract was washed with saturated brine, and dried over anhydrous magnesium sulfate. The solution was concentrated under reduced pressure to obtain Compound 2 (24.76 g). The obtained Compound 2 (24.76 g) was dissolved in tetrahydrofuran (320 mL), 1M lithium hydroxide tri-tert-butoxyaluminum (300 mL) was added dropwise over 45 minutes under a nitrogen stream at room temperature, and the mixture was heated at reflux for 2 hours. To the reaction solution was added saturated brine, and the mixture was filtered through Celite and washed with ethyl acetate. The filtrate was concentrated under reduced pressure, to the concentrated residue were added ethyl acetate and water, and the mixture was extracted with ethyl acetate. The extract was washed with saturated brine, and dried over anhydrous magnesium sulfate. After the solution was concentrated under reduced pressure, the obtained residue was distilled under reduced pressure to obtain Compound 3 (13.52 g).

MS (m/z): 175 [M+H]$^+$ (2)

[Chemistry Formula 128]

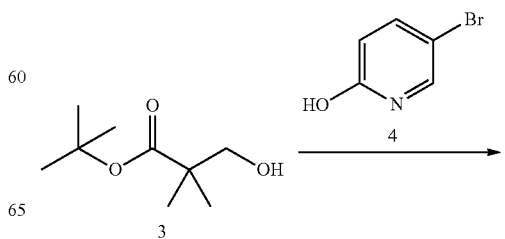

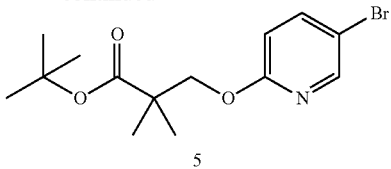

Compound 3 (1005 mg), Compound 4 (500 mg) and triphenylphosphine (1500 mg) were dissolved in tetrahydrofuran (8 mL), a 40% solution of diethyl azodicarboxylate in toluene (2.65 mL) was added, and the mixture was stirred at 80° C. for 3 hours. To the reaction solution was added water, and the mixture was extracted with ethyl acetate. The extract was washed with saturated brine, and dried over anhydrous sodium sulfate. After the solution was concentrated under reduced pressure, the obtained residue was purified by silica gel column chromatography (n-hexane:ethyl acetate=93:7 to 90:10) to obtain Compound 5 (810 mg) as a pink liquid.

MS (m/z): 330/332 [M+H]$^+$ (3)

[Chemical Formula 129]

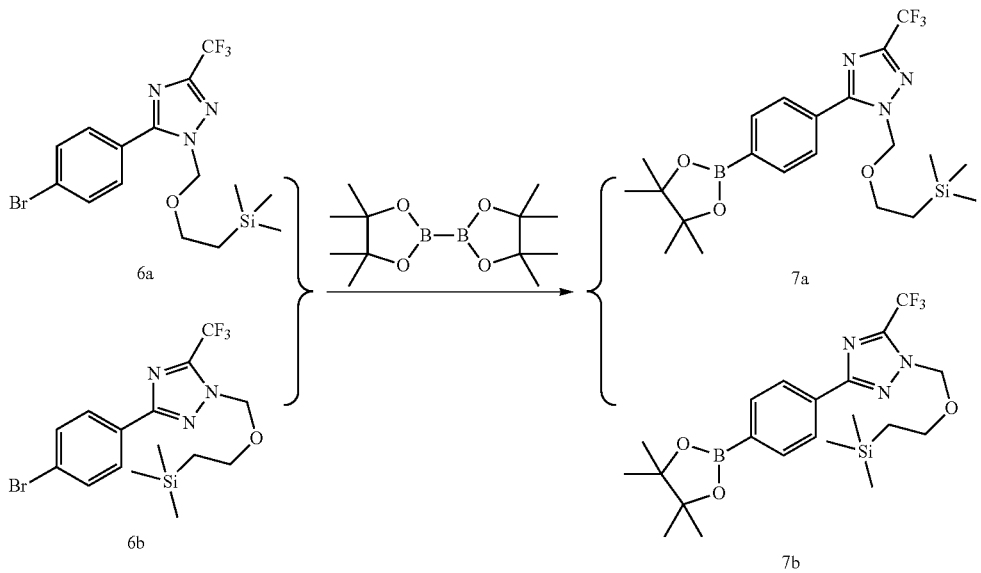

To a mixture of Compounds 6a and 6b (1000 mg), potassium acetate (700 mg) and bis(pinacolato)diboron (755 mg) was added 1,4-dioxane (24 mL), and the mixture was subjected to nitrogen substitution. Then, a [1,1'-bis(diphenylphosphino)ferrocene]palladium(II) dichloride dichloromethane complex (58 mg) and (diphenylphosphino)ferrocene (40 mg) were added, and the mixture was subjected to nitrogen substitution again and stirred at 80° C. for 21 hours. To the reaction solution were added water and ethyl acetate, and the mixture was stirred and subsequently filtered through Celite. The filtrate was extracted with ethyl acetate, washed with saturated brine and dried. After the solution was concentrated under reduced pressure, the obtained residue was purified by silica gel column chromatography (n-hexane:ethyl acetate=95:5 to 85:15) to obtain a mixture of Compounds 7a and 7b (986 mg) as a white solid.

MS (m/z): 470 [M+H]$^+$ (4)

[Chemical Formula 130]

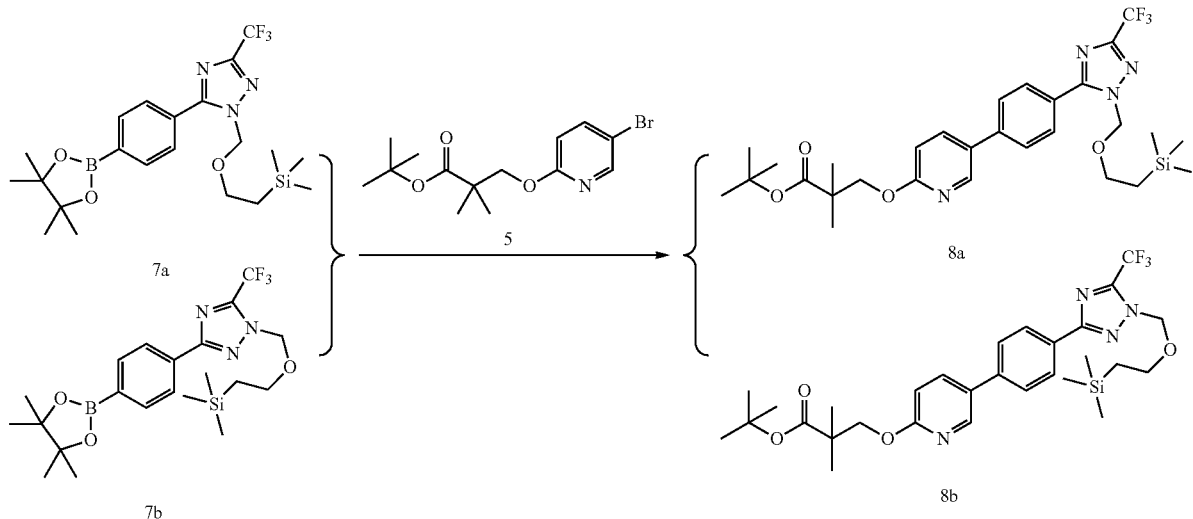

A mixture of the mixture of Compounds 7a and 7b (150 mg), Compound 5 (135 mg), N,N-dimethylformamide (3 mL) and a 2M aqueous sodium carbonate solution (0.64 mL) was subjected to nitrogen substitution, then a [1,1'-bis(diphenylphosphino)ferrocene]palladium(II) dichloride dichloromethane complex (29 mg) was subsequently added, and the mixture was stirred at 80° C. for 15 hours. To the reaction solution was added water, and the mixture was extracted with ethyl acetate, washed with saturated brine and dried over anhydrous sodium sulfate. After the solution was concentrated under reduced pressure, the obtained residue was purified by silica gel column chromatography (n-hexane:ethyl acetate=95:5 to 90:10) to obtain a mixture of Compounds 8a and 8b (125 mg) as a pale yellow viscous material.

MS (m/z): 593 [M+H]$^+$ (5)

[Chemical Formula 131]

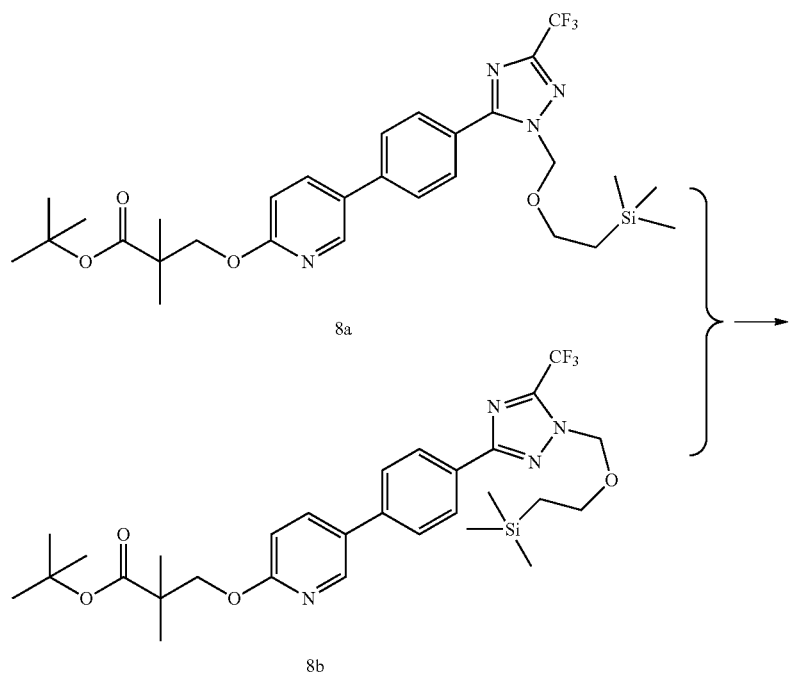

-continued

[Structure of Compound 9: 5-[4-(5-trifluoromethyl-1H-1,2,4-triazol-3-yl)phenyl]pyridin-2-yloxy-2,2-dimethylpropanoic acid]

9

To the mixture of Compounds 8a and 8b (125 mg) were added trifluoroacetic acid (2.5 mL) and water (0.25 mL), and the mixture was stirred at room temperature for 16 hours. The reaction solution was concentrated under reduced pressure, the residue was dissolved in tetrahydrofuran, the solution was neutralized with 1N sodium hydroxide, and 0.1M phosphate buffer having pH 7 (2 mL) was added. This was washed with ethyl acetate, and the aqueous layer was concentrated under reduced pressure. The obtained residue was purified by silica gel column chromatography (n-hexane:ethyl acetate=80:20 to 60:40) to obtain Compound 9 (26 mg) as a white solid.

MS (m/z): 407 [M+H]$^+$

Example 52

(1)

[Chemical Formula 132]

[Reaction scheme: Compound 1 (6-chloro-3-cyanopyridine) → Compound 2 (ethyl imidate HCl salt) with HCl/EtOH]

A reaction was carried out in a manner similar to the Example 50-(1) using Compound 1 (5 g) to obtain Compound 2 (7.98 g) as a pale yellow powder.

MS (m/z): 185/187 [M+H]$^+$ (2)

[Chemical Formula 133]

[Reaction scheme: Compound 2 → Compound 3 (amidine HCl salt) with NH$_3$]

A reaction was carried out in a manner similar to the Example 50-(2) using Compound 2 (7.98 g) to obtain Compound 3 (6.29 g) as a red powder.

MS (m/z): 156/158 [M+H]$^+$ (3)

[Chemical Formula 134]

[Reaction scheme: Compound 3 → Compound 4 (free amidine) with NaOH]

A reaction was carried out in a manner similar to the Example 50-(3) using Compound 3 (6.29 g) to obtain Compound 4 (2.49 g) as a pink powder.

MS (m/z): 156/158 [M+H]$^+$ (4)

[Chemical Formula 135]

[Reaction scheme: Compound 4 + F$_3$C-C(O)-OEt / NH$_2$NH$_2$·H$_2$O → Compound 5 (2-chloro-5-(5-trifluoromethyl-1H-1,2,4-triazol-3-yl)pyridine)]

5

A reaction was carried out in a manner similar to the Example 50-(4) using Compound 4 (2.48 g) to obtain Compound 5 (2.91 g) as a pink powder.

MS (m/z): 249 [M+H]$^+$ (5)
[Chemical Formula 136]
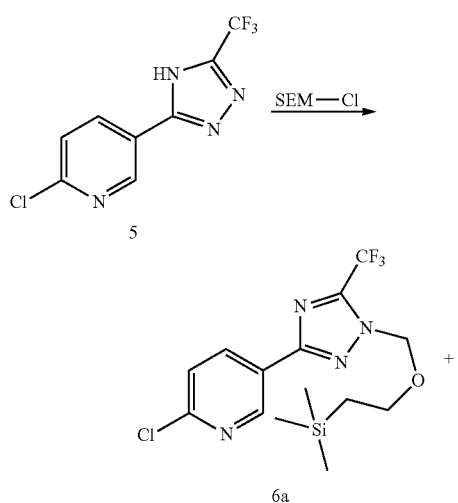
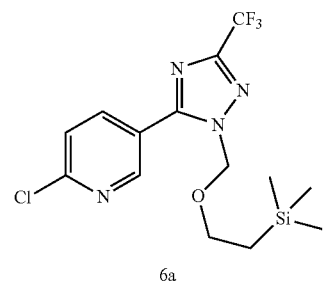
A reaction was carried out in a manner similar to the Example 50-(5) using Compound 5 (2.91 g) to obtain Compound 6a (2.18 g) as a colorless solid and Compound 6b (2.09 g) as a colorless oil.
MS (m/z): 379/381 [M+H]$^+$
(6)
[Chemical Formula 137]
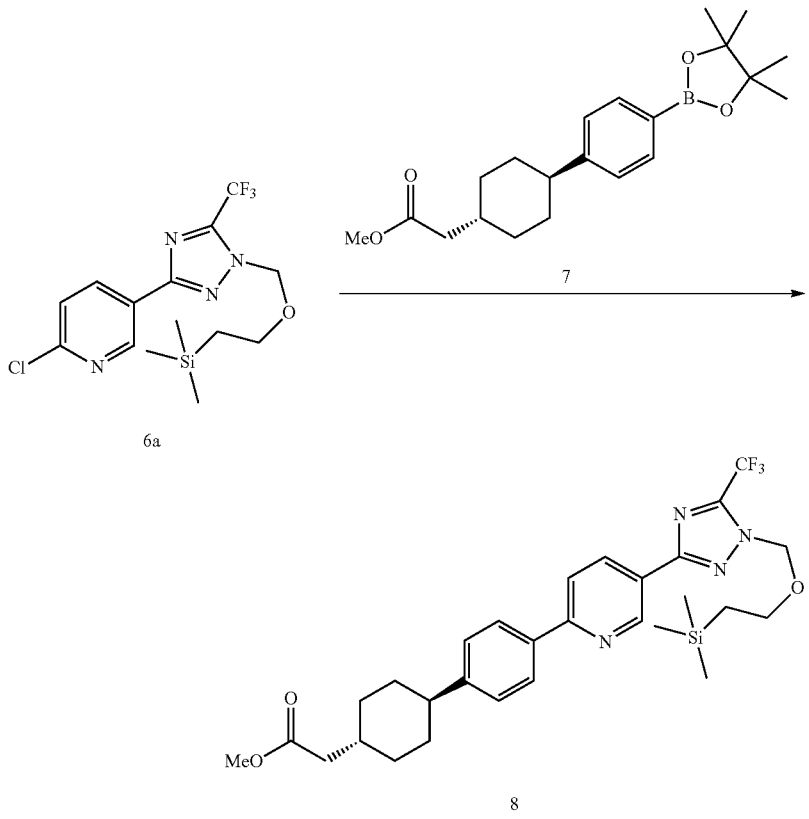
A reaction was carried out in a manner similar to the Example 50-(6) using Compound 6a (500 mg) and Compound 7 (881 mg) to obtain Compound 8 (563 mg) as a colorless powder.
MS (m/z): 575 [M+H]$^+$ (7)

[Chemical Formula 138]

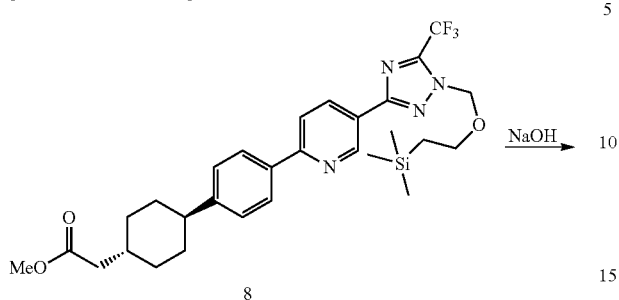

NaOH →

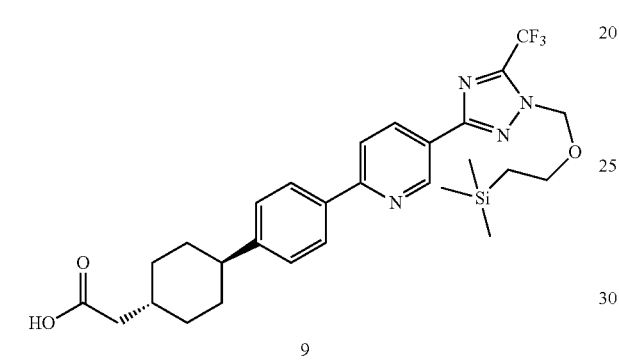

A mixture of Compound 8 (563 mg), methanol (5.6 mL), tetrahydrofuran (9.6 mL) and a 2N aqueous sodium hydroxide solution (3.92 mL) was stirred at room temperature for 14 hours. After the mixture was neutralized by addition of acetic acid, the mixture was concentrated under reduced pressure, to the obtained residue was added water, the mixture was extracted with ethyl acetate. The extract was washed with 0.1N phosphate buffer having pH 7, filtered and concentrated under reduced pressure. The obtained solid was recrystallized from methanol to obtain Compound 9 (353 mg) as a colorless powder. Further, the concentrated residue of the mother liquid was purified by silica gel column chromatography (chloroform:methanol=100:0 to 96:4) to obtain Compound 9 (67 mg) as a white solid.

MS (m/z): 561 [M+H]$^+$ (8)

[Chemical Formula 139]

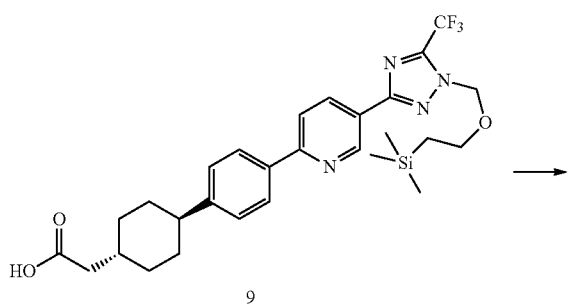

-continued

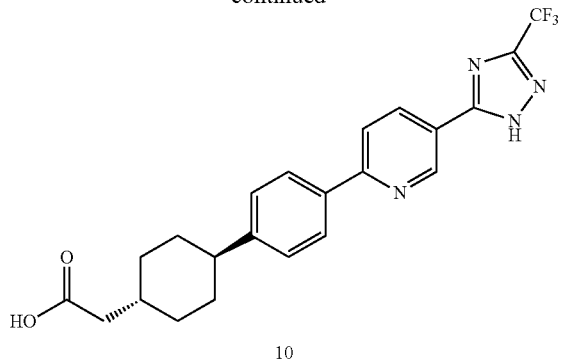

Compound 9 (419 mg) was dissolved in trifluoroacetic acid (8.38 mL) and water (0.84 mL), and the mixture was stirred at room temperature for 16 hours. The reaction solution was concentrated under reduced pressure, and the obtained deposit was washed with acetonitrile, and recrystallized from acetonitrile. The crystals were collected by filtration and dried under reduced pressure at 50° C. to obtain Compound 10 (223 mg) as a white solid.

MS (m/z): 431 [M+H]$^+$

Example 53

(1)

[Chemical Formula 140]

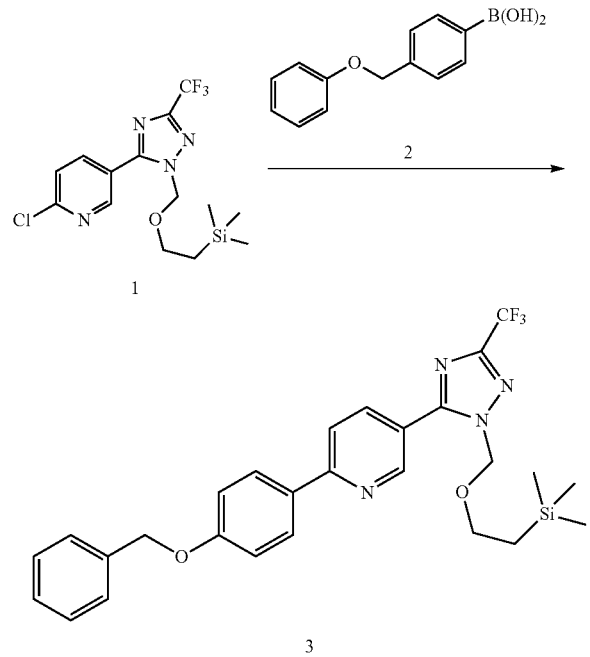

A mixed solution of Compound 1 (1000 mg), Compound 2 (1085 mg), a 2M aqueous sodium carbonate solution (4736 μL) and N,N-dimethylformamide (20 mL) was subject to nitrogen substitution, and subsequently a [1,1'-bis(diphenylphosphino)ferrocene]palladium(II) dichloride dichloromethane complex (193 mg) was added, and the mixture was stirred at 80° C. overnight. To the reaction solution were added water and ethyl acetate, and the mixture was stirred at room temperature for 30 minutes, and filtered through Celite. The filtrate was extracted with ethyl acetate, and the extract was washed with water, and dried over anhydrous sodium sulfate. The solution was concentrated under reduced pressure, and the obtained residue was purified by silica gel column chromatography (n-hexane:ethyl acetate=95:5 to 80:20) to obtain Compound 3 (1288 mg) as a colorless solid.

MS (m/z): 527 $[M+H]^+$ (2)

[Chemical Formula 141]

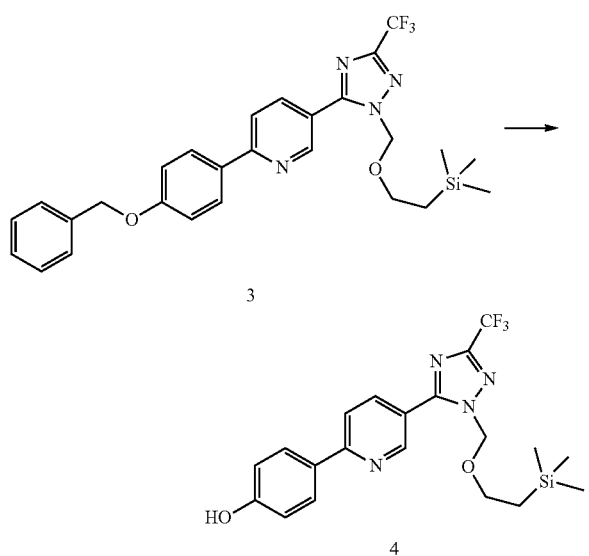

Compound 3 (1285 mg) was dissolved in ethanol (26 mL), and the mixture was subjected to nitrogen substitution. Subsequently, palladium carbon (386 mg) was added, and the mixture was stirred under a hydrogen atmosphere at room temperature for 6 hours. The reaction solution was filtered through Celite and washed with tetrahydrofuran. After the filtrate was concentrated under reduced pressure, the obtained residue was purified by silica gel column chromatography (n-hexane:ethyl acetate=80:20 to 60:40) to obtain Compound 4 (966 mg) as a colorless solid.

MS (m/z): 437 $[M+H]^+$ (3)

[Chemical Formula 142]

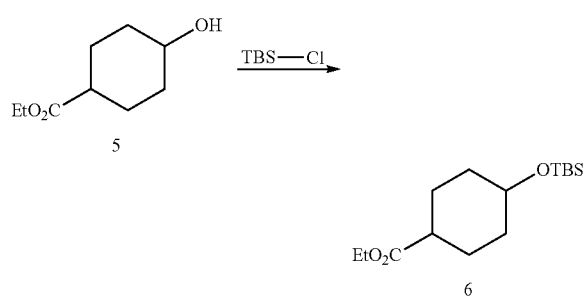

Compound 5 (20.04 g) and imidazole (15.84 g) were dissolved in N,N-dimethylformamide (116 mL), tert-butyldimethylsilyl chloride (19.47 g) was added under ice cooling, and the mixture was stirred at room temperature for 15 hours. The reaction solution was added to ice water, and the mixture was extracted with diethyl ether. The extract was washed with water and saturated brine. The solution was dried over anhydrous magnesium sulfate, and concentrated under reduced pressure to obtain Compound 6 (34.94 g) as a colorless oil.

MS (m/z): 287 $[M+H]^+$ (4)

[Chemical Formula 143]

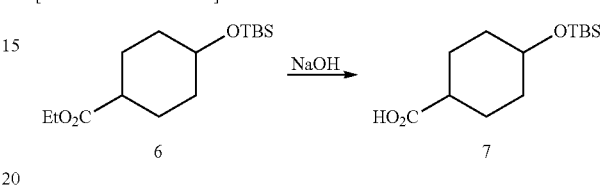

Compound 6 (34.93 g) was dissolved in tetrahydrofuran (241 mL), a 2N aqueous sodium hydroxide solution (244 mL) was added, and the mixture was stirred at 70° C. for 15 hours. Tetrahydrofuran was distilled off under reduced pressure, and the aqueous solution was washed with n-hexane and diethyl ether. The aqueous layer was adjusted to pH=4 with a 1N aqueous citric acid solution, and the mixture was extracted with diethyl ether. The extract was dried over anhydrous magnesium sulfate and concentrated under reduced pressure to obtain Compound 7 (26.17 g) as a colorless solid.

MS (m/z): 259 $[M+H]^+$ (5)

[Chemical Formula 144]

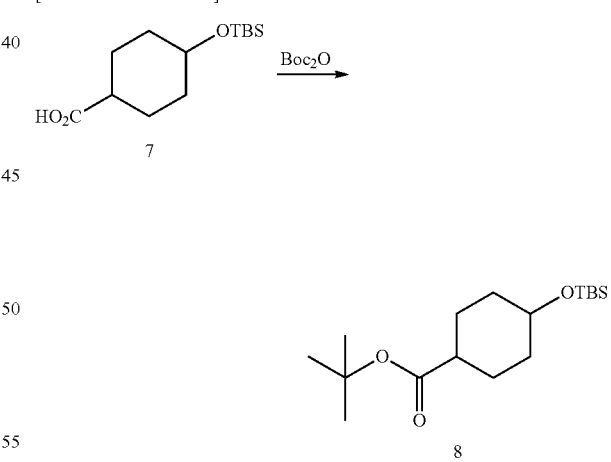

Compound 7 (33.75 g) and Boc$_2$O (34.2 g) were dissolved in tert-butanol (338 mL), and 4-dimethylaminopyridine (4.79 g) was added, and the mixture was stirred at room temperature for 17 hours. After the reaction solution was concentrated under reduced pressure, the obtained residue was purified by silica gel column chromatography (n-hexane:ethyl acetate=99:1 to 91:9) to obtain Compound 8 (40.68 g) as a colorless oil.

MS (m/z): 315 $[M+H]^+$ (6)

[Chemical Formula 145]

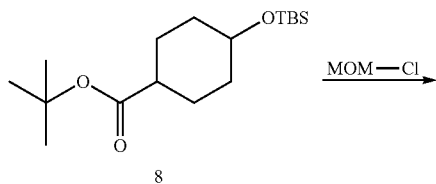

8

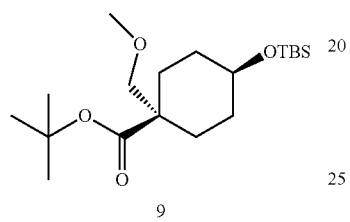

9

A solution of diisopropyl amine (1.94 mL) in tetrahydrofuran (30 mL) was cooled to −70° C., 2.6M n-butyl lithium (5.3 mL) was added dropwise, and the mixture was stirred at the same temperature for 10 minutes. Subsequently, the temperature was elevated to 0° C. The reaction solution was again cooled to −70° C., and a solution of Compound 8 (2.9 g) in tetrahydrofuran (10 mL) was added dropwise. After the mixture was stirred at the same temperature for 10 minutes, the temperature was elevated to 0° C. The reaction solution was again cooled to −70° C., and methoxymethyl chloride (1.4 mL) was added dropwise. After the mixture was stirred at the same temperature for 30 minutes, the temperature was elevated to room temperature, and the mixture was stirred for 13 hours. To the reaction solution was added a saturated aqueous ammonium chloride solution, and the mixture was extracted with ethyl acetate. The extract was washed with saturated brine. After the mixture was dried over anhydrous magnesium sulfate, and concentrated under reduced pressure, and the obtained residue was purified by silica gel column chromatography to obtain a cis form of Compound 9 (1.5 g) as a colorless oil.

MS (m/z): 359 [M+H]⁺

(7)

[Chemical Formula 146]

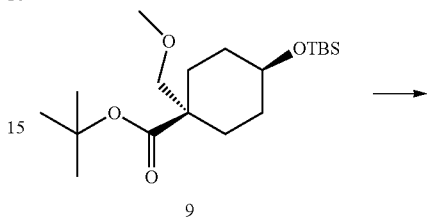

9

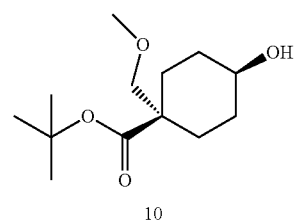

10

To Compound 9 (31.56 g) was added a 1M solution of n-tetrabutylammonium fluoride in tetrahydrofuran (175 mL), and the mixture was stirred at room temperature for 21 hours. Additionally, a 1M solution of n-tetrabutylammonium fluoride in tetrahydrofuran (85 mL) was added, and the mixture was stirred at room temperature for 4 hours. The reaction solution was concentrated under reduced pressure, to the obtained residue was added a saturated aqueous ammonium chloride solution, and the mixture was extracted with ethyl acetate. The extract was washed with saturated brine, and dried over anhydrous magnesium sulfate. The extract was concentrated under reduced pressure, and the obtained residue was purified by silica gel column chromatography to obtain Compound 10 (18.56 g) as a colorless oil.

MS (m/z): 245 [M+H]⁺

(8)

[Chemical Formula 147]

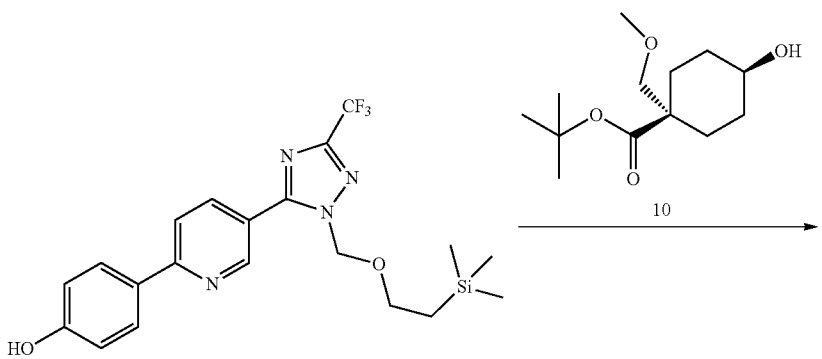

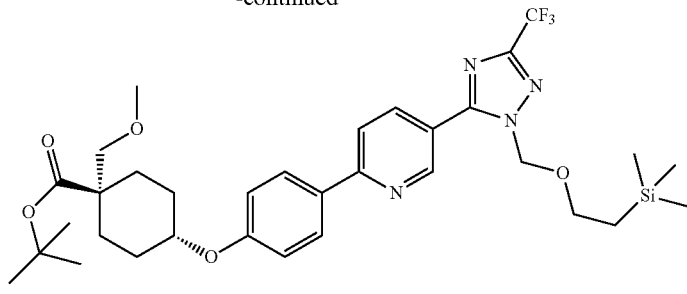

11

A solution of Compound 4 (150 mg), Compound 10 (126 mg), tributylphosphine (127 μL) and ADDP (130 mg) in tetrahydrofuran (3 mL) was heated at reflux overnight. The reaction solution was concentrated under reduced pressure, and the residue was washed with diethyl ether and filtered. The filtrate was concentrated under reduced pressure, and the obtained residue was purified by silica gel column chromatography (n-hexane:ethyl acetate=90:10 to 80:20) to obtain Compound 11 (162 mg) a colorless viscous material.

MS (m/z): 663 [M+H]$^+$ (9)

[Chemical Formula 148]

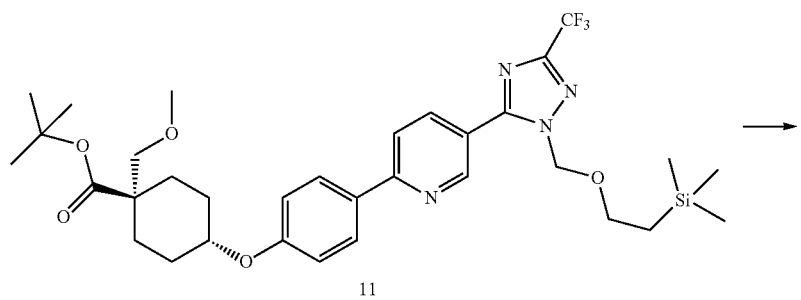

11

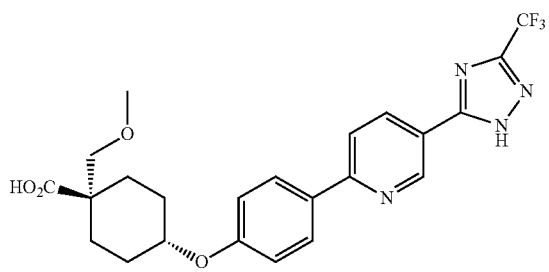

12

Compound 11 (162 mg) was dissolved in trifluoroacetic acid (3 mL) and water (0.3 mL), and the mixture was stirred at room temperature overnight. The reaction solution was concentrated under reduced pressure, to the obtained residue was added acetic acid, and the mixture was concentrated under reduced pressure. The residue was crystallized from ethyl acetate, and the obtained solid was filtered and dried to obtain Compound 12 (96 mg) as an ivory solid.

MS (m/z): 477 [M+H]$^+$

Example 54

(1)

[Chemical Formula 149]

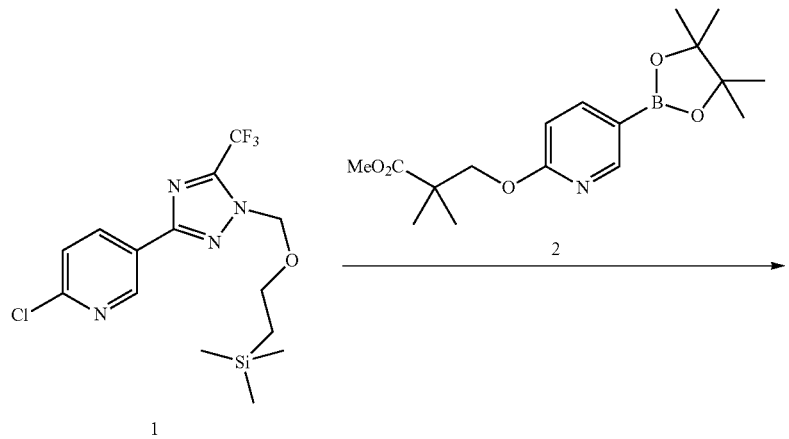

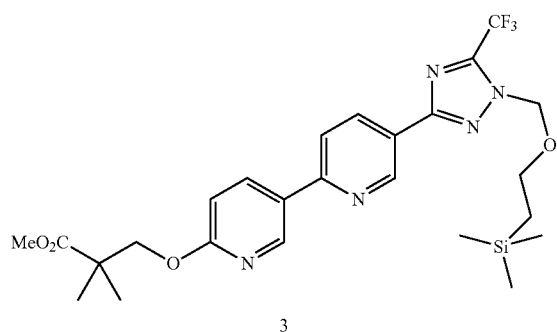

A reaction was carried out in a manner similar to the Example 52-(6) using Compound 1 (207 mg) and Compound 2 (293 mg) to obtain Compound 3 (252 mg) as a colorless solid.

MS (m/z): 552 [M+H]$^+$ (2)

[Chemical Formula 150]

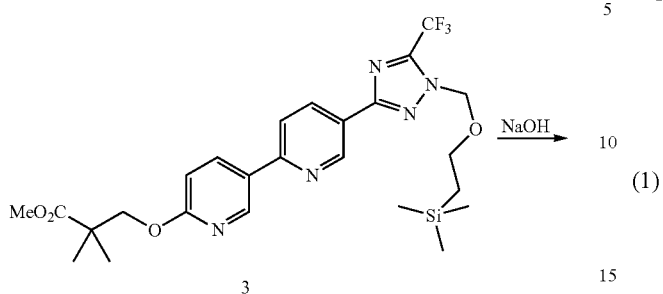

A reaction was carried out in a manner similar to the Example 52-(7) using Compound 3 (244 mg) to obtain Compound 4 (223 mg) as a colorless solid.

MS (m/z): 538 [M+H]$^+$ (3)

[Chemical Formula 151]

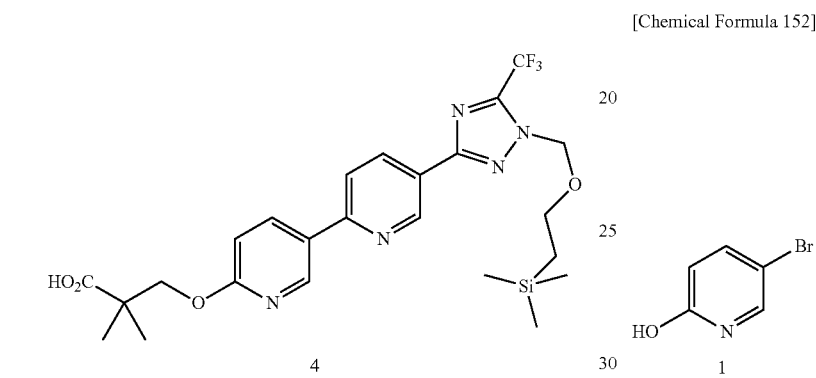

A reaction was carried out in a manner similar to the Example 52-(8) using Compound 4 (216 mg) to obtain Compound 5 (157 mg) as a colorless solid.

MS (m/z): 408 [M+H]$^+$

Example 55

(1)

[Chemical Formula 152]

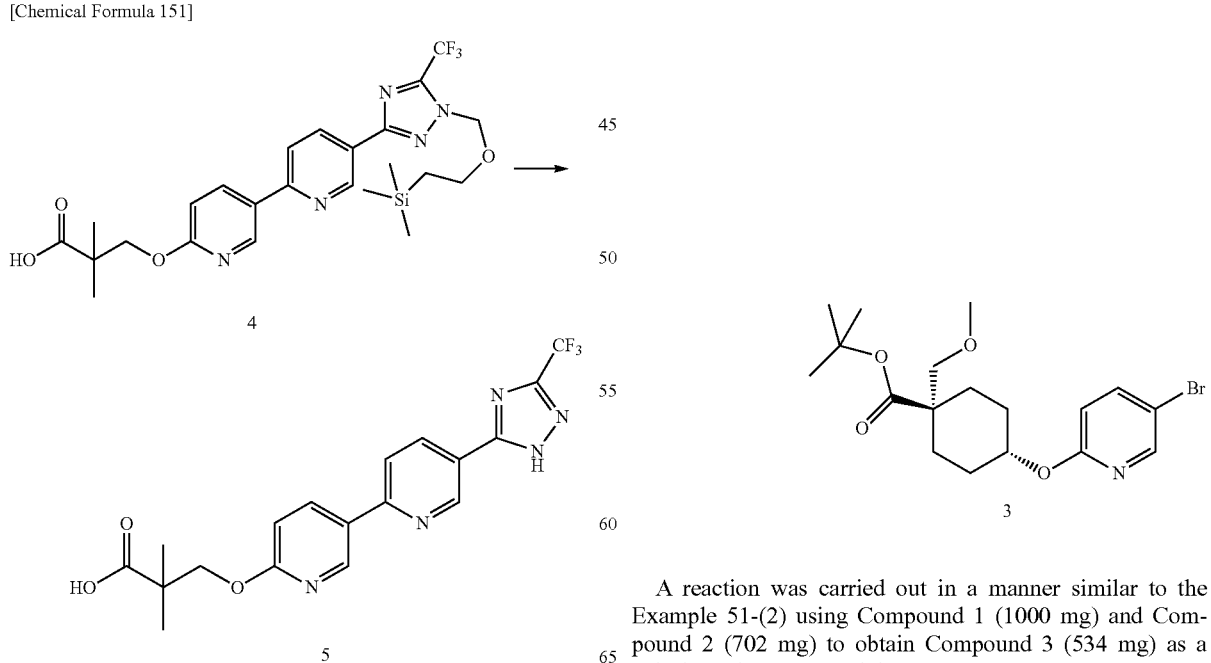

A reaction was carried out in a manner similar to the Example 51-(2) using Compound 1 (1000 mg) and Compound 2 (702 mg) to obtain Compound 3 (534 mg) as a colorless viscous material.

MS (m/z): 400/402 [M+H]$^+$ (2)

[Chemical Formula 153]

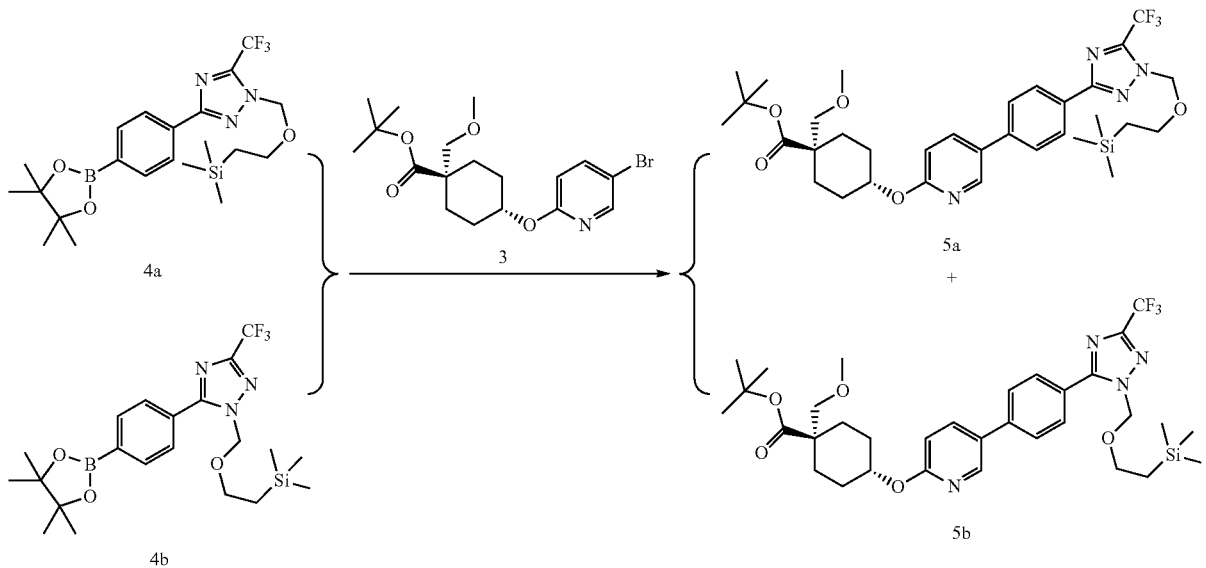

A reaction was carried out in a manner similar to the Example 51-(4) using Compound 3 (200 mg) and a mixture of Compounds 4a and 4b (469 mg) to obtain Compound 5a (151 mg) and Compound 5b (104 mg) as colorless viscous materials respectively.

MS (m/z): 663 [M+H]$^+$ (3)

[Chemical Formula 154]

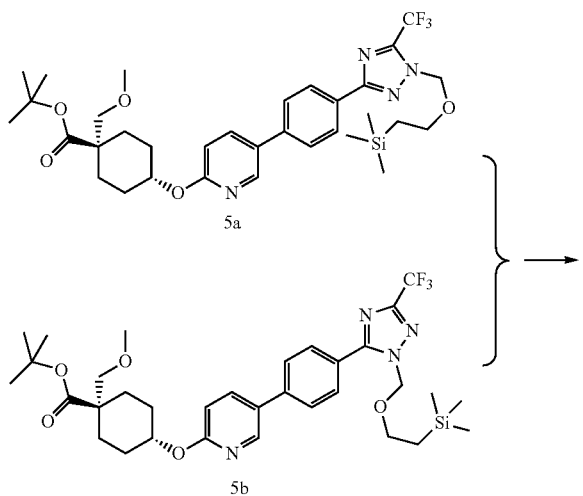

-continued

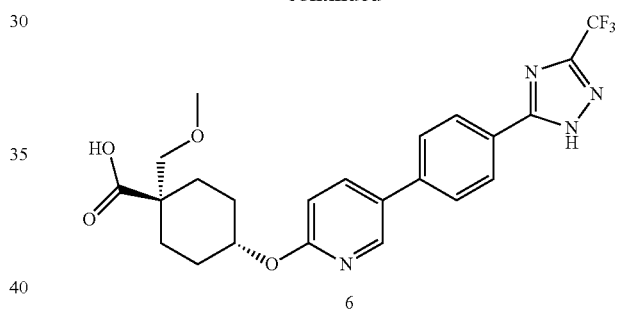

A reaction was carried out in a manner similar to the Example 53-(9) using a mixture of Compound 5a and Compound 5b (250 mg) to obtain Compound 6 (158 mg).

MS (m/z): 477 [M+H]$^+$

Example 56

(1)

[Chemical Formula 155]

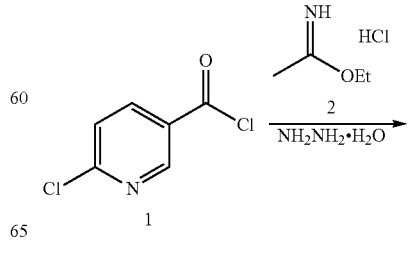

-continued

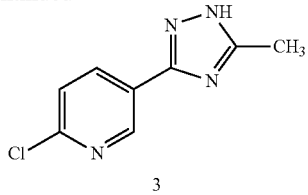

3

To Compound 2 (4.21 g) were added toluene (100 mL) and triethylamine (9.9 mL) at room temperature, and the mixture was stirred for 5 minutes. Subsequently, Compound 1 (5 g) was added, and the mixture was stirred at room temperature for 5 days. The reaction solution was filtered through Celite, and the filtrate was concentrated under reduced pressure. To the obtained residue were added carbon tetrachloride (66.4 mL) and hydrazine hydrate (1.42 mL), and the mixture was stirred at room temperature overnight. The reaction solution was diluted with ethyl acetate and filtered through Celite. The filtrate was concentrated under reduced pressure, to the obtained residue were added water, ethyl acetate and a saturated aqueous ammonium chloride solution, and the mixture was extracted with ethyl acetate. The extract was concentrated under reduced pressure, and the obtained residue was washed with diethyl ether and filtered to obtain Compound 3 (928 mg) as a light pink powder.

MS (m/z): 195/197 [M+H]$^+$ (2)

[Chemical Formula 156]

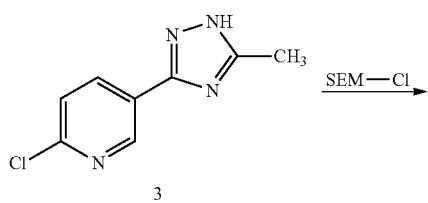

-continued

4a

4b

A reaction was carried out in a manner similar to the Example 50-(5) using Compound 3 (819 mg) to obtain a mixture of Compounds 4a and 4b (1.014 g) as colorless crystals.

MS (m/z): 325/327 [M+H]$^+$ (3)

[Chemical Formula 157]

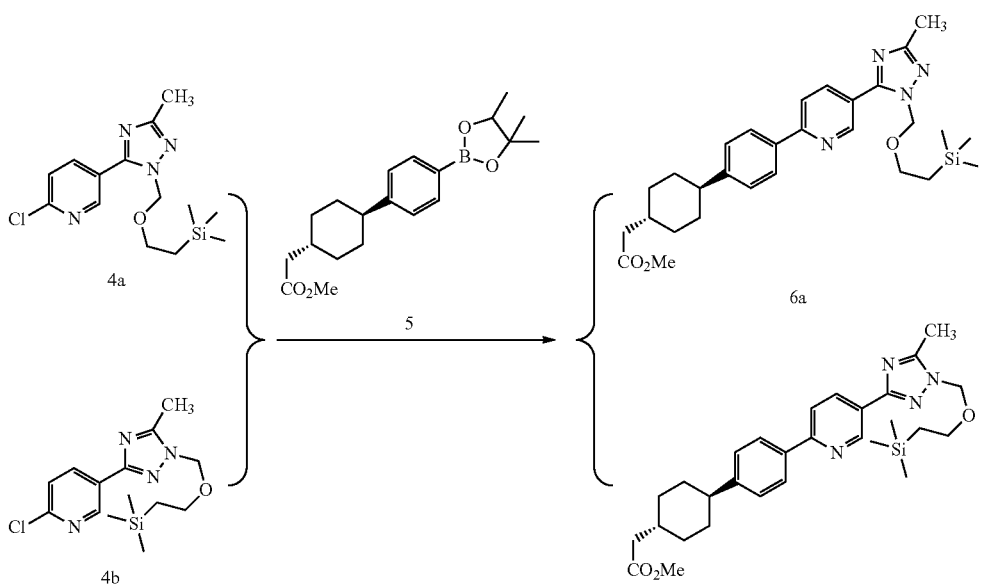

A reaction was carried out in a manner similar to the Example 52-(6) using the mixture of Compounds 4a and 4b (200 mg) and Compound 5 (309 mg) to obtain Compound 6a (84 mg) and Compound 6b (78 mg) as colorless powders each.

MS (m/z): 521 [M+H]$^+$ (4)

[Chemical Formula 158]

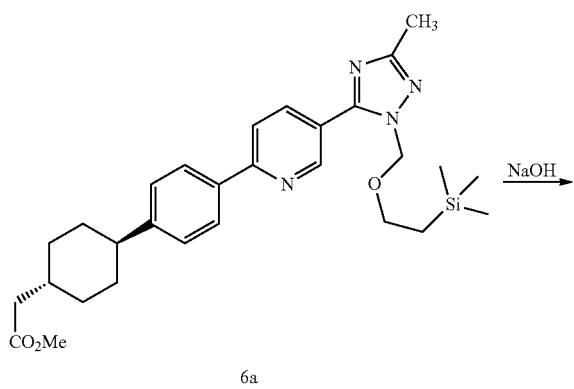

6a

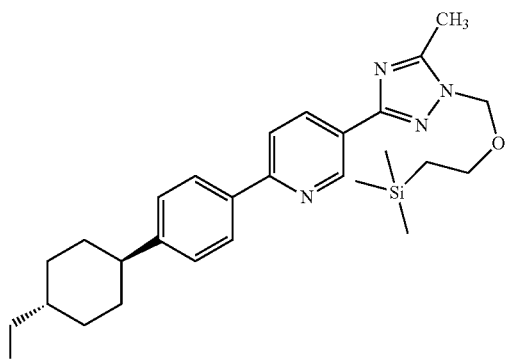

7b

A reaction was carried out in a manner similar to the Example 52-(7) using Compound 6a (83 mg) to obtain Compound 7a (77 mg) as a colorless powder. Further, the similar reaction was carried out using Compound 6b (83 mg) to obtain Compound 7b (69 mg) as a colorless powder.

MS (m/z): 507 [M+H]$^+$ (5)

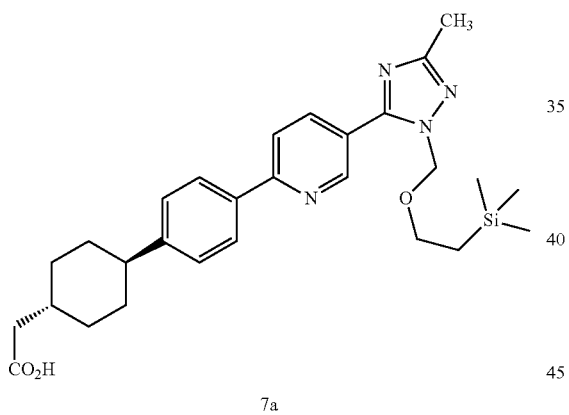

7a

[Chemical Formula 159]

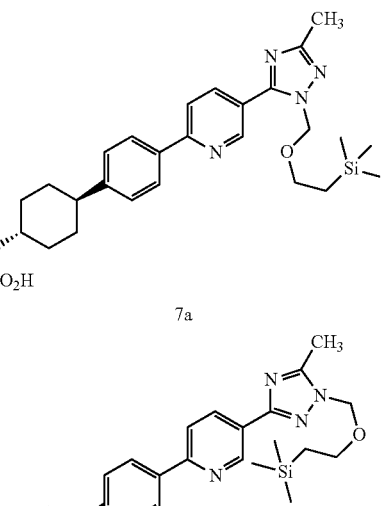

7a

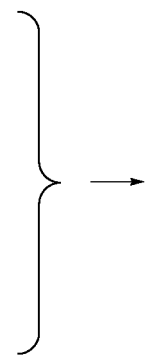

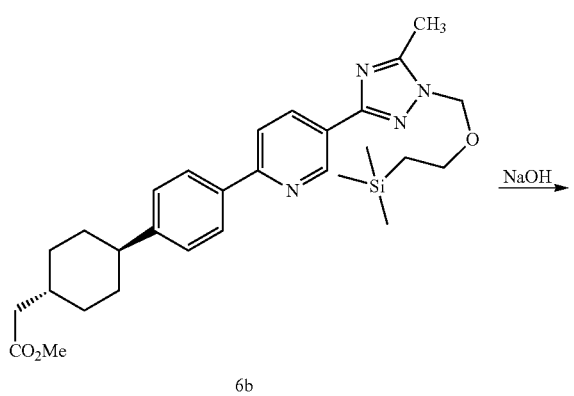

6b

7b

Example 58

(1)

[Chemical Formula 161]

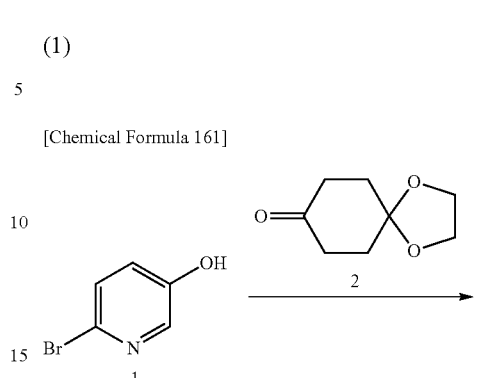

A solution of Compound 1 (5 g) in tetrahydrofuran (96 mL) was cooled to −78° C., a solution of n-butyl lithium in n-hexane (18.3 mL) was added dropwise over 10 minutes, and the mixture was stirred at the same temperature for 20 minutes. Then, a solution of sec-butyl lithium in n-hexane (40.7 mL) was added dropwise over 10 minutes at the same temperature, and the mixture was stirred at the same temperature for 1 hour. Further, a solution of Compound 2 (6.73 g) in tetrahydrofuran (44 mL) was added dropwise at the same temperature over 20 minutes, and the mixture was stirred at the same temperature for 3 hours. To the reaction solution was added dropwise a saturated aqueous ammonia chloride solution (60 mL), and the temperature was elevated to room temperature. Water was added, the mixture was extracted with ethyl acetate, and the extract was washed with saturated brine, and dried over anhydrous magnesium sulfate. After the solution was concentrated under reduced pressure, the obtained residue was purified by silica gel column chromatography (n-hexane:2-propanol=85:15 to 70:30 and chloroform:methanol=100:0 to 93:7) to obtain Compound 3 (2.207 g) as a colorless powder.

MS (m/z): 252 $[M+H]^+$ (2)

[Chemical Formula 162]

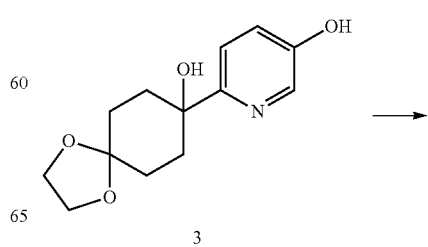

-continued

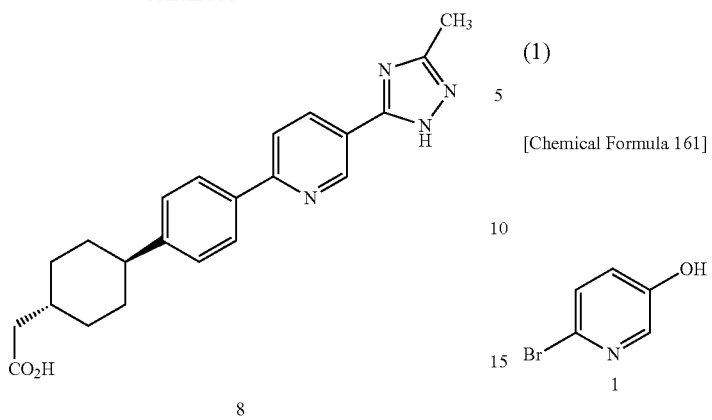

A reaction was carried out in a manner similar to the Example 52-(8) using a mixture of Compounds 7a and 7b (146 mg) to obtain Compound 8 (94 mg) a colorless powder.

MS (m/z): 377 $[M+H]^+$

Example 57

[Chemical Formula 160]

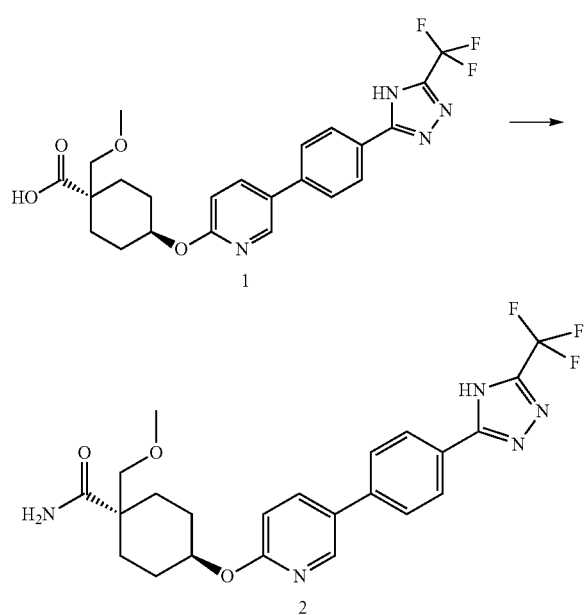

Compound 1 (73 mg), EDC-HCl (88 mg), HOBt (62 mg), ammonium chloride (25 mg) and triethylamine (64 µL) were dissolved in dimethylsulfoxide (1 mL), and the mixture was stirred at room temperature overnight. To the reaction solution was added water, and the mixture was extracted with ethyl acetate and washed with water. After the solution was dried and concentrated under reduced pressure, the obtained residue was purified by silica gel column chromatography (chloroform:methanol=97:3 to 90:10) to obtain Compound 2 (46 mg) as a colorless solid.

MS (m/z): 476 $[M+H]^+$

-continued

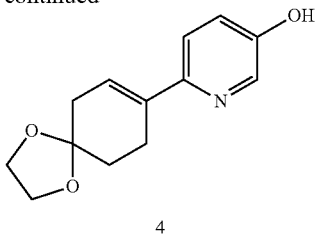
4

To a solution of Compound 3 (1.944 g) in tetrahydrofuran (57 mL) was added the Burgess reagent, and the mixture was heated at reflux for 20 hours. The reaction solution was ice cooled, an aqueous saturated sodium hydrogen carbonate solution was added, and the mixture was extracted with ethyl acetate. The extract was dried over anhydrous magnesium sulfate and subsequently concentrated under reduced pressure, and the obtained residue was purified by silica gel column chromatography (n-hexane:2-propanol=91:9 to 80:20) to obtain Compound 4 (953 mg) as a yellow viscous material.

MS (m/z): 234 [M+H]$^+$ (3)

[Chemical Formula 163]

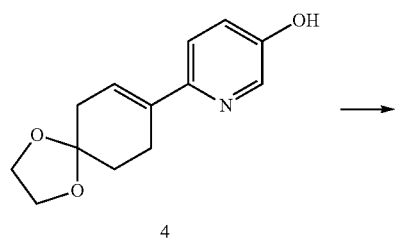
4

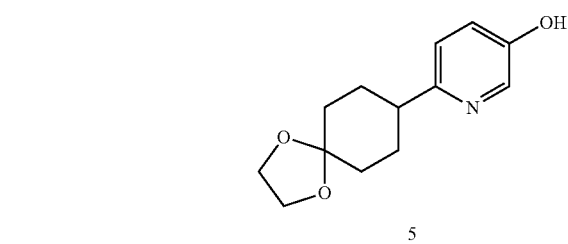
5

To a solution of Compound 4 (953 mg) in methanol (33 mL) was added palladium carbon (286 mg), and the mixture was stirred under a hydrogen atmosphere at room temperature for 2.5 hours. The reaction solution was filtered, and the filtrate was concentrated under reduced pressure. The obtained residue was washed with isopropyl ether to obtain Compound 5 (627 mg) as a colorless powder.

MS (m/z): 236 [M+H]$^+$ (4)

[Chemical Formula 164]

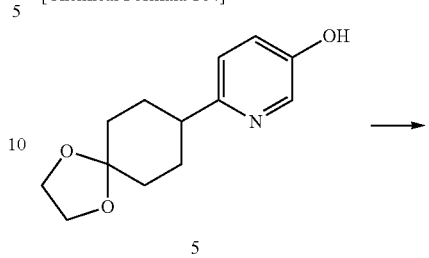
5

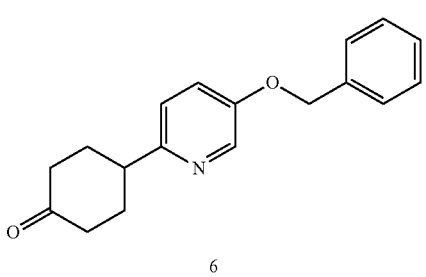
6

A solution of Compound 5 (915 mg) in tetrahydrofuran (4.2 mL) was ice cooled, and sodium hydride (233 mg) was added, and the mixture was stirred at the same temperature for 30 minutes. A solution of benzyl bromide (509 μL) in dimethylsulfoxide (4.2 mL) was then added dropwise at the same temperature, and the mixture was stirred at room temperature for 3 hours. To the reaction solution was added water, the mixture was extracted with ethyl acetate, and the extract was washed with brine. The solution was dried over anhydrous magnesium sulfate, and concentrated under reduced pressure to obtain a yellow solid (1.45 g). This yellow solid (1.26 g) was dissolved in tetrahydrofuran (38 mL), 2N hydrochloric acid (19 mL) was added, and the mixture was stirred at 50° C. for 19 hours. The reaction solution was concentrated under reduced pressure, ethyl acetate was added, and the solution was neutralized with a 1N aqueous sodium hydroxide solution. The mixture was extracted with ethyl acetate, and the extract was washed with brine and dried over anhydrous sodium sulfate. The solution was concentrated under reduced pressure, and the obtained solid was washed with isopropyl ether and filtered. The obtained powder was vacuum-dried at 50° C. to obtain Compound 6 (979 mg) as a pale yellow powder.

MS (m/z): 282 [M+H]$^+$ (5)

[Chemical Formula 165]

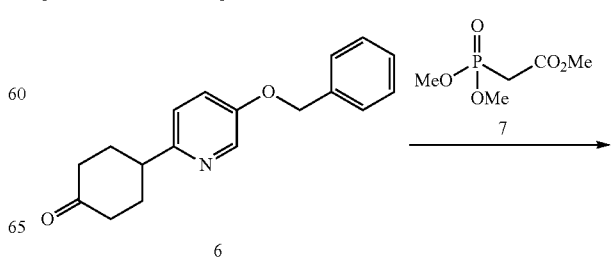
6     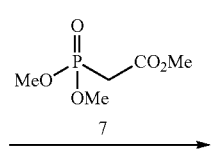 7

-continued (7)

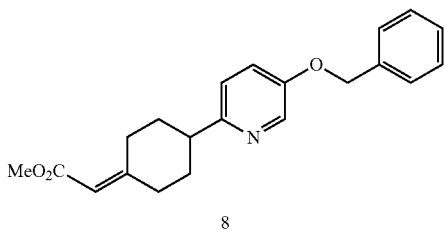

8

[Chemical Formula 167]

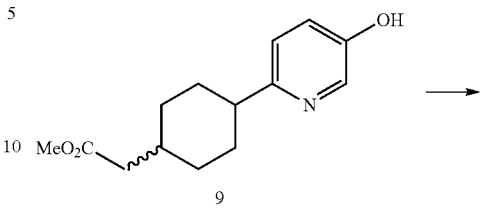

A solution of Compound 7 (760 mg) in tetrahydrofuran (3 mL) was ice cooled, and 60% sodium hydride (174 mg) was added, and the mixture was stirred at room temperature for 30 minutes. Compound 6 (979 mg) was then added, and the mixture was stirred for 17 hours. The reaction solution was ice cooled, water was added, and the mixture was extracted with ethyl acetate. The extract was washed with brine, dried over anhydrous sodium sulfate and concentrated under reduced pressure. The obtained solid was washed with isopropyl ether and collected by filtration. The solid was vacuum-dried at 50° C. to obtain Compound 8 (1.005 g) as a pale yellow powder. Further, the filtrate was concentrated under reduced pressure and the obtained residue was purified by silica gel column chromatography (n-hexane:ethyl acetate=80:20 to 67:33) to obtain Compound 8 (129 mg) as a pale yellow powder.

MS (m/z): 338 [M+H]$^+$ (6)

[Chemical Formula 166]

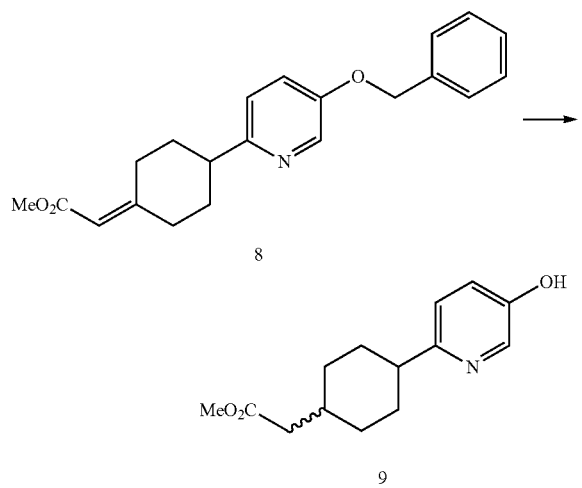

To a solution of Compound 8 (1133 mg) of ethyl acetate (23 mL) was added palladium carbon (340 mg), and the mixture was stirred under a hydrogen atmosphere at room temperature for 3 days. The reaction solution was filtered, the filtrate was concentrated under reduced pressure, and the obtained residue was washed with diethyl ether and vacuum-dried at 50° C. to obtain Compound 9 (497 mg) as a pale yellow powder. Further, the filtrate was concentrated and treated in a similar procedure to obtain Compound 9 (327 mg).

MS (m/z): 250 [M+H]$^+$

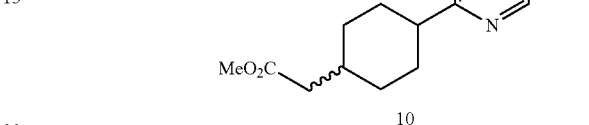

A suspension of Compound 9 (824 mg) in methylene chloride (16 mL) was ice cooled, trifluoromethanesulfonic anhydride (695 μL) was added, and triethylamine (691 μL) was then added, and the mixture was stirred at room temperature for 16 hours. To the reaction solution was added an aqueous saturated sodium hydrogen carbonate solution, and the mixture was extracted with methylene chloride. The extract was dried over anhydrous sodium sulfate and concentrated under reduced pressure. The obtained residue was purified by silica gel column chromatography (n-hexane:ethyl acetate=95:5 to 75:25) to obtain Compound 10 (1.214 g) as a pale yellow oil.

MS (m/z): 382 [M+H]$^+$ (8)

[Chemical Formula 168]

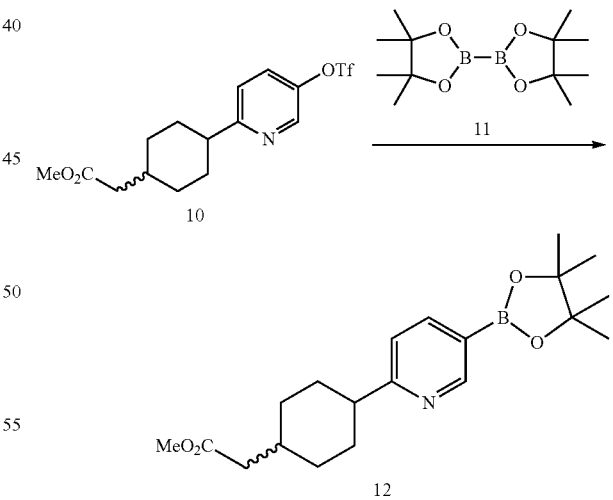

Compound 10 (1214 mg), Compound 11 (889 mg), (diphenylphosphino)ferrocene (53 mg) and potassium acetate (937 mg) were added to 1,4-dioxane (16 mL), and the mixture was subjected to nitrogen substitution. A [1,1'-bis(diphenylphosphino)ferrocene]palladium(II) dichloride dichloromethane complex (78 mg) was then added, and the mixture was subjected to nitrogen substitution again, and stirred at 80° C. for 16 hours. To the reaction solution was added water and ethyl acetate, and the mixture was stirred and filtered through Celite. After the filtrate was extracted with ethyl acetate, the extract was washed with saturated brine and dried. After concentration under reduced pressure, the obtained residue was purified by diol silica gel column chromatography (n-hexane:ethyl acetate=83:17 to 67:33) to obtain Compound 12 (570 mg) as a pale yellow oil.

MS (m/z): 360 [M+H]$^+$ (9)

[Chemical Formula 169]

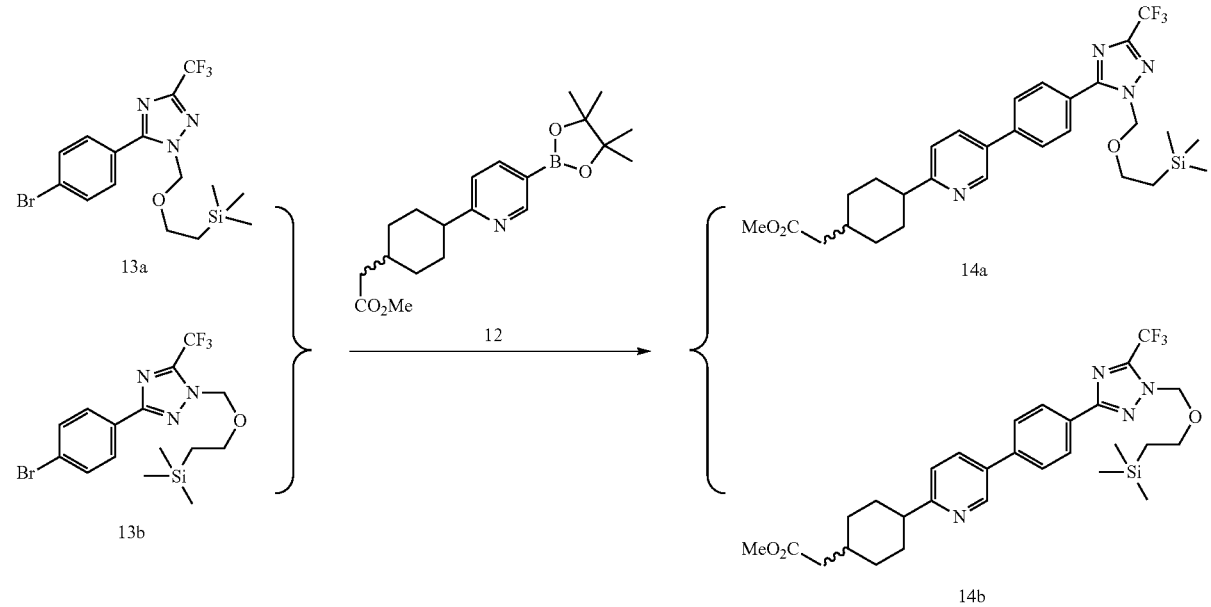

A reaction was carried out in a manner similar to the Example 50-(6) using a mixture of Compounds 13a and 13b (250 mg) and Compound 12 (255 mg) to obtain a mixture of Compounds 14a and 14b (199 mg) as a colorless oil.

MS (m/z): 575 [M+H]$^+$ (10)

[Chemical Formula 170]

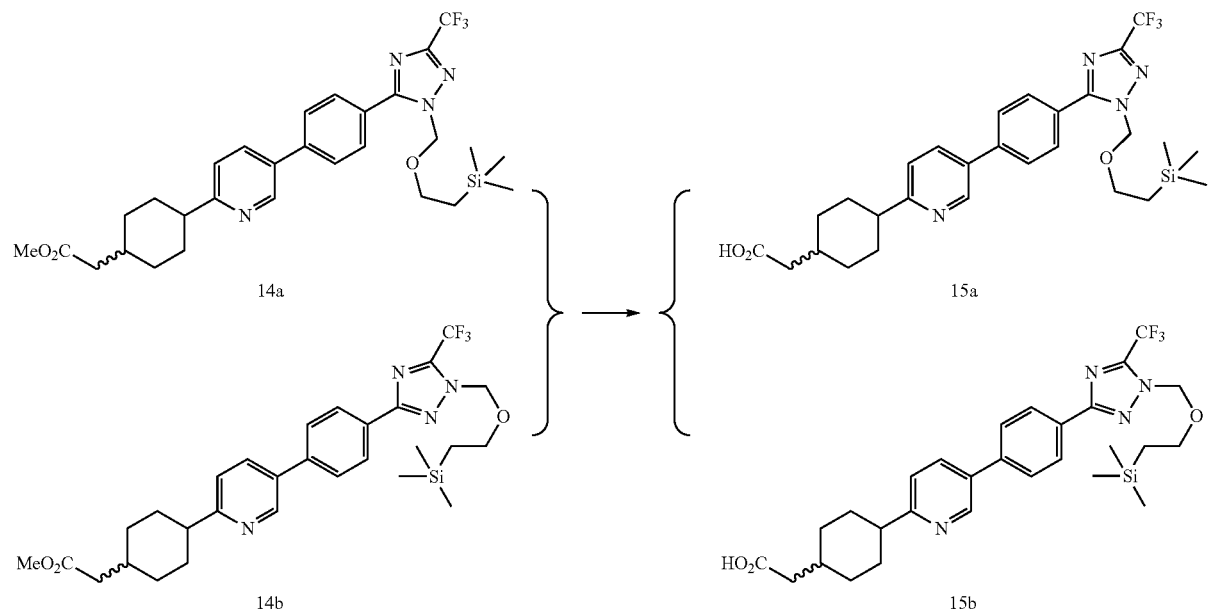

A reaction was carried out in a manner similar to the Example 52-(7) using the mixture of Compounds 14a and 14b (199 mg) to obtain a mixture of Compounds 15a and 15b (197 mg) as a pale yellow oil.

MS (m/z): 561 [M+H]$^+$ (11)

[Chemical Formula 171]

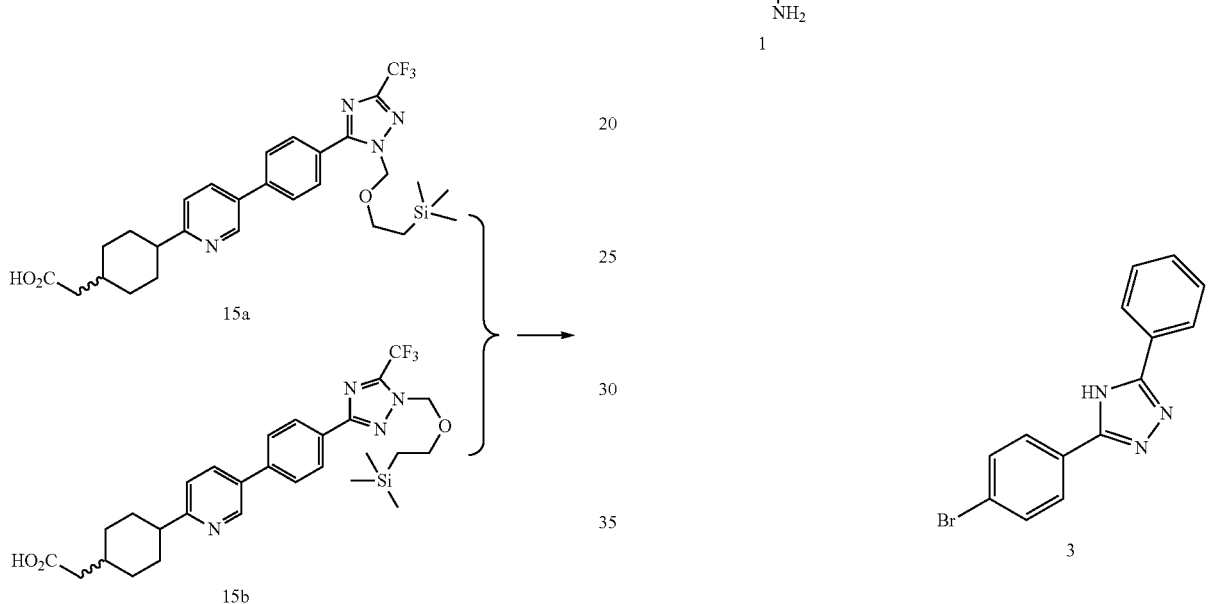

A reaction was carried out in a manner similar to the Example 52-(8) using the mixture of Compounds 15a and 15b (196 mg) to obtain Compound 16 (67 mg) of a colorless powder as a mixture of cis/trans forms.

MS (m/z): 431 [M+H]$^+$

Example 59

(1)

[Chemical Formula 172]

A mixture of Compound 1 (500 mg), Compound 2 (458 mg), sodium methylate (821 mg) and ethanol (7 mL) was heated at reflux for 4 days. The reaction solution was cooled and diluted with a saturated aqueous ammonium chloride solution, and the deposit was collected by filtration, washed with water and then dried at 45° C. overnight. After drying, the solid was dissolved in tetrahydrofuran, and dried over potassium carbonate, then concentrated under reduced pressure to obtain Compound 3 (505 mg) as a pale yellow solid.

MS (m/z): 300/302 [M+H]$^+$ (2)

[Chemical Formula 173]

(3)
[Chemical Formula 174]
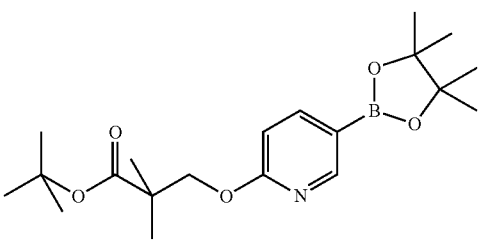
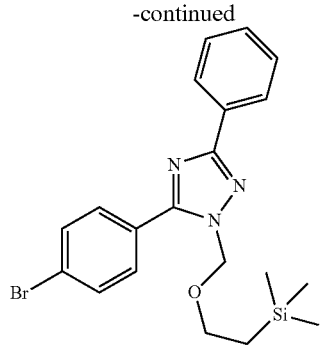
A reaction was carried out in a manner similar to the Example 51-(3) using Compound 3 (1011 mg) to obtain Compound 5 (952 mg) as a colorless solid.
MS (m/z): 378 [M+H]+
(4)
A reaction was carried out in a manner similar to the Example 50-(5) using Compound 1 (505 mg) to obtain a mixture of Compounds 2a and 2b (397 mg) as a pale yellow oil.
MS (m/z): 430/432 [M+H]+
[Chemical Formula 175]
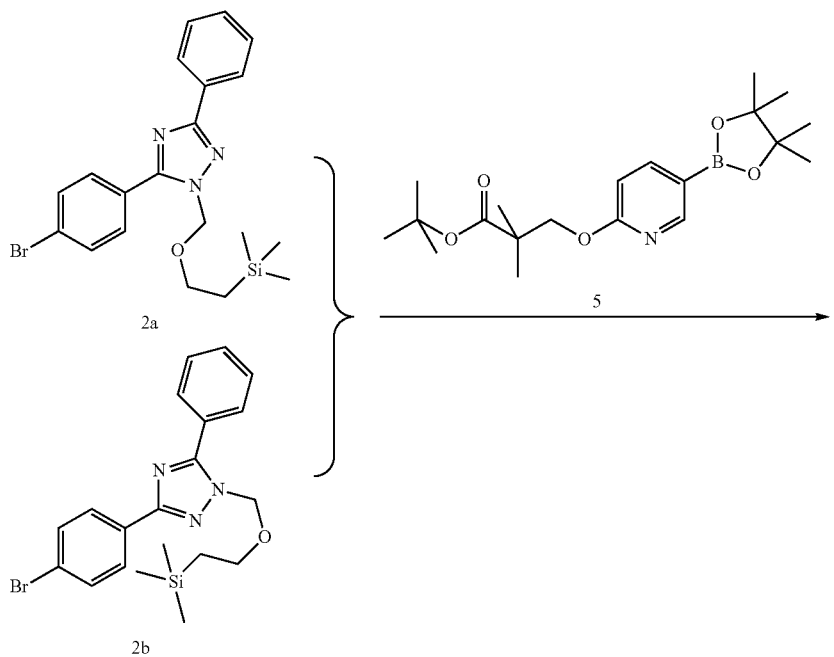

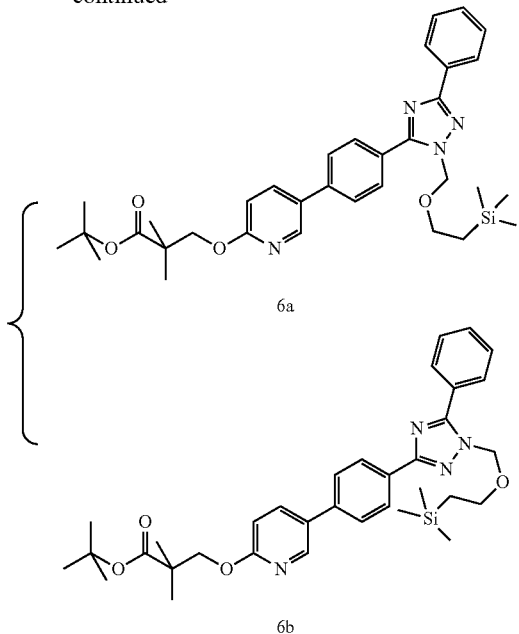

6a

6b

A reaction was carried out in a manner similar to the Example 51-(4) using the mixture of Compounds 2a and 2b (300 mg) to obtain a mixture of Compounds 6a and 6b (298 mg) as a pale yellow oil.

MS (m/z): 601 [M+H]$^+$ (5)

[Chemical Formula 176]

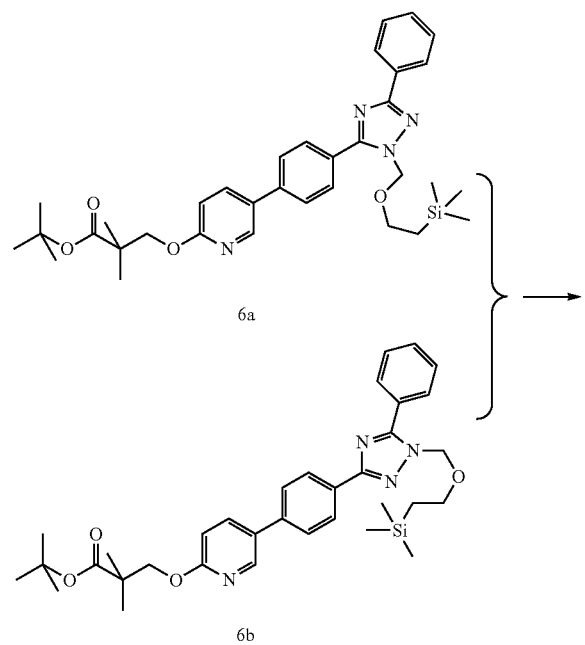

6a

6b

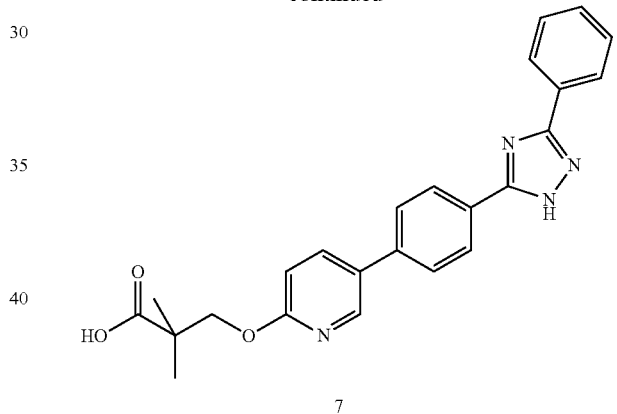

7

A reaction was carried out in a manner similar to the Example 51-(5) using the mixture of Compounds 6a and 6b (298 mg) to obtain Compound 7 (186 mg) as an ivory solid.

MS (m/z): 415 [M+H]$^+$

Example 60

(1)

[Chemical Formula 177]

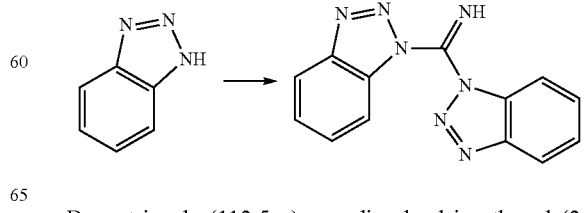

Benzotriazole (112.5 g) was dissolved in ethanol (2 L), and a solution of cyano bromide (50 g) in acetone (200 mL)

was added dropwise under ice cooling. An aqueous solution of sodium hydroxide (18.9 g) dissolved in water (170 mL) was then added dropwise, and the mixture was stirred at the same temperature for 15 minutes. The deposit was filtered, washed with cold ethanol and subsequent dried to obtain Compound 1 (71.21 g) as a colorless solid.

MS (m/z): 264 [M+H]$^+$ (2)

[Chemical Formula 178]

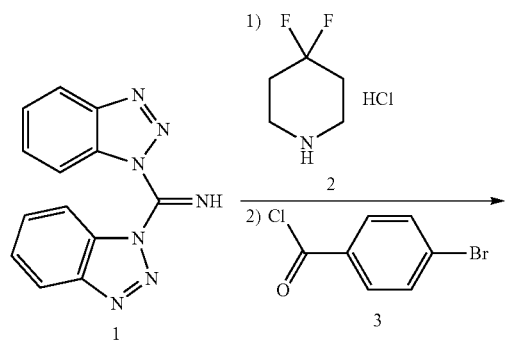

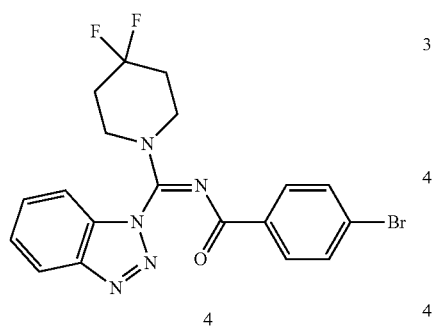

To a solution of Compound 1 (1000 mg) in tetrahydrofuran (20 mL) were added Compound 2 (599 mg) and triethylamine (529 μL), and the mixture was stirred at room temperature overnight. The reaction solution was concentrated under reduced pressure, to the residue were added methylene chloride and an aqueous potassium carbonate solution, and the organic layer was separated, washed with saturated brine, and concentrated under reduced pressure. To the residue was added 20 mL of chloroform, and Compound 3 (834 mg) and triethylamine (529 μL) were added under ice cooling, and the mixture was stirred at room temperature overnight. The reaction solution was extracted with chloroform, and the extract was washed with saturated brine, and dried over anhydrous sodium sulfate. After the solution was concentrated under reduced pressure, the obtained residue was purified by silica gel column chromatography (n-hexane:2-propanol=97:3 to 55:45) to obtain Compound 4 (311 mg) as a colorless solid.

MS (m/z): 448/450 [M+H]$^+$ (3)

[Chemical Formula 179]

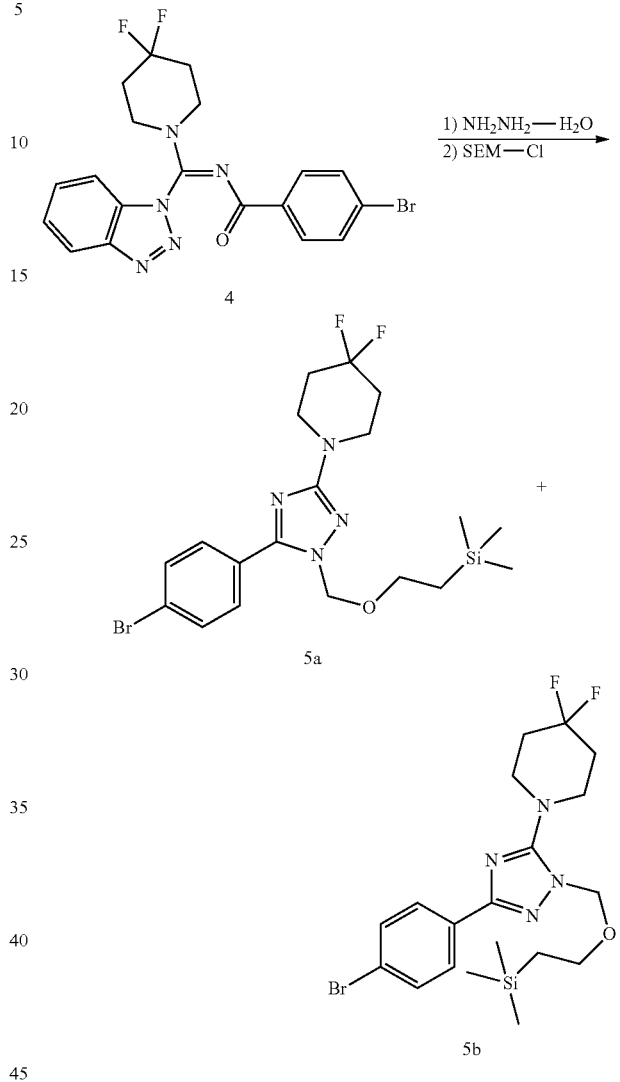

To a solution of Compound 4 (311 mg) in chloroform (6 mL) was added hydrazine hydrate (22 μL), and the mixture was stirred at room temperature overnight. The reaction solution was concentrated under reduced pressure, and the residue was dissolved in N,N-dimethylformamide (6 mL), and ice-cooled. To this was added sodium hydride (69 mg), and the mixture was stirred at room temperature for 1 hour. The reaction solution was ice-cooled, and (trimethylsilyl) ethoxymethyl chloride (307 μL) was added dropwise. The temperature of the reaction solution was elevated to room temperature, and the reaction solution was stirred for 3 days. To the reaction solution was added a saturated aqueous ammonium chloride solution, and the mixture was extracted with ethyl acetate. The extract was washed with saturated brine, and dried over anhydrous sodium sulfate. After the solution was concentrated under reduced pressure, the obtained residue was purified by silica gel column chromatography (n-hexane:2-propanol=99:1 to 85:15) to obtain a mixture of Compounds 5a and 5b (125 mg) as a colorless oil.

MS (m/z): 473/475 [M+H]$^+$ (4)
[Chemical Formula 180]
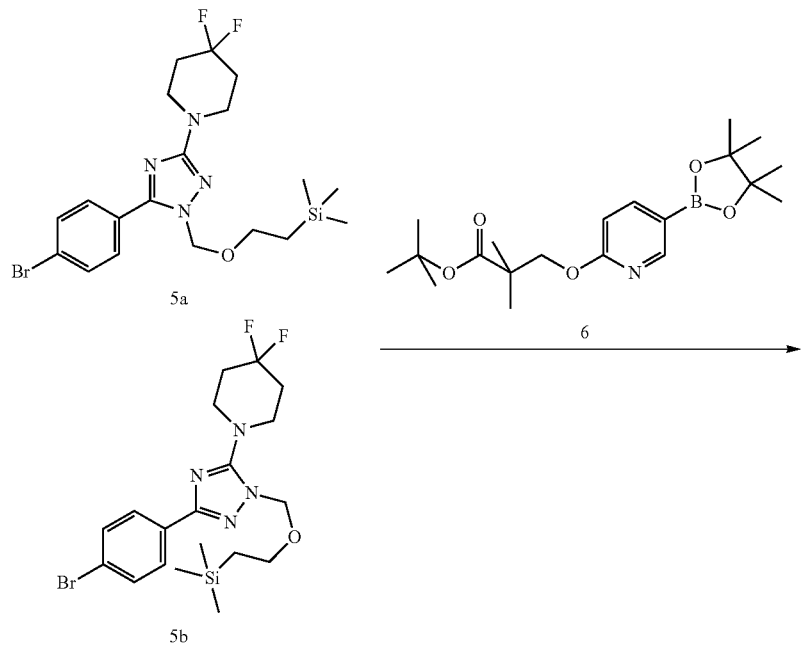
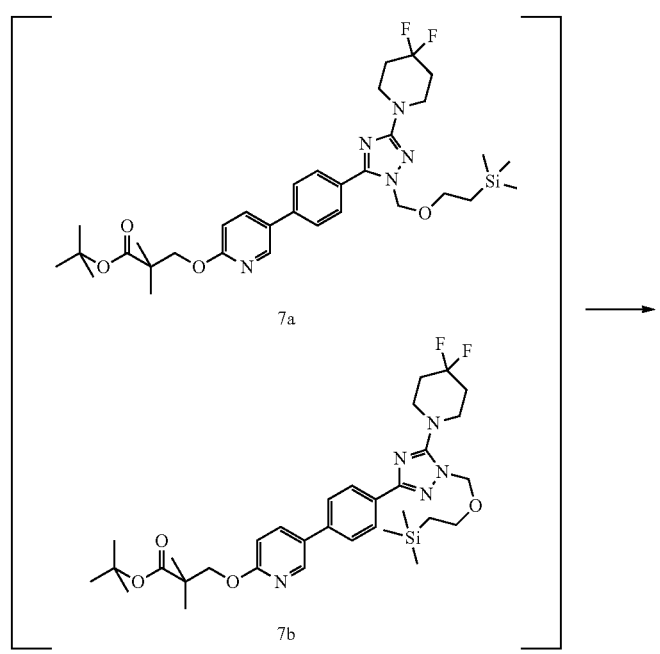

-continued

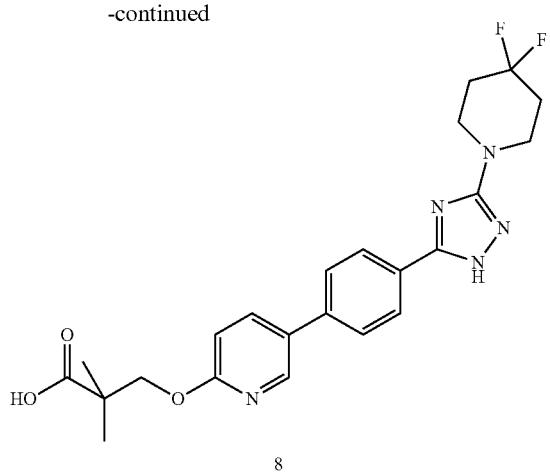

8

After the reaction was carried out in a manner similar to the Example 50-(6) using the mixture of Compounds 5a and 5b (125 mg) and Compound 6 (150 mg), the reaction solution was filtered through silica gel, and washed with ethyl acetate. The filtrate was concentrated under reduced pressure, to the residue were added trifluoroacetic acid (5 mL) and water (0.5 mL), and the mixture was stirred at room temperature overnight. The reaction solution was concentrated, the residue was dissolved by adding acetic acid thereto, and the solution was concentrated again under reduced pressure. The obtained residue was purified by LC-MS to obtain Compound 8 (32 mg) as a beige solid.

MS (m/z): 458 [M+H]$^+$

Example 61

(1)

[Chemical Formula 181]

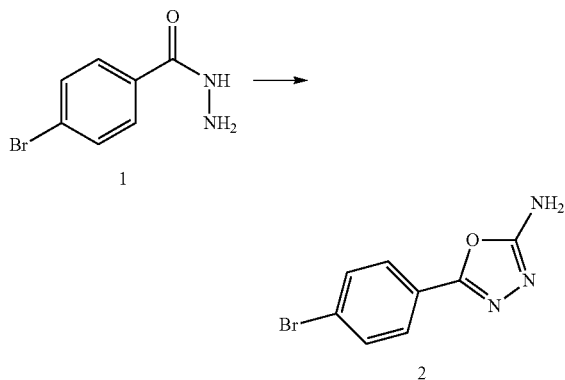

To a solution of Compound 1 (2.00 g) in 1,4-dioxane (20 mL) was added an aqueous sodium hydrogen carbonate solution prepared from sodium hydrogen carbonate (781 mg) and water (15 mL), and the mixture was stirred at room temperature for 5 minutes. To this was added cyano bromide (985 mg), and the mixture was stirred at room temperature for 2 hours and then at elevated temperature of 65° C. for two days. The obtained crystals were collected by filtration, sequentially washed with water and diethyl ether, and dried to obtain Compound 2 (1.81 g) as a colorless solid.

MS (m/z): 240/242 [M+H]$^+$ (2)

[Chemical Formula 182]

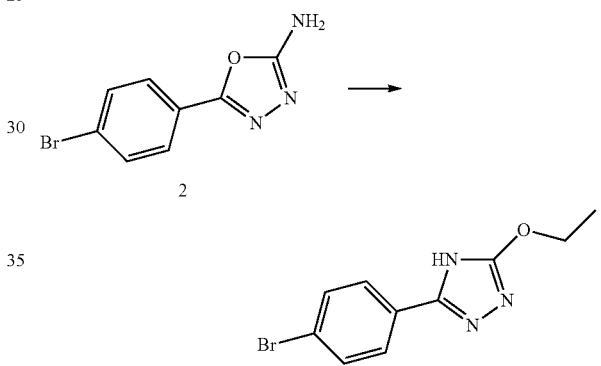

Compound 2 (500 mg) was dissolved in ethanol (15 mL), potassium hydroxide (467 mg) was added, and at the temperature of 90° C., and the mixture was stirred for 8 hours. After the mixture was allowed to cool to room temperature, it was neutralized by addition of a 2N aqueous hydrochloric acid solution. Ethyl acetate and water were added to the reaction solution to carry out a liquid separation. The organic layer was separated, washed with saturated brine, passed through the phase separator and concentrated under reduced pressure. The obtained residue was purified by silica gel column chromatography (chloroform:methanol=100:0 to 93:7) to obtain Compound 3 (396 mg) as a colorless solid.

MS (m/z): 268/270 [M+H]$^+$ (3)

[Chemical Formula 183]

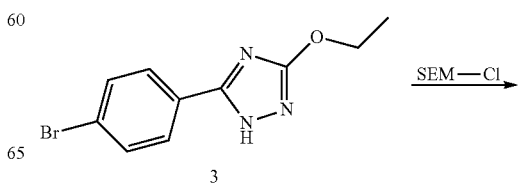

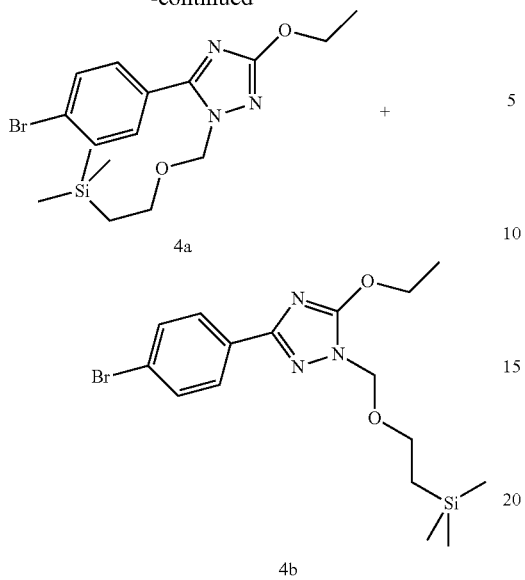

4a

4b

To a solution of Compound 3 (500 mg) dissolved in N,N-dimethylformamide (5 mL) was added 60% sodium hydride (112 mg) under a nitrogen atmosphere under ice cooling, and the mixture was stirred for 15 minutes. 2-(Trimethylsilyl)ethoxymethyl chloride (491 μL) was added under ice-cooling, and the mixture was stirred for 1 hour. To the reaction solution was added a saturated aqueous ammonium chloride solution, and the mixture was extracted with ethyl acetate. The organic layer was washed with saturated brine, passed through the phase separator and concentrated under reduced pressure. The obtained residue was purified by silica gel column chromatography (n-hexane:ethyl acetate=99:1 to 60:40) to obtain a mixture of Compounds 4a and 4b (773 mg) as a pale yellow powder.

MS (m/z): 398/400 [M+H]$^+$ (4)

[Chemical Formula 184]

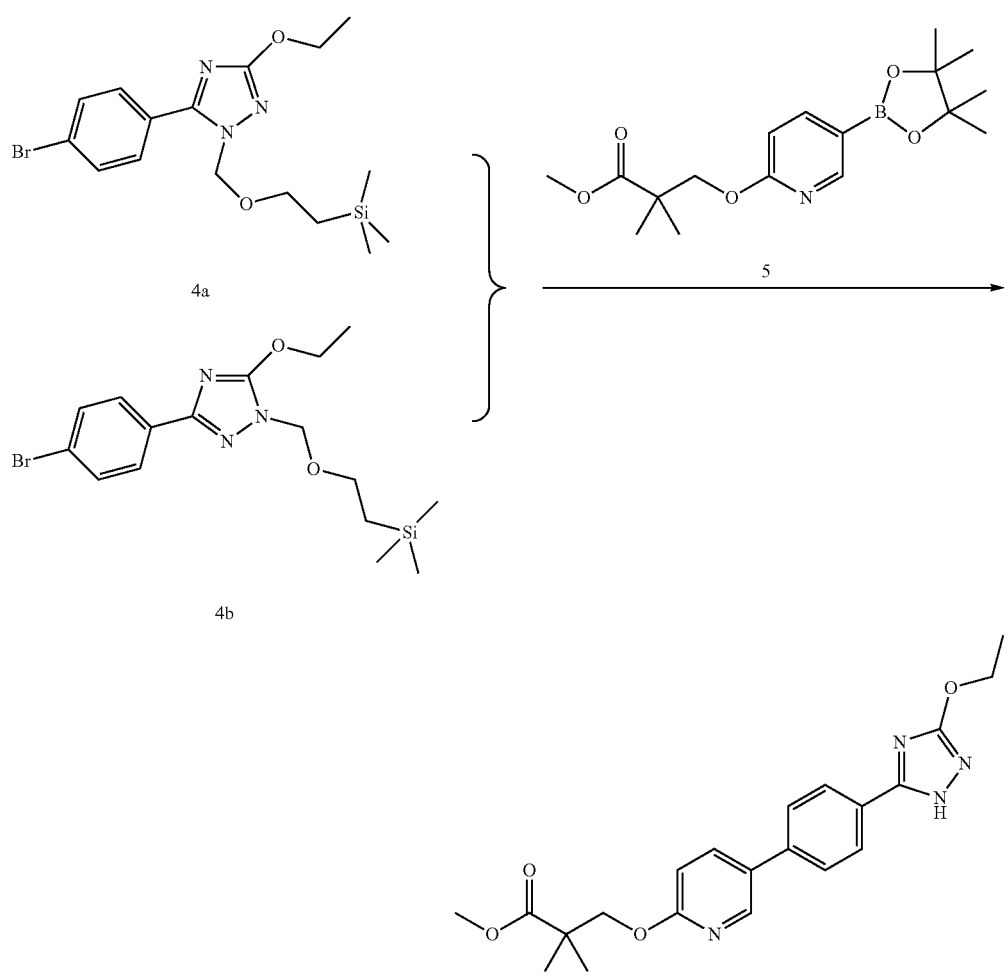

A solution of the mixture of Compounds 4a and 4b (740 mg), palladium acetate (21 mg), 2-dicyclohexylphosphino-2',6'-dimethoxybiphenyl (76 mg), Compound 5 (747 mg) and tripotassium phosphate (789 mg) in tetrahydrofuran (10 mL) was stirred at the temperature of 50° C. under a nitrogen atmosphere overnight. After the reaction solution was allowed to cool to room temperature, a saturated aqueous sodium hydrogen carbonate solution was added, and the mixture was stirred. Ethyl acetate was added to carry out a liquid separation. The organic layer was washed with saturated brine, passed through the phase separator and concentrated under reduced pressure. To the obtained residue were added trifluoroacetic acid (3 mL) and water (0.15 mL), and the mixture was stirred at room temperature overnight. To the reaction solution was added a 2N aqueous sodium hydroxide solution to adjust the pH to about 2 to 3, and ethyl acetate was added to carry out a liquid separation. The organic layer was separated, washed with saturated brine, passed through the phase separator and concentrated under reduced pressure. The obtained residue was purified by silica gel column chromatography (n-hexane:ethyl acetate=80:20 to 50:50) to obtain Compound 6 (351 mg) as a pale yellow viscous material.

MS (m/z): 397 [M+H]$^+$ (5)

[Chemical Formula 185]

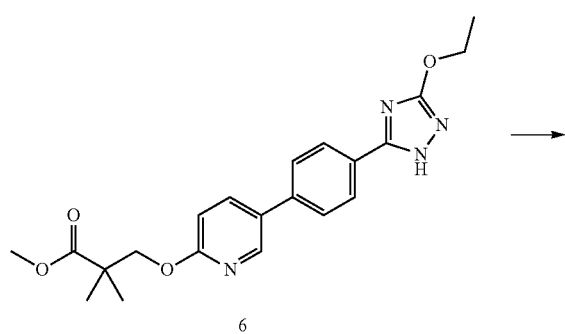

6

Compound 6 (348 mg) were dissolved in tetrahydrofuran (2 mL) and methanol (2 mL), a 2N aqueous sodium hydroxide solution (3 mL) was added, and the mixture was stirred at 50° C. for 2 hours. After the reaction solution was neutralized by addition of 2N hydrochloric acid, ethyl acetate was added to carry out a liquid separation. The organic layer was separated, washed with saturated brine, passed through the phase separator, and concentrated under reduced pressure. The obtained residue was triturated with addition of dichloromethane and a small amount of methanol, and collected by filtration to obtain Compound 7 (186 mg) as a colorless solid.

MS (m/z): 383 [M+H]$^+$

Example 62

(1)

[Chemical Formula 186]

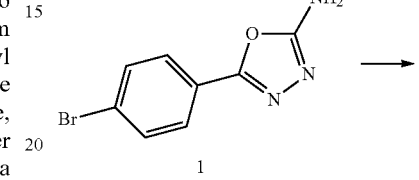

1

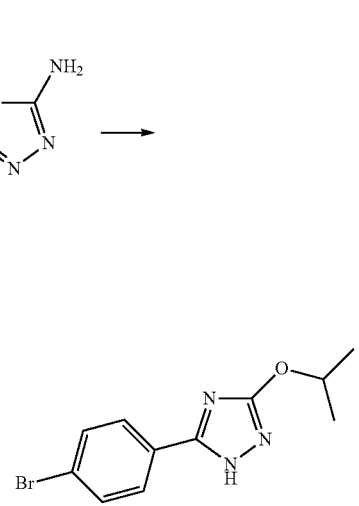

2

A treatment was carried out in a manner similar to the Example 61-(2) using Compound 1 (2.00 g) and 2-propanol (60 mL) to obtain Compound 2 (618 mg) as a colorless solid.

MS (m/z): 282/284 [M+H]$^+$ (2)

[Chemical Formula 187]

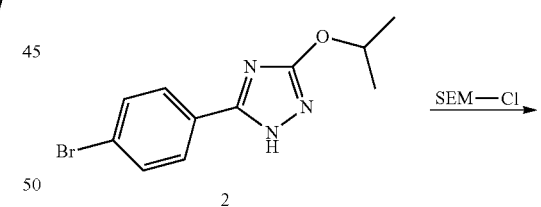

2

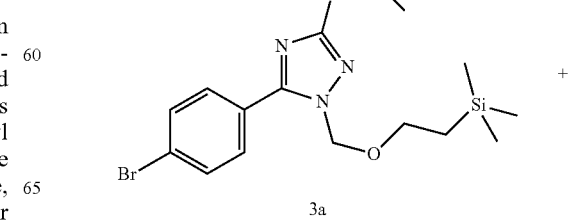

3a

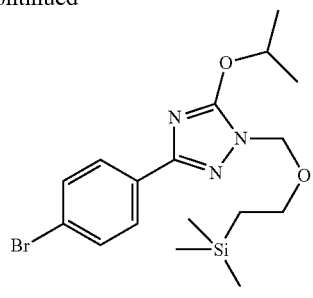
Starting from Compound 2 (610 mg), a treatment was carried out in a manner similar to the Example 61-(3) to obtain a mixture of Compounds 3a and 3b (476 mg) as a colorless solid.
MS (m/z): 412/414 [M+H]$^+$
(3)
[Chemical Formula 188]
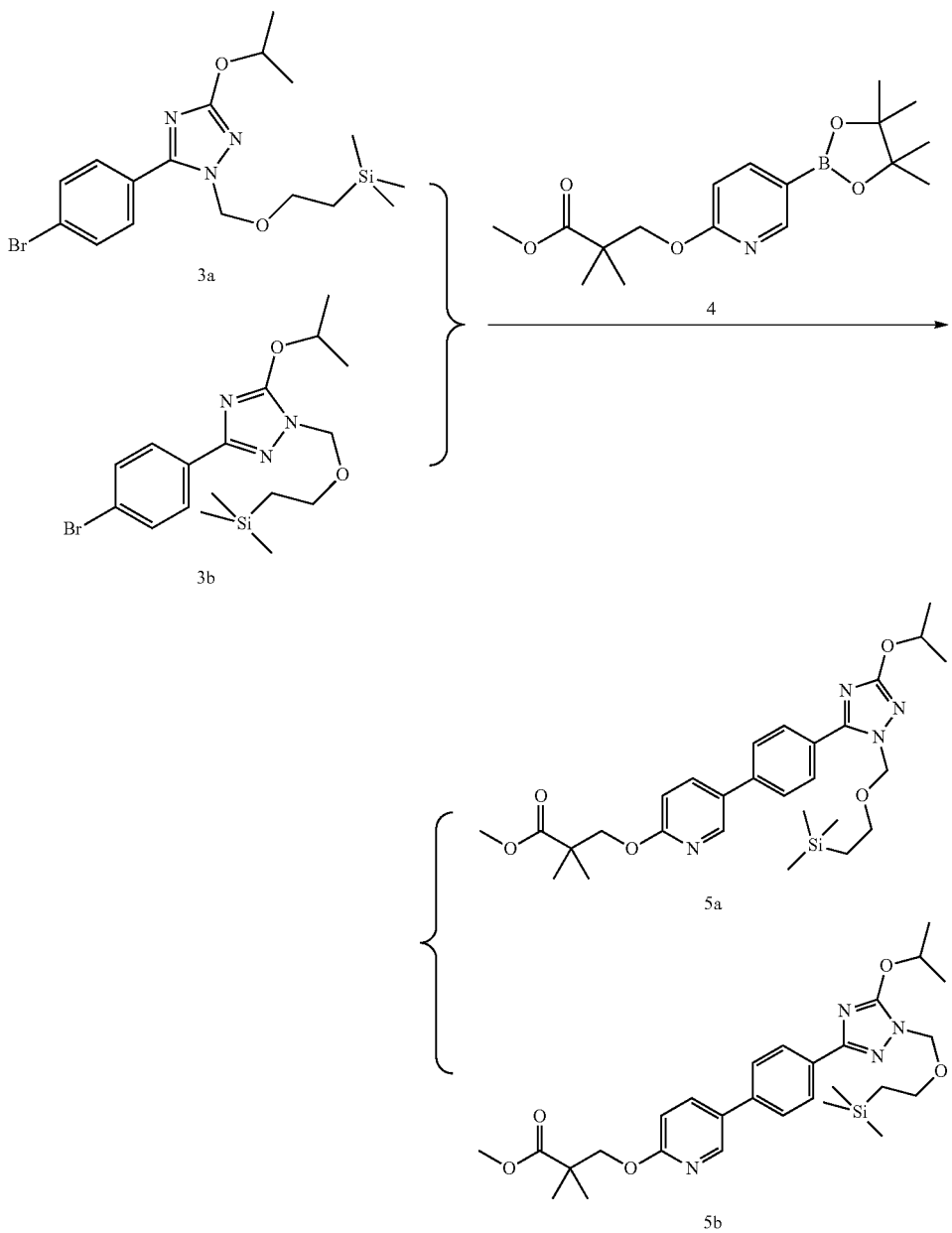

A solution of the mixture of Compounds 3a and 3b (473 mg), palladium acetate (13 mg), 2-dicyclohexylphosphino-2',6'-dimethoxybiphenyl (47 mg), Compound 4 (461 mg) and tripotassium phosphate (487 mg) in tetrahydrofuran (6 mL) was stirred at the temperature of 70° C. under a nitrogen atmosphere overnight. After the reaction solution was allowed to cool to room temperature, a saturated aqueous sodium hydrogen carbonate solution was added to the reaction solution, and the mixture was stirred. Ethyl acetate was added to carry out a liquid separation. The organic layer was washed with saturated brine, passed through the phase separator and concentrated under reduced pressure. The obtained residue was purified by silica gel column chromatography (n-hexane:ethyl acetate=98:2 to 65:35) to obtain a mixture of Compounds 5a and 5b (460 mg) as a pale yellow viscous material.

MS (m/z): 541 [M+H]$^+$ (4)

To the mixture of Compounds 5a and 5b (460 mg) were added trifluoroacetic acid (2 mL) and water (0.1 mL), and the mixture was stirred at room temperature overnight. To the reaction solution was added a 2N aqueous sodium hydroxide solution to adjust the pH to about 2 to 3, and ethyl acetate was added to carry out a liquid separation. The organic layer was separated, washed with saturated brine, passed through the phase separator and concentrated under reduced pressure. The obtained residue was purified by silica gel column chromatography (n-hexane:ethyl acetate=80:20 to 50:50) to obtain Compound 6 (144 mg) as a colorless viscous material.

MS (m/z): 411 [M+H]$^+$ (5)

[Chemical Formula 189]

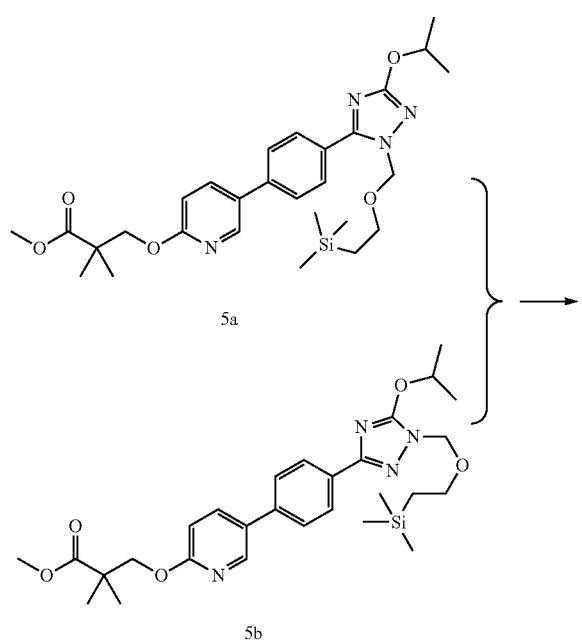

[Chemical Formula 190]

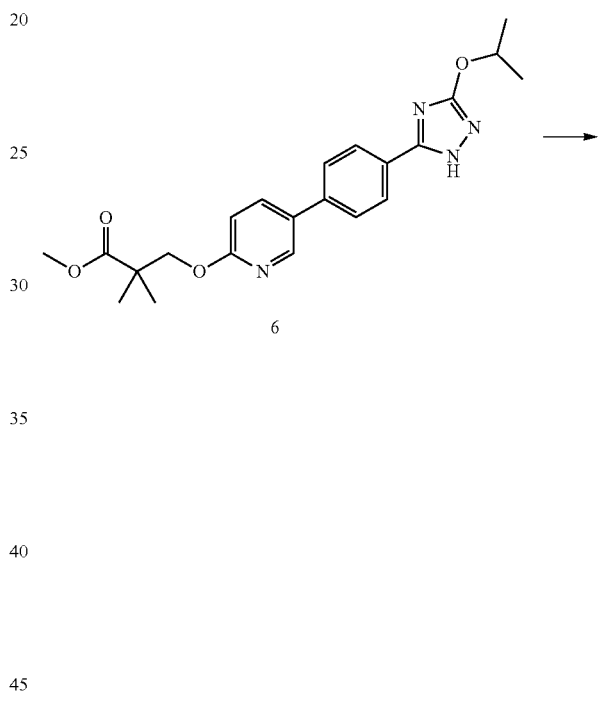

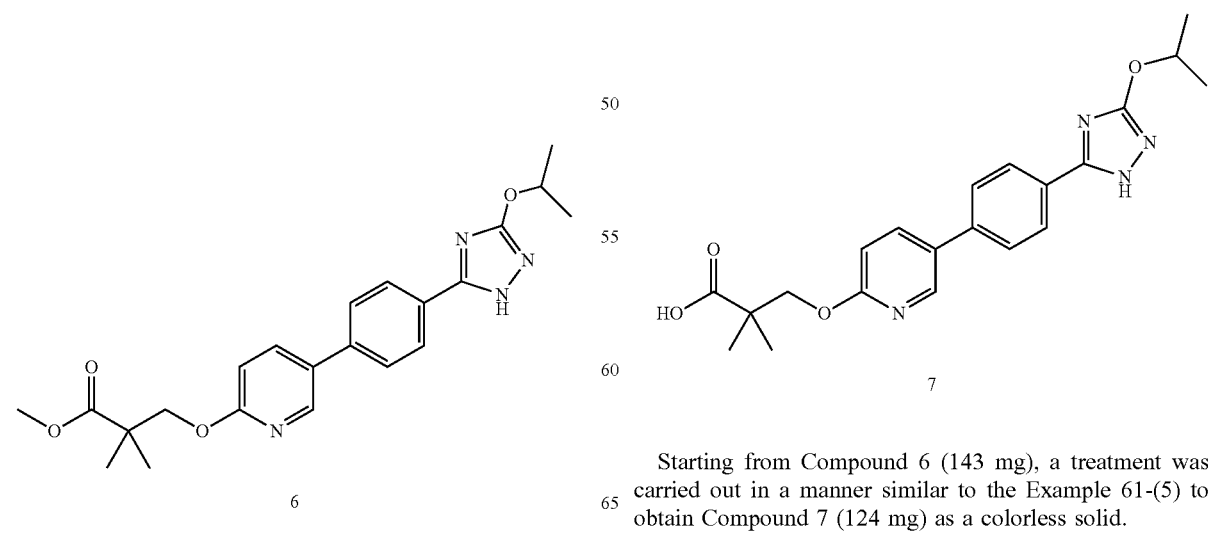

Starting from Compound 6 (143 mg), a treatment was carried out in a manner similar to the Example 61-(5) to obtain Compound 7 (124 mg) as a colorless solid.

MS (m/z): 397 [M+H]$^+$

Example 63
(1)
[Chemical Formula 191]
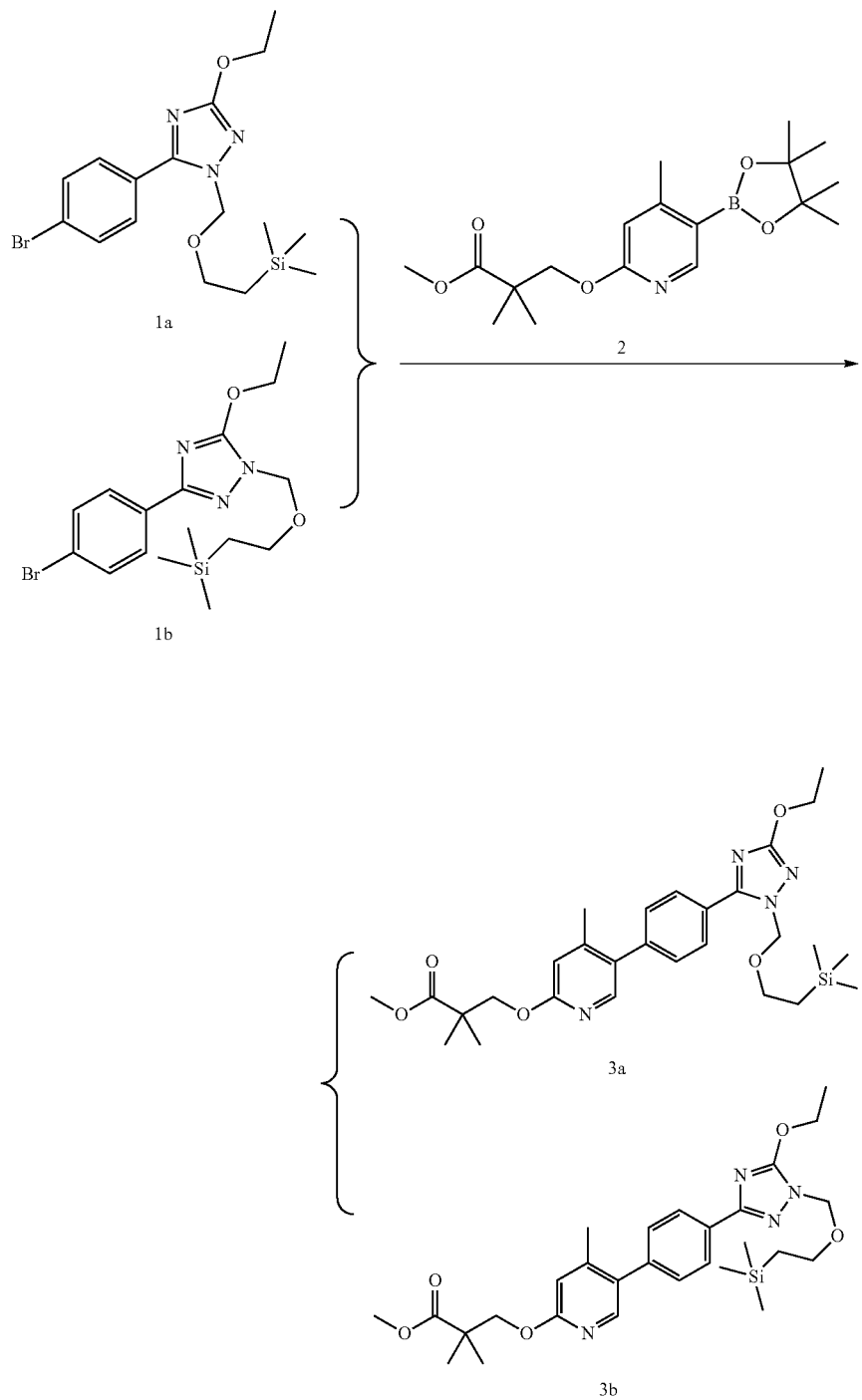
Starting from a mixture of Compounds 1a and 1b (500 mg) and Compound 2 (526 mg), a treatment was carried out in a manner similar to the Example 62-(3) to obtain a mixture of Compounds 3a and 3b (355 mg) as a pale yellow viscous material.
MS (m/z): 541 [M+H]$^+$ (2)

[Chemical Formula 192]

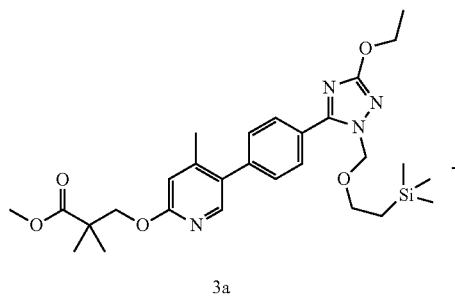

3a

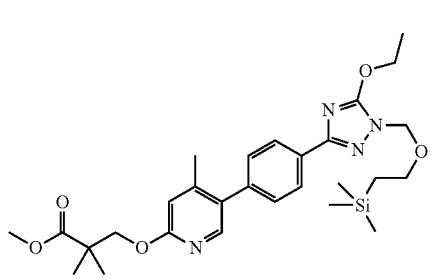

3b (3)

[Chemical Formula 193]

[structure of compound 4] →

4

[structure of compound 4]

4

[structure of compound 5]

5

Starting from a mixture of Compounds 3a and 3b (352 mg), a treatment was carried out in a manner similar to the Example 62-(4) to obtain Compound 4 (43.5 mg) as a colorless viscous material.

MS (m/z): 411 [M+H]$^+$

Starting from Compound 4 (43.0 mg), a treatment was carried out in a manner similar to the Example 61-(5) to obtain Compound 5 (32.9 mg) as a white solid.

MS (m/z): 397 [M+H]$^+$

Example 64

(1)

[Chemical Formula 194]

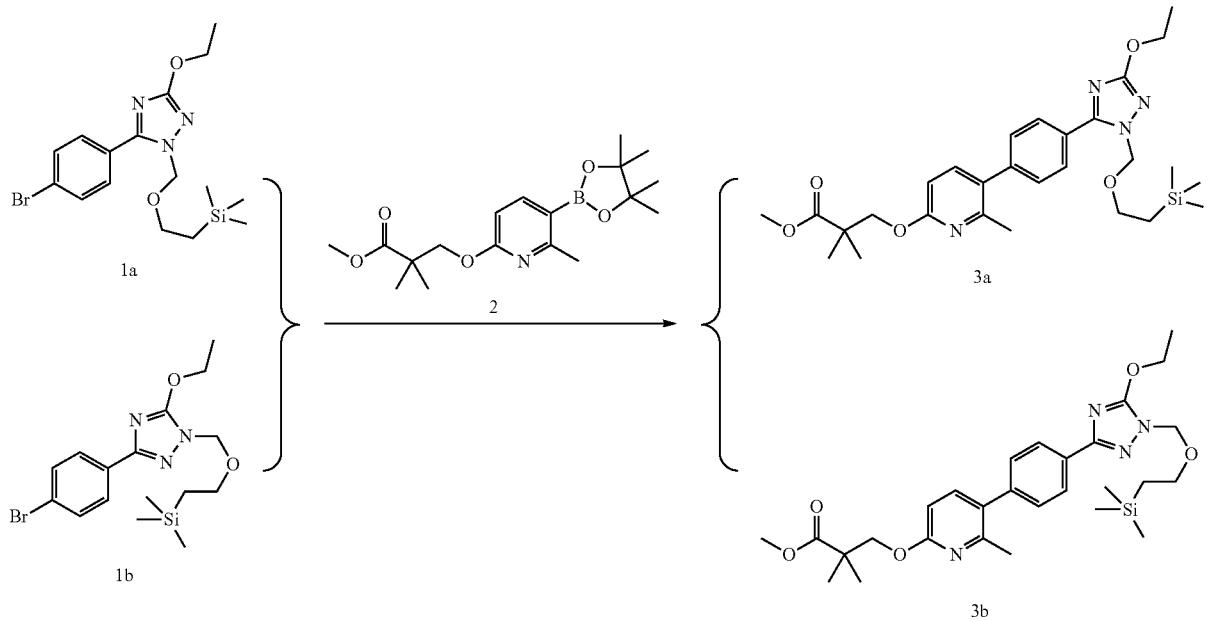

Starting from a mixture of Compounds 1a and 1b (500 mg) and Compound 2 (526 mg), a treatment was carried out in a manner similar to the Example 62-(3) to obtain a mixture of Compounds 3a and 3b (708 mg) as a pale yellow viscous material.

MS (m/z): 541 [M+H]$^+$ (2)

[Chemical Formula 195]

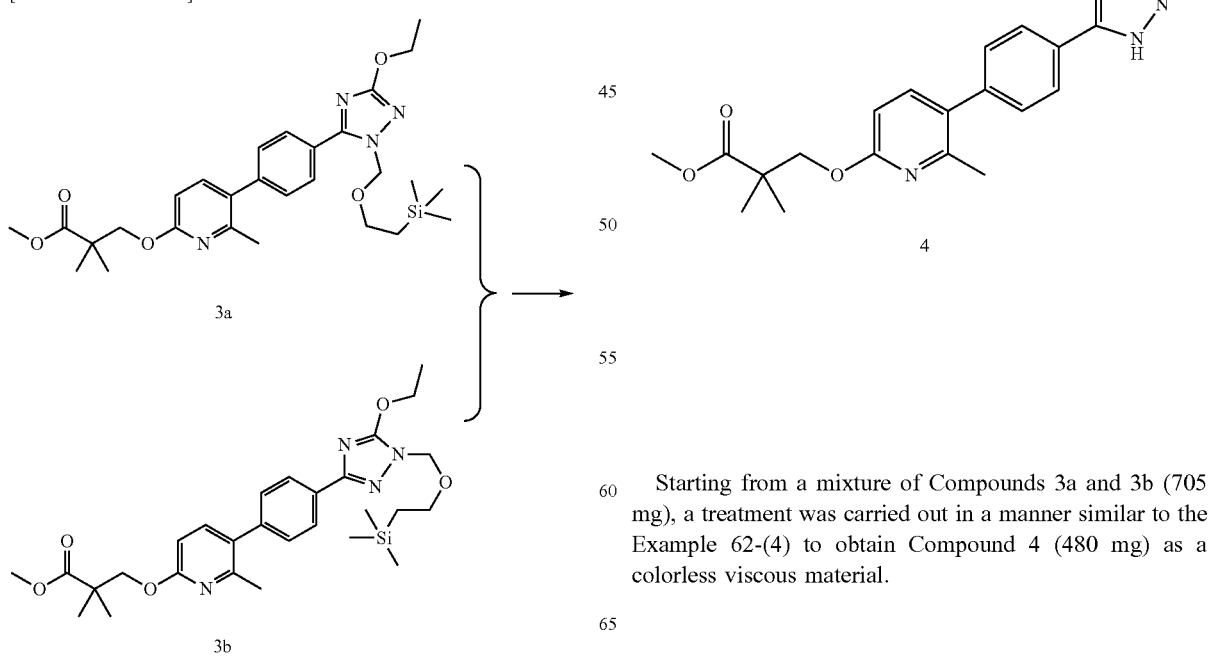

Starting from a mixture of Compounds 3a and 3b (705 mg), a treatment was carried out in a manner similar to the Example 62-(4) to obtain Compound 4 (480 mg) as a colorless viscous material.

MS (m/z): 411 [M+H]$^+$ (3)
[Chemical Formula 196]
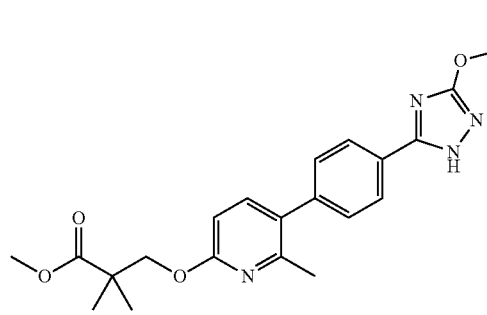
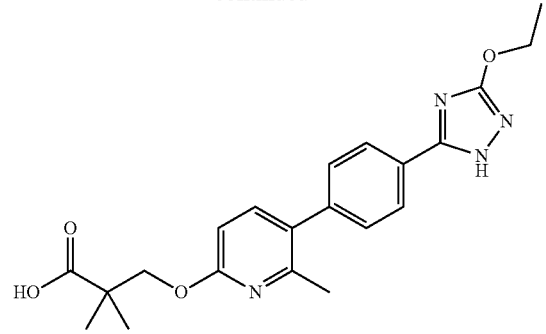
Starting from Compound 4 (478 mg), a treatment was carried out in a manner similar to the Example 61-(5) to obtain Compound 5 (288 mg) as a colorless solid.
MS (m/z): 397 [M+H]$^+$
Example 65
(1)
[Chemical Formula 197]
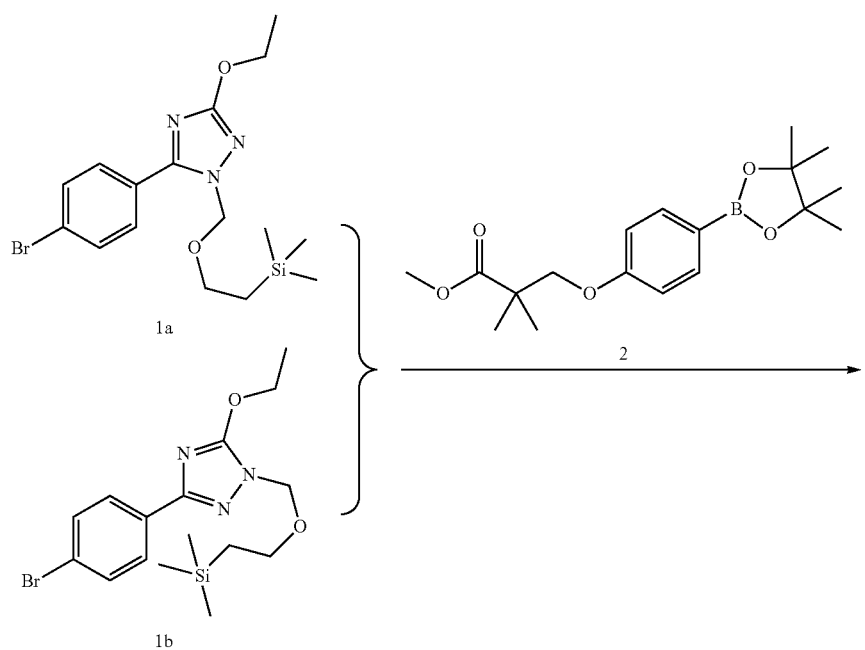

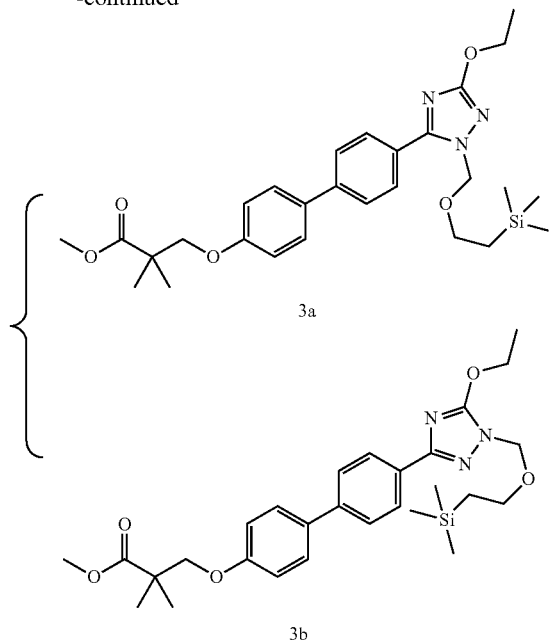

3a

3b

Starting from a mixture of Compounds 1a and 1b (500 mg) and Compound 2 (526 mg), a treatment was carried out in a manner similar to the Example 62-(3) to obtain a mixture of Compounds 3a and 3b (723 mg) as a pale yellow viscous material.

MS (m/z): 526 [M+H]$^+$ (2)

[Chemical Formula 198]

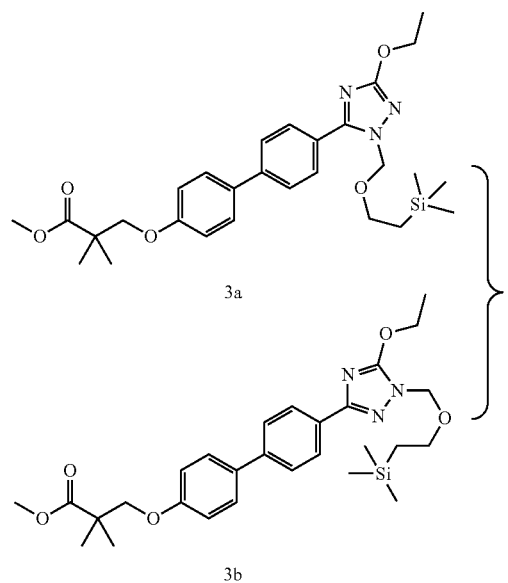

3a

3b

-continued

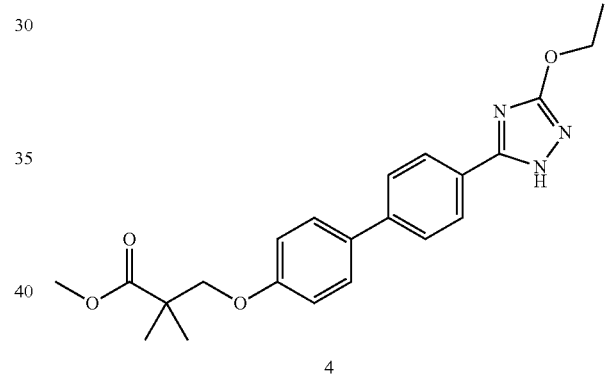

4

Starting from a mixture of Compounds 3a and 3b (720 mg), a treatment was carried out in a manner similar to the Example 62-(4) to obtain Compound 4 (463 mg) as a colorless solid.

MS (m/z): 396 [M+H]$^+$ (3)

[Chemical Formula 199]

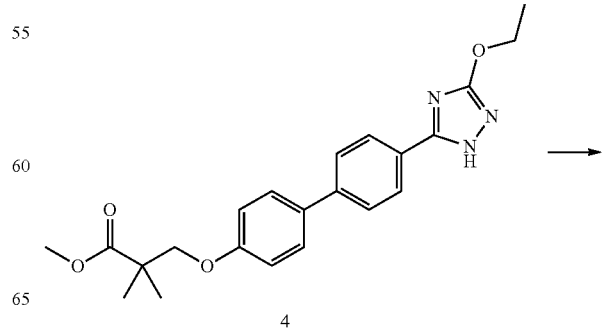

4

-continued
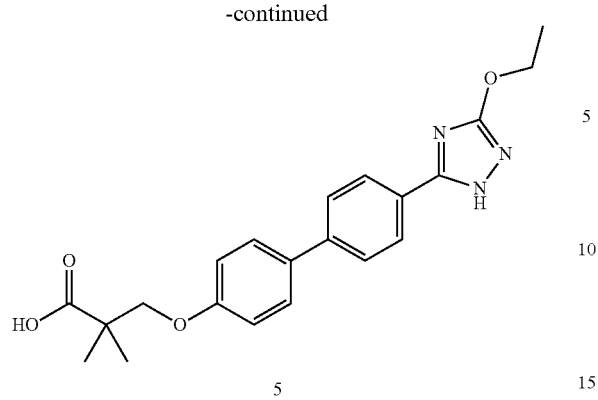
Starting from Compound 4 (463 mg), a treatment was carried out in a manner similar to the Example 61-(5) to obtain Compound 5 (356 mg) as a colorless solid.
MS (m/z): 382 [M+H]$^+$
Example 66
(1)
[Chemical Formula 200]
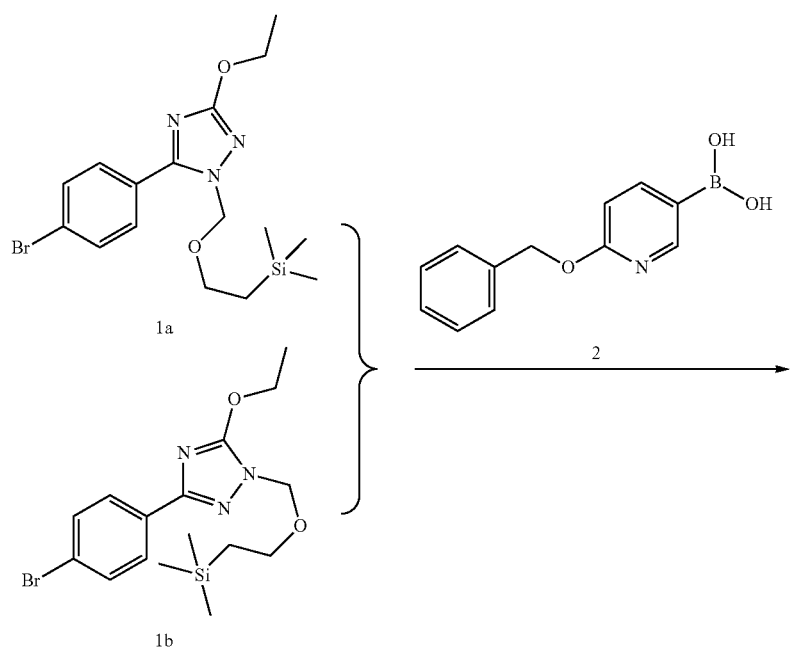

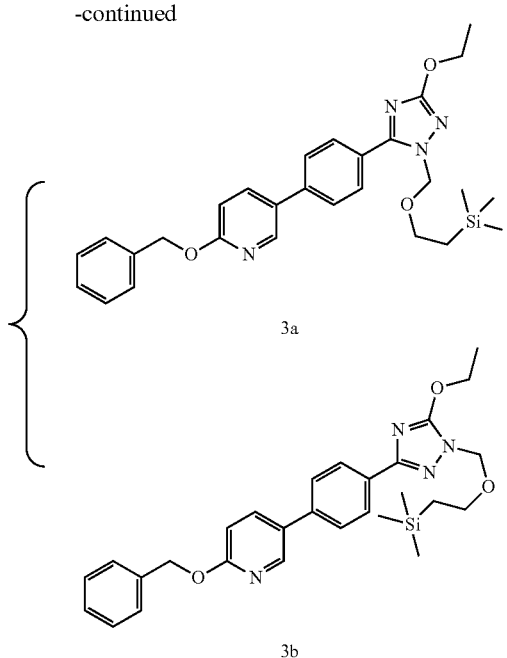
Starting from a mixture of Compounds 1a and 1b (1500 mg) and Compound 2 (1035 mg), a treatment was carried out in a manner similar to the Example 62-(3) to obtain a mixture of Compounds 3a and 3b (1226 mg) as a white solid.
MS (m/z): 503 [M+H]$^+$
(2)
[Chemical Formula 201]
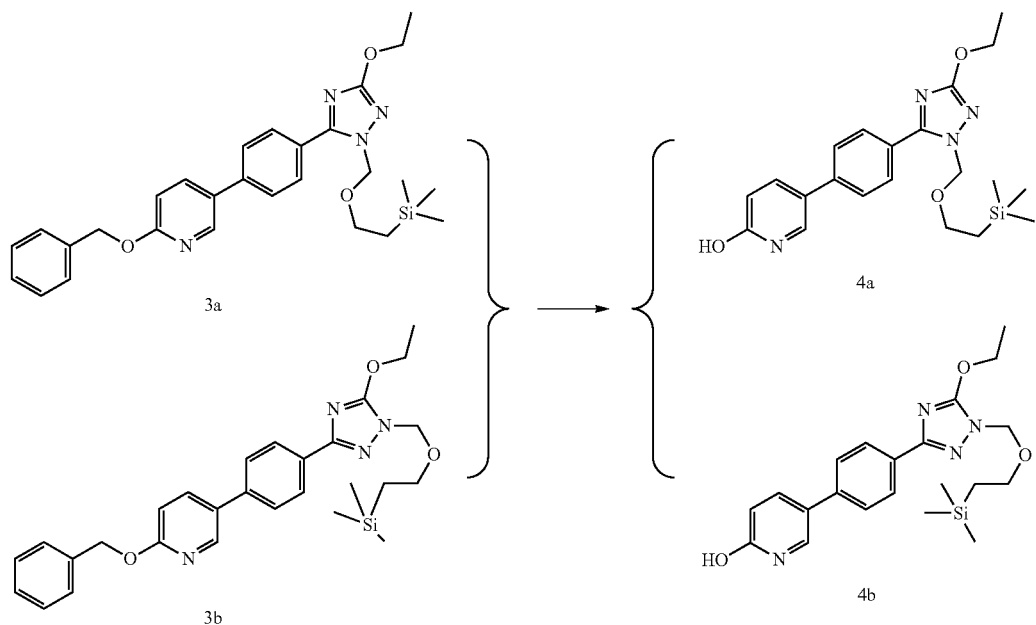

To a mixture of Compounds 3a and 3b (1220 mg) were added methanol (20 mL) and tetrahydrofuran (20 mL), 10% palladium carbon (244 mg) was added under a hydrogen atmosphere, and the mixture was stirred at room temperature for 6 hours. After the catalyst was filtered off over a membrane filter, the filtrate was concentrated under reduced pressure, and the obtained residue was purified by silica gel column chromatography (chloroform:methanol=100:0 to 93:7) to obtain a mixture of Compounds 4a and 4b (902 mg) as a colorless viscous material.

MS (m/z): 413 $[M+H]^+$ (3)

[Chemical Formula 202]

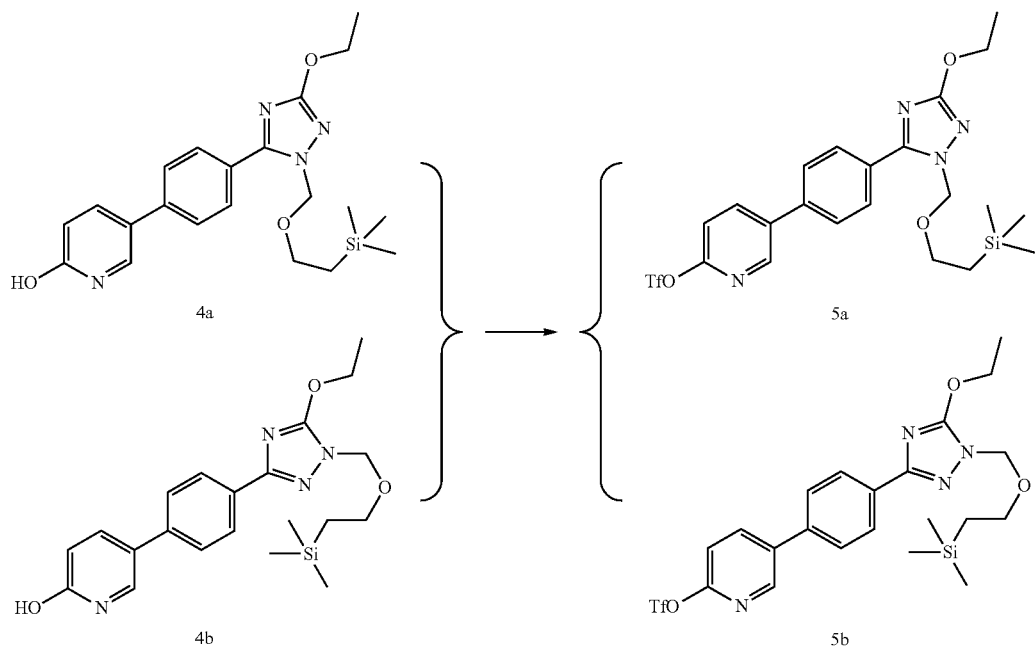

To a solution of a mixture of Compounds 4a and 4b (500 mg) in methylene chloride (10 mL) was added triethylamine (0.34 mL), trifluoromethanesulfonic anhydride (0.24 mL) was added dropwise under ice cooling, and the mixture was stirred for 1 hour. A saturated aqueous sodium hydrogen carbonate solution was added to carry out extraction. The organic layer was separated, washed with saturated brine, passed through the phase separator and concentrated under reduced pressure. The obtained residue was purified by silica gel column chromatography (n-hexane:ethyl acetate=90:10 to 65:35) to obtain Compounds 5a and 5b (542 mg) as a colorless solid.

MS (m/z): 545 $[M+H]^+$ (4)

[Chemical Formula 203]

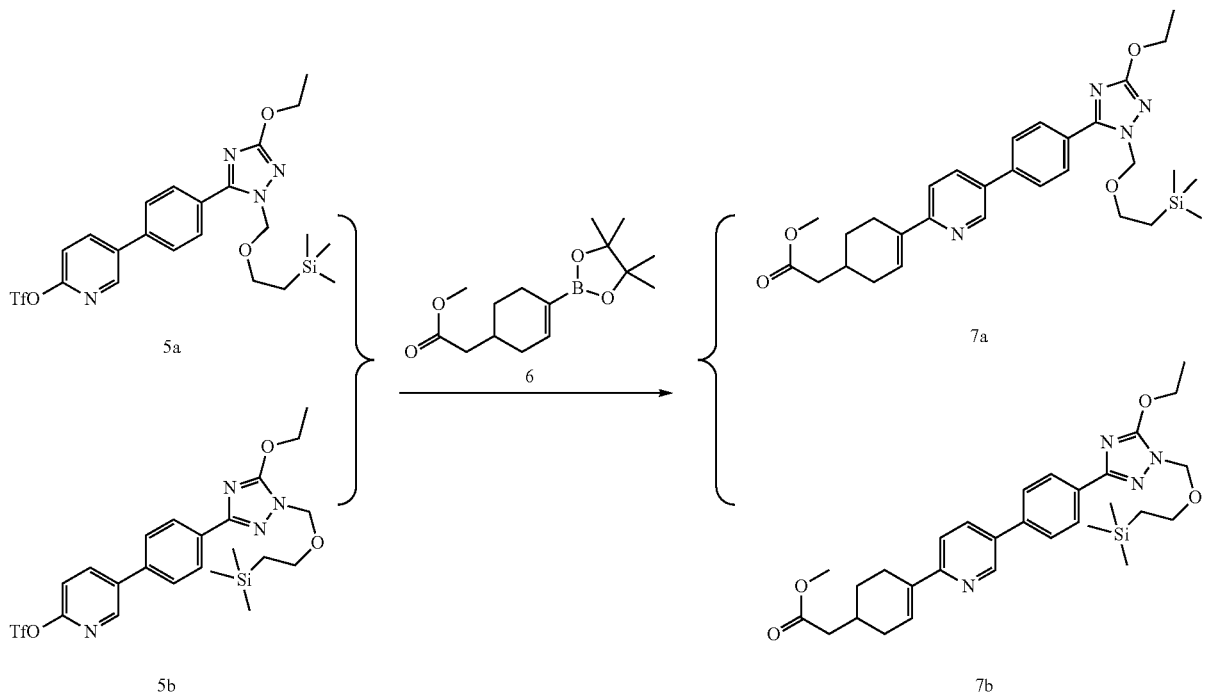

Starting from a mixture of Compounds 5a and 5b (535 mg) and Compound 6 (330 mg), a treatment was carried out in a manner similar to the Example 62-(3) to obtain a mixture of Compounds 7a and 7b (382 mg) as a pale yellow viscous material.

MS (m/z): 549 [M+H]$^+$ (5)

[Chemical Formula 204]

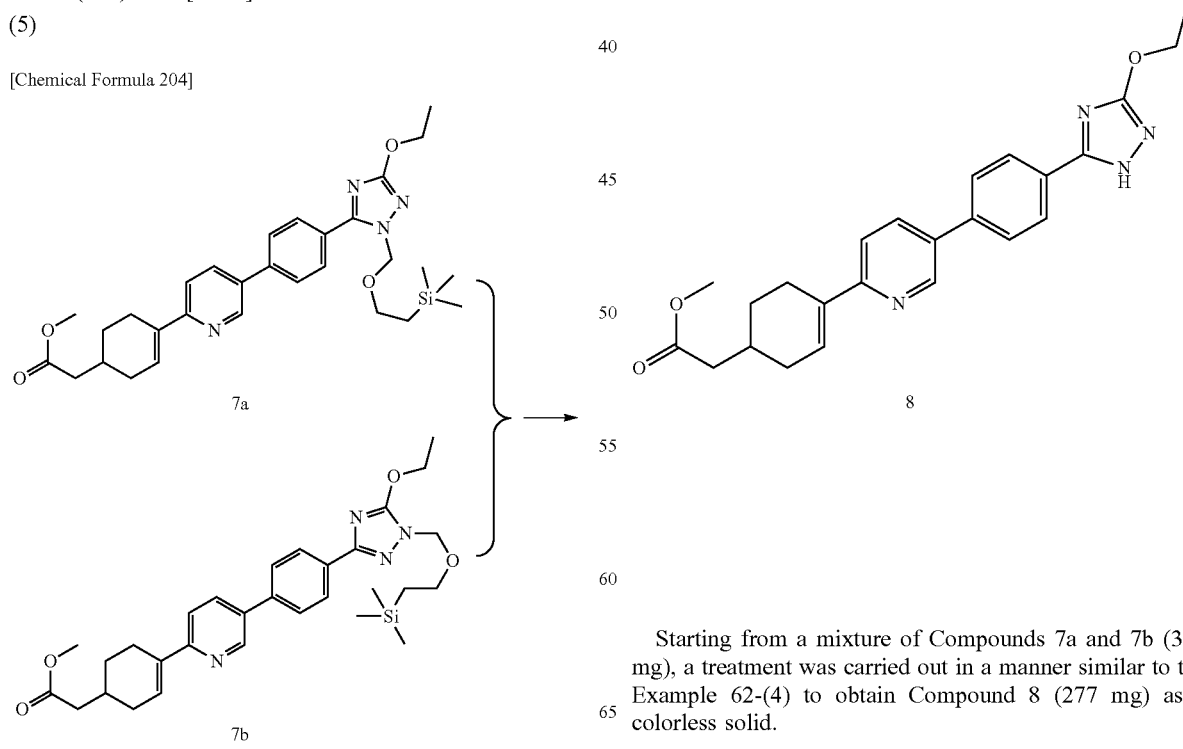

Starting from a mixture of Compounds 7a and 7b (382 mg), a treatment was carried out in a manner similar to the Example 62-(4) to obtain Compound 8 (277 mg) as a colorless solid.

MS (m/z): 419 [M+H]$^+$ (6)

[Chemical Formula 205]

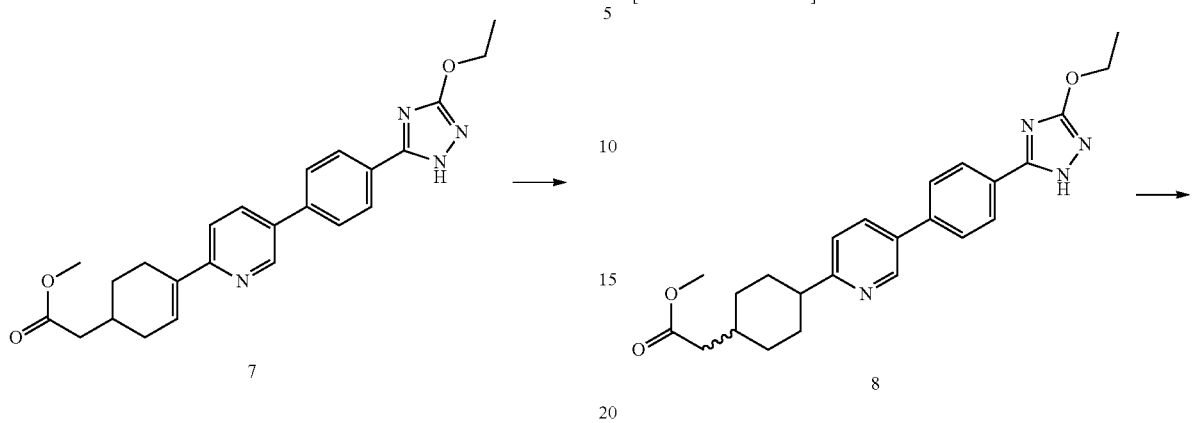

To a suspension of Compound 7 (250 mg) in methanol (4 mL) and tetrahydrofuran (4 mL) was added 10% palladium carbon (50 mg) under a nitrogen atmosphere, and the mixture was subjected to hydrogen substitution and stirred under a hydrogen atmosphere at room temperature for 4 hours. The reaction solution was filtered and concentrated under reduced pressure to obtain a mixture of geometrical isomers of Compound 8 (219 mg) as a colorless liquid.

MS (m/z): 421 [M+H]$^+$ (7)

[Chemical Formula 206]

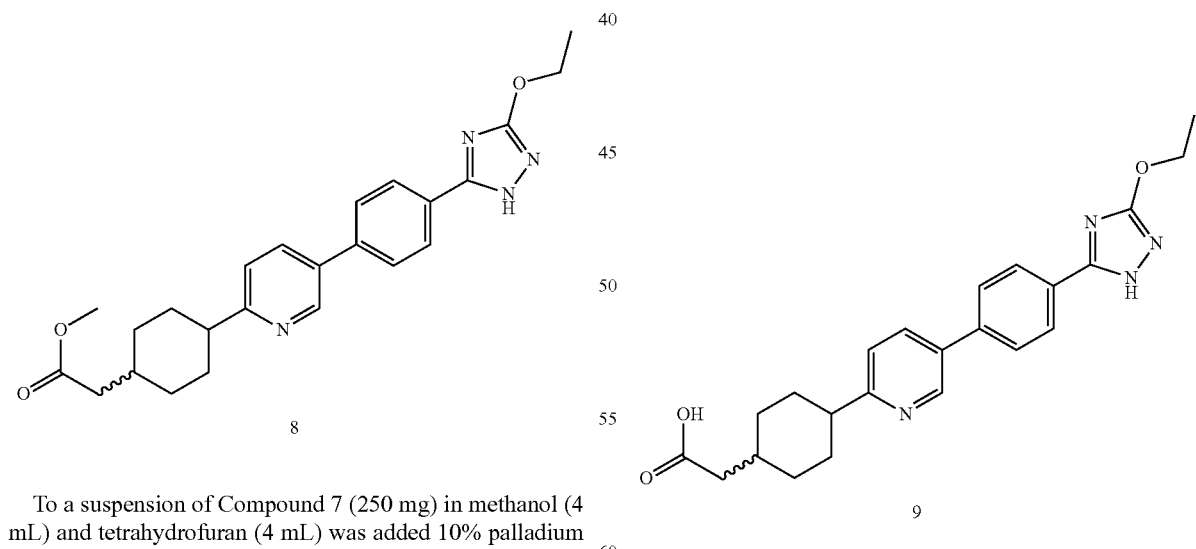

Starting from Compound 8 (218 mg), a treatment was carried out in a manner similar to the Example 61-(5) to obtain a mixture of geometrical isomers of Compound 9 (199 mg) as a colorless solid.

MS (m/z): 407 [M+H]$^+$

Example 67

(1)

[Chemical Formula 207]

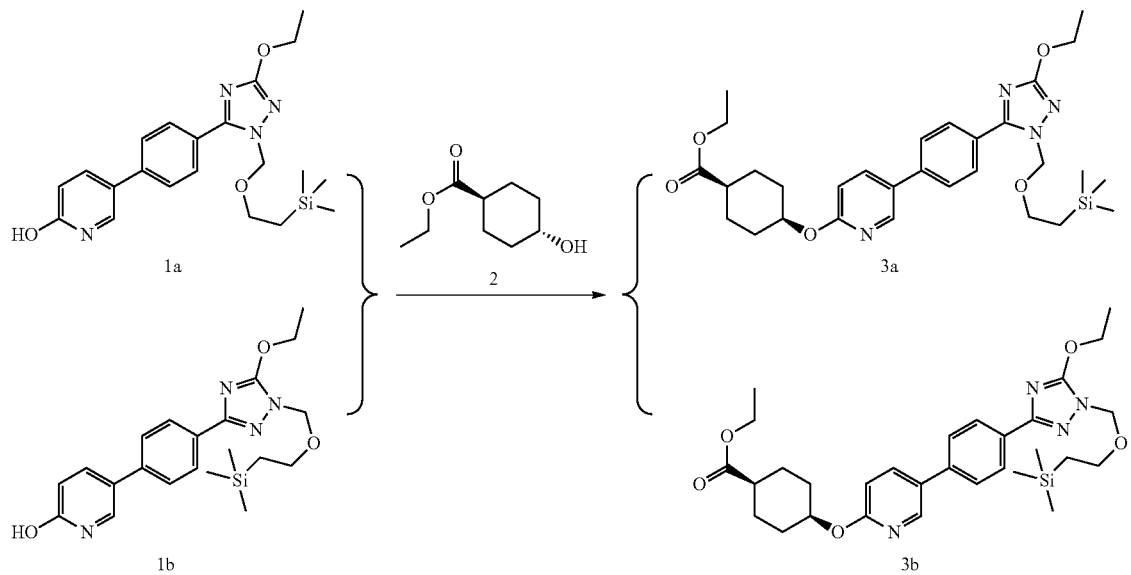

To a solution of a mixture of Compounds 1a and 1b (400 mg), Compound 2 (200 mg) and triphenylphosphine (763 mg) in tetrahydrofuran (8 mL) were added dropwise a 40 wt % solution of diethyl azodicarboxylate in toluene (1324 μL) under ice cooling, and the mixture was stirred at 70° C. overnight. After the mixture was allowed to cool to room temperature, the residue obtained by concentration under reduced pressure was purified by silica gel column chromatography (n-hexane:ethyl acetate=83:17 to 50:50) to obtain a mixture of Compounds 3a and 3b (421 mg) as a colorless viscous material.

MS (m/z): 567 [M+H]$^+$ (2)

[Chemical Formula 208]

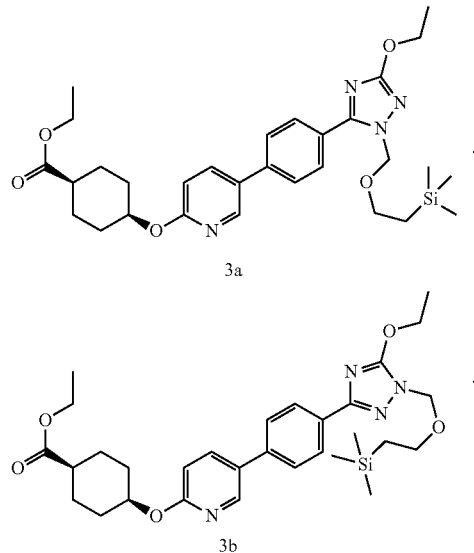

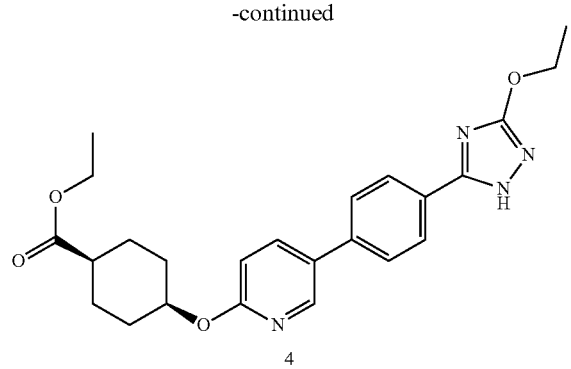

A mixture of Compounds 3a and 3b (415 mg) was treated in a manner similar to the Example 62-(4) to obtain Compound 4 (328 mg) as a colorless viscous material.

MS (m/z): 437 [M+H]$^+$ (3)

[Chemical Formula 209]

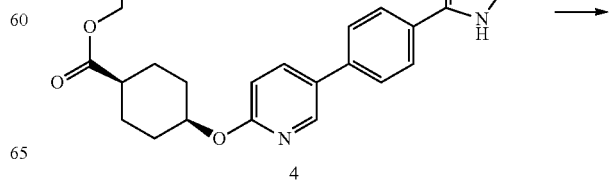

-continued

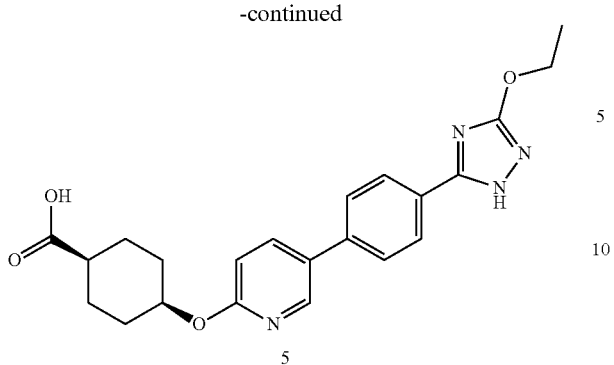

5

Compound 4 (324 mg) was treated in a manner similar to the Example 61-(5) to obtain Compound 5 (183 mg) as a colorless solid.
MS (m/z): 409 [M+H]⁺

Example 68

(1)

[Chemical Formula 210]

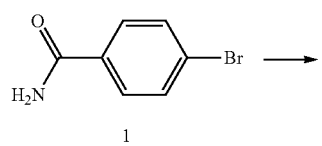

1

To a solution of Compound 1 (19.0 g), carbon disulfide (22.9 mL) and methyl iodide (17.7 mL) in tetrahydrofuran (380 mL) was added sodium hydride (7.6 g) at 0° C., the temperature was brought to room temperature, and the mixture was stirred for 8 hours. Water and ethyl acetate were added and stirred to carry out a liquid separation. The organic layer was separated, washed with saturated brine, dried over anhydrous magnesium sulfate and concentrated under reduced pressure. The obtained residue was purified by silica gel column chromatography (n-hexane:ethyl acetate=98:2 to 85:15) to obtain Compound 2 (10.8 g) as a pale yellow solid.
MS (m/z): 304/306 [M+H]⁺

(2)

[Chemical Formula 211]

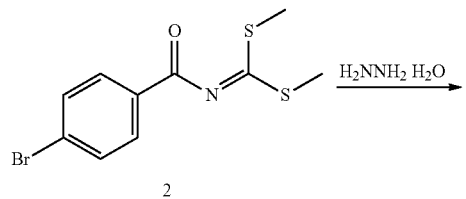

-continued

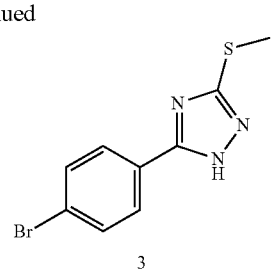

3

To a solution of Compound 2 (10.8 g) in methanol (50 mL) and tetrahydrofuran (50 mL) was added dropwise hydrazine.monohydrate (1.90 mL), and the mixture was stirred at room temperature for 1 hour. After the solvent was distilled off, to the residue was added diethyl ether, and the mixture was stirred. The crystals was collected by filtration and vacuum-dried to obtain Compound 3 (9.13 g) as a colorless solid.
MS (m/z): 270/272 [M+H]⁺

(3)

[Chemical Formula 212]

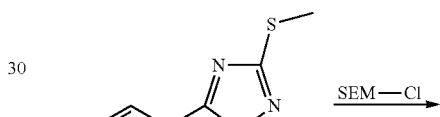

3

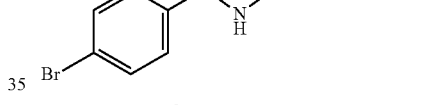

4a

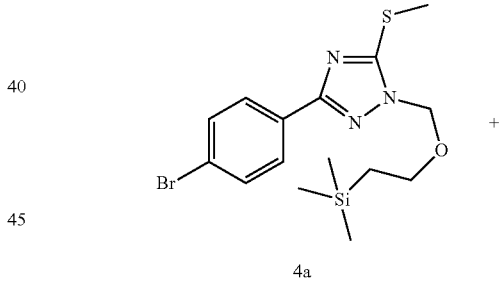

4b

Compound 3 (7 g) was treated in a manner similar to the Example 61-(3) to obtain Compound 4a (6.53 g) and Compound 4b (3.02 g) as a colorless viscous material and a colorless solid, respectively.
MS (m/z): 400/402 [M+H]⁺

(4)

[Chemical Formula 213]

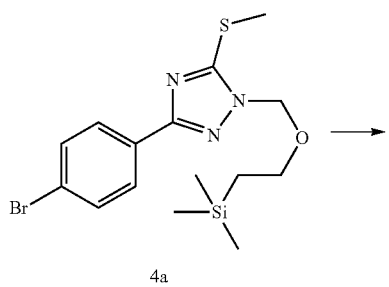

4a

→

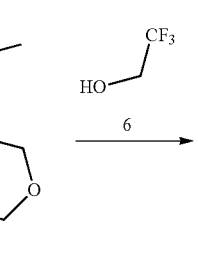

5

To a solution of Compound 4a (6.53 g) in methylene chloride (80 mL) was added 3-chloroperbenzoic acid (11.2 g) at 0° C., and the mixture was stirred at room temperature for 2 hours. A saturated aqueous sodium hydrogen carbonate solution was added, and the mixture was stirred and extracted with methylene chloride. The organic layer was separated, washed with saturated brine, dried over anhydrous magnesium sulfate and concentrated under reduced pressure. The obtained residue was purified by silica gel column chromatography (n-hexane:ethyl acetate=92:8 to 80:20) to obtain Compound 5 (7.44 g) as a colorless solid.

MS (m/z): 432/434 [M+H]$^+$ (5)

[Chemical Formula 214]

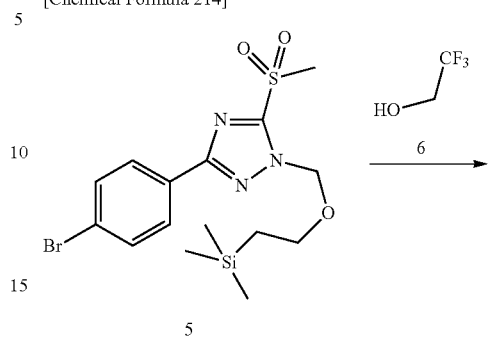

To a solution of sodium hydride (14.6 mg) in tetrahydrofuran (0.5 mL) was added dropwise 2,2,2-trifluoroethanol 6 (26.1 μL) under ice cooling, and the mixture was stirred at the same temperature for 15 minutes. To this was added a solution of Compound 5 (79 mg) in tetrahydrofuran (1.5 mL), and the mixture was stirred at room temperature for 2 hours. A saturated aqueous ammonium chloride solution was added, and the mixture was stirred. Subsequently, water and ethyl acetate were added and stirred to carry out a liquid separation. The organic layer was separated, washed with saturated brine, dried over anhydrous magnesium sulfate and concentrated under reduced pressure. The obtained residue was purified by silica gel column chromatography (n-hexane:ethyl acetate=98:2 to 92:8) to obtain Compound 7 (77.3 mg) as a colorless solid.

MS (m/z): 452/454 [M+H]$^+$ (6)

[Chemical Formula 215]

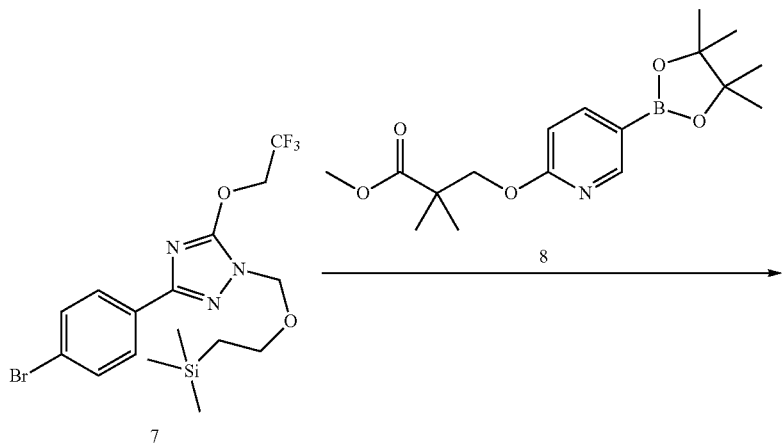

To a solution of Compound 7 (75 mg), a [1,1'-bis(diphenylphosphino)ferrocene]palladium(II) dichloride dichloromethane complex (6.8 mg) and Compound 8 (67 mg) in N,N-dimethylformamide (1 mL) was added dropwise a 2N aqueous sodium carbonate solution (249 µL) under a nitrogen stream, and the mixture was stirred at 60° C. for 6 hours. After the mixture was cooled to room temperature, water and ethyl acetate were added and stirred to carry out a liquid separation. The organic layer was separated, washed with saturated brine, passed through the phase separator, and concentrated under reduced pressure. The obtained residue was purified by silica gel column chromatography (n-hexane:ethyl acetate=95:5 to 85:15) to obtain Compound 9 (74.3 mg) as a colorless viscous material.

MS (m/z): 581 [M+H]$^+$ (7)

[Chemical Formula 216]

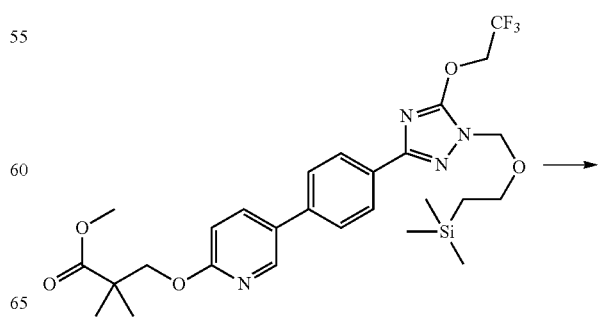

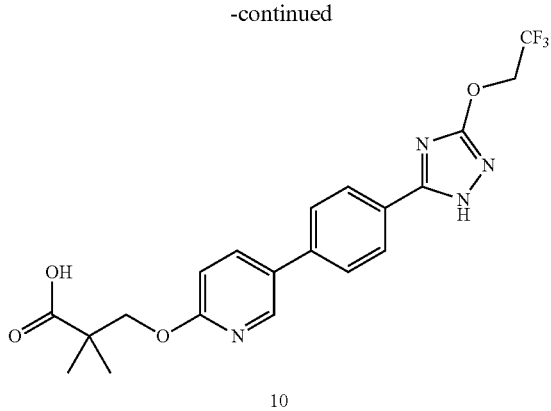

10

To Compound 9 (73 mg) were added trifluoroacetic acid (1 mL) and water (0.05 mL), and the mixture was stirred at room temperature for 6 hours. A 2N aqueous sodium hydroxide solution was added to adjust the pH to about 2-3, and an extraction with ethyl acetate was carried out. The organic layer was separated, washed with saturated brine, passed through the phase separator, and concentrated under reduced pressure. To the obtained residue were added methanol (0.5 mL), tetrahydrofuran (0.5 mL) and a 2N aqueous sodium hydroxide solution (0.5 mL), and the mixture was stirred at 50° C. for 2 hours. After the mixture was neutralized with addition of ethyl acetate and a 1N aqueous hydrochloric acid solution, an extraction was carried out. The organic layer was separated, washed with saturated brine, passed through the phase separator, and concentrated under reduced pressure. To the obtained residue was added diethyl ether, and the mixture was stirred. The obtained crystals were collected by filtration and vacuum-dried to obtain Compound 10 (34 mg) as a colorless solid.

MS (m/z): 437 [M+H]$^+$

Example 69

(1)

[Chemical Formula 217]

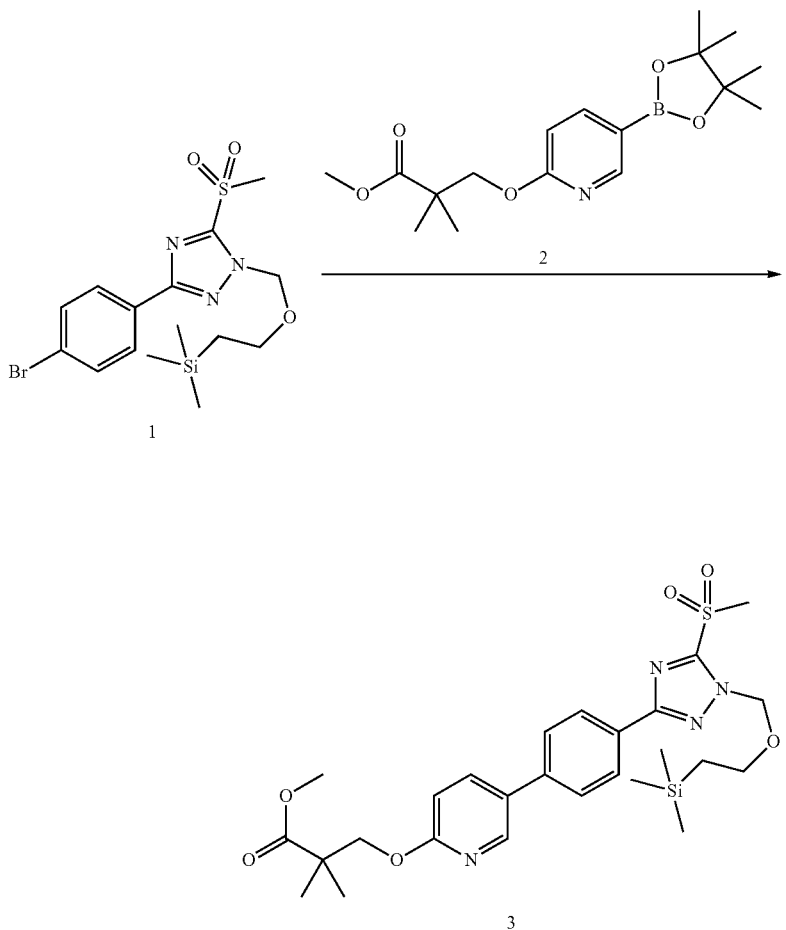

Starting from Compound 1 (5.00 g) and Compound 2 (4.65 g), a treatment was carried out in a manner similar to the Example 68-(6) to obtain Compound 3 (4.45 g) as a pale yellow powder.

MS (m/z): 561 [M+H]$^+$ (2)

[Chemical Formula 218]

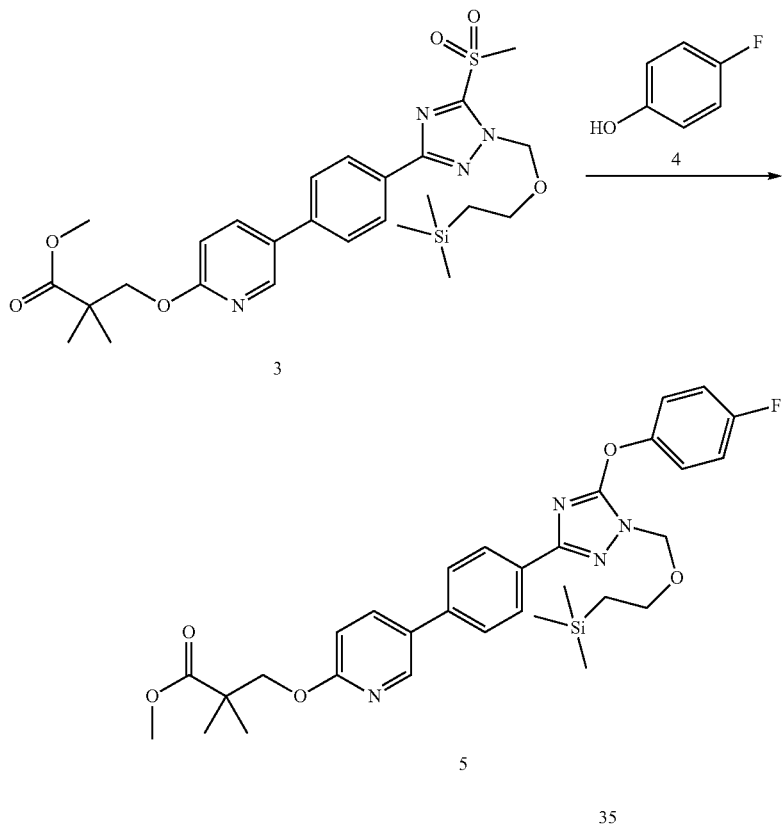

A suspension of Compound 3 (48 mg), Compound 4 (19.2 mg) and sodium carbonate (59 mg) in N-methylpyrrolidone (0.5 mL) was stirred at 120° C. for 1 hour. After the mixture was cooled to room temperature, water and ethyl acetate were added and stirred to carry out a liquid separation. The organic layer was separated, washed with saturated brine, passed through the phase separator and concentrated under reduced pressure. The obtained residue was purified by silica gel column chromatography (n-hexane:ethyl acetate=88:12 to 70:30) to obtain Compound 5 (40 mg) as a colorless viscous material.

MS (m/z): 593 [M+H]$^+$ (3)

[Chemical Formula 219]

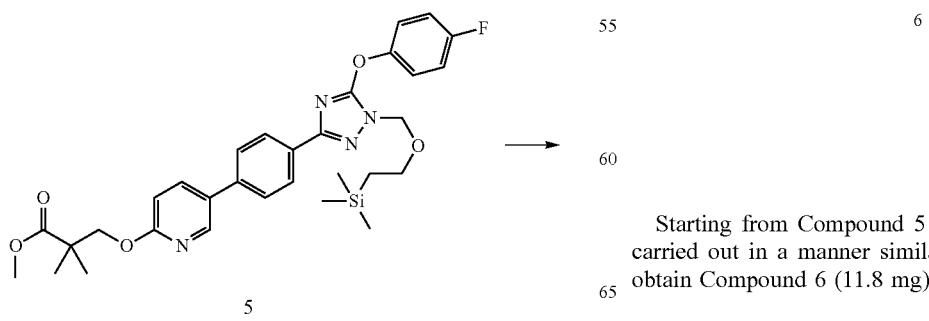

Starting from Compound 5 (21.0 mg), a treatment was carried out in a manner similar to the Example 68-(7) to obtain Compound 6 (11.8 mg) as a colorless solid.

MS (m/z): 449 [M+H]$^+$ (4)

[Chemical Formula 220]

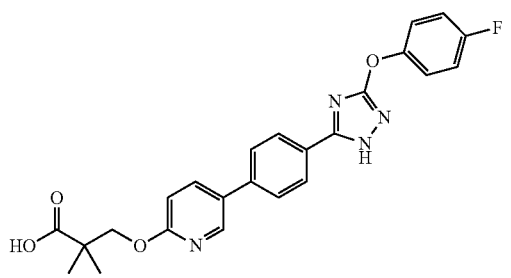

6

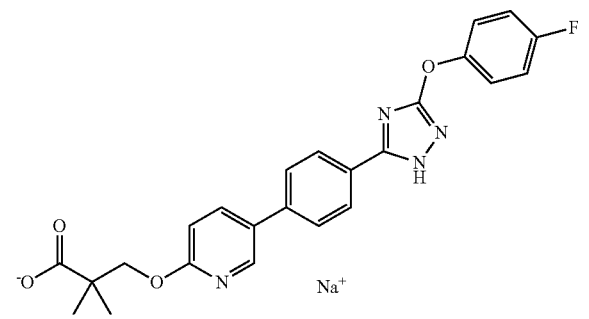

7

To a suspension of Compound 6 (266 mg) in acetonitrile (2 mL) was added dropwise a 1N aqueous sodium hydroxide solution (593 µL), and the mixture was stirred at room temperature for 8 hours. After the solvent was distilled off under reduced pressure, the residue crystals were triturated with diethyl ether, collected by filtration and vacuum-dried to obtain Compound 7 (253 mg) as a colorless solid.

MS (m/z): 447 [M−Na]⁻

Example 70

(1)

[Chemical Formula 221]

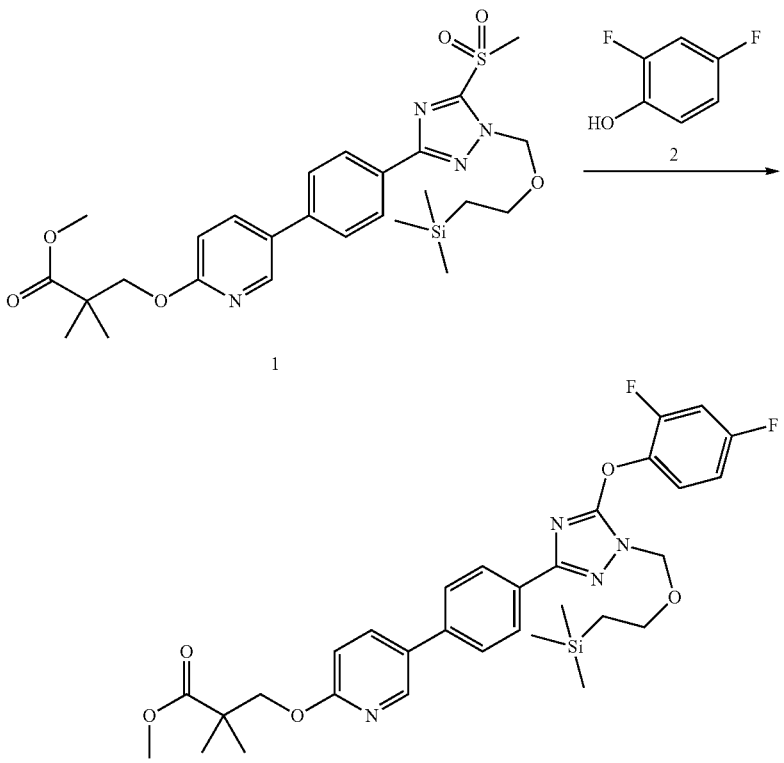

Starting from Compound 1 (400 mg) and Compound 2 (186 mg), a treatment was carried out in a manner similar to the Example 69-(2) to obtain Compound 3 (363 mg) as a colorless viscous material.

MS (m/z): 611 [M+H]$^+$ (2)

[Chemical Formula 222]

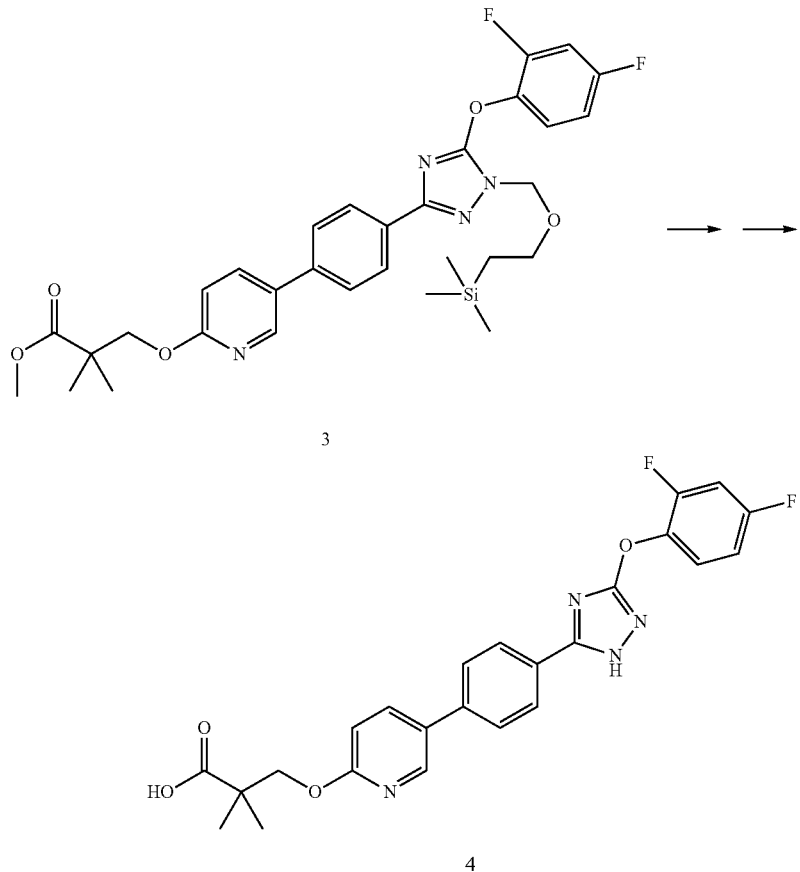

Starting from Compound 3 (360 mg), a treatment was carried out in a manner similar to the Example 68-(7) to obtain Compound 4 (205 mg) as a colorless solid.

MS (m/z): 467 [M+H]$^+$

Example 71

(1)

[Chemical Formula 223]

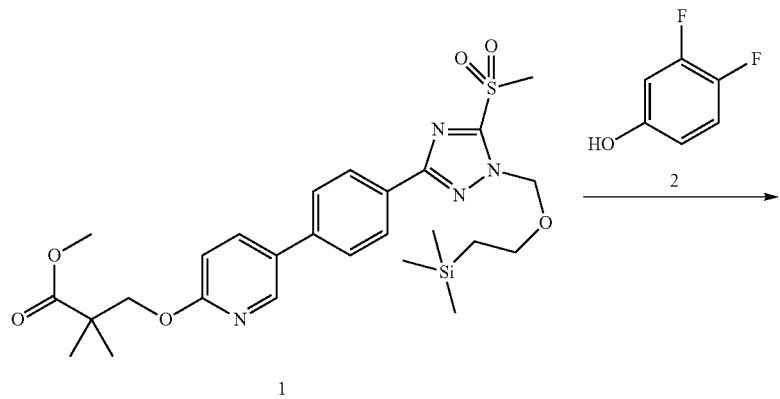

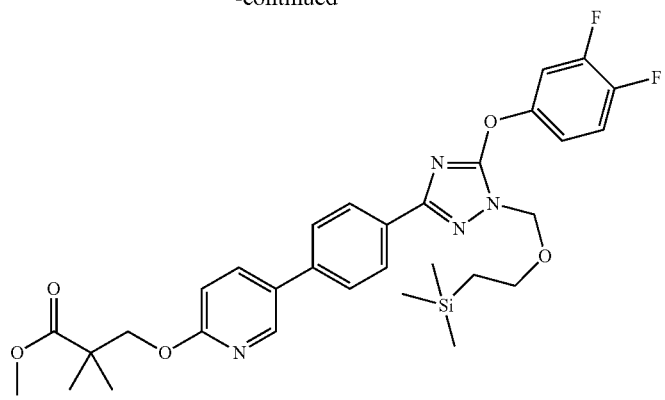
3
Starting from Compound 1 (400 mg) and Compound 2 (186 mg), a treatment was carried out in a manner similar to the Example 69-(2) to obtain Compound 3 (403 mg) as a colorless viscous material.
MS (m/z): 611 [M+H]⁺
(2)
[Chemical Formula 224]
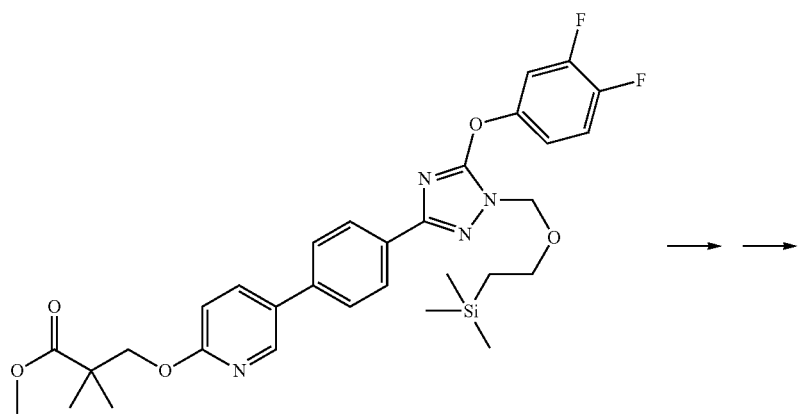
3 → →
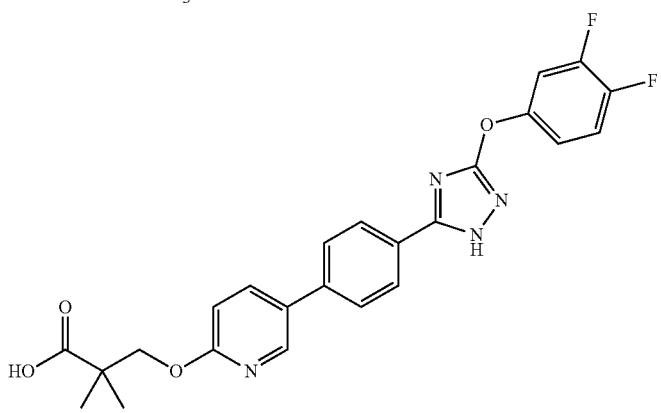
4
Starting from Compound 3 (400 mg), a treatment was carried out in a manner similar to the Example 68-(7) to obtain Compound 4 (220 mg) as a colorless solid.
MS (m/z): 467 [M+H]⁺

Example 72

(1)

[Chemical Formula 225]

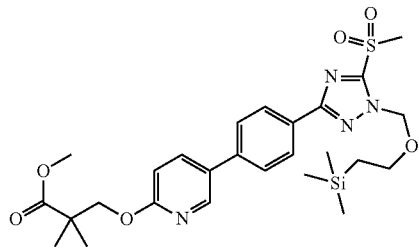

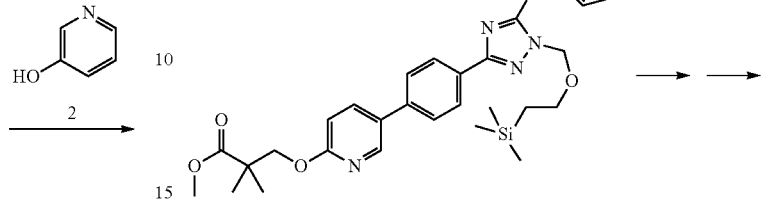

[Chemical Formula 226]

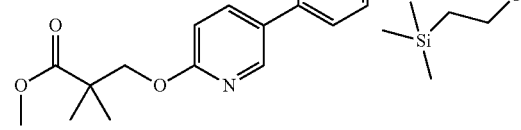

Starting from Compound 1 (100 mg) and Compound 2 (33.9 mg), a treatment was carried out in a manner similar to the Example 69-(2) to obtain Compound 3 (83 mg) as a colorless viscous material.

MS (m/z): 576 [M+H]$^+$ (2)

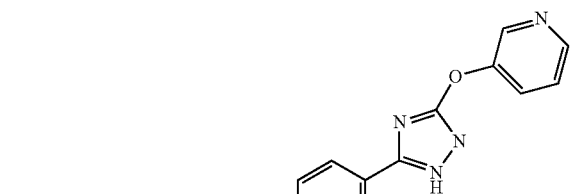

Starting from Compound 3 (82 mg), a treatment was carried out in a manner similar to the Example 68-(7) to obtain Compound 4 (52 mg) as a colorless solid.

MS (m/z): 432 [M+H]$^+$

Example 73

(1)

[Chemical Formula 227]

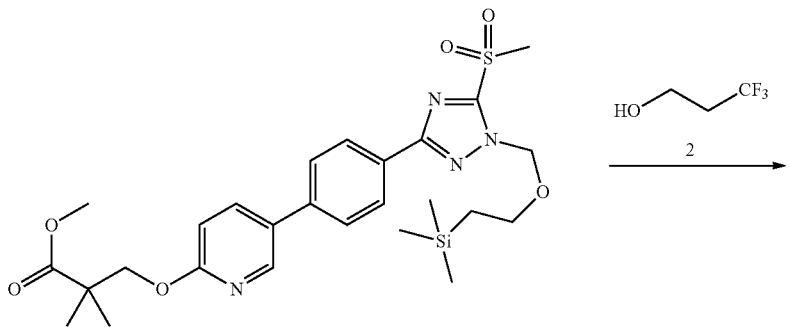

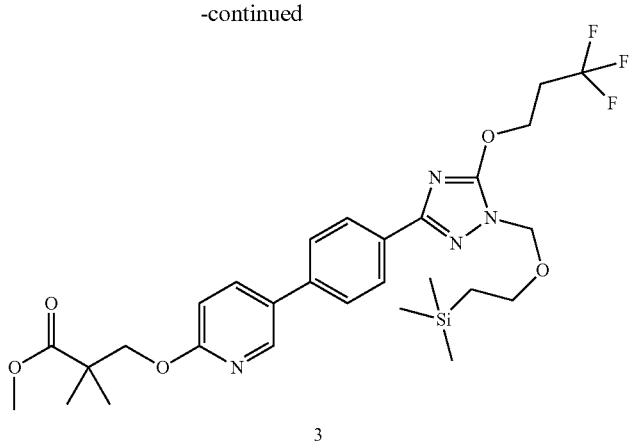

3

Starting from Compound 1 (400 mg) and Compound 2 (163 mg), a treatment was carried out in a manner similar to the Example 68-(5) to obtain Compound 3 (262 mg) as a colorless viscous material.

MS (m/z): 595 [M+H]$^+$ (2)

[Chemical Formula 228]

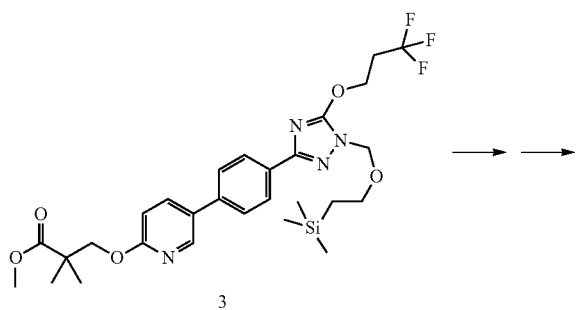

3

⟶ ⟶

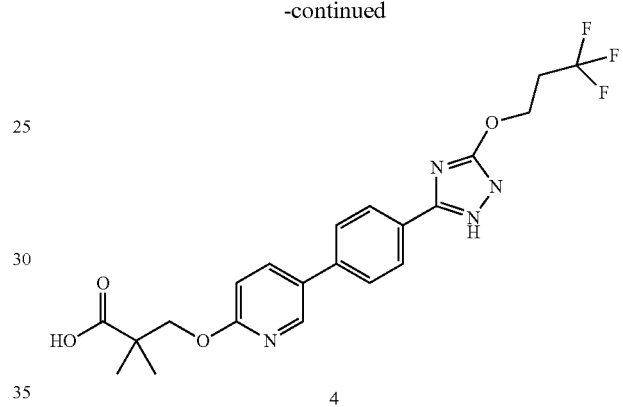

4

Starting from Compound 3 (260 mg), a treatment was carried out in a manner similar to the Example 68-(7) to obtain Compound 4 (157 mg) as a colorless solid.

MS (m/z): 451 [M+H]$^+$

Example 74

(1)

[Chemical Formula 229]

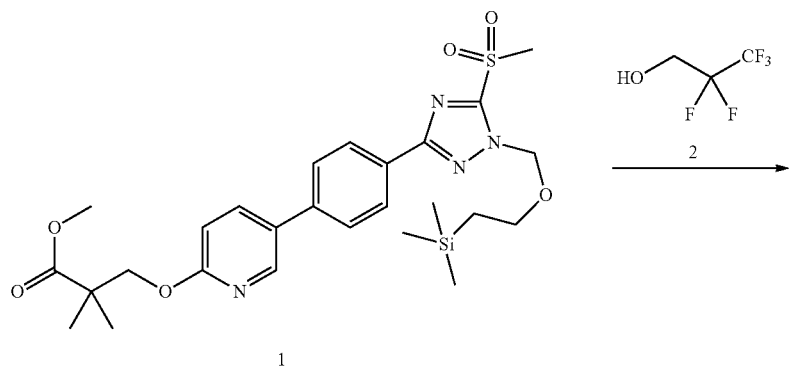

1

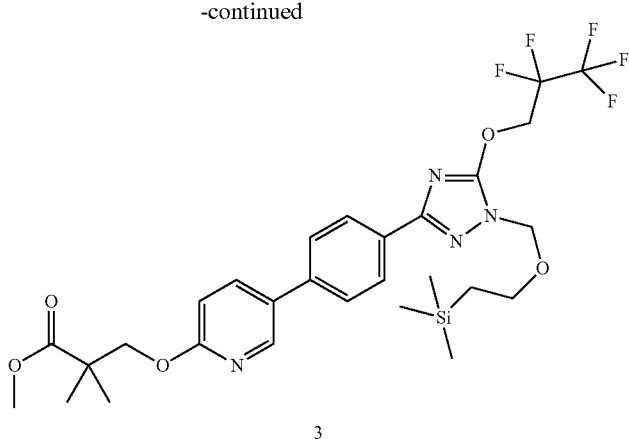

3

Starting from Compound 1 (400 mg) and Compound 2 (214 mg), a treatment was carried out in a manner similar to the Example 68-(5) to obtain Compound 3 (406 mg) as a colorless solid.

MS (m/z): 631 [M+H]$^+$ (2)

[Chemical Formula 230]

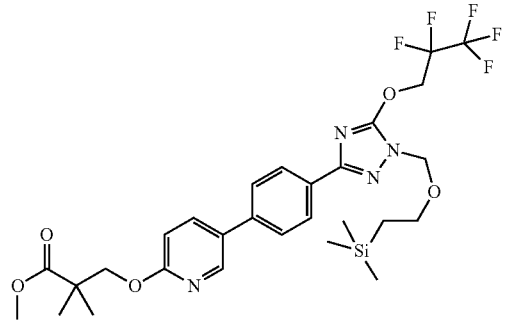

3

→

-continued (structure of Compound 4, sodium salt)

4

To the carboxylic acid compound synthesized from Compound 3 (402 mg) by treating it in a manner similar to the Example 68-(7) were added 1 mL of acetonitrile and an equal amount of a 1 N aqueous sodium hydroxide solution, and additionally diethyl ether was added until complete dissolution. After the solvent was distilled off under reduced pressure, the residue was stirred in a small amount of ethyl acetate and diethyl ether, and the crystals were collected by filtration and dried under reduced pressure to obtain Compound 4 (271 mg) as a colorless solid.

MS (m/z): 485 [M−Na]$^-$

Example 75

(1)

[Chemical Formula 231]

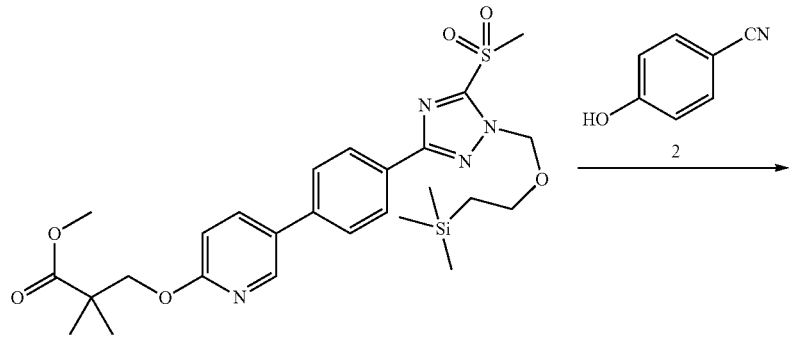

1

-continued
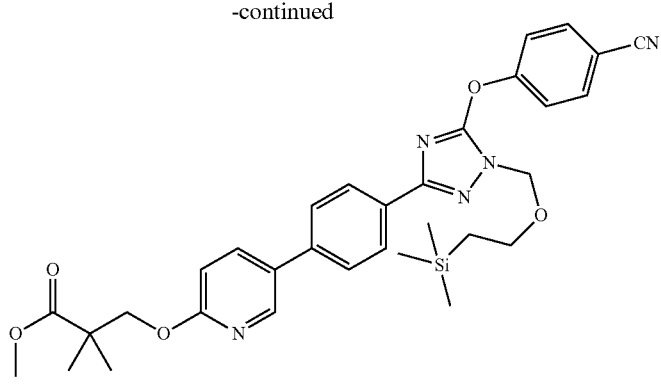
3
Starting from Compound 1 (300 mg) and Compound 2 (128 mg), a treatment was carried out in a manner similar to the Example 69-(2) to obtain Compound 3 (144 mg) as a colorless viscous material.
MS (m/z): 600 [M+H]$^+$
(2)
[Chemical Formula 232]
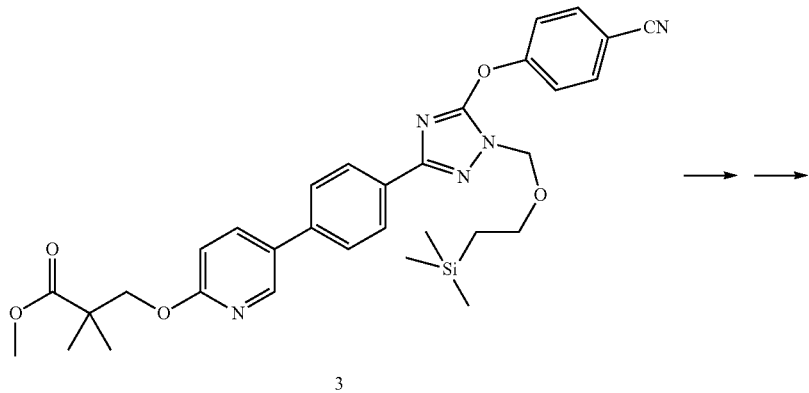
3
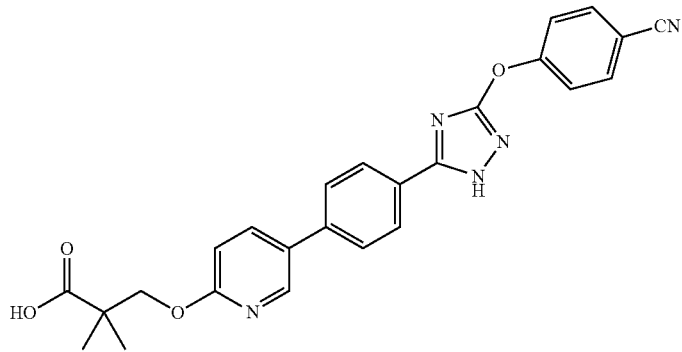
4
Starting from Compound 3 (142 mg), a treatment was carried out in a manner similar to the Example 68-(7) to obtain Compound 4 (57 mg) as a colorless solid.
MS (m/z): 456 [M+H]$^+$

Example 76

(1)

[Chemical Formula 233]

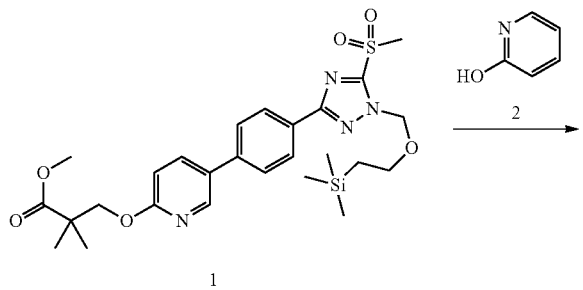

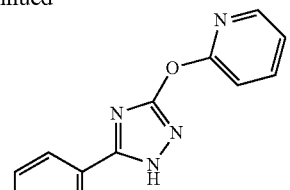

Starting from Compound 1 (100 mg) and Compound 2 (33.9 mg), a treatment was carried out in a manner similar to the Example 69-(2) to obtain Compound 3 (13.9 mg) as a colorless solid.

MS (m/z): 576 [M+H]$^+$ (2)

[Chemical Formula 234]

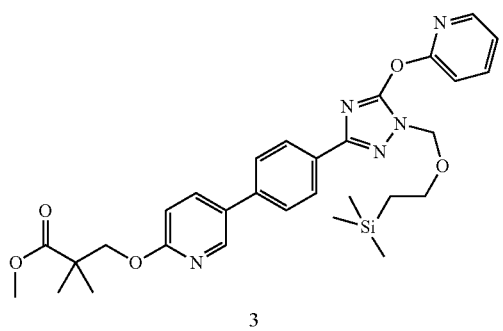

Starting from Compound 3 (30 mg), a treatment was carried out in a manner similar to the Example 68-(7) to obtain Compound 4 (18.7 mg) as a colorless solid.

MS (m/z): 432 [M+H]$^+$

Example 77

(1)

[Chemical Formula 235]

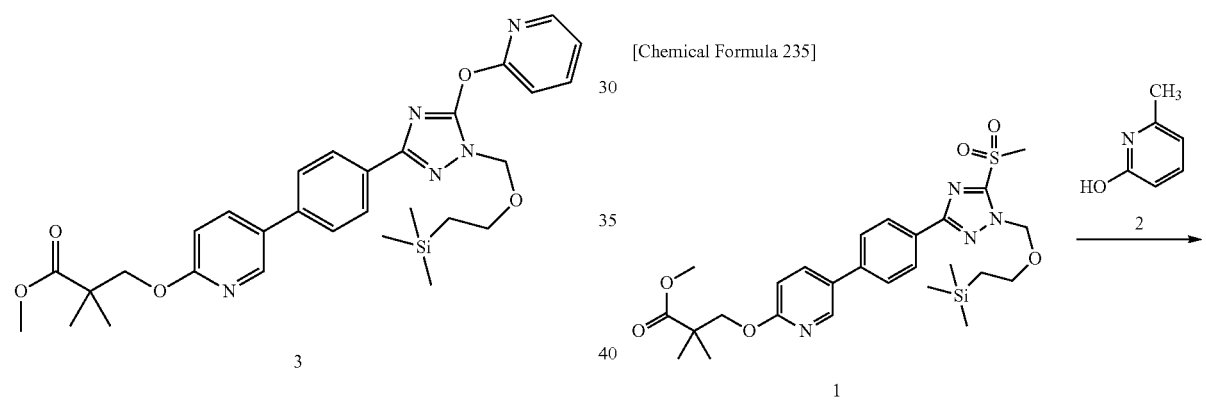

From Compound 1 (200 mg) and Compound 2 (77.8 mg), a treatment was carried out in a manner similar to the Example 69-(2) to obtain Compound 3 (38 mg) as a colorless solid.

MS (m/z): 590 [M+H]$^+$ (2)

[Chemical Formula 236]

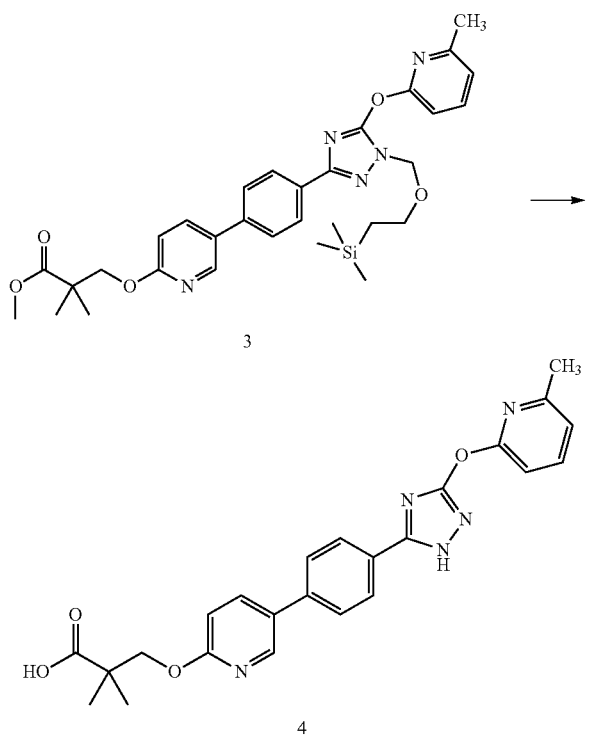

Starting from Compound 3 (36 mg), a treatment was carried out in a manner similar to the Example 68-(7) to obtain Compound 4 (24.8 mg) as a colorless solid.

MS (m/z): 446 [M+H]$^+$

Example 78

(1)

[Chemical Formula 237]

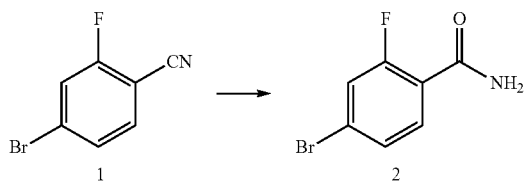

To a solution of Compound 1 (3.00 g) and potassium carbonate (311 mg) in dimethylsulfoxide (45 mL) was added an aqueous 30% hydrogen peroxide solution (1.7 mL) under ice cooling, and the mixture was stirred at room temperature overnight. To this was added an additional aqueous 30% hydrogen peroxide solution (0.5 mL), and the mixture was further stirred at room temperature for 4 days. Water was slowly added dropwise, and the obtained crystals were collected by filtration, washed with diethyl ether and subsequently vacuum-dried to obtain Compound 2 (1284 mg) as a colorless solid.

MS (m/z): 218/220 [M+H]$^+$ (2)

[Chemical Formula 238]

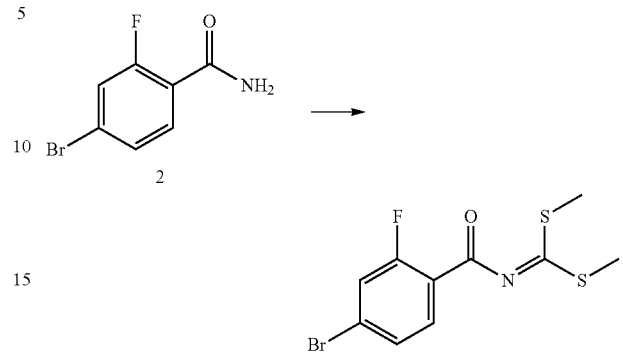

Starting from Compound 2 (1200 mg), a treatment was carried out in a manner similar to the Example 68-(1) to obtain Compound 3 (621 mg) as a pale yellow solid.

MS (m/z): 322/324 [M+H]$^+$ (3)

[Chemical Formula 239]

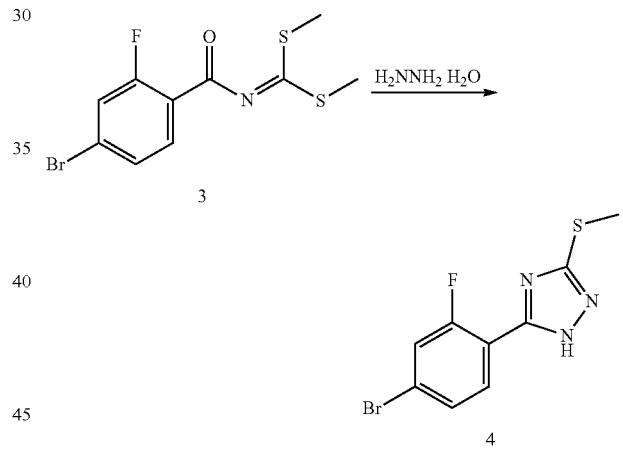

Starting from Compound 3 (640 mg), a treatment was carried out in a manner similar to the Example 68-(2) to obtain Compound 4 (479 mg) as a colorless solid.

MS (m/z): 288/290 [M+H]$^+$ (4)

[Chemical Formula 240]

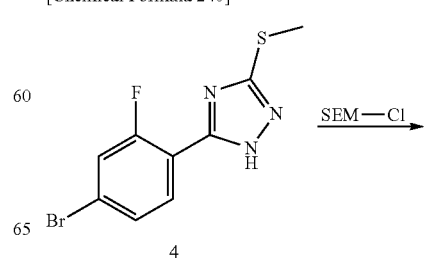

-continued

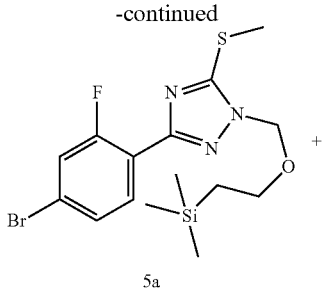

5a

-continued

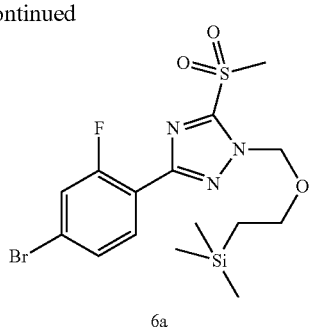

6a

Starting from Compound 5a (325 mg), a treatment was carried out in a manner similar to the Example 68-(4) to obtain Compound 6a (331 mg) as a colorless viscous material.

MS (m/z): 450/452 [M+H]$^+$ (6)

[Chemical Formula 242]

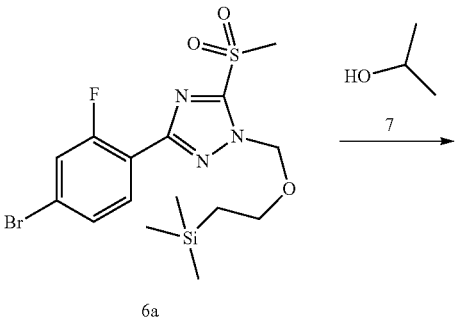

6a

Starting from Compound 4 (445 mg), a treatment was carried out in a manner similar to the Example 61-(3) to obtain Compound 5a (328 mg) and Compound 5b (351 mg) both as colorless viscous materials.

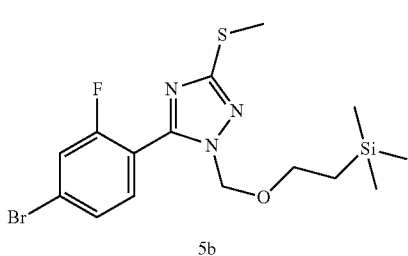

5b

Compound 5a: MS (m/z): 418/420 [M+H]$^+$
Compound 5b: MS (m/z): 418/420 [M+H]$^+$ (5)

[Chemical Formula 241]

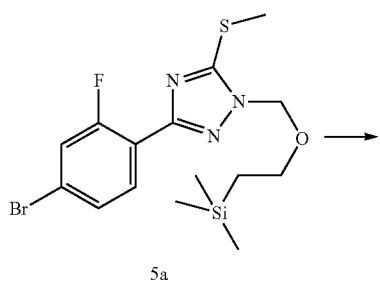

5a

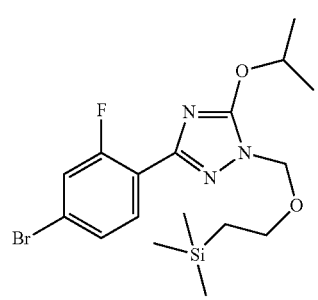

8a

Starting from Compound 6a (330 mg) and Compound 7 (112 μL), a treatment was carried out in a manner similar to the Example 68-(5) to obtain Compound 8a (265 mg) as a colorless viscous material.

MS (m/z): 430/432 [M+H]$^+$ (7)

[Chemical Formula 243]

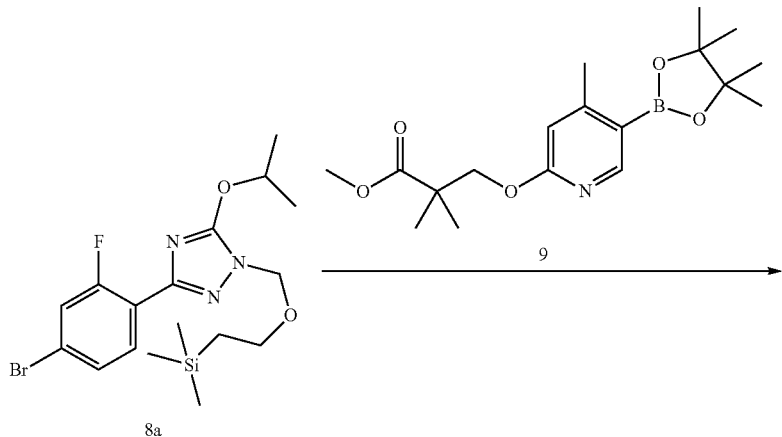

Starting from Compound 8a (260 mg) and Compound 9 (253 mg), a treatment was carried out in a manner similar to the Example 68-(6) to obtain Compound 10a (333 mg) as a colorless viscous material.

MS (m/z): 573 [M+H]$^+$ (8)

[Chemical Formula 244]

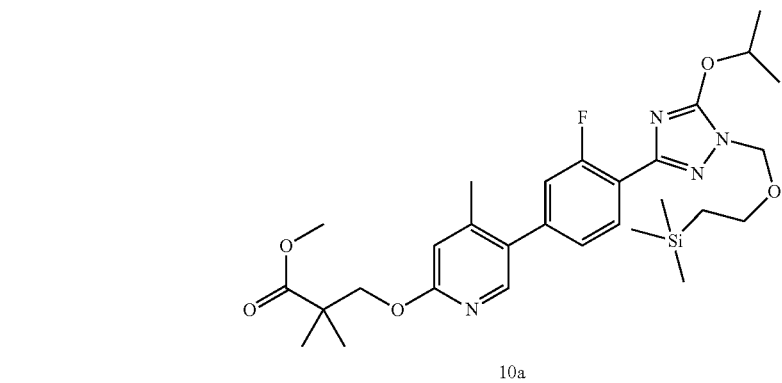

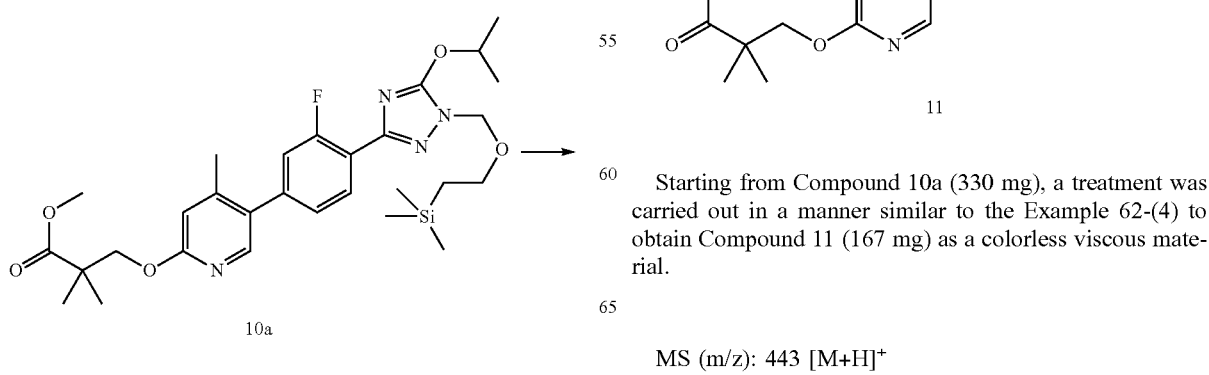

Starting from Compound 10a (330 mg), a treatment was carried out in a manner similar to the Example 62-(4) to obtain Compound 11 (167 mg) as a colorless viscous material.

MS (m/z): 443 [M+H]$^+$ (9)

[Chemical Formula 245]

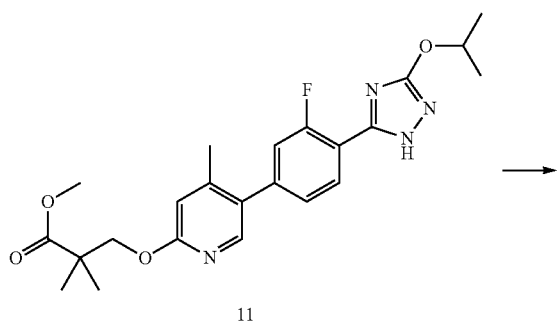

11

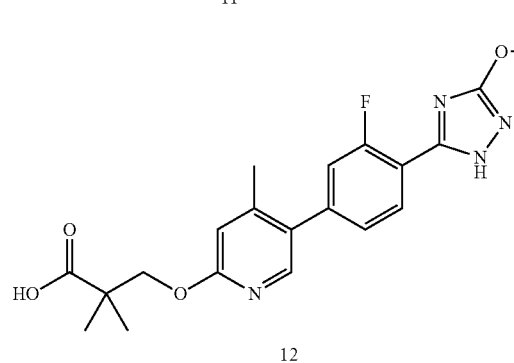

12

Starting from Compound 11 (166 mg), a treatment was carried out in a manner similar to the Example 61-(5) to obtain Compound 12 (132 mg) as a colorless solid.
MS (m/z): 429 [M+H]⁺

Example 79

(1)

[Chemical Formula 246]

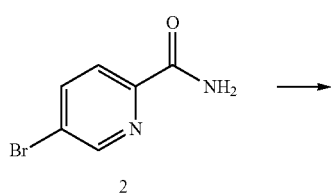

Starting from Compound 1 (3000 mg), a treatment was carried out in a manner similar to the Example 78-(1) to obtain Compound 2 (2842 mg) as a colorless solid.
MS (m/z): 201/203 [M+H]⁺

(2)

[Chemical Formula 247]

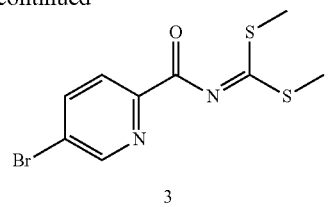

-continued

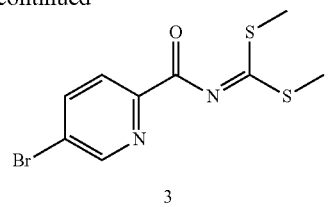

Starting from Compound 2 (2800 mg), a treatment was carried out in a manner similar to the Example 68-(1) to obtain Compound 3 (257 mg) as a pale yellowish-orange solid.
MS (m/z): 305/307 [M+H]⁺

(3)

[Chemical Formula 248]

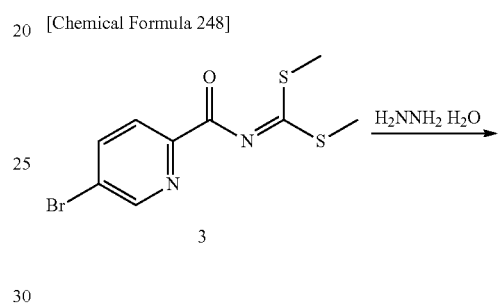

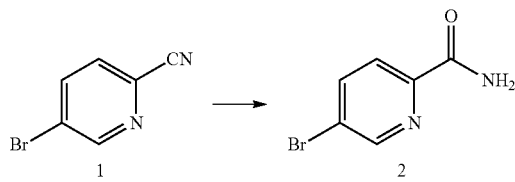

Starting from Compound 3 (255 mg), a treatment was carried out in a manner similar to the Example 68-(2) to obtain Compound 4 (166 mg) a pale yellow solid.
MS (m/z): 271/273 [M+H]⁺

(4)

[Chemical Formula 249]

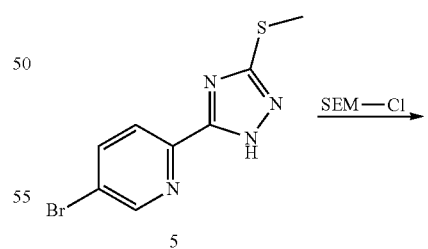

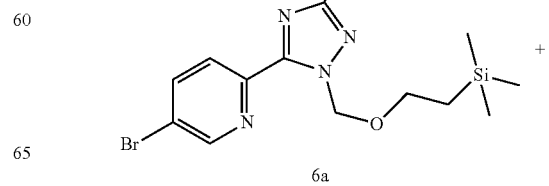

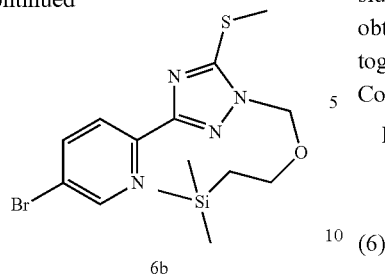

6b

Starting from Compound 5 (162 mg), a treatment was carried out in a manner similar to the Example 61-(3) to obtain Compound 6a (92.9 mg) as a colorless viscous material and Compound 6b (89.1 mg) as a pale yellow solid, respectively.

Compound 6a: MS (m/z): 401/403 [M+H]+
Compound 6b: MS (m/z): 401/403 [M+H]+

(5)

[Chemical formula 250]

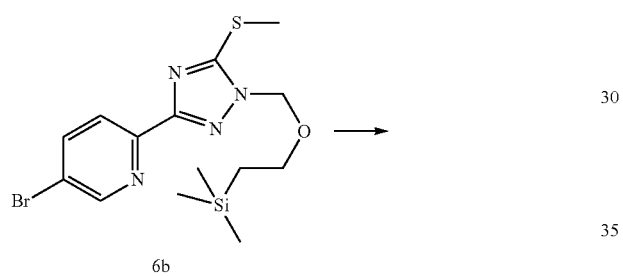

To a solution of Compound 6b (88.0 mg) in methylene chloride (1 mL) was added acetic acid (50 μL), 3-chloroperbenzoic acid (151 mg) was added under ice cooling, and the mixture was stirred at room temperature for 3 hours. A saturated aqueous sodium hydrogen carbonate solution was added, and the mixture was stirred and extracted with methylene chloride. The organic layer was separated, washed with saturated brine, dried over anhydrous magnesium sulfate, and concentrated under reduced pressure. The obtained residue was purified by silica gel column chromatography (n-hexane:ethyl acetate=85:15 to 66:34) to obtain Compound 7b (53.2 mg) as a pale yellowish-orange solid.

MS (m/z): 433/435 [M+H]+

(6)

[Chemical Formula 251]

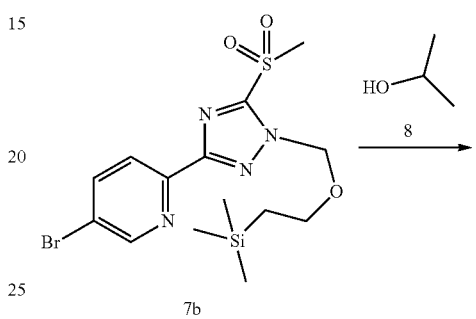

7b

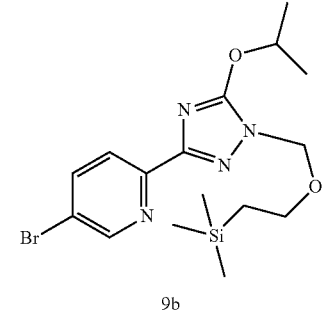

9b

Starting from Compound 7b (53.0 mg) and Compound 8 (19 μL), a treatment was carried out in a manner similar to the Example 68-(5) to obtain Compound 9b (27.0 mg) as a colorless viscous material.

MS (m/z): 413/415 [M+H]+

(7)
[Chemical Formula 252]
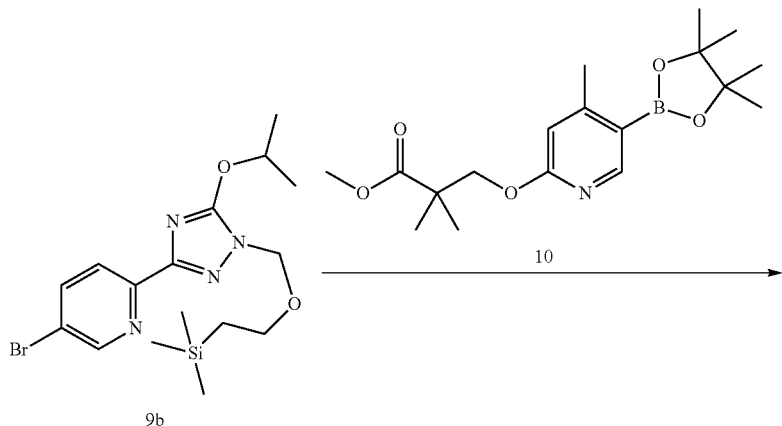
Starting from Compound 9b (26.0 mg) and Compound 10 (43.9 mg), a treatment was carried out in a manner similar to the Example 68-(6) to obtain Compound 11b (31.6 mg) as a colorless viscous material.
MS (m/z): 556 [M+H]$^+$
(8)
[Chemical Formula 226]
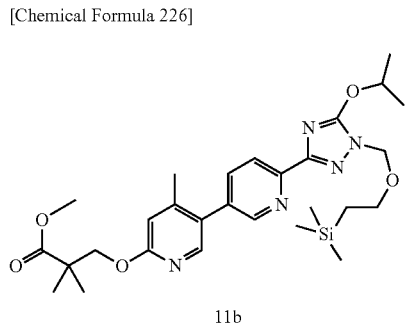
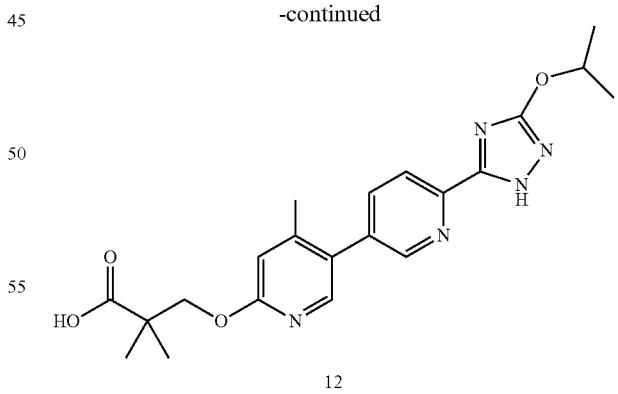
Starting from Compound 11b (31.0 mg), a treatment was carried out in a manner similar to the Example 68-(7) to obtain Compound 12 (13.8 mg) as a colorless solid.
MS (m/z): 412 [M+H]$^+$

Example 80

(1)

[Chemical Formula 254]

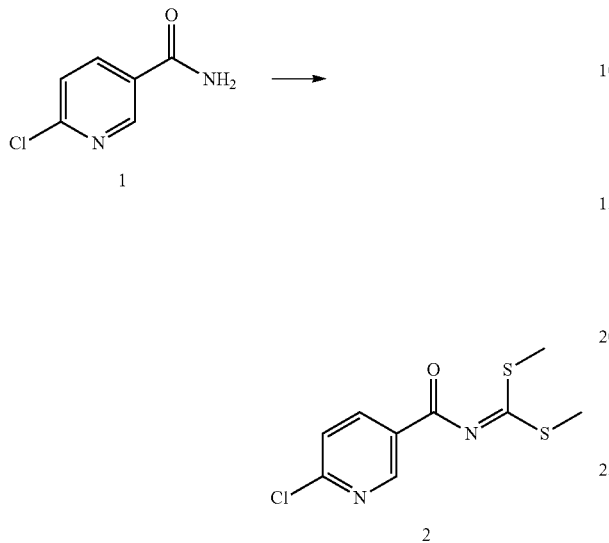

Starting from Compound 1 (2000 mg), a treatment was carried out in a manner similar to the Example 68-(1) to obtain Compound 2 (1153 mg) as a white solid.

MS (m/z): 261/263 [M+H]$^+$ (2)

[Chemical Formula 255]

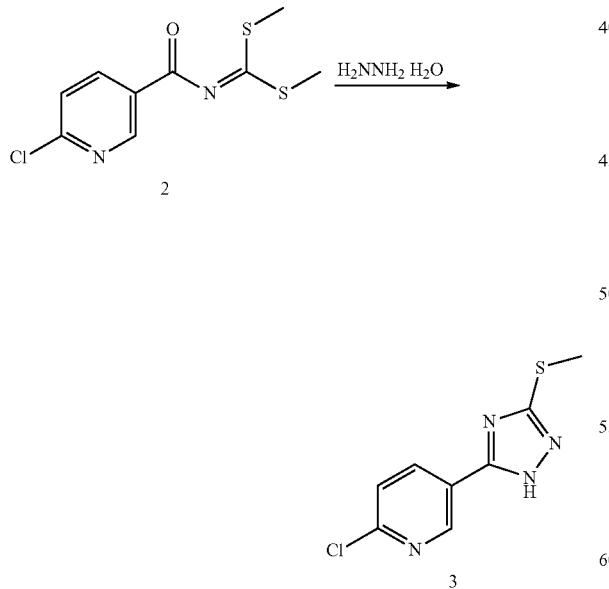

Starting from Compound 2 (1150 mg), a treatment was carried out in a manner similar to the Example 68-(2) to obtain Compound 3 (829 mg) as a colorless solid.

MS (m/z): 227/229 [M+H]$^+$ (3)

[Chemical Formula 256]

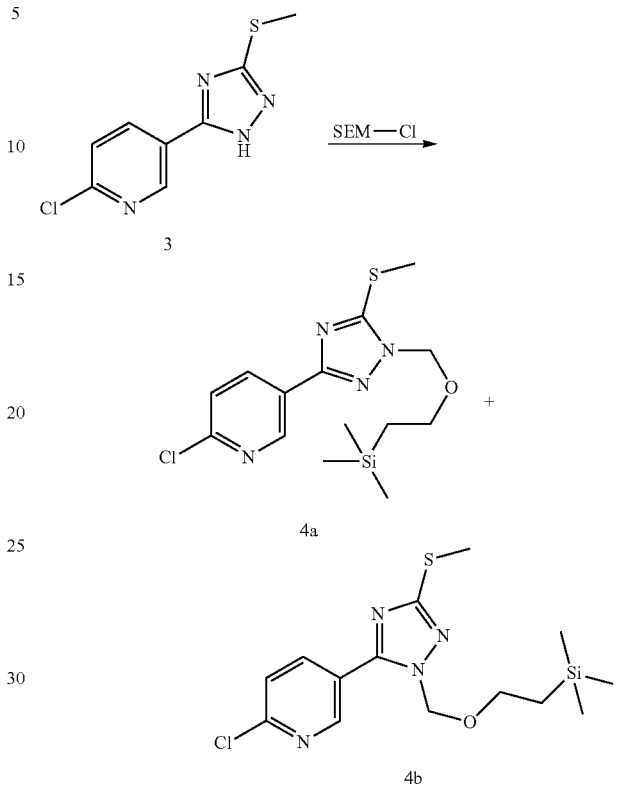

Starting from Compound 3 (500 mg), a treatment was carried out in a manner similar to the Example 61-(3) to obtain Compound 4a (478 mg) and Compound 4b (215 mg) both as colorless viscous materials.

Compound 4a: MS (m/z): 357/359 [M+H]$^+$
Compound 4b: MS (m/z): 357/359 [M+H]$^+$ (4)

[Chemical Formula 257]

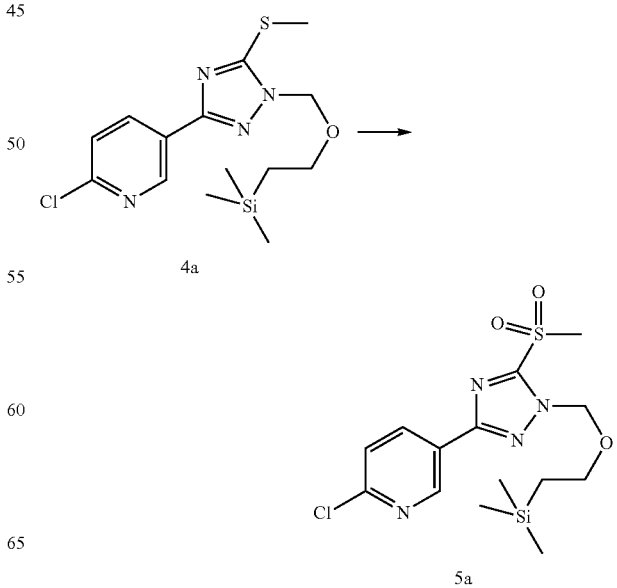

Starting from Compound 4a (470 mg), a treatment was carried out in a manner similar to the Example 79-(5) to obtain Compound 5a (363 mg) as a colorless viscous material.

MS (m/z): 389/391 [M+H]$^+$ (5)

[Chemical Formula 258]

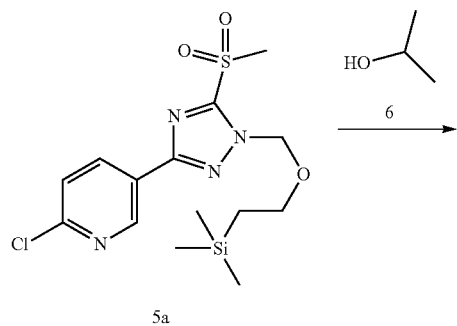

5a

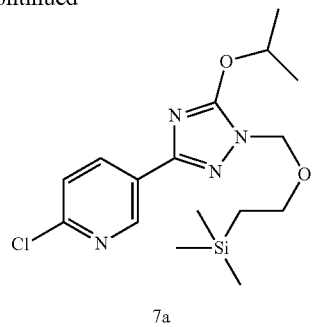

7a

Starting from Compound 5a (360 mg) and Compound 6 (141 μL), a treatment was carried out in a manner similar to the Example 68-(5) to obtain Compound 7a (272 mg) as a colorless solid.

MS (m/z): 369/371 [M+H]$^+$ (6)

[Chemical Formula 259]

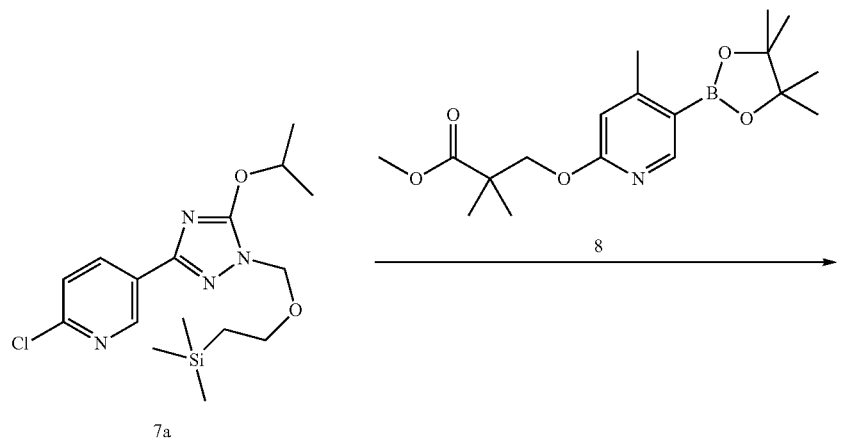

7a

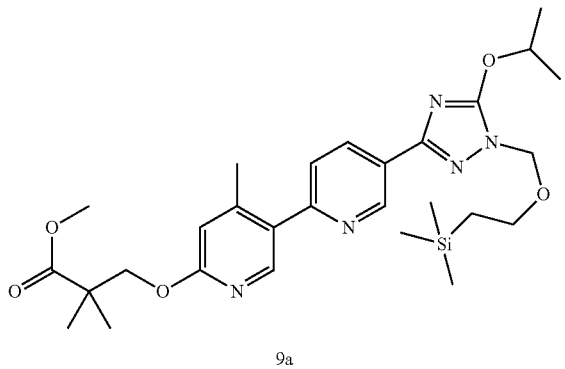

9a

Starting from Compound 7a (200 mg) and Compound 8 (454 mg), a treatment was carried out in a manner similar to the Example 68-(6) to obtain Compound 9a (258 mg) as a colorless viscous material.

MS (m/z): 556 [M+H]$^+$ (7)

[Chemical Formula 260]

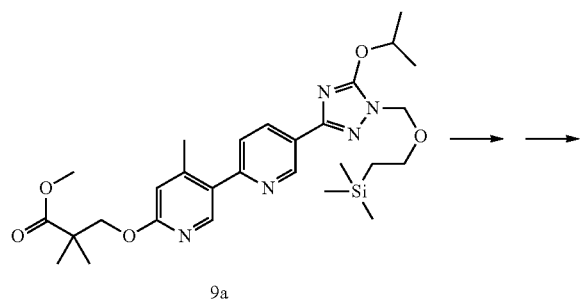

9a

-continued

10

Starting from Compound 9a (254 mg), a treatment was carried out in a manner similar to the Example 68-(7) to obtain Compound 10 (156 mg) as a colorless solid.
MS (m/z): 412 [M+H]$^+$ Example 81

(1)

[Chemical Formula 261]

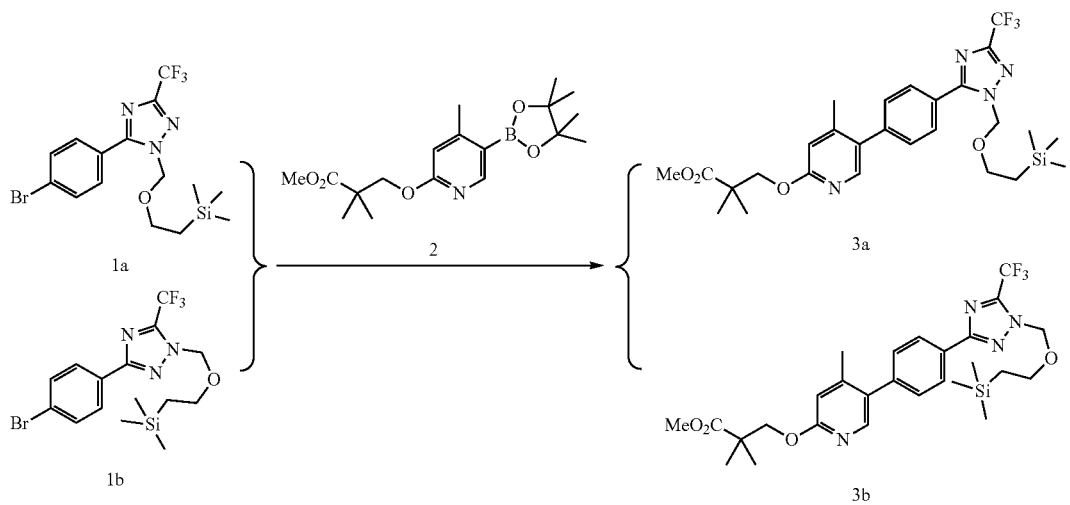

A reaction was carried out in a manner similar to the Example 68-(6) using Compound 2 (400 mg) and a mixture of Compounds 1a and 1b (363 mg) to obtain a mixture of Compounds 3a and 3b (379 mg) as a colorless viscous material.

MS (m/z): 565 [M+H]$^+$ (2)

[Chemical Formula 262]

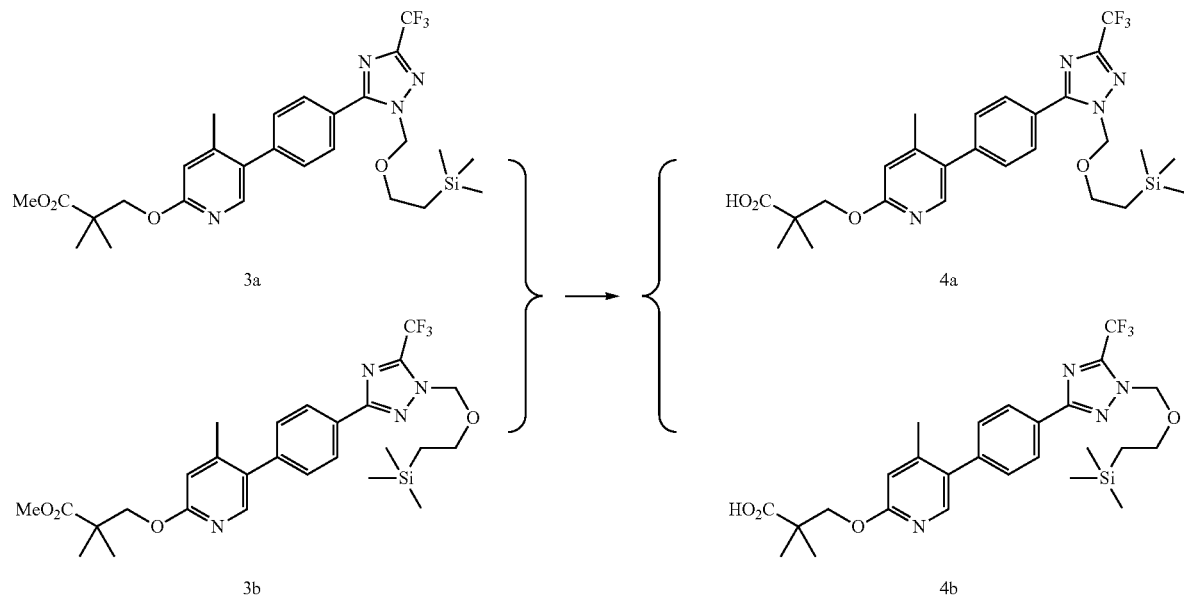

A reaction was carried out in a manner similar to the Example 52-(7) using the mixture of Compounds 3a and 3b (375 mg) to obtain a mixture of Compounds 4a and 4b (366 mg) as a colorless viscous material.

MS (m/z): 551 [M+H]$^+$ (3)

[Chemical Formula 263]

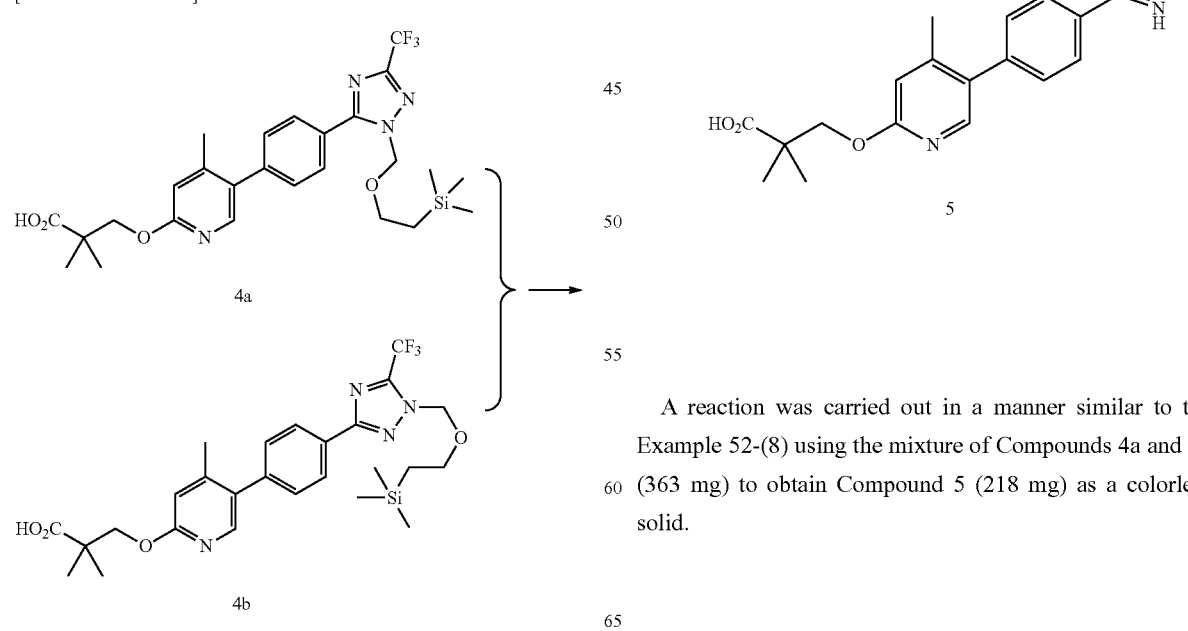

A reaction was carried out in a manner similar to the Example 52-(8) using the mixture of Compounds 4a and 4b (363 mg) to obtain Compound 5 (218 mg) as a colorless solid.

MS (m/z): 421 [M+H]$^+$

Example 82

(1)

[Chemical Formula 264]

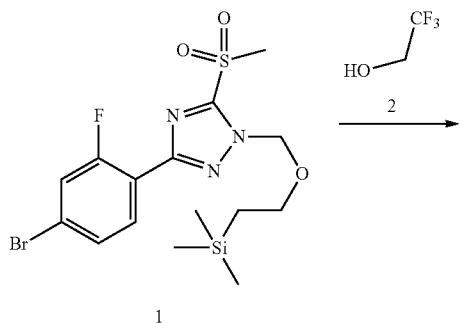

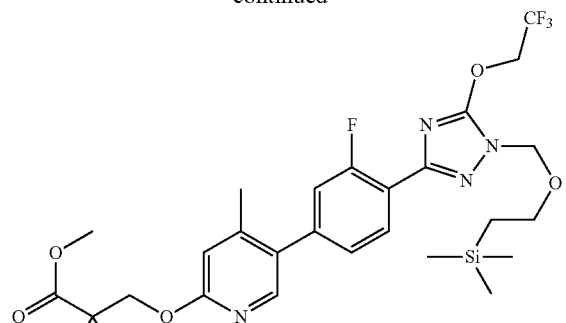

Starting from Compound 3 (341 mg) and Compound 4 (304 mg), a treatment was carried out in a manner similar to the Example 68-(6) to obtain Compound 5 (436 mg) as a colorless viscous material.

MS (m/z): 613 [M+H]$^+$ (3)

[Chemical Formula 266]

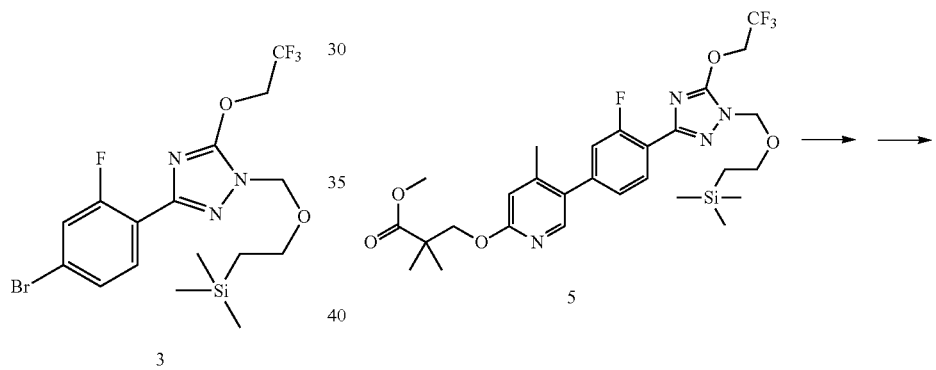

Starting from Compound 1 (500 mg), a treatment was carried out in a manner similar to the Example 68-(5) to obtain Compound 3 (343 mg) as a colorless solid.

MS (m/z): 470/472 [M+H]$^+$ (2)

[Chemical Formula 265]

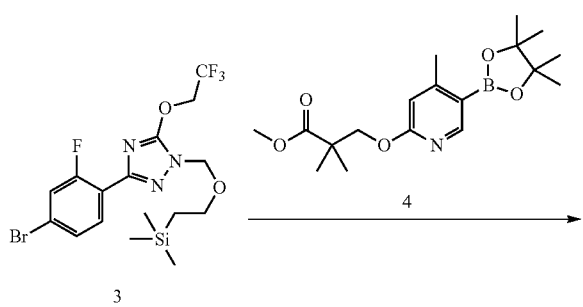

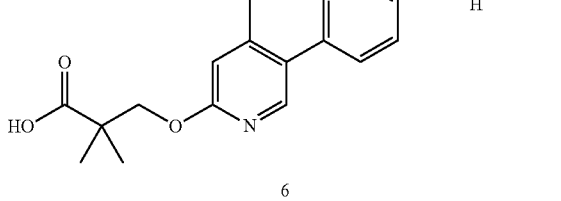

Starting from Compound 5 (435 mg), a treatment was carried out in a manner similar to the Example 68-(7) to obtain Compound 6 (290 mg) as a colorless solid.

MS (m/z): 469 [M+H]$^+$

Example 83

(1)

[Chemical Formula 267]

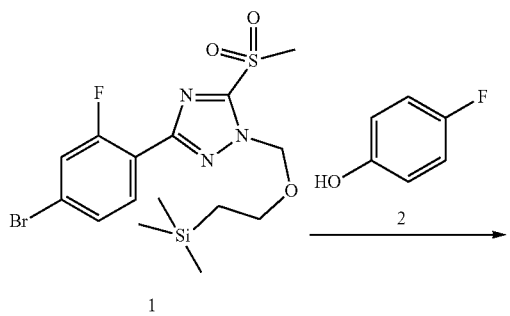

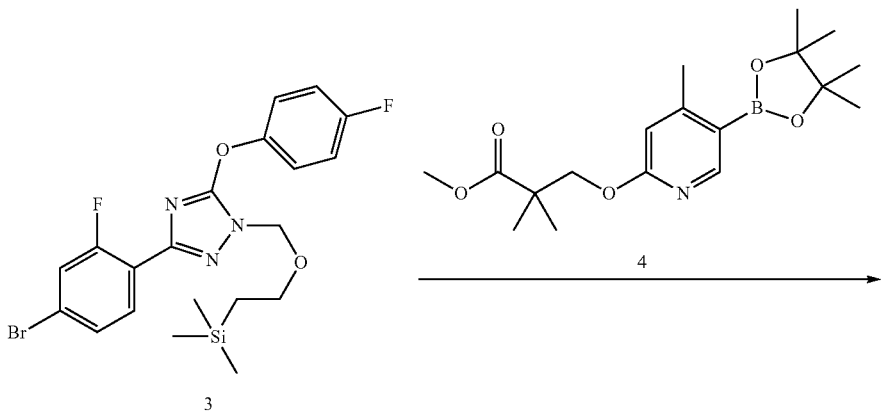

Starting from Compound 1 (500 mg), a treatment was carried out in a manner similar to the Example 69-(2) to obtain Compound 3 (357 mg) as a colorless viscous material.

MS (m/z): 482/484 [M+H]+

(2)

[Chemical Formula 268]

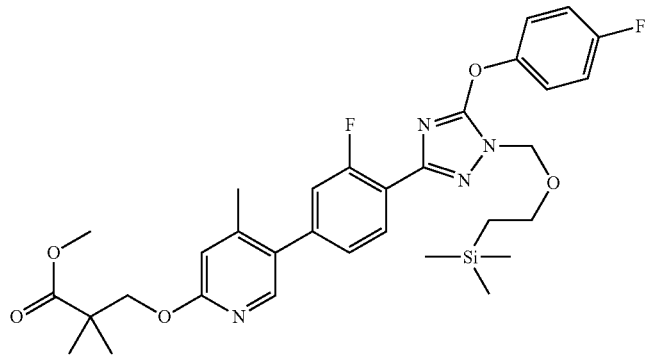

Starting from Compound 3 (355 mg) and Compound 4 (308 mg), a treatment was carried out in a manner similar to Example 68-(6) to obtain Compound 5 (464 mg) as a colorless viscous material.

MS (m/z): 625 [M+H]+

(3)

[Chemical Formula 269]

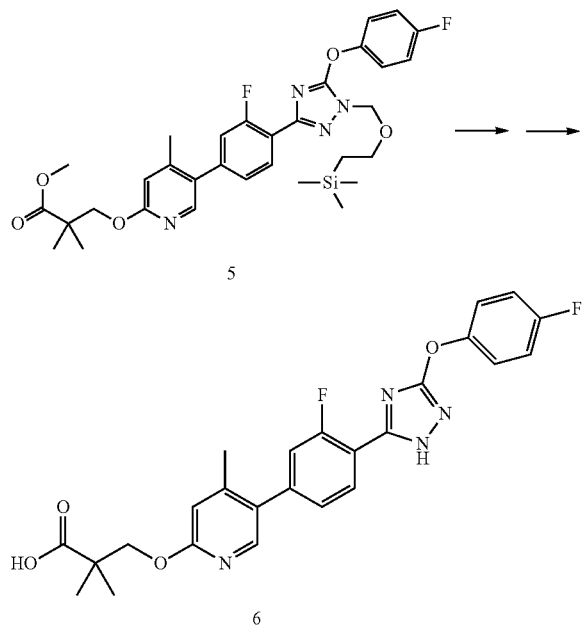

Starting from Compound 5 (450 mg), a treatment was carried out in a manner similar to Example 68-(7) to obtain Compound 6 (293 mg) as a colorless solid.

MS (m/z): 481 [M+H]$^+$

Example 84

(1)

[Chemical Formula 270]

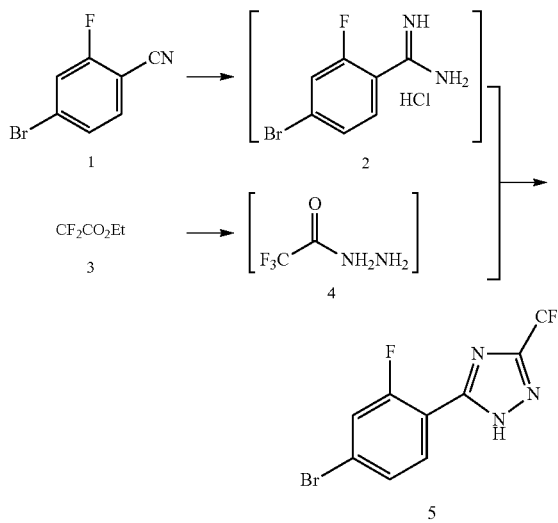

Under ice cooling, to a solution of Compound 1 (2 g) in tetrahydrofuran (10 mL) was added dropwise a 1.6M lithium bis(trimethylsilyl)amide/tetrahydrofuran solution (7.5 mL), and the mixture was stirred at room temperature for 3 hours. The reaction solution was ice cooled, and 4N hydrogen chloride-1,4-dioxane (6.2 mL) was added. Diethyl ether was added, and the deposit was collected by filtration. The filtrate was concentrated under reduced pressure, and the deposit was washed with diethyl ether and collected by filtration. The obtained deposits were combined to be used for the next reaction. A solution of Compound 3 (0.75 mL) and hydrazine hydrate (0.29 mL) in tetrahydrofuran (8 mL) was stirred at 65° C. for 1 hour. The reaction solution was cooled to room temperature, the deposit obtained above was added, and the mixture was stirred at 65° C. for 2 hours. To the reaction solution was added water, and the mixture was extracted with ethyl acetate. The extract was washed with saturated brine, dried over anhydrous magnesium sulfate, and concentrated under reduced pressure. The obtained residue was purified by silica gel column chromatography (n-hexane:ethyl acetate=100:0 to 80:20) to obtain Compound 5 (165 mg) as a colorless solid.

MS (m/z): 310/312 [M+H]$^+$ (2)

[Chemical Formula 271]

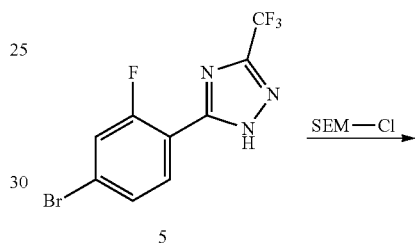

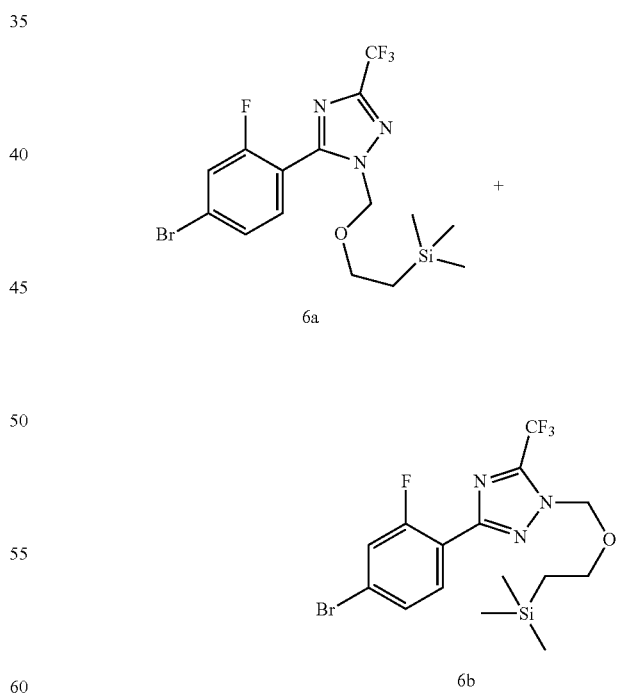

A reaction was carried out in a manner similar to the Example 50-(5) using Compound 5 (164 mg) to obtain a mixture of Compounds 6a and 6b (228 mg) as a colorless viscous material.

MS (m/z): 440/442 [M+H]$^+$ (3)

[Chemical Formula 272]

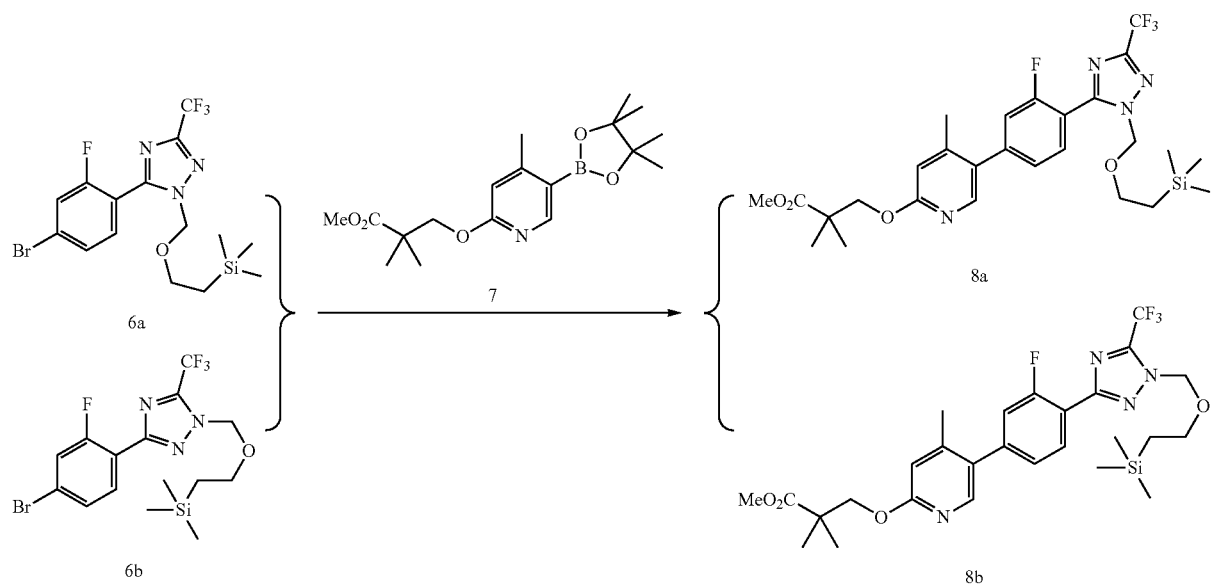

A reaction was carried out in a manner similar to the Example 50-(6) using the mixture of Compounds 6a and 6b (220 mg), and Compound 7 (174 mg) to obtain a mixture of Compounds 8a and 8b (263 mg) as a colorless viscous material.

MS (m/z): 583 [M+H]⁺

(4)

[Chemical Formula 273]

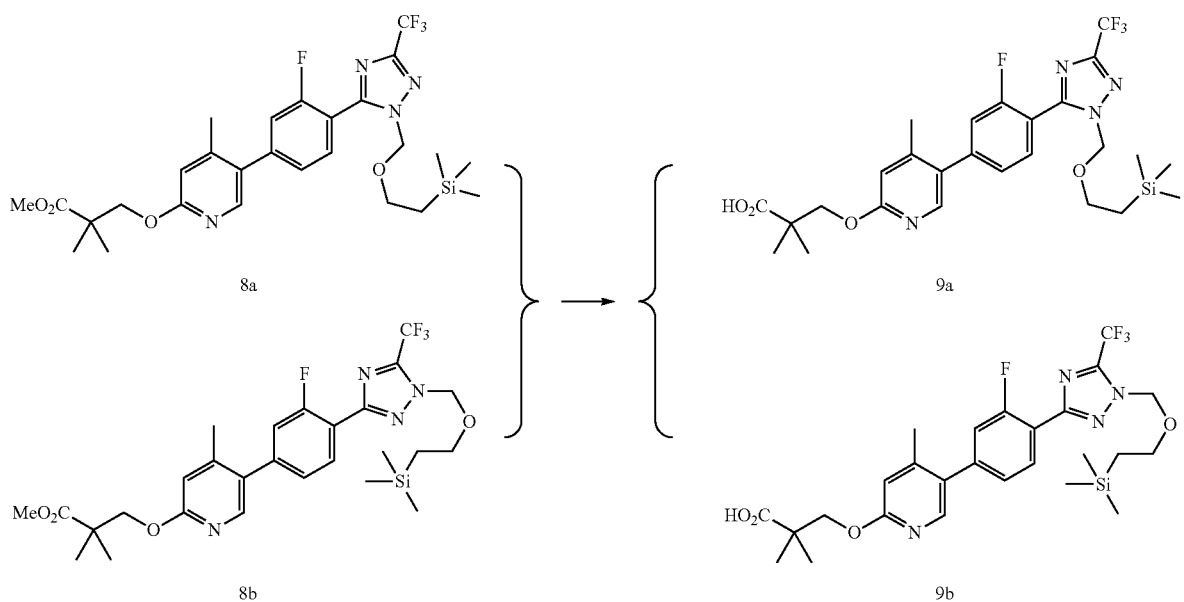

A reaction was carried out in a manner similar to the Example 52-(7) using the mixture of Compounds 8a and 8b (260 mg) to obtain a mixture of Compounds 9a and 9b (259 mg) as a colorless viscous material.

MS (m/z): 569 [M+H]⁺

(5)

[Chemical Formula 274]

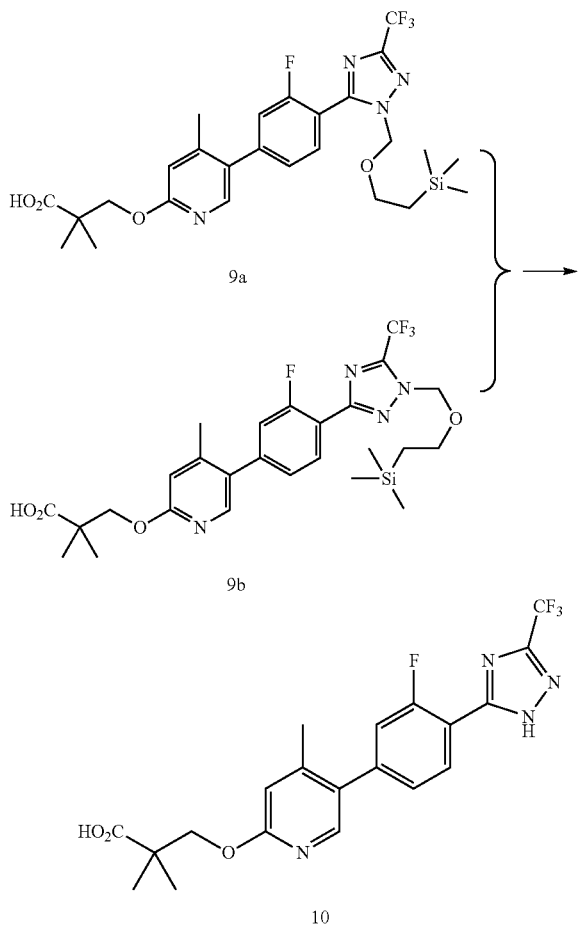

A reaction was carried out in a manner similar to the Example 52-(8) using Compounds 9a and 9b (254 mg) to obtain Compound 10 (130 mg) as a colorless solid.

MS (m/z): 439 [M+H]$^+$

Example 85

(1)

[Chemical Formula 275]

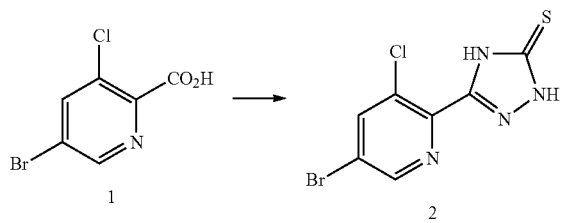

To a solution of Compound 1 (10 g) in methylene chloride (200 mL) were added oxalyl chloride (4.43 mL) and N,N-dimethylformamide (0.16 mL) at room temperature, and the mixture was stirred at room temperature for 2 hours. The reaction solution was concentrated under reduced pressure, the residue was dissolved in tetrahydrofuran (50 mL), and this was added dropwise to a suspension of thiosemicarbazide (3.85 g) and pyridine (75 mL) under ice cooling over 10 minutes. After dropwise addition, the mixture was stirred at room temperature for 2 hours and concentrated under reduced pressure. The residue was dissolved in a 2N aqueous sodium hydroxide solution (210 mL), and heated at reflux for 16 hours. The reaction solution was ice cooled and neutralized with concentrated hydrochloric acid (35 mL). The deposit was collected by filtration and washed with water and methanol. The obtained solid was suspended and washed in diethyl ether (50 mL), collected by filtration and dried at 50° C. under reduced pressure to obtain Compound 2 (9.46 g) as a beige solid.

MS (m/z): 291/293/295 [M+H]$^+$ (2)

[Chemical Formula 276]

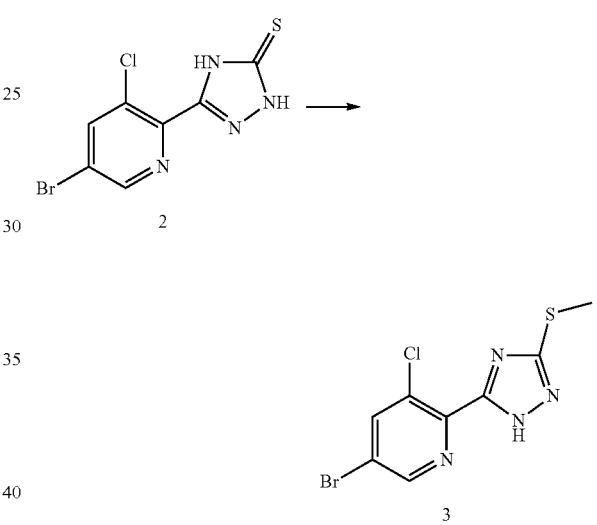

Compound 2 (9.44 g) was suspended in ethanol (24 mL), and a 2N aqueous sodium hydroxide solution (17.8 mL) and methyl iodide (2.2 mL) were added at room temperature. After the reaction solution was stirred at room temperature for 30 minutes, the deposit was collected by filtration, washed with ethanol and vacuum-dried at 50° C. to obtain Compound 3 (7.815 g) as a beige solid.

MS (m/z): 305/307/309 [M+H]$^+$ (3)

[Chemical Formula 277]

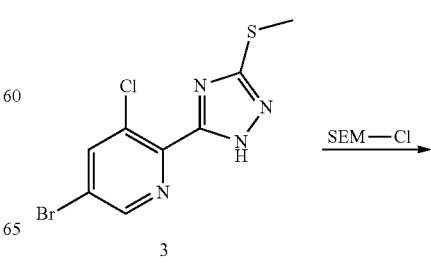

-continued

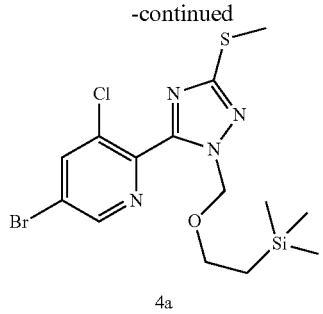

4a

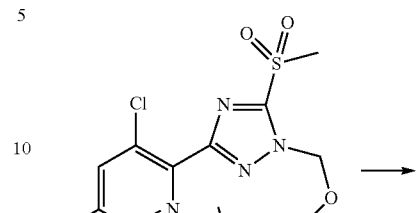

4b

A reaction was carried out in a manner similar to the Example 61-(3) using Compound 3 (7.815 g) to obtain Compound 4a (7.335 g) and Compound 4b (4.294 g) as yellow viscous materials respectively.

MS (m/z): 435/437/439 [M+H]$^+$ (4)

[Chemical Formula 278]

4b

A reaction was carried out in a manner similar to the Example 68-(4) using Compound 4b (3.69 g) to obtain Compound 5 (3.323 g) as a colorless solid.

MS (m/z): 466/468/470 [M+H]$^+$ (5)

[Chemical Formula 279]

5

6

A reaction was carried out in a manner similar to the Example 68-(5) using Compound 5 (1 g) to obtain Compound 6 (826 mg) as a colorless viscous material.

MS (m/z): 447/449/451 [M+H]$^+$ (6)

[Chemical Formula 280]

6

8

A reaction was carried out in a manner similar to the Example 68-(6) using Compound 6 (400 mg) to obtain Compound 8 (429 mg) as a colorless viscous material.

MS (m/z): 590/592 [M+H]$^+$ (7)

[Chemical Formula 281]

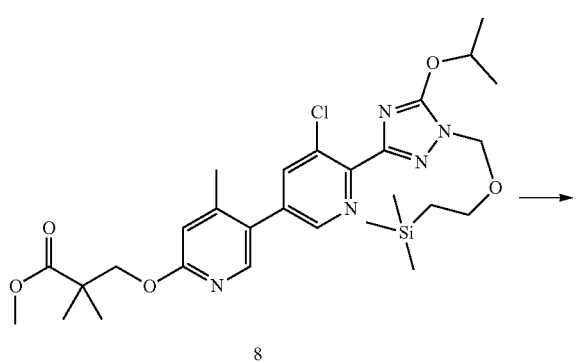

8

A reaction was carried out in a manner similar to the Example 68-(7) using Compound 8 (242 mg) to obtain Compound 9 (210 mg) as a colorless solid.

MS (m/z): 576/578 [M+H]⁺

(8)

[Chemical Formula 282]

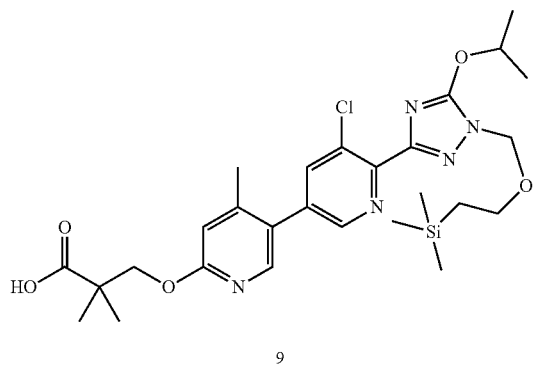

9

-continued

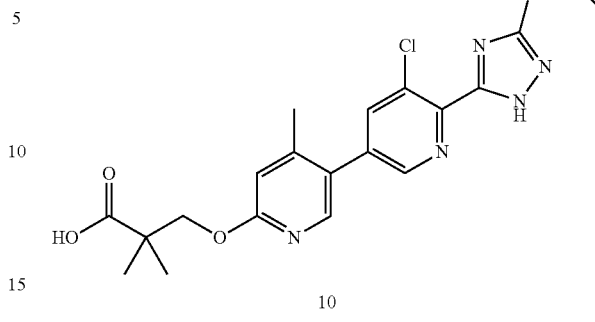

10

To a solution of Compound 9 (205 mg) in tetrahydrofuran (4 mL) was added a 1M solution of tetrabutylammonium fluoride in tetrahydrofuran (1.78 mL), and the mixture was stirred at 70° C. for 23 hours. A saturated aqueous ammonia chloride solution was added, and the mixture was extracted with ethyl acetate. The organic layer was washed with saturated brine, dried over anhydrous magnesium sulfate and concentrated under reduced pressure. The obtained residue was purified by silica gel column chromatography (chloroform:methanol=100/0 to 90/10) to obtain a mixture of Compounds 9 and 10. To this were added 2 mL of trifluoroacetic acid and 0.2 mL of water, and the mixture was stirred at room temperature for 2 hours. After the reaction solution was ice cooled and neutralized with a 1N aqueous sodium hydroxide solution, its pH was adjusted to 4 with 1N hydrochloric acid, and then it was extracted with ethyl acetate. The organic layer was washed with saturated brine, dried over anhydrous magnesium sulfate and concentrated under reduced pressure. The obtained residue was purified by silica gel column chromatography (chloroform:methanol=100/0 to 90/10) to obtain Compound 10 (109 mg) as a colorless solid.

MS (m/z): 446/448 [M+H]⁺

Example 86

(1)

[Chemical Formula 283]

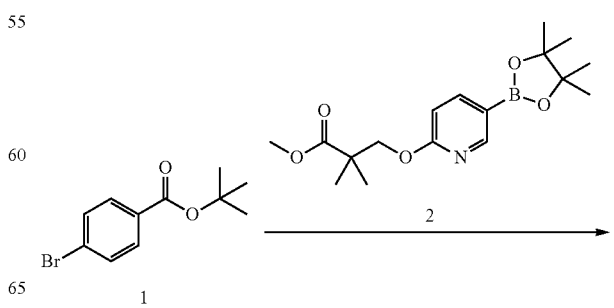

(3)

[Chemical Formula 285]

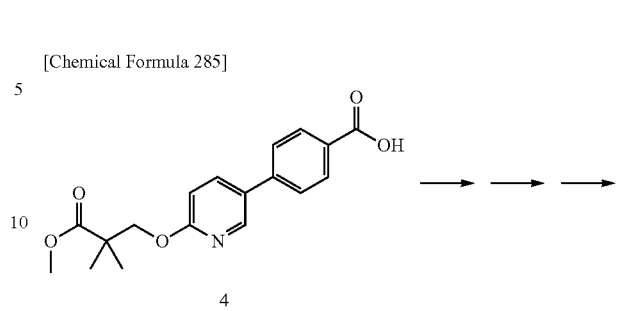

4

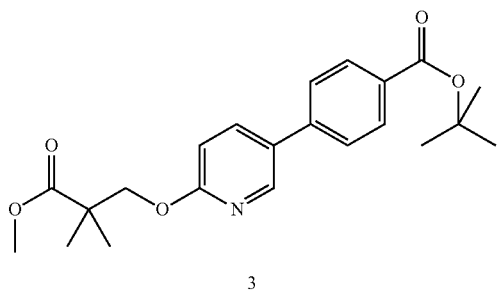

3

Starting from Compound 1 (4400 mg), a treatment was carried out in a manner similar to the Example 68-(6) to obtain Compound 3 (4750 mg) as a pale yellow solid.

MS (m/z): 386 [M+H]$^+$ (2)

[Chemical Formula 284]

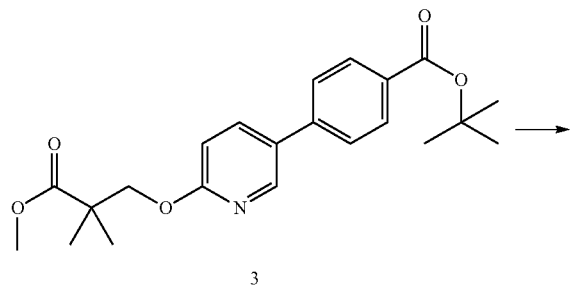

3

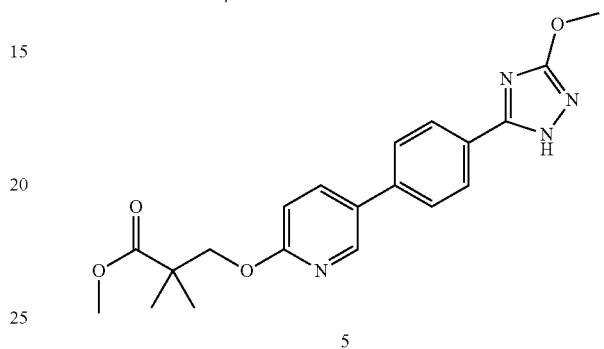

5

To a solution of Compound 4 (200 mg) in methylene chloride (8 mL) was added N,N-dimethylformamide (7 μL), thionyl chloride (266 μL) was added dropwise, and the mixture was stirred at room temperature for 2 hours. The solvent was distilled off under reduced pressure, and azeotroped to dry with toluene. To the residue were added toluene (8 mL) and potassium thiocyanate (354 mg), and the mixture was stirred at room temperature for 1 hour. After the supernatant (4 mL) was removed, to the solution containing the residual insoluble salt was added methanol (0.4 mL), the temperature was brought to 70° C., and the mixture was stirred for 2 hours. After the reaction solution was cooled to room temperature, to this was added hydrazine.monohydrate (59 μL), and the mixture was stirred at room temperature for 1 hour. Ethyl acetate and saturated brine were added, and the mixture was stirred to carry out a separation. The organic layer was passed through the phase separator and subsequently concentrated under reduced pressure. The obtained residue was purified by silica gel column chromatography (n-hexane:ethyl acetate=70:30 to 40:60) to obtain Compound 5 (29.4 mg) as a white solid.

MS (m/z): 383 [M+H]$^+$ (4)

[Chemical Formula 286]

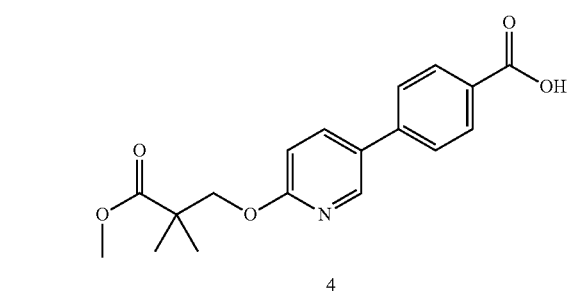

4

To a solution of Compound 3 (4740 mg) in methylene chloride (20 mL) was added trifluoroacetic acid (20 mL), and the mixture was stirred at room temperature for 4 hours. The solvent was distilled off under reduced pressure, and azeotroped with toluene. To the residue was added diethyl ether, and the mixture was stirred. The obtained crystals were collected by filtration and subsequently vacuum-dried to obtain Compound 4 (3144 mg) as a colorless solid.

MS (m/z): 330 [M+H]$^+$

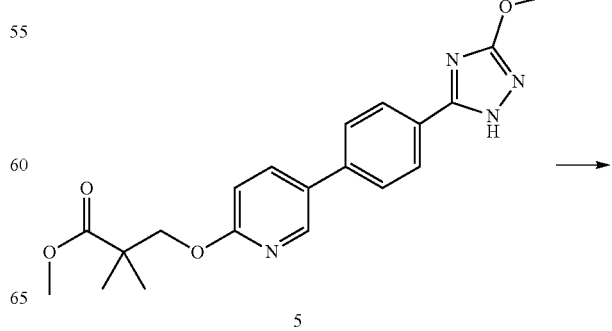

5

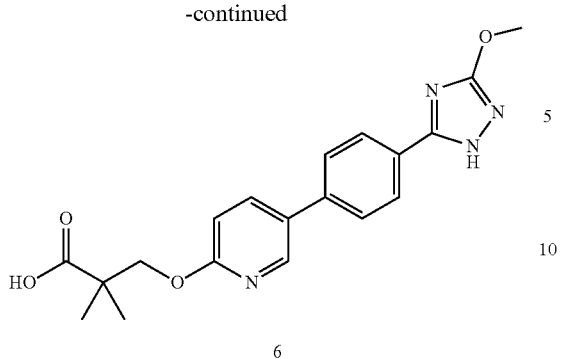
5
6
Starting from Compound 5 (29.0 mg), a treatment was carried out in a manner similar to the Example 61-(5) to obtain Compound 6 (21.8 mg) as a colorless solid.
MS (m/z): 369 [M+H]⁺
Example 87
(1)
[Chemical Formula 287]
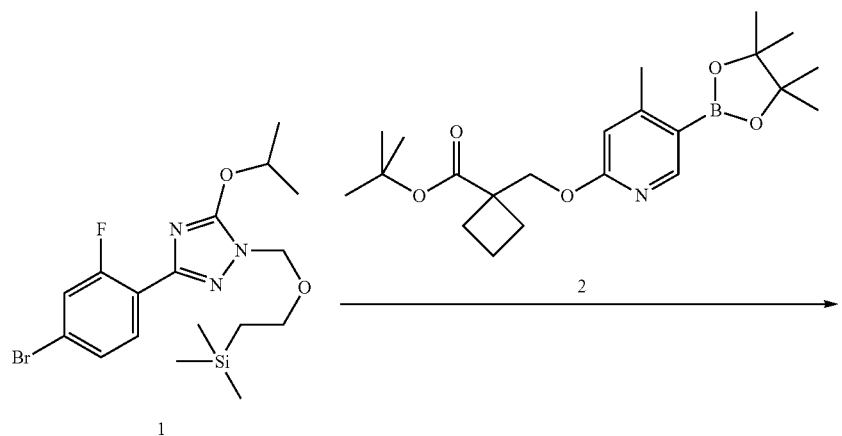
1
2
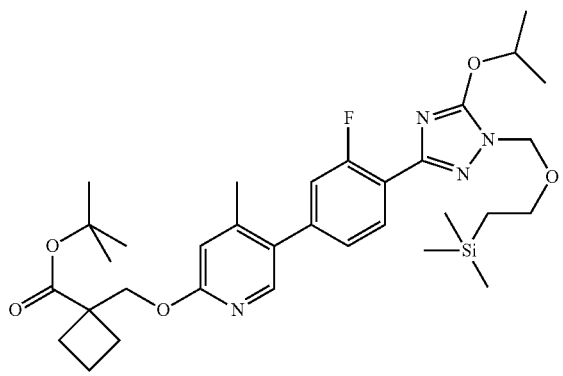
3
Starting from Compound 1 (300 mg) and Compound 2 (309 mg), a treatment was carried out in a manner similar to the Example 68-(6) to obtain Compound 3 (294 mg) as a colorless viscous material.
MS (m/z): 627 [M+H]⁺

(2)

[Chemical Formula 288]

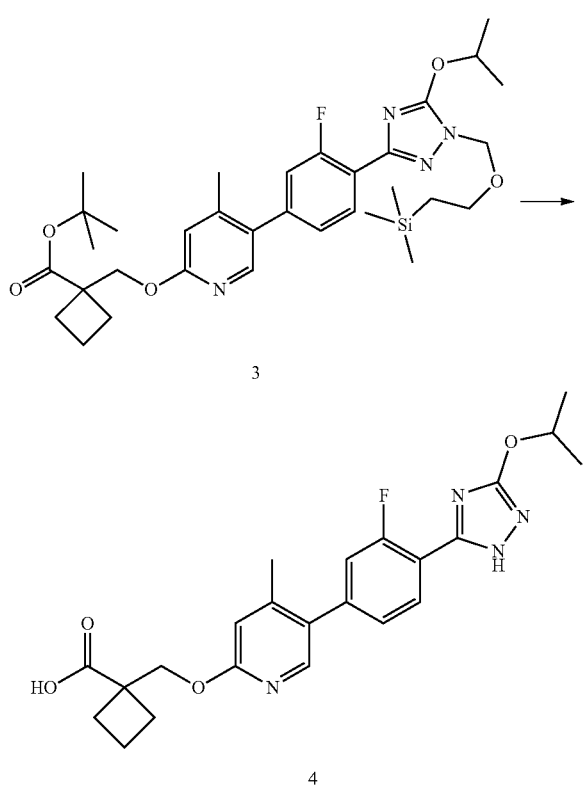

To Compound 3 (293 mg) were added trifluoroacetic acid (1 mL) and water (0.05 mL), and the mixture was stirred at room temperature for 3 hours. The reaction solution was neutralized by addition of a 2N aqueous sodium hydroxide solution, and stirred at room temperature for 1 hour. Subsequently, ethyl acetate was added to carry out a liquid separation. The organic layer was separated, washed with saturated brine, passed through the phase separator and concentrated under reduced pressure. The obtained residue was purified by silica gel column chromatography (n-hexane:ethyl acetate=60:40 to 20:80). The solvent of the fraction including the target compound was distilled off under reduced pressure, to the residue were added diisopropyl ether and a small amount of ethyl acetate, and the obtained crystals were collected by filtration and vacuum-dried to obtain Compound 4 (147 mg) as a colorless solid.

MS (m/z): 441 [M+H]$^+$

Example 88

(1)

[Chemical Formula 289]

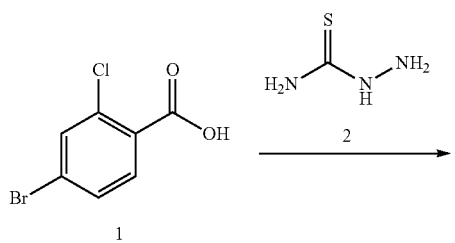

-continued

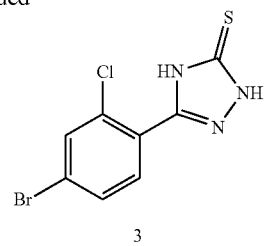

To a solution of Compound 1 (10.0 g) in tetrahydrofuran (50 mL) was added N, N-dimethylformamide (0.5 mL) and thionyl chloride (12.4 mL) was added dropwise, and the mixture was stirred at 50° C. for 2 hours. After the solvent was distilled off under reduced pressure, the residue was dissolved in tetrahydrofuran (25 mL), and the solution was added slowly dropwise to a suspension of Compound 2 (3.87 g) in pyridine (50 mL) under ice cooling. The mixture was stirred at the same temperature for 30 minutes and at room temperature for 3 hours. After the solvent was distilled off under reduced pressure, water (50 mL) and a 2N aqueous sodium hydroxide solution (200 mL) were added, and the mixture was stirred at 110° C. for 3 hours. The mixture was neutralized by slow addition of concentrated hydrochloric acid (about 40 mL) under ice cooling, and the obtained crystals were collected by filtration. The crystals were washed with diethyl ether and vacuum-dried to obtain Compound 3 (8.36 g) as a pale yellow solid.

MS (m/z): 290/292 [M+H]$^+$ (2)

[Chemical Formula 290]

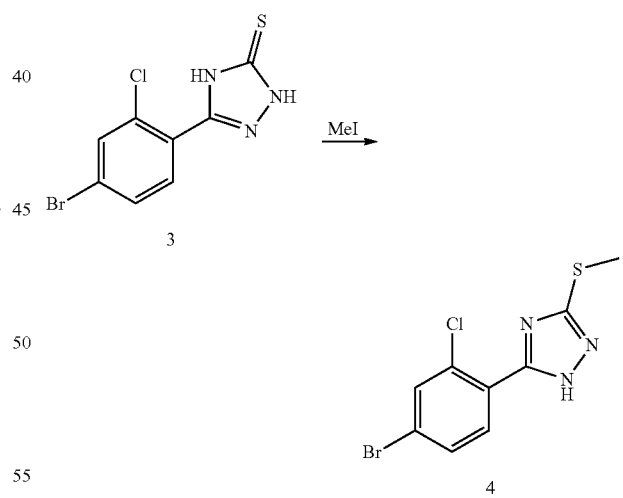

To a suspension of Compound 3 (8.20 g) in ethanol (19 mL) was added dropwise a 2N aqueous sodium hydroxide solution (15.5 mL) and methyl iodide (1.93 mL) was further added, and the mixture was stirred at room temperature for 5 minutes. The obtained crystals were collected by filtration, washed with water and diethyl ether, and subsequently dried to obtain Compound 4 (3.95 g) as a pale yellowish brown solid.

MS (m/z): 304/306 [M+H]$^+$ (3)

[Chemical Formula 291]

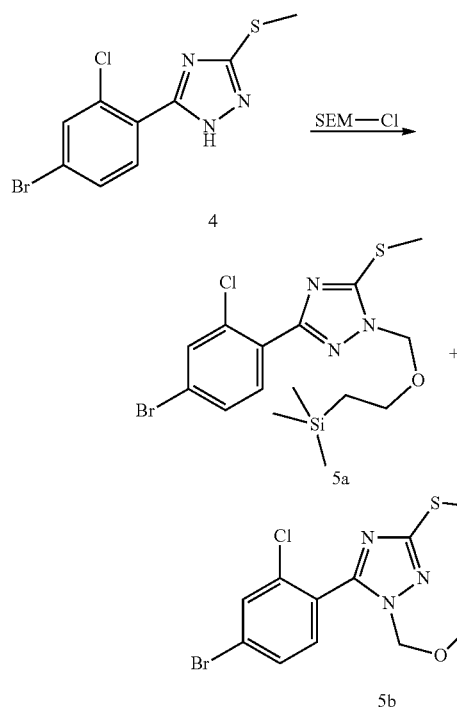

Starting from Compound 4 (3940 mg), a treatment was carried out in a manner similar to the Example 61-(3) to obtain Compound 5a (1353 mg) and Compound 5b (1020 mg) as colorless viscous materials respectively.
Compound 5a: MS (m/z): 434/436 [M+H]+
Compound 5b: MS (m/z): 434/436 [M+H]+

(4)

[Chemical Formula 292]

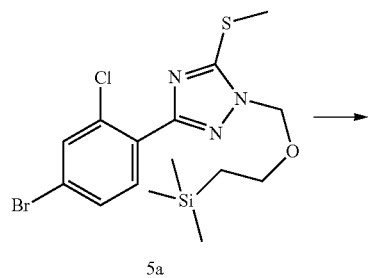

Starting from Compound 5a (1330 mg), a treatment was carried out in a manner similar to the Example 68-(4) to obtain Compound 6a (1221 mg) as a pale yellow viscous material.

MS (m/z): 466/468 [M+H]+

(5)

[Chemical Formula 293]

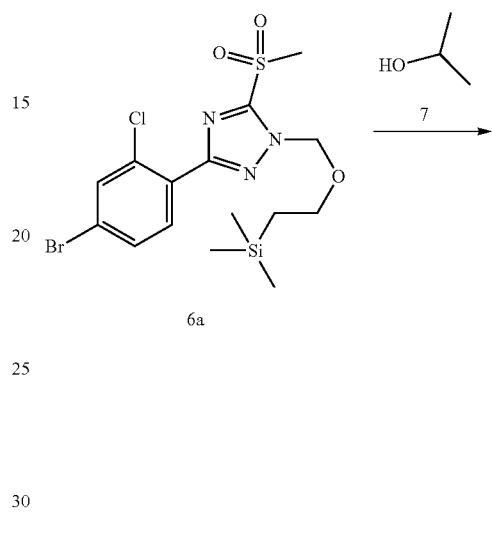

Starting from Compound 6a (800 mg) and Compound 7 (261 μL), a treatment was carried out in a manner similar to the Example 68-(5) to obtain Compound 8a (481 mg) as a colorless viscous material.

MS (m/z): 446/448 [M+H]+

(6)

[Chemical Formula 294]

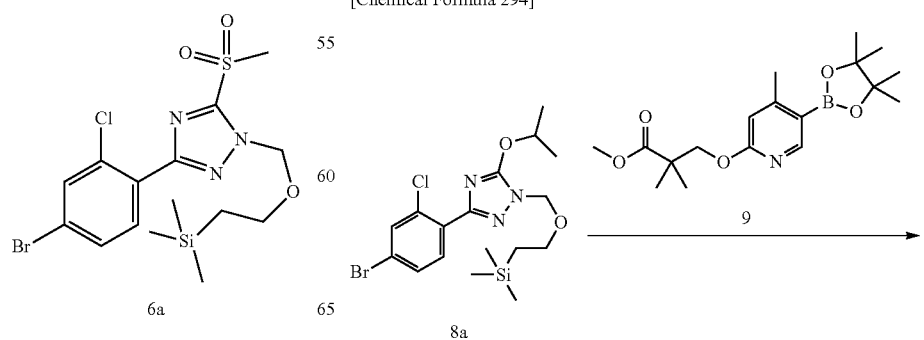

-continued

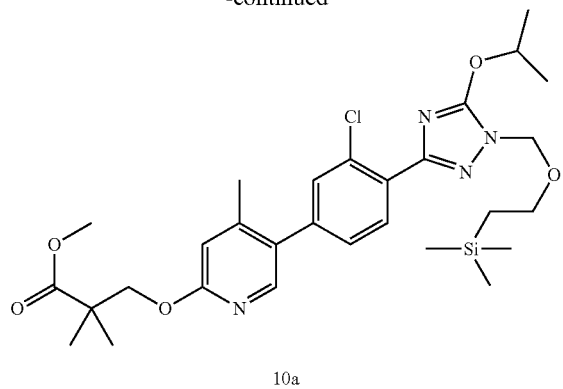

10a

Starting from Compound 8a (479 mg) and Compound 9 (393 mg), a treatment was carried out in a manner similar to the Example 68-(6) to obtain Compound 10a (538 mg) as a colorless viscous material.

MS (m/z): 589/591 [M+H]$^+$ (7)

[Chemical Formula 295]

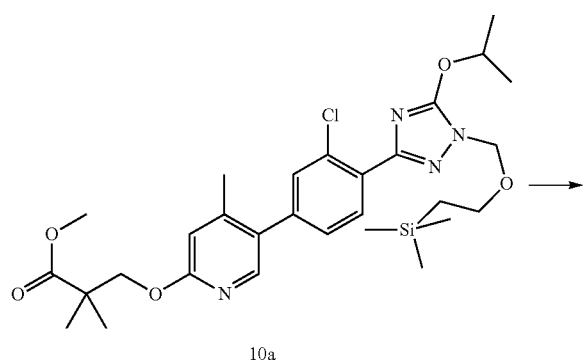

10a

To Compound 10a (300 mg) in tetrahydrofuran (4 mL) was added dropwise a 1M tetrabutylammonium fluoride in tetrahydrofuran (2.5 mL), and the mixture was stirred at 70° C. for 4 days. After neutralization by addition of 1N aqueous hydrochloric acid solution, an extraction with ethyl acetate was carried out. The organic layer was washed with saturated brine, passed through the phase separator and concentrated under reduced pressure. The obtained residue was purified by silica gel column chromatography (n-hexane: ethyl acetate=65:35 to 5:95) to obtain Compound 11 (136 mg) as a colorless solid.

MS (m/z): 445/447 [M+H]$^+$

Example 89

(1)

[Chemical Formula 296]

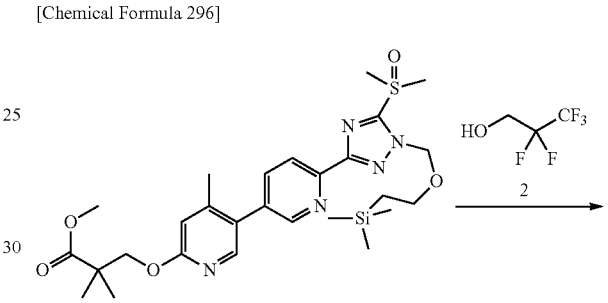

1

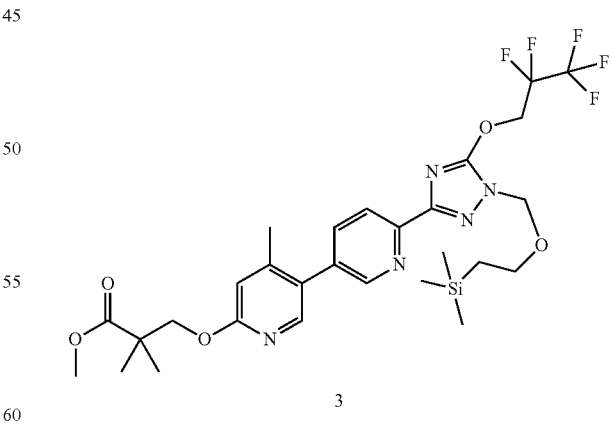

3

Starting from Compound 1 (400 mg) and Compound 2 (209 mg), a treatment was carried out in a manner similar to the Example 68-(5) to obtain Compound 3 (368 mg) as a pale yellow viscous material.

MS (m/z): 646 [M+H]$^+$ (2)
[Chemical Formula 297]
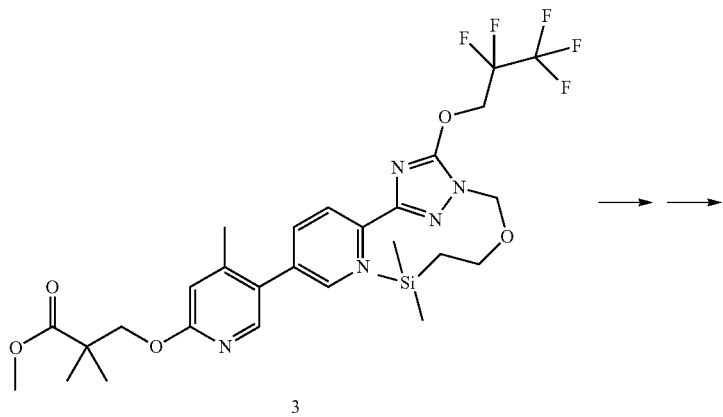
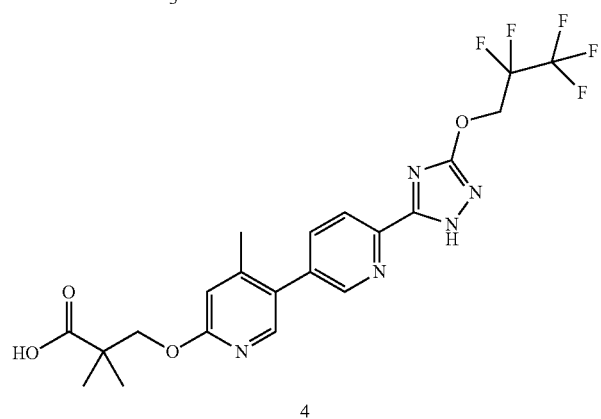
Starting from Compound 3 (366 mg), a treatment was carried out in a manner similar to the Example 68-(7) to obtain Compound 4 (218 mg) as a colorless solid.
MS (m/z): 502 [M+H]+
Example 90
(1)
[Chemical Formula 298]
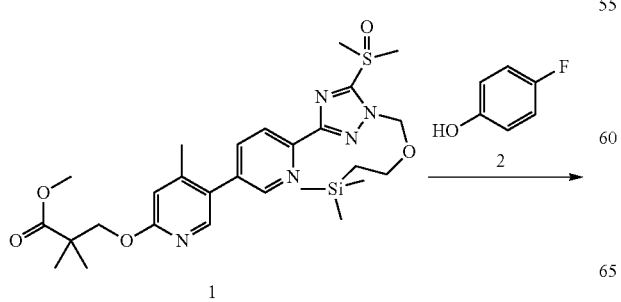
-continued
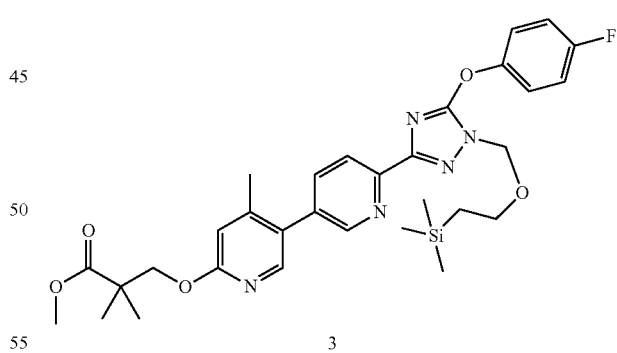
Starting from Compound 1 (300 mg), a treatment was carried out in a manner similar to the Example 69-(2) to obtain Compound 3 (257 mg) as a colorless viscous material.
MS (m/z): 608 [M+H]+

(2)
[Chemical Formula 299]
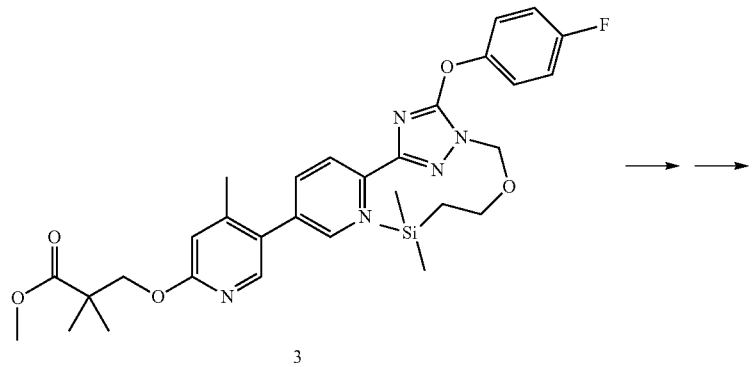
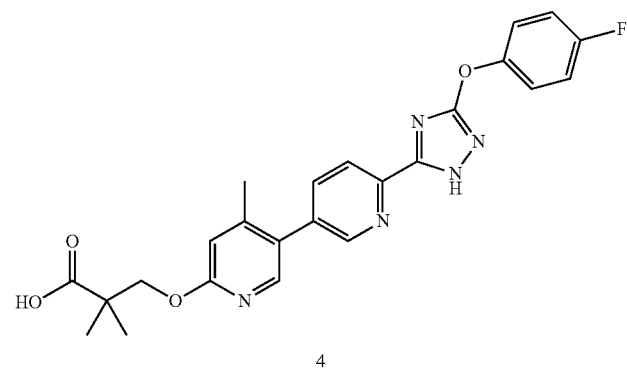
Starting from Compound 3 (255 mg), a treatment was carried out in a manner similar to the Example 68-(7) to obtain Compound 4 (150 mg) as a colorless solid.
MS (m/z): 464 $[M+H]^+$
Example 91
(1)
[Chemical Formula 300]
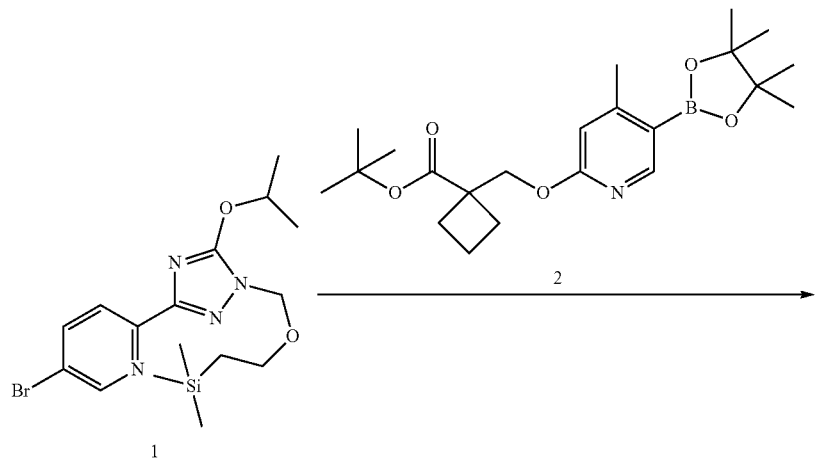

-continued

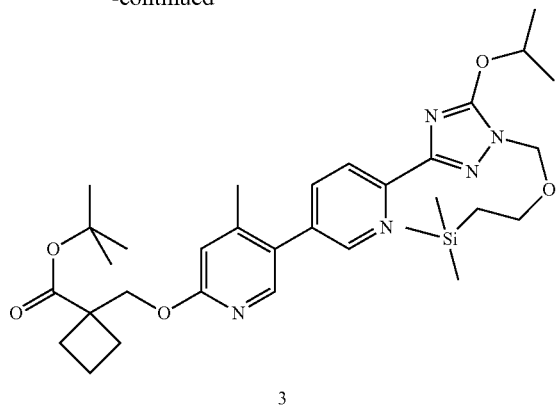

3

Starting from Compound 1 (260 mg) and Compound 2 (304 mg), a treatment was carried out in a manner similar to the Example 68-(6) to obtain Compound 3 (279 mg) as a pale yellow viscous material.

MS (m/z): 610 $[M+H]^+$ (2)

[Chemical Formula 301]

Example 92

(1)

[Chemical Formula 302]

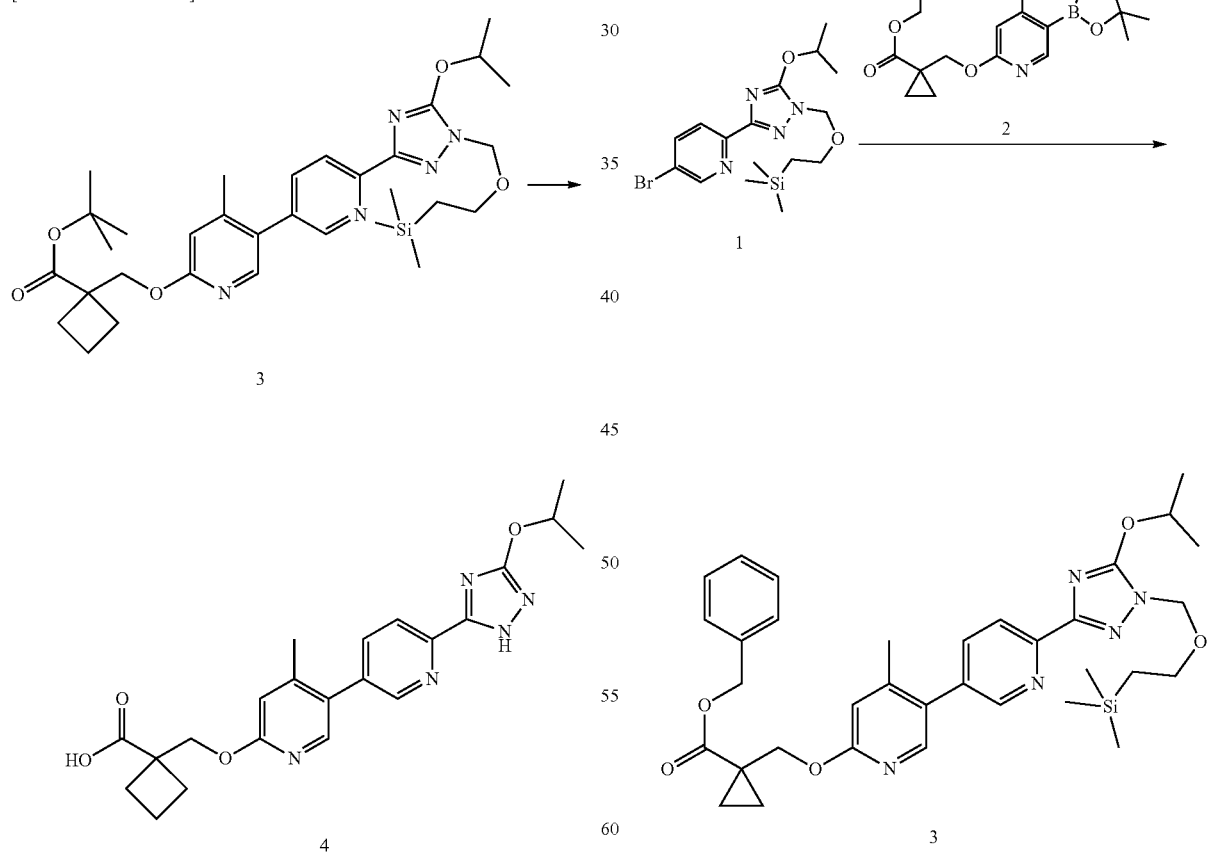

Starting from Compound 3 (278 mg), a treatment was carried out in a manner similar to the Example 87-(2) to obtain Compound 4 (83.4 mg) as a colorless solid.

MS (m/z): 424 $[M+H]^+$

Starting from Compound 1 (330 mg) and Compound 2 (473 mg), a treatment was carried out in a manner similar to the Example 68-(6) to obtain Compound 3 (511 mg) as a pale brown viscous material.

MS (m/z): 630 $[M+H]^+$+

(2)

[Chemical Formula 303]

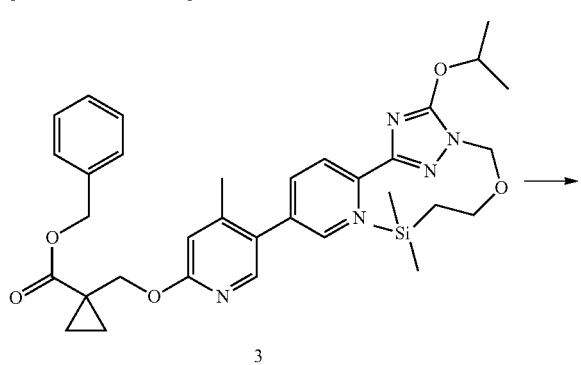

3

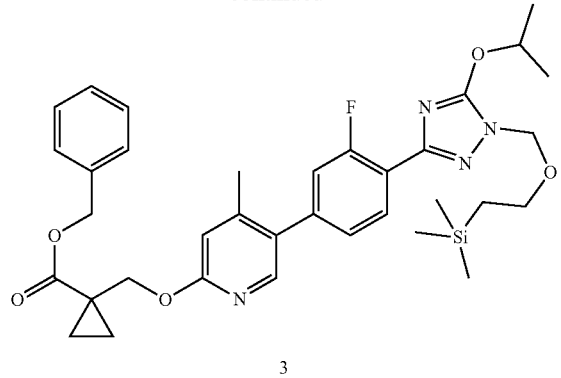

3

Starting from Compound 1 (380 mg) and Compound 2 (523 mg), a treatment was carried out in a manner similar to the Example 68-(6) to obtain Compound 3 (432 mg) as a colorless viscous material.

MS (m/z): 647 [M+H]$^+$ (2)

[Chemical Formula 305]

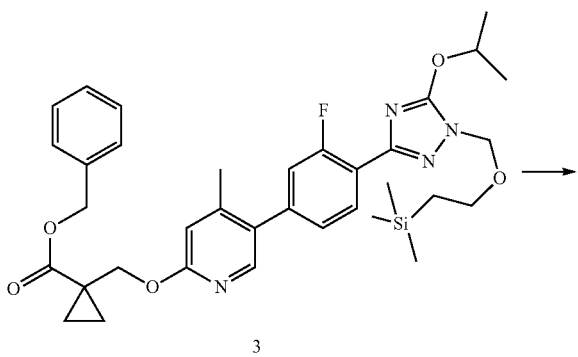

3

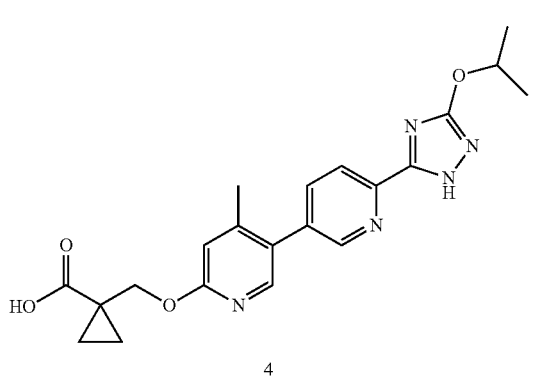

4

Starting from Compound 3 (508 mg), a treatment was carried out in a manner similar to the Example 88-(7) to obtain Compound 4 (217 mg) as a colorless solid.

MS (m/z): 410 [M+H]$^+$

Example 93

(1)

[Chemical Formula 304]

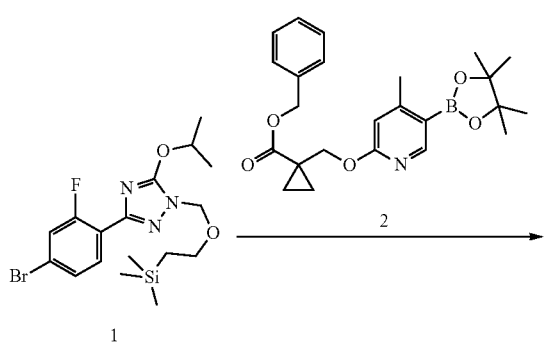

1

2

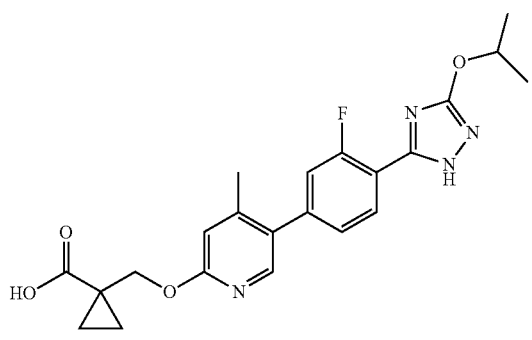

4

Starting from Compound 3 (428 mg), a treatment was carried out in a manner similar to the Example 88-(7) to obtain Compound 4 (204 mg) as a colorless solid.

MS (m/z): 427 [M+H]$^+$

Example 94

(1)

[Chemical Formula 306]

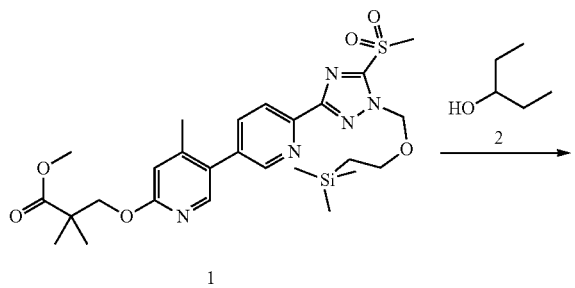

Starting from Compound 1 (200 mg) and Compound 2 (104 mg), a treatment was carried out in a manner similar to the Example 68-(5) to obtain Compound 3 (85.2 mg) as a colorless viscous material.

MS (m/z): 584 [M+H]$^+$ (2)

[Chemical Formula 307]

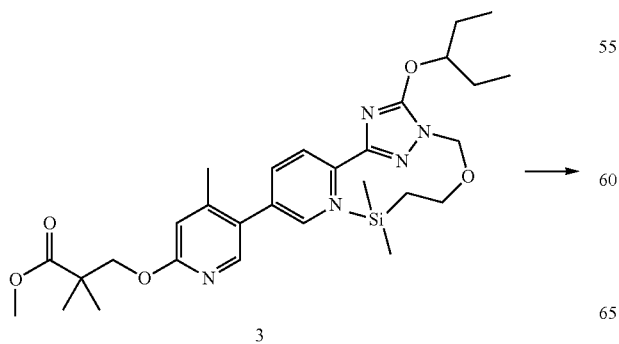

Starting from Compound 3 (85.0 mg), a treatment was carried out in a manner similar to the Example 88-(7) to obtain Compound 4 (36.5 mg) as a colorless solid.

MS (m/z): 440 [M+H]$^+$

Example 95

(1)

[Chemical Formula 308]

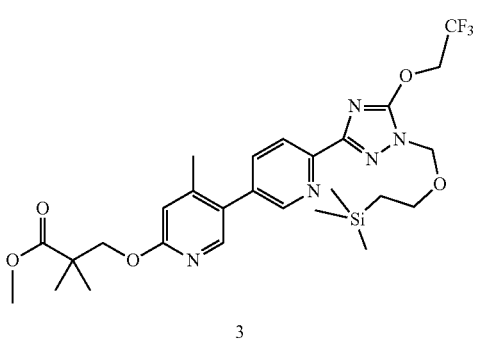

Starting from Compound 1 (400 mg) and Compound 2 (99 μL), a treatment was carried out in a manner similar to the Example 68-(5) to obtain Compound 3 (385 mg) as a pale yellow viscous material.

MS (m/z): 596 [M+H]$^+$ (2)
[Chemical Formula 309]
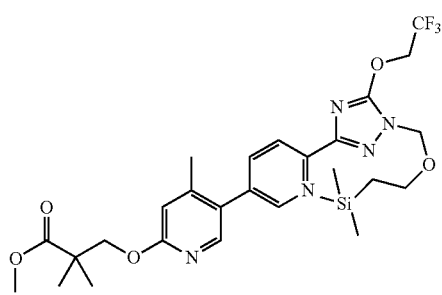
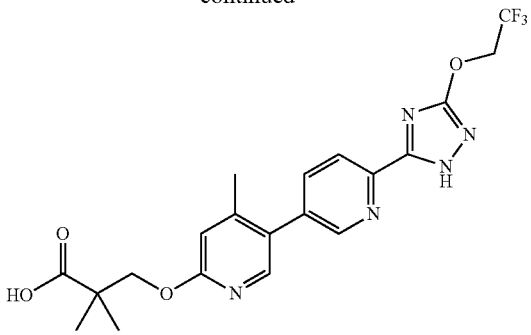
Starting from Compound 3 (338 mg), a treatment was carried out in a manner similar to the Example 68-(7) to obtain Compound 4 (252 mg) as a colorless solid.
MS (m/z): 452 [M+H]⁺
Example 96
(1)
[Chemical Formula 310]
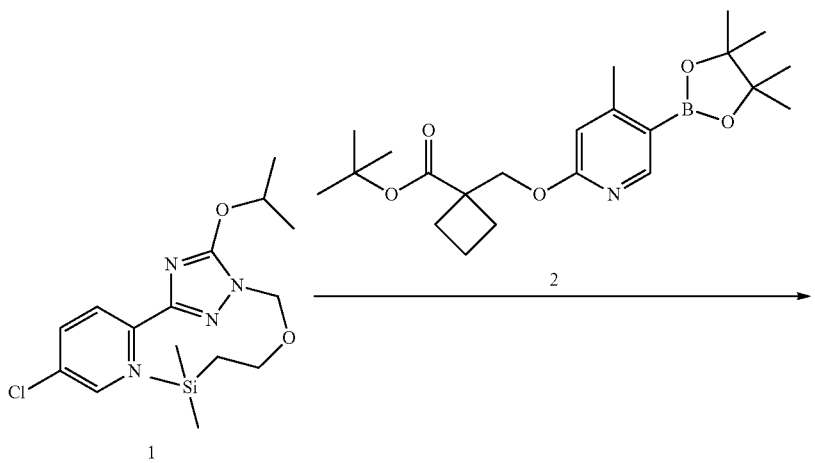
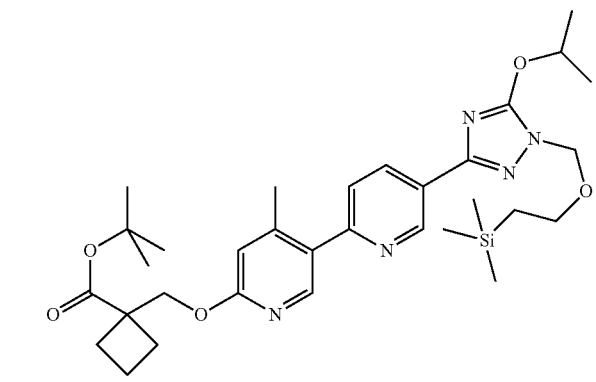
Starting from Compound 1 (230 mg) and Compound 2 (302 mg), a treatment was carried out in a manner similar to the Example 68-(6) to obtain Compound 3 (274 mg) as a colorless viscous material.
MS (m/z): 610 [M+H]⁺

(2)

[Chemical Formula 311]

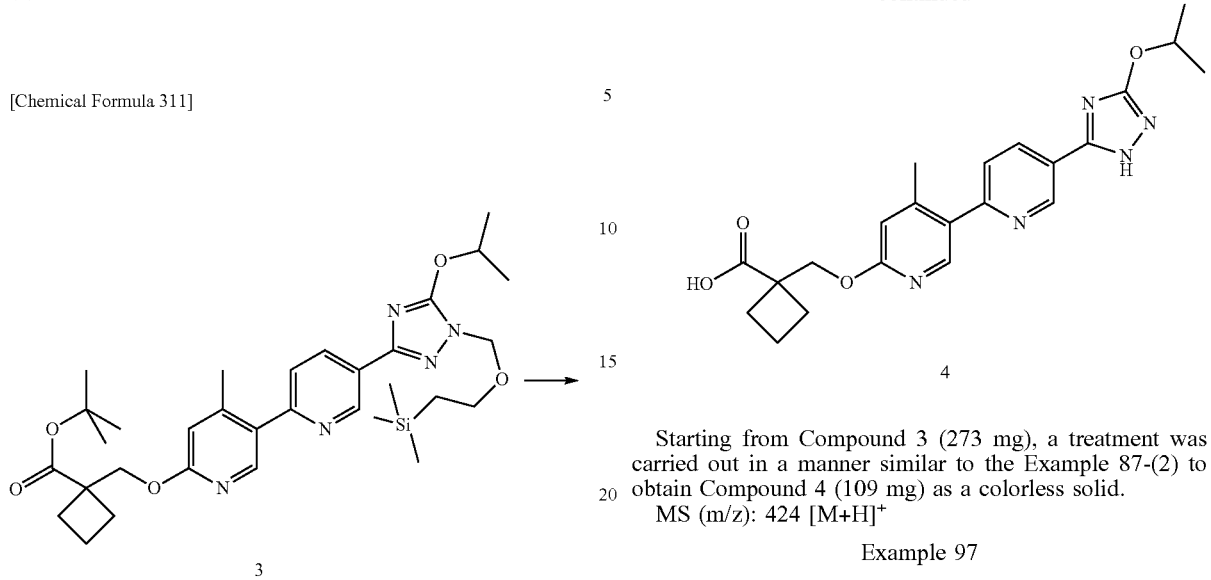

Starting from Compound 3 (273 mg), a treatment was carried out in a manner similar to the Example 87-(2) to obtain Compound 4 (109 mg) as a colorless solid.

MS (m/z): 424 [M+H]$^+$

Example 97

(1)

[Chemical Formula 312]

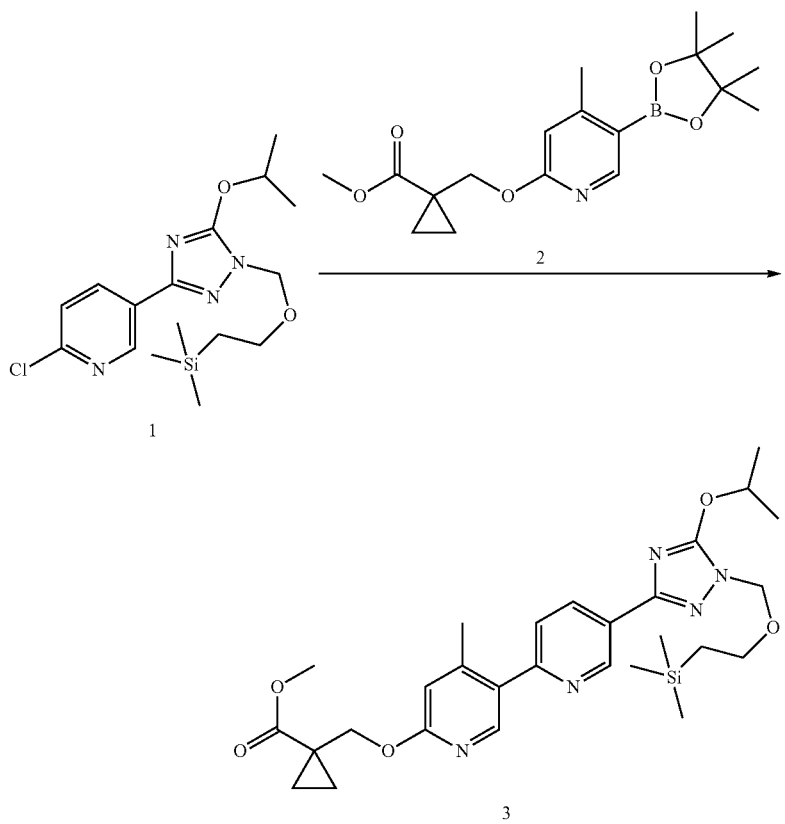

Starting from Compound 1 (230 mg) and Compound 2 (292 mg), a treatment was carried out in a manner similar to the Example 68-(6) to obtain Compound 3 (195 mg) as a pale yellowish brown viscous material.

MS (m/z): 554 [M+H]$^+$ (2)

[Chemical Formula 313]

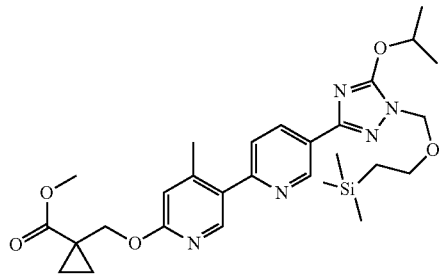

3

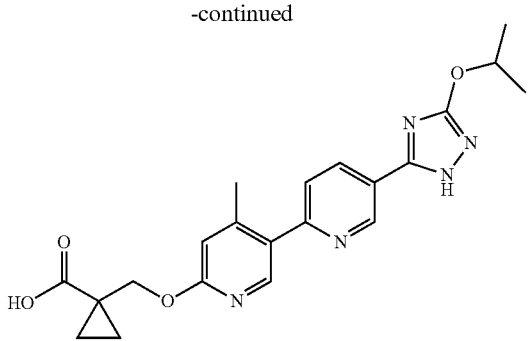

4

Starting from Compound 3 (194 mg), a treatment was carried out in a manner similar to the Example 68-(7) to obtain Compound 4 (109 mg) as a colorless solid.
MS (m/z): 410 [M+H]$^+$ Example 98

(1)

[Chemical Formula 314]

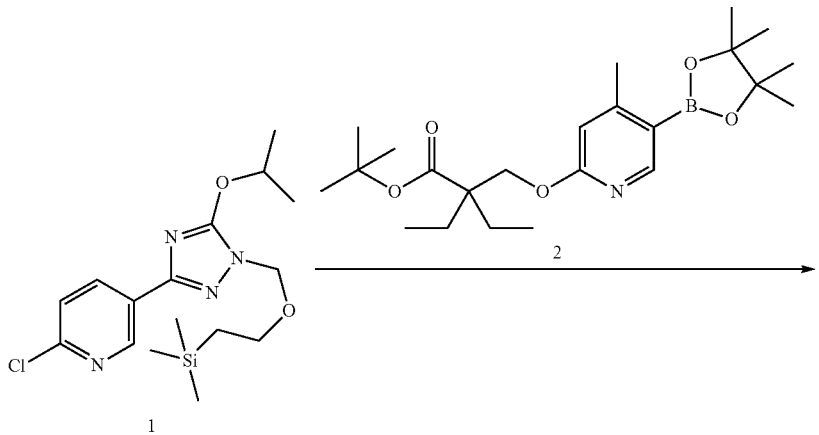

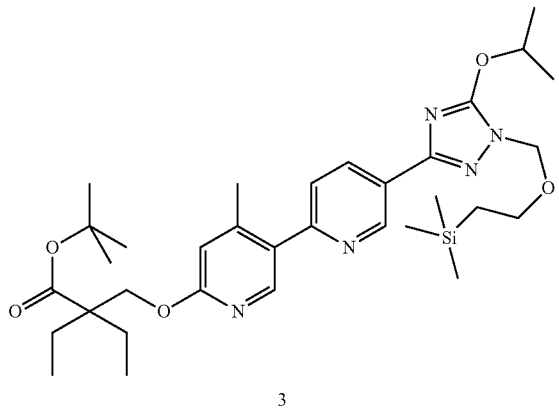

3

Starting from Compound 1 (230 mg) and Compound 2 (314 mg), a treatment was carried out in a manner similar to the Example 68-(6) to obtain Compound 3 (145 mg) as a colorless viscous material.
MS (m/z): 626 [M+H]$^+$ (2)

[Chemical Formula 315]

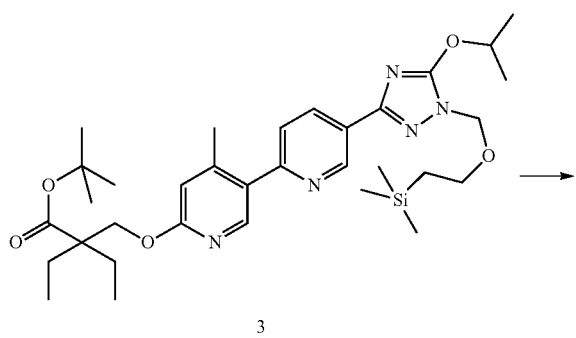

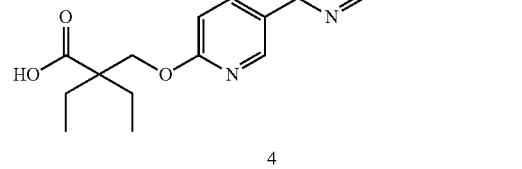

Starting from Compound 3 (144 mg), a treatment was carried out in a manner similar to the Example 87-(2) to obtain Compound 4 (65.8 mg) as a colorless solid.

MS (m/z): 440 [M+H]$^+$

Example 99

(1)

[Chemical Formula 316]

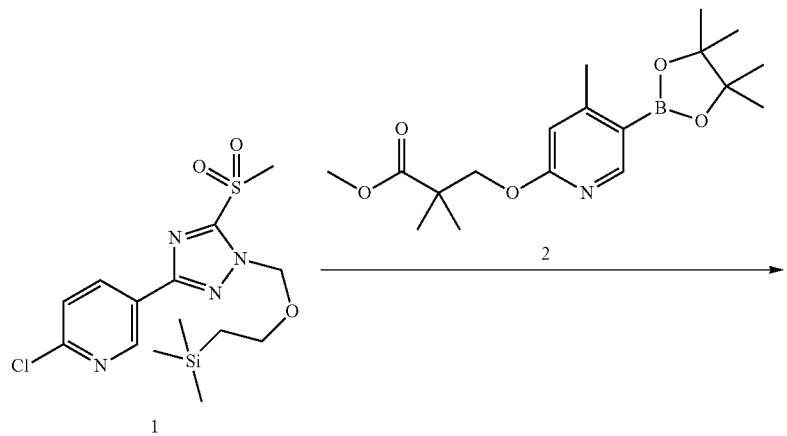

Starting from Compound 1 (1350 mg) and Compound 2 (1273 mg), a treatment was carried out in a manner similar to the Example 68-(6) to obtain Compound 3 (1610 mg) as a pale yellowish brown viscous material.

MS (m/z): 576 [M+H]$^+$ (2)
[Chemical Formula 317]
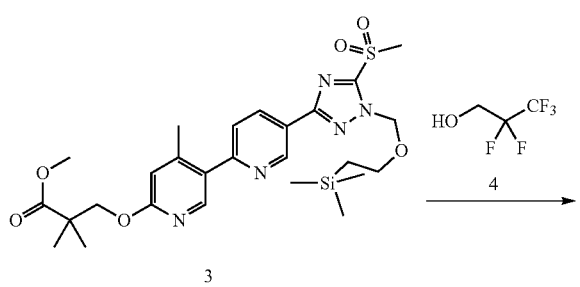
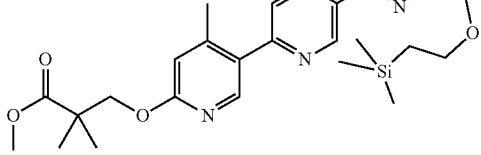
Starting from Compound 3 (400 mg) and Compound 4 (209 mg), a treatment was carried out in a manner similar to the Example 68-(5) to obtain Compound 5 (331 mg) as a pale yellowish brown viscous material.
MS (m/z): 646 [M+H]+
(3)
[Chemical Formula 318]
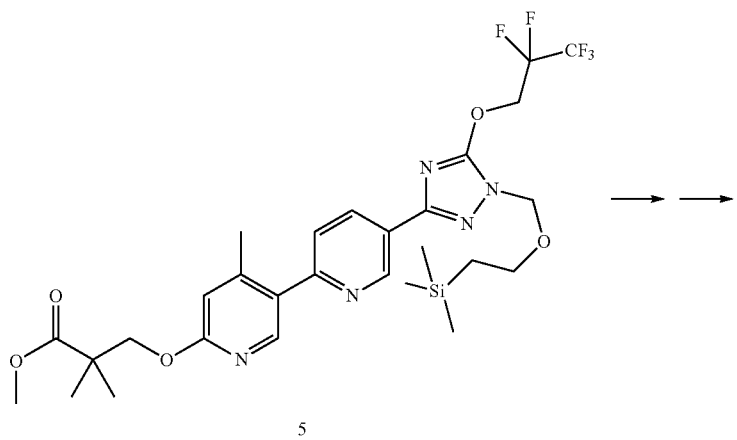
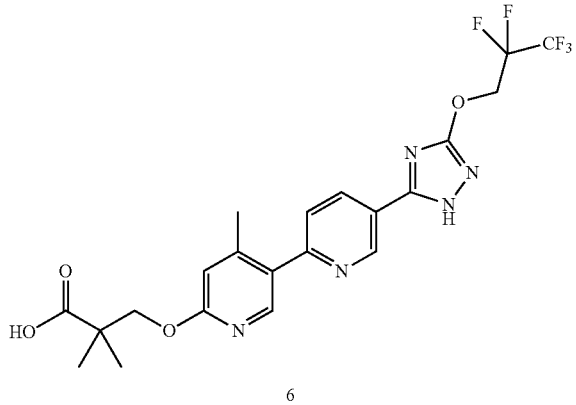
Starting from Compound 5 (329 mg), a treatment was carried out in a manner similar to the Example 68-(7) to obtain Compound 6 (208 mg) as a colorless solid.
MS (m/z): 502 [M+H]+

Example 100
(1)
[Chemical Formula 319]
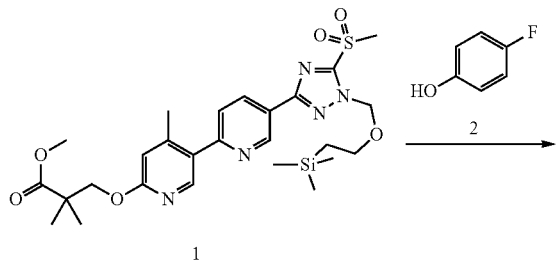
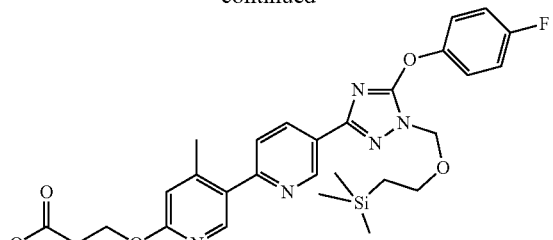
Starting from Compound 1 (400 mg) and Compound 2 (156 mg), a treatment was carried out in a manner similar to the Example 69-(2) to obtain Compound 3 (260 mg) as a colorless viscous material.
MS (m/z): 608 [M+H]⁺
(2)
[Chemical Formula 320]
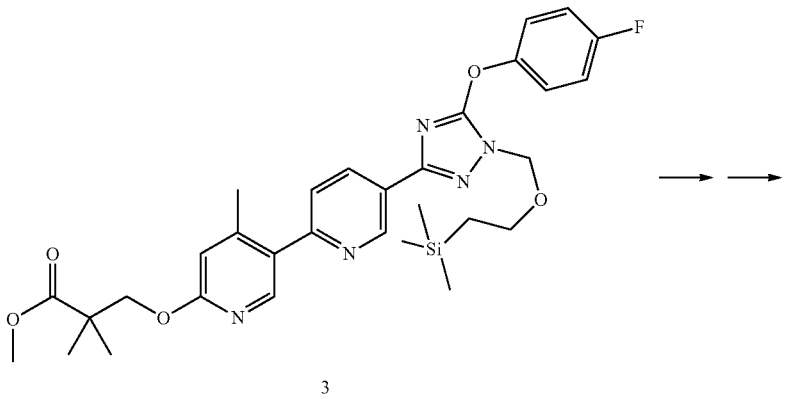
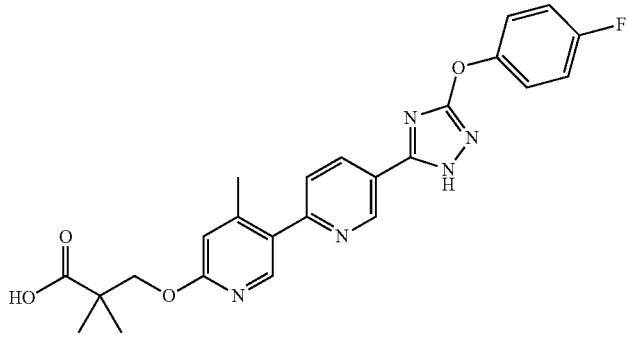
Starting from Compound 3 (258 mg), a treatment was carried out in a manner similar to the Example 68-(7) to obtain Compound 4 (175 mg) as a colorless solid.
MS (m/z): 464 [M+H]⁺

Example 101

(1)

[Chemical Formula 321]

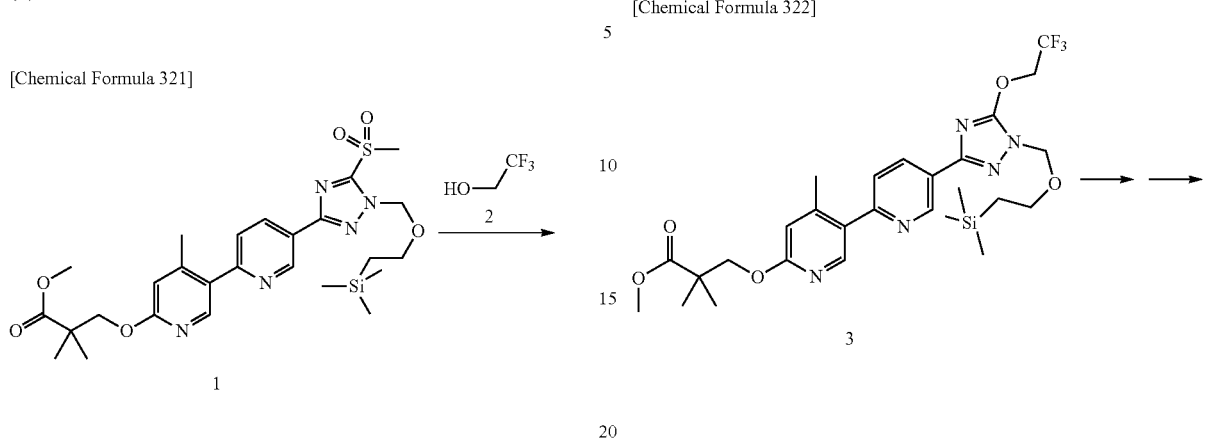

Starting from Compound 1 (400 mg) and Compound 2 (99 μL), a treatment was carried out in a manner similar to the Example 68-(5) to obtain Compound 3 (340 mg) as a colorless solid.

MS (m/z): 596 [M+H]+

(2)

[Chemical Formula 322]

Starting from Compound 3 (338 mg), a treatment was carried out in a manner similar to the Example 68-(7) to obtain Compound 4 (200 mg) as a colorless solid.

MS (m/z): 452 [M+H]+

Example 102

(1)

[Chemical Formula 323]

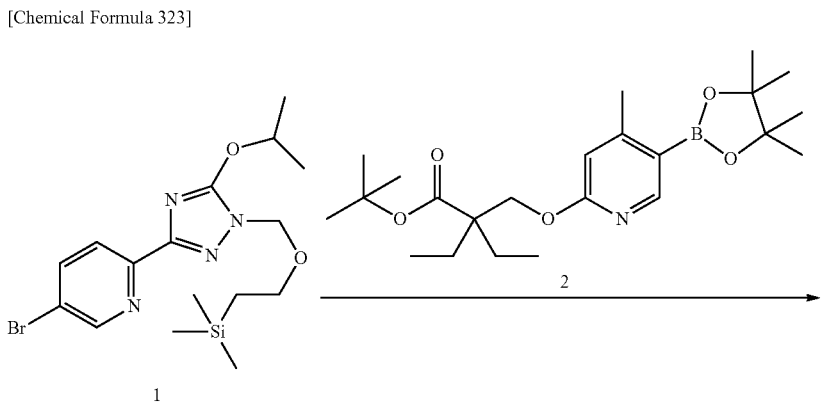

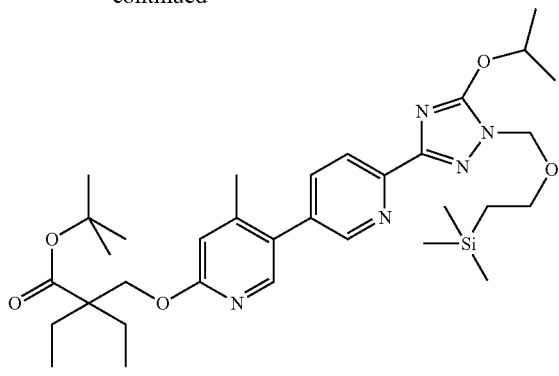

3

Starting from Compound 1 (260 mg) and Compound 2 (317 mg), a treatment was carried out in a manner similar to the Example 68-(6) to obtain Compound 3 (259 mg) as a pale yellow viscous material.

MS (m/z): 626 [M+H]$^+$ (2)

[Chemical Formula 324]

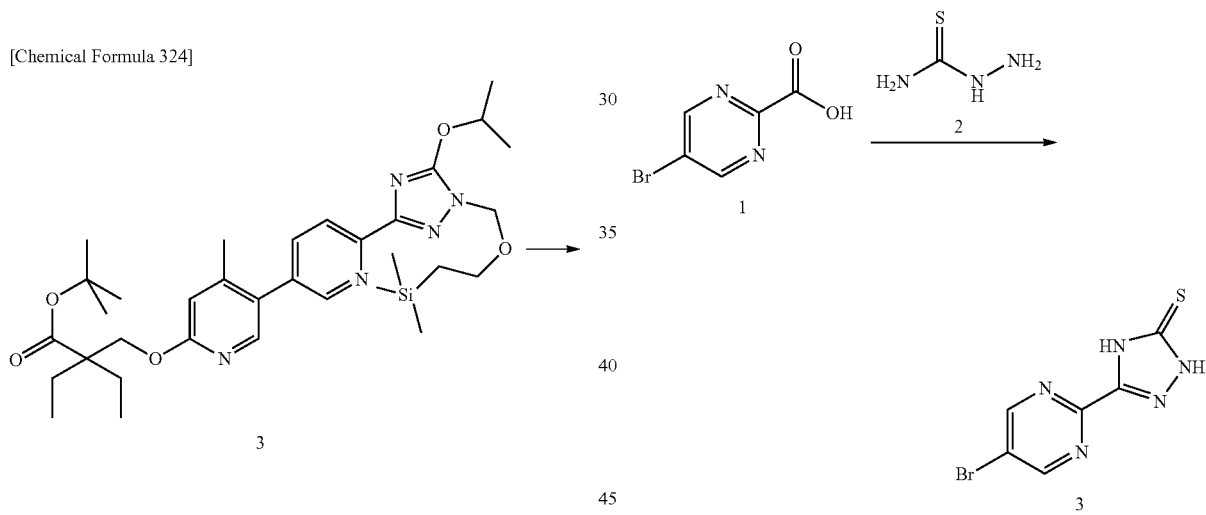

Starting from Compound 3 (258 mg), a treatment was carried out in a manner similar to the Example 87-(2) to obtain Compound 4 (143 mg) as a pale yellow solid.

MS (m/z): 440 [M+H]$^+$

Example 103

(1)

[Chemical Formula 325]

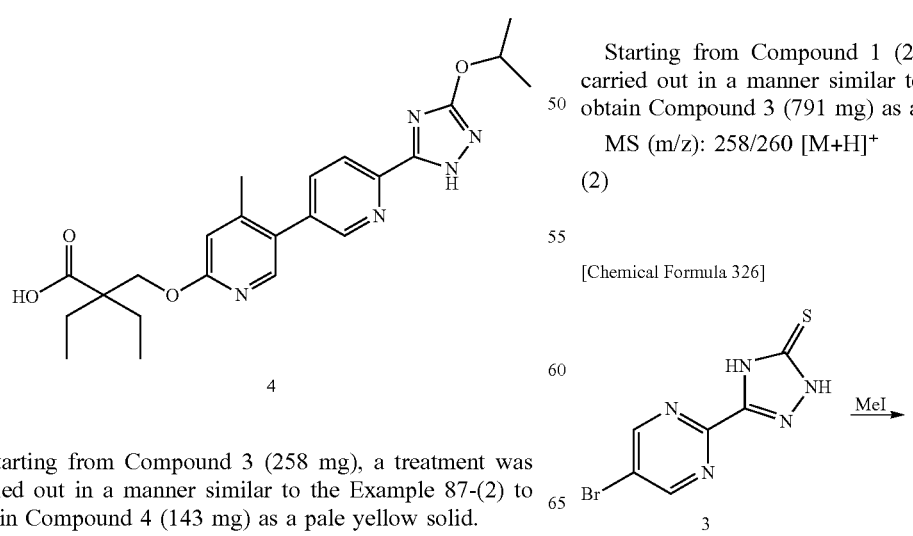

Starting from Compound 1 (2.03 g), a treatment was carried out in a manner similar to the Example 88-(1) to obtain Compound 3 (791 mg) as a yellowish brown solid.

MS (m/z): 258/260 [M+H]$^+$ (2)

[Chemical Formula 326]

-continued

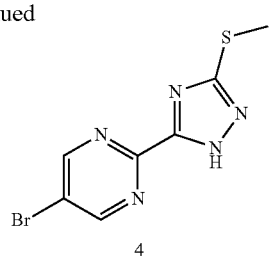

Starting from Compound 3 (785 mg), a treatment was carried out in a manner similar to the Example 88-(2) to obtain Compound 4 (593 mg) as a yellowish brown solid.

MS (m/z): 272/274 [M+H]$^+$ (3)

[Chemical Formula 327]

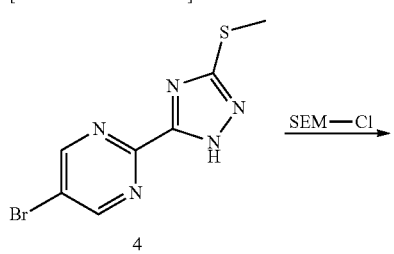

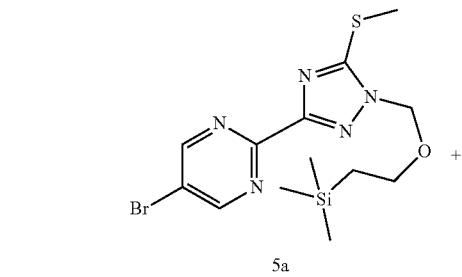

Starting from Compound 4 (560 mg), a treatment was carried out in a manner similar to the Example 61-(3) to obtain Compound 5a (131 mg) and Compound 5b (369 mg) as a colorless solid and a pale yellow solid respectively.

Compound 5a: MS (m/z): 402/404 [M+H]$^+$

Compound 5b: MS (m/z): 402/404 [M+H]$^+$ (4)

[Chemical Formula 328]

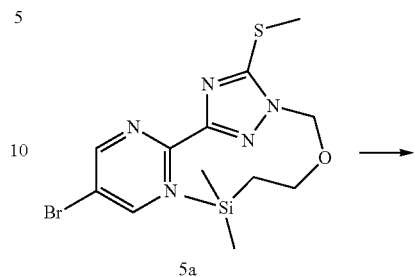

Starting from Compound 5a (127 mg), a treatment was carried out in a manner similar to the Example 79-(5) to obtain Compound 6a (110 mg) as a colorless solid.

MS (m/z): 434/436 [M+H]$^+$ (5)

[Chemical Formula 329]

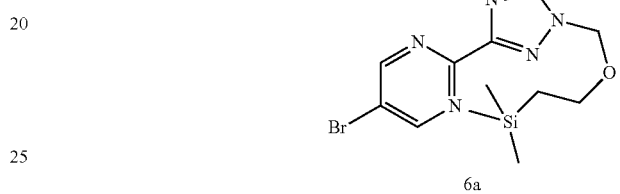

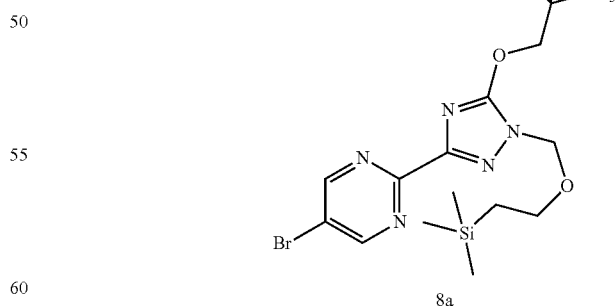

Starting from Compound 6a (108 mg) and Compound 7 (74.6 mg), a treatment was carried out in a manner similar to the Example 68-(5) to obtain Compound 8a (121 mg) as a colorless solid.

MS (m/z): 504/506 [M+H]$^+$ (6)
[Chemical Formula 330]
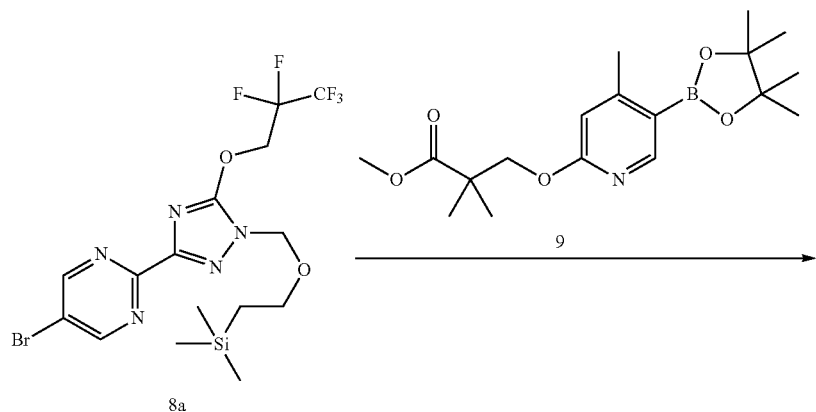
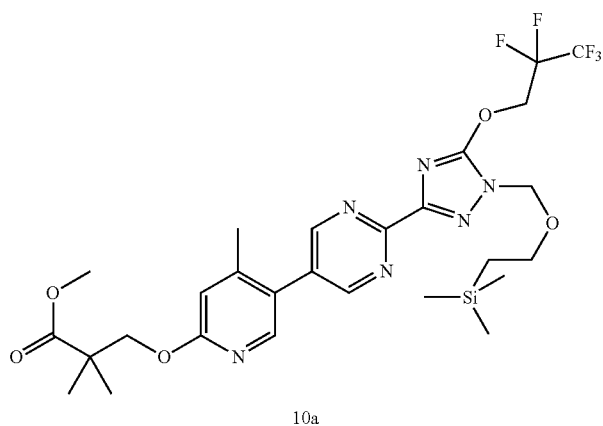
Starting from Compound 8a (120 mg) and Compound 9 (87.3 mg), a treatment was carried out in a manner similar to the Example 68-(6) to obtain Compound 10a (123 mg) as a colorless solid.
MS (m/z): 647 [M+H]$^+$
(7)
[Chemical Formula 331]
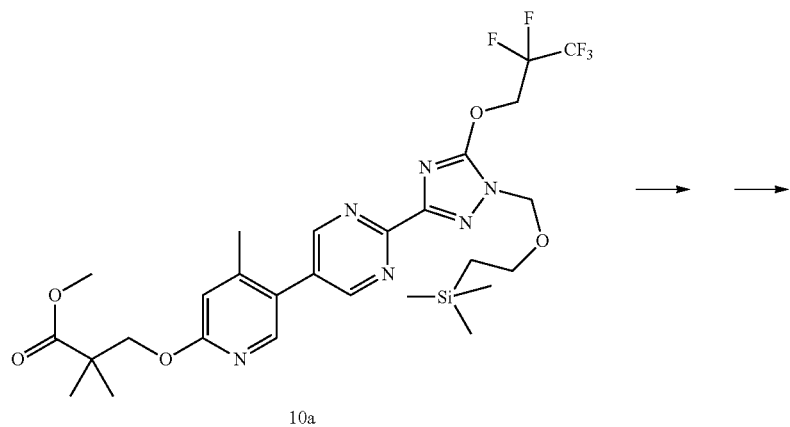

-continued

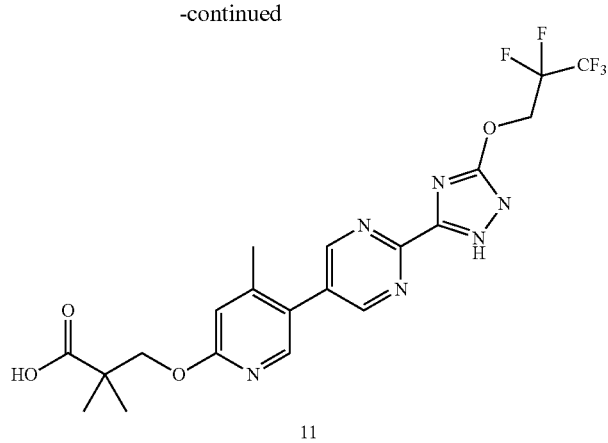

11

Starting from Compound 10a (123 mg), a treatment was carried out in a manner similar to the Example 68-(7) to obtain Compound 11 (84.2 mg) as a pale yellow solid.

MS (m/z): 503 [M+H]$^+$

Example 104

(1)

[Chemical Formula 332]

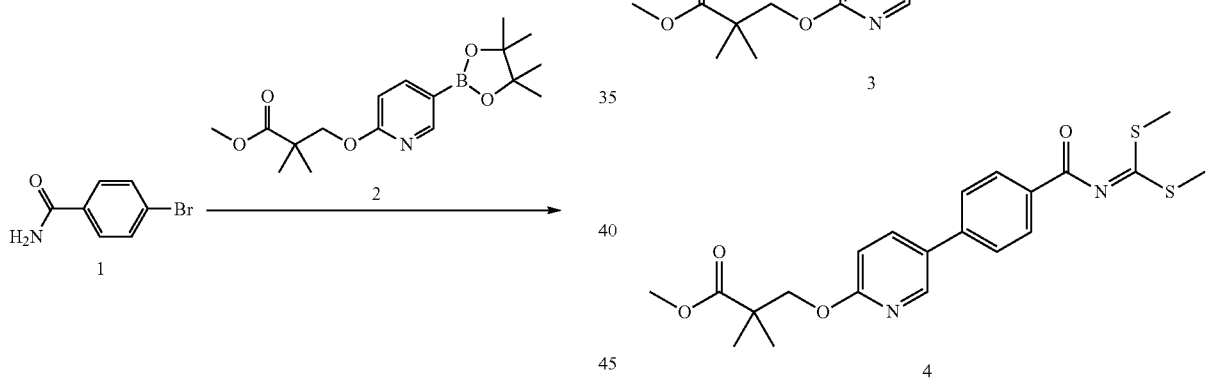

Starting from Compound 1 (3.00 g) and Compound 2 (6.03 g), a treatment was carried out in a manner similar to the Example 68-(6) to obtain Compound 3 (2.07 g) as a pale yellow powder.

MS (m/z): 329 [M+H]$^+$ (2)

[Chemical Formula 333]

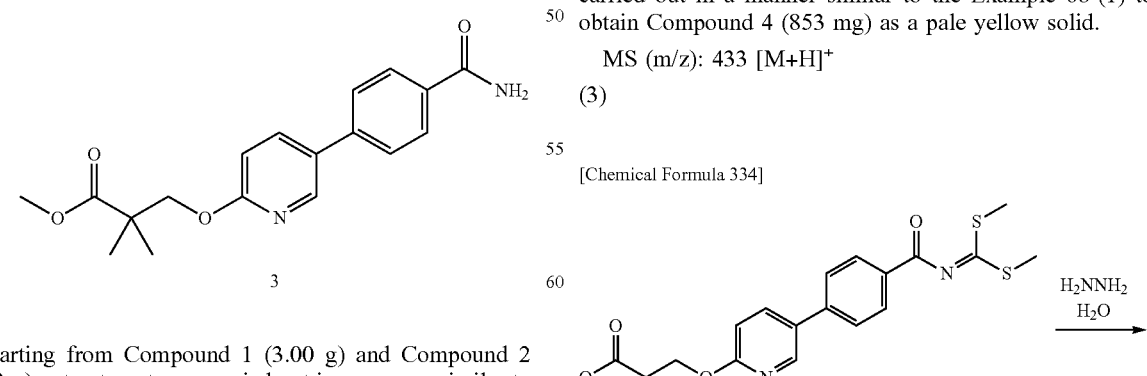

Starting from Compound 3 (2060 mg), a treatment was carried out in a manner similar to the Example 68-(1) to obtain Compound 4 (853 mg) as a pale yellow solid.

MS (m/z): 433 [M+H]$^+$ (3)

[Chemical Formula 334]

-continued

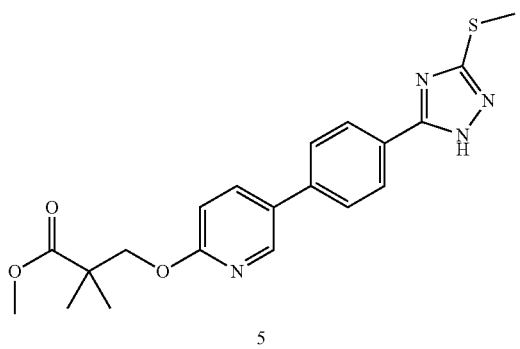

5

Starting from Compound 4 (850 mg), a treatment was carried out in a manner similar to the Example 68-(2) to obtain Compound 5 (480 mg) as a colorless solid.

MS (m/z): 399 [M+H]⁺

(4)

[Chemical Formula 335]

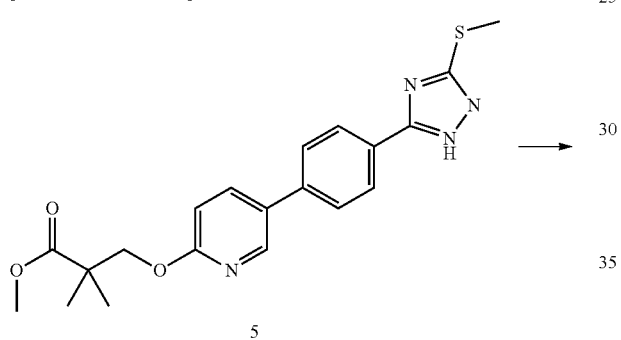

5

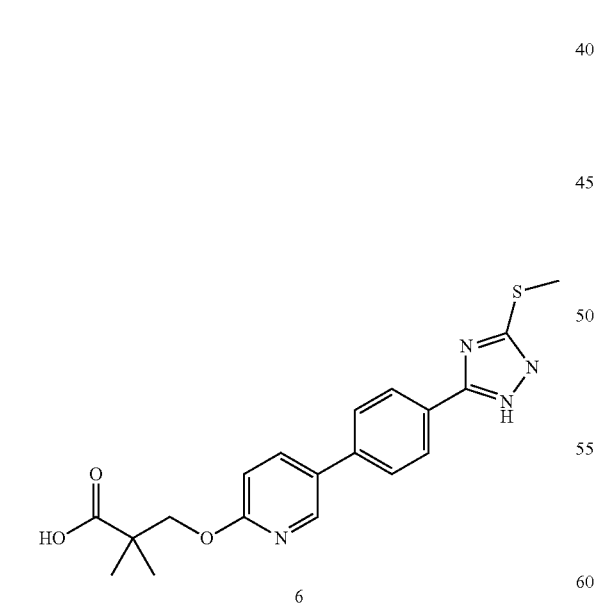

6

Starting from Compound 5 (64.0 mg), a treatment was carried out in a manner similar to the Example 61-(5) to obtain Compound 6 (52.4 mg) as a colorless solid.

MS (m/z): 385 [M+H]⁺

Example 105

(1)

[Chemical Formula 336]

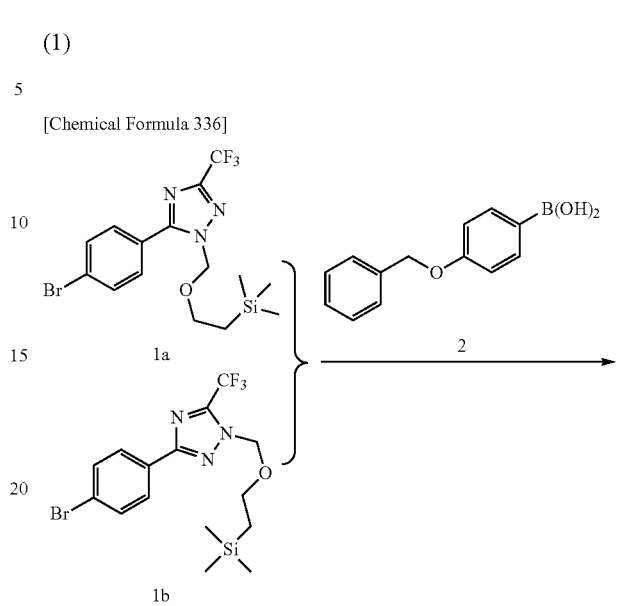

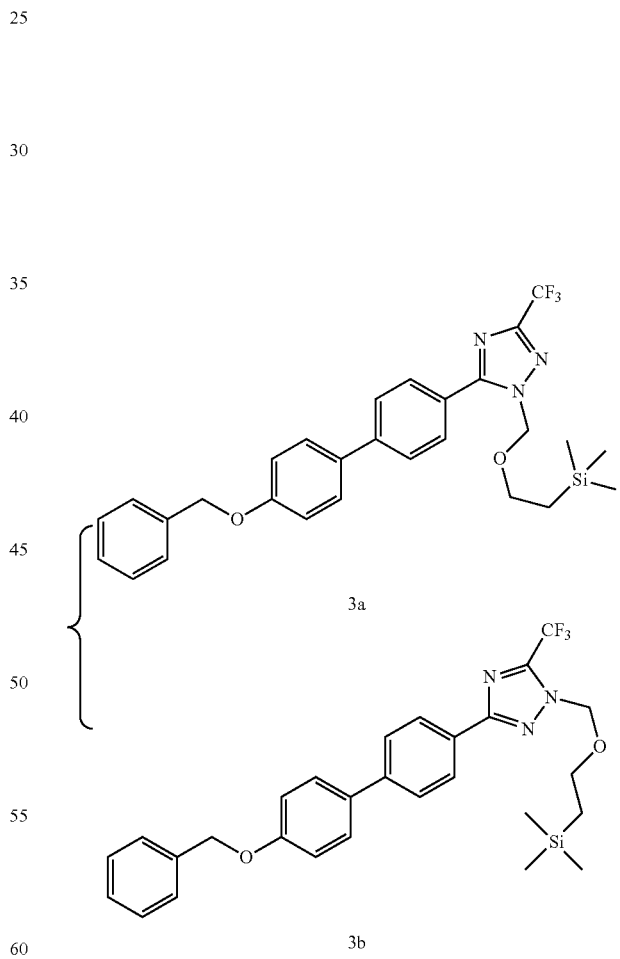

A reaction was carried out in a manner similar to the Example 53-(1) using a mixture of Compounds 1a and 1b (200 mg) and Compound 2 (216 mg) to obtain a mixture of Compounds 3a and 3b (243 mg) as a pale yellow solid.

MS (m/z): 526 [M+H]⁺

(2)
[Chemical Formula 337]
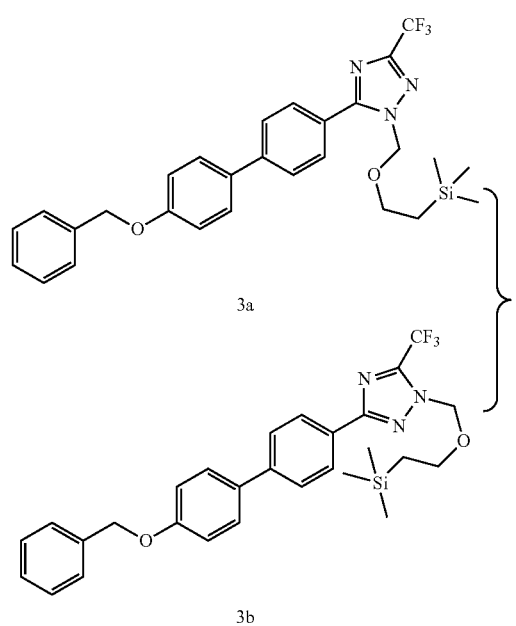
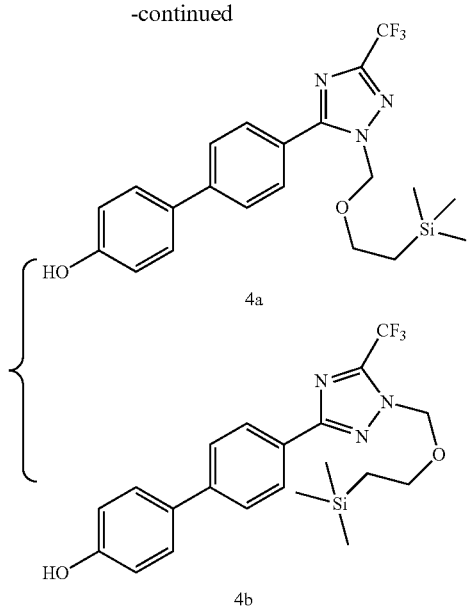
A reaction was carried out in a manner similar to the Example 53-(2) using the mixture of Compounds 3a and 3b (240 mg) to obtain a mixture of Compounds 4a and 4b (245 mg) as a pale yellow oil.
MS (m/z): 436 [M+H]$^+$
(3)
[Chemical Formula 338]
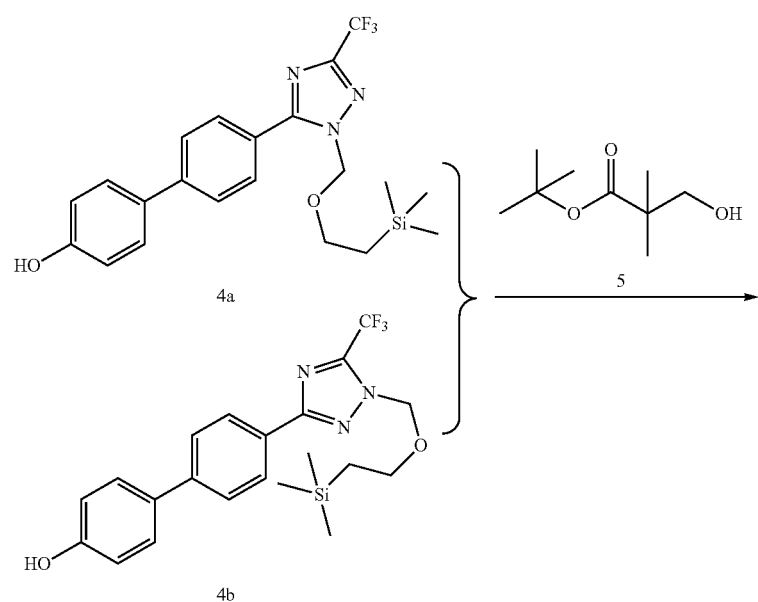

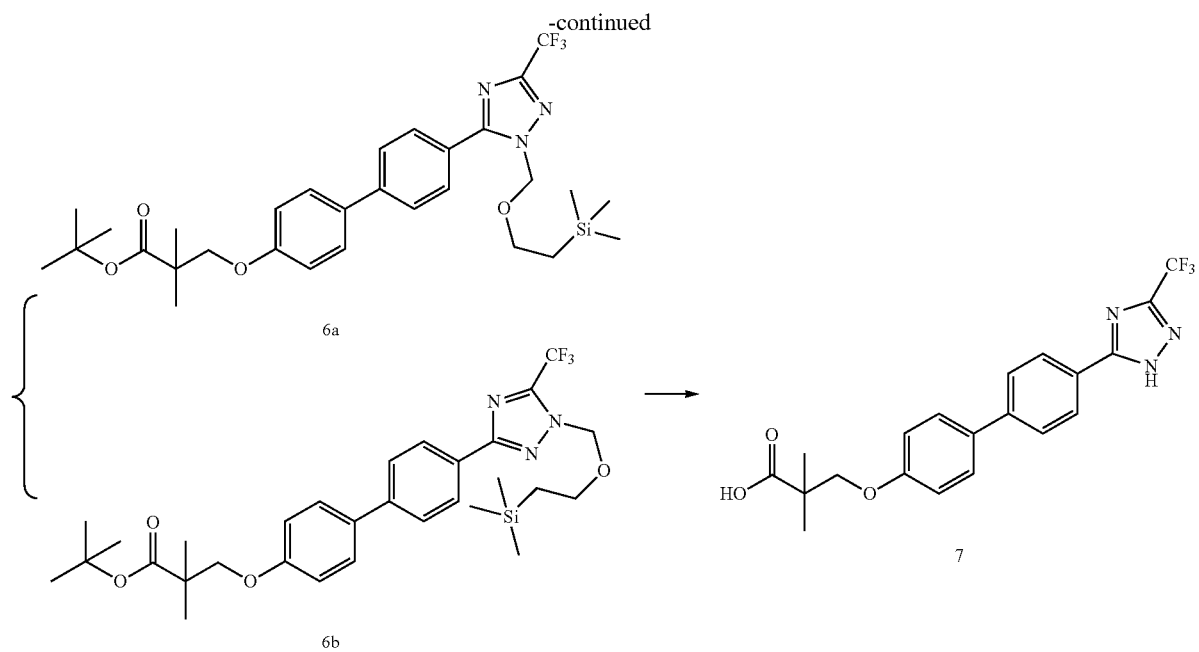
A reaction was carried out in a manner similar to the Example 55-(1) using the mixture of Compounds 4a and 4b (140 mg) and Compound 5 (140 mg) to obtain a mixture of Compounds 6a and 6b (111 mg) as a pale yellow oil. A reaction was carried out in a manner similar to the Example 51-(5) using the mixture of Compounds 6a and 6b (110 mg) to obtain Compound 7 (17 mg) as a white solid.
MS (m/z): 406 [M+H]$^+$
Example 106
(1)
[Chemical Formula 339]
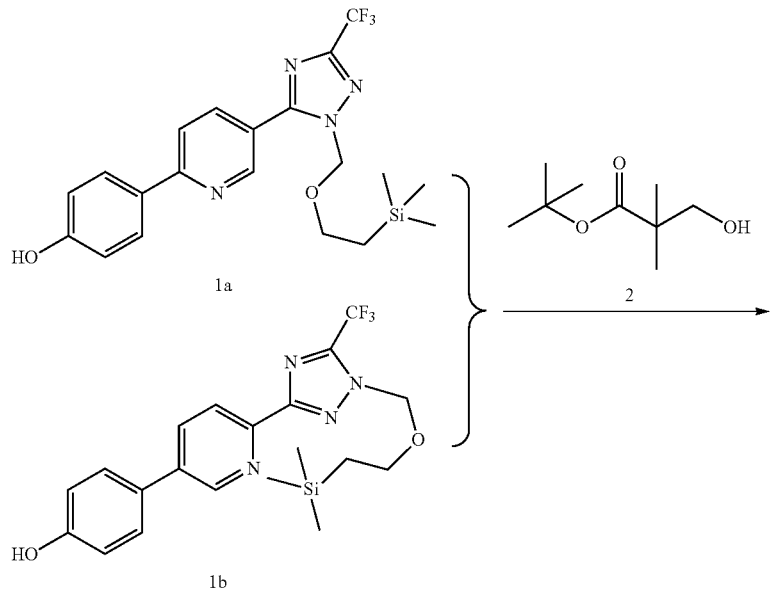

-continued
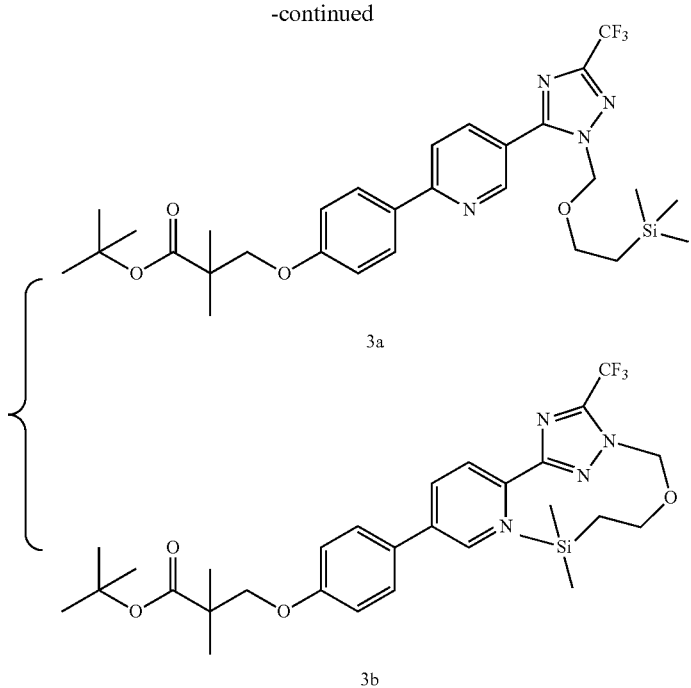
A reaction was carried out in a manner similar to the Example 55-(1) using a mixture of Compounds 1a and 1b (150 mg) and Compound 2 (120 mg) to obtain a mixture of Compounds 3a and 3b (140 mg) as a colorless solid.
MS (m/z): 593 [M+H]$^+$
(2)
[Chemical Formula 340]
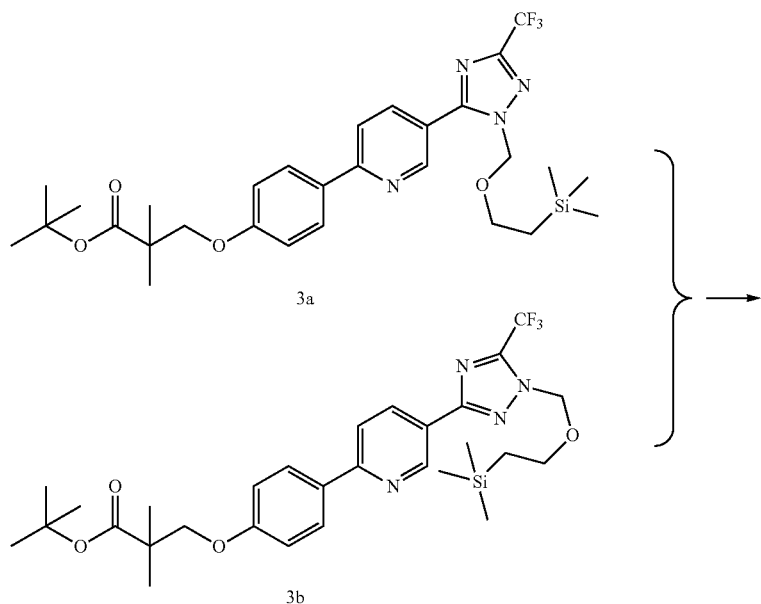

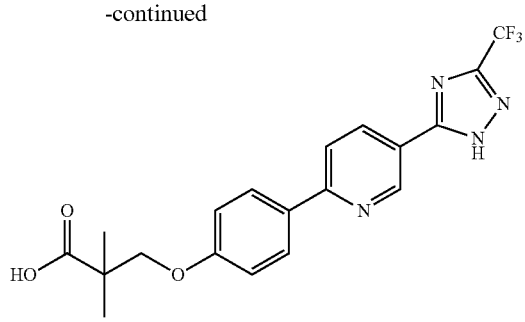

4

A reaction was carried out in a manner similar to the Example 51-(5) using the mixture of Compounds 3a and 3b (140 mg) to obtain Compound 4 (39 mg) as a colorless solid.

MS (m/z): 407 [M+H]$^+$

Example 107

(1)

[Chemical Formula 341]

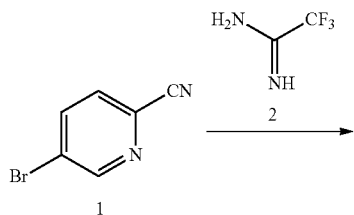

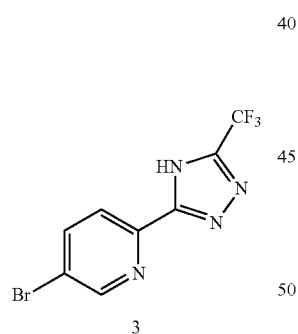

A mixture of Compound 1 (1.02 g), Compound 2 (1.10 g), copper(I) bromide (40 mg), cesium carbonate (5.45 g) and dimethylsulfoxide (20 mL) was stirred at 100° C. for 16 hours. To the reaction solution were added 1N hydrochloric acid and ethyl acetate, and the insoluble matter was removed by celite-filtration. The filtrate was extracted with ethyl acetate, and the extract was washed with water and saturated brine. The extract was dried over anhydrous magnesium sulfate and concentrated, and the residue was purified by silica gel column chromatography (n-hexane:ethyl acetate=90:10 to 70:30) to obtain Compound 3 (721 mg) as a colorless solid.

MS (m/z): 293/295 [M+H]$^+$ (2)

[Chemical Formula 342]

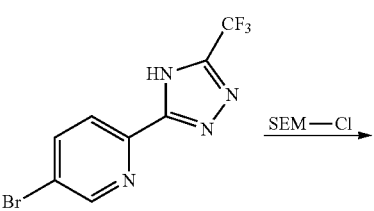

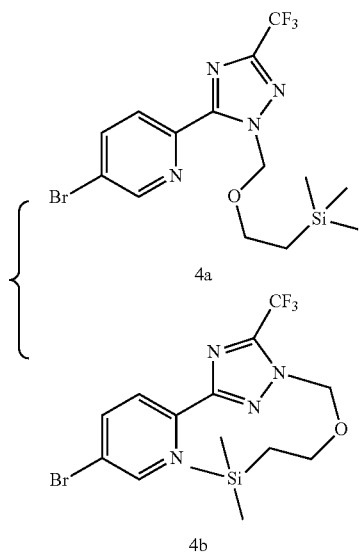

A reaction was carried out in a manner similar to the Example 50-(5) using Compound 3 (715 mg) to obtain Compound 4a (827 mg) and Compound 4b (144 mg) as colorless oils.

MS (m/z): 423/425 [M+H]$^+$ (3)

[Chemical Formula 343]

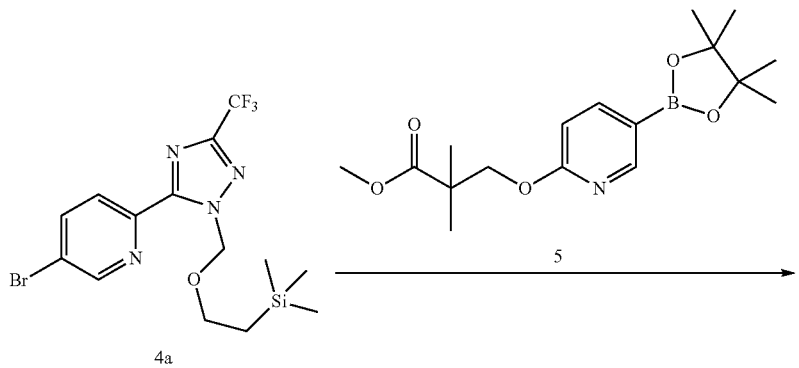

A reaction was carried out in a manner similar to the Example 50-(6) using Compound 4a (285 mg) and Compound 5 (362 mg) to obtain Compound 6a (294 mg) as a pale yellow viscous material.

MS (m/z): 552 [M+H]$^+$ (4)

[Chemcial Formula 344]

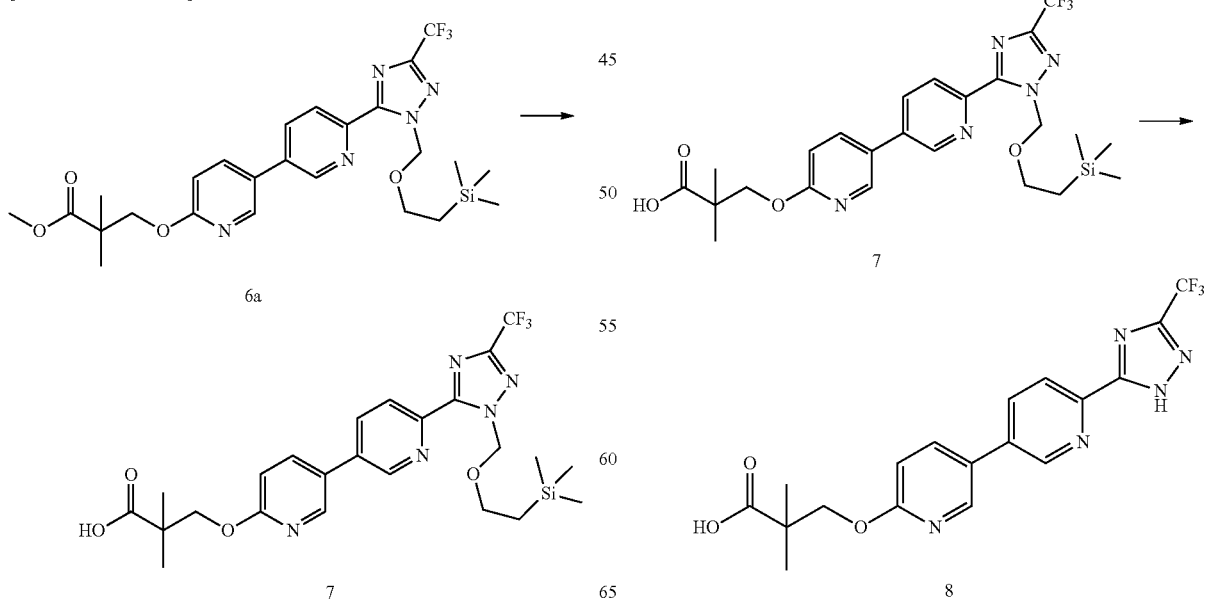

A reaction was carried out in a manner similar to the Example 52-(7) using Compound 6a (287 mg) to obtain Compound 7 (251 mg) as a pale yellow viscous material.

MS (m/z): 538 [M+H]$^+$ (5)

[Chemical Formula 345]

A reaction was carried out in a manner similar to the Example 52-(8) using Compound 7 (243 mg) to obtain Compound 8 (114 mg) as a colorless powder.

MS (m/z): 408 [M+H]$^+$

Example 108

(1)

[Chemical Formula 346]

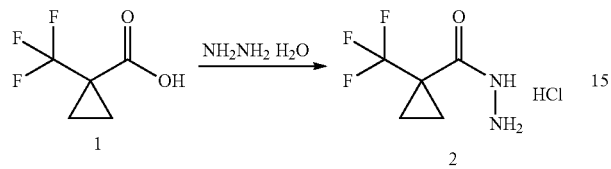

A solution of Compound 1 (5 g), EDC hydrochloride (7.46 g) and HOBt (5.26 g) in N,N-dimethylformamide (50 mL) was stirred at room temperature for 2 hours. This solution was added dropwise to a solution of hydrazine hydrate (3.16 mL) in acetonitrile (50 mL) at 0° C., and the mixture was stirred at the same temperature for 1 hour and further at room temperature for 30 minutes. The deposit was removed by filtration, and a saturated aqueous sodium hydrogen carbonate solution and ethyl acetate were added to the filtrate, and the mixture was extracted. The extract was washed with saturated brine and dried over anhydrous sodium sulfate, and the solvent was distilled off. To the residue were added 4N hydrogen chloride/dioxane (3 mL) and diethyl ether, and the mixture was stirred. The deposit was filtered and vacuum-dried to obtain Compound 2 (1335 mg) as a colorless powder.

MS (m/z): 169 [M+H]$^+$ (2)

[Chemical Formula 347]

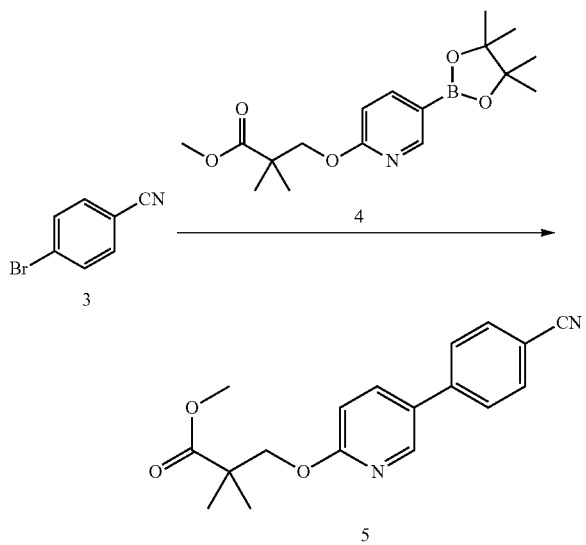

A reaction was carried out in a manner similar to the Example 50-(6) using Compound 3 (4 g) and Compound 4 (7.37 g) to obtain Compound 5 (6.26 g) as a colorless solid.

MS (m/z): 311 [M+H]$^+$ (3)

[Chemical Formula 348]

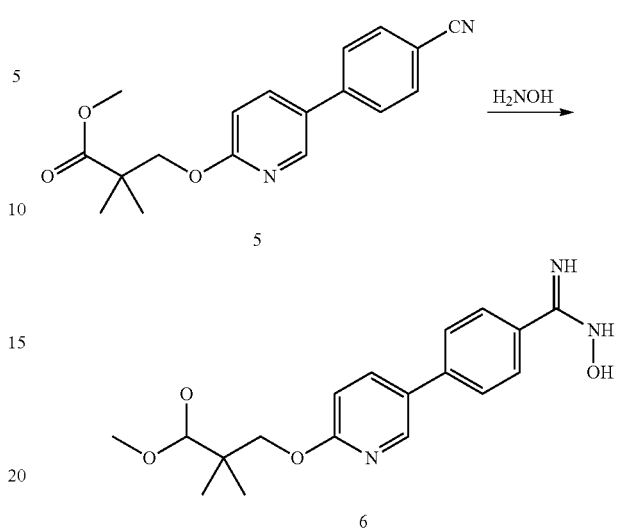

A mixture of Compound 5 (6.24 g), a 50% aqueous hydroxyamine solution (26.6 g), methanol (45 mL) and tetrahydrofuran (45 mL) was stirred at 80° C. for 2 hours. After the solvent was distilled off, chloroform and water were added and the mixture was extracted. The extract was washed with saturated brine, and dried over anhydrous magnesium sulfate. The solvent was distilled off and vacuum-dried to obtain Compound 6 (6.93 g) as a colorless solid.

MS (m/z): 344 [M+H]$^+$ (4)

[Chemical Formula 349]

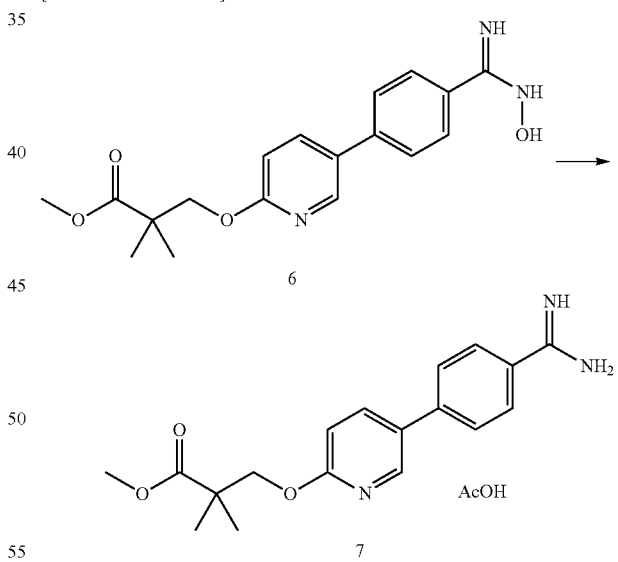

To a solution of Compound 6 (6.92 g) in acetic acid (20 mL) was added acetic anhydride (3.34 mL), and the mixture was stirred at room temperature for 2 hours. The solvent was distilled off, the residue was dissolved in methanol (100 mL), 10% palladium-carbon was added under a nitrogen stream, and the mixture was stirred under a hydrogen atmosphere at room temperature for 6 hours. The catalyst was filtered off by a membrane-filter, the solvent was distilled off, and subsequently diethyl ether was added. The deposit was collected by filtration and vacuum-dried to obtain Compound 7 (6.71 g) as a pale yellow solid.

MS (m/z): 328 [M+H]$^+$ (5)

[Chemical Formula 350]

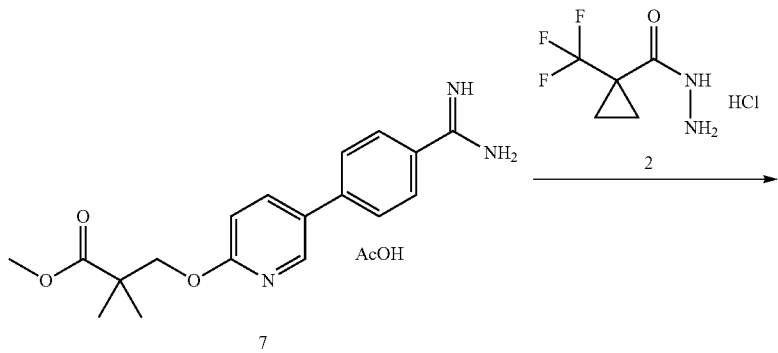

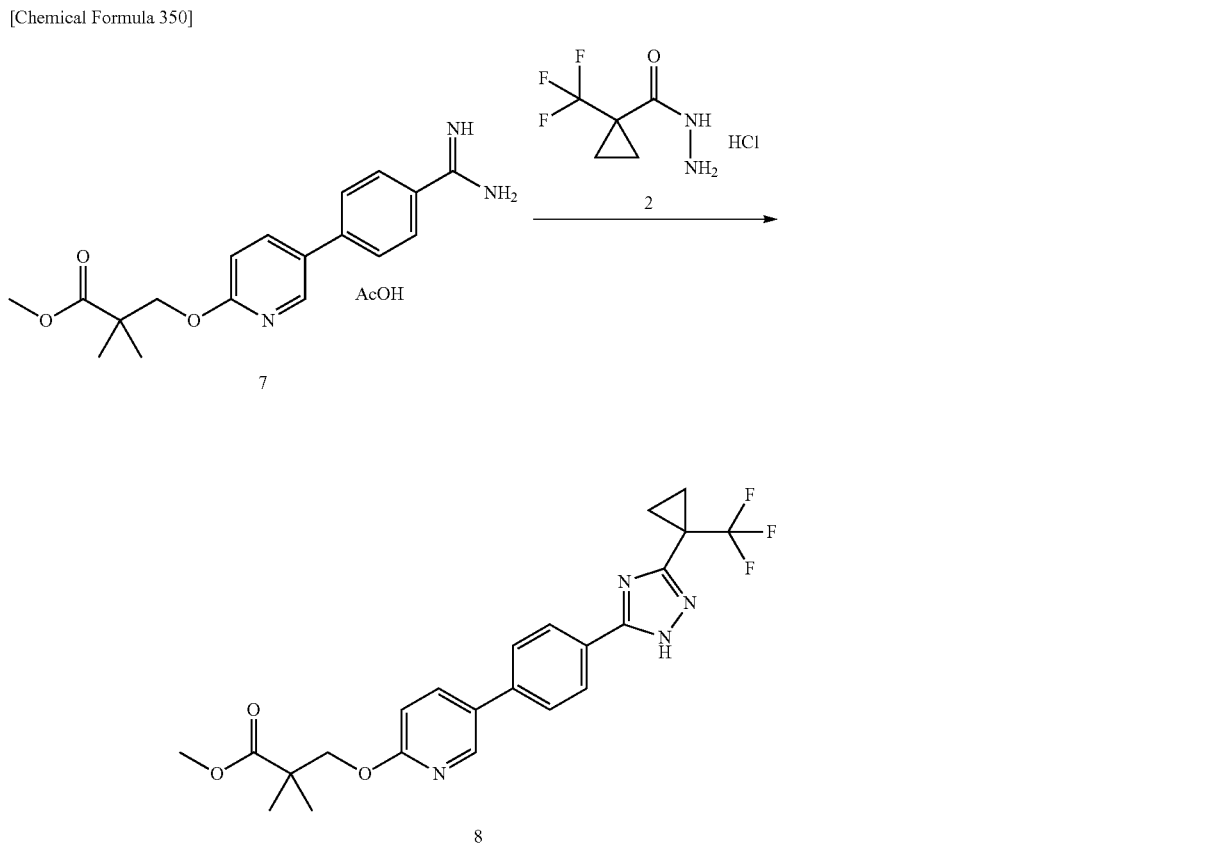

A mixture of Compound 7 (400 mg), Compound 2 (211 mg), sodium methylate (167 mg) and ethanol (6 mL) was stirred at 100° C. for 17 hours. The temperature of the reaction solution was brought to room temperature, and ethyl acetate, 1N hydrochloric acid and water were added, and the reaction solution was extracted. After the extract was washed with saturated brine and passed through the phase separator, the solvent was distilled off. The residue was purified by silica gel column chromatography (n-hexane:ethyl acetate=70:30 to 45:55) to obtain Compound 8 (276 mg) as a colorless oil.

MS (m/z): 461 [M+H]$^+$ (6)

[Chemical Formula 351]

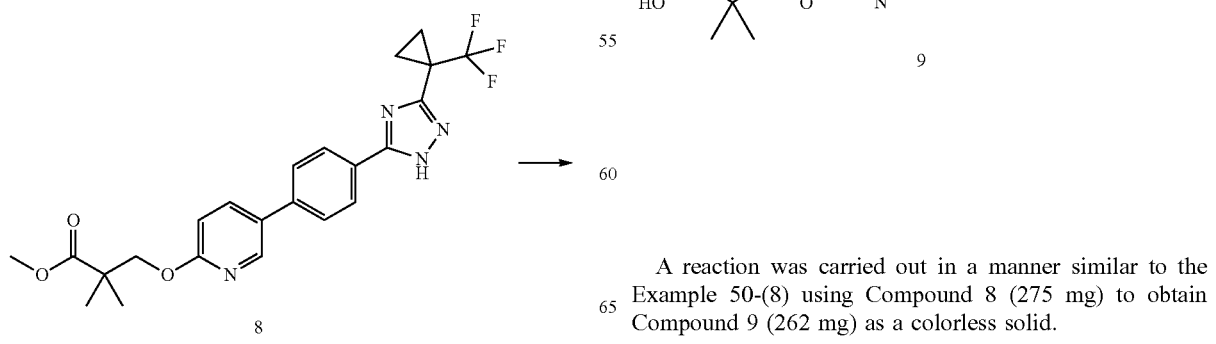

A reaction was carried out in a manner similar to the Example 50-(8) using Compound 8 (275 mg) to obtain Compound 9 (262 mg) as a colorless solid.

MS (m/z): 447 [M+H]$^+$

Example 109

(1)

[Chemical Formula 352]

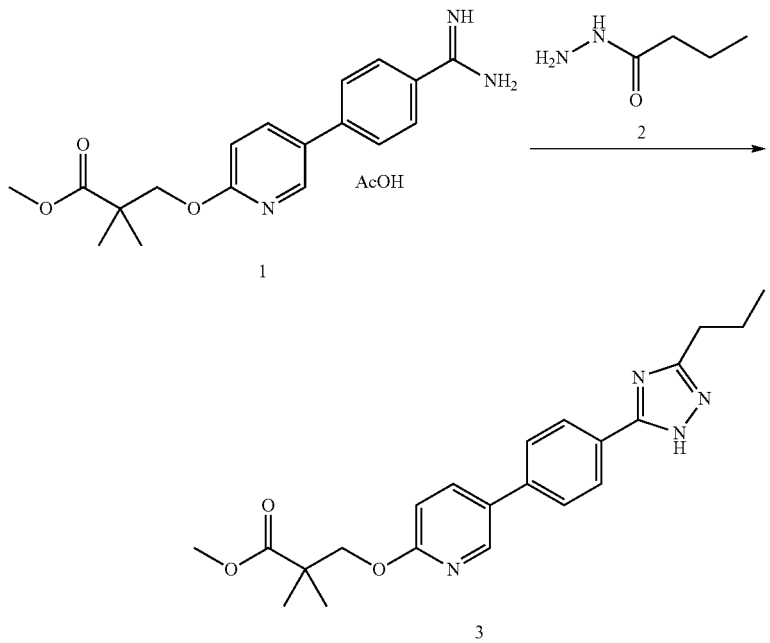

A mixture of Compound 1 (400 mg), Compound 2 (127 mg), sodium methylate (112 mg), ammonium chloride (55 mg) and N,N-dimethylformamide (6 mL) was stirred at 100° C. for 25 hours. The reaction solution was cooled to room temperature, and ethyl acetate, a saturated aqueous ammonium chloride solution and water were added, and the mixture was extracted. After the extract was washed with saturated brine and passed through the phase separator, the solvent was distilled off. The residue was purified by silica gel column chromatography (n-hexane:ethyl acetate=70:30 to 45:55) to obtain Compound 3 (112 mg) as a pale yellow viscous material.

MS (m/z): 395 $[M+H]^+$ (2)

[Chemical Formula 353]

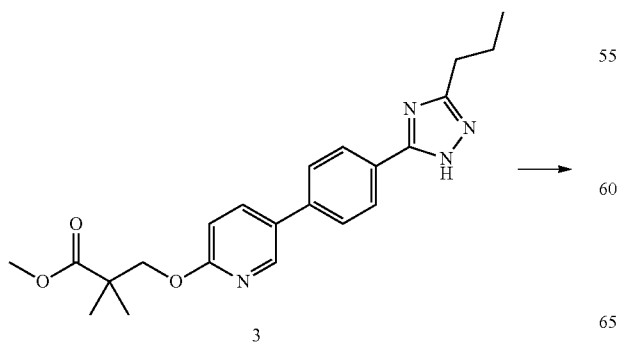

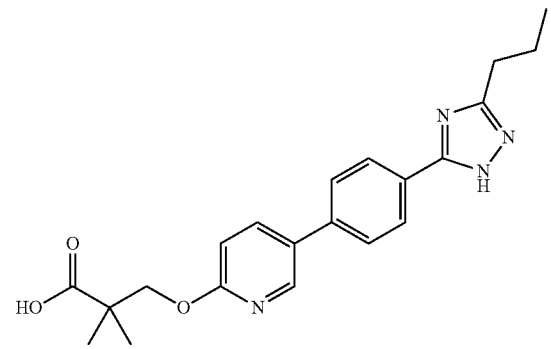

A reaction was carried out in a manner similar to the Example 50-(8) using Compound 3 (112 mg) to obtain Compound 4 (72 mg) as a pale yellow solid.

MS (m/z): 381 $[M+H]^+$

Example 110
(1)
[Chemical Formula 354]
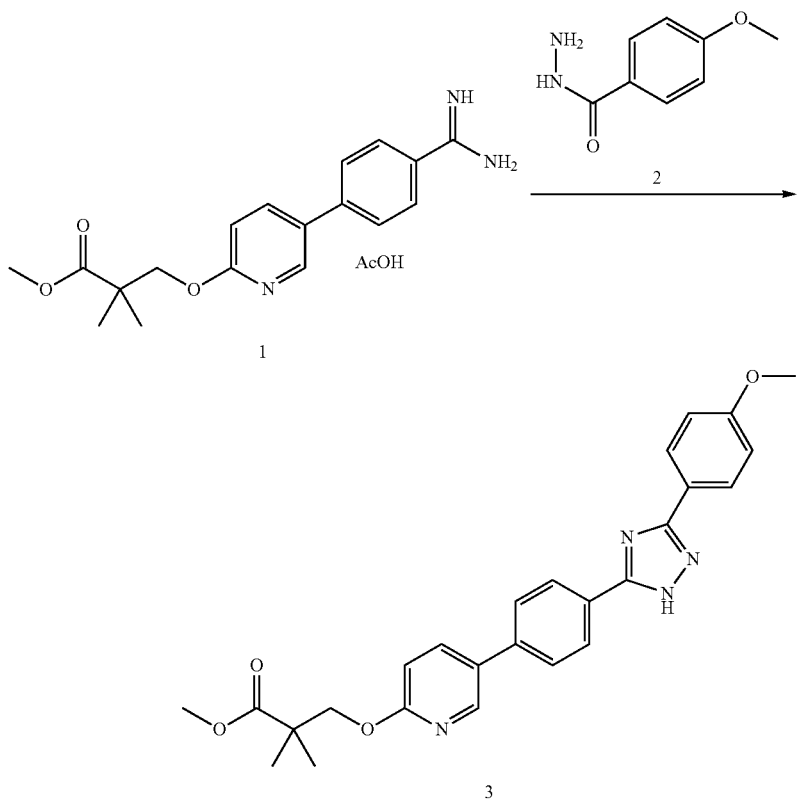
A reaction was carried out in a manner similar to the Example 109-(1) using Compound 1 (200 mg) and Compound 2 (103 mg) to obtain Compound 3 (65 mg) as a pale yellow viscous material.
MS (m/z): 459 [M+H]$^+$
(2)
[Chemical Formula 355]
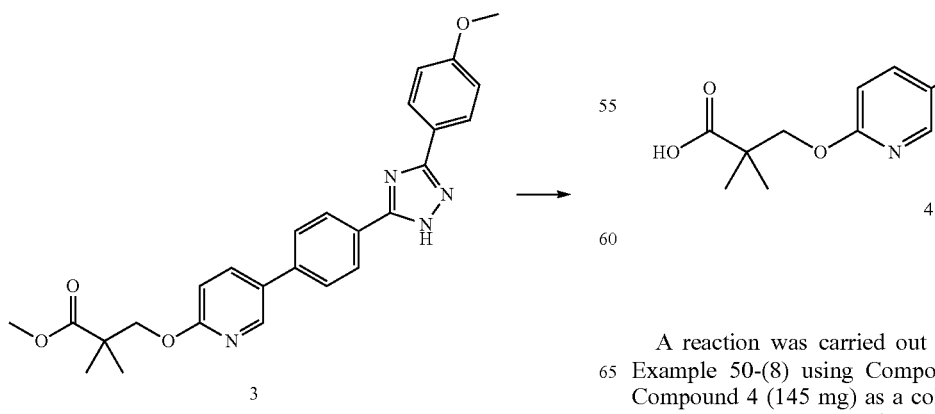
A reaction was carried out in a manner similar to the Example 50-(8) using Compound 3 (180 mg) to obtain Compound 4 (145 mg) as a colorless solid.
MS (m/z): 445 [M+H]$^+$

Example 111
(1)
[Chemical Formula 356]
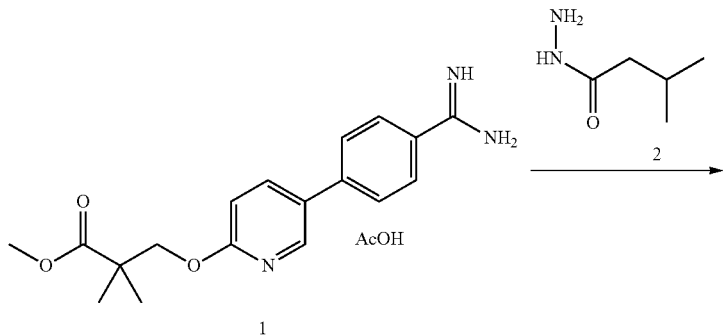
A reaction was carried out in a manner similar to the Example 109-(1) using Compound 1 (400 mg) and Compound 2 (180 mg) to obtain Compound 3 (234 mg) as a pale yellow viscous material.
MS (m/z): 409 [M+H]$^+$
(2)
[Chemical Formula 357]
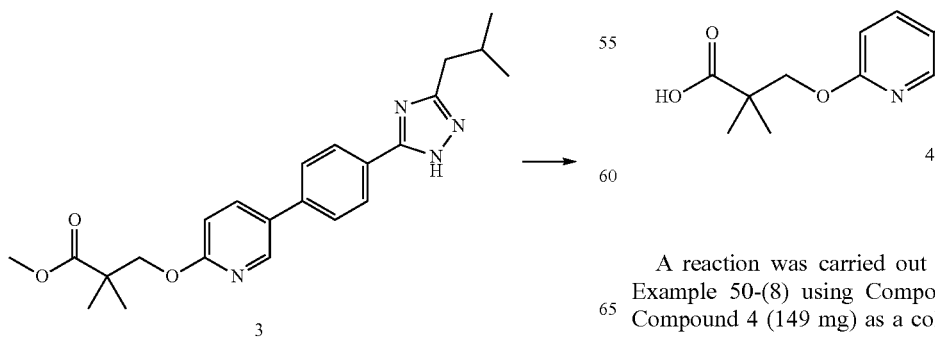
A reaction was carried out in a manner similar to the Example 50-(8) using Compound 3 (218 mg) to obtain Compound 4 (149 mg) as a colorless solid.
MS (m/z): 395 [M+H]$^+$ Example 112

(1)

[Chemical Formula 358]

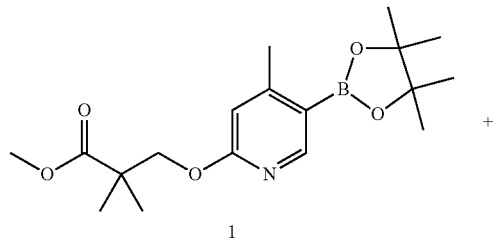

1

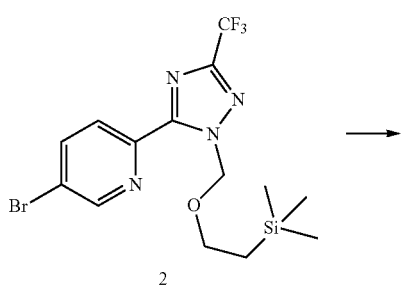

2

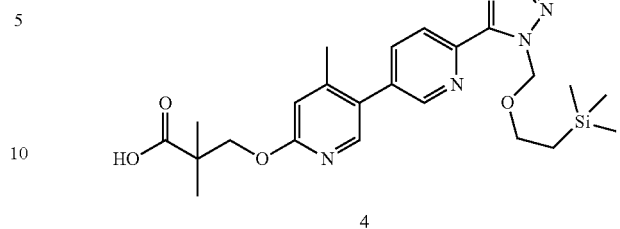

4

A reaction was carried out in a manner similar to the Example 50-(6) using Compound 1 (297 mg) and Compound 2 (300 mg) to obtain Compound 3 (292 mg) as a colorless viscous material.

MS (m/z): 566 [M+H]$^+$ (2)

[Chemical Formula 359]

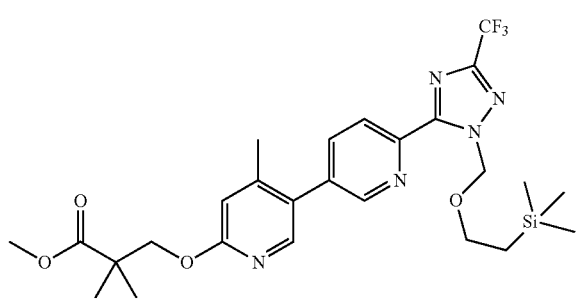

3

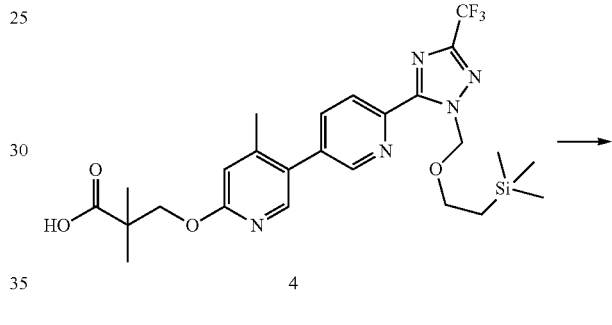

4

A reaction was carried out in a manner similar to the Example 52-(7) using Compound 3 (288 mg) to obtain Compound 4 (305 mg) as a colorless viscous material.

MS (m/z): 552 [M+H]$^+$ (3)

[Chemical Formula 360]

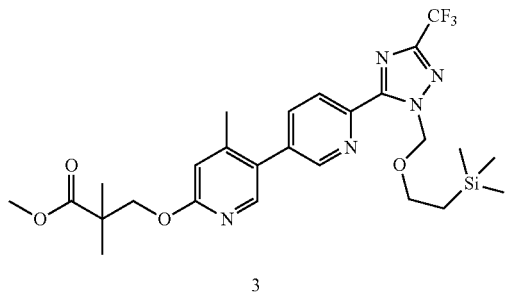

3

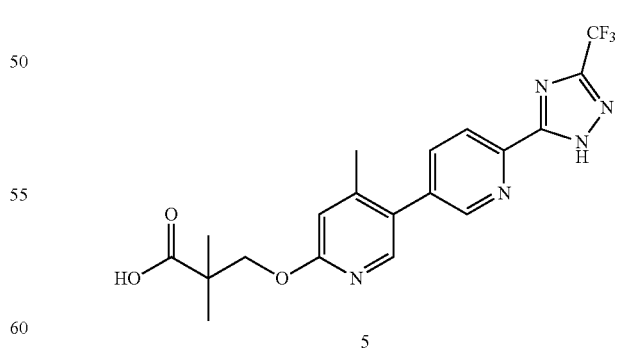

5

A reaction was carried out in a manner similar to the Example 52-(8) using Compound 4 (280 mg) to obtain Compound 5 (149 mg) as a colorless solid.

MS (m/z): 422 [M+H]$^+$

Example 113

(1)

[Chemical Formula 361]

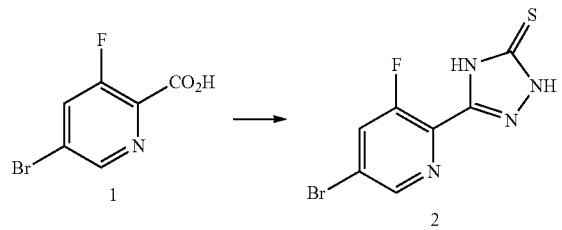

A reaction was carried out in a manner similar to the Example 85-(1) using Compound 1 (5.3 g) to obtain Compound 2 (4.05 g) as a beige solid.

MS (m/z): 275/277 [M+H]$^+$ (2)

[Chemical Formula 362]

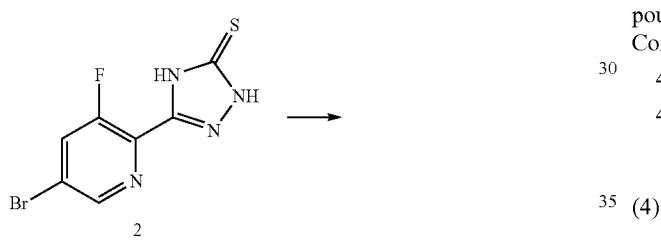

A reaction was carried out in a manner similar to the Example 85-(2) using Compound 2 (4.03 g) to obtain Compound 3 (3.13 g) as a yellow solid.

MS (m/z): 289/291 [M+H]$^+$ (3)

[Chemical Formula 363]

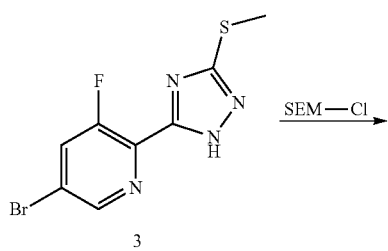

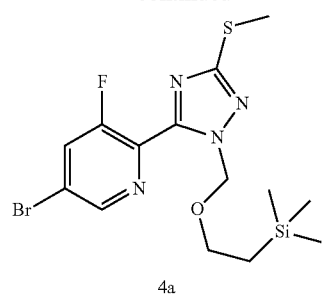

4a

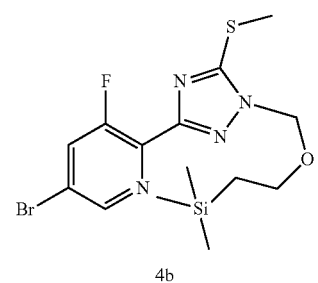

4b

A reaction was carried out in a manner similar to the Example 50-(5) using Compound 3 (3.1 g) to obtain Compound 4a (2.55 g) as a colorless viscous material and Compound 4b (1.70 g) as a colorless solid.

4a: MS (m/z): 419/421 [M+H]$^+$

4b: MS (m/z): 419/421 [M+H]$^+$ (4)

[Chemical Formula 364]

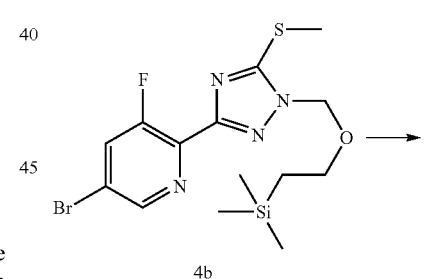

4b

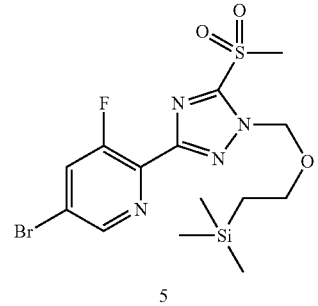

5

A reaction was carried out in a manner similar to the Example 68-(4) using Compound 4b (1.62 g) to obtain Compound 5 (1.355 g) as a colorless solid.

MS (m/z): 451/453 [M+H]$^+$ (5)

[Chemical Formula 365]

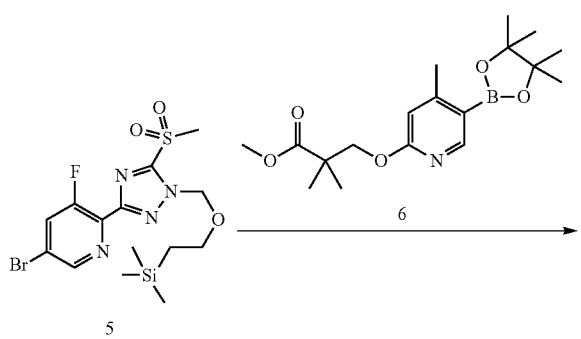

5

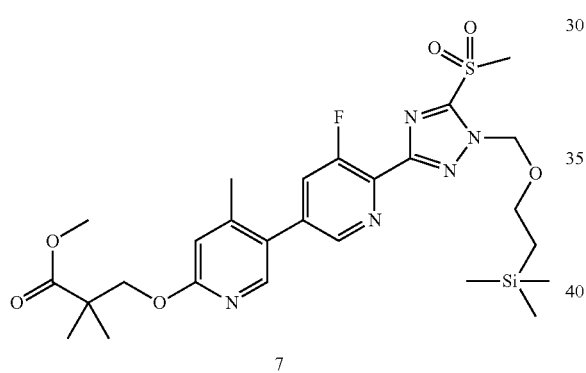

7

A reaction was carried out in a manner similar to the Example 50-(6) using Compound 5 (300 mg) and Compound 6 (255 mg) to obtain Compound 7 (347 mg) as a colorless solid.

MS (m/z): 594 [M+H]⁺

(6)

[Chemical Formula 366]

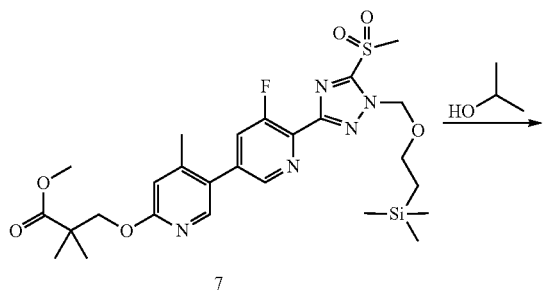

7

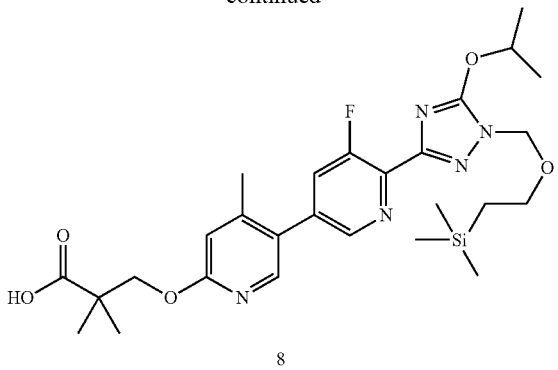

8

To a solution of isopropanol (77 mg) in tetrahydrofuran (3 mL) was added 60% sodium hydride (35 mg) at 0° C., and the mixture was stirred for 10 minutes. To this was added a solution of Compound 7 (345 mg) in tetrahydrofuran (3 mL), and the mixture was stirred for 10 minutes. A 2N aqueous sodium hydroxide solution (2.9 mL) and methanol (3 mL) were then added, and the mixture was stirred at room temperature overnight. The reaction solution was concentrated, the residue was neutralized with 1N hydrochloric acid, and the mixture was extracted with ethyl acetate. The extract was washed with saturated brine, and dried over anhydrous magnesium sulfate. After the extract was concentrated under reduced pressure, the obtained residue was purified by silica gel column chromatography (n-hexane:ethyl acetate=100:0 to 90:10) to obtain Compound 8 (279 mg) as a colorless viscous material.

MS (m/z): 560 [M+H]⁺

(7)

[Chemical Formula 367]

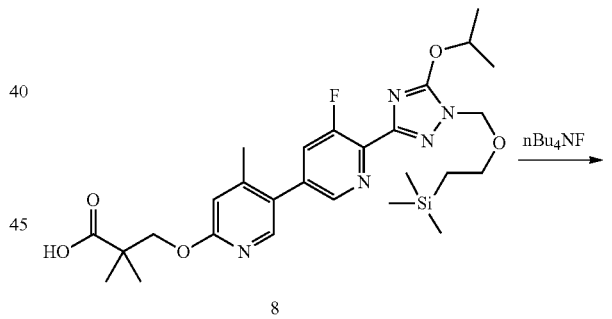

8

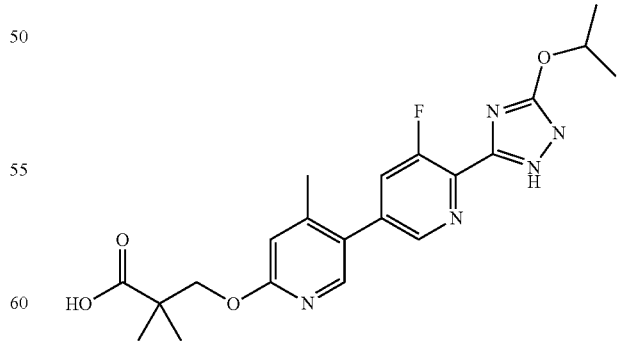

9

A reaction was carried out in a manner similar to the Example 88-(7) using Compound 8 (278 mg) to obtain Compound 9 (60 mg) as a colorless solid.

MS (m/z): 430 [M+H]⁺

Example 114
(1)
[Chemical Formula 368]
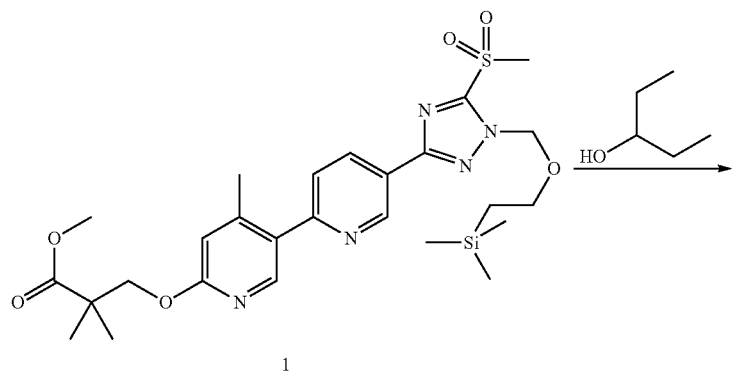
Starting from Compound 1 (389 mg) and 3-pentanol (120 mg), a reaction was carried out in a manner similar to the Example 113-(6) to obtain Compound 2 (292 mg) as a colorless viscous material.
MS (m/z): 570 [M+H]$^+$
(2)
[Chemical Formula 369]
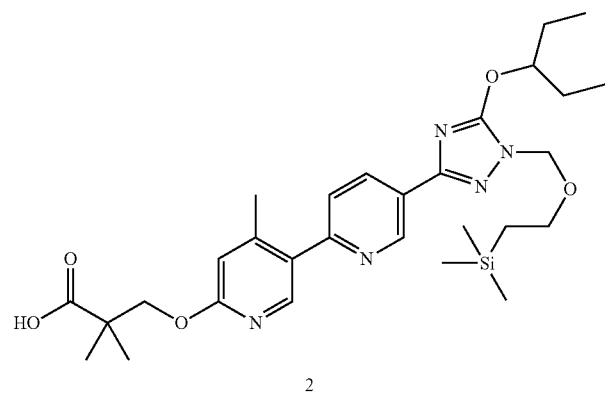
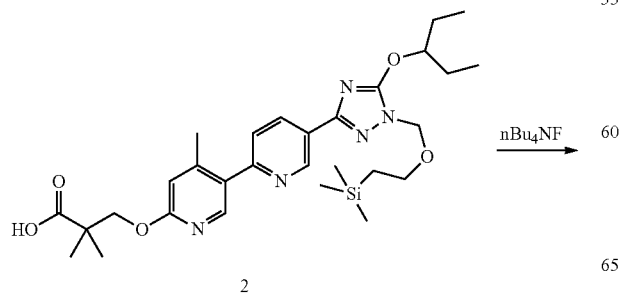
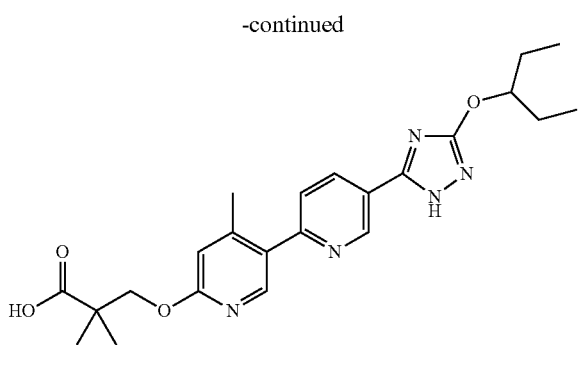
Starting from Compound 2 (290 mg), a reaction was carried out in a manner similar to the Example 88-(7) to obtain Compound 3 (60 mg) as a colorless solid.
MS (m/z): 439 [M+H]$^+$

Example 115

(1)

[Chemical Formula 370]

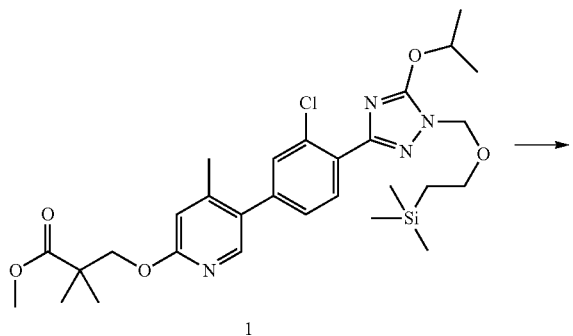

A mixture of Compound 1 (230 mg), potassium ferrocyanide (II) tetrahydrate (66 mg), palladium acetate (9 mg), butyl di-1-adamantylphosphine (42 mg), sodium carbonate (17 mg) and N-methylpyrrolidone (5 mL) was stirred under a nitrogen atmosphere at 160° C. for 18 hours. To the reaction solution was added water, and the mixture was extracted with ethyl acetate. The extract was washed with saturated brine and dried over anhydrous magnesium sulfate. After the extract was concentrated under reduced pressure, the obtained residue was purified by silica gel column chromatography (n-hexane:ethyl acetate=100:0 to 80:20) to obtain Compound 2 (24 mg) as a colorless viscous material.

MS (m/z): 580 [M+H]$^+$ (2)

[Chemical Formula 371]

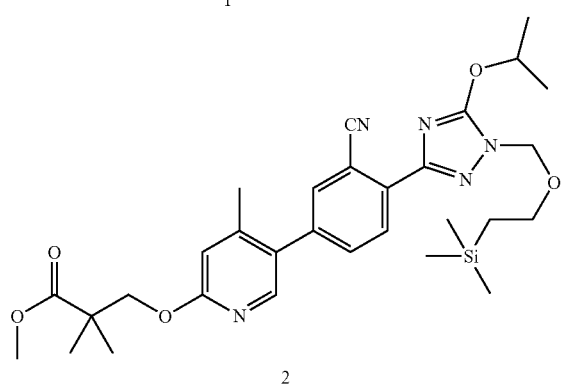

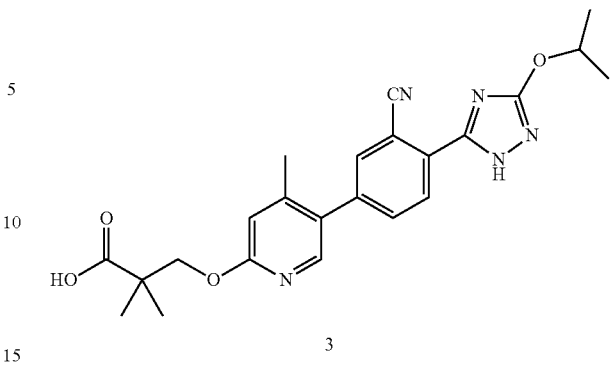

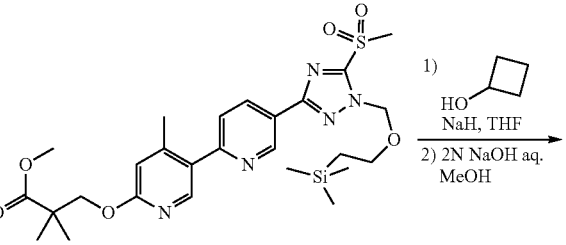

A reaction was carried out in a manner similar to the Example 88-(7) using Compound 2 (20 mg) to obtain Compound 3 (11 mg) as a colorless solid.

MS (m/z): 436 [M+H]$^+$

Example 116

(1)

[Chemical Formula 372]

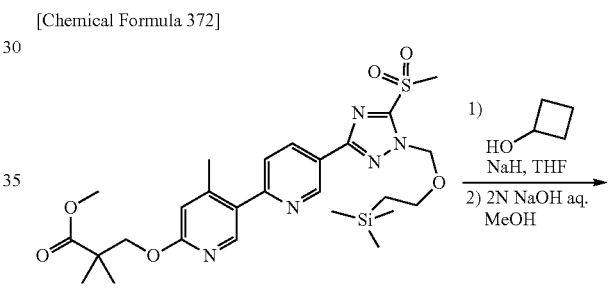

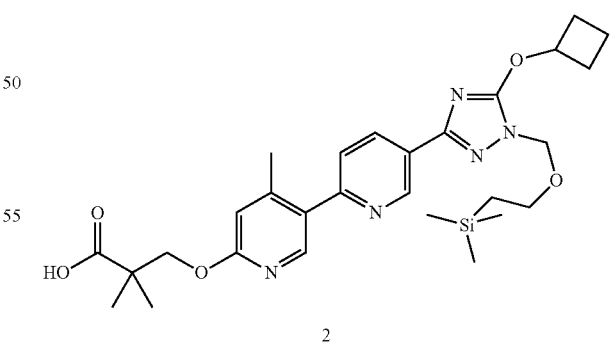

Starting from Compound 1 (300 mg) and cyclobutanol (75 mg), the reaction was carried out in a manner similar to the Example 113-(6) to obtain Compound 2 (270 mg) as a colorless powder.

MS (m/z): 554 [M+H]$^+$ (2)

[Chemical Formula 373]

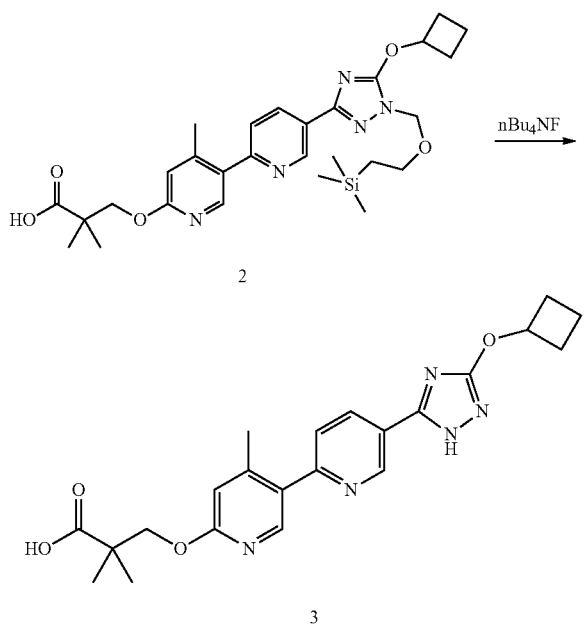

A reaction was carried out in a manner similar to the Example 88-(7) using Compound 2 (270 mg) to obtain Compound 3 (110 mg) as a colorless solid.

MS (m/z): 424 [M+H]$^+$

Example 117

(1)

[Chemical Formula 374]

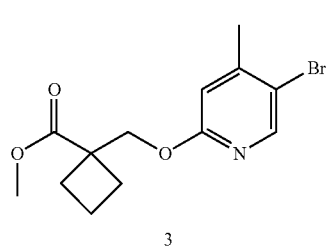

A reaction was carried out in a manner similar to the Example 51-(2) using Compound 1 (2.15 g) and Compound 2 (2.8 g) to obtain Compound 3 (2.82 g) as a pale pink solid.

MS (m/z): 314/316 [M+H]$^+$ (2)

[Chemical Formula 375]

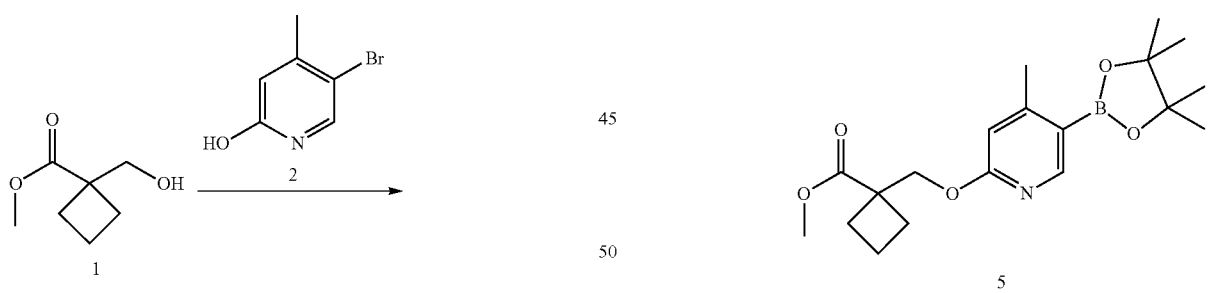

A mixture of Compound 3 (2.81 g), Compound 4 (2.73 g), bis(triphenylphosphine)palladium(II) chloride (190 mg), potassium acetate (2.63 g) and dioxane (56 mL) was stirred under a nitrogen atmosphere at 100° C. for 4 hours. The reaction solution was filtered through Celite, and the mixture was washed with ethyl acetate. The filtrate was washed with saturated brine, and dried over anhydrous magnesium sulfate. After the filtrate was concentrated under reduced pressure, the obtained residue was purified by silica gel column chromatography (n-hexane:ethyl acetate=100:0 to 90:10) to obtain Compound 5 (1.384 g) as a colorless solid.

MS (m/z): 362 [M+H]$^+$ (3)
[Chemical Formula 376]
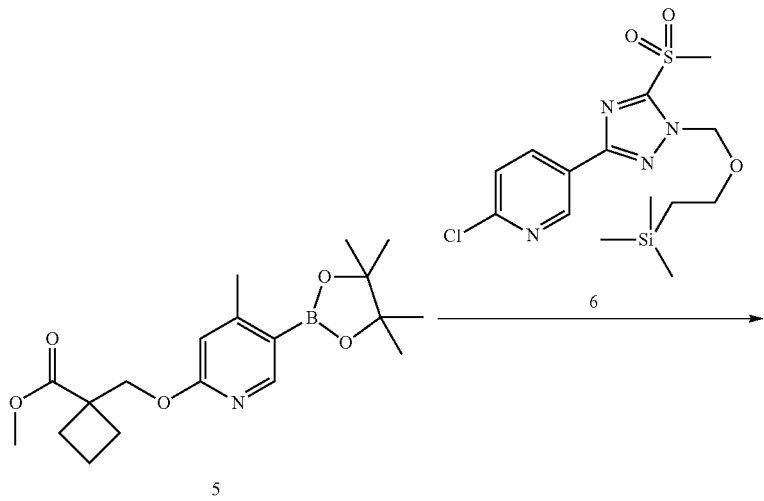
A reaction was carried out in a manner similar to the Example 50-(6) using Compound 5 (392 mg) and Compound 6 (400 mg) to obtain Compound 7 (383 mg) as a colorless viscous material.
MS (m/z): 588 [M+H]$^+$
(4)
[Chemical Formula 377]
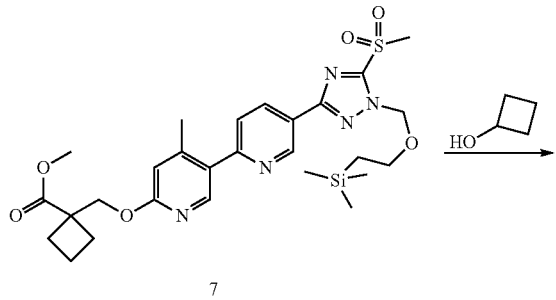
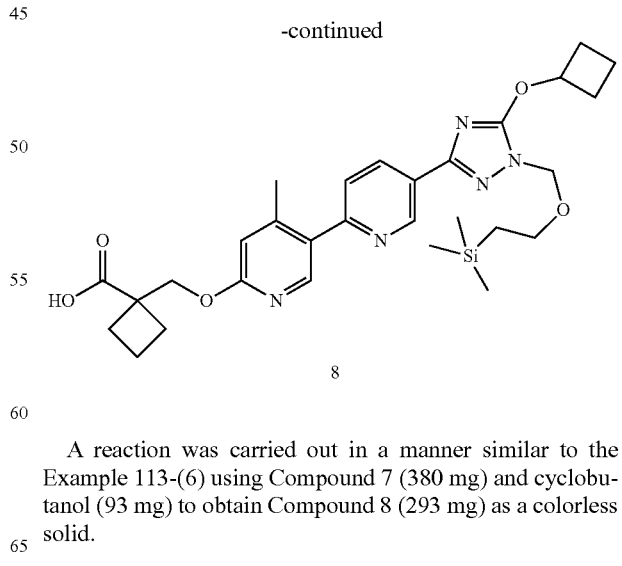
A reaction was carried out in a manner similar to the Example 113-(6) using Compound 7 (380 mg) and cyclobutanol (93 mg) to obtain Compound 8 (293 mg) as a colorless solid.
MS (m/z): 566 [M+H]$^+$ (5)

[Chemical Formula 378]

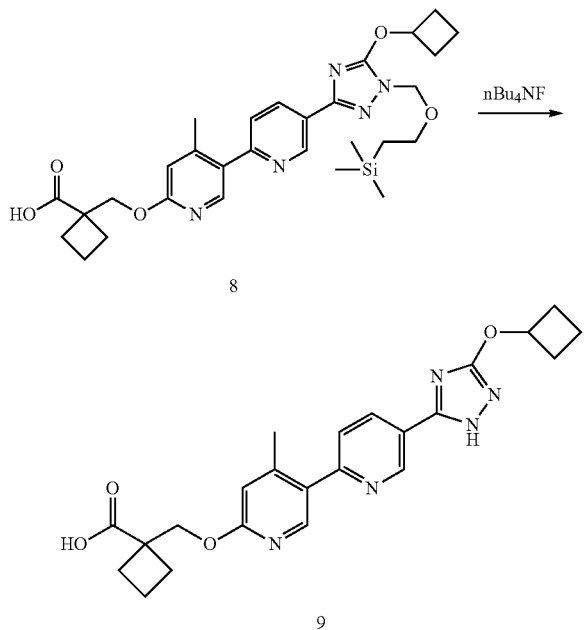

Starting from Compound 8 (290 mg), the reaction was carried out in a manner similar to the Example 88-(7) to obtain Compound 9 (190 mg) as a colorless solid.

MS (m/z): 436 [M+H]$^+$

Example 118

(1)

[Chemical Formula 379]

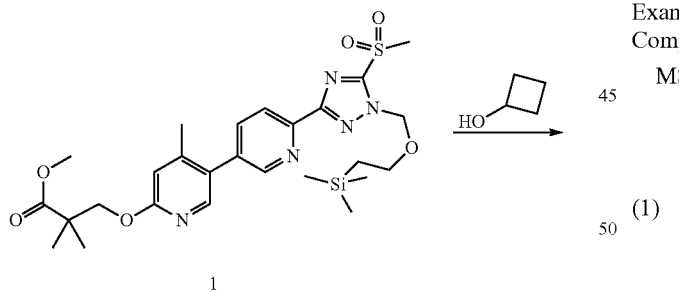

A reaction was carried out in a manner similar to the Example 113-(6) using Compound 1 (300 mg) and cyclobutanol (56 mg) to obtain Compound 2 (305 mg) as a colorless viscous material.

MS (m/z): 554 [M+H]$^+$ (2)

[Chemical Formula 380]

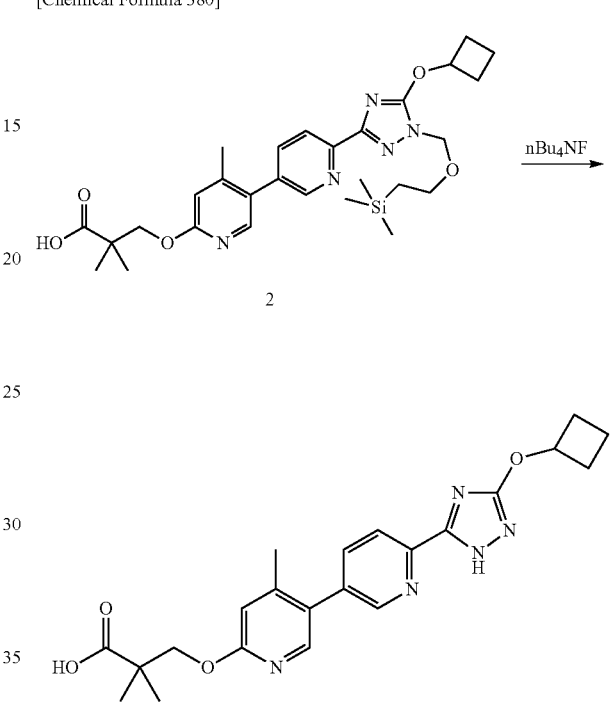

A reaction was carried out in a manner similar to the Example 88-(7) using Compound 2 (304 mg) to obtain Compound 3 (142 mg) as a colorless solid.

MS (m/z): 424 [M+H]$^+$

Example 119

(1)

[Chemical Formula 381]

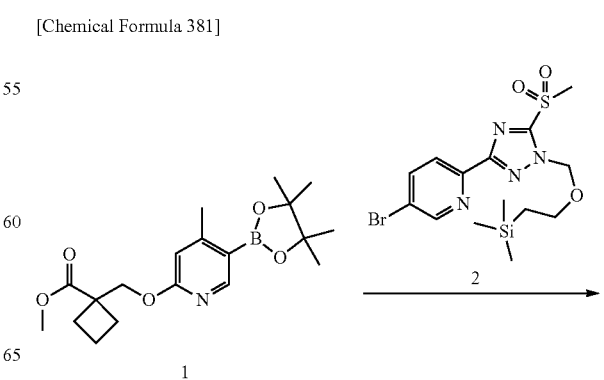

-continued

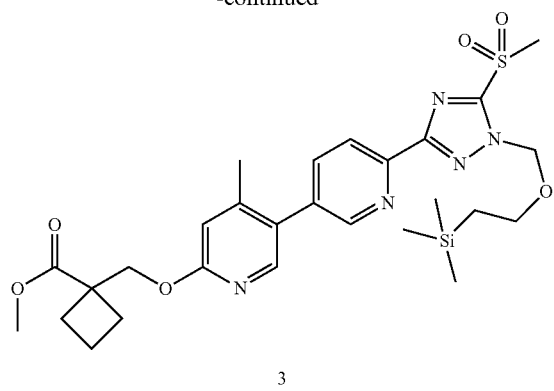

3

A reaction was carried out in a manner similar to the Example 50-(6) using Compound 1 (367 mg) and Compound 2 (400 mg) to obtain Compound 3 (515 mg) as a colorless viscous material.

MS (m/z): 588 [M+H]$^+$ (2)

[Chemical Formula 382]

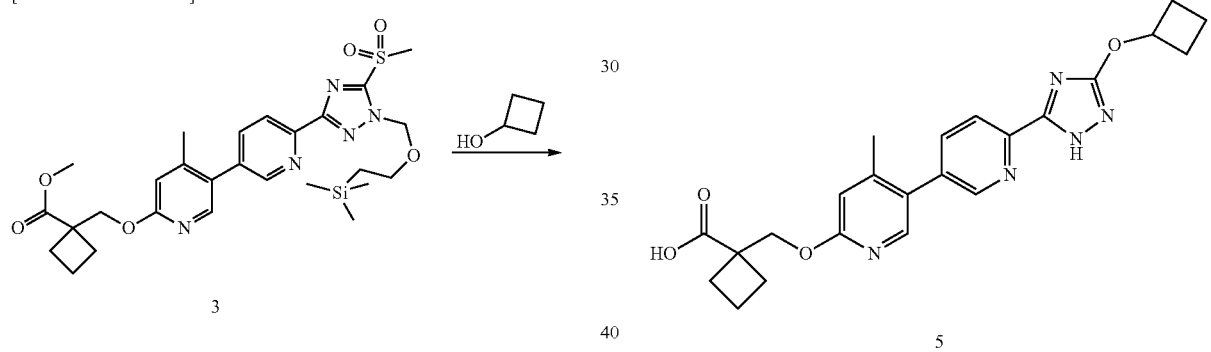

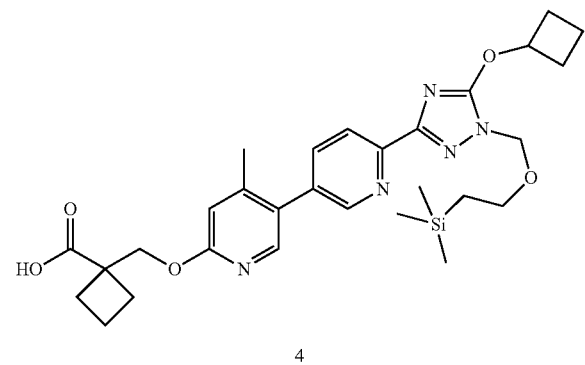

4

A reaction was carried out in a manner similar to the Example 113-(6) using Compound 3 (513 mg) and cyclobutanol (126 mg) to obtain Compound 4 (463 mg) as a colorless solid.

MS (m/z): 566 [M+H]$^+$ (3)

[Chemical Formula 383]

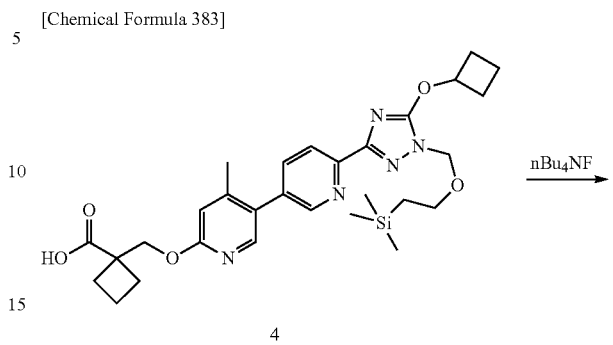

4

A reaction was carried out in a manner similar to the Example 88-(7) using Compound 4 (460 mg) to obtain Compound 5 (286 mg) as a colorless solid.

MS (m/z): 436 [M+H]$^+$

Example 120

(1)

[Chemical Formula 384]

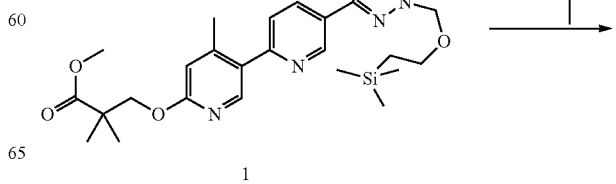

1

Example 121

(1)

[Chemical Formula 386]

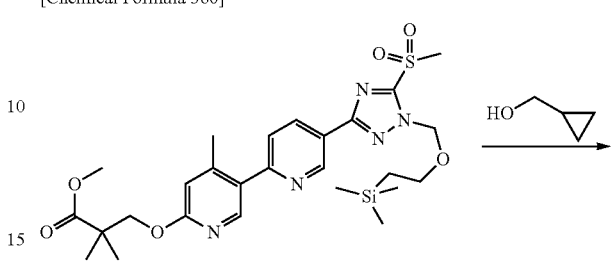

Starting from Compound 1 (290 mg) and 2-methyl-1-propanol (56 mg), the reaction was carried out in a manner similar to the Example 113-(6) to obtain Compound 2 (199 mg) as a colorless viscous material.

MS (m/z): 556 [M+H]$^+$ (2)

[Chemical Formula 385]

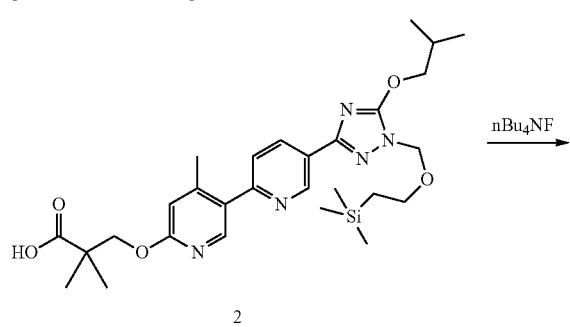

Starting from Compound 2 (198 mg), the reaction was carried out in a manner similar to the Example 88-(7) to obtain Compound 3 (74 mg) as a colorless solid.

MS (m/z): 426 [M+H]$^+$

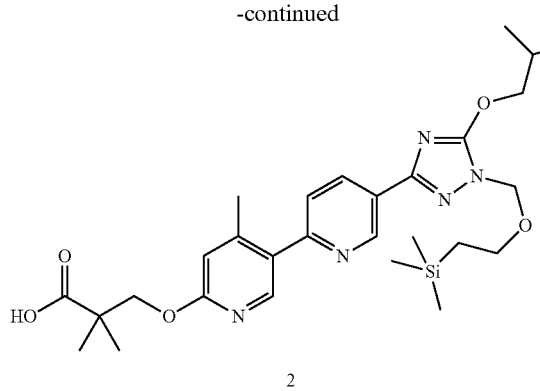

A reaction was carried out in a manner similar to the Example 113-(6) using Compound 1 (290 mg) and cyclopropylmethanol (54 mg) to obtain Compound 2 (287 mg) as a colorless viscous material.

MS (m/z): 554 [M+H]$^+$ (2)

[Chemical Formula 387]

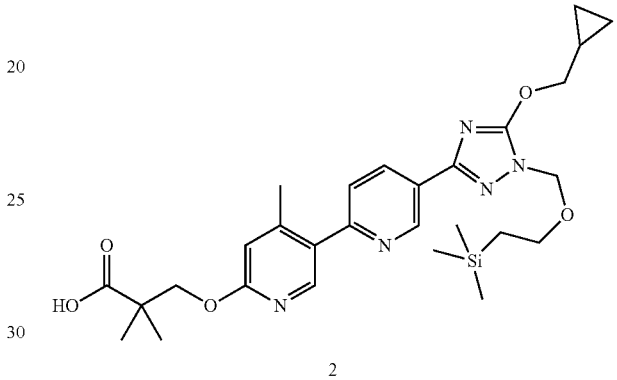

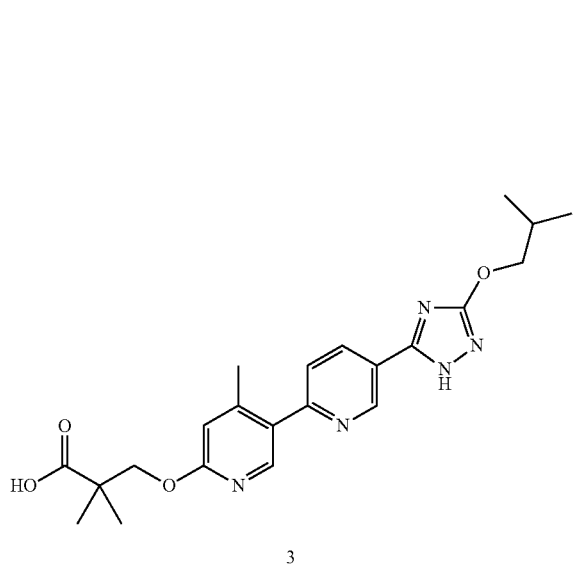

Starting from Compound 2 (286 mg), the reaction was carried out in a manner similar to the Example 88-(7) to obtain Compound 3 (61 mg) as a colorless solid.

MS (m/z): 424 [M+H]$^+$

Example 122

(1)

[Chemical Formula 388]

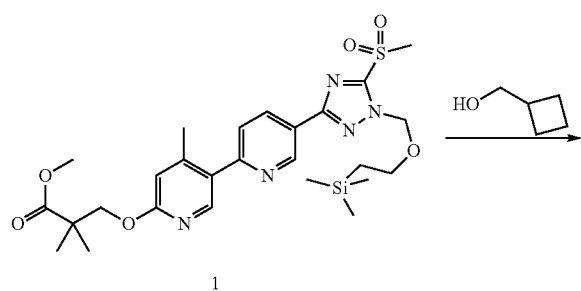

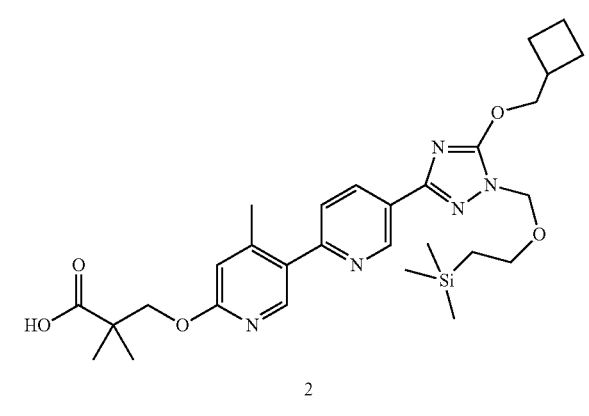

A treatment was carried out in a manner similar to the Example 113-(6) using Compound 1 (290 mg) and cyclobutylmethanol (65 mg) to obtain Compound 2 (279 mg) as a colorless viscous material.

MS (m/z): 568 [M+H]$^+$ (2)

[Chemical Formula 389]

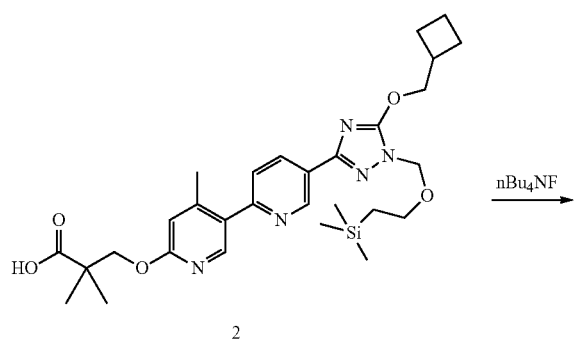

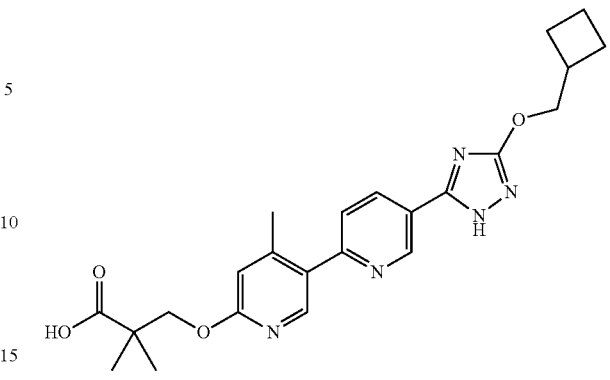

A reaction was carried out in a manner similar to the Example 88-(7) using Compound 2 (278 mg) to obtain Compound 3 (107 mg) as a colorless solid.

MS (m/z): 438 [M+H]$^+$

Example 123

(1)

[Chemical Formula 390]

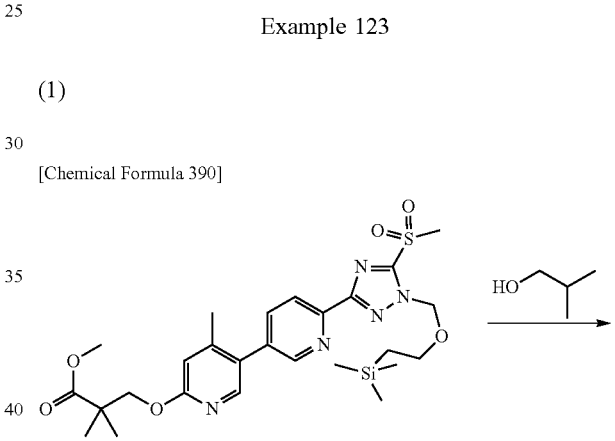

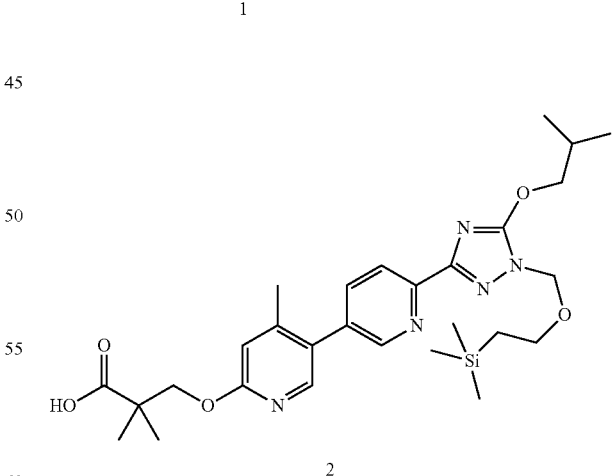

Starting from Compound 1 (350 mg) and 2-methyl-1-propanol (90 mg), the reaction was carried out in a manner similar to the Example 113-(6) to obtain Compound 2 (319 mg) as a colorless viscous material.

MS (m/z): 556 [M+H]$^+$ (2)

[Chemical Formula 391]

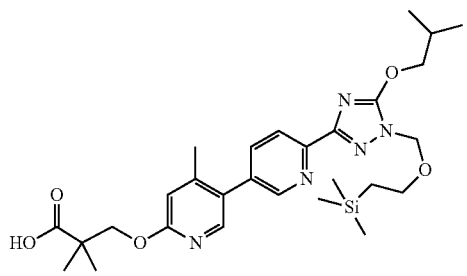 → 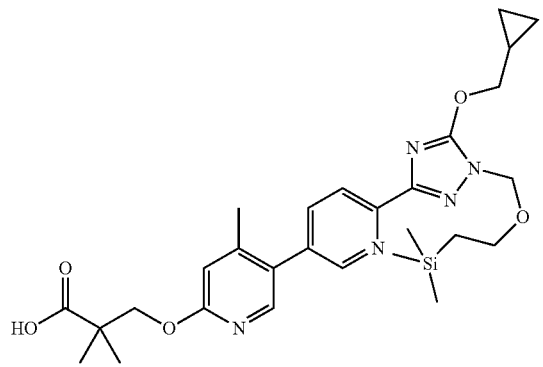

A reaction was carried out in a manner similar to the Example 113-(6) using Compound 1 (350 mg) and cyclopropylmethanol (88 mg) to obtain Compound 2 (345 mg) as a colorless viscous material.

MS (m/z): 554 [M+H]+

(2)

[Chemical Formula 393]

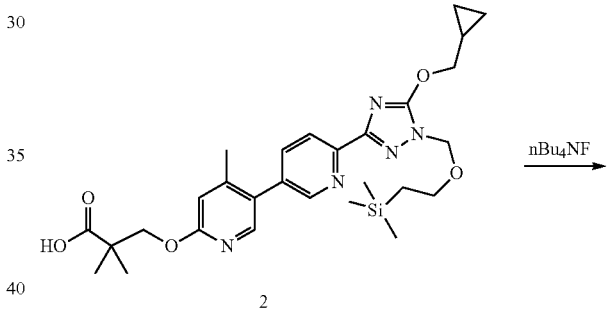

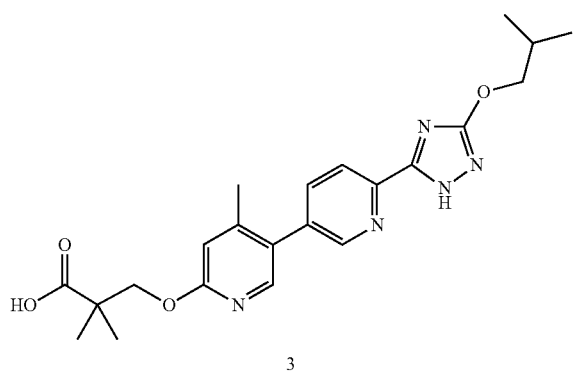

A reaction was carried out in a manner similar to the Example 88-(7) using Compound 2 (317 mg) to obtain Compound 3 (111 mg) as a colorless solid.

MS (m/z): 426 [M+H]+

Example 124

(1)

[Chemical Formula 392]

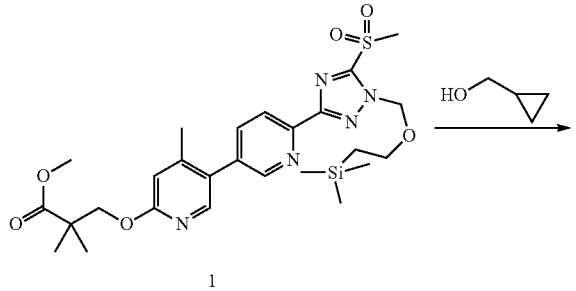

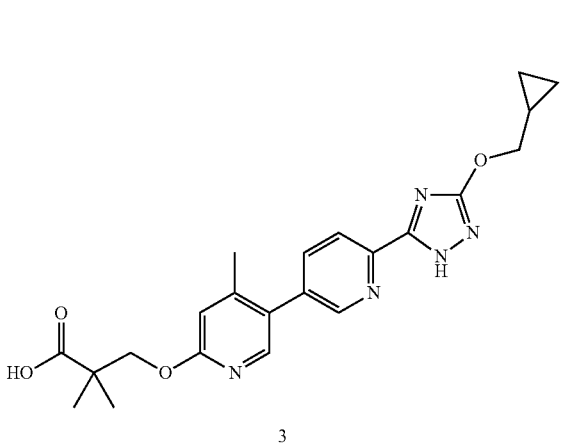

Starting from Compound 2 (343 mg), a reaction was carried out in a manner similar to the Example 88-(7) to obtain Compound 3 (129 mg) as a colorless solid.

MS (m/z): 424 [M+H]+

Example 125

(1)

[Chemical Formula 394]

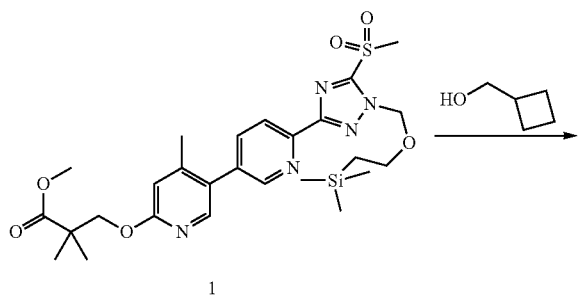

A reaction was carried out in a manner similar to the Example 113-(6) using Compound 1 (350 mg) and cyclobutylmethanol (209 mg) to obtain Compound 2 (345 mg) as a colorless viscous material.

MS (m/z): 568 [M+H]$^+$ (2)

[Chemical Formula 395]

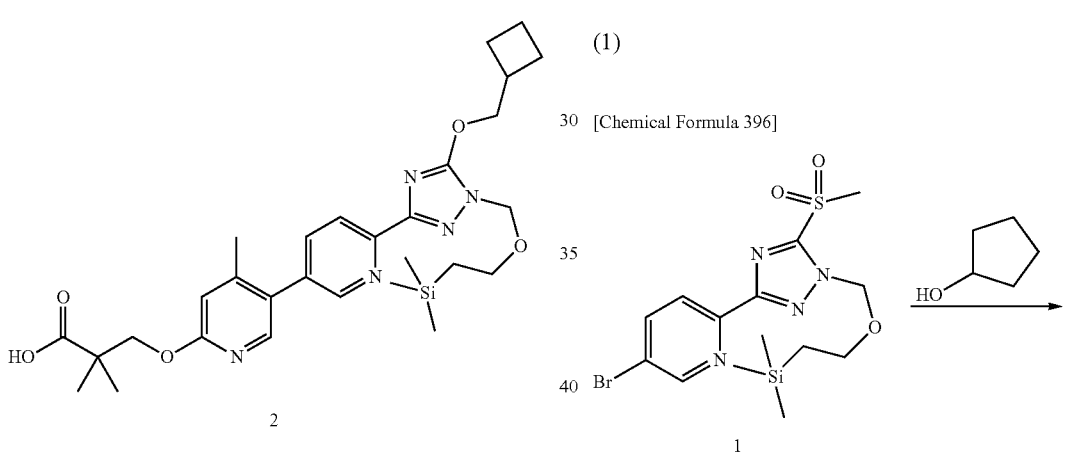

Starting from Compound 2 (343 mg), a reaction was carried out in a manner similar to the Example 88-(7) to obtain Compound 3 (115 mg) as a colorless solid.

MS (m/z): 438 [M+H]$^+$

Example 126

(1)

[Chemical Formula 396]

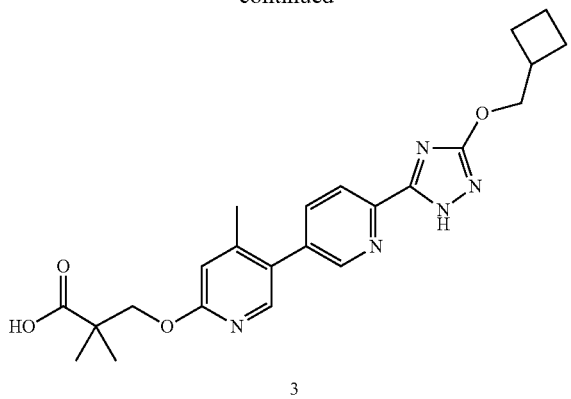

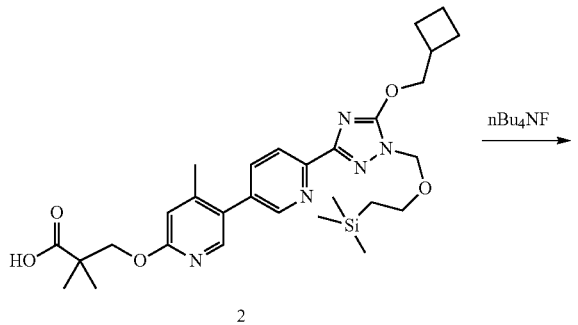

Starting from Compound 1 (300 mg) and cyclopentanol (119 mg), a reaction was carried out in a manner similar to the Example 68-(5) to obtain Compound 2 (300 mg) as a colorless solid.

MS (m/z): 439/441 [M+H]$^+$ (2)
[Chemical Formula 397]
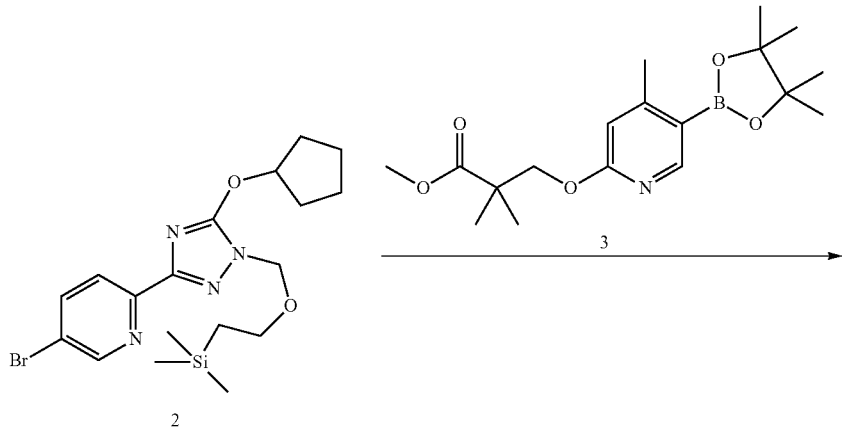
A reaction was carried out in a manner similar to the Example 68-(6) using Compound 2 (298 mg) and Compound 3 (261 mg) to obtain Compound 4 (359 mg) as a colorless viscous material.
MS (m/z): 582 [M+H]+
(3)
[Chemical Formula 398]
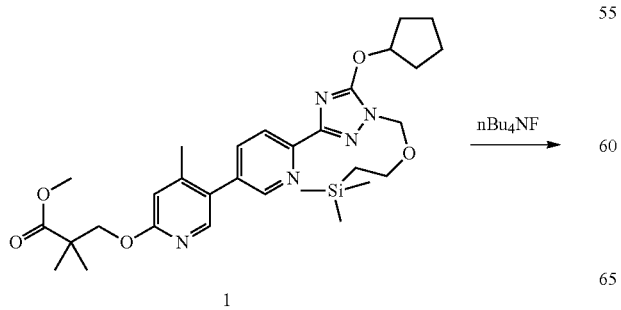
A reaction was carried out in a manner similar to the Example 88-(7) using Compound 2 (355 mg) to obtain Compound 4 (178 mg) as a colorless solid.
MS (m/z): 438 [M+H]+

Example 127

(1)

[Chemical Formula 399]

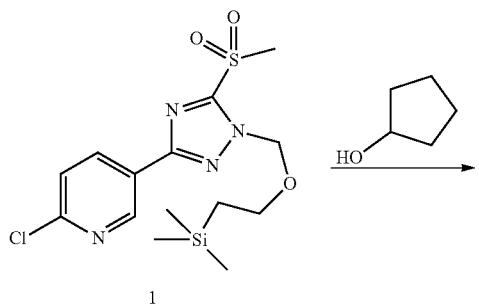

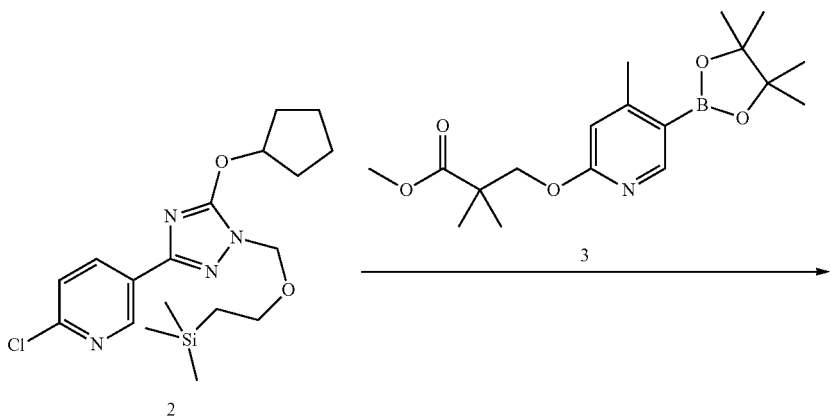

A treatment was carried out in a manner similar to the Example 68-(5) using Compound 1 (400 mg) and cyclopentanol (177 mg) to obtain Compound 2 (332 mg) as a colorless viscous material.

MS (m/z): 395/397 [M+H]$^+$ (2)

[Chemical Formula 400]

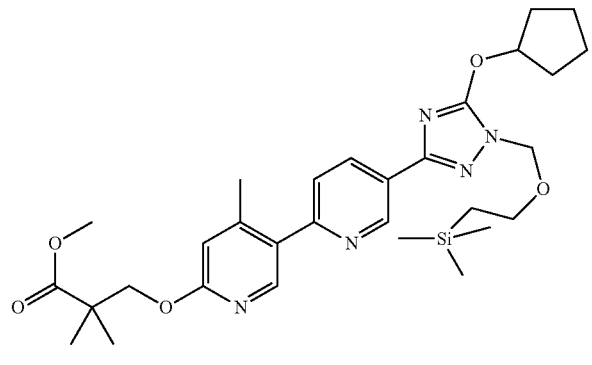

Starting from Compound 2 (330 mg) and Compound 3 (350 mg), a treatment was carried out in a manner similar to the Example 68-(6) to obtain Compound 4 (304 mg) as a colorless viscous material.

MS (m/z): 582 [M+H]$^+$ (3)

[Chemical Formula 401]

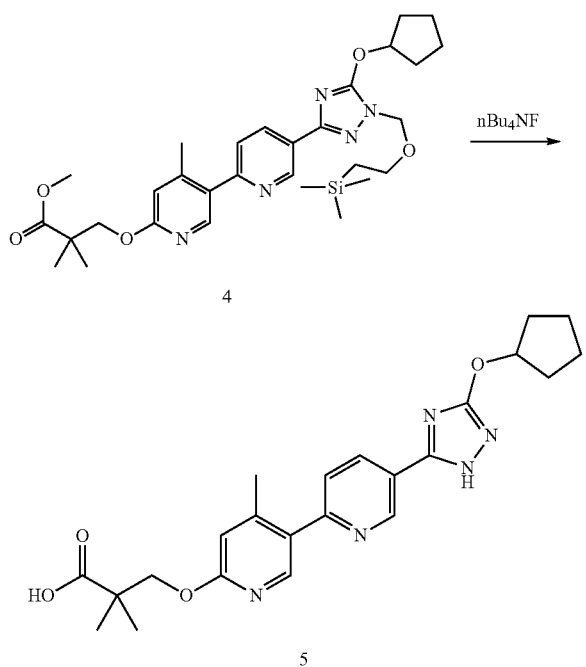

A treatment was carried out in a manner similar to the Example 88-(7) using Compound 4 (303 mg) to obtain Compound 5 (139 mg) as a colorless solid.

MS (m/z): 438 [M+H]$^+$

Reference Example 1

[Chemical Formula 402]

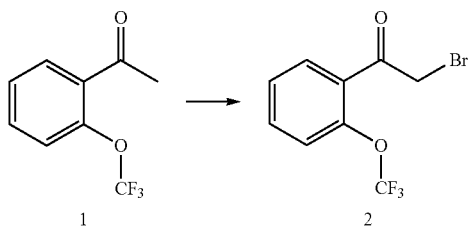

Compound 1 (2'-(trifluoromethoxy)acetophenone) (1.00 g), N-bromosuccinimide (0.87 g) and toluene sulfonic acid monohydrate (84 mg) were stirred at room temperature overnight. Dichloromethane and saturated brine were added to the reaction solution to carry out a liquid separation. The organic layer was separated and dried over anhydrous sodium sulfate, and subsequently the solvent was distilled off under reduced pressure. The obtained residue was purified by silica gel column chromatography (n-hexane:ethyl acetate=99:1 to 94:6) to obtain Compound 2 (1.14 g).

NMR (400 MHz, DMSO-d$_6$): 7.97 (1H, dd, J=8.0, 4.0 Hz), 7.75 (1H, m), 7.57 (1H, t, J=8.0 Hz), 7.53 (1H, d, J=8.0 Hz), 4.85 (1H, s)

Reference Example 2

[Chemical Formula 403]

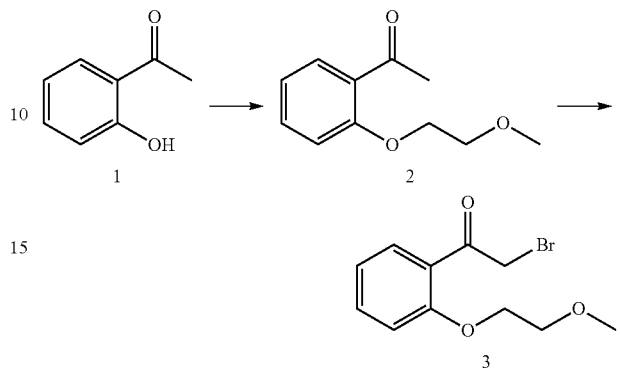

(1) Compound 1 (2'-hydroxyacetophenone) (1.20 mL), 2-bromoethyl methyl ether (1.88 mL) and cesium carbonate (3.26 g) were dissolved in N,N-dimethylformamide (10 mL), and the mixture was stirred at 90° C. overnight. After the temperature of the reaction solution was brought back to room temperature, ethyl acetate and water were added to carry out a liquid separation. The organic layer was separated, washed with saturated brine, and dried over anhydrous magnesium sulfate. The solvent was distilled off under reduced pressure. The obtained residue was purified by silica gel column chromatography (n-hexane:ethyl acetate=95:5 to 80:20) to obtain Compound 2 (1.75 g).

MS (m/z): 195 [M+H]$^+$ (2) A treatment was carried out in a manner similar to Reference Example 1 using Compound 2 (1.74 g) to obtain Compound 3 (2.24 g).

MS (m/z): 273/275 [M+H]$^+$

Reference Example 3

[Chemical Formula 404]

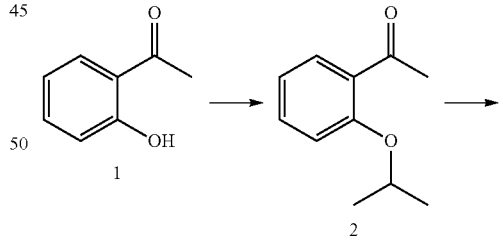

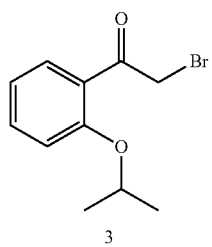

(1) Compound 1 (2'-hydroxyacetophenone) (0.60 mL) was dissolved in dimethylsulfoxide (25 mL), 2-iodopropane (1.70 g) and potassium phosphate (2.12 g) were added, and the mixture was stirred at 60° C. for 4 hours. After the temperature of the reaction solution was brought back to room temperature, ethyl acetate and water were added to carry out a liquid separation. The organic layer was separated, washed with saturated brine, and dried over anhydrous sodium sulfate. The solvent was distilled off under reduced pressure. The obtained residue was purified by silica gel column chromatography (n-hexane:ethyl acetate=98:2 to 92:8) to obtain Compound 2 (0.74 g).

MS (m/z): 179 [M+H]$^+$ (2) Compound 2 (200 mg) was dissolved in ethyl acetate (2.5 mL) and chloroform (2.5 mL), copper bromide (0.50 g) was added, and the mixture was heated at reflux under a nitrogen atmosphere for 4 hours. After the temperature of the reaction solution was brought back to room temperature, the reaction solution was filtered through Celite and washed with ethyl acetate. The filtrate was concentrated under reduced pressure and the obtained residue was purified by silica gel column chromatography (n-hexane:ethyl acetate=98:2 to 92:8) to obtain Compound 3 (267 mg).

MS (m/z): 257/259 [M+H]$^+$

Reference Example 4

[Chemical Formula 405]

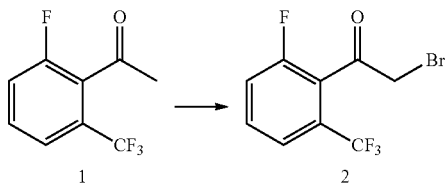

Compound 1 (2'-fluoro-6'-(trifluoromethyl)acetophenone) (500 mg) was dissolved in tetrahydrofuran (10 mL), benzyltrimethylammonium tribromide (1.04 g) was added, and the mixture was stirred at room temperature for 2 hours. The reaction solution was concentrated under reduced pressure, to the residue was added diethyl ether, and the obtained solid was filtered and washed by diethyl ether. The filtrate was concentrated under reduced pressure, and the obtained residue was purified by silica gel column chromatography (n-hexane:ethyl acetate=99:1 to 95:5) to obtain Compound 2 (632 mg).

NMR (400 MHz, DMSO-d$_6$): 7.77 (3H, m), 4.83 (1H, d, J=1.2 Hz)

Reference Example 5

[Chemical Formula 406]

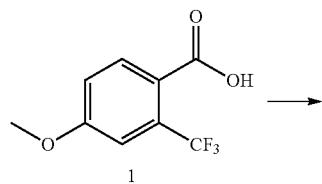

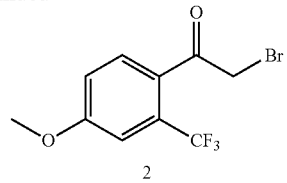

Compound 1 (4-methoxy-2-(trifluoromethyl)benzoic acid) (0.50 g) was dissolved in dichloromethane (10 mL), and oxalyl chloride (0.40 mL) was added dropwise. To this was added N,N-dimethylformamide (5 drops), and the mixture was stirred at room temperature for 1 hour. After the reaction solution was concentrated under reduced pressure, acetonitrile (10 mL) was added. A 2M trimethylsilyldiazomethane-n-hexane solution (2.4 mL) was added dropwise under ice cooling, and the mixture was stirred at room temperature for 1 hour. The reaction solution was ice-cooled, a 48% hydrobromic acid (0.39 mL) was added dropwise, and the mixture was stirred for 1 hour. Ethyl acetate and a saturated aqueous sodium hydrogen carbonate solution were added to the reaction solution to carry out a liquid separation. The organic layer was separated and dried over anhydrous sodium sulfate, and subsequently the solvent was distilled off under reduced pressure. The obtained residue was purified by silica gel column chromatography (n-hexane:ethyl acetate=98:2 to 92:8) to obtain Compound 2 (0.44 g).

MS (m/z): 297/299 [M+H]$^+$

Reference Example 6

[Chemical Formula 407]

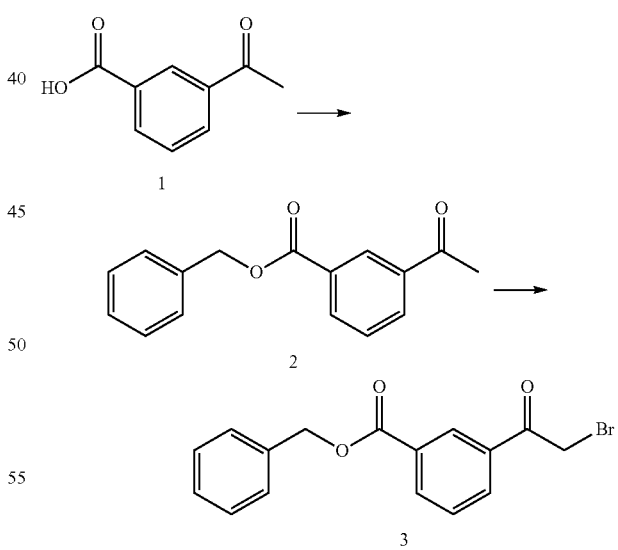

(1) Compound 1 (3-acetylbenzoic acid) (500 mg) was dissolved in N,N-dimethylformamide (10 mL), potassium carbonate (421 mg) and benzyl bromide (362 µL) were added, and the mixture was stirred at room temperature overnight. Ethyl acetate and water were added to the reaction solution to carry out a liquid separation, the organic layer was dried over anhydrous sodium sulfate, and the solvent was distilled off under reduced pressure. The obtained residue was purified by silica gel column chromatography (n-hexane:ethyl acetate=99:1 to 85:15) to obtain Compound 2 (763 mg).

MS (m/z): 272 [M+NH$_4$]$^+$ (2) A treatment was carried out in a manner similar to Reference Example 1 using Compound 2 (760 mg) to obtain Compound 3 (668 mg).

MS (m/z): 333/335 [M+H]$^+$

Reference Example 7-1

[Chemical Formula 408]

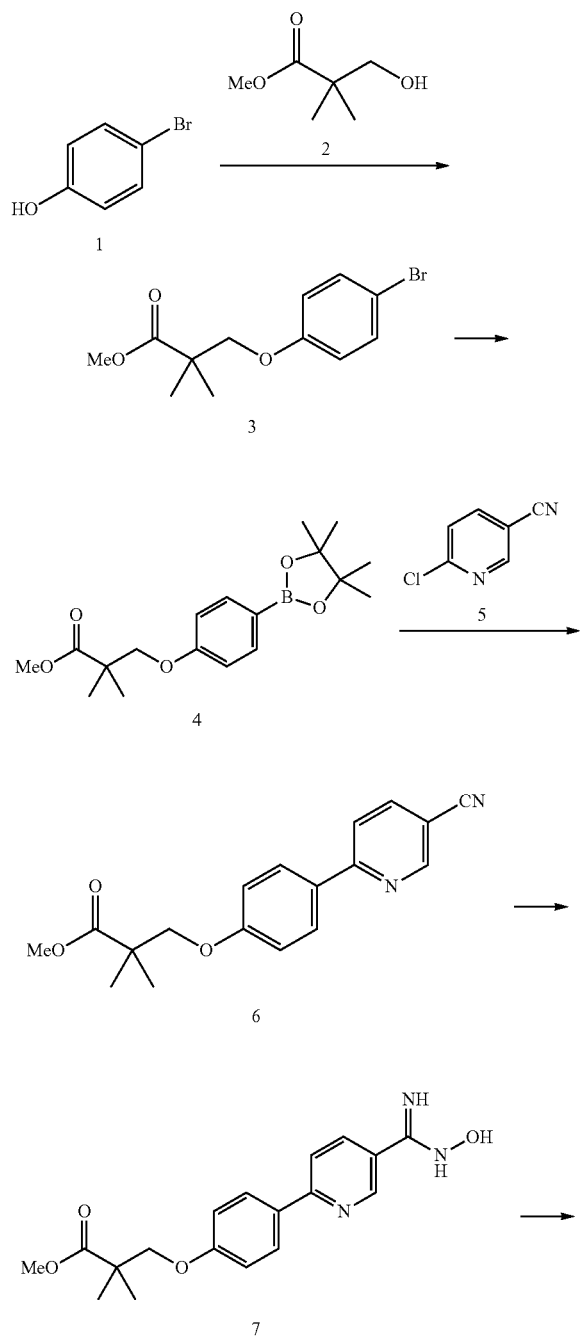

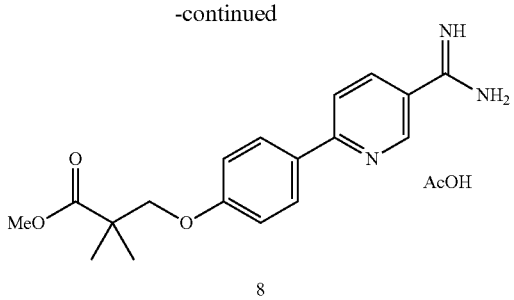

(1) Compound 1 (4-bromophenol) (61.0 g), Compound 2 (methyl hydroxypivalate) (69.9 g) and triphenylphosphine (138.7 g) were dissolved in tetrahydrofuran (350 mL), and the mixture was cooled to 0° C. under a nitrogen atmosphere. Subsequently, a 40% diethyl azodicarboxylate-toluene solution (240 mL) was added dropwise, and the mixture was stirred while the temperature was brought back to room temperature and then at 80° C. overnight. After the temperature of the reaction solution was brought back to room temperature, the reaction solution was concentrated under reduced pressure, to the obtained residue was added diethyl ether (500 mL), and the obtained solid was filtered and washed with diethyl ether. The filtrate was concentrated under reduced pressure and the obtained residue was purified by silica gel column chromatography (n-hexane:ethyl acetate=100:0, 19:1 and to 9:1) to obtain Compound 3 (102.2 g).

MS (m/z): 304/306 [M+NH$_4$]$^+$ (2) Compound 3 (102.2 g), bis(pinacolato)diboron (98.5 g), [1,1'-bis(diphenylphosphino)ferrocene]palladium dichloride (7.73 g), 1,1'-bis(diphenylphosphino)ferrocene (5.86 g), and potassium acetate (103.8 g) were added to 1,4-dioxane (470 mL), and the mixture was stirred under a nitrogen atmosphere at 80° C. overnight. After the temperature of the reaction solution was brought back to room temperature, the reaction solution was concentrated under reduced pressure, and ethyl acetate and water were added to the obtained residue to carry out a liquid separation. The organic layer was separated, washed with saturated brine, and dried over anhydrous sodium sulfate. The solvent was distilled off under reduced pressure. The obtained residue was purified by silica gel column chromatography (n-hexane:ethyl acetate=100:0, 9:1 and to 4:1), to the obtained residue was added n-hexane, and the mixture was stirred under ice-cooling for 1 hour. The obtained solid was collected by filtration and dried to obtain Compound 4 (95.5 g).

MS (m/z): 335 [M+H]$^+$ (3) Compound 4 (87.6 g) and Compound 5 (2-chloro-5-cyanopyridine) (40.0 g) were dissolved in dimethoxyethane (550 mL), and a 2M aqueous sodium carbonate solution (525 mL) was added. To this was added tetrakis(triphenylphosphine)palladium (21.2 g) under a nitrogen atmosphere, and the mixture was stirred at 90° C. overnight. After the temperature of the reaction solution was brought back to room temperature, ethyl acetate and water were added to carry out a liquid separation. The organic layer was separated, washed with saturated brine, and dried over anhydrous magnesium sulfate. The solvent was distilled off under reduced pressure. The obtained residue was purified by silica gel column chromatography (n-hexane:ethyl acetate=9:1, 4:1 and to 2:1) to obtain Compound 6 (77.4 g).

MS (m/z): 311 [M+H]$^+$ (4) Compound 6 (6.27 g) was dissolved in tetrahydrofuran (100 mL) and methanol (100 mL), a 50% aqueous hydroxylamine solution (40 mL) was added, and the mixture was stirred at 80° C. for 4 hours. After the temperature of the reaction solution was brought back to room temperature, the reaction solution was concentrated under reduced pressure, and chloroform and water were added to the obtained residue to carry out a liquid separation. The organic layer was separated, washed with saturated brine, and dried over anhydrous sodium sulfate. The solvent was distilled off under reduced pressure to obtain Compound 7 (6.70 g).

MS (m/z): 344 [M+H]$^+$ (5) Compound 7 (6.68 g) was dissolved in acetic acid (60 mL), acetic anhydride (4 mL) was added, and the mixture was stirred at room temperature for 1.75 hours. After the reaction solution was concentrated under reduced pressure, to the obtained residue were added tetrahydrofuran (70 mL) and methanol (300 mL), 10% palladium/carbon (1.25 g) was added under a nitrogen atmosphere, and the mixture was subjected to hydrogen substitution, and stirred at room temperature for 2 hours. The reaction solution was filtered, and the residue was washed with methanol. After the filtrate was concentrated under reduced pressure, ethyl acetate was added to the residue, and the obtained deposit was washed with ethyl acetate and dried to obtain Compound 8 (6.81 g) as an acetate salt.

MS (m/z): 328 [M+H]$^+$

Reference Examples 7-2 to 7-19

A treatment was carried out in a manner similar to Reference Example 7-1 to obtain compounds of Reference Examples 7-2 to 7-19 in Table 27 below.

TABLE 27

| Reference Example | Intermediate 1 | Intermediate 2 |
|---|---|---|
| 7-2 | | |
| 7-3 | | |
| 7-4 | | |
| 7-5 | | |
| 7-6 | | |
| 7-7 | | |

TABLE 27-continued
| | | |
|---|---|---|
| 7-8 | 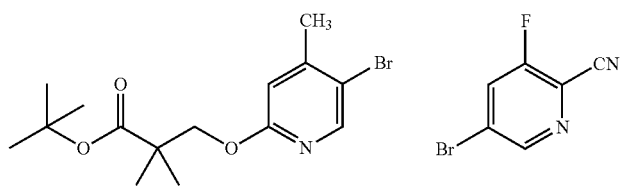 | |
| 7-9 | 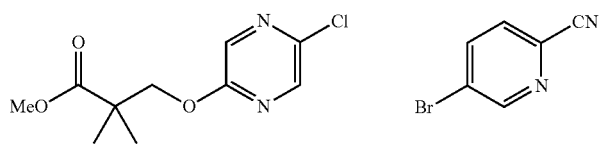 | |
| 7-10 | 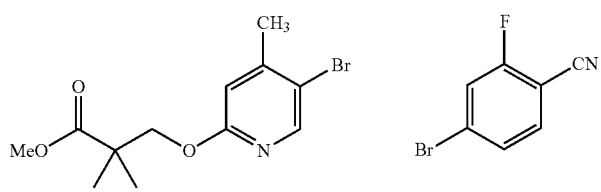 | |
| 7-11 | 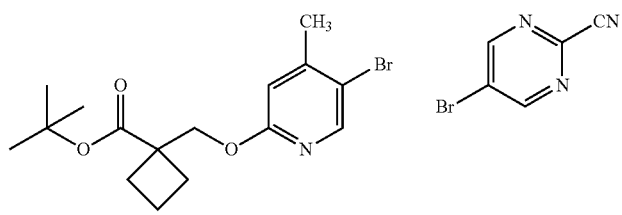 | |
| 7-12 | 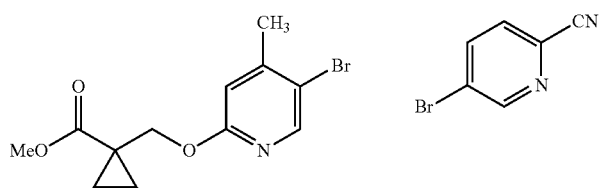 | |
| 7-13 | 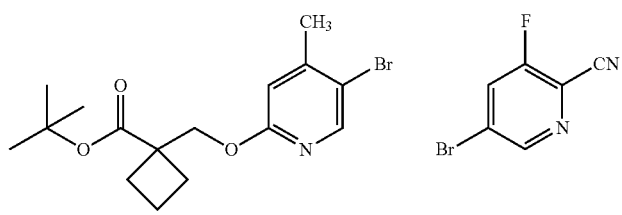 | |
| 7-14 | 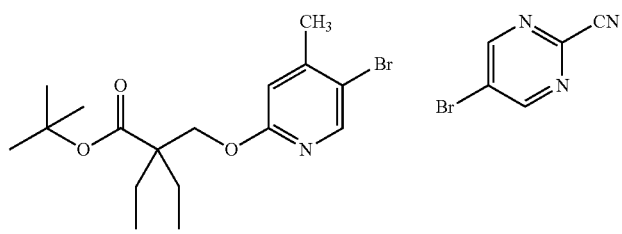 | |
| 7-15 | 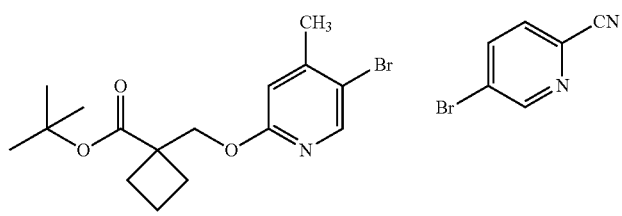 | |

TABLE 27-continued
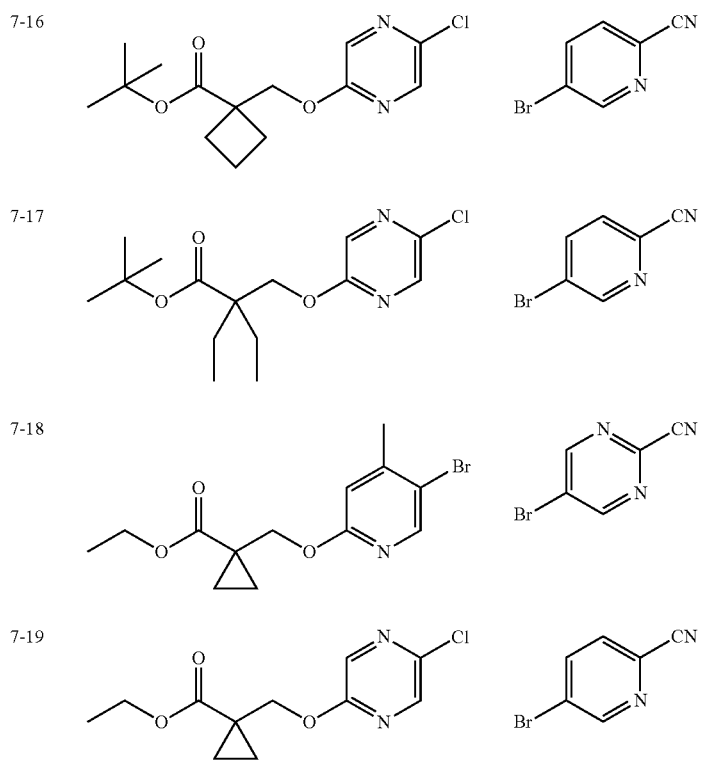
| Reference Example | Product | MS (m/z) |
|---|---|---|
| 7-2 | | 328 [M + H]⁺ |
| 7-3 | | 342 [M + H]⁺ |
| 7-4 | | 342 [M + H]⁺ |
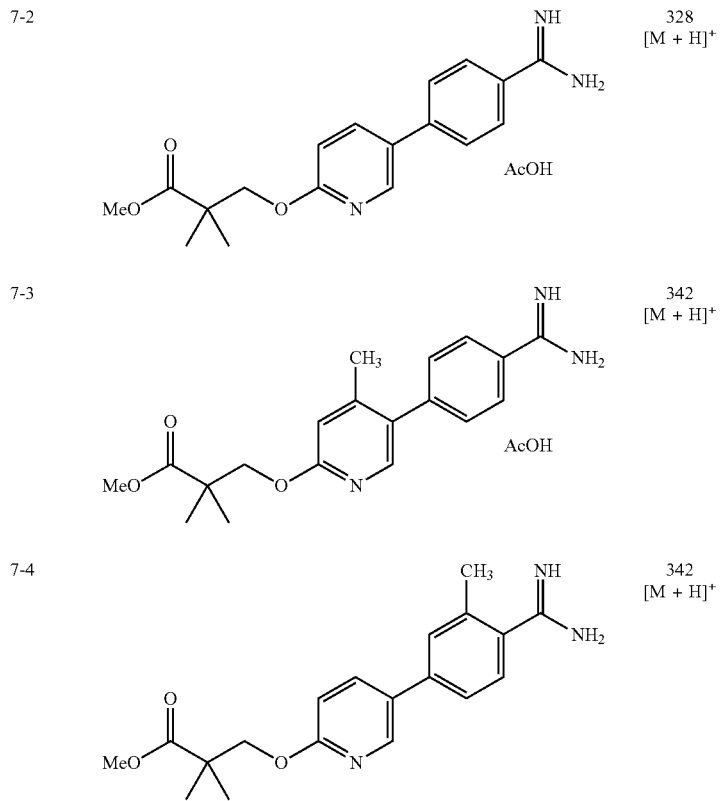

TABLE 27-continued
| | | |
|---|---|---|
| 7-5 | 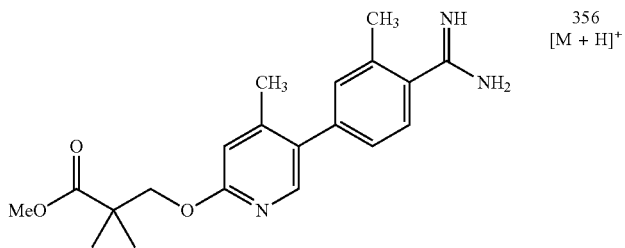 | 356 [M + H]+ |
| 7-6 | 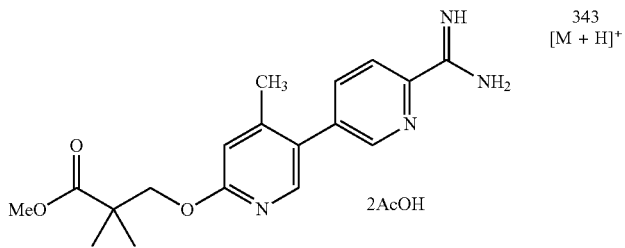 | 343 [M + H]+ |
| 7-7 | 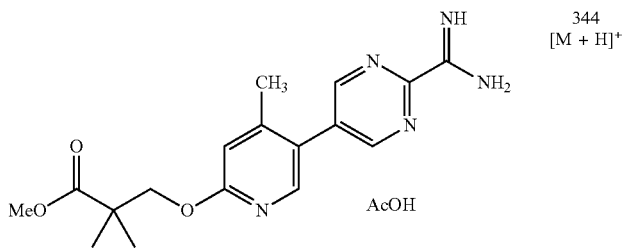 | 344 [M + H]+ |
| 7-8 | 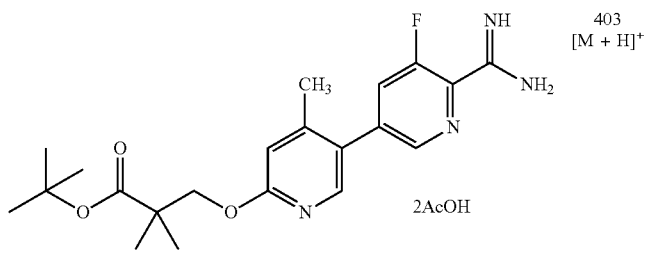 | 403 [M + H]+ |
| 7-9 | 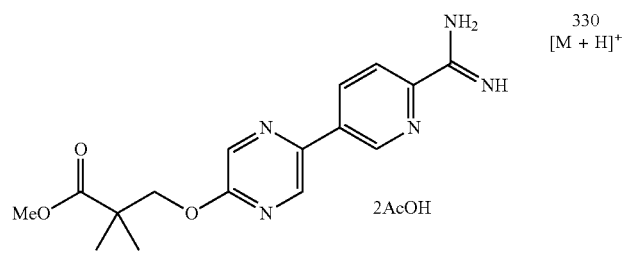 | 330 [M + H]+ |
| 7-10 | 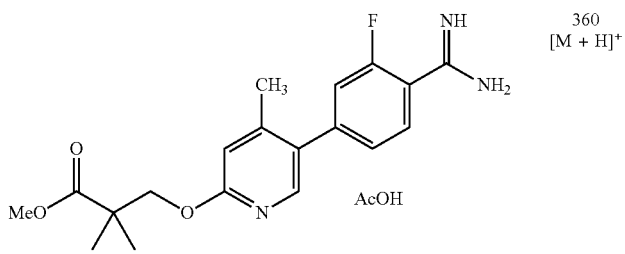 | 360 [M + H]+ |

TABLE 27-continued

| | | |
|---|---|---|
| 7-11 | [structure] AcOH | 398 [M + H]+ |
| 7-12 | [structure] AcOH | 341 [M + H]+ |
| 7-13 | [structure] 2AcOH | 415 [M + H]+ |
| 7-14 | [structure] AcOH | 414 [M + H]+ |
| 7-15 | [structure] 3AcOH | 397 [M + H]+ |
| 7-16 | [structure] | 384 [M + H]+ |

TABLE 27-continued

| | | |
|---|---|---|
| 7-17 | 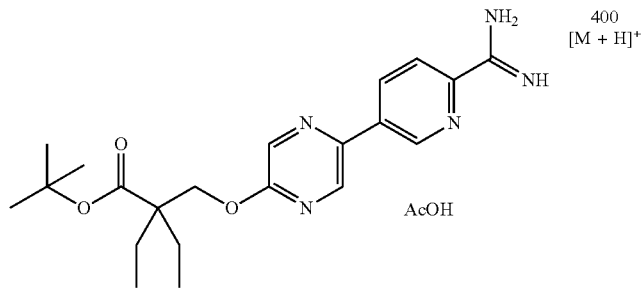 AcOH | 400 [M + H]+ |
| 7-18 | 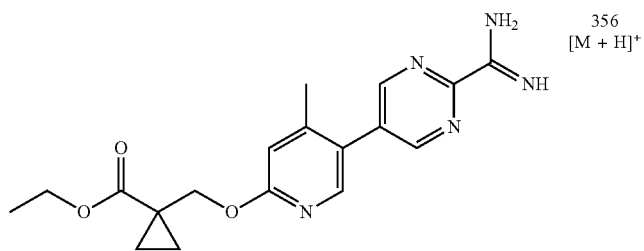 | 356 [M + H]+ |
| 7-19 | 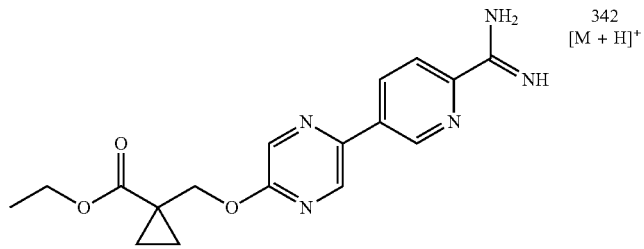 | 342 [M + H]+ |

Reference Example 8

[Chemical Formula 409]

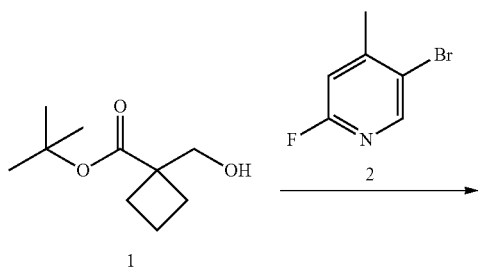

Compound 1 (4.9 g) and Compound 2 (5 g) were dissolved in N,N-dimethylformamide (50 mL), and a 60% sodium hydride (1.16 g) was added portionwise under ice cooling. The temperature of the reaction solution was elevated to room temperature, and the reaction solution was stirred for 4 hours. After a saturated aqueous ammonium chloride solution was added under ice cooling, ethyl acetate and water were added to carry out a liquid separation. The organic layer was separated, washed with water, and dried over sodium sulfate. The solvent was distilled off under reduced pressure. The obtained residue was purified by silica gel column chromatography (n-hexane:ethyl acetate=100:0 to 97:3) to obtain Compound 3 (6.71 g).

MS (m/z): 356/358 [M+H]+

Reference Example 9-1

[Chemical Formula 410]

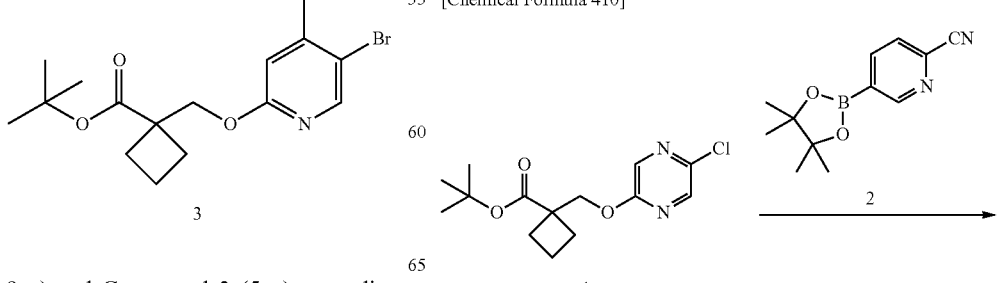

-continued

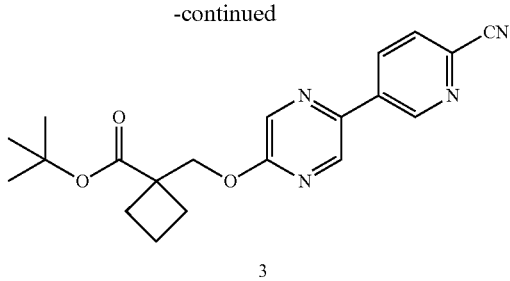

3

Compound 1 (1.46 g), Compound 2 (1.46 g), a dichloro [1,1'-bis(diphenylphosphino)ferrocene]palladium (PdCl₂(dppf))-methylene chloride complex (399 mg) and a 2N aqueous cesium carbonate solution (7.33 mL) were added to 1,4-dioxane (29 mL), and the mixture was stirred at 100° C. for 5 hours. The reaction solution was filtered, and ethyl acetate and water were added to the filtrate to carry out a liquid separation. The organic layer was separated, washed with saturated brine and dried over anhydrous sodium sulfate. The solvent was distilled off under reduced pressure. The obtained residue was purified by silica gel column chromatography (n-hexane:ethyl acetate=95:5 to 80:20) and solidified by n-hexane to obtain Compound 3 (1.39 g).

MS (m/z): 367 [M+H]⁺

Reference Examples 9-2 to 9-3

A treatment was carried out in a manner similar to Reference Example 9-1 to obtain compounds of Reference Examples 9-2 and 9-3 in Table 28 below.

Reference Example 10

[Chemical Formula 411]

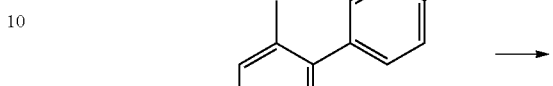

1

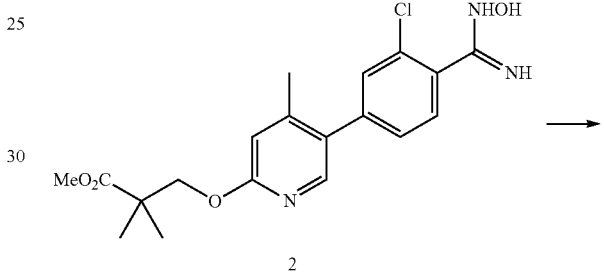

2

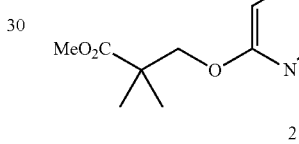

TABLE 28

| Reference Example | Intermediate 1 | Intermediate 2 | Product | MS (m/z) |
|---|---|---|---|---|
| 9-2 | | | | 313 [M + H]⁺ |
| 9-3 | | | | 383 [M + H]⁺ |

-continued

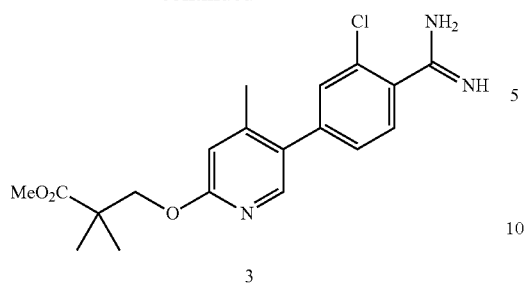

3

(1) A treatment was carried out in a manner similar to Reference Example 7-1 (4) using Compound 1 (850 mg) to obtain Compound 2 (940 mg).

MS (m/z): 392/394 [M+H]$^+$ (2) Compound 2 (925 mg) was dissolved in acetic acid (9 mL) and acetic anhydride (268 μL), and the mixture was stirred at room temperature for 30 minutes. Palladium chloride (46 mg) and triethyl silane (535 μL) were added, and the mixture was stirred at 70° C. for 4 hours. Additional triethyl silane (288 μL) was added, and the mixture was further stirred at the same temperature for 30 minutes. The reaction solution was filtered, and the filtrate was concentrated under reduced pressure. Saturated brine and ethyl acetate were added to the obtained residue to carry out a liquid separation. The organic layer was separated, washed with saturated brine, and dried over anhydrous magnesium sulfate. The solvent was distilled off under reduced pressure. The obtained residue was purified by NH-silica gel column chromatography (chloroform:methanol=100:0 to 90:10) and then silica gel column chromatography (n-hexane:ethyl acetate=90:10 to 67:33) to obtain Compound 3 (201 mg).

MS (m/z): 376/378 [M+H]$^+$

Reference Example 11

[Chemical Formula 412]

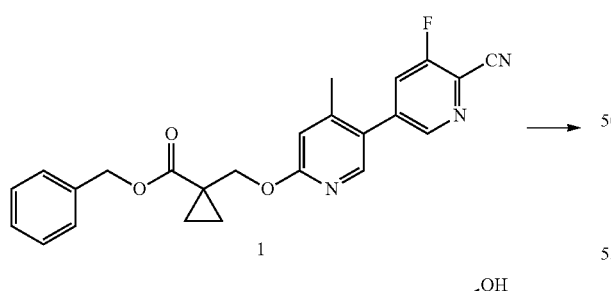

-continued

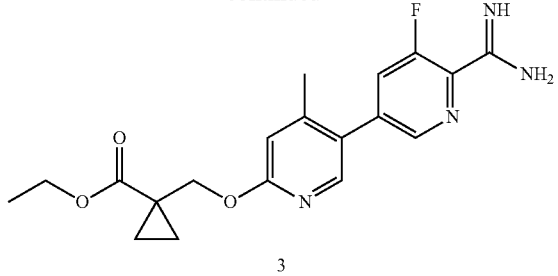

3

(1) A treatment was carried out in a manner similar to Reference Example 7-1 (4) using Compound 1 (1.4 g) to obtain Compound 2 (1.51 g).

MS (m/z): 451 [M+H]$^+$ (2) Compound 2 (1.32 g) was dissolved in acetic acid (30 mL) and acetic anhydride (610 μL), and the mixture was stirred at room temperature for 6 hours. To the reaction solution were added methanol (10 mL) and tetrahydrofuran (10 mL), and 10% palladium-carbon (265 mg) was added under a nitrogen atmosphere. The reaction mixture was stirred under a hydrogen atmosphere at room temperature for 2 hours and subsequently filtered through Celite, and the filtrate was concentrated under reduced pressure. To the obtained residue were added ethanol (20 mL) and a 4N hydrogen chloride-dioxane solution (10 mL), and the mixture was stirred at room temperature overnight and further at 60° C. for 8 hours. Chloroform, methanol and an aqueous saturated sodium hydrogen carbonate solution were added to the reaction solution to carry out a liquid separation. The organic layer was separated, dried over anhydrous sodium sulfate and concentrated under reduced pressure. The obtained residue was solidified with diethyl ether to obtain Compound 3 (675 mg).

MS (m/z): 373 [M+H]$^+$

Reference Example 12

[Chemical Formula 413]

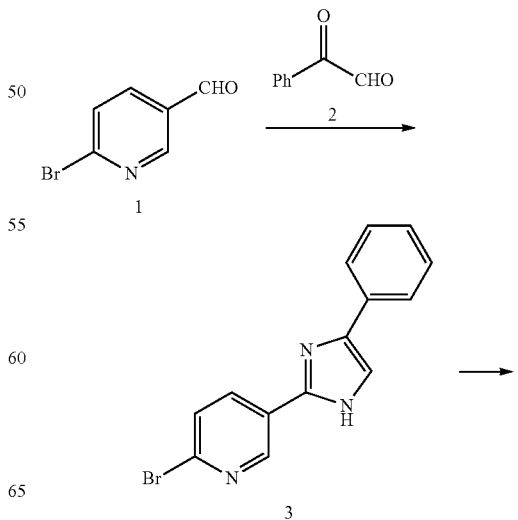

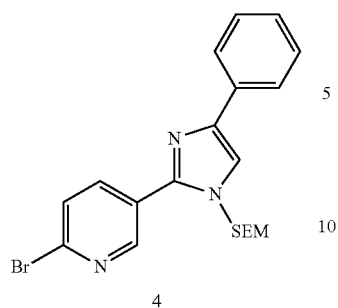

(1) Compound 1 (1.86 g), Compound 2 (3.02 g) and a 28% aqueous ammonia (25 mL) were added to a mixed solvent of water (25 mL) and methanol (100 mL), and the mixture was stirred at room temperature for 5 hours. Chloroform and a saturated aqueous sodium hydrogen carbonate solution were added to the residue obtained by concentration of the reaction solution under reduced pressure to carry out a liquid separation. The organic layer was separated and dried with anhydrous sodium sulfate, and subsequently the solvent was distilled off under reduced pressure. The obtained residue was purified by silica gel column chromatography (n-hexane:ethyl acetate=50:50 to 20:80) to obtain Compound 3 (490 mg).

MS (m/z): 300/302 [M+H]$^+$ (2) To a solution of Compound 3 (475 mg) in N,N-dimethylformamide (5 mL) was added a 60% sodium hydride (95 mg) under a nitrogen atmosphere under ice cooling, and the mixture was stirred at room temperature for 30 minutes. To this was added 2-(trimethylsilyl)ethoxymethyl chloride (420 μL) under ice cooling, and the mixture was stirred at room temperature for 6 hours. To the reaction solution was added a saturated aqueous ammonium chloride solution, and the mixture was extracted with ethyl acetate. The organic layer was washed with saturated brine, and the aqueous layer thus obtained was extracted with ethyl acetate. The organic layers were combined, dried and concentrated under reduced pressure. The obtained residue was purified by silica gel column chromatography (n-hexane:ethyl acetate=87:13 to 74:26) to obtain Compound 4 (651 mg).

MS (m/z): 430/431 [M+H]$^+$

Reference Example 13-1

[Chemical Formula 414]

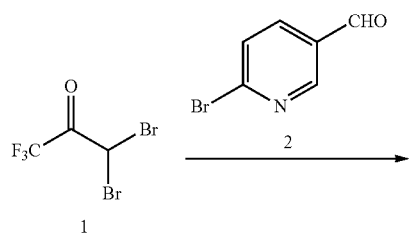

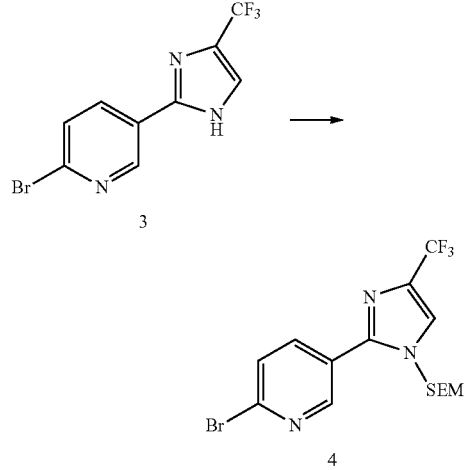

(1) To water (15 mL) were added Compound 1 (3,3-dibromo-1,1,1-trifluoropropan-2-one) (4.05 g) and sodium acetate (2.46 g), and the mixture was stirred at 95° C. for 30 minutes. The reaction solution was ice-cooled, this was added to a solution of Compound 2 (6-bromo-nicotinaldehyde) (1.86 g) dissolved in a 28% aqueous ammonia solution (20 mL) and methanol (60 mL) under ice-cooling, and the mixture was stirred overnight while the temperature was gradually elevated to room temperature. After the reaction solution was concentrated under reduced pressure, water and ethyl acetate were added to carry out a liquid separation, the organic layer was dried over anhydrous sodium sulfate, and the solvent was distilled off under reduced pressure. Diethyl ether was added to the obtained solid residue, the mixture was triturated and solid was collected by filtration and dried to obtain Compound 3 (2-bromo-5-[5-(trifluoromethyl)-1H-imidazole-2-yl]pyridine) (1.25 g).

MS (m/z): 292/294 [M+H]$^+$ (2) To a solution of Compound 3 (2-bromo-5-[5-(trifluoromethyl)-1H-imidazole-2-yl]pyridine) (13.65 g) dissolved in N,N-dimethylformamide (150 mL) was added a 60% sodium hydride (2.62 g) under a nitrogen atmosphere under ice-cooling, and the mixture was stirred for 30 minutes. To this was added 2-(trimethylsilyl)ethoxymethyl chloride (12.4 mL) under ice cooling, and the mixture was stirred overnight while the temperature gradually brought back to room temperature. To the reaction solution was added a saturated aqueous ammonium chloride solution, and the mixture was extracted with ethyl acetate. The organic layer was washed with saturated brine, and the aqueous layer thus obtained was extracted with ethyl acetate. The organic layers were combined, dried and concentrated under reduced pressure. The obtained residue was purified by silica gel column chromatography (n-hexane:ethyl acetate) to obtain Compound 4 (2-bromo-5-[4-(trifluoromethyl)-1-{[2-(trimethylsilyl)ethoxy]methyl}-1H-imidazole-2-yl]pyridine) (9.42 g).

MS (m/z): 422/424 [M+H]$^+$

Reference Examples 13-2 to 13-3

A treatment was carried out in a manner similar to Reference Example 13-1 to obtain compounds of Reference Examples 13-2 to 13-3 in Table 29 below.

TABLE 29

| Reference Example | Starting material 1 | Starting material 2 | Product | MS (m/z) |
|---|---|---|---|---|
| 13-2 | F₃C-CO-CHBr-Br | 5-Br-pyridine-2-CHO | 2-(5-bromopyridin-2-yl)-4-CF₃-1-SEM-imidazole | 422/424 [M + H]⁺ |
| 13-3 | F₃C-CO-CHBr-Br | 4-Br-benzaldehyde | 2-(4-bromophenyl)-4-CF₃-1-SEM-imidazole | 421/423 [M + H]⁺ |

Reference Example 14

[Chemical Formula 415]

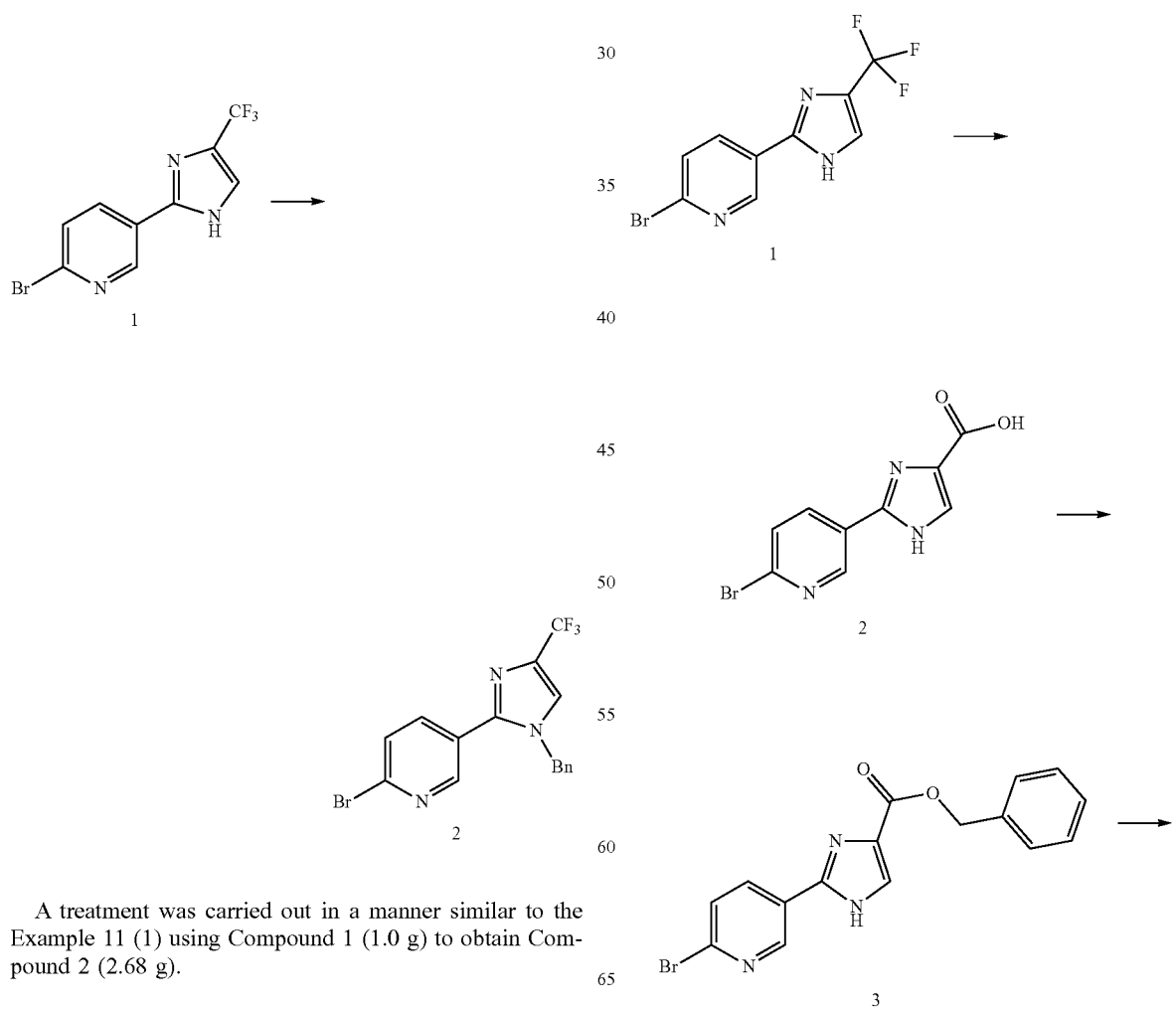

Reference Example 15-1

[Chemical Formula 416]

A treatment was carried out in a manner similar to the Example 11 (1) using Compound 1 (1.0 g) to obtain Compound 2 (2.68 g).

MS (m/z): 382/384 [M+H]⁺

-continued

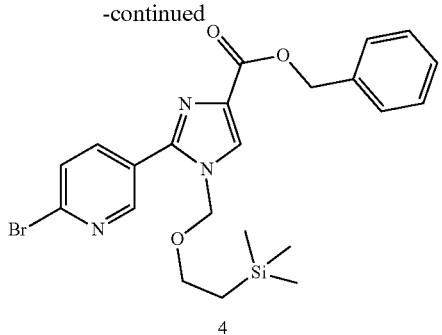

4

(1) Compound 1 (5.9 g) was dissolved in ethanol (70 mL), and an 8M aqueous sodium hydroxide solution (25 mL) was added, and the mixture was stirred at 70° C. for 19 hours. The reaction solution was concentrated under reduced pressure, and ethyl acetate and water were added to the obtained residue to carry out a liquid separation. The aqueous layer was separated, and to this was added a 6M hydrochloric acid to adjust the pH to 5-6. Further, after neutralization by addition of phosphate buffer (pH 7.0), the mixture was extracted with a mixed solvent of ethyl acetate and tetrahydrofuran. The organic layer was separated, dried over anhydrous sodium sulfate, and concentrated under reduced pressure. To the obtained residue was added diethyl ether, and the deposited solid was collected by filtration to obtain Compound 2 (2.56 g).

MS (m/z): 268/270 [M+H]$^+$ (2) Compound 2 (2.62 g), diisopropyl ethyl amine (2.21 mL) and benzyl bromide (2.01 g) were added to N,N-dimethylacetamide (30 mL), and the mixture was stirred at room temperature overnight. The reaction mixture was ice-cooled, water (270 mL) was added, and the obtained solid was collected by filtration and washed with n-hexane to obtain Compound 3 (3.06 g).

MS (m/z): 358/360 [M+H]$^+$ (3) A treatment was carried out in a manner similar to the Example 6 (2) using Compound 3 (2.88 g) to obtain Compound 4 (1.76 g).

MS (m/z): 488/490 [M+H]$^+$

Reference Example 15-2

A treatment was carried out in a manner similar to Reference Example 15-1 to obtain a compound of Reference Example 15-2 in Table 30 below.

Reference Example 16

[Chemical Formula 417]

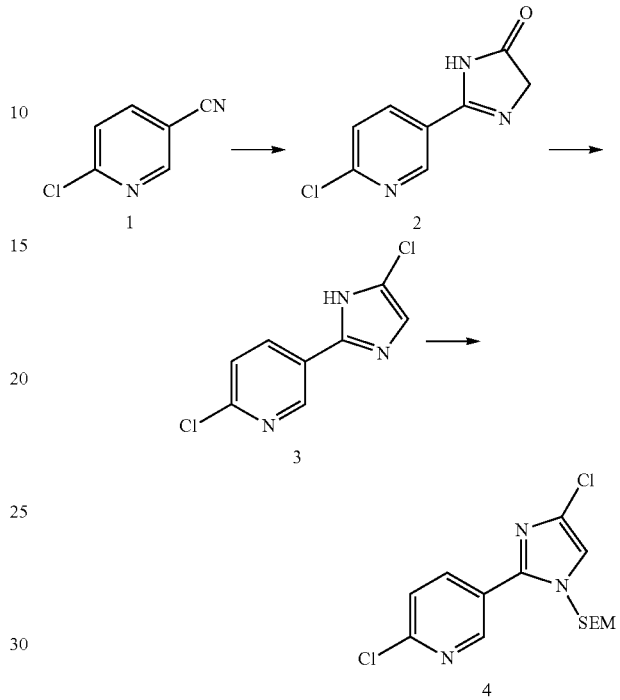

(1) To a solution of sodium methylate (1.39 g) in methanol (28.9 mL) was added Compound 1 (6-chloronicotinonitrile) (10 g), and the mixture was stirred at 40° C. for 30 minutes. The reaction solution was concentrated under reduced pressure, to the obtained residue was added tetrahydrofuran (30 mL) to be mixed, and the mixture was concentrated under reduced pressure. To the residue was added tetrahydrofuran (100 mL), glycine methyl ester hydrochloride (9.06 g) and triethylamine (11.07 mL) were added, and the mixture was stirred at 55° C. for 6.5 hours. The deposited solid was collected by filtration, washed with ethyl acetate and dried to obtain Compound 2 (19.05 g).

MS (m/z): 196/198 [M+H]$^+$ (2) Compound 2 (19.05 g) was heated in phosphorous oxychloride (45.4 mL) at reflux for 1.5 hours. The insoluble

TABLE 30

| Reference Example | Intermediate | Product | MS (m/z) |
|---|---|---|---|
| 15-2 | | | 487/489 [M + H]$^+$ | matter was filtered, and the filtrate was neutralized by addition of a ethyl acetate and a 2N aqueous sodium hydroxide solution. Tetrahydrofuran and activated charcoal were added, the mixture was stirred and filtered thought Celite, and water and ethyl acetate were added to the filtrate to carry out a liquid separation. The organic layer was separated, washed with brine, and dried over anhydrous magnesium sulfate. The solvent was distilled off under reduced pressure. To the obtained solid was added acetonitrile, and the solid was collected by filtration and dried to obtain Compound 3 (4.87 g).

MS (m/z): 214/216 [M+H]$^+$ (3) A treatment was carried out in a manner similar to the Example 6 (2) using Compound 3 (5.09 g) to obtain Compound 4 (5.96 g).

MS (m/z): 344/346 [M+H]$^+$

Reference Example 17-1

[Chemical Formula 418]

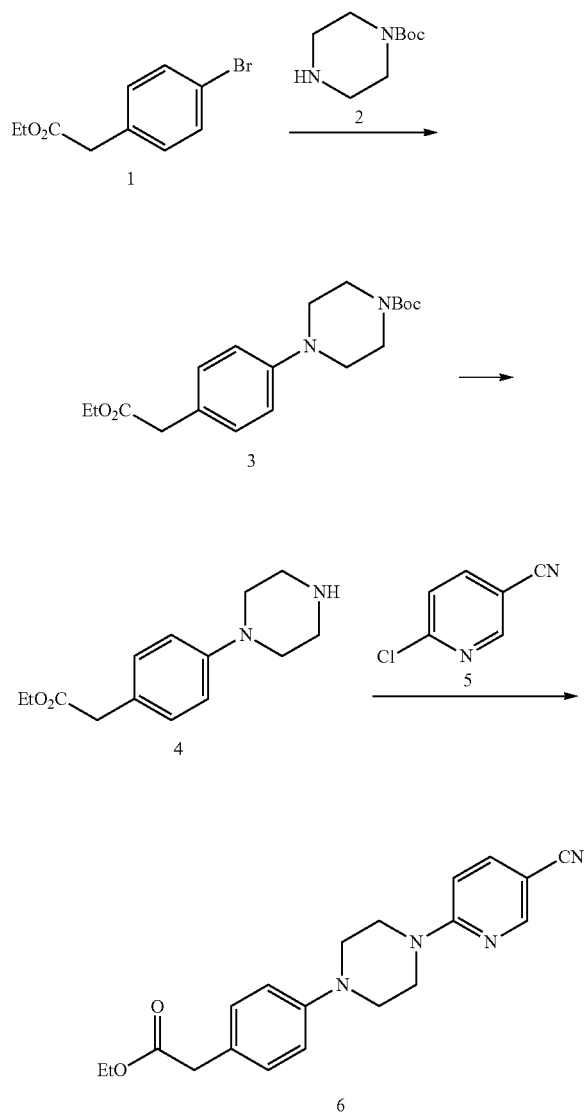

(1) Palladium acetate (924 mg) and 2-dicyclohexylphosphino-2',4',6'-triisopropyl-1,1'-biphenyl (X-PHOS) (5.88 g) were added to a mixed solvent of 1,4-dioxane (500 mL) and water (297 μL) under a nitrogen atmosphere, and the mixture was stirred at 80° C. for 10 minutes. After the reaction solution was cooled to room temperature, a separately prepared solution of Compound 1 (50.00 g), Compound 2 (45.97 g) and cesium carbonate (100.52 g) in 1,4-dioxane (500 mL) was added, and the mixture was stirred at 100° C. for 4 hours. The reaction solution was cooled and subsequently filtered through Celite, and Celite was washed with ethyl acetate. The obtained filtrate was washed with water and then saturated brine, and dried over anhydrous sodium sulfate. Subsequently, the solvent was distilled off under reduced pressure. The obtained residue was purified by silica gel column chromatography (n-hexane:ethyl acetate=100:0 to 80:20) to obtain Compound 3 (69.14 g).

MS (m/z): 349 [M+H]$^+$ (2) Compound 3 (186.80 g) was dissolved in tetrahydrofuran (525 mL), and the solution was ice-cooled. A 4N hydrochloric acid-1,4-dioxane solution (656 mL) was slowly added, and the mixture was stirred at room temperature overnight. The reaction solution was concentrated under reduced pressure, the obtained residue was crystallized after addition of t-butyl methyl ether, and the crystals were collected by filtration. The obtained crystals were suspended in ethyl acetate, a 2M aqueous sodium hydroxide solution was added to adjust the pH to 9, and the mixture was extracted with ethyl acetate. The organic layer was dried over anhydrous sodium sulfate, and subsequently the solvent was distilled off under reduced pressure. The obtained residue was purified by silica gel column chromatography (n-hexane:ethyl acetate=80:20 to 0:100) to obtain Compound 4 (129.64 g).

MS (m/z): 249 [M+H]$^+$ (3) Compound 4 (3.32 g), Compound 5 (2.36 g) and potassium carbonate (2.35 g) were added to dimethylsulfoxide (50 mL), and the mixture was stirred at 100° C. for 2 hours. After the mixture was cooled to room temperature, ethyl acetate and water were added to carry out a liquid separation. The organic layer was separated, washed with saturated brine, and dried over anhydrous sodium sulfate. The solvent was distilled off under reduced pressure. The obtained residue was purified by silica gel column chromatography (n-hexane:ethyl acetate=80:20 to 0:100). The purified product was triturated in diethyl ether and collected by filtration to obtain Compound 6 (3.24 g).

MS (m/z): 351 [M+H]$^+$

Reference Example 17-2

A treatment was carried out in a manner similar to Reference Example 17-1 to obtain a compound of Reference Example 17-2 in Table 31 below.

TABLE 31

| Reference Example | Starting material 1 | Starting material 2 | Product | MS (m/z) |
|---|---|---|---|---|
| 17-2 | 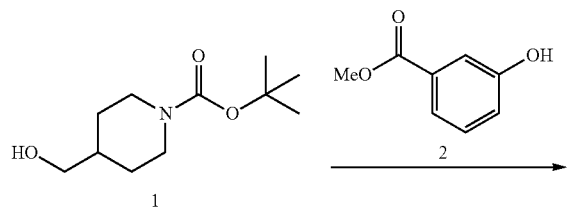 | | | 318 [M + H]⁺ |

Reference Example 18

[Chemical Formula 419]

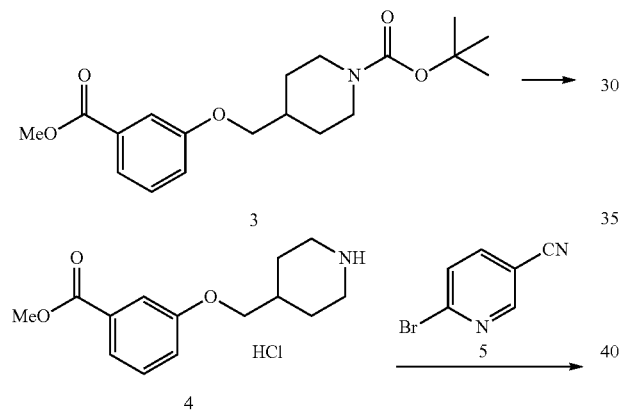

(1) A treatment was carried out in a manner similar to Reference Example 7-1) using Compound 1 (7.08 g) and Compound 2 (2.5 g) to obtain Compound 3 (2.78 g).
MS (m/z): 350 [M+H]⁺
(2) Compound 3 (2.78 g) was dissolved in 1,4-dioxane (10 mL), and a 4N hydrogen chloride-1,4-dioxane solution (20 mL) was added under ice cooling. The reaction solution was stirred at room temperature overnight, and diethyl ether was added. The deposited solid was collected by filtration, washed with diethyl ether and then dried to obtain Compound 4 (2.27 g).
MS (m/z): 250 [M+H]⁺
(3) Compound 4 (600 mg), Compound 5 (500 mg), potassium carbonate (871 mg) and 1,8-diazabicyclo[5.4.0]undec-7-ene (345 μL) were added to 1,4-dioxane (15 mL), and the mixture was stirred at 99° C. for two days. After the reaction solution was concentrated under reduced pressure, ethyl acetate and water were added to carry out a liquid separation. The organic layer was separated, washed with water and saturated brine, and dried over anhydrous sodium sulfate. The solvent was distilled off under reduced pressure. The obtained residue was purified by silica gel column chromatography (n-hexane:ethyl acetate=100:0 to 70:30). To the obtained solid were added ethyl acetate and n-hexane under ice cooling, and the deposit was collected by filtration to obtain Compound 6 (515 mg).
MS (m/z): 352 [M+H]⁺

Reference Example 19

[Chemical Formula 420]

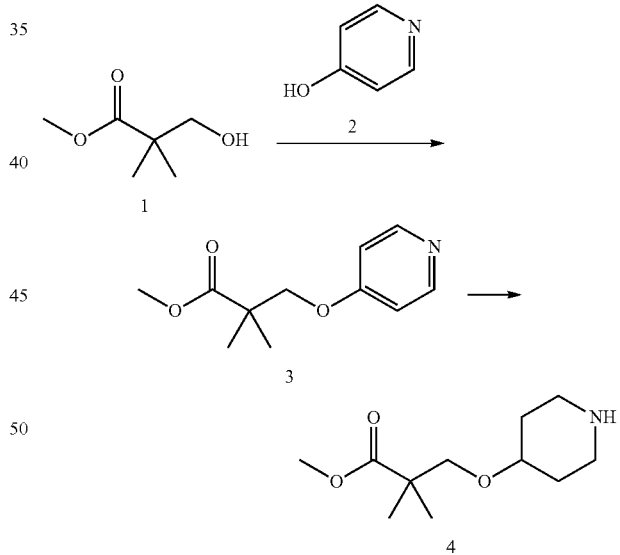

(1) A treatment was carried out in a manner similar to Reference Example 7-1 (1) using Compound 1 (7.64 g) and Compound 2 (5.0 g) to obtain Compound 3 (8.27 g).
MS (m/z): 210 [M+H]⁺
(2) Compound 3 (3.0 g) was dissolved in diethyl ether (20 mL), benzyl bromide (3.4 mL) was added, and the mixture was stirred at room temperature for two days. Subsequently, the deposited solid was collected by filtration. The solid was dissolved in methanol (60 mL), sodium borohydride (2.17 g) was added portionwise, and the mixture was stirred at room temperature for 2 hours. After a saturated aqueous ammonium chloride solution and methylene chloride were added to carry out a liquid separation, the organic layer was separated, washed with saturated brine, and concentrated under reduced pressure. The obtained residue was dissolved in methanol (60 mL), a 10% palladium-carbon (300 mg) was added, and the mixture was stirred under a hydrogen atmosphere for 7 hours. The 10% palladium-carbon was filtered out and the filtrate was concentrated under reduced pressure. The residue was dissolved in acetic acid (50 mL), a 10% palladium-carbon (300 mg) was added, and the mixture was stirred under a hydrogen atmosphere at 70° C. for 7 hours. The 10% palladium-carbon was filtered out, the filtrate was concentrated under reduced pressure, and the obtained residue was purified by NH-silica gel column chromatography (chloroform:methanol=100:0 to 98:2) to obtain Compound 4 (1.34 g).

MS (m/z): 216 [M+H]$^+$

Reference Example 20-1

[Chemical Formula 421]

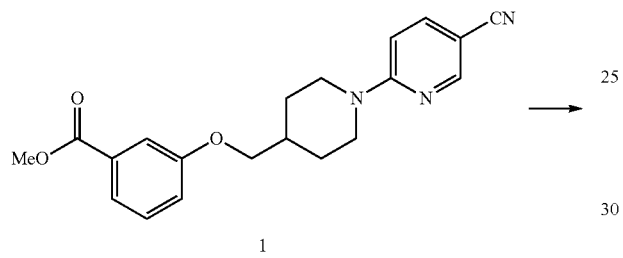

1

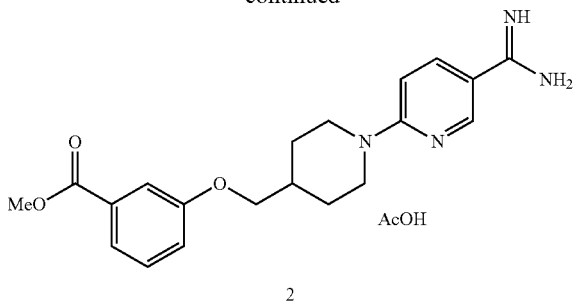

2

A treatment was carried out in a manner similar to Reference Example 7-1 (4) and Reference Example 7-1 (5) using Compound 1 (514 mg) to obtain Compound 2 (416 mg) as an acetate salt.

MS (m/z): 369 [M+H]$^+$

Reference Examples 20-2 to 20-3

A treatment was carried out in a manner similar to Reference Example 20-1 to obtain compounds of Reference Examples 20-2 and 20-3 in Table 32 below.

TABLE 32

| Reference Example | Intermediate | Product | MS (m/z) |
|---|---|---|---|
| 20-2 | | | 368 [M + H]$^+$ |
| 20-3 | | | 335 [M + H]$^+$ |

Reference Example 21-1

[Chemical Formula 422]

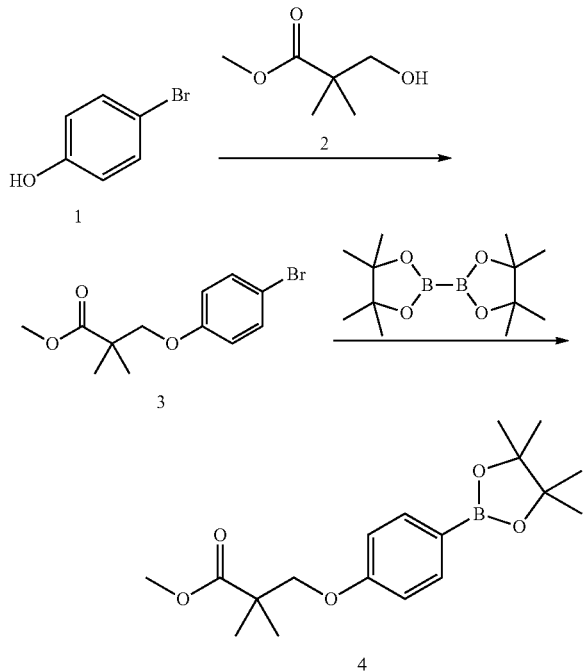

(1) Compound 1 (4-bromophenol) (61.0 g), Compound 2 (methyl hydroxypivalate) (69.9 g) and triphenylphosphine (138.7 g) were dissolved in tetrahydrofuran (350 mL), and the mixture was cooled to 0° C. under a nitrogen atmosphere. Subsequently, a 40% diethyl azodicarboxylate-toluene solution (240 mL) was added dropwise, and the mixture was stirred while the temperature brought back to room temperature and then at 80° C. overnight. After the temperature of the reaction solution was brought back to room temperature, the reaction solution was concentrated under reduced pressure, and to the obtained residue was added diethyl ether (500 mL). The obtained solid was filtered and washed with diethyl ether. The filtrate was concentrated under reduced pressure and the obtained residue was purified by silica gel column chromatography (n-hexane:ethyl acetate=100:0, 19:1 and to 9:1) to obtain Compound 3 (102.2 g).

MS (m/z): 304/306 [M+NH$_4$]$^+$ (2) Compound 3 (102.2 g), bis(pinacolato)diboron (98.5 g), a [1,1'-bis(diphenylphosphino)ferrocene]palladium(II) dichloride dichloromethane complex (7.73 g), 1,1'-bis(diphenylphosphino)ferrocene (5.86 g) and potassium acetate (103.8 g) were dissolved in 1,4-dioxane (470 mL), and the mixture was stirred under a nitrogen atmosphere at 80° C. overnight. After the temperature of the mixture was brought back to room temperature, the mixture was concentrated under reduced pressure, and ethyl acetate and water were added to the obtained residue to carry out a liquid separation. The organic layer was separated, washed with saturated brine, and dried over anhydrous sodium sulfate. The solvent was distilled off under reduced pressure. The obtained residue was purified by silica gel column chromatography (n-hexane:ethyl acetate=100:0, 9:1 and to 4:1), and to the obtained residue was added n-hexane, and the mixture was stirred under ice-cooling for 1 hour. The solid was collected by filtration and dried to obtain Compound 4 (95.5 g).

MS (m/z): 335 [M+H]$^+$

Reference Examples 21-2 to 21-9

A reaction was carried out in a manner similar to Reference Example 21-1 using the following raw materials 1 and 2 to obtain compounds of Reference Examples 21-2 to 21-9 in Table 33 below.

TABLE 33

| Reference Example | Raw Material 1 | Raw Material 2 | Product 4 | MS (m/z) |
|---|---|---|---|---|
| 21-2 | (5-bromo-2-hydroxypyridine) | (methyl hydroxypivalate) | (pyridine boronate ester product) | 336 [M + H]$^+$ |
| 21-3 | (3-bromo-6-hydroxy-2-methylpyridine) | (methyl hydroxypivalate) | (pyridine boronate ester product) | 350 [M + H]$^+$ |

TABLE 33-continued

| Reference Example | Raw Material 1 | Raw Material 2 | Product 4 | MS (m/z) |
|---|---|---|---|---|
| 21-4 | | | | 350 [M + H]+ |
| 21-5 | | | | 348 [M + H]+ |
| 21-6 | | | | 362 [M + H]+ |
| 21-7 | | | | 404 [M + H]+ |
| 21-8 | | | | 420 [M + H]+ |
| 21-9 | | | | 424 [M + H]+ |

Reference Example 22-1

[Chemical Formula 423]

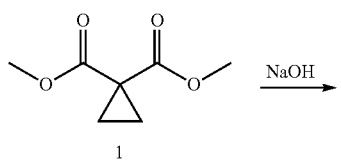

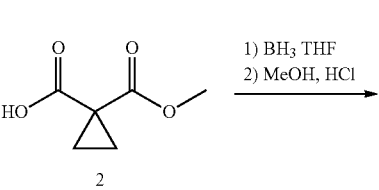

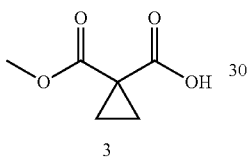

(1) To a solution of dimethyl 1,1-cyclohexanedicarboxylate (2.08 g) in methanol (15 mL) was added a 1N aqueous sodium hydroxide solution (13.2 mL), and the mixture was stirred at room temperature for 23 hours. The methanol was distilled off under reduced pressure, and the residue was washed with n-hexane. To an aqueous layer was added 1N hydrochloric acid (10 mL), and the mixture was extracted with chloroform. The extract was washed with saturated brine, and dried over anhydrous magnesium sulfate. After drying, concentration under reduced pressure provided Compound 2 (1.58 g) as a colorless oil.

(2) A solution of Compound 2 (1.57 g) in tetrahydrofuran (15 mL) was ice-cooled under a nitrogen stream, and a 1M solution of a borane/tetrahydrofuran complex in tetrahydrofuran (12 mL) was added dropwise. After dropwise addition, the reaction solution was stirred at room temperature for 1.5 hours. The reaction solution was ice-cooled, and methanol was added. After the mixture was concentrated under reduced pressure, the residue was dissolved in methanol (15 mL), 20% hydrochloric acid/methanol (4 mL) was added, and the mixture was stirred at 70° C. for 18 hours. The reaction solution was concentrated under reduced pressure, to the residue was added an aqueous saturated sodium bicarbonate solution, and the mixture was extracted with chloroform. The extract was washed with saturated brine, and dried over anhydrous magnesium sulfate. To this was added NH silica gel, and the mixture was stood. The mixture was filtered and concentrated under reduced pressure to obtain Compound 3 (1.14 g) as a colorless oil.

MS (m/z): 131 [M+H]$^+$

Reference Example 22-2

[Chemical Formula 424]

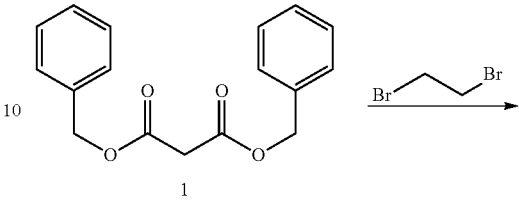

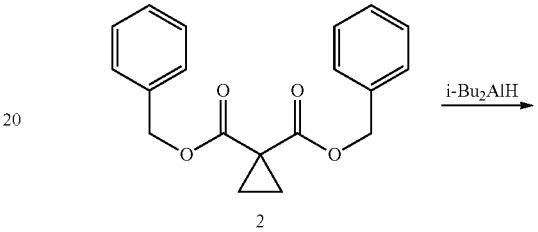

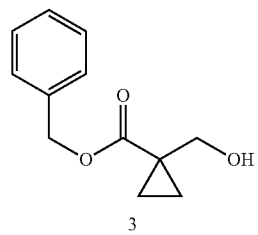

(1) To a solution of dibenzyl malonate (25 g) in N,N-dimethylformamide (250 mL) were added potassium carbonate (121.5 g) and dibromoethane (22.7 mL), and the mixture was stirred at room temperature overnight. To the reaction solution was added water, and the mixture was extracted with ethyl acetate. The extract was washed with water, dried over anhydrous sodium sulfate, and then concentrated under reduced pressure. The obtained residue was purified by silica gel column chromatography (n-hexane: ethyl acetate=90:10 to 80:20) to obtain Compound 2 (25.33 g) as a colorless oil.

(2) A solution of Compound 2 (16.9 g) in methylene chloride (338 mL) was cooled to −65° C. or lower, and a 1M diisobutylaluminum hydride/toluene solution (119.8 mL) was added dropwise. After dropwise addition, the temperature of the reaction solution was elevated to −15° C. over 30 minutes. To the reaction solution were added a saturated aqueous ammonia chloride solution (170 mL) and 1N hydrochloric acid (170 mL), and the mixture was stirred for 10 minutes. To the obtained gel-like mixture was added further 1N hydrochloric acid (300 mL) to dissolve the mixture. The organic layer was separated, washed with saturated sodium bicarbonate water, and dried over anhydrous sodium sulfate. After concentration under reduced pressure, the residue was purified by silica gel column chromatography (n-hexane: ethyl acetate=90:10 to 50:50) to obtain Compound 3 (5.18 g) as a colorless oil.

MS (m/z): 207 [M+H]$^+$

Reference Example 22-3

[Chemical Formula 425]

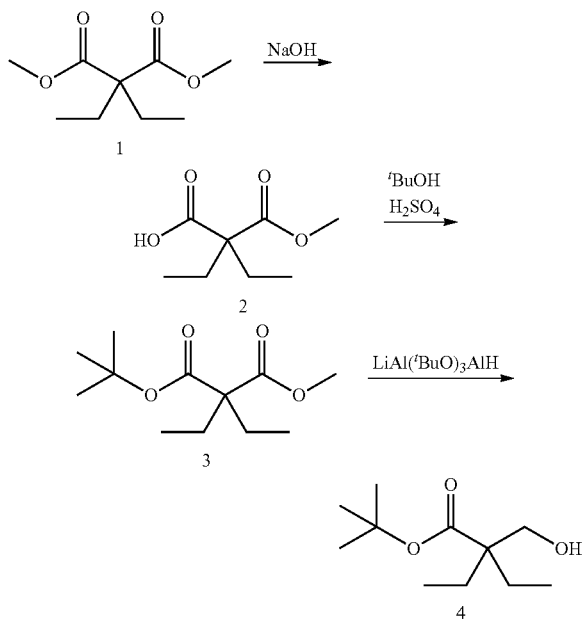

(1) To a solution of dimethyl diethylmalonate (25 g) in methanol (250 mL) was added a 1N aqueous sodium hydroxide solution (132.8 mL), and the mixture was stirred at room temperature overnight. The methanol was distilled off under reduced pressure, and the residue was washed with methylene chloride. To the aqueous layer was added 1N hydrochloric acid to adjust the pH to 3, and the mixture was extracted with diethyl ether. The extract was washed with water, dried over anhydrous magnesium sulfate. After drying, concentration under reduced pressure provided Compound 2 (23.1 g) as a colorless oil.

(2) Anhydrous magnesium sulfate (63.85 g) was suspended in methylene chloride (230 mL), concentrated sulfuric acid (7.07 mL) was added dropwise at room temperature, and the mixture was stirred for 15 minutes. To this was added a solution of Compound 2 (23.1 g) in methylene chloride (115 mL), and then tert-butanol (63.5 mL) was added. The reaction solution was stirred at room temperature overnight. The reaction mixture was filtered, and the filtrate was ice-cooled and rendered alkaline with an aqueous saturated sodium hydrogen carbonate solution. The organic layer was separated, washed with saturated brine, dried over anhydrous sodium sulfate and concentrated under reduced pressure to obtain Compound 3 (26.09 g) as a colorless oil.

(3) To a solution of the obtained Compound 3 (14 g) in tetrahydrofuran (140 mL) was added dropwise a 1M solution of lithium tri(tert-butoxy)aluminum hydride in tetrahydrofuran (150 mL) at room temperature, and the mixture was gradually heated and then at reflux for 8 hours. The reaction solution was ice-cooled, and 1N hydrochloric acid (500 mL) was added dropwise. The reaction mixture was extracted with diethyl ether, and the extract was washed with water and an aqueous saturated sodium bicarbonate solution, and dried over anhydrous magnesium sulfate. After concentration under reduced pressure, the residue was purified by silica gel column chromatography (n-hexane:ethyl acetate=90:10 to 80:20) to obtain Compound 4 (7.41 g) as a colorless oil.

$^1$H NMR (DMSO-$d_6$, 400 MHz) (ppm): δ 4.48 (t, J=5.2 Hz, 1H), 3.42 (d, J=5.1 Hz, 2H), 1.46 (m, 4H), 1.38 (s, 9H), 0.74 (t, J=7.2 Hz, 6H)

Reference Example 22-4

[Chemical Formula 426]

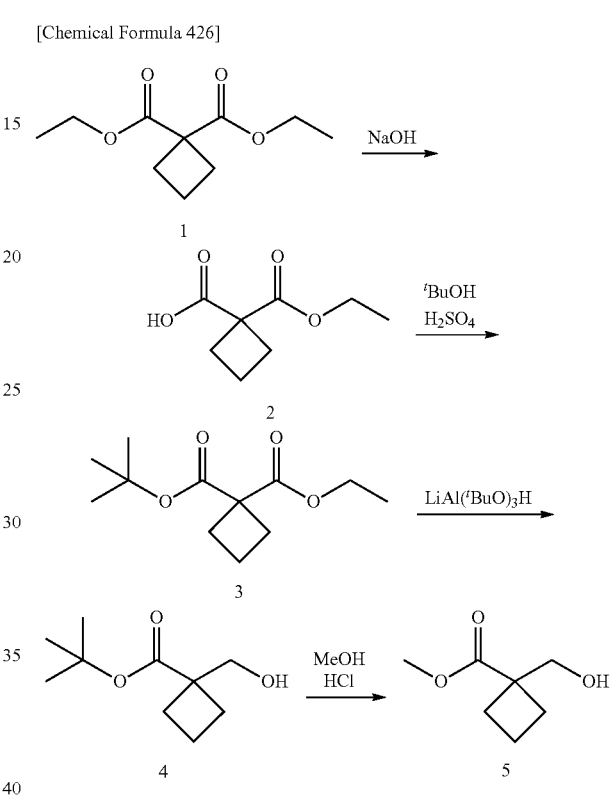

(1) To a solution of diethyl 1,1-cyclobutanedicarboxylate (25 g) in ethanol (250 mL) was added a 1N aqueous sodium hydroxide solution (125 mL), and the mixture was stirred at room temperature for 6 days. The ethanol was distilled off under reduced pressure, and the residue was washed with diethyl ether. To the aqueous layer was added 1N hydrochloric acid to adjust the pH to 3, and the mixture was extracted with chloroform. The extract was washed with water, dried over anhydrous magnesium sulfate. After drying, concentration under reduced pressure provided Compound 2 (20.67 g) as a colorless oil.

(2) Anhydrous magnesium sulfate (52 g) was suspended in methylene chloride (186 mL), concentrated sulfuric acid (5.8 mL) was added dropwise at room temperature, and the mixture was stirred for 15 minutes. To this was added a solution of Compound 2 (18.6 g) in methylene chloride (93 mL), and then tert-butanol (52 mL) was added. The reaction solution was stirred at room temperature overnight. The reaction mixture was filtered, and the filtrate was ice-cooled and rendered alkaline with an aqueous saturated sodium bicarbonate solution. The organic layer was separated, washed with saturated brine, dried over anhydrous sodium sulfate, and concentrated under reduced pressure to obtain Compound 3 (24.7 g) as a colorless oil.

(3) To a solution of the obtained Compound 3 (15.9 g) in tetrahydrofuran (160 mL) was added dropwise a 1M solution of lithium tri(tert-butoxy)aluminum hydride (153 mL) in tetrahydrofuran at room temperature, and the mixture was gradually heated and then at reflux for 3.5 hours. The reaction solution was ice-cooled, a saturated aqueous ammonium chloride solution was added, and the mixture was stirred at room temperature. The obtained gel-like mixture was filtered, and concentrated under reduced pressure. Subsequently, the residue was purified by silica gel column chromatography (n-hexane:ethyl acetate=100:0 to 75:25) to obtain Compound 4 (11.02 g) as a colorless oil.

MS (m/z): 187 [M+H]$^+$ (4) To a solution of Compound 4 (3 g) in methanol (60 mL) was added 2N hydrochloric acid/methanol (6 mL), and the mixture was heated at reflux for 5.5 hours. The reaction solution was diluted with methylene chloride, washed with an aqueous saturated sodium bicarbonate solution and saturated brine, dried over anhydrous magnesium sulfate and concentrated under reduced pressure to obtain Compound 5 (2.16 g) as a colorless oil.

MS (m/z): 149 [M+H]$^+$

Experimental Example 1

DGAT1 Inhibitory Activity

Experimental Method (1) Cloning of Human DGAT1 Gene and Preparation of Recombinant Baculovirus Human DGAT1 gene was obtained by using a human cDNA library as a temple, and amplifying the base sequence (245-1711 in Genbank Accession No. NM_012079) which codes DGAT1 by PCR reaction.

Thus obtained human DGAT1 gene was ligated into a plasmid, pVL1392 (BD Biosciences) to prepare an expression plasmid, pVL1392-DGAT1. Further, a recombinant baculovirus was prepared by using BD BaculoGold Baculovirus Expression vector system (BD Biosciences).

(2) Preparation of Microsome of Human DGAT 1 Enzyme Highly Expressed-Insect Cell The preparation of human DGAT 1 enzyme was carried out by infecting the recombinant baculovirus obtained in the previous item with expresSF+® insect cell (Nosan Corporation). After the recombinant baculovirus was added to the expresSF+® cell and the mixture was cultivated for 72 hours, the cells were collected by centrifugation, and freeze-preserved at −80° C. The freeze-preserved cells were fused in an ice water, suspended in a buffer (200 mM Sucrose, 1 mM EDTA, 100 mM Tris-HCl (pH7.4)) to which Complete Protease Inhibitor (Roche) had been added, and subjected to a sonication. Then, a microsome fraction was obtained by an ordinary method and freeze-preserved at −80° C. as a highly DGAT1-expressing microsome.

(3) Measurement of DGAT1 Inhibitory Activity

As a buffer used for the enzymatic reaction of DGAT1, 100 mM Tris-HCl (pH7.4), 200 mM Sucrose, and 20 mM MgCl$_2$, 0.125% Bovin Serum Albumin (BSA) were used. To this buffer, a test compound with predetermined concentration of test compound, 15 µM dioleoylglycerol, 5 µM [$^{14}$C]-palmitoyl-CoA, 100 µg-protein/mL, highly DGAT1-expressing expresSF+® microsome, 0.75% acetone, and 1% dimethylsulfoxide were added, and a triglyceride (TG) synthesis reaction in a volume of 100 µL was carried out at 30° C. for 20 minutes. 90 µL of the reaction solution was added to 810 µL of methanol to cease the reaction. The reaction solution was added to Oasis® µ Elution plate (Waters) and eluted with 150 µL of mixture of acetonitrile:isopropanol (=2:3). 150 µL of MicroScinti™-40 (Perkin-Elmer Corp.) were added to the eluted solution and the mixture was sufficiently stirred, and an amount of [$^{14}$C]-TG produced in the reaction was determined by measuring using Top-Count™-NXT (Perkin-Elmer Corp.).

The inhibitory ratio was calculated by the following equation.

Inhibitory ratio (%)=(1−(TG amount when the test compound was added−blank TG amount)/(control TG amount−blank TG amount))×100

Here, a count of [$^{14}$C]-TG in the solution where the reaction was carried out without adding the test compound was regarded "control TG amount", and a count of [$^{14}$C]-TG in the solution to which the test compound and highly DGAT1 expressing expresSF+® microsome were not added was regarded as "blank TG amount". Further, a concentration of test compound required to inhibit the synthesis of [$^{14}$C]-TG by 50% (IC$_{50}$ value) was calculated by Prism 5.01 (GraphPad Softwear).

Experimental Result

The experimental results are shown in Table 34 as below.

TABLE 34

| Example | IC$_{50}$ (nM) | Example | IC$_{50}$ (nM) |
| --- | --- | --- | --- |
| 1-1 | 8.0 | 1-3 | 6.9 |
| 1-17 | 11 | 1-28 | 16.9 |
| 1-31 | 26.6 | 1-34 | 2.1 |
| 1-35 | 13 | 1-37 | 11 |
| 1-44 | 4.2 | 1-58 | 11 |
| 1-63 | 3.3 | 1-68 | 19 |
| 2-7 | 2.5 | 2-8 | 2.9 |
| 2-11 | 3.7 | 2-16 | 5.7 |
| 3-7 | 2.5 | 4-1 | 1.7 |
| 4-3 | 2.1 | 4-15 | 0.94 |
| 5-2 | 3.2 | 6 | 9.1 |
| 7 | 11 | 8 | 6.1 |
| 9 | 7.9 | 10 | 6.4 |
| 11 | 44.4 | 12 | 4.7 |
| 14 | 3.2 | 17 | 2.9 |
| 21-2 | 6.9 | 23-1 | 3.3 |
| 24-2 | 26 | 25 | 36 |
| 29-3 | 15 | 30 | 29 |
| 31-2 | 6.8 | 32-2 | 1.7 |
| 34 | 8.8 | 35-1 | 2.7 |
| 37-3 | 4.3 | 37-4 | 14 |
| 37-6 | 21 | 38-5 | 20 |
| 39 | 16 | 40-1, Compound 4 | 12 |
| 42 | 24 | 43-1 | 8.5 |
| 43-2 | 16 | 43-3 | 16 |
| 43-7 | 17 | 44-6 | 0.78 |
| 44-11 | 25 | 45-1 | 1.5 |
| 46-1 | 9.0 | 46-4 | 4.4 |
| 46-5 | 1.2 | 47-1 | 9.0 |
| 48 | 8.2 | 49 | 17 |
| 51 | 15 | 52 | 21 |
| 55 | 8.1 | 57 | 76 |
| 59 | 2.6 | 60 | 18 |
| 61 | 5.2 | 67 | 3.9 |
| 108 | 5.0 | 109 | 12 |
| 110 | 1.1 | 72 | 2.2 |
| 75 | 1.1 | 74 | 1.1 |
| 77 | 28 | 78 | 1.7 |
| 80 | 3.3 | 82 | 4.6 |
| 83 | 1.8 | 104 | 6.8 |

Experimental Example 2

Triglyceride (TG) Elevation-Suppressing Action in Plasma by Lipid Administration

Experimental Method

Male ICR mice, 6 to 9 weeks old, were fasted overnight, and a test compound was suspended in 0.2% carboxymethylcellulose solution and the suspension was orally administered. After 30 minutes, lipid (Intralipos, 20%, Otsuka Pharmaceutical, 10 mL/kg) was orally administered. Blood was sampled through the caudal vein immediately before and 2 hours after the administration of the lipid to obtain plasma. TG in the plasma was determined by using Triglyceride E-Test Wako (Wako Pure Chemical), and the elevation value of TG in the plasma by the lipid administration was calculated. By using the plasma TG elevation value in the solvent control group as the control, the plasma TG elevation-suppressing ratio was calculated in the test compound administrating group.

Experimental Result

As a result as the above, the test compound of the example showed the plasma TG elevation-suppressing ratio at the dose of 5 mg/kg as shown in Table 35 as below.

TABLE 35

| Example | Plasma TG elevation suppressing ratio (5 mg/kg) | Example | Plasma TG elevation suppressing ratio (5 mg/kg) |
|---|---|---|---|
| 1-58 | 66% | 2-11 | 62% |
| 4-1 | 74% | 7 | 47% |
| 10 | 53% | 31-2 | 74% |
| 32-2 | 63% | 37-3 | 64% |
| 37-4 | 69% | 43-1 | 66% |
| 43-2 | 66% | 46-5 | 59% |
| 48 | 61% | 51 | 49.3% |
| 52 | 70.8% | 59 | 72.0% |
| 61 | 77.4% | 67 | 56.8% |
| 110 | 73.0% | 75 | 74.6% |
| 74 | 67.5% | 78 | 73.8% |
| 82 | 67.9% | 83 | 79.5% |

Experimental Example 3

Food Intake-Suppressing Action

Experimental Method

Male C57BL/6J mice, 7 to 10 weeks old, were fasted overnight, and a test compound was suspended in 0.2% carboxymethylcellulose solution and the suspension was orally administered. Immediately, the animals were given high fat diet (Oriental Yeast, 60 cal % fat) and allowed to take freely. The food intake for 4 hours was determined, and the decrease ratio of the food intake (food intake-suppressing ratio) was calculated in the test compound administrating group, relative to the food intake in the solvent control group as a control.

Experimental Result

The test compound of the example showed the food intake-suppressing ratio at the dose of 5 mg/kg as shown in Table 36 as below.

TABLE 36

| Example | Food intake-suppressing ratio (5 mg/kg) | Example | Food intake-suppressing ratio (5 mg/kg) |
|---|---|---|---|
| 1-58 | 68% | 2-11 | 55% |
| 4-1 | 79% | 7 | 73% |
| 10 | 67% | 31-2 | 74% |
| 32-2 | 65% | 37-3 | 69% |
| 37-4 | 82% | 43-1 | 40% |
| 43-2 | 82% | 46-5 | 54% |
| 48 | 64% | 51 | 65% |
| 52 | 75% | 59 | 73% |
| 61 | 60% | 67 | 50% |
| 110 | 68% | 75 | 70% |
| 74 | 82% | 78 | 44% |
| 82 | 60% | 83 | 59% |

Experiment Example 4

Body Weight Gain-Suppressing Action, Hypoglycemic Action and Plasma Insulin-Decreasing Action in KK-Ay Mouse

Experimental Method

Male KK-Ay mice, 8 weeks old, were given high fat diet (Oriental Yeast, 60 cal % fat), the test compound was suspended in 0.2% carboxymethylcellulose solution and the suspension was orally administered once a day. After the oral administration was repeated for 2 weeks, the body weight gain-suppressing ratio of the test compound was calculated, relative to the body weight gain of the solvent control group during the test period as 100%. After the final administration, the animals were fasted overnight, and blood was sampled through the caudal vein. The blood sugar and the insulin in the plasma were determined by using Glucose C II-Test Wako (Wako Pure Chemical) and Mouse Insulin Measurement Kit (Morinaga Institute of Biological Science), respectively.

Experimental Result

As a result as above, the test compound of the example showed the hypoglycemic action, the plasma insulin-decreasing action, and the body weight gain-suppressing action at the dose of 30 mg/kg/day as shown in Table 37 as below, relative to the solvent control group.

TABLE 37

| Example | Hypoglycemic action (30 mg/kg/day) | Plasma insulin-decreasing action (30 mg/kg/day) | Body weight gain-suppressing action (30 mg/kg/day) |
|---|---|---|---|
| 7 | 42% | 34% | 34% |
| 10 | 37% | 40% | 32% |
| 31-2 | 55% | 45% | 41% |
| 43-1 | 36% | 53% | 21% |
| 51 | 26% | 21% | 41% |
| 61 | 44% | 50% | 36% |
| 67 | 47% | 14% | 43% |
| 74 | 32% | 29% | 41% |
| 78 | 57% | 69% | 56% |

INDUSTRIAL APPLICABILITY

The continuation aromatic cyclic compound of the present invention or a pharmaceutically acceptable salt thereof has an excellent DGAT1 inhibitory action and can be used as a prevention/treatment agent of obesity.

The invention claimed is:

1. The compound represented by the general formula (1-B):

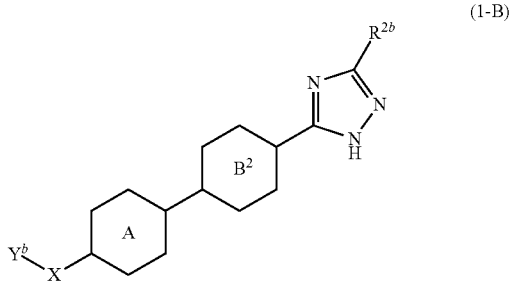

wherein ring A represents pyridine which may be substituted with 1 to 3 alkyl;
ring $B^2$ represents pyridine which may be substituted with 1 to 3 substituent groups which are halogen atoms or cyano;
$R^{2b}$ represents alkyl which may be substituted with 1 to 6 halogen atoms, alkoxy which may be substituted with 1 to 6 halogen atoms, alkylthio, an aromatic hydrocarbon group which may be substituted with 1 to 3 alkoxy, cycloalkyl which may be substituted with 1 to 7 halogen atoms, aryloxy which may be substituted with halogen atom or cyano, cycloalkyloxy, or cycloalkylalkoxy;
X represents a single bond or —O—;
$Y^b$ represents alkyl which may be substituted with carboxy or cycloalkyl which may be substituted with 1 to 3 substituent groups which are carboxyalkyl, carboxy, alkoxyalkyl or aminocarbonyl;
or a pharmaceutically acceptable salt thereof;
wherein when 2 or more substituent groups are present, the substituent groups may be the same or different.

2. The compound according to claim 1 wherein $R^{2b}$ is alkyl which may be substituted, alkoxy which may be substituted, an aromatic hydrocarbon group which may be substituted, or aryloxy which may be substituted, or a pharmaceutically acceptable salt thereof.

3. The compound according to claim 1 wherein X is —O—, and $Y^b$ is alkyl which may be substituted with carboxy, or a pharmaceutically acceptable salt thereof.

4. The compound according to claim 1 which is selected from
2,2-dimethyl-3-({4'-methyl-5-[3-(propan-2-yloxy)-1H-1,2,4-triazol-5-yl]-2,3'-bipyridin-6'-yl}oxy)propanoic acid, and
2,2-dimethyl-3-({4-methyl-6'-[3-(propan-2-yloxy)-1H-1,2,4-triazol-5-yl]-3,3'-bipyridin-6-yl}oxy)propanoic acid,
or a pharmaceutically acceptable salt thereof.

5. A diacylglycerol acyltransferase (DGAT) 1 inhibitor composition comprising the compound according to claim 1 or a pharmaceutically acceptable salt thereof as active ingredient, and a pharmaceutically acceptable carrier.

* * * * *